(12) United States Patent
Phogat et al.

(10) Patent No.: US 8,586,056 B2
(45) Date of Patent: Nov. 19, 2013

(54) HIV-1 ENVELOPE GLYCOPROTEIN

(75) Inventors: Sanjay K. Phogat, Frederick, MD (US);
Wayne C. Koff, Stony Brook, NY (US);
Charles Richter King, Washington, DC (US); Denise Wagner, Brooklyn, NY (US); Simon Hoffenberg, Hartsdale, NY (US)

(73) Assignee: International AIDS Vaccine Initiative, New York, NY (US)

( * ) Notice: Subject to any disclaimer, the term of this patent is extended or adjusted under 35 U.S.C. 154(b) by 184 days.

(21) Appl. No.: 13/039,086

(22) Filed: Mar. 2, 2011

(65) Prior Publication Data

US 2011/0262488 A1    Oct. 27, 2011

Related U.S. Application Data

(60) Provisional application No. 61/309,685, filed on Mar. 2, 2010.

(51) Int. Cl.
*A61K 39/12* (2006.01)
*A61K 39/21* (2006.01)
*C07K 1/00* (2006.01)

(52) U.S. Cl.
USPC .................. 424/208.1; 424/186.1; 424/187.1; 424/188.1; 530/395

(58) Field of Classification Search
USPC ...................................... 424/208.1
See application file for complete search history.

(56) References Cited

U.S. PATENT DOCUMENTS

| | | | | |
|---|---|---|---|---|
| 6,897,301 B2 * | 5/2005 | Hahn et al. | ................... | 536/23.72 |
| 6,908,612 B2 * | 6/2005 | Devico et al. | ............... | 424/185.1 |
| 7,211,659 B2 * | 5/2007 | zur Megede et al. | ...... | 536/23.72 |
| 7,323,557 B2 * | 1/2008 | Wagner et al. | ................ | 536/23.1 |
| 7,358,334 B1 * | 4/2008 | Chaplin | ......................... | 530/350 |
| 7,655,774 B2 * | 2/2010 | Mullins et al. | ................ | 536/23.1 |
| 2009/0123485 A1 | 5/2009 | Koff et al. | | |
| 2011/0044994 A1 * | 2/2011 | Chan-Hui et al. | ......... | 424/148.1 |

OTHER PUBLICATIONS

Yang et al., (2000).Modifications that stabilize HIV envelope glycoprotein trimers in solution. J.Virol. 74(10): 4746-4754.*
GenBank: ABA61516.1 (2006) envelope glycoprotein [Human immunodeficiency virus 1, Submitted by Wu et al.,(2006) Neutralization escapte variants of HIV type 1 are transmitted from mother to infants. J.Virol. 80 (2), 835-844.*
U.S. Appl. No. 61/161,010, filed Mar. 2009, Chan-Hui et al.*
Walker et al.,2009. Broad and Potent Neutralizing Antibodies from an African Donor Reveal a New HIV-1 Vaccine Target. Science 326, 285-289.*
GenBank Accession No. EF117268: Kulkarni, et al., HIV-1 Isolate HIV-16055-2 Clone 3 From India Glycoprotein (ENV) Gene, Complete CDS, Apr. 17, 2009.

* cited by examiner

*Primary Examiner* — Louise Humphrey
*Assistant Examiner* — Yunus Abdul
(74) *Attorney, Agent, or Firm* — Vedder Price P.C.; Thomas J. Kowalski; Deborah L. Lu

(57) ABSTRACT

The present application relates to a novel HIV-1 envelope glycoprotein which may be utilized as an HIV-1 vaccine immunogen, antigens for crystallization and for the identification of broad neutralizing antibodies. The present invention encompasses the preparation and purification of immunogenic compositions which are formulated into the vaccines of the present invention.

8 Claims, 206 Drawing Sheets

FIG. 1

| Virus/Antibody | PG9 | PG16 |
|---|---|---|
| a) Good Binders | | |
| 16055 (EF117268) | <0.01 | <0.01 |
| 0013095 (EF117267) | <0.01 | <0.01 |
| 25925 (EF117273) | 0.15 | 0.11 |
| 25710 (EF117271) | <0.01 | <0.01 |
| CAAN (AY835452) | 11.87 | 12.87 |
| 6535 (AY835438) | 0.6 | >25 |
| Zm109F (AY424138) | 0.46 | >25 |
| B) Weak /Moderate Binders | | |
| DU422 | 1.64 | 2.34 |
| CAP45 | <0.01 | <0.01 |
| Du172 | 0.49 | 0.06 |
| Zm197 | 0.61 | 1.68 |
| JRCSF | <0.01 | <0.01 |
| YU2 | <0.01 | <0.01 |
| Bal | <0.01 | <0.01 |
| PVO | 9.76 | 21.92 |
| AC10 | 0.05 | <0.01 |
| b) Non Binders | | |
| 6936 | >25 | >25 |
| QH0692 | >25 | >25 |
| ZM214 | >25 | >25 |
| JRFL | >25 | >25 |
| SF162 | >25 | >25 |
| Zm135 | 17.56 | >25 |
| Control | | |
| MulV | >25 | >25 |

| | |
|---|---|
| >25 ug/ml | No neut |
| 10-25 ug/ml | |
| 1-10 ug/ml | |
| <1 ug/ml | |

FIG. 2

| HIV-1 Viruses | IC50 in ug/ml | | | | |
|---|---|---|---|---|---|
| | IgG b12 | IgG PG9 | IgG PG16 | IgG 4E10 | CD4BS Ab |
| Clade C | | | | | |
| 13095 | >25 | <0.01 | <0.01 | 0.89 | 0.16 |
| 16055 | >25 | <0.01 | <0.01 | 7.02 | 0.05 |
| 25925 | >25 | 0.15 | 0.11 | >25 | 2.49 |
| 16936 | >25 | >25 | >25 | 3.85 | 0.15 |
| 25710 | >25 | <0.01 | <0.01 | 0.77 | 0.37 |

>25 ug/ml  No neut
10-25 ug/ml
1-10 ug/ml
<1 ug/ml

FIG. 3C

| | HIV-1 Virus | Neutralization | | | Shed gp120 Binding | | |
|---|---|---|---|---|---|---|---|
| | | PG9 | PG16 | b12 | PG9 | PG16 | b12 |
| A | UG037 | 0.02 | 0.01 | >25 | Weak | No | NT |
| | RW020 | 0.05 | 0.037 | 10 | Weak | No | Moderate |
| | Q842 | 0.02 | 0.009 | >25 | No | No | weak |
| B | JRCSF | 0.002 | 0.001 | 0.096 | Moderate | No | Good |
| | REJO451 | 0.001 | 0.004 | 5.92 | Weak | No | Moderate |
| | WITO4160 | 0.005 | 0.002 | 8.58 | Weak | No | Moderate |
| | YU2 | 1.73 | 0.114 | 2.18 | Weak | No | Good |
| | JRFL | >25 | >25 | 0.022 | No | No | Good |
| | SF162 | >25 | >25 | 0.07 | No | No | Good |
| | QH0692 | >25 | >25 | 0.97 | No | No | Good |
| C | CAP45 | 0.003 | 0.002 | 0.37 | Weak | No | Moderate |
| | 16055 | 0.01 | 0.01 | >25 | Good | Moderate | Moderate |
| | DU422 | 0.178 | 0.042 | 0.464 | Weak | No | Moderate |
| | DU172 | 0.24 | 0.023 | 0.3 | Weak | No | Moderate |
| | ZM197 | 0.287 | 0.765 | >25 | Moderate | No | Weak |
| | 16936 | >25 | >25 | >25 | No | No | Weak |
| | ZM135 | >25 | >25 | >25 | No | No | Weak |
| | ZM214 | >25 | >25 | 13.6 | No | No | Weak |
| | MuLv | >25 | >25 | >25 | No | No | No |

ELISA binding:

•No binding (0.2 OD above background at 50ug/ml),

•Weak (>0.5-1 OD at 12.5 ug/ml), Moderate (>0.5-1 OD at 0.2 ug/ml)

•Good binding (>1 OD at 0.2 ug/ml).

Neutralization (IC 50 Value)

| >25 ug/ml | No neut |
|---|---|
| 10-25 ug/ml | |
| 1-10 ug/ml | |
| <1 ug/ml | |

B) Selected PG9 non-binders [Two of clade B (Sf162 and QH0692), one each of C (ZM214), Indian C (6936) and founder virus (700010058) Envs]

FIG. 4I-III depicts shed gp120 based screening and selection of HIV-1 Env A) PG9 binders, a) HIV-1 clade B, b) HIV-1 clade C and B) A few PG9 non-binders

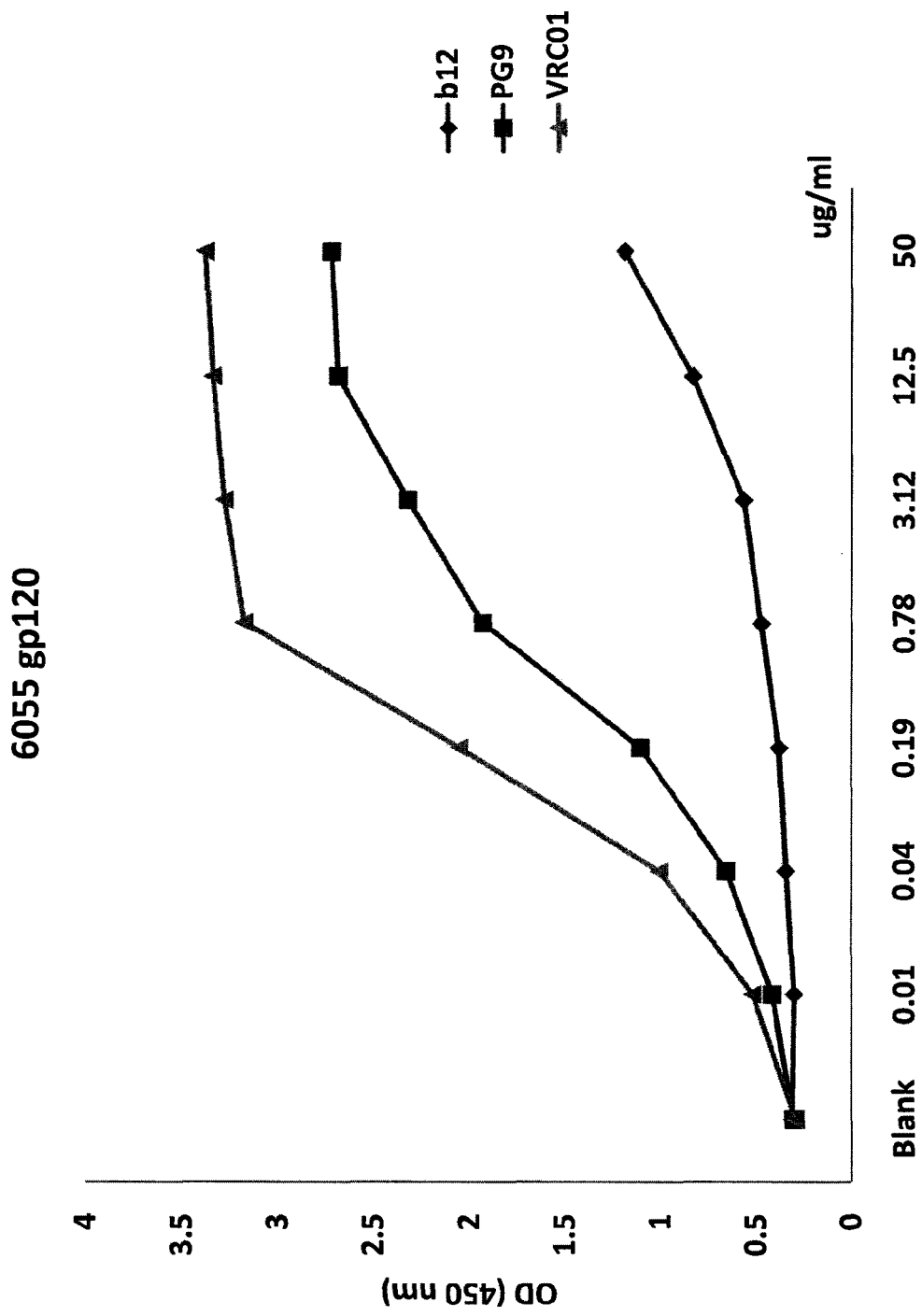

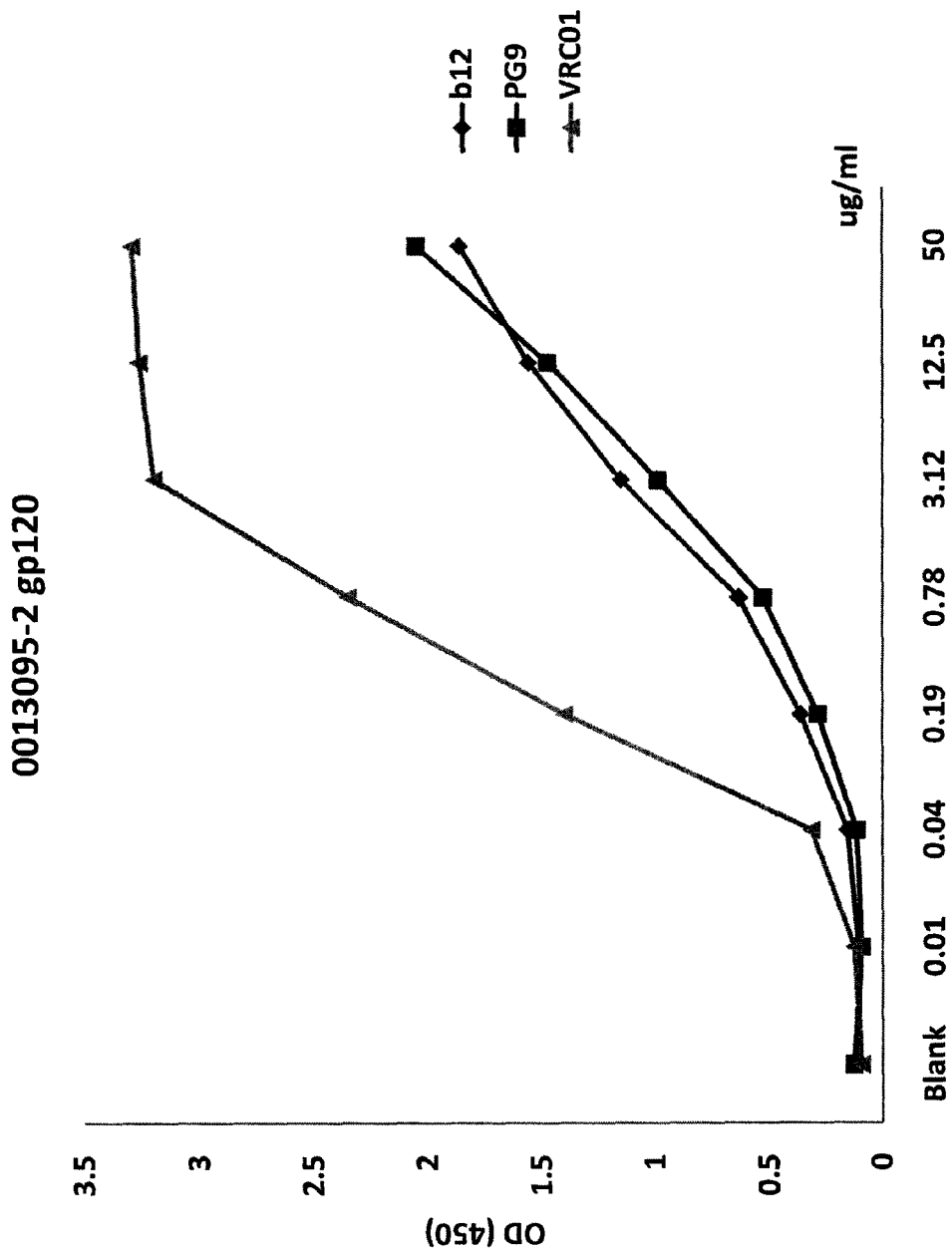

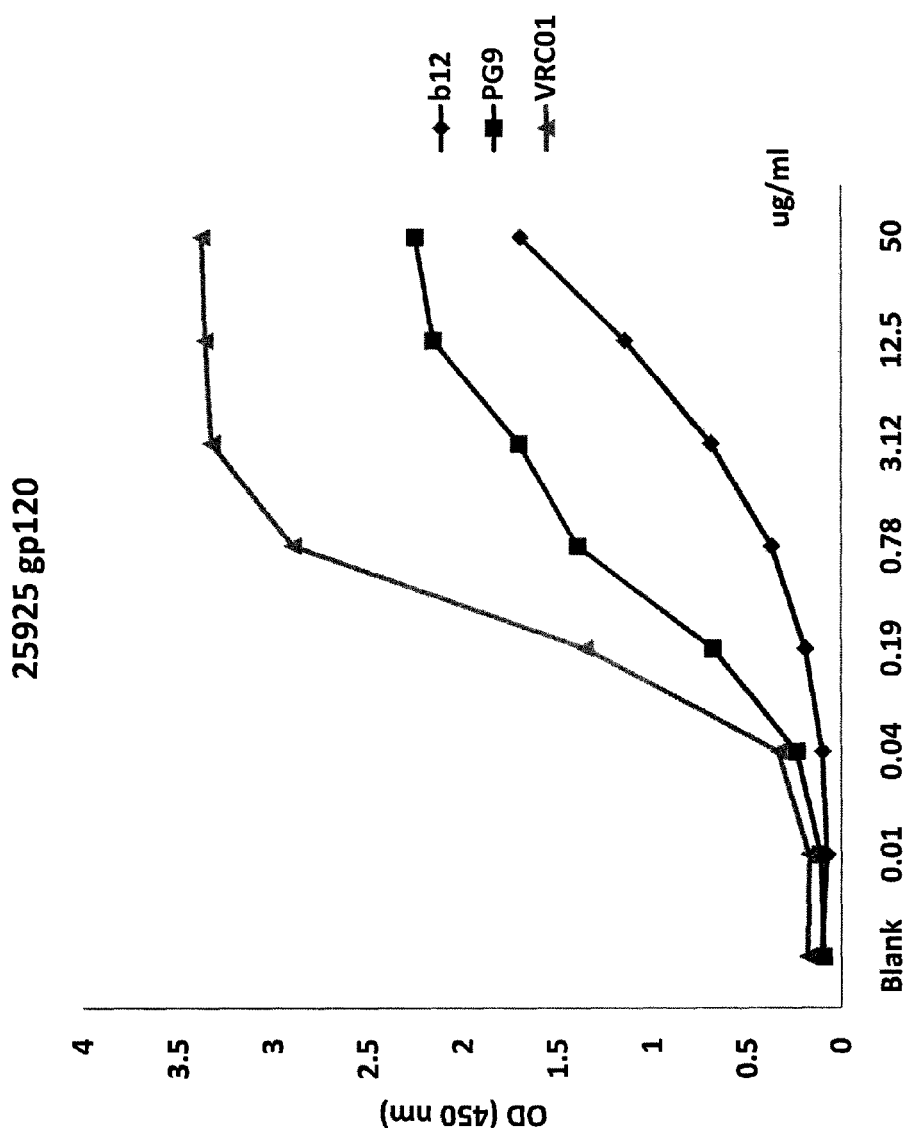

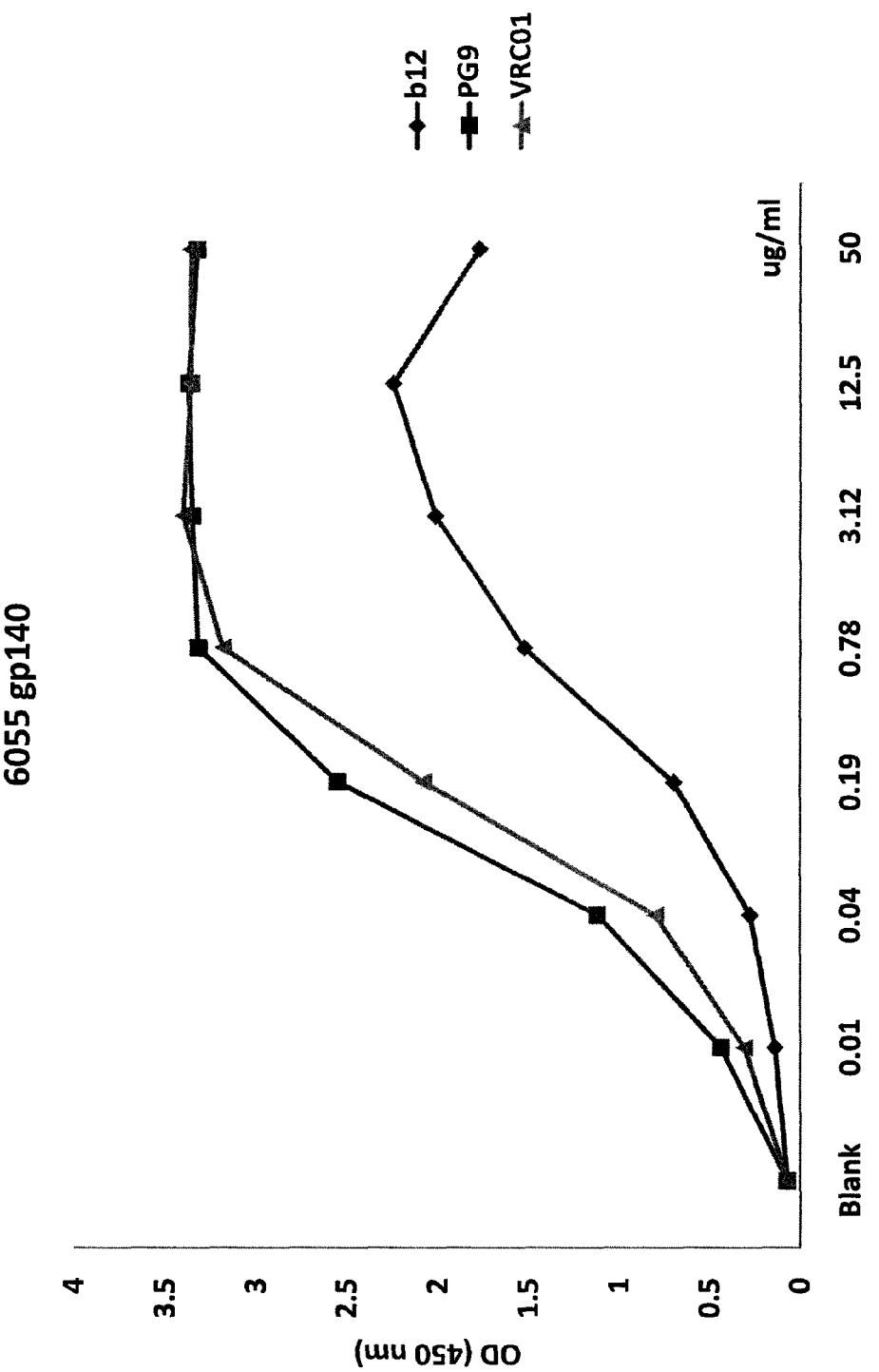

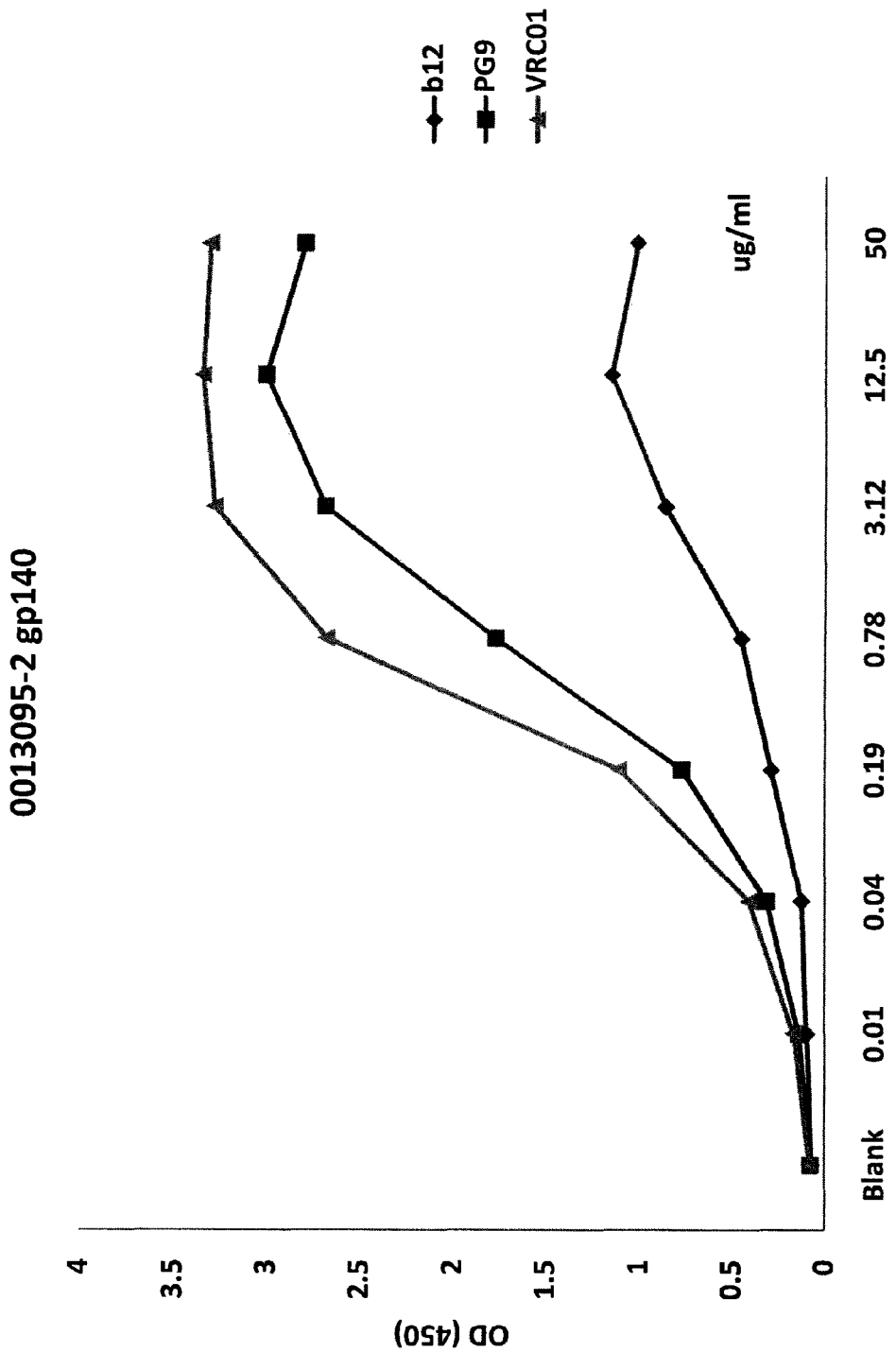

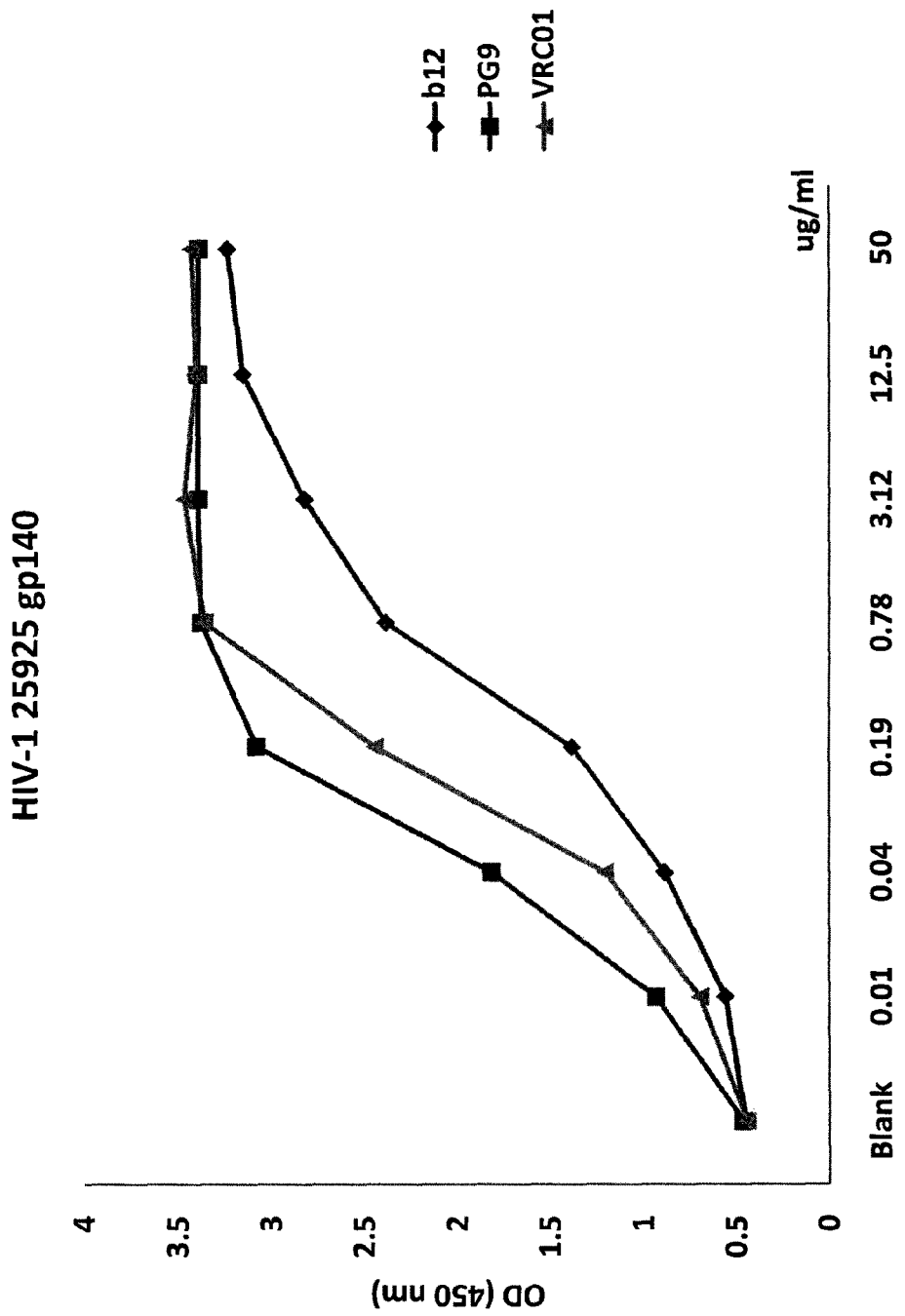

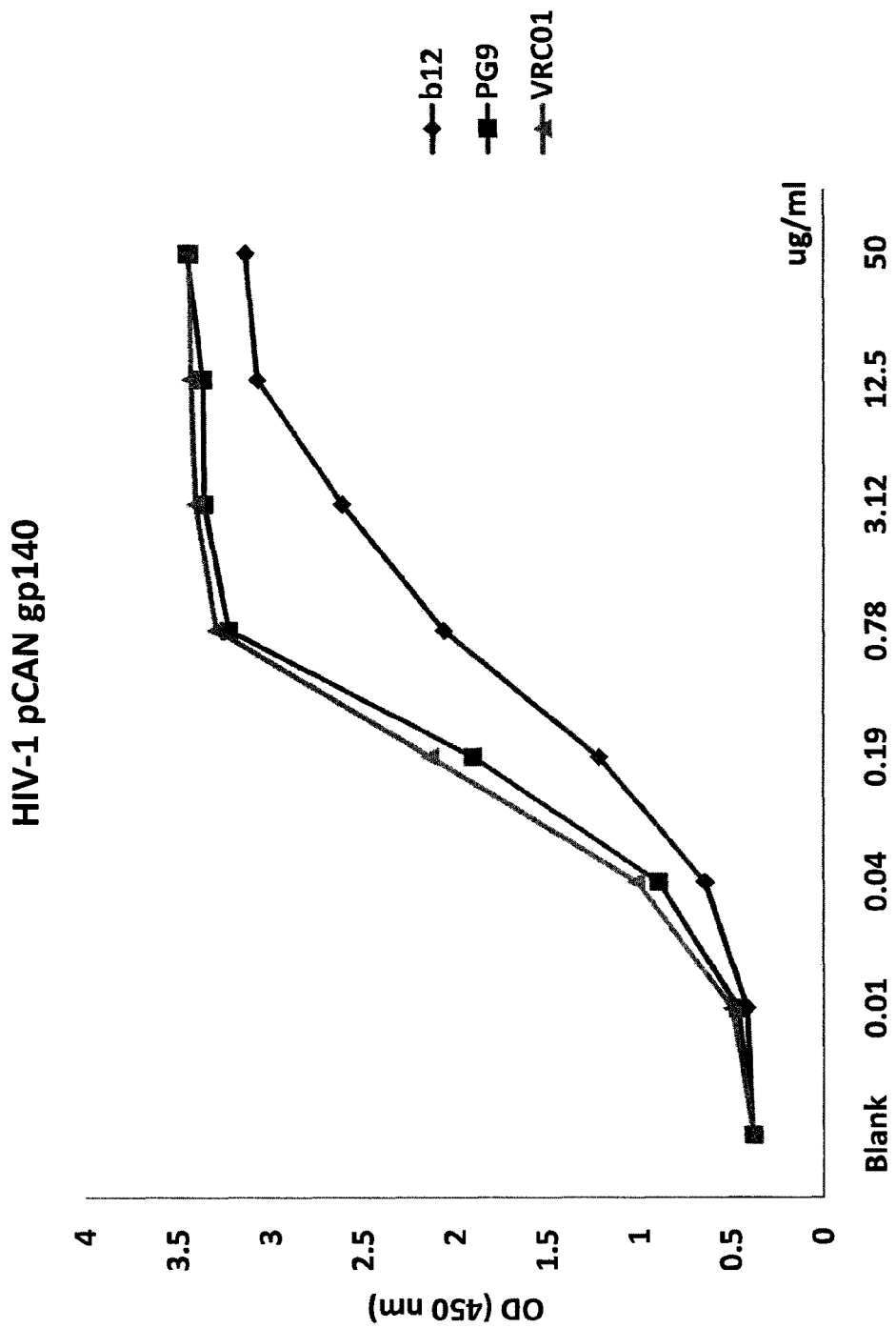

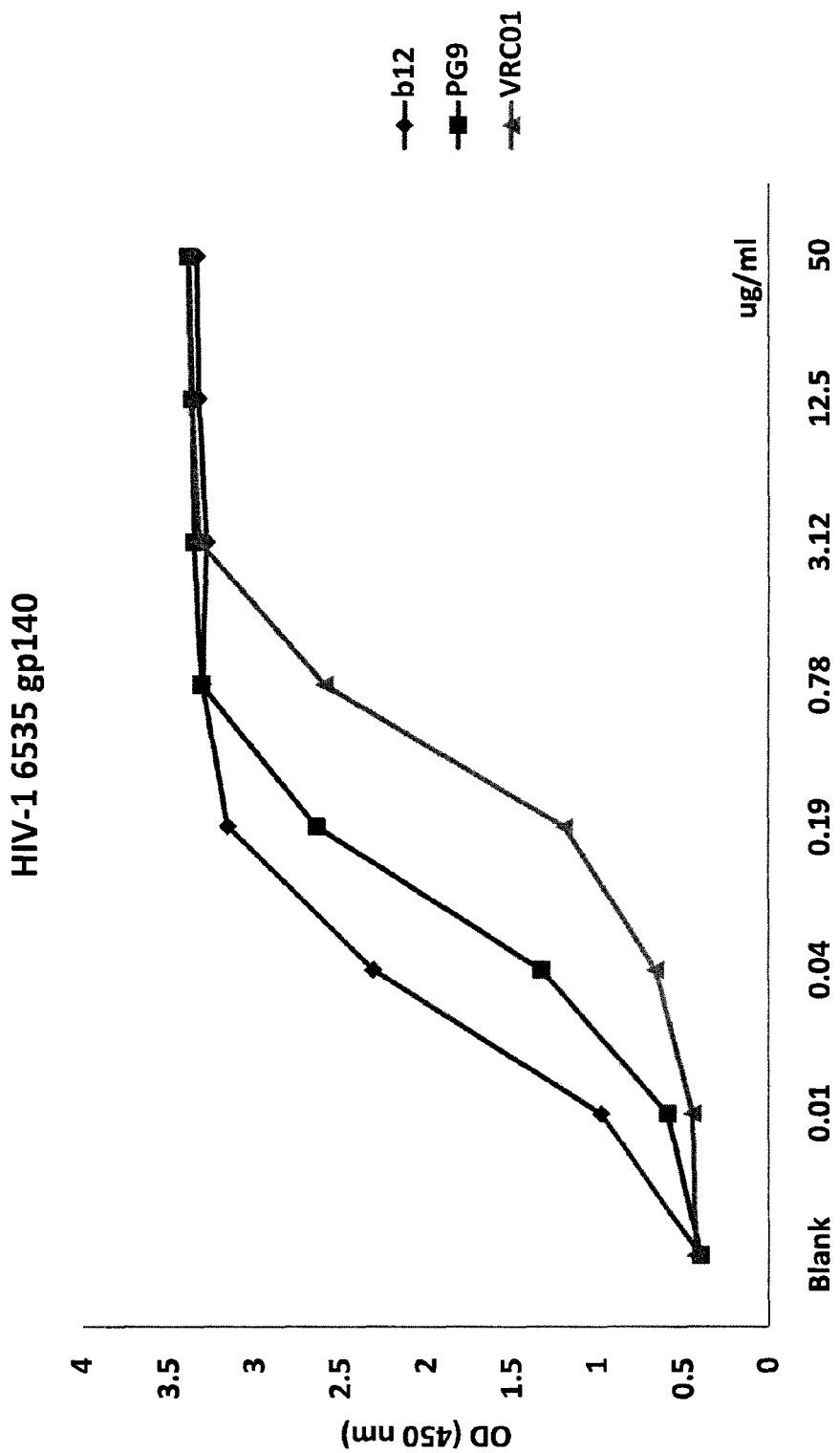

FIG. 6
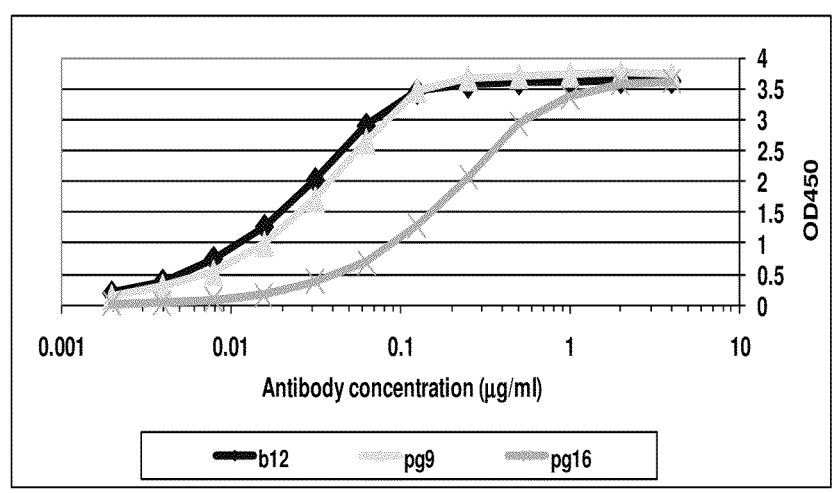
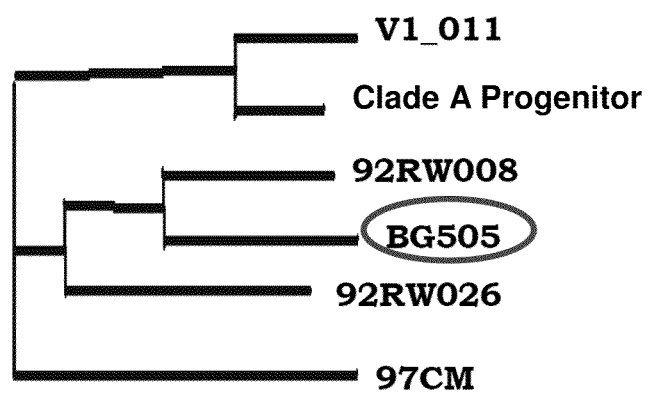

FIG. 7
A)
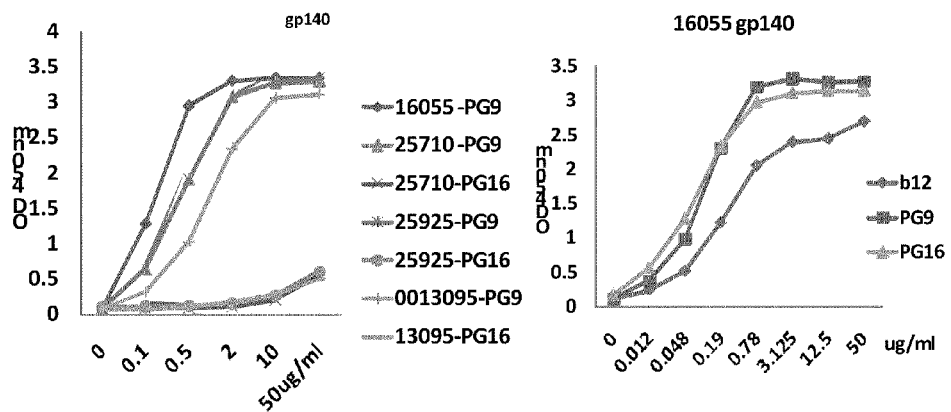
B)
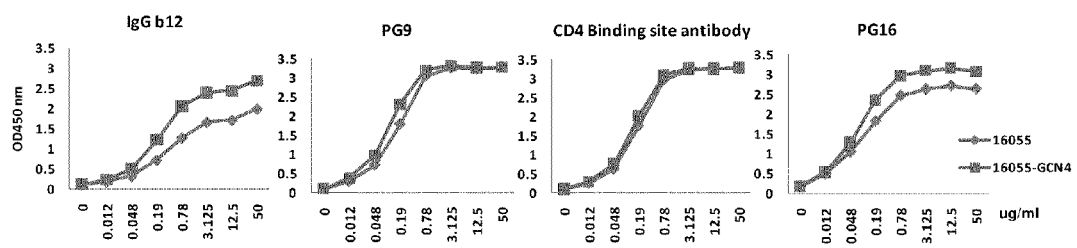

FIG. 8

|  | Ligand | $K_{ON}$ (1/Ms) | $K_{OFF}$ (1/s) | KD (M) | $R^2$ |
|---|---|---|---|---|---|
| Neutralizing ligands | PG9 | $6.82 \times 10^3$ | $3.09 \times 10^{-4}$ | $4.5 \times 10^{-8}$ | 0.995 |
|  | b12 | $8.79 \times 10^3$ | $1.07 \times 10^{-3}$ | $1.2 \times 10^{-7}$ | 0.989 |
|  | VRC01 | $4.78 \times 10^3$ | $2.94 \times 10^{-4}$ | $6.1 \times 10^{-8}$ | 0.997 |
|  | CD4IgG | $8.46 \times 10^3$ | $1.68 \times 10^{-4}$ | $1.9 \times 10^{-8}$ | 0.999 |
| Non-Neutralizing ligands | F105 | $8.43 \times 10^3$ | $1.69 \times 10^{-3}$ | $2.0 \times 10^{-7}$ | 0.993 |
|  | b13 | No Binding | | | |
|  | b6 | $1.1 \times 10^4$ | $8.66 \times 10^{-5}$ | $7.7 \times 10^{-9}$ | 0.999 |
|  | A32 | $1.56 \times 10^4$ | $8.23 \times 10^{-5}$ | $5.2 \times 10^{-9}$ | 0.999 |
|  | C11 | $7.4 \times 10^3$ | $3.57 \times 10^{-4}$ | $4.8 \times 10^{-8}$ | 0.998 |
|  | 17b | $3.29 \times 10^3$ | $2.71 \times 10^{-4}$ | $8.2 \times 10^{-8}$ | 0.997 |

FIG. 9A

```
EF117267_GB    LWVTVYYGVPVWKEAKTTLFCASDAKAYEKEVHNVWATHACVPTDPNPQEMVLENVTENF
EF117271_GB    LWVTVYYGVPVWKEATTTLFCASDAKAYDKEVHNVWATHACVPTDPNPQEMVLGNVTENF
EF117273_GB    LWVTVYYGVPVWKEAKATLFCASDAKAYETEVHNVWATHACVPTDPNPQEIVLENVTENF
EF117265_NB    LWVTVYYGVPVWKEAKTTLFCASDAKAHEREVHNVWATYACVPTDPNPQEIVLKNVTENF
EF117268_GB    LWVTVYYGVPVWKEAKTTLFCASDAKAYEKEVHNVWATHACVPTDPNPQEMVLENVTENF
EF117266_WB    LWVTVYYGVPVWKEARTTLFCASDAKAYETEVHNVWATHACVPTDPNPQEMVLGNVTENF
EF117270_NB    LWVTVYYGVPVWKEAKTTLFCASDAKAYETEVHNVWATHACVPTDPNPQELVLENVTENF
EF117269_WB    LWVTVYYGVPVWREAKTTLFCASDAKAYEKEVHNVWATHACVPTDPNPQEIDL-NVTENF
EF117274_NB    LWVTVYYGVPVWKEAKTTLFCASDAKAYEKEVHNVWATHACVPTDPNPQEIVLGNVTEDF
AY423984_WB    LWVTVYYGVPVWREAKTTLFCASDAKAYEREVHNVWATHACVPTDPNPQEMVLENVTENF
EF117272_NB    LWVTVYYGVPVWKEAKTTLFCASDAKGYDKEVHNVWATHACVPTDPNPQEMPLENVTENF
DQ411854_WB    LWVTVYYGVPVWKEAKTTLFCASDAKAYDKEVHNVWATHACVPTDPNPQEIVLENVTENF
DQ435682_WB    LWVTVYYGVPVWKEAKATLFCASDARAYEKEVHNVWATHACVPTDPNPQEIYLGNVTENF
DQ388514_WB    LWVTVYYGVPVWREAKTTLFCASDAKAYEKEVHNVWVTHACVPTDPNPQEMNLENVTENF
DQ388516_NB    LWVTVYYGVPVWREAKTTLFCASDAKAYEKEVHNVWATHACVPTDPNPQELVLENVTENF
DQ388517_WB    LWVTVYYGVPVWREAKTTLFCASDAKAYETEAHSVWATHACVPTDPNPQEMVLENVTENF
DQ435683_WB    LWVTVYYGVPVWKEAKTTLFCASDAKGYDTEVHNVWATHACVPTDPNPQEIVLENVTENF
DQ411853_WB    LWVTVYYGVPVWKEAKTTLFCASDAKAHKEEVHNIWATHACVPTDPNPQEIVLKNVTENF
DQ388515_WB    LWVTVYYGVPVWKEAKATLFCASDAKAYEKEVHNVWATHACVPTDPNPQEIPLGNVTENF
AY424079_NB    LWVTVYYGVPVWREAKTTLFCASDAKAYEKEVHNVWATHACVPTDPNPQELVLGNVTENF
AY424138_GB    LWVTVYYGVPVWKEAKTTLFCASDAKSYEREVHNVWATHACVPTDPDPQELVMANVTENF
AY835438_GB    LWVTVYYGVPVWKEATTTLFCASEAKAYDTEVHNVWATHACVPTDPNPQEVELGNVTENF
AY835450_WB    LWVTVYYGVPVWKEATTTLFCASDAKAYETEVHNVWATHACVPTDPNPQELVLENVTEYF
AY835449_wB    LWVTVYYGVPVWKEATTTLFCASDAKAYDQEIHNIWATHACVPTDPNPQEVELKNVTENF
AY835445_WB    LWVTVYYGVPVWKDASTTLFCASDAKAYDTEVHNVWATHACVPTDPNPQEVVLGNVTENF
AY835447_WB    LWVTVYYGVPVWKEANTTLFCASDAKAYDTEAHNVWATHACVPTDPNPQEVVLENVTENF
AY835451_WB    LWVTVYYGVPVWREANTTLFCASDAKAYDTEVHNVWATHACVPTDPNPQEVVMGNVTEDF
AY835441_WB    LWVTVYYGVPVWKEATTTLFCASDAKAYETEKHNVWATHACVPTDPDPQEVVLGNVTENF
AY835439_NB    LWVTVYYGVPVWKEATTTLFCASDAKAYETEKHNVWATHACVPTDPNPQEVVLGNVTENF
JRCSF_WB       LWVTVYYGVPVWKETTTTLFCASDAKAYDTEVHNVWATHACVPTDPNPQEVVLENVTEDF
JRFL_NB        LWVTVYYGVPVWKEATTTLFCASDAKAYDTEVHNVWATHACVPTDPNPQEVVLENVTEHF
Bal_WB         LWVTVYYGVPVWKEATTTLFCASDAKAYDTEVHNVWATHACVPTDPNPQEVKMENVTENF
HXBC2_WB       LWVTVYYGVPVWKEATTTLFCASDAKAYDTEVHNVWATHACVPTDPNPQEVVLVNVTENF
SF162_NB       LWVTVYYGVPVWKEATTTLFCASDAKAYDTEVHNVWATHACVPTDPNPQEIVLENVTENF
AY835446_WB    -WVTVYYGVPVWKEANTTLFCASDAKAYNTEVHNVWATHACVPTDPNPQEVELENVTENF
AY835448_NB    LWVTVYYGVPVWKEAVTTLFCASDAKAYDTEVHNVWATHACVPTDPDPQEVVLENVTENF
AY835452_GB    LWVTVYYGVPVWKEATTTLFCASDAKGYEKEVHNVWATHACVPTDPNPQEVVLENVTENF
AY835444_WB    LWVTVYYGVPVWKEATTTLFCASDAKAYNTEVHNVWATHACVPTDPNPQEVGLENVTENF
               **********:::  :******:*:..  *  *.:*.*:******:***:  : **** *
```

FIG. 9B

```
EF117267_GB    NMWENDVVDQMHEDVISLWDQSLKPCVKLTPLCVTLNCSKAKNITEEV--------IKNNTY
EF117271_GB    NMWKNEMVNQMHEDVISLWDQSLKPCVKLTPLCVTLECSN----------------VTYNES
EF117273_GB    NMWENDMVNQMHEDVISLWDQSLKPCVKLTPLCVTLDCENVDGND-----------TYNGT
EF117265_NB    NMWENDMVDQMQEDVISLWDQSLKPCIKLTPLCVTLECTNVNIING---------TIHNET
EF117268_GB    NMWKNDMVEQMHEDVISLWDQSLKPCVKLTPLCVTLECRQVNTTN-AT--------SSVNVT
EF117266_WB    NMWKNDMVDQMHEDVISLWAQSLKPCVKLTPLCVTLECTQVNATQGNT--------TQVNVT
EF117270_NB    NMWRNDMVDQMHEDVISLWDQSLKPCVKLTPLCVTLECRNATS-------------KMVNDT
EF117269_WB    NMWKNDMVEQMHEDVISLWDQSLKPICVKLTPICVTLECTDANITCNST--------TSSNNC
EF117274_NB    NMWKNDMVDQMHEDISLWDQSLKPCVKLTPLCVTLDC--ANVTSNIT-------NGE---
AY423984_WB    NMWKNDMVDQMQEDIISLWDQSLKPCVKLTPLCVTLNCSKLNN-----------------
EF117272_NB    NMWENDMVNQMHEDVISLWDESLKPCVKLTPLCVTLNCTDVNKNVSSS--------DTDNYK
DQ411854_WB    NMWKNDMVDQMHEDIISLWDQSLKPCVKLTPLCVTLNCKNVNISANANA----T-ATLNSS
DQ435682_WB    NMWKNDMVDQMHEDIISLWDQSLKPCVKLTPLCVTLRCTN----------------ATINGS
DQ388514_WB    NMWKNDMVDQMHEDIISLWDQSLKPCVKLTPLCVTLNCNNVNVTHN---------STYNNT
DQ388516_NB    NMWKNDMVNQMHEDIISLWDQSLKPCVKLTPLCVTLNCSNVNINETSID---FNVTSNIS
DQ388517_WB    NMWKNDMVDQMHEDVISIWDQSLKPCVKLTPLCVTLDCS----------------TYNNT
DQ435683_WB    NMWKNDMVDQMHQDIISLWDQSLKPCVKLTPLCVTLNCSDA---------------TYNNG
DQ411853_WB    NMWKNDMVDQMHEDIISLWDQSLKPCVKLTPLCVTLNCSDVKIKGTNA---------TYNNA
DQ388515_WB    NMWKNDMADQMHEDIISLWDQSLKPCVKLTPLCVTLNCSDATSNTTKNATNTNTTSTDNR
AY424079_NB    NMWENDMVDQMHEDIISLWDQSLKPCVKLTPLCVTLECKNATR--------SNQTTYYDN-
AY424138_GB    NMWKNDMVDQMHEDIISLWDQSLKPCVKLTPLCVTLNCTSP---------------AAHNES
AY835438_GB    NMWKNDMVEQMHEDIISLWDQSLKPCVRLTPLCVTLDCTDLNN-----------TTNTNNTT
AY835450_WB    DMWKNNMVEQMHEDIISLWDQSLKPCVKLTPLCVTLNCTDWTNGTDWN-----TTNSNNTT
AY835449_wB    NMWKSNMVEQMHEDIISLWDQSLKPCVKLTPLCVTLKCTDLNV------------TNSNSTD
AY835445_WB    NMWKNNMVDQMHEDIISLWDQSLKPCVKLTPLCVTLNCTDNITNT---------NTNSSKNS
AY835447_WB    NMWKNHMVEQMHEDIISLWDQSLKPCVKLTPLCVTLNCTDLVN------------------S
AY835451_WB    NMWKNNMVEQMHEDIISLWDQSLKPCVKLTPLCVTLHCTNVTISS----------------T
AY835441_WB    NMWKNNMVEQMHEDIISLWDQSLKPCVKLTPLCVTLNCTDELRNG---------TYANVTVT
AY835439_NB    NMWKNNMVEQMHEDIISLWDESLKPCVKLTPLCVTLNCTDEVKT---------SYANKTSN
JRCSF_WB       NMWKNNMVEQMQEDVINLWDQSLKPCVKLTPLCVTLNCKDVN----------------ATNTT
JRFL_NB        NMWKNNMVEQMQEDIISLWDQSLKPCVKLTPLCVTLNCKDVN--------------ATNTT
Bal_WB         NMWKNNMVEQMHEDIISLWDQSLKPCVKLTPLCVTLNCTDLRNAT----------SRNVTNTT
HXBC2_WB       NMWKNDMVEQMHEDIISLWDQSLKPCVKLTPLCVSLKCTDLKN--------------DTNTN
SF162_NB       NMWKNNMVEQMHEDIISLWDQSLKPCVKLTPLCVTLHCTNLKN--------------ATNTK
AY835446_WB    NMWKNNMVDQMHEDIISLWDQSLKPCVKLTPLCVTLSCTDNVG-------------NDTST
AY835448_NB    NMWKNNMVEQMHEDIISLWDQSLKPCVKLTPLCVTLNCTDYNNTATNT----TSSATTTA
AY835452_GB    NMWKNNMVEQMHEDIISLWDQSLKPCVKLTPLCVTLNCSDVNT------------------TS
AY835444_WB    NMWKNNMVEQMHEDIISLWDQSLKPCVKLTPLCVTLNCSDLRNATN---------TTNPTV
               :**...:.:**::*:*.:* :*****::***:**:* *
```

FIG. 9C

```
                    N156,S158,F159,N160,T162, Y173,F176,V181
EF117267_GB  ----------KEDIKNCSFNATTEVKDKKQKVHALFYRLDIVPLNKRNSSESEEENSSGYY
EF117271_GB  ----------MKEVKNCSFNITTELRDKKQKVHALFYRLDIVPLN------DTEKKNSSRPY
EF117273_GB  ----------NE-MKNCSFNTTTELRDKKQKVSALFYRLDIVPLNR------SSSSNSSDYY
EF117265_NB  --------YESMKNCSFNTTTELKDKKQSVYALFYRLDIVPLN---------NSNEYY
EF117268_GB  ---------NGEEIKNCSFNATTEIRDKKQKVYALFYRLDIVPLEE----ERKGNS---SKY
EF117266_WB  QV--------NGDEMKNCSFNTTTEIRDKKQKAYALFYRLDIVPLER---ENRGDSNSASKY
EF117270_NB  R--------NVEEMKNCSFNTTTELRDRKQTVYASFYKLDIVPLNE------NKSTSSENY
EF117269_WB  TSYEINKEDMGEIKNCSFNTTTELIDKKQKKVHALFYRLDIVSLEK--DNSSKKNDSNEYY
EF117274_NB  ----------EIKNCSFNATTDVRDKKKTVYSLFYRLDIVQLD------GRSNTSN--Y
AY423984_WB  --------ATDGEMKNCSFNATTELRDKKKQVYALFYKLDIVPLDG---------RNNSSEY
EF117272_NB  -------ETMKERKNCTFNMTTELRDKNQKKYALFYKLDIVPLDD---------NDNAS-Y
DQ411854_WB  M---------NGEIKNCSFNTTTELRDKKQKVYALFYKPDVVPLN--------GGEHNETGEY
DQ435682_WB  L---------TEEVKNCSFNITTELRDKKQKAYALFYRPDVVPLNK------NSPSGNSSEY
DQ388514_WB  E---------GEQIKNCSFNITTELRDKKQKVYALFYKLDILPLN---------GNNDSNEY
DQ388516_NB  M--------KEEMKNCSFKVNSELRDKNRREHALFYKLDIVQLN--------DEGNDSYSY
DQ388517_WB  ------HNISKEMKICSFNMTTELRDKKRKVNVLFYKLDIVPLTN---------SSNTTNY
DQ435683_WB  --------TNSTDTMKICSFNATTELRDKKKKEYALFYRLDIVPLKNE------SESQNFSEY
DQ411853_WB  TYN--NNNTISDMKNCSFNTTTEITDKKKREYALFYKLDVVALDGKE----TNSTNSSEY
DQ388515_WB  NATSNDTEMKGEIKDCTFNITTEVRDRKTKQRALFYKLDVVPLEEE-KNSSSKNSSYKEY
AY424079_NB  --------MDKEIKNCSFNVTTELTDKKKNMRALFYRADIEPLDGN-SNESINSSEGDKY
AY424138_GB  ---------ETRVKHCSFNITTDVKDRKQKVNATFYDLDIVPLSS------SDNSSNSSLY
AY835438_GB  NTNSSKIEG-GEMKNCSFNITTNRGDKRQKEYALLYRTDIVSIEN---------TSSSY
AY835450_WB  ISKEETIEG-GEMKNCSFNITTATGDKK-KERAFFYKLDVAPIDN---------SNTSY
AY835449_wB  HSTNSSLEAKGEIKNCSFNITTTPRDKIQKEYAIFYKQDVVPIKN----------DNISY
AY835445_WB  STHSYNNSLEGEMKNCSFNITAGIRDKVKKKYALFYKLDVVPIEEDKDTN------KTTY
AY835447_WB  NITRVDNTTEKEMKNCSFNVTSGIRDKVQKEYALLYKLDIVQIDNDNTSHR----DNTSY
AY835451_WB  NGSTANVTMREEMKNCSFNITTVIRDKIQKEYALFYKLDIVPIE-GKNTN-------TGY
AY835441_WB  EK--------GEIKNCSFNITTAIRDKVQKTYALFYRLDVVPIDNNHGNSSSN---YSNY
AY835439_NB  ETYKTSNETFGEIKNCSFSVPTGIKDKVQNVYALFYKLDVIPIDDNNNSSKNNNGSYSSY
JRCSF_WB     SSS-EGMMERGEIKNCSFNITKSIRDKVQKEYALFYKLDVVPIDNK---------NNTKY
JRFL_NB      NDS-EGTMERGEIKNCSFNITTSIRDEVQKEYALFYKLDVVPIDN---------NNTSY
Bal_WB       SSS-RGMVGGGEMKNCSFNITTGIRGKVQKEYALFYELDIVPIDN---------KIDRY
HXBC2_WB     SSSGRMIMEKGEIKNCSFNISTSIRGKVQKEYAFFYKLDIIPIDN---------DTTSY
SF162_NB     SSN-WKEMDRGEIKNCSFKVTTSIRNKMQKEYALFHKLDVVPIDN---------DNTSY
AY835446_WB  NNSRWDKMEKGEIKNCSFNITTNMRDKMQKQYALFYKLDVVPIEEGKNNNS----SFTDY
AY835448_NB  SSANKTAKEEAVMKNCSFNITTNVRDKVKREYALFYNLDVVKLEE---------GETSY
AY835452_GB  VNTTASSMEGGEIKNCSFNTTTSMSDKMQKEYALFYTLDVVPIVK----------ENNTY
AY835444_WB  SSRVIKKEMMGEVKNCSFNVTTDIRDRMQKVYALFYRPDVVPIQDHTIENNNTIENNTTY
                          : *:*.    ..    :: *: :                    *
```

FIG. 9D

```
EF117267_GB  RLINCNTSAVTQACPKVTFDPIPIHYCTPAGYAILKCNEETFNGTGPCHNVSTVQCTHGI
EF117271_GB  RLINCNTSAITQACPKVTFDPIPIHYCTPAGYAILKCNDKKFNGTGPCHKVSTVQCTHGI
EF117273_GB  RLISCNTSAITQACPKVTFDPIPIHYCAPAGFAILKCNNKTFNGTGPCHNVSTVQCTHGI
EF117265_NB  RLINCNTSAIKQACPKVTFDPIPIHYCAPAGYAILKCNDKTFSGTGPCHNVSTVQCTHGI
EF117268_GB  RLINCNTSAITQACPKVTFDPIPIHYCAPAGYAILKCNNKTFNGTGPCNNVSTVQCTHGI
EF117266_WB  ILINCNTSAITQACPKVNFDPIPIHYCTPAGYAILKCNNKTFNGTGSCNNVSTVQCTHGI
EF117270_NB  RLINCNTSAITQACPKVNFDPIPIHYCTPAGYAILKCNNKTFNGTGPCSNVSTVQCTHGI
EF117269_WB  RLINCNTSAITQACPKVTFDPIPIHYCAPAGYAILKCKNKTFNGTGPCNNVSTVQCTHGI
EF117274_NB  RLINCNTSTITQACPKVSFDPIPIHYCAPAGYAILKCNNKTFNGKGPCHNISTVQCTHGI
AY423984_WB  RLINCNTSTITQACPKVSFDPIPIHYCAPAGYAILKCNNKTFNGTGPCHNVSTVQCTHGI
EF117272_NB  RLINCNTSLTQACPKVSFDPIPIHYCAPAGYAILKCKNKTFNGIGPCNKVSTVQCTHGI
DQ411854_WB  ILINCNSSTITQACPKVSFDPIPIHYCAPAGYAILKCNNKTFNGTGPCNNVSTVQCTHGI
DQ435682_WB  ILINCNTSTITQACPKVSFDPIPIHYCAPAGYAILKCNNKTFNGTGPCNNVSTVQCTHGI
DQ388514_WB  RLINCNTSAITQACPKVSFDPIPIHYCAPAGYAILKCNNKTFNGKGPCNNVSTVQCTHGI
DQ388516_NB  RLINCNTSTIKQACPKVSFEPIPIHYCAPAGYAILKCNNETFNGSGPCNNVSTVQCTHGI
DQ388517_WB  RLISCNTSTITQACPKVSFDPIPIHYCAPAGYAILKCNNKTFNGTGPCNNVSTVQCTHGI
DQ435683_WB  ILINCNTSTIAQACPKVSFDPIPIHYCAPAGYAILKCNNKTFNGTGPCNNVSTVQCTHGI
DQ411853_WB  RLINCNTSAVTQACPKVSFDPIPIHYCAPAGYAILKCNNKTFNGTGPCNNVSTVQCTHGI
DQ388515_WB  RLISCNTSTITQACPKVSFDPIPIHYCAPAGYAILKCNNKTFNGTGPCHNVSTVQCTHGI
AY424079_NB  ILINCNTSTIAQACPKVTFDPIPIHYCAPAGYAILKCNNKTFNGIGPCKNVSTVQCTHGI
AY424138_GB  RLISCNTSTITQACPKVSFDPIPIHYCAPAGYAILKCNNKTFSGKGPCSNVSTVQCTHGI
AY835438_GB  RLISCNTSVITQACPKVTFEPIPIHYCAPAGFAILKCNEDKFNGTGPCKNVSTVQCTHGI
AY835450_WB  RLISCNTSVITQACPKISFEPIPIHYCAPAGFAILKCNDKKFNGTGSCTNVSTVQCTHGI
AY835449_wB  RLISCNTSVITQACPKVTFEPIPIHYCAPAGFAILKCNDKGFNGTGPCTNVSTVQCTHGI
AY835445_WB  RLRSCNTSVITQACPKVTFEPIPIHYCAPAGFAILKCNDKKFNGTGPCTNVSTVQCTHGI
AY835447_WB  RLISCNTSVITQACPKISFEPIHFCAPAGFAILKCNDKKFNGTGPCTNVSTVQCTHGI
AY835451_WB  RLINCNTSVITQACPKVSFEPIPIHYCAPAGFAILKCNNKTFNGKGPCRNVSTVQCTHGI
AY835441_WB  RLINCNTSVITQACPKVSFEPIPIHYCAPAGFAILKCNNKKFNGTGPCKNVSTVQCTHGI
AY835439_NB  RLINCNTSVITQACPKVSFEPIPIHYCAPAGFAILKCNNKTFNGTGPCTNVSTVQCTHGI
JRCSF_WB     RLISCNTSVITQACPKVSFEPIPIHYCAPAGFAILKCNNKTFNGKGQCKNVSTVQCTHGI
JRFL_NB      RLISCDTSVITQACPKISFEPIPIHYCAPAGFAILKCNDKTFNGKGPCKNVSTVQCTHGI
Bal_WB       RLISCNTSVITQACPKVSFEPIPIHYCAPAGFAILKCKDKKFNGKGPCTNVSTVQCTHGI
HXBC2_WB     KLTSCNTSVITQACPKVSFEPIPIHYCAPAGFAILKCNNKTFNGTGPCTNVSTVQCTHGI
SF162_NB     KLINCNTSVITQACPKVSFEPIPIHYCAPAGFAILKCNDKKFNGSGPCTNVSTVQCTHGI
AY835446_WB  RLISCNTSVITQACPKVTFEPIPIHYCAPAGFALLKCKDKKFNGTGPCKNVSTVQCTHGI
AY835448_NB  RLVSCNTSVVTQACPKITFEPIPIHYCAPAGFAILKCNNKTFNGTGPCTNVSTVQCTHGI
AY835452_GB  RLISCNTSVITQACPKVSFEPIPIHYCAPAGFAILMCNNKTFDGKGPCNNVSTVQCTHGI
AY835444_WB  RLISCNTSVITQACPKISFEPIPIHYCTPAGFAILKCNDKKFNGSGPCTNVSTVQCTHGI
              *  .*::*.: *****:.*:*****:*:***:*:*  *::.  *.* * *  ::*********
```

FIG. 9E

```
                                                                            P299, K305
EF117267_GB    KPVVSTQLLLNGSLAEG-EIIIRSKNLTDNAKTIIVHLNQSVEIVCTRPNENRRKSIRI-
EF117271_GB    KPVVSTQLLLNGSLAEG-EIIIRSENLTNNAKTIIVHLNQSVEIVCARPSNNTRTSIRI-
EF117273_GB    KPVVSTQLLLNGSLAEK-EIIIRSKNLSDNVKTIIVHLNESVEIVCTRPNNNTRKSIRI-
EF117265_NB    KPVVSTQLLLNGSLAEG-EIIIRSKKLDDNANTIIVHLDEPVKIECTRPNNNTRKSIRI-
EF117268_GB    KPVVSTQLLLNGSLAEG-EIIIRSENLTNNVKTIIVHLNESVEIVCTRPNNNTRKSIRI-
EF117266_WB    KPVVSTQLLLNGSLAEE-EIIIRSENLTDNVKTIIVHLDQSVEIVCTRPNNNTRKSIRI-
EF117270_NB    KPVVSTQLLLNGSLAEE-GIIIRSENLTDNVKTIIVHLEEPVEIVCTRPNNNTRKSVRI-
EF117269_WB    KPVVSTQLLLNGSLAEE-EIIIRSENLTNNAKIIIVHLNQAVEIVCTRPGNNTRKSIRI-
EF117274_NB    KPVVSTQLLLNGSLAEE-EIIIRSENLTNNVKTIIVHLNKPVKIVCTRPGNNTRKSIRI-
AY423984_WB    KPVISTQLLLNGSTAEE-DIIIRSENLTNNAKTIIVHLNESIEIECTRPGNNTRKSIRI-
EF117272_NB    KPVVSTQLLLNGSLAEE-DIVIRSENITDNAKTIIVHLNESVEIVCIRPNNNTRKSIRI-
DQ411854_WB    KPVVSTQLLLNGSLAEE-EIIVRSENLTNNIKTIIVHLNKSVEIKCTRPNNNTRKSVRI-
DQ435682_WB    KPVVSTQLLLNGSLAEE-DIIIRSENLTNNIKTIIVHLNKSVEIVCRRPNNNTRKSIRI-
DQ388514_WB    KPVVSTQLLLNGSLAEK-EIIIRSENITDNVKTIIVHLNESVEINCTRPNNNTRKSIRI-
DQ388516_NB    KPVVSTQLLLNGSLAEK-EIMIRSENLTNNAKTIIVQLTEAVNITCMRPGNNTRKSVRI-
DQ388517_WB    KPVVSTQLLLNGSLAEE-EIIIRFENLTDNVKIIIVQLNETINITCTRPNNNTRKSIRI-
DQ435683_WB    KPVVSTQLLLNGSLAEE-EVVIRSENISNNVKTIIVHLNESVNITCIRPGNNTRRSIRI-
DQ411853_WB    KPVVSTQLLLNGSLAEE-EVVIRFENLTNNAKIIIVHLNESVEINCTRPSNNTRKSVRI-
DQ388515_WB    KPVVSTQLLLNGSLAEE-EIIIRSENLTDNTKTIIVHLNESVEIECVRPNNNTRKSVRI-
AY424079_NB    KPVVSTQLLLNGSLSEE-GIIIRSKNLTDNTKTIIVHLNESVAIVCTRPNNNTRKSIRI-
AY424138_GB    RPVVSTQLLLNGSLAEE-EIVIRSENLTDNAKTIIVHLNKSVEIECIRPGNNTRKSIRL-
AY835438_GB    RPTVSTQLLLNGSLAKE-EVIIRSANLSDNAKIIIVQLKDPVEINCTRPNNNTRKSINL-
AY835450_WB    RPVVSTQLLLNGSLAEE-EVVIRSKNFSDNAKIIIVHLNKSVEIPINCTRPHNNTRKSIHI-
AY835449_wB    RPAISTQLLLNGSLAED-KVVIRSENFTDNAKIIIVHLNETVKINCTRPNNNTRKSIHI-
AY835445_WB    RPVVSTQLLLNGSLAEE-EVVIRSENFTNNAKTIIVQLNESIAINCTRPNNNTRRSIHI-
AY835447_WB    RPVVSTQLLLNGSLAEE-EVVIRSENFTNNVKNIIVQLNESVQINCTRHNNNTRKSINI-
AY835451_WB    KPVVSTQLLLNGSLAEE-DIIIRSENFTNNGKNIIVQLKEPVKINCTRPGNNTRRSINI-
AY835441_WB    RPVVSTQLLLNGSLAEE-EVVIRSENFTDNAKTIIVQLNDSVIINCTRPNNNTRKGITI-
AY835439_NB    RPVVSTQLLLNGSLAEE-EVVIRSENFTNNAKTIIVHLKKSVEINCTRPGNNTRKSIHI-
JRCSF_WB       RPVVSTQLLLNGSLAEE-KVVIRSDNFTDNAKTIIVQLNESVKINCTRPSNNTRKSIHI-
JRFL_NB        RPVVSTQLLLNGSLAEE-EVVIRSDNFTNNAKTIIVQLKESVEINCTRPNNNTRKSIHI-
Bal_WB         RPVVSTQLLLNGSLAEE-EVVIRSENFTNNAKTIIVQLNESVEINCTRPNNNTRKSIHI-
HXBC2_WB       RPVVSTQLLLNGSLAEE-EVVIRSVNFTDNAKTIIVQLNTSVEINCTRPNNNTRKRIRIQ
SF162_NB       RPVVSTQLLLNGSLAEE-GVVIRSENFTDNAKTIIVQLKESVEINCTRPNNNTRKSITI-
AY835446_WB    KPVVSTQLLLNGSLAEE-EVVIRSENFSNNARTIIVQLNTSVEIKCIRPNNNTRKSIHI-
AY835448_NB    KPVVSTQLLLNGSLAEGGEVMIRSANFTNNAKTIIVQLSKSVAINCTRPNNNTSKSIHM-
AY835452_GB    KPVVSTQLLLNGSLAEE-EVVIRSDNFTDNAKTIIVHLNESIEITCTRPNNNTSKSITI-
AY835444_WB    RPVVSTQLLLNGSRAEE-EVIIRSENFTNNAKTIIVQLNKTVEINCTRPNNNTRKSISI-
               :*.:*********  ::    ::::   :: :* . ***:*    .: * * *  :*     : :
```

FIG. 9F

```
EF117267_GB    -GPGQAFYATGDIIGDIRQARCNISEEKWNETLQRVGRKLAEHFPN--KTIKFKSSSGGD
EF117271_GB    -GPGQTFYATGAITGDIRQAHCNISKDKWNETLQRVGEKLAEHFPN--KTIKFNSSSGGD
EF117273_GB    -GPGQTFYATGAIIGNIREAHCNISRDKWNETLQRVGKKLEEQFPN--KTINFTSSSGGD
EF117265_NB    -GPGQTFYATGEIIGNIRQAHCDISEDQWNETLQRVGKKLAELFPN--KTITFNSSSGGD
EF117268_GB    -GPGQTFYATGDIIGNIRQAYCNIKKDDWIRTLQRVGKKLAEHFPR--RIINFTSPAGGD
EF117266_WB    -GPGQTFYATGDIIGNIREAHCNISEKKWHEMLRRVSEKLAEHFPN--KTIKFTSSSGGD
EF117270_NB    -GPGQTFYATGEIIGDIRQAHCNISEAKWNETLQNVTKKLKEHFPN--KTIIFNSSSGGD
EF117269_WB    -GPGQTFYATGDIIGDIRQAHCNISEAKWNKTLREVSKKLAEHFPN--KTIIFNSSSGGD
EF117274_NB    -GPGQTFYATGEIIGNIRQAHCNISKEEWNKTLQGVGEKLAEHFPN--KTIEFTSPSGGD
AY423984_WB    -GPGQAFFATTNIIGDIRQAYCIINKANWTNTLHRVSKKLEEHFPN--KTINFNSSSGGD
EF117272_NB    -GPGQTFYATGDIVGDIRQAYCNISEGKWNKTLQRVSEKLAEHFPN--STINFNSSSGGD
DQ411854_WB    -GPGQTFYATGEIIGDIREAHCNISRETWNSTLIQVKEKLREHY-N--KTIKFEPSSGGD
DQ435682_WB    -GPGQAFYATNDIIGDIRQAHCNINNSTWNRTLEQIKKKLREHFLN--RTIEFEPPSGGD
DQ388514_WB    -GPGQTFYATGEIIGDIRQAHCNISKEKWNKTLLRVAKKLREHFPG--KAIKFEPSSGGD
DQ388516_NB    -GPGQTFYATGEIIGDIRQAHCNISKDKWNQILQNVRAKLGEHFHD--KTIKFEPSSGGD
DQ388517_WB    -GPGQSFYATGEIVGNIREAHCNISASKWNKTLERVRTKLKEHFPN--KTIEFEPSSGGD
DQ435683_WB    -GPGQAFYAMGDIIGNIREAHCNISEKAWNETLKKVVEKLVKYFPN--KTIEFAPPVGGD
DQ411853_WB    -GPGQTFFATGDIIGDIRQAHCNISRKKWNTTLQRVKEKLKEKFPN--KTIQFAPSSGGD
DQ388515_WB    -GPGQTFFATGEIIGDIRQAHCDLSKSNWTTTLKRIEKKLKEHFNN--ATIKFESSAGGD
AY424079_NB    -GPGQTFYATGEVIGDIRQAHCNISGEQWNRTLERIKDKLTEYFPD--KIIKFNHSSGGD
AY424138_GB    -GPGQTFYATGDVIGDIRKAYCKINGSEWNETLTKVSEKLKEYF-N--KTIRFAQHSGGD
AY835438_GB    -GPGRAFYATGDIIGDIRQAHCNISRAKWNDTLREIAKKLAEQFNN--RTIVFNQSSGGD
AY835450_WB    -GPGRAWYATGDIIGDIRKAYCNISEAKWNNTLKQITEKLKEQFNK---TIIVFNQPSGGD
AY835449_wB    -APGRAFYATGEIIGDIRKAYCTINESEWNNTLQKIVVTLREQFRN--KTIVFNQSSGGD
AY835445_WB    -GPGRAFYATGDIIGDIRQAHCNISRTEWNSTLRQIVTKLREQLGDPNKTIIFNQSSGGD
AY835447_WB    -GPGRAFYATGKIIGDIRQAHCNISREKWQNTLKQIVKKLREQFK---NKTIAFAPSSGGD
AY835451_WB    -GPGRAFYATGAIIGDIRKAHCNISTEQWNNTLQIVDKLREQFG---NKTIIFNQSSGGD
AY835441_WB    -GPGRVFY-TGEIVGDIRQVHCNLSSAKWNSTLKQVVTKLREQFG---NKTIVFNQSSGGD
AY835439_NB    -GPGRAFYATGDIIGDIRQAHCNLSSVQWNDTLKQIVIKLGEQFGT-NKTIAFNQSSGGD
JRCSF_WB       -GPGRAFYTTGEIIGDIRQAHCNISRAQWNNTLKQIVEKLREQFNN--KTIVFTHSSGGD
JRFL_NB        -GPGRAFYTTGEIIGDIRQAHCNISRAKWNDTLKQIVIKLREQFEN--KTIVFNHSSGGD
Bal_WB         -GPGRAFYTTGEIIGDIRQAHCNLSRAKWNDTLNKIVIKLREQFGN--KTIVFKHSSGGD
HXBC2_WB       RGPGRAFVTIGK-IGNMRQAHCNISRAKWNNTLKQIASKLREQFGN-NKTIIFKQSGGD
SF162_NB       -GPGRAFYATGDIIGDIRQAHCNISGEKWNNTLKQIVTKLQAQFGN--KTIVFKQSSGGD
AY835446_WB    -GPGRAFYTTGDIIGDIRQAHCNISRQNWNNTLKQIAEKLREQFGN--KTIVFRNSSGGD
AY835448_NB    -GPGGAFFATGRIIGDIRKAYCTVNGTEWNTTLRQIVEKFKKQFGE-NKTIVFKPSAGGD
AY835452_GB    -GPGRAFYATGRIIGDIRKAHCNISGEKWHNALEQIVKKLGEKFEN-ATTIRFNQSSGGD
AY835444_WB    -GPGRAFYATGDIIGDIRQAHCNLSRAEWNKTLKYISTKLREQFGN--KTIIFNGSSGGD
                .**   :        *.:*:. * :.  *   *    : .:       * *    ***
```

FIG. 9G

```
EF117267_GB    LEITTHSFNCRGEFFYCNTSGLFNGTYMPTYM--------PNSTNSNSSSNITIPCRIKQV
EF117271_GB    LEITTHSFNCRGEFFYCNTSGLFNGTFNGTYVS--------PNSTDSNSSSIITIPCRIKQI
EF117273_GB    LEITTHSFNCRGEFFYCNTSKLFNSTYIPTYR--------PNNTQGNSSSTITIPCRIKQI
EF117265_NB    LEITTHSFNCRGEFFYCNTSSLFKGTYRPNGT--------SNSTSG---SIITLPCYIKQV
EF117268_GB    LEITTHSFNCRGEFFYCNTSSLFNSTYNPNDTN--------SNSSSSNSSLDITIPCRIKQI
EF117266_WB    LEITTHSFNCRGEFFYCNTSGLFNSTYMPNGTY--------MPNGTNNSNSTIILPCRIKQI
EF117270_NB    LEITTHSFNCRGEFFYCNTSKLFNGIYNGTQS-----------NSSNSNSTIIIPCKIKQI
EF117269_WB    LEITTHSFNCGGEFFYCNTSSLFNSTFNSTYM--------TNDTDMNSNSTISIPCRIKQI
EF117274_NB    LEITTHSFNCRGEFFYCNTSDLFNGIYNGTYI--------PKG---NLNSTITIQCKIKQF
AY423984_WB    LEITTHSFNCGGEFFYCNTSSLFNGTYN----------------DTDIYNSTDIILLCRIKQI
EF117272_NB    LEITTHSFNCGGEFFYCNTSGLFNGTYMNNDTK-------SNDTKSNSSSIITIPCRIKQI
DQ411854_WB    LEVTTHSFNCREFFYCDTTKLFNETKLFNESE--------------YVDNKTIIILPCRIKQI
DQ435682_WB    LEVTTHSFNCGGEFFYCNT-------TRLFKWSS-------------NVTNDTITIPCRIKQF
DQ388514_WB    LEITTHSFNCRGEFFYCTTSKLFNSTYNPNDTE---------S--NSNNSNETLTLTCKIKQI
DQ388516_NB    LEITTHSFNCGGEFFYCNTTNLFSRTYTNGSNS---------NVNITSATITLPCRIKQI
DQ388517_WB    LEITTHSFNCGGEFFYCNTSGLFNSAIN------------------GTLTSNVTLPCRIKQI
DQ435683_WB    LEITTHSFNCGGEFFYCNTTKLFNSTHNSTDSTVNSTDSTAETGNSTNTNITLPCRIRQI
DQ411853_WB    LEITTHSFNCRGEFFYCYTSDLFNSTYMSN---------------NTGGANITLQCRIKQI
DQ388515_WB    LEITTHSFNCRGEFFYCNTSGLFNSSLLNDTDG--------TSNSTSNATITLPCRIKQI
AY424079_NB    LEITTHTFNCRGEFFYCNTSILF-------------------TENENSSDNITLPCRIKQF
AY424138_GB    LEVTTHSFNCRGEFFYCNTSELFNS---------------------NATESNITLPCRIKQI
AY835438_GB    PEIVMHSFNCAGEFFYCDTSQLFN-STWNSNST-----WNDTNNNNSTE-KIILSCRIRQI
AY835450_WB    PEVTMHSFNCGGEFFYCNTSKLFN-GTWNSTKR-----ANNTEG-------IIIILQCRIKQI
AY835449_wB    PEVTMHTFNCGGEFFYCNTAQLFN-SSWDTNTN-----GNDTQGPSENN-TIILPCRIKQI
AY835445_WB    TEITMHSFNCGGEFFYCNTTKLFN-STWNGN-N-----TTESDSTGEN---ITLPCRIKQI
AY835447_WB    PEIVMHSFNCNGEFFYCNTTKLFT-STWNSTWN-----STWNNTEGSNSTVITLPCRIRQI
AY835451_WB    PEVVMHTFNCGGEFFYCNTSQLFN-STWFNNGT-----STWN-STADN---ITLPCRIKQV
AY835441_WB    PEIVMHSFNCGGEFFFCNTTQLFN-STWNINGT-----WHGT---TVSN--KTIILPCRIKQI
AY835439_NB    PEIVMHSFNCGGEFFYCNTTQLFN-STWEFHGN-----WTRSNFTESNSTTITLPCRIKQI
JRCSF_WB       PEIVMHSFNCGGEFFYCNSTQLFN-STWN---------DTEKSSGTEGNDTIIILPCRIKQI
JRFL_NB        PEIVMHSFNCGGEFFYCNSTQLFN-STWNN--------NTEGSNNTEGN-TITLPCRIKQI
Bal_WB         PEIVTHSFNCGGEFFYCNSTQLFN-STWN---------VTEESNNTVENNTITLPCRIKQI
HXBC2_WB       PEIVTHSFNCGGEFFYCNSTQLFN-STWFNSTW-----STEGSNNTEGSDTITLPCRIKQI
SF162_NB       PEIVMHSFNCGGEFFYCNSTQLFN-STWN---------NTIGPNNTNGT--ITLPCRIKQI
AY835446_WB    PEIVMHTFNCAGEFFYCNTAELFN-STWYANGT-----ISIGGGNKTN----IILPCRIKQF
AY835448_NB    PEIVTHSFNCGGEFFYCNTTNLFNSSSTELNST-----WSGNSNDTGKNDTITLPCRIKQI
AY835452_GB    QEIVMHTFNCGGEFFYCNSTQLFN-STWWPNGT-----TTEWSNETSNG-TITLPCRIKQI
AY835444_WB    PEIVTHSFNCGGEFFYCNTTKLFN-STWDANGN-----CTGCDESDGNN-TITLPCRIKQI
               *:. *:*** ****:*  :                              :  : * *:*.
```

FIG. 9H

```
EF117267_GB    INMWQEVGRAMYAPPIEGEITCKSNITGLLLVRDGGNGNDTN---------KTEIFRPEGGD
EF117271_GB    INMWQEVGRAMYAPPIAGNITCKSNITGLLLVRDGGTGSESN---------KTEIFRPGGGD
EF117273_GB    INMWQEVGRAMYAPPIAGNITCKSHITGLLLVRDGGTGLNS----------STETFRPGGGD
EF117265_NB    INLWQEVGRAIYAPPIEGNITCISNITGLLLVRDGGNHEEAN--------TTETFRPGGGN
EF117268_GB    INMWQEVGRAMYAPPIEGNITCKSNITGLLLVRDG--GVESN---------ETEIFRPGGGD
EF117266_WB    INMWQEVGRAMYAPPIAGNITCNSNITGLLLVRDG--GK-NN---------NTEIFRPGGGD
EF117270_NB    VNMWQKVGRAMYAPPIAGNITCTSNITGLLLVRDGG----PDN--------VTEIFRPGGGD
EF117269_WB    INMWQEVGRAMYAPPIAGNITCKSNITGLLLVRDGGNSNDTN---------EPEIFRPQGGD
EF117274_NB    INMWQEVGRAMYAPPIQGNITCESNITGLLLVRDGGNSNST----------EEIFRPGGGD
AY423984_WB    INMWQEVGRAMYAPPIEGNITCSSNITGLLLTRDGGLTNESK----------ETFRPGGGD
EF117272_NB    INMWQEVGRAVYAPPIAGNITCKSNITGILLTRDGGRGEEVKN-------DTETFRPGGGN
DQ411854_WB    INMWQEVGRAMYAPPIEGNITCKSNITGLLLTWDGG----ENS--------TEGVFRPGGGN
DQ435682_WB    INMWQGAGRAMYAPPIEGNITCNSSITGLLLTRDGGK-TDRN---------DTEIFRPGGGN
DQ388514_WB    INMWQGVGRAMYAPPIEGSITCNSTITGLLLTRDGG--SKNN---------TEEIFRPGGGN
DQ388516_NB    INMWQEVGRAMYAPPIGNITCISNITGLLLTRDGGNGNDTN---------DTETFRPAGGD
DQ388517_WB    INMWQEVGRAMYAPPIAGNITCKSNITGLLLTRDGGENSS---S-------TTETFRPTGGD
DQ435683_WB    INMWQEVGRAMYAPPSKGNITCISNITGLLLTRDGGENKTENN-------DTEIFRPGGGD
DQ411853_WB    IRMWQGVGQAMYAPPIAGNITCKSNITGLLLTRDGGKEKN-----------DTETFRPGGGD
DQ388515_WB    INMWQEVGRAMYASPIAGIITCKSNITGLLLTRDGG--NKSA---------GIETFRPGGGN
AY424079_NB    VNMWQEVGRAMYAPPIAGNITCNSSITGLLLTRDGGLNNKEN--------GTETFRPQGGD
AY424138_GB    INMWQGVGRAMYAPPIRGEIKCTSNITGLLLTRDGGNNNNST---------EEIFRPEGGN
AY835438_GB    INRWQEVGKAMYAPPISGPIKCSSNITGLLLARDGGN----------ETN-VTETFRPAGGD
AY835450_WB    INRWQEVGKAMYAPPIEGQIKCSSNITGLLLTRDGGK-----------TANNTTEFFRPGGGN
AY835449_wB    INMWQRVGKAIYAPPISGQIRCLSNITGLILTRDGGN----------SSLSSPEIFRPGGGD
AY835445_WB    INLWQEVGKAMYAPPIKGQISCSSNITGLLLTRDGGNN----------NSSGPETFRPGGGN
AY835447_WB    INMWQEVGKAMYAPPIQGQIKCSSNITGLLLTRDGGVD---------TTK--ETFRPGGGN
AY835451_WB    INMWQEVGKAMYAPPIRGQIDCSSNITGLILTRDGGSN---------SSQN-ETFRPGGGN
AY835441_WB    INMWQEVGKAMYAPPIRGQIRCSSNITGLLLTRDGGN----------NNSTTEIFRPGGGN
AY835439_NB    VNMWQEVGKAMYAPPIRGQIRCSSNITGLLLTRDGGV--------NG-TRETFRPGGGD
JRCSF_WB       INMWQEVGKAMYAPPIKGQIRCSSNITGLLLTRDGGK-----------NESEIEIFRPGGGD
JRFL_NB        INMWQEVGKAMYAPPIRGQIRCSSNITGLLLTRDGGI-----------NENGTEIFRPGGGD
Bal_WB         INMWQEVGKAMYAPPIRGQIRCSSNITGLLLTRDGGP----------EDNKTEVFRPGGGD
HXBC2_WB       INMWQKVGKAMYAPPISGQIRCSSNITGLLLTRDGGN-----------SNNESEIFRPGGGD
SF162_NB       INRWQEVGKAMYAPPIRGQIRCSSNITGLLLTRDGGKE--------ISNTTEIFRPGGGD
AY835446_WB    INMWQEVGKAMYAPPISGQIRCSSNITGLLLTRDGGRGN--------QTDNQTEIFRPVGGD
AY835448_NB    INMWQQVGKAMYAPPISGKINCLSNITGLLLTRDGGSDGGSKNSSKNETGTEIFRPGGGD
AY835452_GB    INMWQEVGKAMYAPPISGPISCSSNITGLLLVRDGGND---------NETNGTETFRPGGGD
AY835444_WB    VNMWQEVGKAMYAPPIKGLIKCTSNITGLLLTRDGGAN----------NTNETFRPGGGD
               :. **  .*:*:**.*  * *  * ***::*. **             ***  **:
```

FIG. 9I

```
EF117267_GB      MRDNWRSELYKYKVVEIKPLGIAPT---------------
EF117271_GB      MRDNWRSELYKYKVVEIKPLGVAPT---------------
EF117273_GB      MRDNWRSELYKYKVVEIKPLGVAPTAAKRRVVQREKR
EF117265_NB      MRDNWRSELYKYKVVEIKPLGVAPT-------------
EF117268_GB      MRNNWRSELYKYKVVEIKPLGIAPT---------------
EF117266_WB      MRDNWRSELYKYKVVEIKPLGVAPT---------------
EF117270_NB      MRDNWRSELYKYKVVEIKPLGIAPT-------------
EF117269_WB      MRDNWRSELYKYKVVEIKPLGVAPTAAKRRVVGREKR
EF117274_NB      MRDNWRSELYKYKVVEIKPLGVAPTDAKRRVVERGKR
AY423984_WB      MRDNWRSELYKYKVVEIKPLGIAPT---------------
EF117272_NB      MKDNWRSELYKYKVVEIKPLGVAPT-------------
DQ411854_WB      MKDNWRSELYKYKVVEIKPLGVAPTKSKRKVVGREKR
DQ435682_WB      MKDNWRNELYKYKVVEIKPLGVAPT---------------
DQ388514_WB      MKDNWRSELYKYKVVEIKPLGVAPT---------------
DQ388516_NB      MRDNWRSELYKYKVVEIKPLGIAPTKAKRRVVGREKR
DQ388517_WB      MKNNWRSELYKYKVVEIKPLGIAPT---------------
DQ435683_WB      MKDNWRSELYKYKVVEIKPLGVAPT---------------
DQ411853_WB      MRDNWRSELYKYKVVEIKPLGIAP----------------
DQ388515_WB      MKDNWRSELYKYKVVEIKPLGIAPTSAKRRVVEREKR
AY424079_NB      MRDNWRSELYKYKVVEIRPLGVAPT-------------
AY424138_GB      MRDNWRSELYKYKVVEIKPLGIAPTEAKRRVVQREKR
AY835438_GB      MRDNWRSELYKYKVVQIEPLGIAPTKAKRRVVQREKR
AY835450_WB      MKDNWRSELYKYKVVRIEPLGVAPTKAKRRVVQREKR
AY835449_wB      MRDNWRSELYKYKVVQIEPLGIAPTRAKRRAVQREKR
AY835445_WB      MKDNWRSELYKYKVIKIEPLGVAPTRAKRRVVQREKR
AY835447_WB      MKDNWRSELYKYKVVRIEPLGVAPTKAKRRVVQREKR
AY835451_WB      MKDNWRSELYKYKVVKIEPLGIAPTRAKRRVVQREKR
AY835441_WB      MRDNWRSELYKYKVVKIEPLGIAPTKARRRVVQREKR
AY835439_NB      MRDNWRSELYKYKVVKIEPLGVAPTKAKRRVVQREKR
JRCSF_WB         MRDNWRSELYKYKVVKIEPLGVAPTKAKRRVVQREKR
JRFL_NB          MRDNWRSELYKYKVVKIEPLGVAPTKAKRRVVQREKR
Bal_WB           MRDNWRSELYKYKVVKIEPLGVAPTKAKRRVVQREKR
HXBC2_WB         MRDNWRSELYKYKVVKIEPLGVAPTKAKRRVVQREKR
SF162_NB         MRDNWRSELYKYKVVKIEPLGVAPTKAKRRVVQREKR
AY835446_WB      MKNNWRSELYKYKVVRIEPLGIAPTRAKRRVVQREKR
AY835448_NB      MRDNWRSELYKYKVVRIEPLGVAPTKAKRRAVQREKR
AY835452_GB      MRDNWRSELYKYKVVKIEPLGVAPTKAKRRVVQREKR
AY835444_WB      MRDNWRSELYKYKVVQIEPLGI------------------
                 *::***.*******:.*.***:
```

Legend:

Accession#_GB represents Good Binders
Accession#_WB represents Weak/Moderate Binders
Accession#_NB represents Non Binders a)

```
V1-16936    CR-----NATSKMVNDTRNVEEMKNC
            ||     ||||. ||.| |.||:|||
V1-16055    CRQVNTTNATSS-VNVT-NGEEIKNC
                                  #

V2-16936    SFNTTTELRDRKQTVYASFYKLDIVPLNENKSTSSENYRLINC
            |||.|||:||.|||.|||||.|.:.:|..|||||
V2-16055    SFNATTEIRDKKQKVYALFYRLDIVPLEEERKGNSSKYRLINC
            ### #    #     #  #   #

V3-16936    CTRPNNNTRKSVRIGPGQTFYATGEIIGDIRQAHC
            |||||||||||:|||||||||||||:|||:||||:|
V3-16055    CTRPNNNTRKSIRIGPGQTFYATGDIIGNIRQAYC
                 #    # #       ##
```

\# Residues that effect PG9 binding

\## Residues that effect PG16 binding b)

FIG. 11C c)

| HIV-1 Viruises | IC50 in ug/ml | | | | |
|---|---|---|---|---|---|
|  | IgG b12 | IgG PG9 | IgG PG16 | IgG 4E10 | CD4BS Ab |
| Clade C | | | | | |
| 16055 | >25 | <0.01 | <0.01 | 7.02 | 0.05 |
| 16936 | >25 | >25 | >25 | 3.85 | 0.15 |
| 16936 V1-3 16055 | 20.48 | 0.03 | 0.06 | 2.68 | 0.07 |

>25 ug/ml  No neut
10-25 ug/ml
1-10 ug/ml
<1 ug/ml a) Immunization schedule

Group I : 16055 Env DNA immunization (250 ug/animal/dose)
Group II: control DNA immunization (Empty plasmid vector)
Group III: gp120 Env 16055 protein (50 ug/animal/dose)

Intramuscular immunization
DNA by electroporation
Adjuvant Adjuplex LAP b) Geometric mean HIV-1 Env titer

FIG. 13C c) IC50 neutralization value for tier I and tier II clade B, C and JRCSF N160K mutant viruses

| IC50 Value | | | | | | | | |
|---|---|---|---|---|---|---|---|---|
| Week 0 | 14 | 31 | Week 0 | 14 | 31 | Week 0 | 14 | 31 |
| MW965.3 (Tier I C) | | | SF162 (Tier I B) | | | SS1196 (Tier I B) | | |
| Group 1 DNA Prime - 16055 gp120 Boost | | | | | | | | |
| 19 | >270 | >270 | 13 | >270 | >270 | 15 | 34 | 96 |
| <10 | >270 | >270 | <10 | >270 | >270 | <10 | 40 | 29 |
| 30 | >270 | >270 | 13 | >270 | >270 | 18 | 46 | 105 |
| 30 | >270 | >270 | <10 | >270 | >270 | 11 | 11 | 44 |
| 30 | >270 | >270 | <10 | >270 | >270 | <10 | <10 | 21 |
| 30 | >270 | >270 | 27 | | >270 | 18 | 20 | <10 |
| Group 2 control DNA prime - 16055 gp120 boost | | | | | | | | |
| 23 | <10 | >270 | <10 | <10 | >270 | <10 | <10 | <10 |
| <10 | <10 | >270 | <10 | <10 | >270 | <10 | <10 | <10 |
| <10 | <10 | >270 | <10 | <10 | >270 | <10 | <10 | 11 |
| <10 | <10 | >270 | <10 | <10 | 209 | <10 | <10 | <10 |
| <10 | <10 | >270 | 22 | <10 | >270 | 35 | <10 | 40 |
| <10 | <10 | >270 | <10 | <10 | >270 | <10 | <10 | 42 |
| Group 3 - 16055 gp120 prime - boost | | | | | | | | |
| <10 | >270 | >270 | 16 | >270 | >270 | <10 | 37 | 58 |
| 30 | >270 | >270 | <10 | >270 | >270 | <10 | 49 | >270 |
| 30 | >270 | >270 | 13 | >270 | >270 | <10 | 53 | 42 |
| <10 | >270 | >270 | <10 | >270 | >270 | <10 | 33 | 26 |
| <10 | >270 | >270 | <10 | >270 | >270 | <10 | 108 | 26 |
| <10 | >270 | >270 | <10 | >270 | >270 | <10 | <10 | <10 |
| IC50 Value | | | | | | | | |
| Week 0 | 14 | 31 | Week 0 | 14 | 31 | Week 0 | 14 | 31 |
| 16055 (Tier II C) | | | 93IN905 (Tier II C) | | | MGRM026 (Tier II C) | | |
| Group 1 DNA Prime - 16055 gp120 Boost | | | | | | | | |
| 16 | 12 | 72 | 12 | 48 | 117 | 21 | <10 | <10 |
| <10 | <10 | <10 | <10 | 249 | >270 | <10 | 15 | <10 |
| 16 | 30 | 136 | 30 | 72 | 202 | <10 | <10 | 126 |
| <10 | <10 | <10 | 30 | >270 | >270 | <10 | <10 | 135 |
| 20 | <10 | <10 | 30 | 150 | 262 | <10 | 12 | >270 |
| 29 | <10 | <10 | 30 | 142 | >270 | 30 | 90 | >270 |
| Group 2 control DNA prime - 16055 gp120 boost | | | | | | | | |
| 45 | <10 | <10 | 18 | <10 | 265 | 30 | 20 | 56 |
| 25 | <10 | <10 | <10 | <10 | 133 | <10 | <10 | 14 |
| 47 | <10 | <10 | <10 | <10 | >270 | 30 | 46 | 30 |
| 69 | <10 | <10 | <10 | <10 | >270 | 30 | <10 | 30 |
| 33 | <10 | <10 | <10 | 13 | 113 | 38 | 30 | <10 |
| 10 | <10 | <10 | <10 | <10 | 165 | <10 | <10 | <10 |
| Group 3 - 16055 gp120 prime - boost | | | | | | | | |
| <10 | 14 | 14 | <10 | 49 | 14 | 36 | <10 | >270 |
| 11 | <10 | <10 | 30 | >270 | 31 | 21 | <10 | >270 |
| 16 | <10 | <10 | 30 | 59 | 24 | 30 | <10 | >270 |
| <10 | <10 | <10 | <10 | >270 | 78 | <10 | <10 | >270 |
| 12 | <10 | <10 | <10 | >270 | 212 | <10 | 125 | >270 |
| <10 | <10 | <10 | <10 | 21 | 14 | <10 | <10 | >270 |

FIG. 13D

| IC50 Value | | | | | | | | | | | | | | |
|---|---|---|---|---|---|---|---|---|---|---|---|---|---|---|
| Week 0 | 14 | 31 | Week 0 | 14 | 31 | Week 0 | 14 | 31 | Week 0 | 14 | 31 | Week 0 | 14 | 31 |
| JRCSF (Tier II B) | | | JRCSF N160K | | | JRCSF N156A | | | JRFL E168K N192A | | | YU2 (Tier II B) | | |
| Group 1 DNA Prime - 16055 gp120 Boost | | | | | | | | | | | | | | |
| <10 | <10 | 53 | <10 | <10 | <10 | 12 | >270 | >270 | <10 | <10 | <10 | <10 | <10 | <10 |
| <10 | 18 | 36 | <10 | <10 | <10 | <10 | >270 | >270 | <10 | <10 | <10 | <10 | <10 | <10 |
| <10 | 20 | 96 | <10 | <10 | <10 | 12 | >270 | >270 | <10 | <10 | <10 | <10 | <10 | <10 |
| <10 | 12 | 42 | <10 | <10 | <10 | 16 | >270 | >270 | <10 | <10 | <10 | <10 | <10 | <10 |
| <10 | 13 | 31 | <10 | <10 | <10 | <10 | >270 | >270 | <10 | <10 | <10 | <10 | <10 | <10 |
| 25 | 25 | 16 | 26 | <10 | <10 | <10 | >270 | >270 | 45 | 35 | <10 | <10 | <10 | <10 |
| Group 2 control DNA prime - 16055 gp120 boost | | | | | | | | | | | | | | |
| <10 | <10 | <10 | <10 | <10 | <10 | 32 | <10 | >270 | <10 | <10 | <10 | <10 | <10 | <10 |
| 16 | <10 | <10 | 18 | <10 | <10 | 47 | 11 | >270 | <10 | <10 | <10 | <10 | <10 | <10 |
| <10 | <10 | 23 | <10 | <10 | <10 | 13 | 12 | >270 | <10 | <10 | <10 | <10 | <10 | <10 |
| <10 | <10 | 16 | <10 | <10 | <10 | 15 | <10 | >270 | <10 | <10 | <10 | <10 | <10 | <10 |
| <10 | <10 | <10 | <10 | <10 | <10 | 29 | <10 | >270 | <10 | <10 | <10 | <10 | <10 | <10 |
| <10 | <10 | 32 | <10 | <10 | <10 | 13 | <10 | >270 | <10 | <10 | <10 | <10 | <10 | <10 |
| Group 3 - 16055 gp120 prime - boost | | | | | | | | | | | | | | |
| <10 | 30 | 30 | <10 | <10 | <10 | <10 | >270 | >270 | <10 | <10 | <10 | <10 | <10 | 13 |
| <10 | 52 | 28 | <10 | <10 | <10 | 17 | >270 | >270 | <10 | <10 | <10 | <10 | <10 | <10 |
| <10 | 35 | 32 | <10 | <10 | <10 | <10 | >270 | >270 | <10 | <10 | 11 | <10 | <10 | <10 |
| <10 | 46 | 50 | <10 | <10 | <10 | 15 | >270 | >270 | <10 | 13 | <10 | <10 | <10 | <10 |
| <10 | 46 | 111 | <10 | <10 | 33 | 15 | >270 | >270 | 13 | 149 | 30 | <10 | 12 | <10 |
| <10 | 19 | 18 | <10 | <10 | <10 | <10 | >270 | >270 | <10 | 12 | <10 | <10 | <10 | <10 |

FIG. 14

```
                                HindIII
          NheI   PmeI    AflII                                        PstI
     CCAAGCTGGCTAGCGTTTAAACTTAAGCTTGCCACCATGCCTATGGGCAGCCTGCAGCCT
   1 ---------+---------+---------+---------+---------+---------+
     GGTTCGACCGATCGCAAATTTGAATTCGAACGGTGGTACGGATACCCGTCGGACGTCGGA
                                       M   P   M   G   S   L   Q   P BspMI       SphI                        PvuII
     CTGGCCACCCTGTACCTGCTGGGCATGCTGGTGGCCTCCGTGCTGGCAGCTGGCAACCTG
  61 ---------+---------+---------+---------+---------+---------+
     GACCGGTGGGACATGGACGACCCGTACGACCACCGGAGGCACGACCGTCGACCGTTGGAC
     L   A   T   L   Y   L   L   G   M   L   V   A   S   V   L   A   A   G   N   L TGGGTCACAGTGTACTACGGCGTGCCCGTGTGGAAAGAGGCCAAGGCCACACTGTTCTGC
 121 ---------+---------+---------+---------+---------+---------+
     ACCCAGTGTCACATGATGCCGCACGGGCACACCTTTCTCCGGTTCCGGTGTGACAAGACG
     W   V   T   V   Y   Y   G   V   P   V   W   K   E   A   K   A   T   L   F   C StuI
     GCCAGCGACGCCAAGGCCTACGAGACAGAGGTGCACAACGTCTGGGCCACCCACGCCTGC
 181 ---------+---------+---------+---------+---------+---------+
     CGGTCGCTGCGGTTCCGGATGCTCTGTCTCCACGTGTTGCAGACCCGGTGGGTGCGGACG
     A   S   D   A   K   A   Y   E   T   E   V   H   N   V   W   A   T   H   A   C GTGCCCACCGACCCCAACCCCCAGGAAATCGTCCTGGAAAACGTGACCGAGAACTTCAAC
 241 ---------+---------+---------+---------+---------+---------+
     CACGGGTGGCTGGGGTTGGGGGTCCTTTAGCAGGACCTTTTGCACTGGCTCTTGAAGTTG
     V   P   T   D   P   N   P   Q   E   I   V   L   E   N   V   T   E   N   F   N
```

```
                   HincII                    BclI
         ATGTGGGAGAACGACATGGTCAACCAGATGCACGAGGACGTGATCAGCCTGTGGGACCAG
     301 ---------+---------+---------+---------+---------+---------+
         TACACCCTCTTGCTGTACCAGTTGGTCTACGTGCTCCTGCACTAGTCGGACACCCTGGTC
          M  W  E  N  D  M  V  N  Q  M  H  E  D  V  I  S  L  W  D  Q AGCCTGAAGCCCTGCGTGAAGCTGACCCCCCTGTGCGTGACCCTGGACTGCGAGAACGTG
     361 ---------+---------+---------+---------+---------+---------+
         TCGGACTTCGGGACGCACTTCGACTGGGGGGACACGCACTGGGACCTGACGCTCTTGCAC
          S  L  K  P  C  V  K  L  T  P  L  C  V  T  L  D  C  E  N  V PstI
         GACGGCAACGACACCTACAACGGCACCAACGAGATGAAGAACTGCAGCTTCAACACCACC
     421 ---------+---------+---------+---------+---------+---------+
         CTGCCGTTGCTGTGGATGTTGCCGTGGTTGCTCTACTTCTTGACGTCGAAGTTGTGGTGG
          D  G  N  D  T  Y  N  G  T  N  E  M  K  N  C  S  F  N  T  T ACCGAGCTGCGGGACAAGAAACAGAAGGTGTCCGCCCTGTTCTACCGGCTGGACATCGTG
     481 ---------+---------+---------+---------+---------+---------+
         TGGCTCGACGCCCTGTTCTTTGTCTTCCACAGGCGGGACAAGATGGCCGACCTGTAGCAC
          T  E  L  R  D  K  K  Q  K  V  S  A  L  F  Y  R  L  D  I  V PvuII
                                                      BclI
         CCCCTGAACAGAAGCAGCAGCAGCAACAGCAGCGACTACTACCGGCTGATCAGCTGCAAC
     541 ---------+---------+---------+---------+---------+---------+
         GGGGACTTGTCTTCGTCGTCGTCGTTGTCGTCGCTGATGATGGCCGACTAGTCGACGTTG
          P  L  N  R  S  S  S  S  N  S  S  D  Y  Y  R  L  I  S  C  N StuI
         ACCAGCGCCATCACCCAGGCCTGCCCCAAAGTGACCTTCGACCCTATCCCCATCCACTAC
     601 ---------+---------+---------+---------+---------+---------+
         TGGTCGCGGTAGTGGGTCCGGACGGGGTTTCACTGGAAGCTGGGATAGGGGTAGGTGATG
          T  S  A  I  T  Q  A  C  P  K  V  T  F  D  P  I  P  I  H  Y
```

```
        TGCGCCCCTGCCGGCTTCGCCATCCTGAAGTGCAACAACAAGACCTTCAATGGCACCGGC
661     ---------+---------+---------+---------+---------+---------+
        ACGCGGGGACGGCCGAAGCGGTAGGACTTCACGTTGTTGTTCTGGAAGTTACCGTGGCCG
         C  A  P  A  G  F  A  I  L  K  C  N  N  K  T  F  N  G  T  G

CCCTGCCACAACGTGTCCACCGTGCAGTGCACCCACGGCATCAAGCCCGTGGTGTCCACC
721     ---------+---------+---------+---------+---------+---------+
        GGGACGGTGTTGCACAGGTGGCACGTCACGTGGGTGCCGTAGTTCGGGCACCACAGGTGG
         P  C  H  N  V  S  T  V  Q  C  T  H  G  I  K  P  V  V  S  T

PvuII
        CAGCTGCTGCTGAATGGCAGCCTGGCCGAGAAAGAGATCATCATCAGAAGCAAGAACCTG
781     ---------+---------+---------+---------+---------+---------+
        GTCGACGACGACTTACCGTCGGACCGGCTCTTTCTCTAGTAGTAGTCTTCGTTCTTGGAC
         Q  L  L  L  N  G  S  L  A  E  K  E  I  I  I  R  S  K  N  L

AGCGACAACGTGAAAACCATCATTGTGCACCTGAACGAGAGCGTGGAAATCGTGTGCACC
841     ---------+---------+---------+---------+---------+---------+
        TCGCTGTTGCACTTTTGGTAGTAACACGTGGACTTGCTCTCGCACCTTTAGCACACGTGG
         S  D  N  V  K  T  I  I  V  H  L  N  E  S  V  E  I  V  C  T

CGGCCCAACAACAACACCAGAAAGAGCATCCGGATCGGCCCTGGCCAGACCTTCTACGCC
901     ---------+---------+---------+---------+---------+---------+
        GCCGGGTTGTTGTTGTGGTCTTTCTCGTAGGCCTAGCCGGGACCGGTCTGGAAGATGCGG
         R  P  N  N  N  T  R  K  S  I  R  I  G  P  G  Q  T  F  Y  A

NarI
        KasI
        ACCGGCGCCATCATCGGCAACATCAGAGAGGCCCACTGCAACATCAGCCGGGACAAGTGG
961     ---------+---------+---------+---------+---------+---------+
        TGGCCGCGGTAGTAGCCGTTGTAGTCTCTCCGGGTGACGTTGTAGTCGGCCCTGTTCACC
         T  G  A  I  I  G  N  I  R  E  A  H  C  N  I  S  R  D  K  W
```

```
                    PstI
      AACGAGACACTGCAGAGAGTGGGCAAGAAGCTGGAAGAACAGTTCCCTAACAAGACAATC
1021  ---------+---------+---------+---------+---------+---------+
      TTGCTCTGTGACGTCTCTCACCCGTTCTTCGACCTTCTTGTCAAGGGATTGTTCTGTTAG
       N  E  T  L  Q  R  V  G  K  K  L  E  E  Q  F  P  N  K  T  I

PstI
      AACTTCACCTCCAGCTCTGGCGGCGACCTGGAAATCACCACCCACAGCTTCAACTGCAGA
1081  ---------+---------+---------+---------+---------+---------+
      TTGAAGTGGAGGTCGAGACCGCCGCTGGACCTTTAGTGGTGGGTGTCGAAGTTGACGTCT
       N  F  T  S  S  S  G  G  D  L  E  I  T  T  H  S  F  N  C  R

GGCGAGTTCTTCTACTGCAACACCTCCAAGCTGTTCAACAGCACCTACATCCCCACCTAC
1141  ---------+---------+---------+---------+---------+---------+
      CCGCTCAAGAAGATGACGTTGTGGAGGTTCGACAAGTTGTCGTGGATGTAGGGGTGGATG
       G  E  F  F  Y  C  N  T  S  K  L  F  N  S  T  Y  I  P  T  Y

AGACCCAACAACACCCAGGGCAACAGCTCCAGCACCATCACAATCCCTTGCCGGATCAAG
1201  ---------+---------+---------+---------+---------+---------+
      TCTGGGTTGTTGTGGGTCCCGTTGTCGAGGTCGTGGTAGTGTTAGGGAACGGCCTAGTTC
       R  P  N  N  T  Q  G  N  S  S  S  T  I  T  I  P  C  R  I  K

CAGATCATCAATATGTGGCAGGAAGTGGGCAGGGCTATGTACGCCCCTCCTATCGCCGGC
1261  ---------+---------+---------+---------+---------+---------+
      GTCTAGTAGTTATACACCGTCCTTCACCCGTCCCGATACATGCGGGGAGGATAGCGGCCG
       Q  I  I  N  M  W  Q  E  V  G  R  A  M  Y  A  P  P  I  A  G

BspMI                                          StuI
      AACATTACCTGCAAGAGCCACATCACCGGCCTGCTGCTCGTCCGCGACGGAGGCACAGGC
1321  ---------+---------+---------+---------+---------+---------+
      TTGTAATGGACGTTCTCGGTGTAGTGGCCGGACGACGAGCAGGCGCTGCCTCCGTGTCCG
       N  I  T  C  K  S  H  I  T  G  L  L  L  V  R  D  G  G  T  G

CTGAACAGCAGCACCGAGACATTCAGACCCGGCGGAGGCGACATGCGGGACAATTGGCGG
1381  ---------+---------+---------+---------+---------+---------+
      GACTTGTCGTCGTGGCTCTGTAAGTCTGGGCCGCCTCCGCTGTACGCCCTGTTAACCGCC
       L  N  S  S  T  E  T  F  R  P  G  G  G  D  M  R  D  N  W  R
```

```
             AGCGAGCTGTACAAGTACAAGGTGGTGGAAATCAAGCCCCTGGGCGTGGCCCCTACCGCC
1441         ---------+---------+---------+---------+---------+---------+
             TCGCTCGACATGTTCATGTTCCACCACCTTTAGTTCGGGGACCCGCACCGGGGATGGCGG
              S   E   L   Y   K   Y   K   V   V   E   I   K   P   L   G   V   A   P   T   A

NarI
                                              KasI
             GCCAAGAGAAGAGTGGTGCAGAGCGAGAAGTCCGCCGTGGGACTGGGCGCCGTGTTCCTG
1501         ---------+---------+---------+---------+---------+---------+
             CGGTTCTCTTCTCACCACGTCTCGCTCTTCAGGCGGCACCCTGACCCGCGGCACAAGGAC
              A   K   R   R   V   V   Q   S   E   K   S   A   V   G   L   G   A   V   F   L

GGCTTTCTGGGAGCCGCCGGAAGCACAATGGGCGCTGCCAGCATCACCCTGACCGTGCAG
1561         ---------+---------+---------+---------+---------+---------+
             CCGAAAGACCCTCGGCGGCCTTCGTGTTACCCGCGACGGTCGTAGTGGGACTGGCACGTC
              G   F   L   G   A   A   G   S   T   M   G   A   A   S   I   T   L   T   V   Q

PvuII                          BspMI
             GCCAGACAGCTGCTGAGCGGCATCGTGCAGCAGCAGAGCAACCTGCTGAGAGCTATCGAG
1621         ---------+---------+---------+---------+---------+---------+
             CGGTCTGTCGACGACTCGCCGTAGCACGTCGTCGTCTCGTTGGACGACTCTCGATAGCTC
              A   R   Q   L   L   S   G   I   V   Q   Q   Q   S   N   L   L   R   A   I   E

PvuII                          PvuII
                      PstI                           PstI    SmaI
             GCCCAGCAGCACATGCTGCAGCTGACCGTGTGGGGCATCAAGCAGCTGCAGACCCGGGTG
1681         ---------+---------+---------+---------+---------+---------+
             CGGGTCGTCGTGTACGACGTCGACTGGCACACCCCGTAGTTCGTCGACGTCTGGGCCCAC
              A   Q   Q   H   M   L   Q   L   T   V   W   G   I   K   Q   L   Q   T   R   V

PstI
             CTGGCCATCGAGAGATACCTGAAGGACCAGCAGCTCCTGGGAATCTGGGGCTGCAGCGGC
1741         ---------+---------+---------+---------+---------+---------+
             GACCGGTAGCTCTCTATGGACTTCCTGGTCGTCGAGGACCCTTAGACCCCGACGTCGCCG
              L   A   I   E   R   Y   L   K   D   Q   Q   L   L   G   I   W   G   C   S   G
```

```
                                        PvuII
      AAGCTGATCTGCACCACCGCCGTGCCCTGGAACACCAGCTGGTCCAACAGAAGCCAGGCC
1801  ---------+---------+---------+---------+---------+---------+
      TTCGACTAGACGTGGTGGCGGCACGGGACCTTGTGGTCGACCAGGTTGTCTTCGGTCCGG
       K   L   I   C   T   T   A   V   P   W   N   T   S   W   S   N   R   S   Q   A

GACATCTGGGGCAACATGACCTGGATGCAGTGGGACAGAGAGATCAGCAACTACACCAAC
1861  ---------+---------+---------+---------+---------+---------+
      CTGTAGACCCCGTTGTACTGGACCTACGTCACCCTGTCTCTCTAGTCGTTGATGTGGTTG
       D   I   W   G   N   M   T   W   M   Q   W   D   R   E   I   S   N   Y   T   N

BspMI
      ACCATCTTCCGGCTGCTCGAAGATAGCCAGATCCAGCAGGAAAGCAACGAGAAGGACCTG
1921  ---------+---------+---------+---------+---------+---------+
      TGGTAGAAGGCCGACGAGCTTCTATCGGTCTAGGTCGTCCTTTCGTTGCTCTTCCTGGAC
       T   I   F   R   L   L   E   D   S   Q   I   Q   Q   E   S   N   E   K   D   L

PvuII
      CTGGCCCTGGACAGCTGGAAGAACCTGTGGTCCTGGTTTGACATCACCAACTGGCTGTGG
1981  ---------+---------+---------+---------+---------+---------+
      GACCGGGACCTGTCGACCTTCTTGGACACCAGGACCAAACTGTAGTGGTTGACCGACACC
       L   A   L   D   S   W   K   N   L   W   S   W   F   D   I   T   N   W   L   W

BglII
      TACATCAAGATCTTCATCATGATCGTGGGCGGCCTGATCGGCCTGCGGATCATCTTCGCC
2041  ---------+---------+---------+---------+---------+---------+
      ATGTAGTTCTAGAAGTAGTACTAGCACCCGCCGGACTAGCCGGACGCCTAGTAGAAGCGG
       Y   I   K   I   F   I   M   I   V   G   G   L   I   G   L   R   I   I   F   A

GTGCTGAGCATCGTGGGAGGCGGAGCCAAGTTCGTGGCCGCCTGGACACTGAAAGCCGCT
2101  ---------+---------+---------+---------+---------+---------+
      CACGACTCGTAGCACCCTCCGCCTCGGTTCAAGCACCGGCGGACCTGTGACTTTCGGCGA
       V   L   S   I   V   G   G   A   K   F   V   A   A   W   T   L   K   A   A
```

```
                                            XhoI   XbaI   ApaI   PmeI
        GCTGGCGGCACCGAAACCTCTCAGGTGGCCCCTGCCTGACTCGAGTCTAGAGGGCCCGTT
2161    ---------+---------+---------+---------+---------+---------+
        CGACCGCCGTGGCTTTGGAGAGTCCACCGGGGACGGACTGAGCTCAGATCTCCCGGGCAA
         A   G   G   T   E   T   S   Q   V   A   P   A   *

TAAACCCGC
2221    ---------
        ATTTGGGCG
```

FIG. 15

```
                          HindIII
         NheI   PmeI   AflII                                  PstI
        CCAAGCTGGCTAGCGTTTAAACTTAAGCTTGCCACCATGCCTATGGGCAGCCTGCAGCCT
  1     ---------+---------+---------+---------+---------+---------+
        GGTTCGACCGATCGCAAATTTGAATTCGAACGGTGGTACGGATACCCGTCGGACGTCGGA
                                        M   P   M   G   S   L   Q   P BspMI      SphI
        CTGGCCACCCTGTACCTGCTGGGCATGCTGGTGGCCTCCGTGCTGGCTGCCACCGAGAAC
 61     ---------+---------+---------+---------+---------+---------+
        GACCGGTGGGACATGGACGACCCGTACGACCACCGGAGGCACGACCGACGGTGGCTCTTG
         L   A   T   L   Y   L   L   G   M   L   V   A   S   V   L   A   A   T   E   N CTGTGGGTCACAGTGTACTACGGCGTGCCCGTGTGGAAAGAGGCCACCACCACCCTGTTC
121     ---------+---------+---------+---------+---------+---------+
        GACACCCAGTGTCACATGATGCCGCACGGGCACACCTTTCTCCGGTGGTGGTGGGACAAG
         L   W   V   T   V   Y   Y   G   V   P   V   W   K   E   A   T   T   T   L   F TGCGCCTCTGACGCCAAGGGCTACGAGAAAGAGGTGCACAACGTCTGGGCCACCCACGCC
181     ---------+---------+---------+---------+---------+---------+
        ACGCGGAGACTGCGGTTCCCGATGCTCTTTCTCCACGTGTTGCAGACCCGGTGGGTGCGG
         C   A   S   D   A   K   G   Y   E   K   E   V   H   N   V   W   A   T   H   A TGCGTGCCCACCGACCCCAACCCTCAGGAAGTGGTCCTGGAAAACGTGACCGAGAACTTC
241     ---------+---------+---------+---------+---------+---------+
        ACGCACGGGTGGCTGGGGTTGGGAGTCCTTCACCAGGACCTTTTGCACTGGCTCTTGAAG
         C   V   P   T   D   P   N   P   Q   E   V   V   L   E   N   V   T   E   N   F AACATGTGGAAGAACAACATGGTGGAACAGATGCACGAGGACATCATCAGCCTGTGGGAC
301     ---------+---------+---------+---------+---------+---------+
        TTGTACACCTTCTTGTTGTACCACCTTGTCTACGTGCTCCTGTAGTAGTCGGACACCCTG
         N   M   W   K   N   N   M   V   E   Q   M   H   E   D   I   I   S   L   W   D
```

```
                                                          PstI
        CAGAGCCTGAAGCCCTGCGTGAAGCTGACCCCCCTGTGCGTGACCCTGAACTGCAGCGAC
361     ---------+---------+---------+---------+---------+---------+
        GTCTCGGACTTCGGGACGCACTTCGACTGGGGGGACACGCACTGGGACTTGACGTCGCTG
        Q   S   L   K   P   C   V   K   L   T   P   L   C   V   T   L   N   C   S   D

PstI
        GTGAACACCACCTCCGTGAATACCACCGCCAGCAGCATGGAAGGCGGCGAGATCAAGAAC
421     ---------+---------+---------+---------+---------+---------+
        CACTTGTGGTGGAGGCACTTATGGTGGCGGTCGTCGTACCTTCCGCCGCTCTAGTTCTTG
        V   N   T   T   S   V   N   T   T   A   S   S   M   E   G   G   E   I   K   N

TGCAGCTTCAACACCACCACCAGCATGAGCGACAAGATGCAGAAAGAGTACGCCCTGTTC
481     ---------+---------+---------+---------+---------+---------+
        ACGTCGAAGTTGTGGTGGTGGTCGTACTCGCTGTTCTACGTCTTTCTCATGCGGGACAAG
        C   S   F   N   T   T   T   S   M   S   D   K   M   Q   K   E   Y   A   L   F

PvuII
                                                    BclI
        TACACCCTGGACGTGGTGCCCATCGTGAAAGAGAACAACACCTACCGGCTGATCAGCTGC
541     ---------+---------+---------+---------+---------+---------+
        ATGTGGGACCTGCACCACGGGTAGCACTTTCTCTTGTTGTGGATGGCCGACTAGTCGACG
        Y   T   L   D   V   V   P   I   V   K   E   N   N   T   Y   R   L   I   S   C

BclI         StuI
        AACACCAGCGTGATCACCCAGGCCTGCCCCAAGGTGTCCTTCGAGCCCATCCCCATCCAC
601     ---------+---------+---------+---------+---------+---------+
        TTGTGGTCGCACTAGTGGGTCCGGACGGGGTTCCACAGGAAGCTCGGGTAGGGGTAGGTG
        N   T   S   V   I   T   Q   A   C   P   K   V   S   F   E   P   I   P   I   H

ApaI
        TACTGCGCCCCTGCCGGCTTCGCCATCCTGATGTGCAACAACAAGACCTTCGACGGCAAG
661     ---------+---------+---------+---------+---------+---------+
        ATGACGCGGGGACGGCCGAAGCGGTAGGACTACACGTTGTTGTTCTGGAAGCTGCCGTTC
        Y   C   A   P   A   G   F   A   I   L   M   C   N   N   K   T   F   D   G   K
```

```
           GGCCCCTGCAACAACGTGTCCACCGTGCAGTGCACCCACGGCATCAAGCCCGTGGTGTCC
     721   ----------+---------+---------+---------+---------+---------+
           CCGGGGACGTTGTTGCACAGGTGGCACGTCACGTGGGTGCCGTAGTTCGGGCACCACAGG
            G  P  C  N  N  V  S  T  V  Q  C  T  H  G  I  K  P  V  V  S

PvuII
           ACCCAGCTGCTGCTGAATGGCAGCCTGGCCGAAGAGGAAGTGGTCATCAGAAGCGACAAC
     781   ----------+---------+---------+---------+---------+---------+
           TGGGTCGACGACGACTTACCGTCGGACCGGCTTCTCCTTCACCAGTAGTCTTCGCTGTTG
            T  Q  L  L  L  N  G  S  L  A  E  E  E  V  V  I  R  S  D  N

TTCACCGACAACGCCAAGACCATCATCGTGCACCTGAACGAGAGCATCGAGATCACCTGT
     841   ----------+---------+---------+---------+---------+---------+
           AAGTGGCTGTTGCGGTTCTGGTAGTAGCACGTGGACTTGCTCTCGTAGCTCTAGTGGACA
            F  T  D  N  A  K  T  I  I  V  H  L  N  E  S  I  E  I  T  C

ACCCGGCCCAACAACAACACCAGCAAGAGCATCACCATCGGCCCTGGCAGAGCCTTCTAC
     901   ----------+---------+---------+---------+---------+---------+
           TGGGCCGGGTTGTTGTTGTGGTCGTTCTCGTAGTGGTAGCCGGGACCGTCTCGGAAGATG
            T  R  P  N  N  N  T  S  K  S  I  T  I  G  P  G  R  A  F  Y

EagI
           GCCACCGGCCGGATCATCGGCGACATCAGAAAGGCCCACTGCAACATCAGCGGCGAGAAG
     961   ----------+---------+---------+---------+---------+---------+
           CGGTGGCCGGCCTAGTAGCCGCTGTAGTCTTTCCGGGTGACGTTGTAGTCGCCGCTCTTC
            A  T  G  R  I  I  G  D  I  R  K  A  H  C  N  I  S  G  E  K

TGGCACAACGCCCTGGAACAGATCGTGAAGAAGCTGGGCGAGAAGTTCGAGAACGCCACC
    1021   ----------+---------+---------+---------+---------+---------+
           ACCGTGTTGCGGGACCTTGTCTAGCACTTCTTCGACCCGCTCTTCAAGCTCTTGCGGTGG
            W  H  N  A  L  E  Q  I  V  K  K  L  G  E  K  F  E  N  A  T

ACCATCCGGTTCAACCAGAGCAGCGGAGGCGACCAGGAAATCGTGATGCACACCTTCAAC
    1081   ----------+---------+---------+---------+---------+---------+
           TGGTAGGCCAAGTTGGTCTCGTCGCCTCCGCTGGTCCTTTAGCACTACGTGTGGAAGTTG
            T  I  R  F  N  Q  S  S  G  G  D  Q  E  I  V  M  H  T  F  N
```

```
                                              PvuII
          TGTGGCGGCGAGTTCTTCTACTGCAACAGCACCCAGCTGTTCAACAGCACCTGGTGGCCC
1141      ---------+---------+---------+---------+---------+---------+
          ACACCGCCGCTCAAGAAGATGACGTTGTCGTGGGTCGACAAGTTGTCGTGGACCACCGGG
           C   G   G   E   F   F   Y   C   N   S   T   Q   L   F   N   S   T   W   W   P

PflMI
          AACGGCACCACCACCGAGTGGTCCAACGAGACAAGCAATGGCACCATCACCCTGCCCTGC
1201      ---------+---------+---------+---------+---------+---------+
          TTGCCGTGGTGGTGGCTCACCAGGTTGCTCTGTTCGTTACCGTGGTAGTGGGACGGGACG
           N   G   T   T   T   E   W   S   N   E   T   S   N   G   T   I   T   L   P   C

CGGATCAAGCAGATCATCAATATGTGGCAGGAAGTGGGCAAGGCTATGTACGCCCCTCCC
1261      ---------+---------+---------+---------+---------+---------+
          GCCTAGTTCGTCTAGTAGTTATACACCGTCCTTCACCCGTTCCGATACATGCGGGGAGGG
           R   I   K   Q   I   I   N   M   W   Q   E   V   G   K   A   M   Y   A   P   P

PvuII
          ATCAGCGGCCCCATCAGCTGCTCCAGCAACATCACCGGCCTGCTGCTCGTCCGCGACGGC
1321      ---------+---------+---------+---------+---------+---------+
          TAGTCGCCGGGGTAGTCGACGAGGTCGTTGTAGTGGCCGGACGACGAGCAGGCGCTGCCG
           I   S   G   P   I   S   C   S   S   N   I   T   G   L   L   L   V   R   D   G

GGCAACGACAACGAGACTAACGGCACCGAGACATTCAGACCCGGCGGAGGCGATATGCGG
1381      ---------+---------+---------+---------+---------+---------+
          CCGTTGCTGTTGCTCTGATTGCCGTGGCTCTGTAAGTCTGGGCCGCCTCCGCTATACGCC
           G   N   D   N   E   T   N   G   T   E   T   F   R   P   G   G   G   D   M   R

GACAACTGGCGGAGCGAGCTGTACAAGTACAAGGTGGTCAAAATCGAGCCCCTGGGCGTG
1441      ---------+---------+---------+---------+---------+---------+
          CTGTTGACCGCCTCGCTCGACATGTTCATGTTCCACCAGTTTTAGCTCGGGGACCCGCAC
           D   N   W   R   S   E   L   Y   K   Y   K   V   V   K   I   E   P   L   G   V
```

```
                                    NarI
                                    KasI
           GCCCCCACCAAGGCCAAGAGAAGAGTGGTGCAGGGCGCCCACCACCACCATCACCACTGA
     1501  ---------+---------+---------+---------+---------+---------+
           CGGGGGTGGTTCCGGTTCTCTTCTCACCACGTCCCGCGGGTGGTGGTGGTAGTGGTGACT
           A   P   T   K   A   K   R   R   V   V   Q   G   A   H   H   H   H   H   *

XhoI  XbaI   ApaI   PmeI
           CTCGAGTCTAGAGGGCCCGTTTAAACCCGC
     1561  ---------+---------+---------+
           GAGCTCAGATCTCCCGGGCAAATTTGGGCG
```

FIG. 16

```
                                          HindIII
           BsaI         NheI   PmeI   AflII
       CTCACTATAGGGAGACCCAAGCTGGCTAGCGTTTAAACTTAAGCTTGCCACCATGCCTAT
   1   ---------+---------+---------+---------+---------+---------+
       GAGTGATATCCCTCTGGGTTCGACCGATCGCAAATTTGAATTCGAACGGTGGTACGGATA
                                                              M  P  M PstI                  BspMI    SphI
       GGGCAGCCTGCAGCCTCTGGCCACCCTGTACCTGCTGGGCATGCTGGTGGCCTCCGTGCT
  61   ---------+---------+---------+---------+---------+---------+
       CCCGTCGGACGTCGGAGACCGGTGGGACATGGACGACCCGTACGACCACCGGAGGCACGA
        G  S  L  Q  P  L  A  T  L  Y  L  L  G  M  L  V  A  S  V  L PvuII
       GGCAGCTGGCAACCTGTGGGTCACAGTGTACTACGGCGTGCCCGTGTGGAAAGAGGCCAA
 121   ---------+---------+---------+---------+---------+---------+
       CCGTCGACCGTTGGACACCCAGTGTCACATGATGCCGCACGGGCACACCTTTCTCCGGTT
        A  A  G  N  L  W  V  T  V  Y  Y  G  V  P  V  W  K  E  A  K StuI
       GACCACCCTGTTCTGCGCCAGCGACGCCAAGGCCTACGAGAAAGAGGTGCACAACGTCTG
 181   ---------+---------+---------+---------+---------+---------+
       CTGGTGGGACAAGACGCGGTCGCTGCGGTTCCGGATGCTCTTTCTCCACGTGTTGCAGAC
        T  T  L  F  C  A  S  D  A  K  A  Y  E  K  E  V  H  N  V  W PflMI
       GGCCACCCACGCCTGCGTGCCCACCGACCCCAACCCCCAGGAAATGGTCCTGGAAAACGT
 241   ---------+---------+---------+---------+---------+---------+
       CCGGTGGGTGCGGACGCACGGGTGGCTGGGGTTGGGGGTCCTTTACCAGGACCTTTTGCA
        A  T  H  A  C  V  P  T  D  P  N  P  Q  E  M  V  L  E  N  V
```

```
                                                                BclI
        GACCGAGAACTTCAACATGTGGAAGAACGACATGGTGGAACAGATGCACGAGGACGTGAT
301     ---------+---------+---------+---------+---------+---------+
        CTGGCTCTTGAAGTTGTACACCTTCTTGCTGTACCACCTTGTCTACGTGCTCCTGCACTA
         T  E  N  F  N  M  W  K  N  D  M  V  E  Q  M  H  E  D  V  I

CAGCCTGTGGGACCAGAGCCTGAAGCCCTGCGTGAAGCTGACCCCCCTGTGCGTGACCCT
361     ---------+---------+---------+---------+---------+---------+
        GTCGGACACCCTGGTCTCGGACTTCGGGACGCACTTCGACTGGGGGGACACGCACTGGGA
         S  L  W  D  Q  S  L  K  P  C  V  K  L  T  P  L  C  V  T  L

HincII
        GGAATGCAGACAGGTCAACACCACCAACGCCACCAGCAGCGTGAACGTGACCAACGGCGA
421     ---------+---------+---------+---------+---------+---------+
        CCTTACGTCTGTCCAGTTGTGGTGGTTGCGGTGGTCGTCGCACTTGCACTGGTTGCCGCT
         E  C  R  Q  V  N  T  T  N  A  T  S  S  V  N  V  T  N  G  E PstI
        GGAAATCAAGAACTGCAGCTTCAATGCCACCACCGAGATCCGGGACAAGAAACAGAAGGT
481     ---------+---------+---------+---------+---------+---------+
        CCTTTAGTTCTTGACGTCGAAGTTACGGTGGTGGCTCTAGGCCCTGTTCTTTGTCTTCCA
         E  I  K  N  C  S  F  N  A  T  T  E  I  R  D  K  K  Q  K  V GTACGCCCTGTTCTACCGGCTGGACATCGTGCCCCTGGAAGAGGAACGGAAGGGCAACAG
541     ---------+---------+---------+---------+---------+---------+
        CATGCGGGACAAGATGGCCGACCTGTAGCACGGGGACCTTCTCCTTGCCTTCCCGTTGTC
         Y  A  L  F  Y  R  L  D  I  V  P  L  E  E  E  R  K  G  N  S BclI                            StuI
        CAGCAAGTACCGGCTGATCAACTGCAACACCAGCGCCATCACCCAGGCCTGCCCCAAAGT
601     ---------+---------+---------+---------+---------+---------+
        GTCGTTCATGGCCGACTAGTTGACGTTGTGGTCGCGGTAGTGGGTCCGGACGGGGTTTCA
         S  K  Y  R  L  I  N  C  N  T  S  A  I  T  Q  A  C  P  K  V
```

```
       GACCTTCGACCCTATCCCCATCCACTACTGCGCCCCTGCCGGCTACGCCATCCTGAAGTG
  661  ---------+---------+---------+---------+---------+---------+
       CTGGAAGCTGGGATAGGGGTAGGTGATGACGCGGGGACGGCCGATGCGGTAGGACTTCAC
        T  F  D  P  I  P  I  H  Y  C  A  P  A  G  Y  A  I  L  K  C

CAACAACAAGACCTTCAACGGCACCGGCCCCTGCAACAACGTGTCCACCGTGCAGTGCAC
  721  ---------+---------+---------+---------+---------+---------+
       GTTGTTGTTCTGGAAGTTGCCGTGGCCGGGGACGTTGTTGCACAGGTGGCACGTCACGTG
        N  N  K  T  F  N  G  T  G  P  C  N  N  V  S  T  V  Q  C  T

PvuII
       CCACGGCATCAAGCCCGTGGTGTCCACCCAGCTGCTGCTGAATGGCAGCCTGGCCGAGGG
  781  ---------+---------+---------+---------+---------+---------+
       GGTGCCGTAGTTCGGGCACCACAGGTGGGTCGACGACGACTTACCGTCGGACCGGCTCCC
        H  G  I  K  P  V  V  S  T  Q  L  L  L  N  G  S  L  A  E  G

CGAGATCATCATCAGAAGCGAGAACCTGACCAACAACGTGAAAACCATCATCGTGCACCT
  841  ---------+---------+---------+---------+---------+---------+
       GCTCTAGTAGTAGTCTTCGCTCTTGGACTGGTTGTTGCACTTTTGGTAGTAGCACGTGGA
        E  I  I  I  R  S  E  N  L  T  N  N  V  K  T  I  I  V  H  L

GAACGAGAGCGTGGAAATCGTGTGCACCCGGCCCAACAACAACACCAGAAAGAGCATCCG
  901  ---------+---------+---------+---------+---------+---------+
       CTTGCTCTCGCACCTTTAGCACACGTGGGCCGGGTTGTTGTTGTGGTCTTTCTCGTAGGC
        N  E  S  V  E  I  V  C  T  R  P  N  N  N  T  R  K  S  I  R

StuI
       GATCGGCCCTGGCCAGACCTTTTACGCCACCGGCGACATCATCGGCAACATCCGGCAGGC
  961  ---------+---------+---------+---------+---------+---------+
       CTAGCCGGGACCGGTCTGGAAAATGCGGTGGCCGCTGTAGTAGCCGTTGTAGGCCGTCCG
        I  G  P  G  Q  T  F  Y  A  T  G  D  I  I  G  N  I  R  Q  A

BamHI       PstI
       CTACTGCAACATCAAGAAGGACGACTGGATCCGGACCCTGCAGAGAGTGGGCAAGAAGCT
 1021  ---------+---------+---------+---------+---------+---------+
       GATGACGTTGTAGTTCTTCCTGCTGACCTAGGCCTGGGACGTCTCTCACCCGTTCTTCGA
        Y  C  N  I  K  K  D  D  W  I  R  T  L  Q  R  V  G  K  K  L
```

```
        GGCCGAGCACTTCCCCAGACGGATCATCAACTTCACCAGCCCCGCTGGCGGCGACCTGGA
1081    ---------+---------+---------+---------+---------+---------+
        CCGGCTCGTGAAGGGGTCTGCCTAGTAGTTGAAGTGGTCGGGGCGACCGCCGCTGGACCT
         A   E   H   F   P   R   R   I   I   N   F   T   S   P   A   G   G   D   L   E

PstI
        AATCACCACCCACAGCTTCAACTGCAGAGGCGAGTTCTTCTACTGCAATACCAGCAGCCT
1141    ---------+---------+---------+---------+---------+---------+
        TTAGTGGTGGGTGTCGAAGTTGACGTCTCCGCTCAAGAAGATGACGTTATGGTCGTCGGA
         I   T   T   H   S   F   N   C   R   G   E   F   F   Y   C   N   T   S   S   L

GTTCAACAGCACCTACAACCCCAACGACACCAACAGCAACAGCTCCAGCAGCAACTCCAG
1201    ---------+---------+---------+---------+---------+---------+
        CAAGTTGTCGTGGATGTTGGGGTTGCTGTGGTTGTCGTTGTCGAGGTCGTCGTTGAGGTC
         F   N   S   T   Y   N   P   N   D   T   N   S   N   S   S   S   S   N   S   S

CCTGGACATCACCATCCCTTGCCGGATCAAGCAGATCATCAATATGTGGCAGGAAGTGGG
1261    ---------+---------+---------+---------+---------+---------+
        GGACCTGTAGTGGTAGGGAACGGCCTAGTTCGTCTAGTAGTTATACACCGTCCTTCACCC
         L   D   I   T   I   P   C   R   I   K   Q   I   I   N   M   W   Q   E   V   G

CAGGGCTATGTACGCCCCTCCCATCGAGGGCAACATCACATGCAAGAGCAACATCACCGG
1321    ---------+---------+---------+---------+---------+---------+
        GTCCCGATACATGCGGGGAGGGTAGCTCCCGTTGTAGTGTACGTTCTCGTTGTAGTGGCC
         R   A   M   Y   A   P   P   I   E   G   N   I   T   C   K   S   N   I   T   G

BglII
        CCTGCTCCTGGTCCGCGACGGCGGCGTGGAAAGCAACGAGACAGAGATCTTCAGACCCGG
1381    ---------+---------+---------+---------+---------+---------+
        GGACGAGGACCAGGCGCTGCCGCCGCACCTTTCGTTGCTCTGTCTCTAGAAGTCTGGGCC
         L   L   L   V   R   D   G   G   V   E   S   N   E   T   E   I   F   R   P   G

CGGAGGCGACATGCGGAACAACTGGCGGAGCGAGCTGTACAAGTACAAGGTGGTGGAAAT
1441    ---------+---------+---------+---------+---------+---------+
        GCCTCCGCTGTACGCCTTGTTGACCGCCTCGCTCGACATGTTCATGTTCCACCACCTTTA
         G   D   M   R   N   N   W   R   S   E   L   Y   K   Y   K   V   V   E   I
```

```
        CAAGCCCCTGGGAATCGCCCCCACCGCCGCCAAGCGGAGAGTGGTGGAAGGCGGCGAACA
1501    ---------+---------+---------+---------+---------+---------+
        GTTCGGGGACCCTTAGCGGGGGTGGCGGCGGTTCGCCTCTCACCACCTTCCGCCGCTTGT
         K  P  L  G  I  A  P  T  A  A  K  R  R  V  E  G  G  E  Q

BspMI            PvuII
        GAACGAGAAGGACCTGCTGGCCCTGGACAGCTGGGAGAACCTGTGGAACTGGTTCAGCAT
1561    ---------+---------+---------+---------+---------+---------+
        CTTGCTCTTCCTGGACGACCGGGACCTGTCGACCCTCTTGGACACCTTGACCAAGTCGTA
         N  E  K  D  L  L  A  L  D  S  W  E  N  L  W  N  W  F  S  I

BglII
        CACCAAGTGGCTGTGGTACATCAAGATCTTCATCATGATCGTGGGCGGCCTGATCGGCCT
1621    ---------+---------+---------+---------+---------+---------+
        GTGGTTCACCGACACCATGTAGTTCTAGAAGTAGTACTAGCACCCGCCGGACTAGCCGGA
         T  K  W  L  W  Y  I  K  I  F  I  M  I  V  G  G  L  I  G  L

NarI
                                                KasI
        GCGGATCATCTTCGCCGTGCTGAGCGTGGTGAACAGAGTGCGGCAGGGCGCCCACCACCA
1681    ---------+---------+---------+---------+---------+---------+
        CGCCTAGTAGAAGCGGCACGACTCGCACCACTTGTCTCACGCCGTCCCGCGGGTGGTGGT
         R  I  I  F  A  V  L  S  V  V  N  R  V  R  Q  G  A  H  H  H

XhoI  XbaI  ApaI  PmeI          BclI
        CCATCACCACTGACTCGAGTCTAGAGGGCCCGTTTAAACCCGCTGATCAGCCTCGACTG
1741    ---------+---------+---------+---------+---------+---------
        GGTAGTGGTGACTGAGCTCAGATCTCCCGGGCAAATTTGGGCGACTAGTCGGAGCTGAC
         H  H  H  *
```

FIG. 17

```
                                          HindIII
         BsaI          NheI  PmeI   AflII
     CTCACTATAGGGAGACCCAAGCTGGCTAGCGTTTAAACTTAAGCTTGCCACCATGCCTAT
1    ---------+---------+---------+---------+---------+---------+
     GAGTGATATCCCTCTGGGTTCGACCGATCGCAAATTTGAATTCGAACGGTGGTACGGATA
                                                         M  P  M
```

```
         PstI                        BspMI    SphI
     GGGCAGCCTGCAGCCTCTGGCCACCCTGTACCTGCTGGGCATGCTGGTGGCCTCCGTGCT
61   ---------+---------+---------+---------+---------+---------+
     CCCGTCGGACGTCGGAGACCGGTGGGACATGGACGACCCGTACGACCACCGGAGGCACGA
      G  S  L  Q  P  L  A  T  L  Y  L  L  G  M  L  V  A  S  V  L
```

```
       PvuII
     GGCAGCTGGCAACCTGTGGGTCACAGTGTACTACGGCGTGCCCGTGTGGAAAGAGGCCAA
121  ---------+---------+---------+---------+---------+---------+
     CCGTCGACCGTTGGACACCCAGTGTCACATGATGCCGCACGGGCACACCTTTCTCCGGTT
      A  A  G  N  L  W  V  T  V  Y  Y  G  V  P  V  W  K  E  A  K
```

```
                                StuI
     GACCACCCTGTTCTGCGCCAGCGACGCCAAGGCCTACGAGAAAGAGGTGCACAACGTCTG
181  ---------+---------+---------+---------+---------+---------+
     CTGGTGGGACAAGACGCGGTCGCTGCGGTTCCGGATGCTCTTTCTCCACGTGTTGCAGAC
      T  T  L  F  C  A  S  D  A  K  A  Y  E  K  E  V  H  N  V  W
```

```
                                    PflMI
     GGCCACCCACGCCTGCGTGCCCACCGACCCCAACCCCCAGGAAATGGTCCTGGAAAACGT
241  ---------+---------+---------+---------+---------+---------+
     CCGGTGGGTGCGGACGCACGGGTGGCTGGGGTTGGGGGTCCTTTACCAGGACCTTTTGCA
      A  T  H  A  C  V  P  T  D  P  N  P  Q  E  M  V  L  E  N  V
```

```
                                                                  BclI
         GACCGAGAACTTCAACATGTGGAAGAACGACATGGTGGAACAGATGCACGAGGACGTGAT
301      ---------+---------+---------+---------+---------+---------+
         CTGGCTCTTGAAGTTGTACACCTTCTTGCTGTACCACCTTGTCTACGTGCTCCTGCACTA
          _T__E__N__F__N__M__W__K__N__D__M__V__E__Q__M__H__E__D__V__I_

CAGCCTGTGGGACCAGAGCCTGAAGCCCTGCGTGAAGCTGACCCCCCTGTGCGTGACCCT
361      ---------+---------+---------+---------+---------+---------+
         GTCGGACACCCTGGTCTCGGACTTCGGGACGCACTTCGACTGGGGGGACACGCACTGGGA
          _S__L__W__D__Q__S__L__K__P__C__V__K__L__T__P__L__C__V__T__L_

HincII
         GGAATGCAGACAGGTCAACACCACCAACGCCACCAGCAGCGTGAACGTGACCAACGGCGA
421      ---------+---------+---------+---------+---------+---------+
         CCTTACGTCTGTCCAGTTGTGGTGGTTGCGGTGGTCGTCGCACTTGCACTGGTTGCCGCT
          _E__C__R__Q__V__N__T__T__N__A__T__S__S__V__N__V__T__N__G__E_

PstI
         GGAAATCAAGAACTGCAGCTTCAATGCCACCACCGAGATCCGGGACAAGAAACAGAAGGT
481      ---------+---------+---------+---------+---------+---------+
         CCTTTAGTTCTTGACGTCGAAGTTACGGTGGTGGCTCTAGGCCCTGTTCTTTGTCTTCCA
          _E__I__K__N__C__S__F__N__A__T__T__E__I__R__D__K__K__Q__K__V_

GTACGCCCTGTTCTACCGGCTGGACATCGTGCCCCTGGAAGAGGAACGGAAGGGCAACAG
541      ---------+---------+---------+---------+---------+---------+
         CATGCGGGACAAGATGGCCGACCTGTAGCACGGGGACCTTCTCCTTGCCTTCCCGTTGTC
          _Y__A__L__F__Y__R__L__D__I__V__P__L__E__E__E__R__K__G__N__S_

BclI                              StuI
         CAGCAAGTACCGGCTGATCAACTGCAACACCAGCGCCATCACCCAGGCCTGCCCCAAAGT
601      ---------+---------+---------+---------+---------+---------+
         GTCGTTCATGGCCGACTAGTTGACGTTGTGGTCGCGGTAGTGGGTCCGGACGGGGTTTCA
          _S__K__Y__R__L__I__N__C__N__T__S__A__I__T__Q__A__C__P__K__V_
```

```
        GACCTTCGACCCTATCCCCATCCACTACTGCGCCCCTGCCGGCTACGCCATCCTGAAGTG
661     ---------+---------+---------+---------+---------+---------+
        CTGGAAGCTGGGATAGGGGTAGGTGATGACGCGGGGACGGCCGATGCGGTAGGACTTCAC
         T  F  D  P  I  P  I  H  Y  C  A  P  A  G  Y  A  I  L  K  C

CAACAACAAGACCTTCAACGGCACCGGCCCCTGCAACAACGTGTCCACCGTGCAGTGCAC
721     ---------+---------+---------+---------+---------+---------+
        GTTGTTGTTCTGGAAGTTGCCGTGGCCGGGGACGTTGTTGCACAGGTGGCACGTCACGTG
         N  N  K  T  F  N  G  T  G  P  C  N  N  V  S  T  V  Q  C  T

PvuII
        CCACGGCATCAAGCCCGTGGTGTCCACCCAGCTGCTGCTGAATGGCAGCCTGGCCGAGGG
781     ---------+---------+---------+---------+---------+---------+
        GGTGCCGTAGTTCGGGCACCACAGGTGGGTCGACGACGACTTACCGTCGGACCGGCTCCC
         H  G  I  K  P  V  V  S  T  Q  L  L  L  N  G  S  L  A  E  G

CGAGATCATCATCAGAAGCGAGAACCTGACCAACAACGTGAAAACCATCATCGTGCACCT
841     ---------+---------+---------+---------+---------+---------+
        GCTCTAGTAGTAGTCTTCGCTCTTGGACTGGTTGTTGCACTTTTGGTAGTAGCACGTGGA
         E  I  I  I  R  S  E  N  L  T  N  N  V  K  T  I  I  V  H  L

GAACGAGAGCGTGGAAATCGTGTGCACCCGGCCCAACAACAACACCAGAAAGAGCATCCG
901     ---------+---------+---------+---------+---------+---------+
        CTTGCTCTCGCACCTTTAGCACACGTGGGCCGGGTTGTTGTTGTGGTCTTTCTCGTAGGC
         N  E  S  V  E  I  V  C  T  R  P  N  N  N  T  R  K  S  I  R

StuI
        GATCGGCCCTGGCCAGACCTTTTACGCCACCGGCGACATCATCGGCAACATCCGGCAGGC
961     ---------+---------+---------+---------+---------+---------+
        CTAGCCGGGACCGGTCTGGAAAATGCGGTGGCCGCTGTAGTAGCCGTTGTAGGCCGTCCG
         I  G  P  G  Q  T  F  Y  A  T  G  D  I  I  G  N  I  R  Q  A

BamHI     PstI
        CTACTGCAACATCAAGAAGGACGACTGGATCCGGACCCTGCAGAGAGTGGGCAAGAAGCT
1021    ---------+---------+---------+---------+---------+---------+
        GATGACGTTGTAGTTCTTCCTGCTGACCTAGGCCTGGGACGTCTCTCACCCGTTCTTCGA
         Y  C  N  I  K  K  D  D  W  I  R  T  L  Q  R  V  G  K  K  L
```

```
       GGCCGAGCACTTCCCCAGACGGATCATCAACTTCACCAGCCCCGCTGGCGGCGACCTGGA
1081   ---------+---------+---------+---------+---------+---------+
       CCGGCTCGTGAAGGGGTCTGCCTAGTAGTTGAAGTGGTCGGGGCGACCGCCGCTGGACCT
        A   E   H   F   P   R   R   I   I   N   F   T   S   P   A   G   G   D   L   E

PstI
       AATCACCACCCACAGCTTCAACTGCAGAGGCGAGTTCTTCTACTGCAATACCAGCAGCCT
1141   ---------+---------+---------+---------+---------+---------+
       TTAGTGGTGGGTGTCGAAGTTGACGTCTCCGCTCAAGAAGATGACGTTATGGTCGTCGGA
        I   T   T   H   S   F   N   C   R   G   E   F   F   Y   C   N   T   S   S   L

GTTCAACAGCACCTACAACCCCAACGACACCAACAGCAACAGCTCCAGCAGCAACTCCAG
1201   ---------+---------+---------+---------+---------+---------+
       CAAGTTGTCGTGGATGTTGGGGTTGCTGTGGTTGTCGTTGTCGAGGTCGTCGTTGAGGTC
        F   N   S   T   Y   N   P   N   D   T   N   S   N   S   S   S   S   N   S   S

CCTGGACATCACCATCCCTTGCCGGATCAAGCAGATCATCAATATGTGGCAGGAAGTGGG
1261   ---------+---------+---------+---------+---------+---------+
       GGACCTGTAGTGGTAGGGAACGGCCTAGTTCGTCTAGTAGTTATACACCGTCCTTCACCC
        L   D   I   T   I   P   C   R   I   K   Q   I   I   N   M   W   Q   E   V   G

CAGGGCTATGTACGCCCCTCCCATCGAGGGCAACATCACATGCAAGAGCAACATCACCGG
1321   ---------+---------+---------+---------+---------+---------+
       GTCCCGATACATGCGGGGAGGGTAGCTCCCGTTGTAGTGTACGTTCTCGTTGTAGTGGCC
        R   A   M   Y   A   P   P   I   E   G   N   I   T   C   K   S   N   I   T   G

BglII
       CCTGCTCCTGGTCCGCGACGGCGGCGTGGAAAGCAACGAGACAGAGATCTTCAGACCCGG
1381   ---------+---------+---------+---------+---------+---------+
       GGACGAGGACCAGGCGCTGCCGCCGCACCTTTCGTTGCTCTGTCTCTAGAAGTCTGGGCC
        L   L   L   V   R   D   G   G   V   E   S   N   E   T   E   I   F   R   P   G

CGGAGGCGACATGCGGAACAACTGGCGGAGCGAGCTGTACAAGTACAAGGTGGTGGAAAT
1441   ---------+---------+---------+---------+---------+---------+
       GCCTCCGCTGTACGCCTTGTTGACCGCCTCGCTCGACATGTTCATGTTCCACCACCTTTA
        G   G   D   M   R   N   N   W   R   S   E   L   Y   K   Y   K   V   V   E   I
```

```
         CAAGCCCCTGGGAATCGCCCCCACCGCCGCCAAGCGGAGAGTGGTGGAAGGCGCTCACCA
1501     ---------+---------+---------+---------+---------+---------+
         GTTCGGGGACCCTTAGCGGGGGTGGCGGCGGTTCGCCTCTCACCACCTTCCGCGAGTGGT
          K  P  L  G  I  A  P  T  A  A  K  R  R  V  V  E  G  A  H  H

CCACCATCACCACGGCCTGAACGACATCTTCGAGGCCCAGAAAATCGAGTGGCACGAGTG
1561     ---------+---------+---------+---------+---------+---------+
         GGTGGTAGTGGTGCCGGACTTGCTGTAGAAGCTCCGGGTCTTTTAGCTCACCGTGCTCAC
          H  H  H  H  G  L  N  D  I  F  E  A  Q  K  I  E  W  H  E  *

XhoI  XbaI   ApaI   PmeI        BclI
         ACTCGAGTCTAGAGGGCCCGTTTAAACCCGCTGATCAGCCTCGACTG
1621     ---------+---------+---------+---------+-------
         TGAGCTCAGATCTCCCGGGCAAATTTGGGCGACTAGTCGGAGCTGAC
```

FIG. 18

```
                                             HindIII
         BsaI        NheI  PmeI   AflII
    CTCACTATAGGGAGACCCAAGCTGGCTAGCGTTTAAACTTAAGCTTGCCACCATGCCTAT
1   ----------+---------+---------+---------+---------+---------+
    GAGTGATATCCCTCTGGGTTCGACCGATCGCAAATTTGAATTCGAACGGTGGTACGGATA
                                                          M  P  M PstI                       BspMI    SphI
    GGGCAGCCTGCAGCCTCTGGCCACCCTGTACCTGCTGGGCATGCTGGTGGCCTCCGTGCT
61  ----------+---------+---------+---------+---------+---------+
    CCCGTCGGACGTCGGAGACCGGTGGGACATGGACGACCCGTACGACCACCGGAGGCACGA
    _G__S__L__Q__P__L__A__T__L__Y__L__L__G__M__L__V__A__S__V__L_

PvuII
    GGCAGCTGGCAACCTGTGGGTCACAGTGTACTACGGCGTGCCCGTGTGGAAAGAGGCCAA
121 ----------+---------+---------+---------+---------+---------+
    CCGTCGACCGTTGGACACCCAGTGTCACATGATGCCGCACGGGCACACCTTTCTCCGGTT
    _A__A__G__N__L__W__V__T__V__Y__Y__G__V__P__V__W__K__E__A__K_

StuI
    GACCACCCTGTTCTGCGCCAGCGACGCCAAGGCCTACGAGAAAGAGGTGCACAACGTCTG
181 ----------+---------+---------+---------+---------+---------+
    CTGGTGGGACAAGACGCGGTCGCTGCGGTTCCGGATGCTCTTTCTCCACGTGTTGCAGAC
    _T__T__L__F__C__A__S__D__A__K__A__Y__E__K__E__V__H__N__V__W_

PflMI
    GGCCACCCACGCCTGCGTGCCCACCGACCCCAACCCCCAGGAAATGGTCCTGGAAAACGT
241 ----------+---------+---------+---------+---------+---------+
    CCGGTGGGTGCGGACGCACGGGTGGCTGGGGTTGGGGGTCCTTTACCAGGACCTTTTGCA
    _A__T__H__A__C__V__P__T__D__P__N__P__Q__E__M__V__L__E__N__V_
```

```
                                                                    BclI
            GACCGAGAACTTCAACATGTGGAAGAACGACATGGTGGAACAGATGCACGAGGACGTGAT
      301   ---------+---------+---------+---------+---------+---------+
            CTGGCTCTTGAAGTTGTACACCTTCTTGCTGTACCACCTTGTCTACGTGCTCCTGCACTA
             T  E  N  F  N  M  W  K  N  D  M  V  E  Q  M  H  E  D  V  I

CAGCCTGTGGGACCAGAGCCTGAAGCCCTGCGTGAAGCTGACCCCCCTGTGCGTGACCCT
      361   ---------+---------+---------+---------+---------+---------+
            GTCGGACACCCTGGTCTCGGACTTCGGGACGCACTTCGACTGGGGGGACACGCACTGGGA
             S  L  W  D  Q  S  L  K  P  C  V  K  L  T  P  L  C  V  T  L

HincII
            GGAATGCAGACAGGTCAACACCACCAACGCCACCAGCAGCGTGAACGTGACCAACGGCGA
      421   ---------+---------+---------+---------+---------+---------+
            CCTTACGTCTGTCCAGTTGTGGTGGTTGCGGTGGTCGTCGCACTTGCACTGGTTGCCGCT
             E  C  R  Q  V  N  T  T  N  A  T  S  S  V  N  V  T  N  G  E PstI
            GGAAATCAAGAACTGCAGCTTCAAGGCCACCACCGAGATCCGGGACAAGAAACAGAAGGT
      481   ---------+---------+---------+---------+---------+---------+
            CCTTTAGTTCTTGACGTCGAAGTTCCGGTGGTGGCTCTAGGCCCTGTTCTTTGTCTTCCA
             E  I  K  N  C  S  F  K  A  T  T  E  I  R  D  K  K  Q  K  V GTACGCCCTGTTCTACCGGCTGGACATCGTGCCCCTGGAAGAGGAACGGAAGGGCAACAG
      541   ---------+---------+---------+---------+---------+---------+
            CATGCGGGACAAGATGGCCGACCTGTAGCACGGGGACCTTCTCCTTGCCTTCCCGTTGTC
             Y  A  L  F  Y  R  L  D  I  V  P  L  E  E  E  R  K  G  N  S BclI                                   StuI
            CAGCAAGTACCGGCTGATCAACTGCAACACCAGCGCCATCACCCAGGCCTGCCCCAAAGT
      601   ---------+---------+---------+---------+---------+---------+
            GTCGTTCATGGCCGACTAGTTGACGTTGTGGTCGCGGTAGTGGGTCCGGACGGGGTTTCA
             S  K  Y  R  L  I  N  C  N  T  S  A  I  T  Q  A  C  P  K  V
```

```
       GACCTTCGACCCTATCCCCATCCACTACTGCGCCCCTGCCGGCTACGCCATCCTGAAGTG
661    ---------+---------+---------+---------+---------+---------+
       CTGGAAGCTGGGATAGGGGTAGGTGATGACGCGGGGACGGCCGATGCGGTAGGACTTCAC
        T  F  D  P  I  P  I  H  Y  C  A  P  A  G  Y  A  I  L  K  C

CAACAACAAGACCTTCAACGGCACCGGCCCCTGCAACAACGTGTCCACCGTGCAGTGCAC
721    ---------+---------+---------+---------+---------+---------+
       GTTGTTGTTCTGGAAGTTGCCGTGGCCGGGGACGTTGTTGCACAGGTGGCACGTCACGTG
        N  N  K  T  F  N  G  T  G  P  C  N  N  V  S  T  V  Q  C  T

PvuII
       CCACGGCATCAAGCCCGTGGTGTCCACCCAGCTGCTGCTGAATGGCAGCCTGGCCGAGGG
781    ---------+---------+---------+---------+---------+---------+
       GGTGCCGTAGTTCGGGCACCACAGGTGGGTCGACGACGACTTACCGTCGGACCGGCTCCC
        H  G  I  K  P  V  V  S  T  Q  L  L  L  N  G  S  L  A  E  G

CGAGATCATCATCAGAAGCGAGAACCTGACCAACAACGTGAAAACCATCATCGTGCACCT
841    ---------+---------+---------+---------+---------+---------+
       GCTCTAGTAGTAGTCTTCGCTCTTGGACTGGTTGTTGCACTTTTGGTAGTAGCACGTGGA
        E  I  I  I  R  S  E  N  L  T  N  N  V  K  T  I  I  V  H  L

GAACGAGAGCGTGGAAATCGTGTGCACCCGGCCCAACAACAACACCAGAAAGAGCATCCG
901    ---------+---------+---------+---------+---------+---------+
       CTTGCTCTCGCACCTTTAGCACACGTGGGCCGGGTTGTTGTTGTGGTCTTTCTCGTAGGC
        N  E  S  V  E  I  V  C  T  R  P  N  N  N  T  R  K  S  I  R

StuI
       GATCGGCCCTGGCCAGACCTTTTACGCCACCGGCGACATCATCGGCAACATCCGGCAGGC
961    ---------+---------+---------+---------+---------+---------+
       CTAGCCGGGACCGGTCTGGAAAATGCGGTGGCCGCTGTAGTAGCCGTTGTAGGCCGTCCG
        I  G  P  G  Q  T  F  Y  A  T  G  D  I  I  G  N  I  R  Q  A

BamHI     PstI
       CTACTGCAACATCAAGAAGGACGACTGGATCCGGACCCTGCAGAGAGTGGGCAAGAAGCT
1021   ---------+---------+---------+---------+---------+---------+
       GATGACGTTGTAGTTCTTCCTGCTGACCTAGGCCTGGGACGTCTCTCACCCGTTCTTCGA
        Y  C  N  I  K  K  D  D  W  I  R  T  L  Q  R  V  G  K  K  L
```

```
                GGCCGAGCACTTCCCCAGACGGATCATCAACTTCACCAGCCCCGCTGGCGGCGACCTGGA
     1081       ---------+---------+---------+---------+---------+---------+
                CCGGCTCGTGAAGGGGTCTGCCTAGTAGTTGAAGTGGTCGGGGCGACCGCCGCTGGACCT
                 A  E  H  F  P  R  R  I  I  N  F  T  S  P  A  G  G  D  L  E

PstI
                AATCACCACCCACAGCTTCAACTGCAGAGGCGAGTTCTTCTACTGCAATACCAGCAGCCT
     1141       ---------+---------+---------+---------+---------+---------+
                TTAGTGGTGGGTGTCGAAGTTGACGTCTCCGCTCAAGAAGATGACGTTATGGTCGTCGGA
                 I  T  T  H  S  F  N  C  R  G  E  F  F  Y  C  N  T  S  S  L

GTTCAACAGCACCTACAACCCCAACGACACCAACAGCAACAGCTCCAGCAGCAACTCCAG
     1201       ---------+---------+---------+---------+---------+---------+
                CAAGTTGTCGTGGATGTTGGGGTTGCTGTGGTTGTCGTTGTCGAGGTCGTCGTTGAGGTC
                 F  N  S  T  Y  N  P  N  D  T  N  S  N  S  S  S  S  N  S  S

CCTGGACATCACCATCCCTTGCCGGATCAAGCAGATCATCAATATGTGGCAGGAAGTGGG
     1261       ---------+---------+---------+---------+---------+---------+
                GGACCTGTAGTGGTAGGGAACGGCCTAGTTCGTCTAGTAGTTATACACCGTCCTTCACCC
                 L  D  I  T  I  P  C  R  I  K  Q  I  I  N  M  W  Q  E  V  G

CAGGGCTATGTACGCCCCTCCCATCGAGGGCAACATCACATGCAAGAGCAACATCACCGG
     1321       ---------+---------+---------+---------+---------+---------+
                GTCCCGATACATGCGGGGAGGGTAGCTCCCGTTGTAGTGTACGTTCTCGTTGTAGTGGCC
                 R  A  M  Y  A  P  P  I  E  G  N  I  T  C  K  S  N  I  T  G

BglII
                CCTGCTCCTGGTCCGCGACGGCGGCGTGGAAAGCAACGAGACAGAGATCTTCAGACCCGG
     1381       ---------+---------+---------+---------+---------+---------+
                GGACGAGGACCAGGCGCTGCCGCCGCACCTTTCGTTGCTCTGTCTCTAGAAGTCTGGGCC
                 L  L  L  V  R  D  G  G  V  E  S  N  E  T  E  I  F  R  P  G

CGGAGGCGACATGCGGAACAACTGGCGGAGCGAGCTGTACAAGTACAAGGTGGTGGAAAT
     1441       ---------+---------+---------+---------+---------+---------+
                GCCTCCGCTGTACGCCTTGTTGACCGCCTCGCTCGACATGTTCATGTTCCACCACCTTTA
                 G  G  D  M  R  N  N  W  R  S  E  L  Y  K  Y  K  V  V  E  I
```

```
            CAAGCCCCTGGGAATCGCCCCCACCGCCGCCAAGCGGAGAGTGGTGGAAGGCGCTCACCA
1501        ---------+---------+---------+---------+---------+---------+
            GTTCGGGGACCCTTAGCGGGGGTGGCGGCGGTTCGCCTCTCACCACCTTCCGCGAGTGGT
             K  P  L  G  I  A  P  T  A  A  K  R  R  V  V  E  G  A  H  H

CCACCATCACCACGGCCTGAACGACATCTTCGAGGCCCAGAAAATCGAGTGGCACGAGTG
1561        ---------+---------+---------+---------+---------+---------+
            GGTGGTAGTGGTGCCGGACTTGCTGTAGAAGCTCCGGGTCTTTTAGCTCACCGTGCTCAC
             H  H  H  H  G  L  N  D  I  F  E  A  Q  K  I  E  W  H  E  *

XhoI  XbaI  ApaI  PmeI         BclI
            ACTCGAGTCTAGAGGGCCCGTTTAAACCCGCTGATCAGCCTCGACTG
1621        ---------+---------+---------+---------+-------
            TGAGCTCAGATCTCCCGGGCAAATTTGGGCGACTAGTCGGAGCTGAC
```

FIG. 19

```
                                                  HindIII
          BsaI         NheI   PmeI   AflII
          CTCACTATAGGGAGACCCAAGCTGGCTAGCGTTTAAACTTAAGCTTGCCACCATGCCTAT
   1      ---------+---------+---------+---------+---------+---------+
          GAGTGATATCCCTCTGGGTTCGACCGATCGCAAATTTGAATTCGAACGGTGGTACGGATA
                                                               M  P  M PstI                    BspMI    SphI
          GGGCAGCCTGCAGCCTCTGGCCACCCTGTACCTGCTGGGCATGCTGGTGGCCTCCGTGCT
  61      ---------+---------+---------+---------+---------+---------+
          CCCGTCGGACGTCGGAGACCGGTGGGACATGGACGACCCGTACGACCACCGGAGGCACGA
           G  S  L  Q  P  L  A  T  L  Y  L  L  G  M  L  V  A  S  V  L PvuII
          GGCAGCTGGCAACCTGTGGGTCACAGTGTACTACGGCGTGCCCGTGTGGAAAGAGGCCAA
 121      ---------+---------+---------+---------+---------+---------+
          CCGTCGACCGTTGGACACCCAGTGTCACATGATGCCGCACGGGCACACCTTTCTCCGGTT
           A  A  G  N  L  W  V  T  V  Y  Y  G  V  P  V  W  K  E  A  K StuI
          GACCACCCTGTTCTGCGCCAGCGACGCCAAGGCCTACGAGAAAGAGGTGCACAACGTCTG
 181      ---------+---------+---------+---------+---------+---------+
          CTGGTGGGACAAGACGCGGTCGCTGCGGTTCCGGATGCTCTTTCTCCACGTGTTGCAGAC
           T  T  L  F  C  A  S  D  A  K  A  Y  E  K  E  V  H  N  V  W PflMI
          GGCCACCCACGCCTGCGTGCCCACCGACCCCAACCCCCAGGAAATGGTCCTGGAAAACGT
 241      ---------+---------+---------+---------+---------+---------+
          CCGGTGGGTGCGGACGCACGGGTGGCTGGGGTTGGGGGTCCTTTACCAGGACCTTTTGCA
           A  T  H  A  C  V  P  T  D  P  N  P  Q  E  M  V  L  E  N  V
```

```
                                                                  BclI
     GACCGAGAACTTCAACATGTGGAAGAACGACATGGTGGAACAGATGCACGAGGACGTGAT
301  ---------+---------+---------+---------+---------+---------+
     CTGGCTCTTGAAGTTGTACACCTTCTTGCTGTACCACCTTGTCTACGTGCTCCTGCACTA
      T  E  N  F  N  M  W  K  N  D  M  V  E  Q  M  H  E  D  V  I

CAGCCTGTGGGACCAGAGCCTGAAGCCCTGCGTGAAGCTGACCCCCCTGTGCGTGACCCT
361  ---------+---------+---------+---------+---------+---------+
     GTCGGACACCCTGGTCTCGGACTTCGGGACGCACTTCGACTGGGGGGACACGCACTGGGA
      S  L  W  D  Q  S  L  K  P  C  V  K  L  T  P  L  C  V  T  L

HincII
     GGAATGCAGACAGGTCAACACCACCAACGCCACCAGCAGCGTGAACGTGACCAACGGCGA
421  ---------+---------+---------+---------+---------+---------+
     CCTTACGTCTGTCCAGTTGTGGTGGTTGCGGTGGTCGTCGCACTTGCACTGGTTGCCGCT
      E  C  R  Q  V  N  T  T  N  A  T  S  S  V  N  V  T  N  G  E GGAAATCAAGAAATGCAGCTTCAATGCCACCACCGAGATCCGGGACAAGAAACAGAAGGT
481  ---------+---------+---------+---------+---------+---------+
     CCTTTAGTTCTTTACGTCGAAGTTACGGTGGTGGCTCTAGGCCCTGTTCTTTGTCTTCCA
      E  I  K  K  C  S  F  N  A  T  T  E  I  R  D  K  K  Q  K  V GTACGCCCTGTTCTACCGGCTGGACATCGTGCCCCTGGAAGAGGAACGGAAGGGCAACAG
541  ---------+---------+---------+---------+---------+---------+
     CATGCGGGACAAGATGGCCGACCTGTAGCACGGGGACCTTCTCCTTGCCTTCCCGTTGTC
      Y  A  L  F  Y  R  L  D  I  V  P  L  E  E  E  R  K  G  N  S BclI                                StuI
     CAGCAAGTACCGGCTGATCAACTGCAACACCAGCGCCATCACCCAGGCCTGCCCCAAAGT
601  ---------+---------+---------+---------+---------+---------+
     GTCGTTCATGGCCGACTAGTTGACGTTGTGGTCGCGGTAGTGGGTCCGGACGGGGTTTCA
      S  K  Y  R  L  I  N  C  N  T  S  A  I  T  Q  A  C  P  K  V GACCTTCGACCCTATCCCCATCCACTACTGCGCCCCTGCCGGCTACGCCATCCTGAAGTG
661  ---------+---------+---------+---------+---------+---------+
     CTGGAAGCTGGGATAGGGGTAGGTGATGACGCGGGGACGGCCGATGCGGTAGGACTTCAC
      T  F  D  P  I  P  I  H  Y  C  A  P  A  G  Y  A  I  L  K  C
```

```
              CAACAACAAGACCTTCAACGGCACCGGCCCCTGCAACAACGTGTCCACCGTGCAGTGCAC
     721      ---------+---------+---------+---------+---------+---------+
              GTTGTTGTTCTGGAAGTTGCCGTGGCCGGGGACGTTGTTGCACAGGTGGCACGTCACGTG
               N  N  K  T  F  N  G  T  G  P  C  N  N  V  S  T  V  Q  C  T

PvuII
              CCACGGCATCAAGCCCGTGGTGTCCACCCAGCTGCTGCTGAATGGCAGCCTGGCCGAGGG
     781      ---------+---------+---------+---------+---------+---------+
              GGTGCCGTAGTTCGGGCACCACAGGTGGGTCGACGACGACTTACCGTCGGACCGGCTCCC
               H  G  I  K  P  V  V  S  T  Q  L  L  L  N  G  S  L  A  E  G

CGAGATCATCATCAGAAGCGAGAACCTGACCAACAACGTGAAAACCATCATCGTGCACCT
     841      ---------+---------+---------+---------+---------+---------+
              GCTCTAGTAGTAGTCTTCGCTCTTGGACTGGTTGTTGCACTTTTGGTAGTAGCACGTGGA
               E  I  I  I  R  S  E  N  L  T  N  N  V  K  T  I  I  V  H  L

GAACGAGAGCGTGGAAATCGTGTGCACCCGGCCCAACAACAACACCAGAAAGAGCATCCG
     901      ---------+---------+---------+---------+---------+---------+
              CTTGCTCTCGCACCTTTAGCACACGTGGGCCGGGTTGTTGTTGTGGTCTTTCTCGTAGGC
               N  E  S  V  E  I  V  C  T  R  P  N  N  N  T  R  K  S  I  R

StuI
              GATCGGCCCTGGCCAGACCTTTTACGCCACCGGCGACATCATCGGCAACATCCGGCAGGC
     961      ---------+---------+---------+---------+---------+---------+
              CTAGCCGGGACCGGTCTGGAAAATGCGGTGGCCGCTGTAGTAGCCGTTGTAGGCCGTCCG
               I  G  P  G  Q  T  F  Y  A  T  G  D  I  I  G  N  I  R  Q  A

BamHI      PstI
              CTACTGCAACATCAAGAAGGACGACTGGATCCGGACCCTGCAGAGAGTGGGCAAGAAGCT
    1021      ---------+---------+---------+---------+---------+---------+
              GATGACGTTGTAGTTCTTCCTGCTGACCTAGGCCTGGGACGTCTCTCACCCGTTCTTCGA
               Y  C  N  I  K  K  D  D  W  I  R  T  L  Q  R  V  G  K  K  L

GGCCGAGCACTTCCCCAGACGGATCATCAACTTCACCAGCCCCGCTGGCGGCGACCTGGA
    1081      ---------+---------+---------+---------+---------+---------+
              CCGGCTCGTGAAGGGGTCTGCCTAGTAGTTGAAGTGGTCGGGGCGACCGCCGCTGGACCT
               A  E  H  F  P  R  R  I  I  N  F  T  S  P  A  G  G  D  L  E
```

```
                        PstI
      AATCACCACCCACAGCTTCAACTGCAGAGGCGAGTTCTTCTACTGCAATACCAGCAGCCT
1141  ---------+---------+---------+---------+---------+---------+
      TTAGTGGTGGGTGTCGAAGTTGACGTCTCCGCTCAAGAAGATGACGTTATGGTCGTCGGA
       I   T   T   H   S   F   N   C   R   G   E   F   F   Y   C   N   T   S   S   L

GTTCAACAGCACCTACAACCCCAACGACACCAACAGCAACAGCTCCAGCAGCAACTCCAG
1201  ---------+---------+---------+---------+---------+---------+
      CAAGTTGTCGTGGATGTTGGGGTTGCTGTGGTTGTCGTTGTCGAGGTCGTCGTTGAGGTC
       F   N   S   T   Y   N   P   N   D   T   N   S   N   S   S   S   S   N   S   S

CCTGGACATCACCATCCCTTGCCGGATCAAGCAGATCATCAATATGTGGCAGGAAGTGGG
1261  ---------+---------+---------+---------+---------+---------+
      GGACCTGTAGTGGTAGGGAACGGCCTAGTTCGTCTAGTAGTTATACACCGTCCTTCACCC
       L   D   I   T   I   P   C   R   I   K   Q   I   I   N   M   W   Q   E   V   G

CAGGGCTATGTACGCCCCTCCCATCGAGGGCAACATCACATGCAAGAGCAACATCACCGG
1321  ---------+---------+---------+---------+---------+---------+
      GTCCCGATACATGCGGGGAGGGTAGCTCCCGTTGTAGTGTACGTTCTCGTTGTAGTGGCC
       R   A   M   Y   A   P   P   I   E   G   N   I   T   C   K   S   N   I   T   G

BglII
      CCTGCTCCTGGTCCGCGACGGCGGCGTGGAAAGCAACGAGACAGAGATCTTCAGACCCGG
1381  ---------+---------+---------+---------+---------+---------+
      GGACGAGGACCAGGCGCTGCCGCCGCACCTTTCGTTGCTCTGTCTCTAGAAGTCTGGGCC
       L   L   L   V   R   D   G   G   V   E   S   N   E   T   E   I   F   R   P   G

CGGAGGCGACATGCGGAACAACTGGCGGAGCGAGCTGTACAAGTACAAGGTGGTGGAAAT
1441  ---------+---------+---------+---------+---------+---------+
      GCCTCCGCTGTACGCCTTGTTGACCGCCTCGCTCGACATGTTCATGTTCCACCACCTTTA
       G   G   D   M   R   N   N   W   R   S   E   L   Y   K   Y   K   V   V   E   I

CAAGCCCCTGGGAATCGCCCCCACCGCCGCCAAGCGGAGAGTGGTGGAAGGCGCTCACCA
1501  ---------+---------+---------+---------+---------+---------+
      GTTCGGGGACCCTTAGCGGGGGTGGCGGCGGTTCGCCTCTCACCACCTTCCGCGAGTGGT
       K   P   L   G   I   A   P   T   A   A   K   R   R   V   V   E   G   A   H   H
```

```
        CCACCATCACCACGGCCTGAACGACATCTTCGAGGCCCAGAAAATCGAGTGGCACGAGTG
1561    ---------+---------+---------+---------+---------+---------+
        GGTGGTAGTGGTGCCGGACTTGCTGTAGAAGCTCCGGGTCTTTTAGCTCACCGTGCTCAC
         H  H  H  H  G  L  N  D  I  F  E  A  Q  K  I  E  W  H  E  *

XhoI XbaI  ApaI  PmeI        BclI
        ACTCGAGTCTAGAGGGCCCGTTTAAACCCGCTGATCAGCCTCGACTG
1621    ---------+---------+---------+---------+-------
        TGAGCTCAGATCTCCCGGGCAAATTTGGGCGACTAGTCGGAGCTGAC
```

FIG. 20

```
                                        HindIII
              BsaI      NheI   PmeI   AflII
       CTCACTATAGGGAGACCCAAGCTGGCTAGCGTTTAAACTTAAGCTTGCCACCATGCCTAT
   1   ---------+---------+---------+---------+---------+---------+
       GAGTGATATCCCTCTGGGTTCGACCGATCGCAAATTTGAATTCGAACGGTGGTACGGATA
                                                          M   P   M PstI                     BspMI     SphI
       GGGCAGCCTGCAGCCTCTGGCCACCCTGTACCTGCTGGGCATGCTGGTGGCCTCCGTGCT
  61   ---------+---------+---------+---------+---------+---------+
       CCCGTCGGACGTCGGAGACCGGTGGGACATGGACGACCCGTACGACCACCGGAGGCACGA
        G   S   L   Q   P   L   A   T   L   Y   L   L   G   M   L   V   A   S   V   L PvuII
       GGCAGCTGGCAACCTGTGGGTCACAGTGTACTACGGCGTGCCCGTGTGGAAAGAGGCCAA
 121   ---------+---------+---------+---------+---------+---------+
       CCGTCGACCGTTGGACACCCAGTGTCACATGATGCCGCACGGGCACACCTTTCTCCGGTT
        A   A   G   N   L   W   V   T   V   Y   Y   G   V   P   V   W   K   E   A   K StuI
       GACCACCCTGTTCTGCGCCAGCGACGCCAAGGCCTACGAGAAAGAGGTGCACAACGTCTG
 181   ---------+---------+---------+---------+---------+---------+
       CTGGTGGGACAAGACGCGGTCGCTGCGGTTCCGGATGCTCTTTCTCCACGTGTTGCAGAC
        T   T   L   F   C   A   S   D   A   K   A   Y   E   K   E   V   H   N   V   W PflMI
       GGCCACCCACGCCTGCGTGCCCACCGACCCCAACCCCCAGGAAATGGTCCTGGAAAACGT
 241   ---------+---------+---------+---------+---------+---------+
       CCGGTGGGTGCGGACGCACGGGTGGCTGGGGTTGGGGGTCCTTTACCAGGACCTTTTGCA
        A   T   H   A   C   V   P   T   D   P   N   P   Q   E   M   V   L   E   N   V
```

```
                                                         BclI
       GACCGAGAACTTCAACATGTGGAAGAACGACATGGTGGAACAGATGCACGAGGACGTGAT
301    ---------+---------+---------+---------+---------+---------+
       CTGGCTCTTGAAGTTGTACACCTTCTTGCTGTACCACCTTGTCTACGTGCTCCTGCACTA
        _T__E__N__F__N__M__W__K__N__D__M__V__E__Q__M__H__E__D__V__I_

CAGCCTGTGGGACCAGAGCCTGAAGCCCTGCGTGAAGCTGACCCCCCTGTGCGTGACCCT
361    ---------+---------+---------+---------+---------+---------+
       GTCGGACACCCTGGTCTCGGACTTCGGGACGCACTTCGACTGGGGGGACACGCACTGGGA
        _S__L__W__D__Q__S__L__K__P__C__V__K__L__T__P__L__C__V__T__L_

HincII
       GGAATGCAGACAGGTCAACACCACCAACGCCACCAGCAGCGTGAACGTGACCAACGGCGA
421    ---------+---------+---------+---------+---------+---------+
       CCTTACGTCTGTCCAGTTGTGGTGGTTGCGGTGGTCGTCGCACTTGCACTGGTTGCCGCT
        _E__C__R__Q__V__N__T__T__N__A__T__S__S__V__N__V__T__N__G__E_

PstI
       GGAAATCAAGAACTGCAGCTACAATGCCACCACCGAGATCCGGGACAAGAAACAGAAGGT
481    ---------+---------+---------+---------+---------+---------+
       CCTTTAGTTCTTGACGTCGATGTTACGGTGGTGGCTCTAGGCCCTGTTCTTTGTCTTCCA
        _E__I__K__N__C__S__Y__N__A__T__T__E__I__R__D__K__K__Q__K__V_

GTACGCCCTGTTCTACCGGCTGGACATCGTGCCCCTGGAAGAGGAACGGAAGGGCAACAG
541    ---------+---------+---------+---------+---------+---------+
       CATGCGGGACAAGATGGCCGACCTGTAGCACGGGGACCTTCTCCTTGCCTTCCCGTTGTC
        _Y__A__L__F__Y__R__L__D__I__V__P__L__E__E__E__R__K__G__N__S_

BclI                        StuI
       CAGCAAGTACCGGCTGATCAACTGCAACACCAGCGCCATCACCCAGGCCTGCCCCAAAGT
601    ---------+---------+---------+---------+---------+---------+
       GTCGTTCATGGCCGACTAGTTGACGTTGTGGTCGCGGTAGTGGGTCCGGACGGGGTTTCA
        _S__K__Y__R__L__I__N__C__N__T__S__A__I__T__Q__A__C__P__K__V_
```

```
             GACCTTCGACCCTATCCCCATCCACTACTGCGCCCCTGCCGGCTACGCCATCCTGAAGTG
     661     ---------+---------+---------+---------+---------+---------+
             CTGGAAGCTGGGATAGGGGTAGGTGATGACGCGGGGACGGCCGATGCGGTAGGACTTCAC
              T  F  D  P  I  P  I  H  Y  C  A  P  A  G  Y  A  I  L  K  C

CAACAACAAGACCTTCAACGGCACCGGCCCCTGCAACAACGTGTCCACCGTGCAGTGCAC
     721     ---------+---------+---------+---------+---------+---------+
             GTTGTTGTTCTGGAAGTTGCCGTGGCCGGGGACGTTGTTGCACAGGTGGCACGTCACGTG
              N  N  K  T  F  N  G  T  G  P  C  N  N  V  S  T  V  Q  C  T

PvuII
             CCACGGCATCAAGCCCGTGGTGTCCACCCAGCTGCTGCTGAATGGCAGCCTGGCCGAGGG
     781     ---------+---------+---------+---------+---------+---------+
             GGTGCCGTAGTTCGGGCACCACAGGTGGGTCGACGACGACTTACCGTCGGACCGGCTCCC
              H  G  I  K  P  V  V  S  T  Q  L  L  L  N  G  S  L  A  E  G

CGAGATCATCATCAGAAGCGAGAACCTGACCAACAACGTGAAAACCATCATCGTGCACCT
     841     ---------+---------+---------+---------+---------+---------+
             GCTCTAGTAGTAGTCTTCGCTCTTGGACTGGTTGTTGCACTTTTGGTAGTAGCACGTGGA
              E  I  I  I  R  S  E  N  L  T  N  N  V  K  T  I  I  V  H  L

GAACGAGAGCGTGGAAATCGTGTGCACCCGGCCCAACAACAACACCAGAAAGAGCATCCG
     901     ---------+---------+---------+---------+---------+---------+
             CTTGCTCTCGCACCTTTAGCACACGTGGGCCGGGTTGTTGTTGTGGTCTTTCTCGTAGGC
              N  E  S  V  E  I  V  C  T  R  P  N  N  N  T  R  K  S  I  R

StuI
             GATCGGCCCTGGCCAGACCTTTTACGCCACCGGCGACATCATCGGCAACATCCGGCAGGC
     961     ---------+---------+---------+---------+---------+---------+
             CTAGCCGGGACCGGTCTGGAAAATGCGGTGGCCGCTGTAGTAGCCGTTGTAGGCCGTCCG
              I  G  P  G  Q  T  F  Y  A  T  G  D  I  I  G  N  I  R  Q  A

BamHI       PstI
             CTACTGCAACATCAAGAAGGACGACTGGATCCGGACCCTGCAGAGAGTGGGCAAGAAGCT
    1021     ---------+---------+---------+---------+---------+---------+
             GATGACGTTGTAGTTCTTCCTGCTGACCTAGGCCTGGGACGTCTCTCACCCGTTCTTCGA
              Y  C  N  I  K  K  D  D  W  I  R  T  L  Q  R  V  G  K  K  L
```

```
          GGCCGAGCACTTCCCCAGACGGATCATCAACTTCACCAGCCCCGCTGGCGGCGACCTGGA
    1081  ---------+---------+---------+---------+---------+---------+
          CCGGCTCGTGAAGGGGTCTGCCTAGTAGTTGAAGTGGTCGGGGCGACCGCCGCTGGACCT
           A  E  H  F  P  R  R  I  I  N  F  T  S  P  A  G  G  D  L  E

PstI
          AATCACCACCCACAGCTTCAACTGCAGAGGCGAGTTCTTCTACTGCAATACCAGCAGCCT
    1141  ---------+---------+---------+---------+---------+---------+
          TTAGTGGTGGGTGTCGAAGTTGACGTCTCCGCTCAAGAAGATGACGTTATGGTCGTCGGA
           I  T  T  H  S  F  N  C  R  G  E  F  F  Y  C  N  T  S  S  L

GTTCAACAGCACCTACAACCCCAACGACACCAACAGCAACAGCTCCAGCAGCAACTCCAG
    1201  ---------+---------+---------+---------+---------+---------+
          CAAGTTGTCGTGGATGTTGGGGTTGCTGTGGTTGTCGTTGTCGAGGTCGTCGTTGAGGTC
           F  N  S  T  Y  N  P  N  D  T  N  S  N  S  S  S  S  N  S  S

CCTGGACATCACCATCCCTTGCCGGATCAAGCAGATCATCAATATGTGGCAGGAAGTGGG
    1261  ---------+---------+---------+---------+---------+---------+
          GGACCTGTAGTGGTAGGGAACGGCCTAGTTCGTCTAGTAGTTATACACCGTCCTTCACCC
           L  D  I  T  I  P  C  R  I  K  Q  I  I  N  M  W  Q  E  V  G

CAGGGCTATGTACGCCCCTCCCATCGAGGGCAACATCACATGCAAGAGCAACATCACCGG
    1321  ---------+---------+---------+---------+---------+---------+
          GTCCCGATACATGCGGGGAGGGTAGCTCCCGTTGTAGTGTACGTTCTCGTTGTAGTGGCC
           R  A  M  Y  A  P  P  I  E  G  N  I  T  C  K  S  N  I  T  G

BglII
          CCTGCTCCTGGTCCGCGACGGCGGCGTGGAAAGCAACGAGACAGAGATCTTCAGACCCGG
    1381  ---------+---------+---------+---------+---------+---------+
          GGACGAGGACCAGGCGCTGCCGCCGCACCTTTCGTTGCTCTGTCTCTAGAAGTCTGGGCC
           L  L  L  V  R  D  G  G  V  E  S  N  E  T  E  I  F  R  P  G

CGGAGGCGACATGCGGAACAACTGGCGGAGCGAGCTGTACAAGTACAAGGTGGTGGAAAT
    1441  ---------+---------+---------+---------+---------+---------+
          GCCTCCGCTGTACGCCTTGTTGACCGCCTCGCTCGACATGTTCATGTTCCACCACCTTTA
           G  G  D  M  R  N  N  W  R  S  E  L  Y  K  Y  K  V  V  E  I
```

```
             CAAGCCCCTGGGAATCGCCCCCACCGCCGCCAAGCGGAGAGTGGTGGAAGGCGCTCACCA
     1501    ---------+---------+---------+---------+---------+---------+
             GTTCGGGGACCCTTAGCGGGGGTGGCGGCGGTTCGCCTCTCACCACCTTCCGCGAGTGGT
              K  P  L  G  I  A  P  T  A  A  K  R  R  V  V  E  G  A  H  H

CCACCATCACCACGGCCTGAACGACATCTTCGAGGCCCAGAAAATCGAGTGGCACGAGTG
     1561    ---------+---------+---------+---------+---------+---------+
             GGTGGTAGTGGTGCCGGACTTGCTGTAGAAGCTCCGGGTCTTTTAGCTCACCGTGCTCAC
              H  H  H  H  G  L  N  D  I  F  E  A  Q  K  I  E  W  H  E  *

XhoI  XbaI  ApaI   PmeI       BclI
             ACTCGAGTCTAGAGGGCCCGTTTAAACCCGCTGATCAGCCTCGACTG
     1621    ---------+---------+---------+---------+-------
             TGAGCTCAGATCTCCCGGGCAAATTTGGGCGACTAGTCGGAGCTGAC
```

FIG. 21

```
                                            HindIII
         BsaI         NheI   PmeI   AflII
      CTCACTATAGGGAGACCCAAGCTGGCTAGCGTTTAAACTTAAGCTTGCCACCATGCCTAT
    1 ---------+---------+---------+---------+---------+---------+
      GAGTGATATCCCTCTGGGTTCGACCGATCGCAAATTTGAATTCGAACGGTGGTACGGATA
                                                            M   P   M PstI                       BspMI    SphI
      GGGCAGCCTGCAGCCTCTGGCCACCCTGTACCTGCTGGGCATGCTGGTGGCCTCCGTGCT
   61 ---------+---------+---------+---------+---------+---------+
      CCCGTCGGACGTCGGAGACCGGTGGGACATGGACGACCCGTACGACCACCGGAGGCACGA
       G   S   L   Q   P   L   A   T   L   Y   L   L   G   M   L   V   A   S   V   L PvuII
      GGCAGCTGGCAACCTGTGGGTCACAGTGTACTACGGCGTGCCCGTGTGGAAAGAGGCCAA
  121 ---------+---------+---------+---------+---------+---------+
      CCGTCGACCGTTGGACACCCAGTGTCACATGATGCCGCACGGGCACACCTTTCTCCGGTT
       A   A   G   N   L   W   V   T   V   Y   Y   G   V   P   V   W   K   E   A   K StuI
      GACCACCCTGTTCTGCGCCAGCGACGCCAAGGCCTACGAGAAAGAGGTGCACAACGTCTG
  181 ---------+---------+---------+---------+---------+---------+
      CTGGTGGGACAAGACGCGGTCGCTGCGGTTCCGGATGCTCTTTCTCCACGTGTTGCAGAC
       T   T   L   F   C   A   S   D   A   K   A   Y   E   K   E   V   H   N   V   W PflMI
      GGCCACCCACGCCTGCGTGCCCACCGACCCCAACCCCCAGGAAATGGTCCTGGAAAACGT
  241 ---------+---------+---------+---------+---------+---------+
      CCGGTGGGTGCGGACGCACGGGTGGCTGGGGTTGGGGGTCCTTTACCAGGACCTTTTGCA
       A   T   H   A   C   V   P   T   D   P   N   P   Q   E   M   V   L   E   N   V
```

```
                                                                   BclI
        GACCGAGAACTTCAACATGTGGAAGAACGACATGGTGGAACAGATGCACGAGGACGTGAT
301     ---------+---------+---------+---------+---------+---------+
        CTGGCTCTTGAAGTTGTACACCTTCTTGCTGTACCACCTTGTCTACGTGCTCCTGCACTA
         T  E  N  F  N  M  W  K  N  D  M  V  E  Q  M  H  E  D  V  I

CAGCCTGTGGGACCAGAGCCTGAAGCCCTGCGTGAAGCTGACCCCCCTGTGCGTGACCCT
361     ---------+---------+---------+---------+---------+---------+
        GTCGGACACCCTGGTCTCGGACTTCGGGACGCACTTCGACTGGGGGGACACGCACTGGGA
         S  L  W  D  Q  S  L  K  P  C  V  K  L  T  P  L  C  V  T  L

HincII
        GGAATGCAGACAGGTCAACACCACCAACGCCACCAGCAGCGTGAACGTGACCAACGGCGA
421     ---------+---------+---------+---------+---------+---------+
        CCTTACGTCTGTCCAGTTGTGGTGGTTGCGGTGGTCGTCGCACTTGCACTGGTTGCCGCT
         E  C  R  Q  V  N  T  T  N  A  T  S  S  V  N  V  T  N  G  E PstI
        GGAAATCAAGAACTGCAGCTTCAAGGCCACCACCGAGATCCGGGACGAGAAACAGAAGGT
481     ---------+---------+---------+---------+---------+---------+
        CCTTTAGTTCTTGACGTCGAAGTTCCGGTGGTGGCTCTAGGCCCTGCTCTTTGTCTTCCA
         E  I  K  N  C  S  F  K  A  T  T  E  I  R  D  E  K  Q  K  V GTACGCCCTGTTCTACCGGCTGGACATCGTGCCCCTGGAAGAGGAACGGAAGGGCAACAG
541     ---------+---------+---------+---------+---------+---------+
        CATGCGGGACAAGATGGCCGACCTGTAGCACGGGGACCTTCTCCTTGCCTTCCCGTTGTC
         Y  A  L  F  Y  R  L  D  I  V  P  L  E  E  E  R  K  G  N  S BclI                              StuI
        CAGCAAGTACCGGCTGATCAACTGCAACACCAGCGCCATCACCCAGGCCTGCCCCAAAGT
601     ---------+---------+---------+---------+---------+---------+
        GTCGTTCATGGCCGACTAGTTGACGTTGTGGTCGCGGTAGTGGGTCCGGACGGGGTTTCA
         S  K  Y  R  L  I  N  C  N  T  S  A  I  T  Q  A  C  P  K  V
```

```
      GACCTTCGACCCTATCCCCATCCACTACTGCGCCCCTGCCGGCTACGCCATCCTGAAGTG
661   ---------+---------+---------+---------+---------+---------+
      CTGGAAGCTGGGATAGGGGTAGGTGATGACGCGGGGACGGCCGATGCGGTAGGACTTCAC
       T  F  D  P  I  P  I  H  Y  C  A  P  A  G  Y  A  I  L  K  C

CAACAACAAGACCTTCAACGGCACCGGCCCCTGCAACAACGTGTCCACCGTGCAGTGCAC
721   ---------+---------+---------+---------+---------+---------+
      GTTGTTGTTCTGGAAGTTGCCGTGGCCGGGGACGTTGTTGCACAGGTGGCACGTCACGTG
       N  N  K  T  F  N  G  T  G  P  C  N  N  V  S  T  V  Q  C  T

PvuII
      CCACGGCATCAAGCCCGTGGTGTCCACCCAGCTGCTGCTGAATGGCAGCCTGGCCGAGGG
781   ---------+---------+---------+---------+---------+---------+
      GGTGCCGTAGTTCGGGCACCACAGGTGGGTCGACGACGACTTACCGTCGGACCGGCTCCC
       H  G  I  K  P  V  V  S  T  Q  L  L  L  N  G  S  L  A  E  G

CGAGATCATCATCAGAAGCGAGAACCTGACCAACAACGTGAAAACCATCATCGTGCACCT
841   ---------+---------+---------+---------+---------+---------+
      GCTCTAGTAGTAGTCTTCGCTCTTGGACTGGTTGTTGCACTTTTGGTAGTAGCACGTGGA
       E  I  I  I  R  S  E  N  L  T  N  N  V  K  T  I  I  V  H  L

GAACGAGAGCGTGGAAATCGTGTGCACCCGGCCCAACAACAACACCAGAAAGAGCATCCG
901   ---------+---------+---------+---------+---------+---------+
      CTTGCTCTCGCACCTTTAGCACACGTGGGCCGGGTTGTTGTTGTGGTCTTTCTCGTAGGC
       N  E  S  V  E  I  V  C  T  R  P  N  N  N  T  R  K  S  I  R

StuI
      GATCGGCCCTGGCCAGACCTTTTACGCCACCGGCGACATCATCGGCAACATCCGGCAGGC
961   ---------+---------+---------+---------+---------+---------+
      CTAGCCGGGACCGGTCTGGAAAATGCGGTGGCCGCTGTAGTAGCCGTTGTAGGCCGTCCG
       I  G  P  G  Q  T  F  Y  A  T  G  D  I  I  G  N  I  R  Q  A

BamHI      PstI
      CTACTGCAACATCAAGAAGGACGACTGGATCCGGACCCTGCAGAGAGTGGGCAAGAAGCT
1021  ---------+---------+---------+---------+---------+---------+
      GATGACGTTGTAGTTCTTCCTGCTGACCTAGGCCTGGGACGTCTCTCACCCGTTCTTCGA
       Y  C  N  I  K  K  D  D  W  I  R  T  L  Q  R  V  G  K  K  L
```

```
            GGCCGAGCACTTCCCCAGACGGATCATCAACTTCACCAGCCCCGCTGGCGGCGACCTGGA
  1081      ---------+---------+---------+---------+---------+---------+
            CCGGCTCGTGAAGGGGTCTGCCTAGTAGTTGAAGTGGTCGGGGCGACCGCCGCTGGACCT
             A   E   H   F   P   R   R   I   I   N   F   T   S   P   A   G   G   D   L   E

PstI
            AATCACCACCCACAGCTTCAACTGCAGAGGCGAGTTCTTCTACTGCAATACCAGCAGCCT
  1141      ---------+---------+---------+---------+---------+---------+
            TTAGTGGTGGGTGTCGAAGTTGACGTCTCCGCTCAAGAAGATGACGTTATGGTCGTCGGA
             I   T   T   H   S   F   N   C   R   G   E   F   F   Y   C   N   T   S   S   L

GTTCAACAGCACCTACAACCCCAACGACACCAACAGCAACAGCTCCAGCAGCAACTCCAG
  1201      ---------+---------+---------+---------+---------+---------+
            CAAGTTGTCGTGGATGTTGGGGTTGCTGTGGTTGTCGTTGTCGAGGTCGTCGTTGAGGTC
             F   N   S   T   Y   N   P   N   D   T   N   S   N   S   S   S   S   N   S   S

CCTGGACATCACCATCCCTTGCCGGATCAAGCAGATCATCAATATGTGGCAGGAAGTGGG
  1261      ---------+---------+---------+---------+---------+---------+
            GGACCTGTAGTGGTAGGGAACGGCCTAGTTCGTCTAGTAGTTATACACCGTCCTTCACCC
             L   D   I   T   I   P   C   R   I   K   Q   I   I   N   M   W   Q   E   V   G

CAGGGCTATGTACGCCCCTCCCATCGAGGGCAACATCACATGCAAGAGCAACATCACCGG
  1321      ---------+---------+---------+---------+---------+---------+
            GTCCCGATACATGCGGGGAGGGTAGCTCCCGTTGTAGTGTACGTTCTCGTTGTAGTGGCC
             R   A   M   Y   A   P   P   I   E   G   N   I   T   C   K   S   N   I   T   G

BglII
            CCTGCTCCTGGTCCGCGACGGCGGCGTGGAAAGCAACGAGACAGAGATCTTCAGACCCGG
  1381      ---------+---------+---------+---------+---------+---------+
            GGACGAGGACCAGGCGCTGCCGCCGCACCTTTCGTTGCTCTGTCTCTAGAAGTCTGGGCC
             L   L   L   V   R   D   G   G   V   E   S   N   E   T   E   I   F   R   P   G

CGGAGGCGACATGCGGAACAACTGGCGGAGCGAGCTGTACAAGTACAAGGTGGTGGAAAT
  1441      ---------+---------+---------+---------+---------+---------+
            GCCTCCGCTGTACGCCTTGTTGACCGCCTCGCTCGACATGTTCATGTTCCACCACCTTTA
             G   G   D   M   R   N   N   W   R   S   E   L   Y   K   Y   K   V   V   E   I
```

```
        CAAGCCCCTGGGAATCGCCCCCACCGCCGCCAAGCGGAGAGTGGTGGAAGGCGCTCACCA
1501    ---------+---------+---------+---------+---------+---------+
        GTTCGGGGACCCTTAGCGGGGGTGGCGGCGGTTCGCCTCTCACCACCTTCCGCGAGTGGT
         K   P   L   G   I   A   P   T   A   A   K   R   R   V   V   E   G   A   H   H

CCACCATCACCACGGCCTGAACGACATCTTCGAGGCCCAGAAAATCGAGTGGCACGAGTG
1561    ---------+---------+---------+---------+---------+---------+
        GGTGGTAGTGGTGCCGGACTTGCTGTAGAAGCTCCGGGTCTTTTAGCTCACCGTGCTCAC
         H   H   H   H   G   L   N   D   I   F   E   A   Q   K   I   E   W   H   E   *

XhoI  XbaI  ApaI   PmeI       BclI
        ACTCGAGTCTAGAGGGCCCGTTTAAACCCGCTGATCAGCCTCGACTG
1621    ---------+---------+---------+---------+-------
        TGAGCTCAGATCTCCCGGGCAAATTTGGGCGACTAGTCGGAGCTGAC
```

FIG. 22

```
                                        HindIII
         BsaI        NheI   PmeI   AflII
      CTCACTATAGGGAGACCCAAGCTGGCTAGCGTTTAAACTTAAGCTTGCCACCATGCCTAT
  1   ---------+---------+---------+---------+---------+---------+
      GAGTGATATCCCTCTGGGTTCGACCGATCGCAAATTTGAATTCGAACGGTGGTACGGATA
                                                          M  P  M PstI                      BspMI    SphI
      GGGCAGCCTGCAGCCTCTGGCCACCCTGTACCTGCTGGGCATGCTGGTGGCCTCCGTGCT
 61   ---------+---------+---------+---------+---------+---------+
      CCCGTCGGACGTCGGAGACCGGTGGGACATGGACGACCCGTACGACCACCGGAGGCACGA
       G  S  L  Q  P  L  A  T  L  Y  L  L  G  M  L  V  A  S  V  L PvuII
      GGCAGCTGGCAACCTGTGGGTCACAGTGTACTACGGCGTGCCCGTGTGGAAAGAGGCCAA
121   ---------+---------+---------+---------+---------+---------+
      CCGTCGACCGTTGGACACCCAGTGTCACATGATGCCGCACGGGCACACCTTTCTCCGGTT
       A  A  G  N  L  W  V  T  V  Y  Y  G  V  P  V  W  K  E  A  K StuI
      GACCACCCTGTTCTGCGCCAGCGACGCCAAGGCCTACGAGAAAGAGGTGCACAACGTCTG
181   ---------+---------+---------+---------+---------+---------+
      CTGGTGGGACAAGACGCGGTCGCTGCGGTTCCGGATGCTCTTTCTCCACGTGTTGCAGAC
       T  T  L  F  C  A  S  D  A  K  A  Y  E  K  E  V  H  N  V  W PflMI
      GGCCACCCACGCCTGCGTGCCCACCGACCCCAACCCCCAGGAAATGGTCCTGGAAAACGT
241   ---------+---------+---------+---------+---------+---------+
      CCGGTGGGTGCGGACGCACGGGTGGCTGGGGTTGGGGGTCCTTTACCAGGACCTTTTGCA
       A  T  H  A  C  V  P  T  D  P  N  P  Q  E  M  V  L  E  N  V
```

```
                                                                      BclI
        GACCGAGAACTTCAACATGTGGAAGAACGACATGGTGGAACAGATGCACGAGGACGTGAT
301     ---------+---------+---------+---------+---------+---------+
        CTGGCTCTTGAAGTTGTACACCTTCTTGCTGTACCACCTTGTCTACGTGCTCCTGCACTA
         T  E  N  F  N  M  W  K  N  D  M  V  E  Q  M  H  E  D  V  I

CAGCCTGTGGGACCAGAGCCTGAAGCCCTGCGTGAAGCTGACCCCCCTGTGCGTGACCCT
361     ---------+---------+---------+---------+---------+---------+
        GTCGGACACCCTGGTCTCGGACTTCGGGACGCACTTCGACTGGGGGGACACGCACTGGGA
         S  L  W  D  Q  S  L  K  P  C  V  K  L  T  P  L  C  V  T  L

HincII
        GGAATGCAGACAGGTCAACACCACCAACGCCACCAGCAGCGTGAACGTGACCAACGGCGA
421     ---------+---------+---------+---------+---------+---------+
        CCTTACGTCTGTCCAGTTGTGGTGGTTGCGGTGGTCGTCGCACTTGCACTGGTTGCCGCT
         E  C  R  Q  V  N  T  T  N  A  T  S  S  V  N  V  T  N  G  E PstI
        GGAAATCAAGAACTGCAGCTTCAATGCCACCACCGAGATCCGGGACAAGAAACAGAAGGT
481     ---------+---------+---------+---------+---------+---------+
        CCTTTAGTTCTTGACGTCGAAGTTACGGTGGTGGCTCTAGGCCCTGTTCTTTGTCTTCCA
         E  I  K  N  C  S  F  N  A  T  T  E  I  R  D  K  K  Q  K  V GTACGCCCTGTACTACCGGCTGGACATCGTGCCCCTGGAAGAGGAACGGAAGGGCAACAG
541     ---------+---------+---------+---------+---------+---------+
        CATGCGGGACATGATGGCCGACCTGTAGCACGGGGACCTTCTCCTTGCCTTCCCGTTGTC
         Y  A  L  Y  Y  R  L  D  I  V  P  L  E  E  E  R  K  G  N  S BclI                           StuI
        CAGCAAGTACCGGCTGATCAACTGCAACACCAGCGCCATCACCCAGGCCTGCCCCAAAGT
601     ---------+---------+---------+---------+---------+---------+
        GTCGTTCATGGCCGACTAGTTGACGTTGTGGTCGCGGTAGTGGGTCCGGACGGGGTTTCA
         S  K  Y  R  L  I  N  C  N  T  S  A  I  T  Q  A  C  P  K  V
```

```
           GACCTTCGACCCTATCCCCATCCACTACTGCGCCCCTGCCGGCTACGCCATCCTGAAGTG
    661    ---------+---------+---------+---------+---------+---------+
           CTGGAAGCTGGGATAGGGGTAGGTGATGACGCGGGGACGGCCGATGCGGTAGGACTTCAC
            T  F  D  P  I  P  I  H  Y  C  A  P  A  G  Y  A  I  L  K  C

CAACAACAAGACCTTCAACGGCACCGGCCCCTGCAACAACGTGTCCACCGTGCAGTGCAC
    721    ---------+---------+---------+---------+---------+---------+
           GTTGTTGTTCTGGAAGTTGCCGTGGCCGGGGACGTTGTTGCACAGGTGGCACGTCACGTG
            N  N  K  T  F  N  G  T  G  P  C  N  N  V  S  T  V  Q  C  T

PvuII
           CCACGGCATCAAGCCCGTGGTGTCCACCCAGCTGCTGCTGAATGGCAGCCTGGCCGAGGG
    781    ---------+---------+---------+---------+---------+---------+
           GGTGCCGTAGTTCGGGCACCACAGGTGGGTCGACGACGACTTACCGTCGGACCGGCTCCC
            H  G  I  K  P  V  V  S  T  Q  L  L  L  N  G  S  L  A  E  G

CGAGATCATCATCAGAAGCGAGAACCTGACCAACAACGTGAAAACCATCATCGTGCACCT
    841    ---------+---------+---------+---------+---------+---------+
           GCTCTAGTAGTAGTCTTCGCTCTTGGACTGGTTGTTGCACTTTTGGTAGTAGCACGTGGA
            E  I  I  I  R  S  E  N  L  T  N  N  V  K  T  I  I  V  H  L

GAACGAGAGCGTGGAAATCGTGTGCACCCGGCCCAACAACAACACCAGAAAGAGCATCCG
    901    ---------+---------+---------+---------+---------+---------+
           CTTGCTCTCGCACCTTTAGCACACGTGGGCCGGGTTGTTGTTGTGGTCTTTCTCGTAGGC
            N  E  S  V  E  I  V  C  T  R  P  N  N  N  T  R  K  S  I  R

StuI
           GATCGGCCCTGGCCAGACCTTTTACGCCACCGGCGACATCATCGGCAACATCCGGCAGGC
    961    ---------+---------+---------+---------+---------+---------+
           CTAGCCGGGACCGGTCTGGAAAATGCGGTGGCCGCTGTAGTAGCCGTTGTAGGCCGTCCG
            I  G  P  G  Q  T  F  Y  A  T  G  D  I  I  G  N  I  R  Q  A

BamHI       PstI
           CTACTGCAACATCAAGAAGGACGACTGGATCCGGACCCTGCAGAGAGTGGGCAAGAAGCT
   1021    ---------+---------+---------+---------+---------+---------+
           GATGACGTTGTAGTTCTTCCTGCTGACCTAGGCCTGGGACGTCTCTCACCCGTTCTTCGA
            Y  C  N  I  K  K  D  D  W  I  R  T  L  Q  R  V  G  K  K  L
```

```
        GGCCGAGCACTTCCCCAGACGGATCATCAACTTCACCAGCCCCGCTGGCGGCGACCTGGA
1081    ---------+---------+---------+---------+---------+---------+
        CCGGCTCGTGAAGGGGTCTGCCTAGTAGTTGAAGTGGTCGGGGCGACCGCCGCTGGACCT
         A   E   H   F   P   R   R   I   I   N   F   T   S   P   A   G   G   D   L   E
```

```
                                        PstI
        AATCACCACCCACAGCTTCAACTGCAGAGGCGAGTTCTTCTACTGCAATACCAGCAGCCT
1141    ---------+---------+---------+---------+---------+---------+
        TTAGTGGTGGGTGTCGAAGTTGACGTCTCCGCTCAAGAAGATGACGTTATGGTCGTCGGA
         I   T   T   H   S   F   N   C   R   G   E   F   F   Y   C   N   T   S   S   L
```

```
        GTTCAACAGCACCTACAACCCCAACGACACCAACAGCAACAGCTCCAGCAGCAACTCCAG
1201    ---------+---------+---------+---------+---------+---------+
        CAAGTTGTCGTGGATGTTGGGGTTGCTGTGGTTGTCGTTGTCGAGGTCGTCGTTGAGGTC
         F   N   S   T   Y   N   P   N   D   T   N   S   N   S   S   S   S   N   S   S
```

```
        CCTGGACATCACCATCCCTTGCCGGATCAAGCAGATCATCAATATGTGGCAGGAAGTGGG
1261    ---------+---------+---------+---------+---------+---------+
        GGACCTGTAGTGGTAGGGAACGGCCTAGTTCGTCTAGTAGTTATACACCGTCCTTCACCC
         L   D   I   T   I   P   C   R   I   K   Q   I   I   N   M   W   Q   E   V   G
```

```
        CAGGGCTATGTACGCCCCTCCCATCGAGGGCAACATCACATGCAAGAGCAACATCACCGG
1321    ---------+---------+---------+---------+---------+---------+
        GTCCCGATACATGCGGGGAGGGTAGCTCCCGTTGTAGTGTACGTTCTCGTTGTAGTGGCC
         R   A   M   Y   A   P   P   I   E   G   N   I   T   C   K   S   N   I   T   G
```

```
                                                        BglII
        CCTGCTCCTGGTCCGCGACGGCGGCGTGGAAAGCAACGAGACAGAGATCTTCAGACCCGG
1381    ---------+---------+---------+---------+---------+---------+
        GGACGAGGACCAGGCGCTGCCGCCGCACCTTTCGTTGCTCTGTCTCTAGAAGTCTGGGCC
         L   L   L   V   R   D   G   G   V   E   S   N   E   T   E   I   F   R   P   G
```

```
        CGGAGGCGACATGCGGAACAACTGGCGGAGCGAGCTGTACAAGTACAAGGTGGTGGAAAT
1441    ---------+---------+---------+---------+---------+---------+
        GCCTCCGCTGTACGCCTTGTTGACCGCCTCGCTCGACATGTTCATGTTCCACCACCTTTA
         G   G   D   M   R   N   N   W   R   S   E   L   Y   K   Y   K   V   V   E   I
```

```
        CAAGCCCCTGGGAATCGCCCCCACCGCCGCCAAGCGGAGAGTGGTGGAAGGCGCTCACCA
1501    ----------+---------+---------+---------+---------+---------+
        GTTCGGGGACCCTTAGCGGGGGTGGCGGCGGTTCGCCTCTCACCACCTTCCGCGAGTGGT
         K  P  L  G  I  A  P  T  A  A  K  R  R  V  V  E  G  A  H  H

CCACCATCACCACGGCCTGAACGACATCTTCGAGGCCCAGAAAATCGAGTGGCACGAGTG
1561    ----------+---------+---------+---------+---------+---------+
        GGTGGTAGTGGTGCCGGACTTGCTGTAGAAGCTCCGGGTCTTTTAGCTCACCGTGCTCAC
         H  H  H  H  G  L  N  D  I  F  E  A  Q  K  I  E  W  H  E  *

XhoI  XbaI  ApaI  PmeI        BclI
        ACTCGAGTCTAGAGGGCCCGTTTAAACCCGCTGATCAGCCTCGACTG
1621    ----------+---------+---------+---------+-------
        TGAGCTCAGATCTCCCGGGCAAATTTGGGCGACTAGTCGGAGCTGAC
```

FIG. 23

```
                                    HindIII
     BsaI         NheI    PmeI    AflII                              PstI
         GAGACCCAAGCTGGCTAGCGTTTAAACTTAAGCTTGCCACCATGCCTATGGGCAGCCTGC
   1  ---------+---------+---------+---------+---------+---------+
         CTCTGGGTTCGACCGATCGCAAATTTGAATTCGAACGGTGGTACGGATACCCGTCGGACG
                                                    M  P  M  G  S  L  Q BspMI     SphI                          PvuII
         AGCCTCTGGCCACCCTGTACCTGCTGGGCATGCTGGTGGCCTCCGTGCTGGCAGCTGGCA
  61  ---------+---------+---------+---------+---------+---------+
         TCGGAGACCGGTGGGACATGGACGACCCGTACGACCACCGGAGGCACGACCGTCGACCGT
          P  L  A  T  L  Y  L  L  G  M  L  V  A  S  V  L  A  A  G  N ACCTGTGGGTCACAGTGTACTACGGCGTGCCCGTGTGGAAAGAGGCCAAGACCACCCTGT
 121  ---------+---------+---------+---------+---------+---------+
         TGGACACCCAGTGTCACATGATGCCGCACGGGCACACCTTTCTCCGGTTCTGGTGGGACA
          L  W  V  T  V  Y  Y  G  V  P  V  W  K  E  A  K  T  T  L  F StuI
         TCTGCGCCAGCGACGCCAAGGCCTACGAGAAAGAGGTGCACAACGTCTGGGCCACCCACG
 181  ---------+---------+---------+---------+---------+---------+
         AGACGCGGTCGCTGCGGTTCCGGATGCTCTTTCTCCACGTGTTGCAGACCCGGTGGGTGC
          C  A  S  D  A  K  A  Y  E  K  E  V  H  N  V  W  A  T  H  A PflMI
         CCTGCGTGCCCACCGACCCCAACCCCCAGGAAATGGTCCTGGAAAACGTGACCGAGAACT
 241  ---------+---------+---------+---------+---------+---------+
         GGACGCACGGGTGGCTGGGGTTGGGGGTCCTTTACCAGGACCTTTTGCACTGGCTCTTGA
          C  V  P  T  D  P  N  P  Q  E  M  V  L  E  N  V  T  E  N  F
```

```
                                                         BclI
         TCAACATGTGGAAGAACGACATGGTGGAACAGATGCACGAGGACGTGATCAGCCTGTGGG
301      ---------+---------+---------+---------+---------+---------+
         AGTTGTACACCTTCTTGCTGTACCACCTTGTCTACGTGCTCCTGCACTAGTCGGACACCC
          N  M  W  K  N  D  M  V  E  Q  M  H  E  D  V  I  S  L  W  D

ACCAGAGCCTGAAGCCCTGCGTGAAGCTGACCCCCCTGTGCGTGACCCTGGAATGCAGAC
361      ---------+---------+---------+---------+---------+---------+
         TGGTCTCGGACTTCGGGACGCACTTCGACTGGGGGGACACGCACTGGGACCTTACGTCTG
          Q  S  L  K  P  C  V  K  L  T  P  L  C  V  T  L  E  C  R  Q

HincII
         AGGTCAACACCACCAACGCCACCAGCAGCGTGAACGTGACCAACGGCGAGGAAATCAAGA
421      ---------+---------+---------+---------+---------+---------+
         TCCAGTTGTGGTGGTTGCGGTGGTCGTCGCACTTGCACTGGTTGCCGCTCCTTTAGTTCT
          V  N  T  T  N  A  T  S  S  V  N  V  T  N  G  E  E  I  K  N PstI
         ACTGCAGCTTCAATGCCACCACCGAGATCCGGGACAAGAAACAGAAGGTGTACGCCCTGT
481      ---------+---------+---------+---------+---------+---------+
         TGACGTCGAAGTTACGGTGGTGGCTCTAGGCCCTGTTCTTTGTCTTCCACATGCGGGACA
          C  S  F  N  A  T  T  E  I  R  D  K  K  Q  K  V  Y  A  L  F TCTACCGGCTGGACATCGTGCCCCTGGAAGAGGAACGGAAGGGCAACAGCAGCAAGTACC
541      ---------+---------+---------+---------+---------+---------+
         AGATGGCCGACCTGTAGCACGGGGACCTTCTCCTTGCCTTCCCGTTGTCGTCGTTCATGG
          Y  R  L  D  I  V  P  L  E  E  E  R  K  G  N  S  S  K  Y  R BclI                      StuI
         GGCTGATCAACTGCAACACCAGCGCCATCACCCAGGCCTGCCCCAAAGTGACCTTCGACC
601      ---------+---------+---------+---------+---------+---------+
         CCGACTAGTTGACGTTGTGGTCGCGGTAGTGGGTCCGGACGGGGTTTCACTGGAAGCTGG
          L  I  N  C  N  T  S  A  I  T  Q  A  C  P  K  V  T  F  D  P
```

```
         CTATCCCCATCCACTACTGCGCCCCTGCCGGCTACGCCATCCTGAAGTGCAACAACAAGA
   661   ---------+---------+---------+---------+---------+---------+
         GATAGGGGTAGGTGATGACGCGGGGACGGCCGATGCGGTAGGACTTCACGTTGTTGTTCT
          _I__P__I__H__Y__C__A__P__A__G__Y__A__I__L__K__C__N__N__K__T

CCTTCAACGGCACCGGCCCCTGCAACAACGTGTCCACCGTGCAGTGCACCCACGGCATCA
   721   ---------+---------+---------+---------+---------+---------+
         GGAAGTTGCCGTGGCCGGGGACGTTGTTGCACAGGTGGCACGTCACGTGGGTGCCGTAGT
          _F__N__G__T__G__P__C__N__N__V__S__T__V__Q__C__T__H__G__I__K

PvuII
         AGCCCGTGGTGTCCACCCAGCTGCTGCTGAATGGCAGCCTGGCCGAGGGCGAGATCATCA
   781   ---------+---------+---------+---------+---------+---------+
         TCGGGCACCACAGGTGGGTCGACGACGACTTACCGTCGGACCGGCTCCCGCTCTAGTAGT
          _P__V__V__S__T__Q__L__L__L__N__G__S__L__A__E__G__E__I__I__I

TCAGAAGCGAGAACCTGACCAACAACGTGAAAACCATCATCGTGCACCTGAACGAGAGCG
   841   ---------+---------+---------+---------+---------+---------+
         AGTCTTCGCTCTTGGACTGGTTGTTGCACTTTTGGTAGTAGCACGTGGACTTGCTCTCGC
          _R__S__E__N__L__T__N__N__V__K__T__I__I__V__H__L__N__E__S__V

TGGAAATCGTGTGCACCCGGCCCAACAACAACACCAGAAAGAGCATCCGGATCGGCCCTG
   901   ---------+---------+---------+---------+---------+---------+
         ACCTTTAGCACACGTGGGCCGGGTTGTTGTTGTGGTCTTTCTCGTAGGCCTAGCCGGGAC
          _E__I__V__C__T__R__P__N__N__N__T__R__K__S__I__R__I__G__P__G

StuI
         GCCAGACCTTTTACGCCACCGGCGACATCATCGGCAACATCCGGCAGGCCTACTGCAACA
   961   ---------+---------+---------+---------+---------+---------+
         CGGTCTGGAAAATGCGGTGGCCGCTGTAGTAGCCGTTGTAGGCCGTCCGGATGACGTTGT
          _Q__T__F__Y__A__T__G__D__I__I__G__N__I__R__Q__A__Y__C__N__I

BamHI       PstI
         TCAAGAAGGACGACTGGATCCGGACCCTGCAGAGAGTGGGCAAGAAGCTGGCCGAGCACT
  1021   ---------+---------+---------+---------+---------+---------+
         AGTTCTTCCTGCTGACCTAGGCCTGGGACGTCTCTCACCCGTTCTTCGACCGGCTCGTGA
          _K__K__D__D__W__I__R__T__L__Q__R__V__G__K__K__L__A__E__H__F
```

```
            TCCCCAGACGGATCATCAACTTCACCAGCCCCGCTGGCGGCGACCTGGAAATCACCACCC
    1081   ---------+---------+---------+---------+---------+---------+
            AGGGGTCTGCCTAGTAGTTGAAGTGGTCGGGGCGACCGCCGCTGGACCTTTAGTGGTGGG
             P   R   R   I   I   N   F   T   S   P   A   G   G   D   L   E   I   T   T   H

PstI
            ACAGCTTCAACTGCAGAGGCGAGTTCTTCTACTGCAATACCAGCAGCCTGTTCAACAGCA
    1141   ---------+---------+---------+---------+---------+---------+
            TGTCGAAGTTGACGTCTCCGCTCAAGAAGATGACGTTATGGTCGTCGGACAAGTTGTCGT
             S   F   N   C   R   G   E   F   F   Y   C   N   T   S   S   L   F   N   S   T

CCTACAACCCCAACGACACCAACAGCAACAGCTCCAGCAGCAACTCCAGCCTGGACATCA
    1201   ---------+---------+---------+---------+---------+---------+
            GGATGTTGGGGTTGCTGTGGTTGTCGTTGTCGAGGTCGTCGTTGAGGTCGGACCTGTAGT
             Y   N   P   N   D   T   N   S   N   S   S   S   S   N   S   S   L   D   I   T

CCATCCCTTGCCGGATCAAGCAGATCATCAATATGTGGCAGGAAGTGGGCAGGGCTATGT
    1261   ---------+---------+---------+---------+---------+---------+
            GGTAGGGAACGGCCTAGTTCGTCTAGTAGTTATACACCGTCCTTCACCCGTCCCGATACA
             I   P   C   R   I   K   Q   I   I   N   M   W   Q   E   V   G   R   A   M   Y

ACGCCCCTCCCATCGAGGGCAACATCACATGCAAGAGCAACATCACCGGCCTGCTCCTGG
    1321   ---------+---------+---------+---------+---------+---------+
            TGCGGGGAGGGTAGCTCCCGTTGTAGTGTACGTTCTCGTTGTAGTGGCCGGACGAGGACC
             A   P   P   I   E   G   N   I   T   C   K   S   N   I   T   G   L   L   L   V

BglII
            TCCGCGACGGCGGCGTGGAAAGCAACGAGACAGAGATCTTCAGACCCGGCGGAGGCGACA
    1381   ---------+---------+---------+---------+---------+---------+
            AGGCGCTGCCGCCGCACCTTTCGTTGCTCTGTCTCTAGAAGTCTGGGCCGCCTCCGCTGT
             R   D   G   G   V   E   S   N   E   T   E   I   F   R   P   G   G   G   D   M

TGCGGAACAACTGGCGGAGCGAGCTGTACAAGTACAAGGTGGTGGAAATCAAGCCCCTGG
    1441   ---------+---------+---------+---------+---------+---------+
            ACGCCTTGTTGACCGCCTCGCTCGACATGTTCATGTTCCACCACCTTTAGTTCGGGGACC
             R   N   N   W   R   S   E   L   Y   K   Y   K   V   V   E   I   K   P   L   G
```

```
                  GAATCGCCCCCACCGCCGCCAAGCGGAGAGTGGTGGAAAGCGAGAAGTCCGCCGTGGGCC
        1501      ---------+---------+---------+---------+---------+---------+
                  CTTAGCGGGGGTGGCGGCGGTTCGCCTCTCACCACCTTTCGCTCTTCAGGCGGCACCCGG
                   I  A  P  T  A  A  K  R  R  V  V  E  S  E  K  S  A  V  G  L

NarI
                      KasI                                NcoI
                  TGGGCGCCGTGATCTTCGGCTTTCTGGGAGCCGCCGGAAGCACCATGGGCGCTGCCAGCA
        1561      ---------+---------+---------+---------+---------+---------+
                  ACCCGCGGCACTAGAAGCCGAAAGACCCTCGGCGGCCTTCGTGGTACCCGCGACGGTCGT
                   G  A  V  I  F  G  F  L  G  A  A  G  S  T  M  G  A  A  S  I

PvuII                    BspMI
                  TCACCCTGACCGTGCAGGCCAGACAGCTGCTGAGCGGCATCGTGCAGCAGCAGAGCAACC
        1621      ---------+---------+---------+---------+---------+---------+
                  AGTGGGACTGGCACGTCCGGTCTGTCGACGACTCGCCGTAGCACGTCGTCGTCTCGTTGG
                   T  L  T  V  Q  A  R  Q  L  L  S  G  I  V  Q  Q  Q  S  N  L

PvuII
                                     PstI                           PvuII
                  TGCTGAAGGCCATCGAGGCCCAGCAGCATCTGCTGCAGCTGACCGTGTGGGGCATCAAGC
        1681      ---------+---------+---------+---------+---------+---------+
                  ACGACTTCCGGTAGCTCCGGGTCGTCGTAGACGACGTCGACTGGCACACCCCGTAGTTCG
                   L  K  A  I  E  A  Q  Q  H  L  L  Q  L  T  V  W  G  I  K  Q

PstI    SmaI
                  AGCTGCAGACCCGGGTGCTGGCCATCGAGAGATACCTGAAGGACCAGCAGCTCCTGGGAA
        1741      ---------+---------+---------+---------+---------+---------+
                  TCGACGTCTGGGCCCACGACCGGTAGCTCTCTATGGACTTCCTGGTCGTCGAGGACCCTT
                   L  Q  T  R  V  L  A  I  E  R  Y  L  K  D  Q  Q  L  L  G  I

PstI                                         PvuII
                  TCTGGGGCTGCAGCGGCAAGCTGATCTGCACCACCGCCGTGCCCTGGAACAGCAGCTGGT
        1801      ---------+---------+---------+---------+---------+---------+
                  AGACCCCGACGTCGCCGTTCGACTAGACGTGGTGGCGGCACGGGACCTTGTCGTCGACCA
                   W  G  C  S  G  K  L  I  C  T  T  A  V  P  W  N  S  S  W  S
```

```
                     BglII
       CCAACAAGAGCCACGACGAGATCTGGGGCAACATGACCTGGATGCAGTGGGACAGAGAGA
1861   ---------+---------+---------+---------+---------+---------+
       GGTTGTTCTCGGTGCTGCTCTAGACCCCGTTGTACTGGACCTACGTCACCCTGTCTCTCT
        _N__K__S__H__D__E__I__W__G__N__M__T__W__M__Q__W__D__R__E__I

TCAGCAACTACACCAACACCATCTACCGCCTGCTGGAAGATAGCCAGAACCAGCAGGAAC
1921   ---------+---------+---------+---------+---------+---------+
       AGTCGTTGATGTGGTTGTGGTAGATGGCGGACGACCTTCTATCGGTCTTGGTCGTCCTTG
        _S__N__Y__T__N__T__I__Y__R__L__L__E__D__S__Q__N__Q__Q__E__Q

BspMI           PvuII
       AGAACGAGAAGGACCTGCTGGCCCTGGACAGCTGGGAGAACCTGTGGAACTGGTTCAGCA
1981   ---------+---------+---------+---------+---------+---------+
       TCTTGCTCTTCCTGGACGACCGGGACCTGTCGACCCTCTTGGACACCTTGACCAAGTCGT
        _N__E__K__D__L__L__A__L__D__S__W__E__N__L__W__N__W__F__S__I

NarI
                                                     KasI
       TCACCAAGTGGCTGTGGTACATCAAGGGCAGCGGCATGGTCCGAGGCATCAGAGGCGCCA
2041   ---------+---------+---------+---------+---------+---------+
       AGTGGTTCACCGACACCATGTAGTTCCCGTCGCCGTACCAGGCTCCGTAGTCTCCGCGGT
        _T__K__W__L__W__Y__I__K__G__S__G__M__V__R__G__I__R__G__A__I

TCACCGTGGAAGAGGACACCCCCGAGGCCATCCACCAGGCCACCAGAGAACTGCTGCTCA
2101   ---------+---------+---------+---------+---------+---------+
       AGTGGCACCTTCTCCTGTGGGGGCTCCGGTAGGTGGTCCGGTGGTCTCTTGACGACGAGT
        _T__V__E__E__D__T__P__E__A__I__H__Q__A__T__R__E__L__L__L__K

AGATGCTGGAAGCCAACGGCATCCAGAGCTACGAGGAACTGGCCGCCGTGATCTTCACCG
2161   ---------+---------+---------+---------+---------+---------+
       TCTACGACCTTCGGTTGCCGTAGGTCTCGATGCTCCTTGACCGGCGGCACTAGAAGTGGC
        _M__L__E__A__N__G__I__Q__S__Y__E__E__L__A__A__V__I__F__T__V
```

```
                                                              SphI
         TGACAGAGGACCTGACCTTCGCCTTCCCCGCCGAAGCCGCCAGACAGATCGGCATGCACC
2221     ---------+---------+---------+---------+---------+---------+
         ACTGTCTCCTGGACTGGAAGCGGAAGGGGCGGCTTCGGCGGTCTGTCTAGCCGTACGTGG
           T  E  D  L  T  F  A  F  P  A  E  A  A  R  Q  I  G  M  H  R

BclI
         GGGTGCCCCTGCTGAGCGCCAGAGAAGTGCCTGTGCCCGGCAGCCTGCCCAGAGTGATCA
2281     ---------+---------+---------+---------+---------+---------+
         CCCACGGGGACGACTCGCGGTCTCTTCACGGACACGGGCCGTCGGACGGGTCTCACTAGT
           V  P  L  L  S  A  R  E  V  P  V  P  G  S  L  P  R  V  I  R

BspMI
         GAGTGCTGGCCCTGTGGAACACCGCCACCCCCCAGGATAGAGTGCGGCACGTGTACCTGC
2341     ---------+---------+---------+---------+---------+---------+
         CTCACGACCGGGACACCTTGTGGCGGTGGGGGGTCCTATCTCACGCCGTGCACATGGACG
           V  L  A  L  W  N  T  A  T  P  Q  D  R  V  R  H  V  Y  L  R

StuI                       XhoI XbaI   ApaI
         GCGAGGCTGTCAGACTGAGGCCTCACCACCACCATCACCACTGACTCGAGTCTAGAGGGC
2401     ---------+---------+---------+---------+---------+---------+
         CGCTCCGACAGTCTGACTCCGGAGTGGTGGTGGTAGTGGTGACTGAGCTCAGATCTCCCG
           E  A  V  R  L  R  P  H  H  H  H  H  *

PmeI
         CCGTTTAAACCCGCTGATC
2461     ---------+---------
         GGCAAATTTGGGCGACTAG
```

FIG. 24

```
            HindIII
  BsaI      NheI   PmeI  AflII                              PstI
     GAGACCCAAGCTGGCTAGCGTTTAAACTTAAGCTTGCCACCATGCCTATGGGCAGCCTGC
  1  ---------+---------+---------+---------+---------+---------+
     CTCTGGGTTCGACCGATCGCAAATTTGAATTCGAACGGTGGTACGGATACCCGTCGGACG
                                            M  P  M  G  S  L  Q BspMI    SphI                             PvuII
     AGCCTCTGGCCACCCTGTACCTGCTGGGCATGCTGGTGGCCTCCGTGCTGGCAGCTGGCA
 61  ---------+---------+---------+---------+---------+---------+
     TCGGAGACCGGTGGGACATGGACGACCCGTACGACCACCGGAGGCACGACCGTCGACCGT
      P  L  A  T  L  Y  L  L  G  M  L  V  A  S  V  L  A  A  G  N ACCTGTGGGTCACAGTGTACTACGGCGTGCCCGTGTGGAAAGAGGCCAAGACCACCCTGT
121  ---------+---------+---------+---------+---------+---------+
     TGGACACCCAGTGTCACATGATGCCGCACGGGCACACCTTTCTCCGGTTCTGGTGGGACA
      L  W  V  T  V  Y  Y  G  V  P  V  W  K  E  A  K  T  T  L  F StuI
     TCTGCGCCAGCGACGCCAAGGCCTACGAGAAAGAGGTGCACAACGTCTGGGCCACCCACG
181  ---------+---------+---------+---------+---------+---------+
     AGACGCGGTCGCTGCGGTTCCGGATGCTCTTTCTCCACGTGTTGCAGACCCGGTGGGTGC
      C  A  S  D  A  K  A  Y  E  K  E  V  H  N  V  W  A  T  H  A PflMI
     CCTGCGTGCCCACCGACCCCAACCCCCAGGAAATGGTCCTGGAAAACGTGACCGAGAACT
241  ---------+---------+---------+---------+---------+---------+
     GGACGCACGGGTGGCTGGGGTTGGGGGTCCTTTACCAGGACCTTTTGCACTGGCTCTTGA
      C  V  P  T  D  P  N  P  Q  E  M  V  L  E  N  V  T  E  N  F
```

```
                                                   BclI
            TCAACATGTGGAAGAACGACATGGTGGAACAGATGCACGAGGACGTGATCAGCCTGTGGG
    301     ---------+---------+---------+---------+---------+---------+
            AGTTGTACACCTTCTTGCTGTACCACCTTGTCTACGTGCTCCTGCACTAGTCGGACACCC
             N  M  W  K  N  D  M  V  E  Q  M  H  E  D  V  I  S  L  W  D

ACCAGAGCCTGAAGCCCTGCGTGAAGCTGACCCCCCTGTGCGTGACCCTGGAATGCAGAC
    361     ---------+---------+---------+---------+---------+---------+
            TGGTCTCGGACTTCGGGACGCACTTCGACTGGGGGGACACGCACTGGGACCTTACGTCTG
             Q  S  L  K  P  C  V  K  L  T  P  L  C  V  T  L  E  C  R  Q

HincII
            AGGTCAACACCACCAACGCCACCAGCAGCGTGAACGTGACCAACGGCGAGGAAATCAAGA
    421     ---------+---------+---------+---------+---------+---------+
            TCCAGTTGTGGTGGTTGCGGTGGTCGTCGCACTTGCACTGGTTGCCGCTCCTTTAGTTCT
             V  N  T  T  N  A  T  S  S  V  N  V  T  N  G  E  E  I  K  N PstI
            ACTGCAGCTTCAAGGCCACCACCGAGATCCGGGACAAGAAACAGAAGGTGTACGCCCTGT
    481     ---------+---------+---------+---------+---------+---------+
            TGACGTCGAAGTTCCGGTGGTGGCTCTAGGCCCTGTTCTTTGTCTTCCACATGCGGGACA
             C  S  F  K  A  T  T  E  I  R  D  K  K  Q  K  V  Y  A  L  F TCTACCGGCTGGACATCGTGCCCCTGGAAGAGGAACGGAAGGGCAACAGCAGCAAGTACC
    541     ---------+---------+---------+---------+---------+---------+
            AGATGGCCGACCTGTAGCACGGGGACCTTCTCCTTGCCTTCCCGTTGTCGTCGTTCATGG
             Y  R  L  D  I  V  P  L  E  E  E  R  K  G  N  S  S  K  Y  R BclI                    StuI
            GGCTGATCAACTGCAACACCAGCGCCATCACCCAGGCCTGCCCCAAAGTGACCTTCGACC
    601     ---------+---------+---------+---------+---------+---------+
            CCGACTAGTTGACGTTGTGGTCGCGGTAGTGGGTCCGGACGGGGTTTCACTGGAAGCTGG
             L  I  N  C  N  T  S  A  I  T  Q  A  C  P  K  V  T  F  D  P
```

```
          CTATCCCCATCCACTACTGCGCCCCTGCCGGCTACGCCATCCTGAAGTGCAACAACAAGA
    661   ---------+---------+---------+---------+---------+---------+
          GATAGGGGTAGGTGATGACGCGGGGACGGCCGATGCGGTAGGACTTCACGTTGTTGTTCT
           _I__P__I__H__Y__C__A__P__A__G__Y__A__I__L__K__C__N__N__K__T

CCTTCAACGGCACCGGCCCCTGCAACAACGTGTCCACCGTGCAGTGCACCCACGGCATCA
    721   ---------+---------+---------+---------+---------+---------+
          GGAAGTTGCCGTGGCCGGGGACGTTGTTGCACAGGTGGCACGTCACGTGGGTGCCGTAGT
           _F__N__G__T__G__P__C__N__N__V__S__T__V__Q__C__T__H__G__I__K

PvuII
          AGCCCGTGGTGTCCACCCAGCTGCTGCTGAATGGCAGCCTGGCCGAGGGCGAGATCATCA
    781   ---------+---------+---------+---------+---------+---------+
          TCGGGCACCACAGGTGGGTCGACGACGACTTACCGTCGGACCGGCTCCCGCTCTAGTAGT
           _P__V__V__S__T__Q__L__L__L__N__G__S__L__A__E__G__E__I__I__I

TCAGAAGCGAGAACCTGACCAACAACGTGAAAACCATCATCGTGCACCTGAACGAGAGCG
    841   ---------+---------+---------+---------+---------+---------+
          AGTCTTCGCTCTTGGACTGGTTGTTGCACTTTTGGTAGTAGCACGTGGACTTGCTCTCGC
           _R__S__E__N__L__T__N__N__V__K__T__I__I__V__H__L__N__E__S__V

TGGAAATCGTGTGCACCCGGCCCAACAACAACACCAGAAAGAGCATCCGGATCGGCCCTG
    901   ---------+---------+---------+---------+---------+---------+
          ACCTTTAGCACACGTGGGCCGGGTTGTTGTTGTGGTCTTTCTCGTAGGCCTAGCCGGGAC
           _E__I__V__C__T__R__P__N__N__N__T__R__K__S__I__R__I__G__P__G

StuI
          GCCAGACCTTTTACGCCACCGGCGACATCATCGGCAACATCCGGCAGGCCTACTGCAACA
    961   ---------+---------+---------+---------+---------+---------+
          CGGTCTGGAAAATGCGGTGGCCGCTGTAGTAGCCGTTGTAGGCCGTCCGGATGACGTTGT
           _Q__T__F__Y__A__T__G__D__I__I__G__N__I__R__Q__A__Y__C__N__I

BamHI       PstI
          TCAAGAAGGACGACTGGATCCGGACCCTGCAGAGAGTGGGCAAGAAGCTGGCCGAGCACT
   1021   ---------+---------+---------+---------+---------+---------+
          AGTTCTTCCTGCTGACCTAGGCCTGGGACGTCTCTCACCCGTTCTTCGACCGGCTCGTGA
           _K__K__D__D__W__I__R__T__L__Q__R__V__G__K__K__L__A__E__H__F
```

```
          TCCCCAGACGGATCATCAACTTCACCAGCCCCGCTGGCGGCGACCTGGAAATCACCACCC
1081      ---------+---------+---------+---------+---------+---------+
          AGGGGTCTGCCTAGTAGTTGAAGTGGTCGGGGCGACCGCCGCTGGACCTTTAGTGGTGGG
           _P__R__R__I__I__N__F__T__S__P__A__G__G__D__L__E__I__T__T__H
```

```
                  PstI
          ACAGCTTCAACTGCAGAGGCGAGTTCTTCTACTGCAATACCAGCAGCCTGTTCAACAGCA
1141      ---------+---------+---------+---------+---------+---------+
          TGTCGAAGTTGACGTCTCCGCTCAAGAAGATGACGTTATGGTCGTCGGACAAGTTGTCGT
           _S__F__N__C__R__G__E__F__F__Y__C__N__T__S__S__L__F__N__S__T
```

```
          CCTACAACCCCAACGACACCAACAGCAACAGCTCCAGCAGCAACTCCAGCCTGGACATCA
1201      ---------+---------+---------+---------+---------+---------+
          GGATGTTGGGGTTGCTGTGGTTGTCGTTGTCGAGGTCGTCGTTGAGGTCGGACCTGTAGT
           _Y__N__P__N__D__T__N__S__N__S__S__S__S__N__S__S__L__D__I__T
```

```
          CCATCCCTTGCCGGATCAAGCAGATCATCAATATGTGGCAGGAAGTGGGCAGGGCTATGT
1261      ---------+---------+---------+---------+---------+---------+
          GGTAGGGAACGGCCTAGTTCGTCTAGTAGTTATACACCGTCCTTCACCCGTCCCGATACA
           _I__P__C__R__I__K__Q__I__I__N__M__W__Q__E__V__G__R__A__M__Y
```

```
          ACGCCCCTCCCATCGAGGGCAACATCACATGCAAGAGCAACATCACCGGCCTGCTCCTGG
1321      ---------+---------+---------+---------+---------+---------+
          TGCGGGGAGGGTAGCTCCCGTTGTAGTGTACGTTCTCGTTGTAGTGGCCGGACGAGGACC
           _A__P__P__I__E__G__N__I__T__C__K__S__N__I__T__G__L__L__L__V
```

```
                                                  BglII
          TCCGCGACGGCGGCGTGGAAAGCAACGAGACAGAGATCTTCAGACCCGGCGGAGGCGACA
1381      ---------+---------+---------+---------+---------+---------+
          AGGCGCTGCCGCCGCACCTTTCGTTGCTCTGTCTCTAGAAGTCTGGGCCGCCTCCGCTGT
           _R__D__G__G__V__E__S__N__E__T__E__I__F__R__P__G__G__G__D__M
```

```
          TGCGGAACAACTGGCGGAGCGAGCTGTACAAGTACAAGGTGGTGGAAATCAAGCCCCTGG
1441      ---------+---------+---------+---------+---------+---------+
          ACGCCTTGTTGACCGCCTCGCTCGACATGTTCATGTTCCACCACCTTTAGTTCGGGGACC
           _R__N__N__W__R__S__E__L__Y__K__Y__K__V__V__E__I__K__P__L__G
```

```
         GAATCGCCCCCACCGCCGCCAAGCGGAGAGTGGTGGAAAGCGAGAAGTCCGCCGTGGGCC
1501     ---------+---------+---------+---------+---------+---------+
         CTTAGCGGGGGTGGCGGCGGTTCGCCTCTCACCACCTTTCGCTCTTCAGGCGGCACCCGG
          I  A  P  T  A  A  K  R  R  V  V  E  S  E  K  S  A  V  G  L

NarI
         KasI                                      NcoI
         TGGGCGCCGTGATCTTCGGCTTTCTGGGAGCCGCCGGAAGCACCATGGGCGCTGCCAGCA
1561     ---------+---------+---------+---------+---------+---------+
         ACCCGCGGCACTAGAAGCCGAAAGACCCTCGGCGGCCTTCGTGGTACCCGCGACGGTCGT
          G  A  V  I  F  G  F  L  G  A  A  G  S  T  M  G  A  A  S  I

PvuII                         BspMI
         TCACCCTGACCGTGCAGGCCAGACAGCTGCTGAGCGGCATCGTGCAGCAGCAGAGCAACC
1621     ---------+---------+---------+---------+---------+---------+
         AGTGGGACTGGCACGTCCGGTCTGTCGACGACTCGCCGTAGCACGTCGTCGTCTCGTTGG
          T  L  T  V  Q  A  R  Q  L  L  S  G  I  V  Q  Q  Q  S  N  L

PvuII
                             PstI                            PvuII
         TGCTGAAGGCCATCGAGGCCCAGCAGCATCTGCTGCAGCTGACCGTGTGGGGCATCAAGC
1681     ---------+---------+---------+---------+---------+---------+
         ACGACTTCCGGTAGCTCCGGGTCGTCGTAGACGACGTCGACTGGCACACCCCGTAGTTCG
          L  K  A  I  E  A  Q  Q  H  L  L  Q  L  T  V  W  G  I  K  Q

PstI    SmaI
         AGCTGCAGACCCGGGTGCTGGCCATCGAGAGATACCTGAAGGACCAGCAGCTCCTGGGAA
1741     ---------+---------+---------+---------+---------+---------+
         TCGACGTCTGGGCCCACGACCGGTAGCTCTCTATGGACTTCCTGGTCGTCGAGGACCCTT
          L  Q  T  R  V  L  A  I  E  R  Y  L  K  D  Q  Q  L  L  G  I

PstI                                          PvuII
         TCTGGGGCTGCAGCGGCAAGCTGATCTGCACCACCGCCGTGCCCTGGAACAGCAGCTGGT
1801     ---------+---------+---------+---------+---------+---------+
         AGACCCCGACGTCGCCGTTCGACTAGACGTGGTGGCGGCACGGGACCTTGTCGTCGACCA
          W  G  C  S  G  K  L  I  C  T  T  A  V  P  W  N  S  S  W  S
```

```
                         BglII
            CCAACAAGAGCCACGACGAGATCTGGGGCAACATGACCTGGATGCAGTGGGACAGAGAGA
      1861  ---------+---------+---------+---------+---------+---------+
            GGTTGTTCTCGGTGCTGCTCTAGACCCCGTTGTACTGGACCTACGTCACCCTGTCTCTCT
             _N__K__S__H__D__E__I__W__G__N__M__T__W__M__Q__W__D__R__E__I

TCAGCAACTACACCAACACCATCTACCGCCTGCTGGAAGATAGCCAGAACCAGCAGGAAC
      1921  ---------+---------+---------+---------+---------+---------+
            AGTCGTTGATGTGGTTGTGGTAGATGGCGGACGACCTTCTATCGGTCTTGGTCGTCCTTG
             _S__N__Y__T__N__T__I__Y__R__L__L__E__D__S__Q__N__Q__Q__E__Q

BspMI           PvuII
            AGAACGAGAAGGACCTGCTGGCCCTGGACAGCTGGGAGAACCTGTGGAACTGGTTCAGCA
      1981  ---------+---------+---------+---------+---------+---------+
            TCTTGCTCTTCCTGGACGACCGGGACCTGTCGACCCTCTTGGACACCTTGACCAAGTCGT
             _N__E__K__D__L__L__A__L__D__S__W__E__N__L__W__N__W__F__S__I

TCACCAAGTGGCTGTGGTACATCAAGGGCAGCGGCATGAAGCAGATCGAGGACAAGATCG
      2041  ---------+---------+---------+---------+---------+---------+
            AGTGGTTCACCGACACCATGTAGTTCCCGTCGCCGTACTTCGTCTAGCTCCTGTTCTAGC
             _T__K__W__L__W__Y__I__K__G__S__G__M__K__Q__I__E__D__K__I__E

AGGAAATCGAGAGCAAGATCAAGAAGATCGAGAACGAGATCGCCCGGATCAAGAAGCTGA
      2101  ---------+---------+---------+---------+---------+---------+
            TCCTTTAGCTCTCGTTCTAGTTCTTCTAGCTCTTGCTCTAGCGGGCCTAGTTCTTCGACT
             _E__I__E__S__K__I__K__K__I__E__N__E__I__A__R__I__K__K__L__I

TCGGCGAGAGCGGCCACCACCACCATCACCACGGCCTGAACGACATCTTCGAGGCCCAGA
      2161  ---------+---------+---------+---------+---------+---------+
            AGCCGCTCTCGCCGGTGGTGGTGGTAGTGGTGCCGGACTTGCTGTAGAAGCTCCGGGTCT
             _G__E__S__G__H__H__H__H__H__G__L__N__D__I__F__E__A__Q__K

XhoI  XbaI   ApaI    PmeI
            AAATCGAGTGGCACGAGTGACTCGAGTCTAGAGGGCCCGTTTAAACCCGCTGATC
      2221  ---------+---------+---------+---------+---------+-----
            TTTAGCTCACCGTGCTCACTGAGCTCAGATCTCCCGGGCAAATTTGGGCGACTAG
             _I__E__W__H__E__*_
```

FIG. 25

```
                              SfiI         PacI     SfiI
         ACTGGAAAGCGGGCAGTGAAAGGAAGGCCCATGAGGCCAGTTAATTAAGGCCATCGAGGC
    1    ---------+---------+---------+---------+---------+---------+
         TGACCTTTCGCCCGTCACTTTCCTTCCGGGTACTCCGGTCAATTAATTCCGGTAGCTCCG
                                                             A  I  E  A

PvuII                  PvuII
                 PstI                    PstI       SmaI
         CCAGCAGCATCTGCTGCAGCTGACCGTGTGGGGCATCAAGCAGCTGCAGACCCGGGTGCT
   61    ---------+---------+---------+---------+---------+---------+
         GGTCGTCGTAGACGACGTCGACTGGCACACCCCGTAGTTCGTCGACGTCTGGGCCCACGA
          Q  Q  H  L  L  Q  L  T  V  W  G  I  K  Q  L  Q  T  R  V  L

PstI
         GGCCATCGAGAGATACCTGAAGGACCAGCAGCTCCTGGGAATCTGGGGCTGCAGCGGCAA
  121    ---------+---------+---------+---------+---------+---------+
         CCGGTAGCTCTCTATGGACTTCCTGGTCGTCGAGGACCCTTAGACCCCGACGTCGCCGTT
          A  I  E  R  Y  L  K  D  Q  Q  L  L  G  I  W  G  C  S  G  K

PvuII                 BglII
         GCTGATCTGCACCACCGCCGTGCCCTGGAACAGCAGCTGGTCCAACAAGAGCCACGACGA
  181    ---------+---------+---------+---------+---------+---------+
         CGACTAGACGTGGTGGCGGCACGGGACCTTGTCGTCGACCAGGTTGTTCTCGGTGCTGCT
          L  I  C  T  T  A  V  P  W  N  S  S  W  S  N  K  S  H  D  E

GATCTGGGGCAACATGACCTGGATGCAGTGGGACAGAGAGATCAGCAACTACACCAACAC
  241    ---------+---------+---------+---------+---------+---------+
         CTAGACCCCGTTGTACTGGACCTACGTCACCCTGTCTCTCTAGTCGTTGATGTGGTTGTG
          I  W  G  N  M  T  W  M  Q  W  D  R  E  I  S  N  Y  T  N  T
```

```
                                                          BspMI
          CATCTACCGCCTGCTGGAAGATAGCCAGAACCAGCAGGAACAGAACGAGAAGGACCTGCT
301       ---------+---------+---------+---------+---------+---------+
          GTAGATGGCGGACGACCTTCTATCGGTCTTGGTCGTCCTTGTCTTGCTCTTCCTGGACGA
           I   Y   R   L   L   E   D   S   Q   N   Q   Q   E   Q   N   E   K   D   L   L

PvuII
          GGCCCTGGACAGCTGGGAGAACCTGTGGAACTGGTTCAGCATCACCAAGTGGCTGTGGTA
361       ---------+---------+---------+---------+---------+---------+
          CCGGGACCTGTCGACCCTCTTGGACACCTTGACCAAGTCGTAGTGGTTCACCGACACCAT
           A   L   D   S   W   E   N   L   W   N   W   F   S   I   T   K   W   L   W   Y

CATCAAGGGCAGCGGCGGCATGAAGCAGATCGAGGACAAGATCGAGGAAATCGAGAGCAA
421       ---------+---------+---------+---------+---------+---------+
          GTAGTTCCCGTCGCCGCCGTACTTCGTCTAGCTCCTGTTCTAGCTCCTTTAGCTCTCGTT
           I   K   G   S   G   G   M   K   Q   I   E   D   K   I   E   E   I   E   S   K

GATCAAGAAGATCGAGAACGAGATCGCCCGGATCAAGAAGCTGATCGGCGAGAGCGGCCA
481       ---------+---------+---------+---------+---------+---------+
          CTAGTTCTTCTAGCTCTTGCTCTAGCGGGCCTAGTTCTTCGACTAGCCGCTCTCGCCGGT
           I   K   K   I   E   N   E   I   A   R   I   K   K   L   I   G   E   S   G   H

StuI
                             BssHII  SfiI
                       XhoI AscI    AvrII
          CCACCACCATCACCACTGACTCGAGGCGCGCCTAGGCCTTGACGGCCTTCCTTCAATTCG
541       ---------+---------+---------+---------+---------+---------+
          GGTGGTGGTAGTGGTGACTGAGCTCCGCGCGGATCCGGAACTGCCGGAAGGAAGTTAAGC
           H   H   H   H   H   *

CCCTATAGTGAG
601       ---------+--
          GGGATATCACTC
```

FIG. 26

```
                                    HindIII
     BsaI         NheI   PmeI    AflII              NcoI BamHI PstI
     GAGACCCAAGCTGGCTAGCGTTTAAACTTAAGCTTGCCACCATGCCCATGGGATCCCTGC
  1  ---------+---------+---------+---------+---------+---------+
     CTCTGGGTTCGACCGATCGCAAATTTGAATTCGAACGGTGGTACGGGTACCCTAGGGACG
                                              M  P  M  G  S  L  Q SphI
     AGCCTCTGGCCACACTGTATCTGCTGGGCATGCTGGTGGCCTCTGTGCTGGCCGCTGGCA
 61  ---------+---------+---------+---------+---------+---------+
     TCGGAGACCGGTGTGACATAGACGACCCGTACGACCACCGGAGACACGACCGGCGACCGT
      P  L  A  T  L  Y  L  L  G  M  L  V  A  S  V  L  A  A  G  N BstEII
     ATCTGTGGGTCACCGTGTACTACGGCGTGCCCGTGTGGAAAGAGGCCAAGACCACCCTGT
121  ---------+---------+---------+---------+---------+---------+
     TAGACACCCAGTGGCACATGATGCCGCACGGGCACACCTTTCTCCGGTTCTGGTGGGACA
      L  W  V  T  V  Y  Y  G  V  P  V  W  K  E  A  K  T  T  L  F StuI
     TCTGCGCCTCTGACGCCAAGGCCTACGAGACAGAGGTGCACAACGTGTGGGCCACCCACG
181  ---------+---------+---------+---------+---------+---------+
     AGACGCGGAGACTGCGGTTCCGGATGCTCTGTCTCCACGTGTTGCACACCCGGTGGGTGC
      C  A  S  D  A  K  A  Y  E  T  E  V  H  N  V  W  A  T  H  A CCTGTGTGCCCACCGATCCCAACCCTCAGGAACTGGTCCTGGAAAACGTGACCGAGAACT
241  ---------+---------+---------+---------+---------+---------+
     GGACACACGGGTGGCTAGGGTTGGGAGTCCTTGACCAGGACCTTTTGCACTGGCTCTTGA
      C  V  P  T  D  P  N  P  Q  E  L  V  L  E  N  V  T  E  N  F
```

```
                                                     BclI
         TCAACATGTGGCGGAACGACATGGTGGACCAGATGCACGAGGACGTGATCAGCCTGTGGG
301      ---------+---------+---------+---------+---------+---------+
         AGTTGTACACCGCCTTGCTGTACCACCTGGTCTACGTGCTCCTGCACTAGTCGGACACCC
          _N__M__W__R__N__D__M__V__D__Q__M__H__E__D__V__I__S__L__W__D

BspMI
         ACCAGAGCCTGAAGCCCTGCGTGAAGCTGACCCCTCTGTGCGTGACCCTGGAATGCCGGC
361      ---------+---------+---------+---------+---------+---------+
         TGGTCTCGGACTTCGGGACGCACTTCGACTGGGGAGACACGCACTGGGACCTTACGGCCG
          _Q__S__L__K__P__C__V__K__L__T__P__L__C__V__T__L__E__C__R__Q

HincII
         AGGTCAACACCACCAACGCCACCAGCAGCGTGAACGTGACCAACGGCGAGGAAATCAAGA
421      ---------+---------+---------+---------+---------+---------+
         TCCAGTTGTGGTGGTTGCGGTGGTCGTCGCACTTGCACTGGTTGCCGCTCCTTTAGTTCT
          _V__N__T__T__N__A__T__S__S__V__N__V__T__N__G__E__E__I__K__N PstI
         ACTGCAGCTTCAATGCCACCACCGAGATCCGGGACAAGAAACAGAAGGTGTACGCCCTGT
481      ---------+---------+---------+---------+---------+---------+
         TGACGTCGAAGTTACGGTGGTGGCTCTAGGCCCTGTTCTTTGTCTTCCACATGCGGGACA
          _C__S__F__N__A__T__T__E__I__R__D__K__K__Q__K__V__Y__A__L__F TCTACCGGCTGGACATCGTGCCCCTGGAAGAGGAACGGAAGGGCAACAGCAGCAAGTACC
541      ---------+---------+---------+---------+---------+---------+
         AGATGGCCGACCTGTAGCACGGGGACCTTCTCCTTGCCTTCCCGTTGTCGTCGTTCATGG
          _Y__R__L__D__I__V__P__L__E__E__E__R__K__G__N__S__S__K__Y__R BclI                            StuI
         GGCTGATCAACTGCAACACCAGCGCCATCACCCAGGCCTGCCCCAAAGTGAACTTCGACC
601      ---------+---------+---------+---------+---------+---------+
         CCGACTAGTTGACGTTGTGGTCGCGGTAGTGGGTCCGGACGGGGTTTCACTTGAAGCTGG
          _L__I__N__C__N__T__S__A__I__T__Q__A__C__P__K__V__N__F__D__P
```

```
            CCATCCCCATCCACTACTGCACCCCTGCCGGCTACGCCATCCTGAAGTGCAACAACAAGA
    661     ---------+---------+---------+---------+---------+---------+
            GGTAGGGGTAGGTGATGACGTGGGGACGGCCGATGCGGTAGGACTTCACGTTGTTGTTCT
             _I__P__I__H__Y__C__T__P__A__G__Y__A__I__L__K__C__N__N__K__T

PstI
            CCTTCAACGGCACCGGCCCCTGCAGCAATGTGTCCACCGTGCAGTGCACCCACGGCATCA
    721     ---------+---------+---------+---------+---------+---------+
            GGAAGTTGCCGTGGCCGGGGACGTCGTTACACAGGTGGCACGTCACGTGGGTGCCGTAGT
             _F__N__G__T__G__P__C__S__N__V__S__T__V__Q__C__T__H__G__I__K

PvuII
            AGCCTGTGGTGTCCACCCAGCTGCTGCTGAATGGCAGCCTGGCCGAGGAAGGCATCATCA
    781     ---------+---------+---------+---------+---------+---------+
            TCGGACACCACAGGTGGGTCGACGACGACTTACCGTCGGACCGGCTCCTTCCGTAGTAGT
             _P__V__V__S__T__Q__L__L__L__N__G__S__L__A__E__E__G__I__I__I

TCAGAAGCGAGAACCTGACCGACAACGTCAAGACCATCATTGTGCACCTGGAAGAACCCG
    841     ---------+---------+---------+---------+---------+---------+
            AGTCTTCGCTCTTGGACTGGCTGTTGCAGTTCTGGTAGTAACACGTGGACCTTCTTGGGC
             _R__S__E__N__L__T__D__N__V__K__T__I__I__V__H__L__E__E__P__V

TGGAAATCGTGTGCACCCGGCCCAACAACAACACCAGAAAGAGCATCCGGATCGGCCCTG
    901     ---------+---------+---------+---------+---------+---------+
            ACCTTTAGCACACGTGGGCCGGGTTGTTGTTGTGGTCTTTCTCGTAGGCCTAGCCGGGAC
             _E__I__V__C__T__R__P__N__N__N__T__R__K__S__I__R__I__G__P__G

StuI
            GCCAGACCTTTTACGCCACCGGCGACATCATCGGCAACATCAGACAGGCCTACTGCAACA
    961     ---------+---------+---------+---------+---------+---------+
            CGGTCTGGAAAATGCGGTGGCCGCTGTAGTAGCCGTTGTAGTCTGTCCGGATGACGTTGT
             _Q__T__F__Y__A__T__G__D__I__I__G__N__I__R__Q__A__Y__C__N__I
```

```
                           PstI
         TCTCCGAGGCCAAGTGGAACGAGACACTGCAGAATGTGACCAAGAAGCTGAAAGAGCACT
1021     ---------+---------+---------+---------+---------+---------+
         AGAGGCTCCGGTTCACCTTGCTCTGTGACGTCTTACACTGGTTCTTCGACTTTCTCGTGA
          S  E  A  K  W  N  E  T  L  Q  N  V  T  K  K  L  K  E  H  F

TCCCCAACAAGACAATCATCTTCAACAGCAGCTCTGGCGGCGACCTGGAAATCACCACCC
1081     ---------+---------+---------+---------+---------+---------+
         AGGGGTTGTTCTGTTAGTAGAAGTTGTCGTCGAGACCGCCGCTGGACCTTTAGTGGTGGG
          P  N  K  T  I  I  F  N  S  S  S  G  G  D  L  E  I  T  T  H

PstI
         ACAGCTTCAACTGCAGAGGCGAGTTCTTCTACTGCAATACCAGCAAGCTGTTCAACGGCA
1141     ---------+---------+---------+---------+---------+---------+
         TGTCGAAGTTGACGTCTCCGCTCAAGAAGATGACGTTATGGTCGTTCGACAAGTTGCCGT
          S  F  N  C  R  G  E  F  F  Y  C  N  T  S  K  L  F  N  G  I

TCTACAACGGCACCCAGAGCAACAGCTCCAACAGCAACAGCACCATCATCATCCCTTGCA
1201     ---------+---------+---------+---------+---------+---------+
         AGATGTTGCCGTGGGTCTCGTTGTCGAGGTTGTCGTTGTCGTGGTAGTAGTAGGGAACGT
          Y  N  G  T  Q  S  N  S  S  N  S  N  S  T  I  I  I  P  C  K

AGATCAAGCAGATCGTGAACATGTGGCAGAAAGTGGGCAGAGCTATGTACGCCCCTCCTA
1261     ---------+---------+---------+---------+---------+---------+
         TCTAGTTCGTCTAGCACTTGTACACCGTCTTTCACCCGTCTCGATACATGCGGGGAGGAT
          I  K  Q  I  V  N  M  W  Q  K  V  G  R  A  M  Y  A  P  P  I

BspMI
         TCGCCGGCAACATTACCTGCACCAGCAACATCACCGGCCTGCTGCTCGTGCGAGATGGCG
1321     ---------+---------+---------+---------+---------+---------+
         AGCGGCCGTTGTAATGGACGTGGTCGTTGTAGTGGCCGGACGACGAGCACGCTCTACCGC
          A  G  N  I  T  C  T  S  N  I  T  G  L  L  L  V  R  D  G  G
```

```
                              BglII
          GCCCTGACAATGTGACCGAGATCTTTAGACCCGGCGGAGGCGACATGCGGGACAATTGGA
     1381 ---------+---------+---------+---------+---------+---------+
          CGGGACTGTTACACTGGCTCTAGAAATCTGGGCCGCCTCCGCTGTACGCCCTGTTAACCT
            P  D  N  V  T  E  I  F  R  P  G  G  D  M  R  D  N  W  R
```

```
                                                                    NarI
                                                                    KasI
          GAAGCGAGCTGTACAAGTACAAGGTGGTGGAAATCAAGCCCCTGGGAATCGCCCCTACCG
     1441 ---------+---------+---------+---------+---------+---------+
          CTTCGCTCGACATGTTCATGTTCCACCACCTTTAGTTCGGGGACCCTTAGCGGGGATGGC
            S  E  L  Y  K  Y  K  V  V  E  I  K  P  L  G  I  A  P  T  G
```

```
                            NarI
                            KasI                       XhoI    XbaI
          GCGCCAAAAGAAGAGTGGTCGAAGGCGCCCACCACCACCATCACCACTGACTCGAGTCTA
     1501 ---------+---------+---------+---------+---------+---------+
          CGCGGTTTTCTTCTCACCAGCTTCCGCGGGTGGTGGTGGTAGTGGTGACTGAGCTCAGAT
            A  K  R  R  V  V  E  G  A  H  H  H  H  H  H  *
```

```
            ApaI   PmeI
          GAGGGCCCGTTTAAACCCGCTGATC
     1561 ---------+---------+-----
          CTCCCGGGCAAATTTGGGCGACTAG
```

FIG. 27

```
                                      HindIII
    BsaI          NheI   PmeI    AflII              NcoI BamHI PstI
         GAGACCCAAGCTGGCTAGCGTTTAAACTTAAGCTTGCCACCATGCCCATGGGATCCCTGC
   1   ---------+---------+---------+---------+---------+---------+
         CTCTGGGTTCGACCGATCGCAAATTTGAATTCGAACGGTGGTACGGGTACCCTAGGGACG
                                                    M  P  M  G  S  L  Q SphI
         AGCCTCTGGCCACACTGTATCTGCTGGGCATGCTGGTGGCCTCTGTGCTGGCCGCTGGCA
  61   ---------+---------+---------+---------+---------+---------+
         TCGGAGACCGGTGTGACATAGACGACCCGTACGACCACCGGAGACACGACCGGCGACCGT
          P  L  A  T  L  Y  L  L  G  M  L  V  A  S  V  L  A  A  G  N BstEII
         ATCTGTGGGTCACCGTGTACTACGGCGTGCCCGTGTGGAAAGAGGCCAAGACCACCCTGT
 121   ---------+---------+---------+---------+---------+---------+
         TAGACACCCAGTGGCACATGATGCCGCACGGGCACACCTTTCTCCGGTTCTGGTGGGACA
           L  W  V  T  V  Y  Y  G  V  P  V  W  K  E  A  K  T  T  L  F StuI
         TCTGCGCCTCTGACGCCAAGGCCTACGAGAAAGAGGTGCACAACGTCTGGGCCACCCACG
 181   ---------+---------+---------+---------+---------+---------+
         AGACGCGGAGACTGCGGTTCCGGATGCTCTTTCTCCACGTGTTGCAGACCCGGTGGGTGC
           C  A  S  D  A  K  A  Y  E  K  E  V  H  N  V  W  A  T  H  A PflMI
         CCTGTGTGCCCACCGATCCCAACCCCCAGGAAATGGTCCTGGAAAACGTGACCGAGAACT
 241   ---------+---------+---------+---------+---------+---------+
         GGACACACGGGTGGCTAGGGTTGGGGGTCCTTTACCAGGACCTTTTGCACTGGCTCTTGA
           C  V  P  T  D  P  N  P  Q  E  M  V  L  E  N  V  T  E  N  F
```

```
                                                   BclI
         TCAACATGTGGAAGAACGACATGGTCGAGCAGATGCACGAGGACGTGATCAGCCTGTGGG
301      ---------+---------+---------+---------+---------+---------+
         AGTTGTACACCTTCTTGCTGTACCAGCTCGTCTACGTGCTCCTGCACTAGTCGGACACCC
          _N__M__W__K__N__D__M__V__E__Q__M__H__E__D__V__I__S__L__W__D

ACCAGAGCCTGAAGCCCTGCGTGAAGCTGACCCCTCTGTGCGTGACCCTGGAATGCAGAA
361      ---------+---------+---------+---------+---------+---------+
         TGGTCTCGGACTTCGGGACGCACTTCGACTGGGGAGACACGCACTGGGACCTTACGTCTT
          _Q__S__L__K__P__C__V__K__L__T__P__L__C__V__T__L__E__C__R__N

HincII                                        PstI
         ACGCCACCAGCAAGATGGTCAACGACACCCGGAACGTGGAAGAGATGAAGAACTGCAGCT
421      ---------+---------+---------+---------+---------+---------+
         TGCGGTGGTCGTTCTACCAGTTGCTGTGGGCCTTGCACCTTCTCTACTTCTTGACGTCGA
          _A__T__S__K__M__V__N__D__T__R__N__V__E__E__M__K__N__C__S__F TCAACACCACCACCGAGCTGCGGGACCGGAAGCAGACAGTGTACGCCAGCTTCTACAAGC
481      ---------+---------+---------+---------+---------+---------+
         AGTTGTGGTGGTGGCTCGACGCCCTGGCCTTCGTCTGTCACATGCGGTCGAAGATGTTCG
          _N__T__T__T__E__L__R__D__R__K__Q__T__V__Y__A__S__F__Y__K__L BclI
         TGGACATCGTGCCCCTGAACGAGAACAAGAGCACCAGCAGCGAGAACTACCGGCTGATCA
541      ---------+---------+---------+---------+---------+---------+
         ACCTGTAGCACGGGGACTTGCTCTTGTTCTCGTGGTCGTCGCTCTTGATGGCCGACTAGT
          _D__I__V__P__L__N__E__N__K__S__T__S__S__E__N__Y__R__L__I__N StuI
         ACTGCAACACCAGCGCCATCACCCAGGCCTGCCCCAAAGTGACCTTCGACCCCATCCCCA
601      ---------+---------+---------+---------+---------+---------+
         TGACGTTGTGGTCGCGGTAGTGGGTCCGGACGGGGTTTCACTGGAAGCTGGGGTAGGGGT
          _C__N__T__S__A__I__T__Q__A__C__P__K__V__T__F__D__P__I__P__I
```

```
          TCCACTACTGTGCCCCTGCCGGCTACGCCATCCTGAAGTGCAACAACAAGACCTTCAACG
    661   ---------+---------+---------+---------+---------+---------+
          AGGTGATGACACGGGGACGGCCGATGCGGTAGGACTTCACGTTGTTGTTCTGGAAGTTGC
           H  Y  C  A  P  A  G  Y  A  I  L  K  C  N  N  K  T  F  N  G

GCACCGGCCCCTGCAACAACGTGTCCACCGTGCAGTGCACCCACGGCATCAAGCCTGTGG
    721   ---------+---------+---------+---------+---------+---------+
          CGTGGCCGGGGACGTTGTTGCACAGGTGGCACGTCACGTGGGTGCCGTAGTTCGGACACC
           T  G  P  C  N  N  V  S  T  V  Q  C  T  H  G  I  K  P  V  V

PvuII
          TGTCCACCCAGCTGCTGCTGAATGGCTCTCTGGCCGAGGGCGAGATCATCATCAGAAGCG
    781   ---------+---------+---------+---------+---------+---------+
          ACAGGTGGGTCGACGACGACTTACCGAGAGACCGGCTCCCGCTCTAGTAGTAGTCTTCGC
           S  T  Q  L  L  L  N  G  S  L  A  E  G  E  I  I  I  R  S  E

AGAACCTGACCAACAACGTCAAGACCATCATCGTCCACCTGAATGAGAGCGTGGAAATCG
    841   ---------+---------+---------+---------+---------+---------+
          TCTTGGACTGGTTGTTGCAGTTCTGGTAGTAGCAGGTGGACTTACTCTCGCACCTTTAGC
           N  L  T  N  N  V  K  T  I  I  V  H  L  N  E  S  V  E  I  V

TGTGCACCCGGCCCAACAACAACACCAGAAAGAGCGTGCGGATCGGCCCTGGCCAGACCT
    901   ---------+---------+---------+---------+---------+---------+
          ACACGTGGGCCGGGTTGTTGTTGTGGTCTTTCTCGCACGCCTAGCCGGGACCGGTCTGGA
           C  T  R  P  N  N  N  T  R  K  S  V  R  I  G  P  G  Q  T  F

TTTATGCCACCGGGGAGATCATCGGCGACATCAGACAGGCCCACTGCAACATCAAGAAGG
    961   ---------+---------+---------+---------+---------+---------+
          AAATACGGTGGCCCCTCTAGTAGCCGCTGTAGTCTGTCCGGGTGACGTTGTAGTTCTTCC
           Y  A  T  G  E  I  I  G  D  I  R  Q  A  H  C  N  I  K  K  D

BamHI       PstI
          ACGACTGGATCCGGACCCTGCAGAGAGTGGGCAAGAAGCTGGCCGAGCACTTCCCCAGAC
   1021   ---------+---------+---------+---------+---------+---------+
          TGCTGACCTAGGCCTGGGACGTCTCTCACCCGTTCTTCGACCGGCTCGTGAAGGGGTCTG
           D  W  I  R  T  L  Q  R  V  G  K  K  L  A  E  H  F  P  R  R
```

```
          GGATCATCAACTTCACCAGCCCCGCTGGCGGCGACCTGGAAATCACCACCCACAGCTTCA
1081    ---------+---------+---------+---------+---------+---------+
          CCTAGTAGTTGAAGTGGTCGGGGCGACCGCCGCTGGACCTTTAGTGGTGGGTGTCGAAGT
           I  I  N  F  T  S  P  A  G  G  D  L  E  I  T  T  H  S  F  N

PstI
          ACTGCAGAGGCGAGTTCTTCTACTGCAATACCAGCAGCCTGTTCAACAGCACCTACAACC
1141    ---------+---------+---------+---------+---------+---------+
          TGACGTCTCCGCTCAAGAAGATGACGTTATGGTCGTCGGACAAGTTGTCGTGGATGTTGG
           C  R  G  E  F  F  Y  C  N  T  S  S  L  F  N  S  T  Y  N  P

CCAACGACACCAACAGCAACAGCAGCAGCTCCAACAGCAGCCTGGACATCACCATCCCTT
1201    ---------+---------+---------+---------+---------+---------+
          GGTTGCTGTGGTTGTCGTTGTCGTCGTCGAGGTTGTCGTCGGACCTGTAGTGGTAGGGAA
           N  D  T  N  S  N  S  S  S  S  N  S  S  L  D  I  T  I  P  C

GCCGGATCAAGCAGATCATCAATATGTGGCAGGAAGTGGGCAGGGCTATGTACGCCCCTC
1261    ---------+---------+---------+---------+---------+---------+
          CGGCCTAGTTCGTCTAGTAGTTATACACCGTCCTTCACCCGTCCCGATACATGCGGGGAG
           R  I  K  Q  I  I  N  M  W  Q  E  V  G  R  A  M  Y  A  P  P

CCATCGAGGGCAACATCACATGCAAGAGCAACATCACCGGCCTGCTGCTCGTGCGAGATG
1321    ---------+---------+---------+---------+---------+---------+
          GGTAGCTCCCGTTGTAGTGTACGTTCTCGTTGTAGTGGCCGGACGACGAGCACGCTCTAC
           I  E  G  N  I  T  C  K  S  N  I  T  G  L  L  L  V  R  D  G

BglII
          GCGGCGTGGAAAGCAACGAGACAGAGATCTTCAGACCCGGCGGAGGCGACATGCGGAACA
1381    ---------+---------+---------+---------+---------+---------+
          CGCCGCACCTTTCGTTGCTCTGTCTCTAGAAGTCTGGGCCGCCTCCGCTGTACGCCTTGT
           G  V  E  S  N  E  T  E  I  F  R  P  G  G  G  D  M  R  N  N

ATTGGCGGAGCGAGCTGTACAAGTACAAGGTGGTGGAAATCAAGCCCCTGGGAATCGCCC
1441    ---------+---------+---------+---------+---------+---------+
          TAACCGCCTCGCTCGACATGTTCATGTTCCACCACCTTTAGTTCGGGGACCCTTAGCGGG
           W  R  S  E  L  Y  K  Y  K  V  V  E  I  K  P  L  G  I  A  P
```

```
                              NarI
                              KasI                              XhoI
        CTACCGCCGCCAAAAGAAGAGTGGTCGAAGGCGCCCACCACCACCATCACCACTGACTCG
1501    ---------+---------+---------+---------+---------+---------+
        GATGGCGGCGGTTTTCTTCTCACCAGCTTCCGCGGGTGGTGGTGGTAGTGGTGACTGAGC
         T  A  A  K  R  R  V  V  E  G  A  H  H  H  H  H  H  *

XbaI  ApaI  PmeI
        AGTCTAGAGGGCCCGTTTAAACCCGCTGATC
1561    ---------+---------+---------+-
        TCAGATCTCCCGGGCAAATTTGGGCGACTAG
```

FIG. 28

```
     BssHII
 AscI        EcoRI                             PstI                    BspMI
       GGCGCGCCGAATTCGCCACCATGCCTATGGGCAGCCTGCAGCCTCTGGCCACACTGTACC
  1    ---------+---------+---------+---------+---------+---------+
       CCGCGCGGCTTAAGCGGTGGTACGGATACCCGTCGGACGTCGGAGACCGGTGTGACATGG
                             M   P   M   G   S   L   Q   P   L   A   T   L   Y   L
                             1       3       5       7       9      11      13

SphI
       TGCTGGGCATGCTGGTGGCCTCTGTGCTGGCCGCCGAGAACCTGTGGGTGACAGTGTACT
 61    ---------+---------+---------+---------+---------+---------+
       ACGACCCGTACGACCACCGGAGACACGACCGGCGGCTCTTGGACACCCACTGTCACATGA
          L   G   M   L   V   A   S   V   L   A   A   E   N   L   W   V   T   V   Y   Y
         15      17      19      21      23      25      27      29      31      33

StuI
       ACGGCGTGCCCGTGTGGAAGGACGCCGAGACAACCCTGTTCTGCGCCAGCGACGCCAAGG
121    ---------+---------+---------+---------+---------+---------+
       TGCCGCACGGGCACACCTTCCTGCGGCTCTGTTGGGACAAGACGCGGTCGCTGCGGTTCC
          G   V   P   V   W   K   D   A   E   T   T   L   F   C   A   S   D   A   K   A
         35      37      39      41      43      45      47      49      51      53

CCTACGAGACAGAGAAGCACAACGTGTGGGCCACCCACGCCTGCGTGCCAACCGACCCTA
181    ---------+---------+---------+---------+---------+---------+
       GGATGCTCTGTCTCTTCGTGTTGCACACCCGGTGGGTGCGGACGCACGGTTGGCTGGGAT
          Y   E   T   E   K   H   N   V   W   A   T   H   A   C   V   P   T   D   P   N
         55      57      59      61      63      65      67      69      71      73

ACCCCCAGGAAATCCACCTGGAAAACGTGACCGAAGAGTTCAACATGTGGAAGAACAACA
241    ---------+---------+---------+---------+---------+---------+
       TGGGGGTCCTTTAGGTGGACCTTTTGCACTGGCTTCTCAAGTTGTACACCTTCTTGTTGT
          P   Q   E   I   H   L   E   N   V   T   E   E   F   N   M   W   K   N   N   M
         75      77      79      81      83      85      87      89      91      93
```

```
      TGGTGGAACAGATGCACACCGACATCATCAGCCTGTGGGACCAGAGCCTGAAGCCCTGCG
301   ---------+---------+---------+---------+---------+---------+
      ACCACCTTGTCTACGTGTGGCTGTAGTAGTCGGACACCCTGGTCTCGGACTTCGGGACGC
       V   E   Q   M   H   T   D   I   I   S   L   W   D   Q   S   L   K   P   C   V
       95     97      99     101     103     105     107     109     111     113

PstI
      TGAAGCTGACCCCCCTGTGCGTGACCCTGCAGTGCACCAACGTGACCAACAACATCACCG
361   ---------+---------+---------+---------+---------+---------+
      ACTTCGACTGGGGGGACACGCACTGGGACGTCACGTGGTTGCACTGGTTGTTGTAGTGGC
       K   L   T   P   L   C   V   T   L   Q   C   T   N   V   T   N   N   I   T   D
      115     117     119     121     123     125     127     129     131     133

PstI
      ACGACATGCGGGGCGAGCTGAAGAACTGCAGCTTCAACATGACCACCGAGCTGCGGGACA
421   ---------+---------+---------+---------+---------+---------+
      TGCTGTACGCCCCGCTCGACTTCTTGACGTCGAAGTTGTACTGGTGGCTCGACGCCCTGT
       D   M   R   G   E   L   K   N   C   S   F   N   M   T   T   E   L   R   D   K
      135     137     139     141     143     145     147     149     151     153

AGAAACAGAAGGTGTACAGCCTGTTCTACCGGCTGGACGTGGTGCAGATCAACGAGAACC
481   ---------+---------+---------+---------+---------+---------+
      TCTTTGTCTTCCACATGTCGGACAAGATGGCCGACCTGCACCACGTCTAGTTGCTCTTGG
       K   Q   K   V   Y   S   L   F   Y   R   L   D   V   V   Q   I   N   E   N   Q
      155     157     159     161     163     165     167     169     171     173

BclI
      AGGGCAACAGAAGCAACAACAGCAACAAAGAGTACCGGCTGATCAACTGCAACACCAGCG
541   ---------+---------+---------+---------+---------+---------+
      TCCCGTTGTCTTCGTTGTTGTCGTTGTTTCTCATGGCCGACTAGTTGACGTTGTGGTCGC
       G   N   R   S   N   N   S   N   K   E   Y   R   L   I   N   C   N   T   S   A
      175     177     179     181     183     185     187     189     191     193

StuI
      CCATCACCCAGGCCTGCCCCAAGGTGTCCTTCGAGCCCATCCCCATCCACTACTGCGCCC
601   ---------+---------+---------+---------+---------+---------+
      GGTAGTGGGTCCGGACGGGGTTCCACAGGAAGCTCGGGTAGGGGTAGGTGATGACGCGGG
       I   T   Q   A   C   P   K   V   S   F   E   P   I   P   I   H   Y   C   A   P
      195     197     199     201     203     205     207     209     211     213

CTGCCGGCTTCGCCATCCTGAAGTGCAAGGACAAGAAGTTCAACGGCACCGGCCCCTGCC
661   ---------+---------+---------+---------+---------+---------+
      GACGGCCGAAGCGGTAGGACTTCACGTTCCTGTTCTTCAAGTTGCCGTGGCCGGGGACGG
       A   G   F   A   I   L   K   C   K   D   K   K   F   N   G   T   G   P   C   P
      215     217     219     221     223     225     227     229     231     233

PvuII
      CCAGCGTGTCCACAGTGCAGTGTACCCACGGCATCAAGCCCGTGGTGTCCACCCAGCTGC
721   ---------+---------+---------+---------+---------+---------+
      GGTCGCACAGGTGTCACGTCACATGGGTGCCGTAGTTCGGGCACCACAGGTGGGTCGACG
       S   V   S   T   V   Q   C   T   H   G   I   K   P   V   V   S   T   Q   L   L
      235     237     239     241     243     245     247     249     251     253

BclI
      TGCTGAACGGCAGCCTGGCCGAAGAGGAAGTGATGATCAGAAGCGAGAACATCACCAACA
781   ---------+---------+---------+---------+---------+---------+
      ACGACTTGCCGTCGGACCGGCTTCTCCTTCACTACTAGTCTTCGCTCTTGTAGTGGTTGT
       L   N   G   S   L   A   E   E   E   V   M   I   R   S   E   N   I   T   N   N
      255     257     259     261     263     265     267     269     271     273
```

```
      ACGCCAAGAACATCCTGGTGCAGTTCAACACCCCCGTGCAGATTAACTGCACCCGGCCCA
 841  ---------+---------+---------+---------+---------+---------+
      TGCGGTTCTTGTAGGACCACGTCAAGTTGTGGGGGCACGTCTAATTGACGTGGGCCGGGT
       A   K   N   I   L   V   Q   F   N   T   P   V   Q   I   N   C   T   R   P   N
       275     277     279     281     283     285     287     289     291     293

StuI
      ACAACAACACCAGAAAGAGCATCCGGATCGGCCCAGGCCAGGCCTTCTACGCCACCGGCG
 901  ---------+---------+---------+---------+---------+---------+
      TGTTGTTGTGGTCTTTCTCGTAGGCCTAGCCGGGTCCGGTCCGGAAGATGCGGTGGCCGC
       N   N   T   R   K   S   I   R   I   G   P   G   Q   A   F   Y   A   T   G   D
       295     297     299     301     303     305     307     309     311     313

ACATCATCGGCGACATCCGGCAGGCCCACTGCACCGTGTCCAAGGCCACCTGGAACGAGA
 961  ---------+---------+---------+---------+---------+---------+
      TGTAGTAGCCGCTGTAGGCCGTCCGGGTGACGTGGCACAGGTTCCGGTGGACCTTGCTCT
       I   I   G   D   I   R   Q   A   H   C   T   V   S   K   A   T   W   N   E   T
       315     317     319     321     323     325     327     329     331     333

PvuII
      CACTGGGCAAGGTGGTGAAACAGCTGCGGAAGCACTTCGGGAACAACACCATCATCCGCT
1021  ---------+---------+---------+---------+---------+---------+
      GTGACCCGTTCCACCACTTTGTCGACGCCTTCGTGAAGCCCTTGTTGTGGTAGTAGGCGA
       L   G   K   V   V   K   Q   L   R   K   H   F   G   N   N   T   I   I   R   F
       335     337     339     341     343     345     347     349     351     353

TCGCCAACAGCTCTGGCGGCGACCTGGAAGTGACCACCCACAGCTTCAACTGTGGCGGCG
1081  ---------+---------+---------+---------+---------+---------+
      AGCGGTTGTCGAGACCGCCGCTGGACCTTCACTGGTGGGTGTCGAAGTTGACACCGCCGC
       A   N   S   S   G   G   D   L   E   V   T   T   H   S   F   N   C   G   G   E
       355     357     359     361     363     365     367     369     371     373

AGTTCTTCTACTGCAATACCTCCGGCCTGTTCAACAGCACCTGGATCAGCAATACCAGCG
1141  ---------+---------+---------+---------+---------+---------+
      TCAAGAAGATGACGTTATGGAGGCCGGACAAGTTGTCGTGGACCTAGTCGTTATGGTCGC
       F   F   Y   C   N   T   S   G   L   F   N   S   T   W   I   S   N   T   S   V
       375     377     379     381     383     385     387     389     391     393

TGCAGGGCAGCAACAGCACCGGCAGCAACGACAGCATCACCCTGCCCTGCCGGATCAAGC
1201  ---------+---------+---------+---------+---------+---------+
      ACGTCCCGTCGTTGTCGTGGCCGTCGTTGCTGTCGTAGTGGGACGGGACGGCCTAGTTCG
       Q   G   S   N   S   T   G   S   N   D   S   I   T   L   P   C   R   I   K   Q
       395     397     399     401     403     405     407     409     411     413

AGATCATCAATATGTGGCAGCGGATTGGCCAGGCTATGTACGCCCCACCCATCCAGGGCG
1261  ---------+---------+---------+---------+---------+---------+
      TCTAGTAGTTATACACCGTCGCCTAACCGGTCCGATACATGCGGGGTGGGTAGGTCCCGC
       I   I   N   M   W   Q   R   I   G   Q   A   M   Y   A   P   P   I   Q   G   V
       415     417     419     421     423     425     427     429     431     433

BclI                                 SmaI
      TGATCAGATGCGTGTCCAATATCACCGGCCTGATCCTGACCCGGGACGGCGGCTCTACCA
1321  ---------+---------+---------+---------+---------+---------+
      ACTAGTCTACGCACAGGTTATAGTGGCCGGACTAGGACTGGGCCCTGCCGCCGAGATGGT
       I   R   C   V   S   N   I   T   G   L   I   L   T   R   D   G   G   S   T   N
       435     437     439     441     443     445     447     449     451     453

ACAGCACCACCGAAACCTTCAGACCCGGCGGAGGCGACATGAGAGACAACTGGCGGAGCG
1381  ---------+---------+---------+---------+---------+---------+
      TGTCGTGGTGGCTTTGGAAGTCTGGGCCGCCTCCGCTGTACTCTCTGTTGACCGCCTCGC
       S   T   T   E   T   F   R   P   G   G   G   D   M   R   D   N   W   R   S   E
       455     457     459     461     463     465     467     469     471     473
```

```
      AGCTGTACAAGTACAAAGTGGTGAAAATCGAGCCCCTGGGCGTGGCCCCCACCAGAGCCA
1441  ------------+---------+---------+---------+---------+---------+
      TCGACATGTTCATGTTTCACCACTTTTAGCTCGGGGACCCGCACCGGGGGTGGTCTCGGT
       L  Y  K  Y  K  V  V  K  I  E  P  L  G  V  A  P  T  R  A  K
       475   477   479   481   483   485   487   489   491   493

NotI
                                                               EagI
      AGAGAAGAGTGGTCGGAAGCGAGAAGTCCGGCCACCACCACCATCACCACTGAGCGGCCG
1501  ---------+---------+---------+---------+---------+---------+
      TCTCTTCTCACCAGCCTTCGCTCTTCAGGCCGGTGGTGGTGGTAGTGGTGACTCGCCGGC
       R  R  V  V  G  S  E  K  S  G  H  H  H  H  H  *
       495   497   499   501   503   505   507   509   511

PacI
      CTTAATTAA
1561  ---------
      GAATTAATT
```

FIG. 29

```
  BssHII
  AscI     EcoRI                             PstI                      BspMI
       GGCGCGCCGAATTCGCCACCATGCCTATGGGCAGCCTGCAGCCTCTGGCCACACTGTACC
  1    ---------+---------+---------+---------+---------+---------+
       CCGCGCGGCTTAAGCGGTGGTACGGATACCCGTCGGACGTCGGAGACCGGTGTGACATGG
                           M  P  M  G  S  L  Q  P  L  A  T  L  Y  L
                           1     3     5     7     9     11    13

SphI
       TGCTGGGCATGCTGGTGGCCTCTGTGCTGGCCGCCGAGAACCTGTGGGTGACAGTGTACT
  61   ---------+---------+---------+---------+---------+---------+
       ACGACCCGTACGACCACCGGAGACACGACCGGCGGCTCTTGGACACCCACTGTCACATGA
        L  G  M  L  V  A  S  V  L  A  A  E  N  L  W  V  T  V  Y  Y
        15    17    19    21    23    25    27    29    31    33

StuI
       ACGGCGTGCCCGTGTGGAAGGACGCCGAGACAACCCTGTTCTGCGCCAGCGACGCCAAGG
  121  ---------+---------+---------+---------+---------+---------+
       TGCCGCACGGGCACACCTTCCTGCGGCTCTGTTGGGACAAGACGCGGTCGCTGCGGTTCC
        G  V  P  V  W  K  D  A  E  T  T  L  F  C  A  S  D  A  K  A
        35    37    39    41    43    45    47    49    51    53

CCTACGAGACAGAGAAGCACAACGTGTGGGCCACCCACGCCTGCGTGCCAACCGACCCTA
  181  ---------+---------+---------+---------+---------+---------+
       GGATGCTCTGTCTCTTCGTGTTGCACACCCGGTGGGTGCGGACGCACGGTTGGCTGGGAT
        Y  E  T  E  K  H  N  V  W  A  T  H  A  C  V  P  T  D  P  N
        55    57    59    61    63    65    67    69    71    73

ACCCCCAGGAAATCCACCTGGAAAACGTGACCGAAGAGTTCAACATGTGGAAGAACAACA
  241  ---------+---------+---------+---------+---------+---------+
       TGGGGGTCCTTTAGGTGGACCTTTTGCACTGGCTTCTCAAGTTGTACACCTTCTTGTTGT
        P  Q  E  I  H  L  E  N  V  T  E  E  F  N  M  W  K  N  N  M
        75    77    79    81    83    85    87    89    91    93
```

```
     TGGTGGAACAGATGCACACCGACATCATCAGCCTGTGGGACCAGAGCCTGAAGCCCTGCG
301  ---------+---------+---------+---------+---------+---------+
     ACCACCTTGTCTACGTGTGGCTGTAGTAGTCGGACACCCTGGTCTCGGACTTCGGGACGC
      V   E   Q   M   H   T   D   I   I   S   L   W   D   Q   S   L   K   P   C   V
       95      97      99     101     103     105     107     109     111     113

PstI
     TGAAGCTGACCCCCCTGTGCGTGACCCTGCAGTGCACCAACGTGACCAACAACATCACCG
361  ---------+---------+---------+---------+---------+---------+
     ACTTCGACTGGGGGGACACGCACTGGGACGTCACGTGGTTGCACTGGTTGTTGTAGTGGC
      K   L   T   P   L   C   V   T   L   Q   C   T   N   V   T   N   N   I   T   D
      115     117     119     121     123     125     127     129     131     133

PstI
     ACGACATGCGGGGCGAGCTGAAGAACTGCAGCTTCAACATGACCACCGAGCTGCGGGACA
421  ---------+---------+---------+---------+---------+---------+
     TGCTGTACGCCCCGCTCGACTTCTTGACGTCGAAGTTGTACTGGTGGCTCGACGCCCTGT
      D   M   R   G   E   L   K   N   C   S   F   N   M   T   T   E   L   R   D   K
      135     137     139     141     143     145     147     149     151     153

AGAAACAGAAGGTGTACAGCCTGTTCTACCGGCTGGACGTGGTGCAGATCAACGAGAACC
481  ---------+---------+---------+---------+---------+---------+
     TCTTTGTCTTCCACATGTCGGACAAGATGGCCGACCTGCACCACGTCTAGTTGCTCTTGG
      K   Q   K   V   Y   S   L   F   Y   R   L   D   V   V   Q   I   N   E   N   Q
      155     157     159     161     163     165     167     169     171     173

BclI
     AGGGCAACAGAAGCAACAACAGCAACAAAGAGTACCGGCTGATCAACTGCAACACCAGCG
541  ---------+---------+---------+---------+---------+---------+
     TCCCGTTGTCTTCGTTGTTGTCGTTGTTTCTCATGGCCGACTAGTTGACGTTGTGGTCGC
      G   N   R   S   N   N   S   N   K   E   Y   R   L   I   N   C   N   T   S   A
      175     177     179     181     183     185     187     189     191     193

StuI
     CCATCACCCAGGCCTGCCCCAAGGTGTCCTTCGAGCCCATCCCCATCCACTACTGCGCCC
601  ---------+---------+---------+---------+---------+---------+
     GGTAGTGGGTCCGGACGGGGTTCCACAGGAAGCTCGGGTAGGGGTAGGTGATGACGCGGG
      I   T   Q   A   C   P   K   V   S   F   E   P   I   P   I   H   Y   C   A   P
      195     197     199     201     203     205     207     209     211     213

CTGCCGGCTTCGCCATCCTGAAGTGCAAGGACAAGAAGTTCAACGGCACCGGCCCCTGCC
661  ---------+---------+---------+---------+---------+---------+
     GACGGCCGAAGCGGTAGGACTTCACGTTCCTGTTCTTCAAGTTGCCGTGGCCGGGGACGG
      A   G   F   A   I   L   K   C   K   D   K   K   F   N   G   T   G   P   C   P
      215     217     219     221     223     225     227     229     231     233

PvuII
     CCAGCGTGTCCACAGTGCAGTGTACCCACGGCATCAAGCCCGTGGTGTCCACCCAGCTGC
721  ---------+---------+---------+---------+---------+---------+
     GGTCGCACAGGTGTCACGTCACATGGGTGCCGTAGTTCGGGCACCACAGGTGGGTCGACG
      S   V   S   T   V   Q   C   T   H   G   I   K   P   V   V   S   T   Q   L   L
      235     237     239     241     243     245     247     249     251     253

BclI
     TGCTGAACGGCAGCCTGGCCGAAGAGGAAGTGATGATCAGAAGCGAGAACATCACCAACA
781  ---------+---------+---------+---------+---------+---------+
     ACGACTTGCCGTCGGACCGGCTTCTCCTTCACTACTAGTCTTCGCTCTTGTAGTGGTTGT
      L   N   G   S   L   A   E   E   E   V   M   I   R   S   E   N   I   T   N   N
      255     257     259     261     263     265     267     269     271     273
```

```
     ACGCCAAGAACATCCTGGTGCAGTTCAACACCCCCGTGCAGATTAACTGCACCCGGCCCA
841  ---------+---------+---------+---------+---------+---------+
     TGCGGTTCTTGTAGGACCACGTCAAGTTGTGGGGGCACGTCTAATTGACGTGGGCCGGGT
      A   K   N   I   L   V   Q   F   N   T   P   V   Q   I   N   C   T   R   P   N
        275     277     279     281     283     285     287     289     291     293

StuI
     ACAACAACACCAGAAAGAGCATCCGGATCGGCCCAGGCCAGGCCTTCTACGCCACCGGCG
901  ---------+---------+---------+---------+---------+---------+
     TGTTGTTGTGGTCTTTCTCGTAGGCCTAGCCGGGTCCGGTCCGGAAGATGCGGTGGCCGC
      N   N   T   R   K   S   I   R   I   G   P   G   Q   A   F   Y   A   T   G   D
        295     297     299     301     303     305     307     309     311     313

ACATCATCGGCGACATCCGGCAGGCCCACTGCACCGTGTCCAAGGCCACCTGGAACGAGA
961  ---------+---------+---------+---------+---------+---------+
     TGTAGTAGCCGCTGTAGGCCGTCCGGGTGACGTGGCACAGGTTCCGGTGGACCTTGCTCT
      I   I   G   D   I   R   Q   A   H   C   T   V   S   K   A   T   W   N   E   T
        315     317     319     321     323     325     327     329     331     333

PvuII
     CACTGGGCAAGGTGGTGAAACAGCTGCGGAAGCACTTCGGGAACAACACCATCATCCGCT
1021 ---------+---------+---------+---------+---------+---------+
     GTGACCCGTTCCACCACTTTGTCGACGCCTTCGTGAAGCCCTTGTTGTGGTAGTAGGCGA
      L   G   K   V   V   K   Q   L   R   K   H   F   G   N   N   T   I   I   R   F
        335     337     339     341     343     345     347     349     351     353

TCGCCAACAGCTCTGGCGGCGACCTGGAAGTGACCACCCACAGCTTCAACTGTGGCGGCG
1081 ---------+---------+---------+---------+---------+---------+
     AGCGGTTGTCGAGACCGCCGCTGGACCTTCACTGGTGGGTGTCGAAGTTGACACCGCCGC
      A   N   S   S   G   G   D   L   E   V   T   T   H   S   F   N   C   G   G   E
        355     357     359     361     363     365     367     369     371     373

AGTTCTTCTACTGCAATACCTCCGGCCTGTTCAACAGCACCTGGATCAGCAATACCAGCG
1141 ---------+---------+---------+---------+---------+---------+
     TCAAGAAGATGACGTTATGGAGGCCGGACAAGTTGTCGTGGACCTAGTCGTTATGGTCGC
      F   F   Y   C   N   T   S   G   L   F   N   S   T   W   I   S   N   T   S   V
        375     377     379     381     383     385     387     389     391     393

TGCAGGGCAGCAACAGCACCGGCAGCAACGACAGCATCACCCTGCCCTGCCGGATCAAGC
1201 ---------+---------+---------+---------+---------+---------+
     ACGTCCCGTCGTTGTCGTGGCCGTCGTTGCTGTCGTAGTGGGACGGGACGGCCTAGTTCG
      Q   G   S   N   S   T   G   S   N   D   S   I   T   L   P   C   R   I   K   Q
        395     397     399     401     403     405     407     409     411     413

AGATCATCAATATGTGGCAGCGGATTGGCCAGGCTATGTACGCCCCACCCATCCAGGGCG
1261 ---------+---------+---------+---------+---------+---------+
     TCTAGTAGTTATACACCGTCGCCTAACCGGTCCGATACATGCGGGGTGGGTAGGTCCCGC
      I   I   N   M   W   Q   R   I   G   Q   A   M   Y   A   P   P   I   Q   G   V
        415     417     419     421     423     425     427     429     431     433

BclI                              SmaI
     TGATCAGATGCGTGTCCAATATCACCGGCCTGATCCTGACCCGGGACGGCGGCTCTACCA
1321 ---------+---------+---------+---------+---------+---------+
     ACTAGTCTACGCACAGGTTATAGTGGCCGGACTAGGACTGGGCCCTGCCGCCGAGATGGT
      I   R   C   V   S   N   I   T   G   L   I   L   T   R   D   G   G   S   T   N
        435     437     439     441     443     445     447     449     451     453

ACAGCACCACCGAAACCTTCAGACCCGGCGGAGGCGACATGAGAGACAACTGGCGGAGCG
1381 ---------+---------+---------+---------+---------+---------+
     TGTCGTGGTGGCTTTGGAAGTCTGGGCCGCCTCCGCTGTACTCTCTGTTGACCGCCTCGC
      S   T   T   E   T   F   R   P   G   G   D   M   R   D   N   W   R   S   E
        455     457     459     461     463     465     467     469     471     473
```

```
       AGCTGTACAAGTACAAAGTGGTGAAAATCGAGCCCCTGGGCGTGGCCCCCACCAGAGCCA
1441   ---------+---------+---------+---------+---------+---------+
       TCGACATGTTCATGTTTCACCACTTTTAGCTCGGGGACCCGCACCGGGGTGGTCTCGGT
        L   Y   K   Y   K   V   V   K   I   E   P   L   G   V   A   P   T   R   A   K
        475     477     479     481     483     485     487     489     491     493

NarI
                                                KasI
       AGAGAAGAGTGGTCGGAAGCGAGAAGTCCGCCGTGGGCATCGGCGCCGTGTTTCTGGGAT
1501   ---------+---------+---------+---------+---------+---------+
       TCTCTTCTCACCAGCCTTCGCTCTTCAGGCGGCACCCGTAGCCGCGGCACAAAGACCCTA
        R   R   V   V   G   S   E   K   S   A   V   G   I   G   A   V   F   L   G   F
        495     497     499     501     503     505     507     509     511     513

TCCTGGGCGCTGCCGGCTCTACAATGGGAGCCGCCAGCATGACACTGACCGTGCAGGCCA
1561   ---------+---------+---------+---------+---------+---------+
       AGGACCCGCGACGGCCGAGATGTTACCCTCGGCGGTCGTACTGTGACTGGCACGTCCGGT
        L   G   A   A   G   S   T   M   G   A   A   S   M   T   L   T   V   Q   A   R
        515     517     519     521     523     525     527     529     531     533

BspMI                                     BspMI
       GAAACCTGCTGTCCGGCATCGTGCAGCAGCAGAGCAACCTGCTGAGAGCCATCGAGGCCC
1621   ---------+---------+---------+---------+---------+---------+
       CTTTGGACGACAGGCCGTAGCACGTCGTCGTCTCGTTGGACGACTCTCGGTAGCTCCGGG
        N   L   L   S   G   I   V   Q   Q   Q   S   N   L   L   R   A   I   E   A   Q
        535     537     539     541     543     545     547     549     551     553

PvuII
                                            PstI
       AGCAGCATCTCCTCAAACTCACAGTCTGGGGCATCAAGCAGCTGCAGGCCAGGGTGCTGG
1681   ---------+---------+---------+---------+---------+---------+
       TCGTCGTAGAGGAGTTTGAGTGTCAGACCCCGTAGTTCGTCGACGTCCGGTCCCACGACC
        Q   H   L   L   K   L   T   V   W   G   I   K   Q   L   Q   A   R   V   L   A
        555     557     559     561     563     565     567     569     571     573

BspMI                              PstI
       CCGTGGAGAGATACCTGCGGGATCAGCAGCTCCTCGGCATCTGGGGCTGCAGCGGCAAGC
1741   ---------+---------+---------+---------+---------+---------+
       GGCACCTCTCTATGGACGCCCTAGTCGTCGAGGAGCCGTAGACCCCGACGTCGCCGTTCG
        V   E   R   Y   L   R   D   Q   Q   L   L   G   I   W   G   C   S   G   K   L
        575     577     579     581     583     585     587     589     591     593

PvuII                         BglII
       TGATCTGCACCACCAACGTGCCCTGGAACTCCAGCTGGTCCAACCGGAACCTGAGCGAGA
1801   ---------+---------+---------+---------+---------+---------+
       ACTAGACGTGGTGGTTGCACGGGACCTTGAGGTCGACCAGGTTGGCCTTGGACTCGCTCT
        I   C   T   T   N   V   P   W   N   S   S   W   S   N   R   N   L   S   E   I
        595     597     599     601     603     605     607     609     611     613

PstI
       TCTGGGACAACATGACCTGGCTGCAGTGGGACAAAGAGATCAGCAACTACACCCAGATCA
1861   ---------+---------+---------+---------+---------+---------+
       AGACCCTGTTGTACTGGACCGACGTCACCCTGTTTCTCTAGTCGTTGATGTGGGTCTAGT
        W   D   N   M   T   W   L   Q   W   D   K   E   I   S   N   Y   T   Q   I   I
        615     617     619     621     623     625     627     629     631     633

TCTACGGCCTGCTGGAAGAGAGCCAGAACCAGCAGGAAAAGAACGAACAGGATCTCCTGG
1921   ---------+---------+---------+---------+---------+---------+
       AGATGCCGGACGACCTTCTCTCGGTCTTGGTCGTCCTTTTCTTGCTTGTCCTAGAGGACC
        Y   G   L   L   E   E   S   Q   N   Q   Q   E   K   N   E   Q   D   L   L   A
        635     637     639     641     643     645     647     649     651     653
```

```
                PflMI
        CTCTCGATAAGTGGGCCAGCCTGTGGAATTGGTTCGACATCAGCAACTGGCTGTGGTACA
1981    ----------+---------+---------+---------+---------+---------+
        GAGAGCTATTCACCCGGTCGGACACCTTAACCAAGCTGTAGTCGTTGACCGACACCATGT
         L  D  K  W  A  S  L  W  N  W  F  D  I  S  N  W  L  W  Y  I
         655   657   659   661   663   665   667   669   671   673

NotI
                                          EagI    PacI
        TCAAGGGCAGCGGCCACCACCACCATCACCACTGAGCGGCCGCTTAATTAA
2041    ----------+---------+---------+---------+---------+-
        AGTTCCCGTCGCCGGTGGTGGTGGTAGTGGTGACTCGCCGGCGAATTAATT
         K  G  S  G  H  H  H  H  H  *
         675   677   679   681   683   685
```

FIG. 30

```
   BssHII
 AscI       EcoRI              NcoI BamHI PstI
     GGCGCGCCGAATTCGCCACCATGCCCATGGGATCCCTGCAGCCTCTGGCCACACTGTATC
  1  ---------+---------+---------+---------+---------+---------+
     CCGCGCGGCTTAAGCGGTGGTACGGGTACCCTAGGGACGTCGGAGACCGGTGTGACATAG
                          M   P   M   G   S   L   Q   P   L   A   T   L   Y   L
                          1       3       5       7       9       11      13

SphI                                              BstEII
     TGCTGGGCATGCTGGTGGCCTCTGTGCTGGCCGCTGGCAATCTGTGGGTCACCGTGTACT
 61  ---------+---------+---------+---------+---------+---------+
     ACGACCCGTACGACCACCGGAGACACGACCGGCGACCGTTAGACACCCAGTGGCACATGA
      L   G   M   L   V   A   S   V   L   A   A   G   N   L   W   V   T   V   Y   Y
      15      17      19      21      23      25      27      29      31      33

StuI
     ACGGCGTGCCCGTGTGGAAGGACGCCGAGACAACCCTGTTCTGCGCCAGCGACGCCAAGG
121  ---------+---------+---------+---------+---------+---------+
     TGCCGCACGGGCACACCTTCCTGCGGCTCTGTTGGGACAAGACGCGGTCGCTGCGGTTCC
      G   V   P   V   W   K   D   A   E   T   T   L   F   C   A   S   D   A   K   A
      35      37      39      41      43      45      47      49      51      53

CCTACGAGACAGAGAAGCACAACGTGTGGGCCACCCACGCCTGCGTGCCAACCGACCCTA
181  ---------+---------+---------+---------+---------+---------+
     GGATGCTCTGTCTCTTCGTGTTGCACACCCGGTGGGTGCGGACGCACGGTTGGCTGGGAT
      Y   E   T   E   K   H   N   V   W   A   T   H   A   C   V   P   T   D   P   N
      55      57      59      61      63      65      67      69      71      73

ACCCCCAGGAAATCCACCTGGAAAACGTGACCGAAGAGTTCAACATGTGGAAGAACAACA
241  ---------+---------+---------+---------+---------+---------+
     TGGGGGTCCTTTAGGTGGACCTTTTGCACTGGCTTCTCAAGTTGTACACCTTCTTGTTGT
      P   Q   E   I   H   L   E   N   V   T   E   E   F   N   M   W   K   N   N   M
      75      77      79      81      83      85      87      89      91      93

TGGTGGAACAGATGCACACCGACATCATCAGCCTGTGGGACCAGAGCCTGAAGCCCTGCG
301  ---------+---------+---------+---------+---------+---------+
     ACCACCTTGTCTACGTGTGGCTGTAGTAGTCGGACACCCTGGTCTCGGACTTCGGGACGC
      V   E   Q   M   H   T   D   I   I   S   L   W   D   Q   S   L   K   P   C   V
      95      97      99      101     103     105     107     109     111     113
```

```
                                       PstI
            TGAAGCTGACCCCCCTGTGCGTGACCCTGCAGTGCACCAACGTGACCAACAACATCACCG
     361    ---------+---------+---------+---------+---------+---------+
            ACTTCGACTGGGGGGACACGCACTGGGACGTCACGTGGTTGCACTGGTTGTTGTAGTGGC
             K   L   T   P   L   C   V   T   L   Q   C   T   N   V   T   N   N   I   T   D
             115     117     119     121     123     125     127     129     131     133

PstI
            ACGACATGCGGGGCGAGCTGAAGAACTGCAGCTTCAACATGACCACCGAGCTGCGGGACA
     421    ---------+---------+---------+---------+---------+---------+
            TGCTGTACGCCCCGCTCGACTTCTTGACGTCGAAGTTGTACTGGTGGCTCGACGCCCTGT
             D   M   R   G   E   L   K   N   C   S   F   N   M   T   T   E   L   R   D   K
             135     137     139     141     143     145     147     149     151     153

AGAAACAGAAGGTGTACAGCCTGTTCTACCGGCTGGACGTGGTGCAGATCAACGAGAACC
     481    ---------+---------+---------+---------+---------+---------+
            TCTTTGTCTTCCACATGTCGGACAAGATGGCCGACCTGCACCACGTCTAGTTGCTCTTGG
             K   Q   K   V   Y   S   L   F   Y   R   L   D   V   V   Q   I   N   E   N   Q
             155     157     159     161     163     165     167     169     171     173

BclI
            AGGGCAACAGAAGCAACAACAGCAACAAAGAGTACCGGCTGATCAACTGCAACACCAGCG
     541    ---------+---------+---------+---------+---------+---------+
            TCCCGTTGTCTTCGTTGTTGTCGTTGTTTCTCATGGCCGACTAGTTGACGTTGTGGTCGC
             G   N   R   S   N   N   S   N   K   E   Y   R   L   I   N   C   N   T   S   A
             175     177     179     181     183     185     187     189     191     193

StuI
            CCATCACCCAGGCCTGCCCCAAGGTGTCCTTCGAGCCCATCCCCATCCACTACTGCGCCC
     601    ---------+---------+---------+---------+---------+---------+
            GGTAGTGGGTCCGGACGGGGTTCCACAGGAAGCTCGGGTAGGGGTAGGTGATGACGCGGG
             I   T   Q   A   C   P   K   V   S   F   E   P   I   P   I   H   Y   C   A   P
             195     197     199     201     203     205     207     209     211     213

CTGCCGGCTTCGCCATCCTGAAGTGCAAGGACAAGAAGTTCAACGGCACCGGCCCCTGCC
     661    ---------+---------+---------+---------+---------+---------+
            GACGGCCGAAGCGGTAGGACTTCACGTTCCTGTTCTTCAAGTTGCCGTGGCCGGGGACGG
             A   G   F   A   I   L   K   C   K   D   K   K   F   N   G   T   G   P   C   P
             215     217     219     221     223     225     227     229     231     233

PvuII
            CCAGCGTGTCCACAGTGCAGTGTACCCACGGCATCAAGCCCGTGGTGTCCACCCAGCTGC
     721    ---------+---------+---------+---------+---------+---------+
            GGTCGCACAGGTGTCACGTCACATGGGTGCCGTAGTTCGGGCACCACAGGTGGGTCGACG
             S   V   S   T   V   Q   C   T   H   G   I   K   P   V   V   S   T   Q   L   L
             235     237     239     241     243     245     247     249     251     253

BclI
            TGCTGAACGGCAGCCTGGCCGAAGAGGAAGTGATGATCAGAAGCGAGAACATCACCAACA
     781    ---------+---------+---------+---------+---------+---------+
            ACGACTTGCCGTCGGACCGGCTTCTCCTTCACTACTAGTCTTCGCTCTTGTAGTGGTTGT
             L   N   G   S   L   A   E   E   E   V   M   I   R   S   E   N   I   T   N   N
             255     257     259     261     263     265     267     269     271     273

ACGCCAAGAACATCCTGGTGCAGTTCAACACCCCCGTGCAGATTAACTGCACCCGGCCCA
     841    ---------+---------+---------+---------+---------+---------+
            TGCGGTTCTTGTAGGACCACGTCAAGTTGTGGGGGCACGTCTAATTGACGTGGGCCGGGT
             A   K   N   I   L   V   Q   F   N   T   P   V   Q   I   N   C   T   R   P   N
             275     277     279     281     283     285     287     289     291     293
```

```
                                                    StuI
       ACAACAACACCAGAAAGAGCATCCGGATCGGCCCAGGCCAGGCCTTCTACGCCACCGGCG
 901   ---------+---------+---------+---------+---------+---------+
       TGTTGTTGTGGTCTTTCTCGTAGGCCTAGCCGGGTCCGGTCCGGAAGATGCGGTGGCCGC
        N  N  T  R  K  S  I  R  I  G  P  G  Q  A  F  Y  A  T  G  D
            295   297   299   301   303   305   307   309   311   313

ACATCATCGGCGACATCCGGCAGGCCCACTGCACCGTGTCCAAGGCCACCTGGAACGAGA
 961   ---------+---------+---------+---------+---------+---------+
       TGTAGTAGCCGCTGTAGGCCGTCCGGGTGACGTGGCACAGGTTCCGGTGGACCTTGCTCT
        I  I  G  D  I  R  Q  A  H  C  T  V  S  K  A  T  W  N  E  T
            315   317   319   321   323   325   327   329   331   333

PvuII
       CACTGGGCAAGGTGGTGAAACAGCTGCGGAAGCACTTCGGGAACAACACCATCATCCGCT
1021   ---------+---------+---------+---------+---------+---------+
       GTGACCCGTTCCACCACTTTGTCGACGCCTTCGTGAAGCCCTTGTTGTGGTAGTAGGCGA
        L  G  K  V  V  K  Q  L  R  K  H  F  G  N  N  T  I  I  R  F
            335   337   339   341   343   345   347   349   351   353

TCGCCAACAGCTCTGGCGGCGACCTGGAAGTGACCACCCACAGCTTCAACTGTGGCGGCG
1081   ---------+---------+---------+---------+---------+---------+
       AGCGGTTGTCGAGACCGCCGCTGGACCTTCACTGGTGGGTGTCGAAGTTGACACCGCCGC
        A  N  S  S  G  G  D  L  E  V  T  T  H  S  F  N  C  G  G  E
            355   357   359   361   363   365   367   369   371   373

AGTTCTTCTACTGCAATACCTCCGGCCTGTTCAACAGCACCTGGATCAGCAATACCAGCG
1141   ---------+---------+---------+---------+---------+---------+
       TCAAGAAGATGACGTTATGGAGGCCGGACAAGTTGTCGTGGACCTAGTCGTTATGGTCGC
        F  F  Y  C  N  T  S  G  L  F  N  S  T  W  I  S  N  T  S  V
            375   377   379   381   383   385   387   389   391   393

TGCAGGGCAGCAACAGCACCGGCAGCAACGACAGCATCACCCTGCCCTGCCGGATCAAGC
1201   ---------+---------+---------+---------+---------+---------+
       ACGTCCCGTCGTTGTCGTGGCCGTCGTTGCTGTCGTAGTGGGACGGGACGGCCTAGTTCG
        Q  G  S  N  S  T  G  S  N  D  S  I  T  L  P  C  R  I  K  Q
            395   397   399   401   403   405   407   409   411   413

AGATCATCAATATGTGGCAGCGGATTGGCCAGGCTATGTACGCCCCACCCATCCAGGGCG
1261   ---------+---------+---------+---------+---------+---------+
       TCTAGTAGTTATACACCGTCGCCTAACCGGTCCGATACATGCGGGGTGGGTAGGTCCCGC
        I  I  N  M  W  Q  R  I  G  Q  A  M  Y  A  P  P  I  Q  G  V
            415   417   419   421   423   425   427   429   431   433

BclI                                   SmaI
       TGATCAGATGCGTGTCCAATATCACCGGCCTGATCCTGACCCGGGACGGCGGCTCTACCA
1321   ---------+---------+---------+---------+---------+---------+
       ACTAGTCTACGCACAGGTTATAGTGGCCGGACTAGGACTGGGCCCTGCCGCCGAGATGGT
        I  R  C  V  S  N  I  T  G  L  I  L  T  R  D  G  G  S  T  N
            435   437   439   441   443   445   447   449   451   453

ACAGCACCACCGAAACCTTCAGACCCGGCGGAGGCGACATGAGAGACAACTGGCGGAGCG
1381   ---------+---------+---------+---------+---------+---------+
       TGTCGTGGTGGCTTTGGAAGTCTGGGCCGCCTCCGCTGTACTCTCTGTTGACCGCCTCGC
        S  T  T  E  T  F  R  P  G  G  G  D  M  R  D  N  W  R  S  E
            455   457   459   461   463   465   467   469   471   473

AGCTGTACAAGTACAAAGTGGTGAAAATCGAGCCCCTGGGCGTGGCCCCCACCAGAGCCA
1441   ---------+---------+---------+---------+---------+---------+
       TCGACATGTTCATGTTTCACCACTTTTAGCTCGGGGACCCGCACCGGGGGTGGTCTCGGT
        L  Y  K  Y  K  V  V  K  I  E  P  L  G  V  A  P  T  R  A  K
            475   477   479   481   483   485   487   489   491   493
```

```
                                            NarI
                                            KasI
      AGAGAAGAGTGGTCGGAAGCGAGAAGTCCGCCGTGGGAATCGGCGCCGTGTTTCTGGGAT
1501  ---------+---------+---------+---------+---------+---------+
      TCTCTTCTCACCAGCCTTCGCTCTTCAGGCGGCACCCTTAGCCGCGGCACAAAGACCCTA
       R  R  V  V  G  S  E  K  S  A  V  G  I  G  A  V  F  L  G  F
       495   497   499   501   503   505   507   509   511   513

TCCTGGGCGCTGCCGGCTCTACAATGGGAGCCGCCAGCATGACACTGACCGTGCAGGCCA
1561  ---------+---------+---------+---------+---------+---------+
      AGGACCCGCGACGGCCGAGATGTTACCCTCGGCGGTCGTACTGTGACTGGCACGTCCGGT
       L  G  A  A  G  S  T  M  G  A  A  S  M  T  L  T  V  Q  A  R
       515   517   519   521   523   525   527   529   531   533

BspMI                                   BspMI
      GAAACCTGCTGTCCGGCATCGTGCAGCAGCAGAGCAACCTGCTGAGAGCCATCGAGGCCC
1621  ---------+---------+---------+---------+---------+---------+
      CTTTGGACGACAGGCCGTAGCACGTCGTCGTCTCGTTGGACGACTCTCGGTAGCTCCGGG
       N  L  L  S  G  I  V  Q  Q  Q  S  N  L  L  R  A  I  E  A  Q
       535   537   539   541   543   545   547   549   551   553

PvuII
                                      PstI
      AGCAGCATCTCCTCAAACTCACAGTCTGGGGCATCAAGCAGCTGCAGGCCAGGGTGCTGG
1681  ---------+---------+---------+---------+---------+---------+
      TCGTCGTAGAGGAGTTTGAGTGTCAGACCCCGTAGTTCGTCGACGTCCGGTCCCACGACC
       Q  H  L  L  K  L  T  V  W  G  I  K  Q  L  Q  A  R  V  L  A
       555   557   559   561   563   565   567   569   571   573

BspMI                              PstI
      CCGTGGAGAGATACCTGCGGGATCAGCAGCTCCTCGGCATCTGGGGCTGCAGCGGCAAGC
1741  ---------+---------+---------+---------+---------+---------+
      GGCACCTCTCTATGGACGCCCTAGTCGTCGAGGAGCCGTAGACCCCGACGTCGCCGTTCG
       V  E  R  Y  L  R  D  Q  Q  L  L  G  I  W  G  C  S  G  K  L
       575   577   579   581   583   585   587   589   591   593

PvuII                     BglII
      TGATCTGCACCACCAACGTGCCCTGGAACTCCAGCTGGTCCAACCGGAACCTGAGCGAGA
1801  ---------+---------+---------+---------+---------+---------+
      ACTAGACGTGGTGGTTGCACGGGACCTTGAGGTCGACCAGGTTGGCCTTGGACTCGCTCT
       I  C  T  T  N  V  P  W  N  S  S  W  S  N  R  N  L  S  E  I
       595   597   599   601   603   605   607   609   611   613

PstI
      TCTGGGACAATATGACCTGGCTGCAGTGGGACAAAGAGATCAGCAACTACACCCAGATCA
1861  ---------+---------+---------+---------+---------+---------+
      AGACCCTGTTATACTGGACCGACGTCACCCTGTTTCTCTAGTCGTTGATGTGGGTCTAGT
       W  D  N  M  T  W  L  Q  W  D  K  E  I  S  N  Y  T  Q  I  I
       615   617   619   621   623   625   627   629   631   633

BspMI
      TCTACGGCCTGCTGGAAGAGAGCCAGAACCAGCAGGAAAAGAACGAGCAGGACCTGCTGG
1921  ---------+---------+---------+---------+---------+---------+
      AGATGCCGGACGACCTTCTCTCGGTCTTGGTCGTCCTTTTCTTGCTCGTCCTGGACGACC
       Y  G  L  L  E  E  S  Q  N  Q  Q  E  K  N  E  Q  D  L  L  A
       635   637   639   641   643   645   647   649   651   653

CCCTGGACAAGTGGGCCTCCCTGTGGAATTGGTTCGACATCTCCAACTGGCTGTGGTACA
1981  ---------+---------+---------+---------+---------+---------+
      GGGACCTGTTCACCCGGAGGGACACCTTAACCAAGCTGTAGAGGTTGACCGACACCATGT
       L  D  K  W  A  S  L  W  N  W  F  D  I  S  N  W  L  W  Y  I
       655   657   659   661   663   665   667   669   671   673
```

```
       TCAAGGGCAGCGGCGGCATGAAGCAGATCGAGGACAAGATCGAAGAGATCGAGTCTAAGA
2041   ---------+---------+---------+---------+---------+---------+
       AGTTCCCGTCGCCGCCGTACTTCGTCTAGCTCCTGTTCTAGCTTCTCTAGCTCAGATTCT
        K   G   S   G   G   M   K   Q   I   E   D   K   I   E   E   I   E   S   K   I
        675     677     679     681     683     685     687     689     691     693

TCAAGAAGATTGAGAACGAGATCGCCCGCATCAAGAAACTGATCGGCGAGAGCGGCCACC
2101   ---------+---------+---------+---------+---------+---------+
       AGTTCTTCTAACTCTTGCTCTAGCGGGCGTAGTTCTTTGACTAGCCGCTCTCGCCGGTGG
        K   K   I   E   N   E   I   A   R   I   K   K   L   I   G   E   S   G   H   H
        695     697     699     701     703     705     707     709     711     713

NotI
                          EagI    PacI
       ACCACCATCACCATTGAGCGGCCGCTTAATTAA
2161   ---------+---------+---------+---
       TGGTGGTAGTGGTAACTCGCCGGCGAATTAATT
        H   H   H   H   *
        715     717     719
```

FIG. 31

```
     BssHII
     AscI     EcoRI              NcoI BamHI PstI
     GGCGCGCCGAATTCGCCACCATGCCCATGGGATCCCTGCAGCCTCTGGCCACACTGTATC
  1  ---------+---------+---------+---------+---------+---------+
     CCGCGCGGCTTAAGCGGTGGTACGGGTACCCTAGGGACGTCGGAGACCGGTGTGACATAG
                       M  P  M  G  S  L  Q  P  L  A  T  L  Y  L
                       1     3     5     7     9    11    13

SphI                                         BstEII
     TGCTGGGCATGCTGGTGGCCTCTGTGCTGGCCGCTGGCAATCTGTGGGTCACCGTGTACT
 61  ---------+---------+---------+---------+---------+---------+
     ACGACCCGTACGACCACCGGAGACACGACCGGCGACCGTTAGACACCCAGTGGCACATGA
      L  G  M  L  V  A  S  V  L  A  A  G  N  L  W  V  T  V  Y  Y
     15    17    19    21    23    25    27    29    31    33

StuI
     ACGGCGTGCCCGTGTGGAAGGACGCCGAGACAACCCTGTTCTGCGCCAGCGACGCCAAGG
121  ---------+---------+---------+---------+---------+---------+
     TGCCGCACGGGCACACCTTCCTGCGGCTCTGTTGGGACAAGACGCGGTCGCTGCGGTTCC
      G  V  P  V  W  K  D  A  E  T  T  L  F  C  A  S  D  A  K  A
     35    37    39    41    43    45    47    49    51    53

CCTACGAGACAGAGAAGCACAACGTGTGGGCCACCCACGCCTGCGTGCCAACCGACCCTA
181  ---------+---------+---------+---------+---------+---------+
     GGATGCTCTGTCTCTTCGTGTTGCACACCCGGTGGGTGCGGACGCACGGTTGGCTGGGAT
      Y  E  T  E  K  H  N  V  W  A  T  H  A  C  V  P  T  D  P  N
     55    57    59    61    63    65    67    69    71    73

ACCCCCAGGAAATCCACCTGGAAAACGTGACCGAAGAGTTCAACATGTGGAAGAACAACA
241  ---------+---------+---------+---------+---------+---------+
     TGGGGGTCCTTTAGGTGGACCTTTTGCACTGGCTTCTCAAGTTGTACACCTTCTTGTTGT
      P  Q  E  I  H  L  E  N  V  T  E  E  F  N  M  W  K  N  N  M
     75    77    79    81    83    85    87    89    91    93

TGGTGGAACAGATGCACACCGACATCATCAGCCTGTGGGACCAGAGCCTGAAGCCCTGCG
301  ---------+---------+---------+---------+---------+---------+
     ACCACCTTGTCTACGTGTGGCTGTAGTAGTCGGACACCCTGGTCTCGGACTTCGGGACGC
      V  E  Q  M  H  T  D  I  I  S  L  W  D  Q  S  L  K  P  C  V
     95    97    99   101   103   105   107   109   111   113
```

```
                                       PstI
           TGAAGCTGACCCCCCTGTGCGTGACCCTGCAGTGCACCAACGTGACCAACAACATCACCG
    361    ---------+---------+---------+---------+---------+---------+
           ACTTCGACTGGGGGGACACGCACTGGGACGTCACGTGGTTGCACTGGTTGTTGTAGTGGC
            K   L   T   P   L   C   V   T   L   Q   C   T   N   V   T   N   N   I   T   D
            115     117     119     121     123     125     127     129     131     133

PstI
           ACGACATGCGGGGCGAGCTGAAGAACTGCAGCTTCAACATGACCACCGAGCTGCGGGACA
    421    ---------+---------+---------+---------+---------+---------+
           TGCTGTACGCCCCGCTCGACTTCTTGACGTCGAAGTTGTACTGGTGGCTCGACGCCCTGT
            D   M   R   G   E   L   K   N   C   S   F   N   M   T   T   E   L   R   D   K
            135     137     139     141     143     145     147     149     151     153

AGAAACAGAAGGTGTACAGCCTGTTCTACCGGCTGGACGTGGTGCAGATCAACGAGAACC
    481    ---------+---------+---------+---------+---------+---------+
           TCTTTGTCTTCCACATGTCGGACAAGATGGCCGACCTGCACCACGTCTAGTTGCTCTTGG
            K   Q   K   V   Y   S   L   F   Y   R   L   D   V   V   Q   I   N   E   N   Q
            155     157     159     161     163     165     167     169     171     173

BclI
           AGGGCAACAGAAGCAACAACAGCAACAAAGAGTACCGGCTGATCAACTGCAACACCAGCG
    541    ---------+---------+---------+---------+---------+---------+
           TCCCGTTGTCTTCGTTGTTGTCGTTGTTTCTCATGGCCGACTAGTTGACGTTGTGGTCGC
            G   N   R   S   N   N   S   N   K   E   Y   R   L   I   N   C   N   T   S   A
            175     177     179     181     183     185     187     189     191     193

StuI
           CCATCACCCAGGCCTGCCCCAAGGTGTCCTTCGAGCCCATCCCCATCCACTACTGCGCCC
    601    ---------+---------+---------+---------+---------+---------+
           GGTAGTGGGTCCGGACGGGGTTCCACAGGAAGCTCGGGTAGGGGTAGGTGATGACGCGGG
            I   T   Q   A   C   P   K   V   S   F   E   P   I   P   I   H   Y   C   A   P
            195     197     199     201     203     205     207     209     211     213

CTGCCGGCTTCGCCATCCTGAAGTGCAAGGACAAGAAGTTCAACGGCACCGGCCCCTGCC
    661    ---------+---------+---------+---------+---------+---------+
           GACGGCCGAAGCGGTAGGACTTCACGTTCCTGTTCTTCAAGTTGCCGTGGCCGGGGACGG
            A   G   F   A   I   L   K   C   K   D   K   K   F   N   G   T   G   P   C   P
            215     217     219     221     223     225     227     229     231     233

PvuII
           CCAGCGTGTCCACAGTGCAGTGTACCCACGGCATCAAGCCCGTGGTGTCCACCCAGCTGC
    721    ---------+---------+---------+---------+---------+---------+
           GGTCGCACAGGTGTCACGTCACATGGGTGCCGTAGTTCGGGCACCACAGGTGGGTCGACG
            S   V   S   T   V   Q   C   T   H   G   I   K   P   V   V   S   T   Q   L   L
            235     237     239     241     243     245     247     249     251     253

BclI
           TGCTGAACGGCAGCCTGGCCGAAGAGGAAGTGATGATCAGAAGCGAGAACATCACCAACA
    781    ---------+---------+---------+---------+---------+---------+
           ACGACTTGCCGTCGGACCGGCTTCTCCTTCACTACTAGTCTTCGCTCTTGTAGTGGTTGT
            L   N   G   S   L   A   E   E   E   V   M   I   R   S   E   N   I   T   N   N
            255     257     259     261     263     265     267     269     271     273

ACGCCAAGAACATCCTGGTGCAGTTCAACACCCCCGTGCAGATTAACTGCACCCGGCCCA
    841    ---------+---------+---------+---------+---------+---------+
           TGCGGTTCTTGTAGGACCACGTCAAGTTGTGGGGGCACGTCTAATTGACGTGGGCCGGGT
            A   K   N   I   L   V   Q   F   N   T   P   V   Q   I   N   C   T   R   P   N
            275     277     279     281     283     285     287     289     291     293
```

```
                                            StuI
         ACAACAACACCAGAAAGAGCATCCGGATCGGCCCAGGCCAGGCCTTCTACGCCACCGGCG
   901   ---------+---------+---------+---------+---------+---------+
         TGTTGTTGTGGTCTTTCTCGTAGGCCTAGCCGGGTCCGGTCCGGAAGATGCGGTGGCCGC
          _N__N__T__R__K__S__I__R__I__G__P__G__Q__A__F__Y__A__T__G__D_
           295   297   299   301   303   305   307   309   311   313

ACATCATCGGCGACATCCGGCAGGCCCACTGCACCGTGTCCAAGGCCACCTGGAACGAGA
   961   ---------+---------+---------+---------+---------+---------+
         TGTAGTAGCCGCTGTAGGCCGTCCGGGTGACGTGGCACAGGTTCCGGTGGACCTTGCTCT
          _I__I__G__D__I__R__Q__A__H__C__T__V__S__K__A__T__W__N__E__T_
           315   317   319   321   323   325   327   329   331   333

PvuII
         CACTGGGCAAGGTGGTGAAACAGCTGCGGAAGCACTTCGGGAACAACACCATCATCCGCT
  1021   ---------+---------+---------+---------+---------+---------+
         GTGACCCGTTCCACCACTTTGTCGACGCCTTCGTGAAGCCCTTGTTGTGGTAGTAGGCGA
          _L__G__K__V__V__K__Q__L__R__K__H__F__G__N__N__T__I__I__R__F_
           335   337   339   341   343   345   347   349   351   353

TCGCCAACAGCTCTGGCGGCGACCTGGAAGTGACCACCCACAGCTTCAACTGTGGCGGCG
  1081   ---------+---------+---------+---------+---------+---------+
         AGCGGTTGTCGAGACCGCCGCTGGACCTTCACTGGTGGGTGTCGAAGTTGACACCGCCGC
          _A__N__S__S__G__G__D__L__E__V__T__T__H__S__F__N__C__G__G__E_
           355   357   359   361   363   365   367   369   371   373

AGTTCTTCTACTGCAATACCTCCGGCCTGTTCAACAGCACCTGGATCAGCAATACCAGCG
  1141   ---------+---------+---------+---------+---------+---------+
         TCAAGAAGATGACGTTATGGAGGCCGGACAAGTTGTCGTGGACCTAGTCGTTATGGTCGC
          _F__F__Y__C__N__T__S__G__L__F__N__S__T__W__I__S__N__T__S__V_
           375   377   379   381   383   385   387   389   391   393

TGCAGGGCAGCAACAGCACCGGCAGCAACGACAGCATCACCCTGCCCTGCCGGATCAAGC
  1201   ---------+---------+---------+---------+---------+---------+
         ACGTCCCGTCGTTGTCGTGGCCGTCGTTGCTGTCGTAGTGGGACGGGACGGCCTAGTTCG
          _Q__G__S__N__S__T__G__S__N__D__S__I__T__L__P__C__R__I__K__Q_
           395   397   399   401   403   405   407   409   411   413

AGATCATCAATATGTGGCAGCGGATTGGCCAGGCTATGTACGCCCCACCCATCCAGGGCG
  1261   ---------+---------+---------+---------+---------+---------+
         TCTAGTAGTTATACACCGTCGCCTAACCGGTCCGATACATGCGGGGTGGGTAGGTCCCGC
          _I__I__N__M__W__Q__R__I__G__Q__A__M__Y__A__P__P__I__Q__G__V_
           415   417   419   421   423   425   427   429   431   433

BclI                                   SmaI
         TGATCAGATGCGTGTCCAATATCACCGGCCTGATCCTGACCCGGGACGGCGGCTCTACCA
  1321   ---------+---------+---------+---------+---------+---------+
         ACTAGTCTACGCACAGGTTATAGTGGCCGGACTAGGACTGGGCCCTGCCGCCGAGATGGT
          _I__R__C__V__S__N__I__T__G__L__I__L__T__R__D__G__G__S__T__N_
           435   437   439   441   443   445   447   449   451   453

ACAGCACCACCGAAACCTTCAGACCCGGCGGAGGCGACATGAGAGACAACTGGCGGAGCG
  1381   ---------+---------+---------+---------+---------+---------+
         TGTCGTGGTGGCTTTGGAAGTCTGGGCCGCCTCCGCTGTACTCTCTGTTGACCGCCTCGC
          _S__T__T__E__T__F__R__P__G__G__G__D__M__R__D__N__W__R__S__E_
           455   457   459   461   463   465   467   469   471   473

AGCTGTACAAGTACAAAGTGGTGAAAATCGAGCCCCTGGGCGTGGCCCCCACCAGAGCCA
  1441   ---------+---------+---------+---------+---------+---------+
         TCGACATGTTCATGTTTCACCACTTTTAGCTCGGGGACCCGCACCGGGGGTGGTCTCGGT
          _L__Y__K__Y__K__V__V__K__I__E__P__L__G__V__A__P__T__R__A__K_
           475   477   479   481   483   485   487   489   491   493
```

```
         AGAGAAGAGTGGTCGGACGCGAGAAGCGGGCCGTGGGAATTGGAGCCGTGTTTCTGGGAT
1501  ----------+----------+----------+----------+----------+----------+
         TCTCTTCTCACCAGCCTGCGCTCTTCGCCCGGCACCCTTAACCTCGGCACAAAGACCCTA
          R   R   V   V   G   R   E   K   R   A   V   G   I   G   A   V   F   L   G   F
         495     497     499     501     503     505     507     509     511     513

TCCTGGGCGCTGCCGGCTCTACAATGGGAGCCGCCAGCATGACACTGACCGTGCAGGCCA
1561  ----------+----------+----------+----------+----------+----------+
         AGGACCCGCGACGGCCGAGATGTTACCCTCGGCGGTCGTACTGTGACTGGCACGTCCGGT
          L   G   A   A   G   S   T   M   G   A   A   S   M   T   L   T   V   Q   A   R
         515     517     519     521     523     525     527     529     531     533

BspMI                                  BspMI
         GAAACCTGCTGTCCGGCATCGTGCAGCAGCAGAGCAACCTGCTGAGAGCCATCGAGGCCC
1621  ----------+----------+----------+----------+----------+----------+
         CTTTGGACGACAGGCCGTAGCACGTCGTCGTCTCGTTGGACGACTCTCGGTAGCTCCGGG
          N   L   L   S   G   I   V   Q   Q   Q   S   N   L   L   R   A   I   E   A   Q
         535     537     539     541     543     545     547     549     551     553

PvuII
                                                  PstI
         AGCAGCATCTCCTCAAACTCACAGTCTGGGGCATCAAGCAGCTGCAGGCCAGGGTGCTGG
1681  ----------+----------+----------+----------+----------+----------+
         TCGTCGTAGAGGAGTTTGAGTGTCAGACCCCGTAGTTCGTCGACGTCCGGTCCCACGACC
          Q   H   L   L   K   L   T   V   W   G   I   K   Q   L   Q   A   R   V   L   A
         555     557     559     561     563     565     567     569     571     573

BspMI                                    PstI
         CCGTGGAGAGATACCTGCGGGATCAGCAGCTCCTCGGCATCTGGGGCTGCAGCGGCAAGC
1741  ----------+----------+----------+----------+----------+----------+
         GGCACCTCTCTATGGACGCCCTAGTCGTCGAGGAGCCGTAGACCCCGACGTCGCCGTTCG
          V   E   R   Y   L   R   D   Q   Q   L   L   G   I   W   G   C   S   G   K   L
         575     577     579     581     583     585     587     589     591     593

PvuII                      BglII
         TGATCTGCACCACCAACGTGCCCTGGAACTCCAGCTGGTCCAACCGGAACCTGAGCGAGA
1801  ----------+----------+----------+----------+----------+----------+
         ACTAGACGTGGTGGTTGCACGGGACCTTGAGGTCGACCAGGTTGGCCTTGGACTCGCTCT
          I   C   T   T   N   V   P   W   N   S   S   W   S   N   R   N   L   S   E   I
         595     597     599     601     603     605     607     609     611     613

PstI
         TCTGGGACAATATGACCTGGCTGCAGTGGGACAAAGAGATCAGCAACTACACCCAGATCA
1861  ----------+----------+----------+----------+----------+----------+
         AGACCCTGTTATACTGGACCGACGTCACCCTGTTTCTCTAGTCGTTGATGTGGGTCTAGT
          W   D   N   M   T   W   L   Q   W   D   K   E   I   S   N   Y   T   Q   I   I
         615     617     619     621     623     625     627     629     631     633

BspMI
         TCTACGGCCTGCTGGAAGAGAGCCAGAACCAGCAGGAAAAGAACGAGCAGGACCTGCTGG
1921  ----------+----------+----------+----------+----------+----------+
         AGATGCCGGACGACCTTCTCTCGGTCTTGGTCGTCCTTTTCTTGCTCGTCCTGGACGACC
          Y   G   L   L   E   E   S   Q   N   Q   Q   E   K   N   E   Q   D   L   L   A
         635     637     639     641     643     645     647     649     651     653

CCCTGGACAAGTGGGCCTCCCTGTGGAATTGGTTCGACATCTCCAACTGGCTGTGGTACA
1981  ----------+----------+----------+----------+----------+----------+
         GGGACCTGTTCACCCGGAGGGACACCTTAACCAAGCTGTAGAGGTTGACCGACACCATGT
          L   D   K   W   A   S   L   W   N   W   F   D   I   S   N   W   L   W   Y   I
         655     657     659     661     663     665     667     669     671     673
```

```
        BglII
        TCAAGATCTTCATCATGATCGTGGGCGGACTGATCGGCCTGCGGATCGTGTTTGCCGTGC
2041    ---------+---------+---------+---------+---------+---------+
        AGTTCTAGAAGTAGTACTAGCACCCGCCTGACTAGCCGGACGCCTAGCACAAACGGCACG
         K   I   F   I   M   I   V   G   G   L   I   G   L   R   I   V   F   A   V   L
         675     677     679     681     683     685     687     689     691     693

NotI
                                                EagI    PacI
        TGAGCGTGATCTCCGGCCACCACCACCATCACCACTGAGCGGCCGCTTAATTAA
2101    ---------+---------+---------+---------+---------+----
        ACTCGCACTAGAGGCCGGTGGTGGTGGTAGTGGTGACTCGCCGGCGAATTAATT
         S   V   I   S   G   H   H   H   H   H   *
         695     697     699     701     703     705
```

FIG. 32

```
                    HindIII
    NheI   PmeI  AflII                              PstI
    CCAAGCTGGCTAGCGTTTAAACTTAAGCTTGCCACCATGCCTATGGGCAGCCTGCAGCCT
  1 ---------+---------+---------+---------+---------+---------+
    GGTTCGACCGATCGCAAATTTGAATTCGAACGGTGGTACGGATACCCGTCGGACGTCGGA
                                        M  P  M  G  S  L  Q  P BspMI    SphI
    CTGGCCACCCTGTACCTGCTGGGCATGCTGGTGGCCTCCGTGCTGGCTGCCACCGAGAAG
 61 ---------+---------+---------+---------+---------+---------+
    GACCGGTGGGACATGGACGACCCGTACGACCACCGGAGGCACGACCGACGGTGGCTCTTC
    L  A  T  L  Y  L  L  G  M  L  V  A  S  V  L  A  A  T  E  K CTGTGGGTCACAGTGTACTACGGCGTGCCCGTGTGGAAAGAGGCCACCACCACCCTGTTC
121 ---------+---------+---------+---------+---------+---------+
    GACACCCAGTGTCACATGATGCCGCACGGGCACACCTTTCTCCGGTGGTGGTGGGACAAG
    L  W  V  T  V  Y  Y  G  V  P  V  W  K  E  A  T  T  T  L  F StuI
    TGCGCCTCTGAGGCCAAGGCCTACGACACCGAGGTGCACAACGTGTGGGCCACCCACGCC
181 ---------+---------+---------+---------+---------+---------+
    ACGCGGAGACTCCGGTTCCGGATGCTGTGGCTCCACGTGTTGCACACCCGGTGGGTGCGG
    C  A  S  E  A  K  A  Y  D  T  E  V  H  N  V  W  A  T  H  A PflMI
    TGCGTGCCAACCGACCCCAACCCCCAGGAAGTGGAACTGGGCAACGTGACCGAGAACTTC
241 ---------+---------+---------+---------+---------+---------+
    ACGCACGGTTGGCTGGGGTTGGGGGTCCTTCACCTTGACCCGTTGCACTGGCTCTTGAAG
    C  V  P  T  D  P  N  P  Q  E  V  E  L  G  N  V  T  E  N  F
```

```
     AACATGTGGAAGAACGACATGGTGGAACAGATGCACGAGGACATCATCAGCCTGTGGGAC
301  ---------+---------+---------+---------+---------+---------+
     TTGTACACCTTCTTGCTGTACCACCTTGTCTACGTGCTCCTGTAGTAGTCGGACACCCTG
      N  M  W  K  N  D  M  V  E  Q  M  H  E  D  I  I  S  L  W  D

CAGAGCCTGAAGCCCTGCGTGCGGCTGACCCCTCTGTGCGTGACCCTGGACTGCACCGAC
361  ---------+---------+---------+---------+---------+---------+
     GTCTCGGACTTCGGGACGCACGCCGACTGGGGAGACACGCACTGGGACCTGACGTGGCTG
      Q  S  L  K  P  C  V  R  L  T  P  L  C  V  T  L  D  C  T  D

CTGAACAACACCACCAACACCAACAATACCACAAACACTAACAGCAGCAAGATCGAGGGC
421  ---------+---------+---------+---------+---------+---------+
     GACTTGTTGTGGTGGTTGTGGTTGTTATGGTGTTTGTGATTGTCGTCGTTCTAGCTCCCG
      L  N  N  T  T  N  T  N  N  T  T  N  T  N  S  S  K  I  E  G

PstI
     GGCGAGATGAAGAACTGCAGCTTCAACATCACCACCAATCGGGGCGACAAGCGGCAGAAA
481  ---------+---------+---------+---------+---------+---------+
     CCGCTCTACTTCTTGACGTCGAAGTTGTAGTGGTGGTTAGCCCCGCTGTTCGCCGTCTTT
      G  E  M  K  N  C  S  F  N  I  T  T  N  R  G  D  K  R  Q  K

GAGTACGCCCTGCTGTACCGGACCGACATCGTGTCCATCGAGAACACCAGCAGCAGCTAC
541  ---------+---------+---------+---------+---------+---------+
     CTCATGCGGGACGACATGGCCTGGCTGTAGCACAGGTAGCTCTTGTGGTCGTCGTCGATG
      E  Y  A  L  L  Y  R  T  D  I  V  S  I  E  N  T  S  S  S  Y

PvuII
        BclI            BclI    StuI
     CGGCTGATCAGCTGCAACACCAGCGTGATCACCCAGGCCTGCCCCAAAGTGACCTTCGAG
601  ---------+---------+---------+---------+---------+---------+
     GCCGACTAGTCGACGTTGTGGTCGCACTAGTGGGTCCGGACGGGGTTTCACTGGAAGCTC
      R  L  I  S  C  N  T  S  V  I  T  Q  A  C  P  K  V  T  F  E

CCCATCCCCATCCACTACTGCGCCCCTGCCGGCTTCGCCATCCTGAAGTGCAACGAGGAC
661  ---------+---------+---------+---------+---------+---------+
     GGGTAGGGGTAGGTGATGACGCGGGGACGGCCGAAGCGGTAGGACTTCACGTTGCTCCTG
      P  I  P  I  H  Y  C  A  P  A  G  F  A  I  L  K  C  N  E  D
```

```
         AAGTTCAACGGCACAGGCCCCTGCAAGAACGTGTCCACCGTGCAGTGCACCCACGGCATC
    721  ---------+---------+---------+---------+---------+---------+
         TTCAAGTTGCCGTGTCCGGGGACGTTCTTGCACAGGTGGCACGTCACGTGGGTGCCGTAG
          K  F  N  G  T  G  P  C  K  N  V  S  T  V  Q  C  T  H  G  I

PvuII                            BclI
         AGACCCACCGTGTCCACCCAGCTGCTGCTGAATGGCAGCCTGGCCAAAGAAGAAGTGATC
    781  ---------+---------+---------+---------+---------+---------+
         TCTGGGTGGCACAGGTGGGTCGACGACGACTTACCGTCGGACCGGTTTCTTCTTCACTAG
          R  P  T  V  S  T  Q  L  L  L  N  G  S  L  A  K  E  E  V  I

PvuII
         ATCAGAAGCGCCAACCTGAGCGACAACGCCAAGATCATCATCGTGCAGCTGAAGGACCCC
    841  ---------+---------+---------+---------+---------+---------+
         TAGTCTTCGCGGTTGGACTCGCTGTTGCGGTTCTAGTAGTAGCACGTCGACTTCCTGGGG
          I  R  S  A  N  L  S  D  N  A  K  I  I  I  V  Q  L  K  D  P

ApaI
         GTGGAAATCAACTGCACCCGGCCCAACAACAACACCAGAAAGAGCATCAACCTGGGCCCT
    901  ---------+---------+---------+---------+---------+---------+
         CACCTTTAGTTGACGTGGGCCGGGTTGTTGTTGTGGTCTTTCTCGTAGTTGGACCCGGGA
          V  E  I  N  C  T  R  P  N  N  N  T  R  K  S  I  N  L  G  P

GGCAGAGCCTTCTACGCCACCGGCGACATCATCGGCGACATCCGGCAGGCCCACTGCAAC
    961  ---------+---------+---------+---------+---------+---------+
         CCGTCTCGGAAGATGCGGTGGCCGCTGTAGTAGCCGCTGTAGGCCGTCCGGGTGACGTTG
          G  R  A  F  Y  A  T  G  D  I  I  G  D  I  R  Q  A  H  C  N

ATCAGCCGGGCCAAGTGGAACGACACCCTGAGAGAGATCGCCAAGAAGCTGGCCGAGCAG
   1021  ---------+---------+---------+---------+---------+---------+
         TAGTCGGCCCGGTTCACCTTGCTGTGGGACTCTCTCTAGCGGTTCTTCGACCGGCTCGTC
          I  S  R  A  K  W  N  D  T  L  R  E  I  A  K  K  L  A  E  Q

TTCAACAATCGGACCATCGTGTTCAACCAGAGCAGCGGAGGCGACCCCGAGATCGTGATG
   1081  ---------+---------+---------+---------+---------+---------+
         AAGTTGTTAGCCTGGTAGCACAAGTTGGTCTCGTCGCCTCCGCTGGGGCTCTAGCACTAC
          F  N  N  R  T  I  V  F  N  Q  S  S  G  G  D  P  E  I  V  M
```

```
                                                        PvuII
       CACAGCTTCAACTGTGCCGGCGAGTTCTTCTACTGCGACACCAGCCAGCTGTTCAACAGC
1141   ---------+---------+---------+---------+---------+---------+
       GTGTCGAAGTTGACACGGCCGCTCAAGAAGATGACGCTGTGGTCGGTCGACAAGTTGTCG
        H   S   F   N   C   A   G   E   F   F   Y   C   D   T   S   Q   L   F   N   S

ACCTGGAACAGCAACTCCACCTGGAACGATACAAACAACAACAATAGCACCGAGAAGATC
1201   ---------+---------+---------+---------+---------+---------+
       TGGACCTTGTCGTTGAGGTGGACCTTGCTATGTTTGTTGTTGTTATCGTGGCTCTTCTAG
        T   W   N   S   N   S   T   W   N   D   T   N   N   N   N   S   T   E   K   I

BamHI              AgeI
       ATCCTGAGCTGTCGGATCCGGCAGATCATCAACCGGTGGCAGGAAGTGGGCAAGGCTATG
1261   ---------+---------+---------+---------+---------+---------+
       TAGGACTCGACAGCCTAGGCCGTCTAGTAGTTGGCCACCGTCCTTCACCCGTTCCGATAC
        I   L   S   C   R   I   R   Q   I   I   N   R   W   Q   E   V   G   K   A   M

TACGCCCCTCCCATCAGCGGCCCCATCAAGTGCAGCAGCAACATCACCGGCCTGCTGCTG
1321   ---------+---------+---------+---------+---------+---------+
       ATGCGGGGAGGGTAGTCGCCGGGGTAGTTCACGTCGTCGTTGTAGTGGCCGGACGACGAC
        Y   A   P   P   I   S   G   P   I   K   C   S   S   N   I   T   G   L   L   L

GCCAGGGACGGCGGCAACGAGACAAATGTGACCGAGACATTCCGGCCTGCCGGCGGAGAC
1381   ---------+---------+---------+---------+---------+---------+
       CGGTCCCTGCCGCCGTTGCTCTGTTTACACTGGCTCTGTAAGGCCGGACGGCCGCCTCTG
        A   R   D   G   G   N   E   T   N   V   T   E   T   F   R   P   A   G   G   D

ATGCGGGACAATTGGCGGAGCGAGCTGTACAAGTACAAGGTCGTGCAGATCGAGCCCCTG
1441   ---------+---------+---------+---------+---------+---------+
       TACGCCCTGTTAACCGCCTCGCTCGACATGTTCATGTTCCAGCACGTCTAGCTCGGGGAC
        M   R   D   N   W   R   S   E   L   Y   K   Y   K   V   V   Q   I   E   P   L
```

```
                                                    NarI
                                                    KasI
          GGAATCGCCCCCACCAAGGCCAAGCGGAGAGTGGTGCAGGGCGCCCACCACCACCATCAC
1501      ---------+---------+---------+---------+---------+---------+
          CCTTAGCGGGGGTGGTTCCGGTTCGCCTCTCACCACGTCCCGCGGGTGGTGGTGGTAGTG
           G  I  A  P  T  K  A  K  R  R  V  V  Q  G  A  H  H  H  H  H

XhoI  XbaI  ApaI  PmeI
          CACTGACTCGAGTCTAGAGGGCCCGTTTAAACCCGC
1561      ---------+---------+---------+------
          GTGACTGAGCTCAGATCTCCCGGGCAAATTTGGGCG
           H  *
```

FIG. 33

```
                               HindIII
          NheI    PmeI    AflII                                    PstI
          CCAAGCTGGCTAGCGTTTAAACTTAAGCTTGCCACCATGCCTATGGGCAGCCTGCAGCCT
    1     ---------+---------+---------+---------+---------+---------+
          GGTTCGACCGATCGCAAATTTGAATTCGAACGGTGGTACGGATACCCGTCGGACGTCGGA
                                           M   P   M   G   S   L   Q   P BspMI       SphI
          CTGGCCACCCTGTACCTGCTGGGCATGCTGGTGGCCTCCGTGCTGGCTGCCACCGAGAAC
    61    ---------+---------+---------+---------+---------+---------+
          GACCGGTGGGACATGGACGACCCGTACGACCACCGGAGGCACGACCGACGGTGGCTCTTG
          L   A   T   L   Y   L   L   G   M   L   V   A   S   V   L   A   A   T   E   N CTGTGGGTCACAGTGTACTACGGCGTGCCCGTGTGGAAAGAGGCCACCACCACCCTGTTC
    121   ---------+---------+---------+---------+---------+---------+
          GACACCCAGTGTCACATGATGCCGCACGGGCACACCTTTCTCCGGTGGTGGTGGGACAAG
          L   W   V   T   V   Y   Y   G   V   P   V   W   K   E   A   T   T   T   L   F TGCGCCTCTGACGCCAAGGGCTACGAGAAAGAGGTGCACAACGTCTGGGCCACCCACGCC
    181   ---------+---------+---------+---------+---------+---------+
          ACGCGGAGACTGCGGTTCCCGATGCTCTTTCTCCACGTGTTGCAGACCCGGTGGGTGCGG
          C   A   S   D   A   K   G   Y   E   K   E   V   H   N   V   W   A   T   H   A TGCGTGCCCACCGACCCCAACCCTCAGGAAGTGGTCCTGGAAAACGTGACCGAGAACTTC
    241   ---------+---------+---------+---------+---------+---------+
          ACGCACGGGTGGCTGGGGTTGGGAGTCCTTCACCAGGACCTTTTGCACTGGCTCTTGAAG
          C   V   P   T   D   P   N   P   Q   E   V   V   L   E   N   V   T   E   N   F AACATGTGGAAGAACAACATGGTGGAACAGATGCACGAGGACATCATCAGCCTGTGGGAC
    301   ---------+---------+---------+---------+---------+---------+
          TTGTACACCTTCTTGTTGTACCACCTTGTCTACGTGCTCCTGTAGTAGTCGGACACCCTG
          N   M   W   K   N   N   M   V   E   Q   M   H   E   D   I   I   S   L   W   D
```

```
                                                       PstI
        CAGAGCCTGAAGCCCTGCGTGAAGCTGACCCCCCTGTGCGTGACCCTGAACTGCAGCGAC
361     ---------+---------+---------+---------+---------+---------+
        GTCTCGGACTTCGGGACGCACTTCGACTGGGGGGACACGCACTGGGACTTGACGTCGCTG
         Q   S   L   K   P   C   V   K   L   T   P   L   C   V   T   L   N   C   S   D

PstI
        GTGAACACCACCTCCGTGAATACCACCGCCAGCAGCATGGAAGGCGGCGAGATCAAGAAC
421     ---------+---------+---------+---------+---------+---------+
        CACTTGTGGTGGAGGCACTTATGGTGGCGGTCGTCGTACCTTCCGCCGCTCTAGTTCTTG
         V   N   T   T   S   V   N   T   T   A   S   S   M   E   G   G   E   I   K   N

TGCAGCTTCAACACCACCACCAGCATGAGCGACAAGATGCAGAAAGAGTACGCCCTGTTC
481     ---------+---------+---------+---------+---------+---------+
        ACGTCGAAGTTGTGGTGGTGGTCGTACTCGCTGTTCTACGTCTTTCTCATGCGGGACAAG
         C   S   F   N   T   T   T   S   M   S   D   K   M   Q   K   E   Y   A   L   F

PvuII
                                                        BclI
        TACACCCTGGACGTGGTGCCCATCGTGAAAGAGAACAACACCTACCGGCTGATCAGCTGC
541     ---------+---------+---------+---------+---------+---------+
        ATGTGGGACCTGCACCACGGGTAGCACTTTCTCTTGTTGTGGATGGCCGACTAGTCGACG
         Y   T   L   D   V   V   P   I   V   K   E   N   N   T   Y   R   L   I   S   C

BclI      StuI
        AACACCAGCGTGATCACCCAGGCCTGCCCCAAGGTGTCCTTCGAGCCCATCCCCATCCAC
601     ---------+---------+---------+---------+---------+---------+
        TTGTGGTCGCACTAGTGGGTCCGGACGGGGTTCCACAGGAAGCTCGGGTAGGGGTAGGTG
         N   T   S   V   I   T   Q   A   C   P   K   V   S   F   E   P   I   P   I   H

ApaI
        TACTGCGCCCCTGCCGGCTTCGCCATCCTGATGTGCAACAACAAGACCTTCGACGGCAAG
661     ---------+---------+---------+---------+---------+---------+
        ATGACGCGGGGACGGCCGAAGCGGTAGGACTACACGTTGTTGTTCTGGAAGCTGCCGTTC
         Y   C   A   P   A   G   F   A   I   L   M   C   N   N   K   T   F   D   G   K
```

```
              GGCCCCTGCAACAACGTGTCCACCGTGCAGTGCACCCACGGCATCAAGCCCGTGGTGTCC
         721  ---------+---------+---------+---------+---------+---------+
              CCGGGGACGTTGTTGCACAGGTGGCACGTCACGTGGGTGCCGTAGTTCGGGCACCACAGG
               G  P  C  N  N  V  S  T  V  Q  C  T  H  G  I  K  P  V  V  S

PvuII
              ACCCAGCTGCTGCTGAATGGCAGCCTGGCCGAAGAGGAAGTGGTCATCAGAAGCGACAAC
         781  ---------+---------+---------+---------+---------+---------+
              TGGGTCGACGACGACTTACCGTCGGACCGGCTTCTCCTTCACCAGTAGTCTTCGCTGTTG
               T  Q  L  L  L  N  G  S  L  A  E  E  E  V  V  I  R  S  D  N

TTCACCGACAACGCCAAGACCATCATCGTGCACCTGAACGAGAGCATCGAGATCACCTGT
         841  ---------+---------+---------+---------+---------+---------+
              AAGTGGCTGTTGCGGTTCTGGTAGTAGCACGTGGACTTGCTCTCGTAGCTCTAGTGGACA
               F  T  D  N  A  K  T  I  I  V  H  L  N  E  S  I  E  I  T  C

ACCCGGCCCAACAACAACACCAGCAAGAGCATCACCATCGGCCCTGGCAGAGCCTTCTAC
         901  ---------+---------+---------+---------+---------+---------+
              TGGGCCGGGTTGTTGTTGTGGTCGTTCTCGTAGTGGTAGCCGGGACCGTCTCGGAAGATG
               T  R  P  N  N  N  T  S  K  S  I  T  I  G  P  G  R  A  F  Y

EagI
              GCCACCGGCCGGATCATCGGCGACATCAGAAAGGCCCACTGCAACATCAGCGGCGAGAAG
         961  ---------+---------+---------+---------+---------+---------+
              CGGTGGCCGGCCTAGTAGCCGCTGTAGTCTTTCCGGGTGACGTTGTAGTCGCCGCTCTTC
               A  T  G  R  I  I  G  D  I  R  K  A  H  C  N  I  S  G  E  K

TGGCACAACGCCCTGGAACAGATCGTGAAGAAGCTGGGCGAGAAGTTCGAGAACGCCACC
        1021  ---------+---------+---------+---------+---------+---------+
              ACCGTGTTGCGGGACCTTGTCTAGCACTTCTTCGACCCGCTCTTCAAGCTCTTGCGGTGG
               W  H  N  A  L  E  Q  I  V  K  K  L  G  E  K  F  E  N  A  T

ACCATCCGGTTCAACCAGAGCAGCGGAGGCGACCAGGAAATCGTGATGCACACCTTCAAC
        1081  ---------+---------+---------+---------+---------+---------+
              TGGTAGGCCAAGTTGGTCTCGTCGCCTCCGCTGGTCCTTTAGCACTACGTGTGGAAGTTG
               T  I  R  F  N  Q  S  S  G  G  D  Q  E  I  V  M  H  T  F  N
```

```
                              PvuII
         TGTGGCGGCGAGTTCTTCTACTGCAACAGCACCCAGCTGTTCAACAGCACCTGGTGGCCC
1141     ---------+---------+---------+---------+---------+---------+
         ACACCGCCGCTCAAGAAGATGACGTTGTCGTGGGTCGACAAGTTGTCGTGGACCACCGGG
         C  G  G  E  F  F  Y  C  N  S  T  Q  L  F  N  S  T  W  W  P

PflMI
         AACGGCACCACCACCGAGTGGTCCAACGAGACAAGCAATGGCACCATCACCCTGCCCTGC
1201     ---------+---------+---------+---------+---------+---------+
         TTGCCGTGGTGGTGGCTCACCAGGTTGCTCTGTTCGTTACCGTGGTAGTGGGACGGGACG
         N  G  T  T  T  E  W  S  N  E  T  S  N  G  T  I  T  L  P  C

CGGATCAAGCAGATCATCAATATGTGGCAGGAAGTGGGCAAGGCTATGTACGCCCCTCCC
1261     ---------+---------+---------+---------+---------+---------+
         GCCTAGTTCGTCTAGTAGTTATACACCGTCCTTCACCCGTTCCGATACATGCGGGGAGGG
         R  I  K  Q  I  I  N  M  W  Q  E  V  G  K  A  M  Y  A  P  P

PvuII
         ATCAGCGGCCCCATCAGCTGCTCCAGCAACATCACCGGCCTGCTGCTCGTCCGCGACGGC
1321     ---------+---------+---------+---------+---------+---------+
         TAGTCGCCGGGGTAGTCGACGAGGTCGTTGTAGTGGCCGGACGACGAGCAGGCGCTGCCG
         I  S  G  P  I  S  C  S  S  N  I  T  G  L  L  L  V  R  D  G

GGCAACGACAACGAGACTAACGGCACCGAGACATTCAGACCCGGCGGAGGCGATATGCGG
1381     ---------+---------+---------+---------+---------+---------+
         CCGTTGCTGTTGCTCTGATTGCCGTGGCTCTGTAAGTCTGGGCCGCCTCCGCTATACGCC
         G  N  D  N  E  T  N  G  T  E  T  F  R  P  G  G  G  D  M  R

GACAACTGGCGGAGCGAGCTGTACAAGTACAAGGTGGTCAAAATCGAGCCCCTGGGCGTG
1441     ---------+---------+---------+---------+---------+---------+
         CTGTTGACCGCCTCGCTCGACATGTTCATGTTCCACCAGTTTTAGCTCGGGGACCCGCAC
         D  N  W  R  S  E  L  Y  K  Y  K  V  V  K  I  E  P  L  G  V
```

```
                                       NarI
                                       KasI
     GCCCCCACCAAGGCCAAGAGAAGAGTGGTGCAGGGCGCCCACCACCACCATCACCACTGA
1501 ---------+---------+---------+---------+---------+---------+
     CGGGGGTGGTTCCGGTTCTCTTCTCACCACGTCCCGCGGGTGGTGGTGGTAGTGGTGACT
      A  P  T  K  A  K  R  R  V  V  Q  G  A  H  H  H  H  H  *

XhoI  XbaI  ApaI   PmeI
     CTCGAGTCTAGAGGGCCCGTTTAAACCCGC
1561 ---------+---------+---------+
     GAGCTCAGATCTCCCGGGCAAATTTGGGCG
```

FIG. 34

```
              PacI   HindIII                             PstI
      GAGCGGAAGGCCCATGAGGCCAGTTAATTAAGCTTGCCACCATGCCTATGGGCAGCCTGC
  1   ---------+---------+---------+---------+---------+---------+
      CTCGCCTTCCGGGTACTCCGGTCAATTAATTCGAACGGTGGTACGGATACCCGTCGGACG
                                              M  P  M  G  S  L  Q BspMI    SphI                          PvuII
      AGCCTCTGGCCACCCTGTACCTGCTGGGCATGCTGGTGGCCTCCGTGCTGGCAGCTGGCA
 61   ---------+---------+---------+---------+---------+---------+
      TCGGAGACCGGTGGGACATGGACGACCCGTACGACCACCGGAGGCACGACCGTCGACCGT
       P  L  A  T  L  Y  L  L  G  M  L  V  A  S  V  L  A  A  G  N ACCTGTGGGTCACAGTGTACTACGGCGTGCCCGTGTGGAAAGAGGCCAAGACCACCCTGT
121   ---------+---------+---------+---------+---------+---------+
      TGGACACCCAGTGTCACATGATGCCGCACGGGCACACCTTTCTCCGGTTCTGGTGGGACA
       L  W  V  T  V  Y  Y  G  V  P  V  W  K  E  A  K  T  T  L  F StuI
      TCTGCGCCAGCGACGCCAAGGCCTACGAGAAAGAGGTGCACAACGTCTGGGCCACCCACG
181   ---------+---------+---------+---------+---------+---------+
      AGACGCGGTCGCTGCGGTTCCGGATGCTCTTTCTCCACGTGTTGCAGACCCGGTGGGTGC
       C  A  S  D  A  K  A  Y  E  K  E  V  H  N  V  W  A  T  H  A PflMI
      CCTGCGTGCCCACCGACCCCAACCCCCAGGAAATGGTCCTGGAAAACGTGACCGAGAACT
241   ---------+---------+---------+---------+---------+---------+
      GGACGCACGGGTGGCTGGGGTTGGGGGTCCTTTACCAGGACCTTTTGCACTGGCTCTTGA
       C  V  P  T  D  P  N  P  Q  E  M  V  L  E  N  V  T  E  N  F
```

```
                                                         BclI
    TCAACATGTGGGAGAACGACGTGGTGGACCAGATGCACGAGGACGTGATCAGCCTGTGGG
301 ---------+---------+---------+---------+---------+---------+
    AGTTGTACACCCTCTTGCTGCACCACCTGGTCTACGTGCTCCTGCACTAGTCGGACACCC
     N  M  W  E  N  D  V  V  D  Q  M  H  E  D  V  I  S  L  W  D

PstI
    ACCAGAGCCTGAAGCCCTGCGTGAAGCTGACCCCCCTGTGCGTGACCCTGAACTGCAGCA
361 ---------+---------+---------+---------+---------+---------+
    TGGTCTCGGACTTCGGGACGCACTTCGACTGGGGGGACACGCACTGGGACTTGACGTCGT
     Q  S  L  K  P  C  V  K  L  T  P  L  C  V  T  L  N  C  S  K

BclI
    AGGCCAAGAACATCACCGAGGAAGTGATCAAGAACAACACCTACAAAGAGGACATCCGGA
421 ---------+---------+---------+---------+---------+---------+
    TCCGGTTCTTGTAGTGGCTCCTTCACTAGTTCTTGTTGTGGATGTTTCTCCTGTAGGCCT
     A  K  N  I  T  E  E  V  I  K  N  N  T  Y  K  E  D  I  R  N

PstI
    ACTGCAGCTTCAACGCCACCACCGAAGTGAAGGACAAGAAACAGAAGGTGCACGCCCTGT
481 ---------+---------+---------+---------+---------+---------+
    TGACGTCGAAGTTGCGGTGGTGGCTTCACTTCCTGTTCTTTGTCTTCCACGTGCGGGACA
      C  S  F  N  A  T  T  E  V  K  D  K  K  Q  K  V  H  A  L  F

TCTACCGGCTGGACATCGTGCCCCTGAACAAGCGGAACAGCAGCGAGAGCGAGGAAGAGA
541 ---------+---------+---------+---------+---------+---------+
    AGATGGCCGACCTGTAGCACGGGGACTTGTTCGCCTTGTCGTCGCTCTCGCTCCTTCTCT
      Y  R  L  D  I  V  P  L  N  K  R  N  S  S  E  S  E  E  N

BclI                            StuI
    ACAGCTCCGGCTACTACCGGCTGATCAACTGCAACACCAGCGCCGTGACCCAGGCCTGCC
601 ---------+---------+---------+---------+---------+---------+
    TGTCGAGGCCGATGATGGCCGACTAGTTGACGTTGTGGTCGCGGCACTGGGTCCGGACGG
      S  S  G  Y  Y  R  L  I  N  C  N  T  S  A  V  T  Q  A  C  P
```

```
          CCAAAGTGACCTTCGACCCCATCCCCATCCACTACTGCACCCCTGCCGGCTACGCCATCC
661       ---------+---------+---------+---------+---------+---------+
          GGTTTCACTGGAAGCTGGGGTAGGGGTAGGTGATGACGTGGGGACGGCCGATGCGGTAGG
           _K__V__T__F__D__P__I__P__I__H__Y__C__T__P__A__G__Y__A__I__L

TGAAGTGCAACGAGGAAACCTTCAACGGCACCGGCCCCTGCCACAACGTGTCCACCGTGC
721       ---------+---------+---------+---------+---------+---------+
          ACTTCACGTTGCTCCTTTGGAAGTTGCCGTGGCCGGGGACGGTGTTGCACAGGTGGCACG
           _K__C__N__E__E__T__F__N__G__T__G__P__C__H__N__V__S__T__V__Q

PvuII
          AGTGCACCCACGGCATCAAGCCCGTGGTGTCCACCCAGCTGCTGCTGAATGGCAGCCTGG
781       ---------+---------+---------+---------+---------+---------+
          TCACGTGGGTGCCGTAGTTCGGGCACCACAGGTGGGTCGACGACGACTTACCGTCGGACC
           _C__T__H__G__I__K__P__V__V__S__T__Q__L__L__L__N__G__S__L__A

CTGAGGGCGAGATCATCATCAGAAGCAAGAACCTGACCGACAACGCCAAGACCATCATTG
841       ---------+---------+---------+---------+---------+---------+
          GACTCCCGCTCTAGTAGTAGTCTTCGTTCTTGGACTGGCTGTTGCGGTTCTGGTAGTAAC
           _E__G__E__I__I__I__R__S__K__N__L__T__D__N__A__K__T__I__I__V

PflMI
          TGCACCTGAACCAGAGCGTGGAAATCGTGTGCACCCGGCCCAACGAGAACCGGCGGAAGT
901       ---------+---------+---------+---------+---------+---------+
          ACGTGGACTTGGTCTCGCACCTTTAGCACACGTGGGCCGGGTTGCTCTTGGCCGCCTTCA
           _H__L__N__Q__S__V__E__I__V__C__T__R__P__N__E__N__R__R__K__S

StuI
          CCATCCGGATCGGCCCAGGCCAGGCCTTTTACGCCACCGGCGACATCATCGGCGACATCC
961       ---------+---------+---------+---------+---------+---------+
          GGTAGGCCTAGCCGGGTCCGGTCCGGAAAATGCGGTGGCCGCTGTAGTAGCCGCTGTAGG
           _I__R__I__G__P__G__Q__A__F__Y__A__T__G__D__I__I__G__D__I__R
```

```
                                                           PstI
            GGCAGGCCCGGTGCAACATCAGCGAAGAGAAGTGGAACGAGACACTGCAGAGAGTGGGCC
1021        ---------+---------+---------+---------+---------+---------+
            CCGTCCGGGCCACGTTGTAGTCGCTTCTCTTCACCTTGCTCTGTGACGTCTCTCACCCGG
             Q   A   R   C   N   I   S   E   E   K   W   N   E   T   L   Q   R   V   G   R

GGAAGCTGGCCGAGCACTTCCCCAACAAGACAATCAAGTTCAAGAGCAGCTCTGGCGGCG
1081        ---------+---------+---------+---------+---------+---------+
            CCTTCGACCGGCTCGTGAAGGGGTTGTTCTGTTAGTTCAAGTTCTCGTCGAGACCGCCGC
             K   L   A   E   H   F   P   N   K   T   I   K   F   K   S   S   S   G   G   D

PstI
            ACCTGGAAATCACCACCCACAGCTTCAACTGCAGAGGCGAGTTCTTCTACTGCAATACCT
1141        ---------+---------+---------+---------+---------+---------+
            TGGACCTTTAGTGGTGGGTGTCGAAGTTGACGTCTCCGCTCAAGAAGATGACGTTATGGA
             L   E   I   T   T   H   S   F   N   C   R   G   E   F   F   Y   C   N   T   S

CCGGCCTGTTCAATGGCACCTACATGCCCACCTATATGCCCAACAGCACCAACTCCAACA
1201        ---------+---------+---------+---------+---------+---------+
            GGCCGGACAAGTTACCGTGGATGTACGGGTGGATATACGGGTTGTCGTGGTTGAGGTTGT
             G   L   F   N   G   T   Y   M   P   T   Y   M   P   N   S   T   N   S   N   S

GCAGCAGCAACATCACCATCCCTTGCCGGATCAAACAGGTCATCAATATGTGGCAGGAAG
1261        ---------+---------+---------+---------+---------+---------+
            CGTCGTCGTTGTAGTGGTAGGGAACGGCCTAGTTTGTCCAGTAGTTATACACCGTCCTTC
             S   S   N   I   T   I   P   C   R   I   K   Q   V   I   N   M   W   Q   E   V

TGGGCAGAGCTATGTACGCCCCTCCCATCGAGGGGGAGATCACATGCAAGTCCAACATCA
1321        ---------+---------+---------+---------+---------+---------+
            ACCCGTCTCGATACATGCGGGGAGGGTAGCTCCCCCTCTAGTGTACGTTCAGGTTGTAGT
             G   R   A   M   Y   A   P   P   I   E   G   E   I   T   C   K   S   N   I   T

BglII
            CCGGCCTGCTGCTCGTCCGCGACGGCGGCAACGGCAACGACACCAACAAGACCGAGATCT
1381        ---------+---------+---------+---------+---------+---------+
            GGCCGGACGACGAGCAGGCGCTGCCGCCGTTGCCGTTGCTGTGGTTGTTCTGGCTCTAGA
             G   L   L   L   V   R   D   G   G   N   G   N   D   T   N   K   T   E   I   F
```

```
          TCCGGCCCGAGGGCGGCGACATGAGAGACAATTGGCGGAGCGAGCTGTACAAGTACAAGG
1441      ---------+---------+---------+---------+---------+---------+
          AGGCCGGGCTCCCGCCGCTGTACTCTCTGTTAACCGCCTCGCTCGACATGTTCATGTTCC
            R  P  E  G  G  D  M  R  D  N  W  R  S  E  L  Y  K  Y  K  V

NarI
                                                                   KasI
          TGGTGGAAATCAAGCCCCTGGGAATCGCCCCCACCGAGGCCAAGCGGAGAGTGGTGGAAG
1501      ---------+---------+---------+---------+---------+---------+
          ACCACCTTTAGTTCGGGGACCCCTTAGCGGGGGTGGCTCCGGTTCGCCTCTCACCACCTTC
            V  E  I  K  P  L  G  I  A  P  T  E  A  K  R  R  V  V  E  G

BssHII StuI
                        XhoI AscI  AvrII
          GCGCCCACCACCACCATCACCACTGACTCGAGGCGCGCCTAGGCCTTGACGGCCTTCCGC
1561      ---------+---------+---------+---------+---------+---------+
          CGCGGGTGGTGGTGGTAGTGGTGACTGAGCTCCGCGCGGATCCGGAACTGCCGGAAGGCG
            A  H  H  H  H  H  H  *

```
                      HindIII
         NheI  PmeI   AflII                              PstI
         CCAAGCTGGCTAGCGTTTAAACTTAAGCTTGCCACCATGCCTATGGGCAGCCTGCAGCCT
    1    ---------+---------+---------+---------+---------+---------+
         GGTTCGACCGATCGCAAATTTGAATTCGAACGGTGGTACGGATACCCGTCGGACGTCGGA
                                         M   P   M   G   S   L   Q   P BspMI      SphI                        PvuII
         CTGGCCACCCTGTACCTGCTGGGCATGCTGGTGGCCTCCGTGCTGGCAGCTGGCAACCTG
    61   ---------+---------+---------+---------+---------+---------+
         GACCGGTGGGACATGGACGACCCGTACGACCACCGGAGGCACGACCGTCGACCGTTGGAC
          L   A   T   L   Y   L   L   G   M   L   V   A   S   V   L   A   A   G   N   L TGGGTCACAGTGTACTACGGCGTGCCCGTGTGGAAAGAGGCCAAGACCACCCTGTTCTGC
   121   ---------+---------+---------+---------+---------+---------+
         ACCCAGTGTCACATGATGCCGCACGGGCACACCTTTCTCCGGTTCTGGTGGGACAAGACG
          W   V   T   V   Y   Y   G   V   P   V   W   K   E   A   K   T   T   L   F   C StuI
         GCCAGCGACGCCAAGGCCTACGAGAAAGAGGTGCACAACGTCTGGGCCACCCACGCCTGC
   181   ---------+---------+---------+---------+---------+---------+
         CGGTCGCTGCGGTTCCGGATGCTCTTTCTCCACGTGTTGCAGACCCGGTGGGTGCGGACG
          A   S   D   A   K   A   Y   E   K   E   V   H   N   V   W   A   T   H   A   C PflMI
         GTGCCCACCGACCCCAACCCCCAGGAAATGGTCCTGGAAAACGTGACCGAGAACTTCAAC
   241   ---------+---------+---------+---------+---------+---------+
         CACGGGTGGCTGGGGTTGGGGGTCCTTTACCAGGACCTTTTGCACTGGCTCTTGAAGTTG
          V   P   T   D   P   N   P   Q   E   M   V   L   E   N   V   T   E   N   F   N
```

```
                                              BclI
      ATGTGGGAGAACGACGTGGTGGACCAGATGCACGAGGACGTGATCAGCCTGTGGGACCAG
301   ---------+---------+---------+---------+---------+---------+
      TACACCCTCTTGCTGCACCACCTGGTCTACGTGCTCCTGCACTAGTCGGACACCCTGGTC
       M  W  E  N  D  V  V  D  Q  M  H  E  D  V  I  S  L  W  D  Q

PstI
      AGCCTGAAGCCCTGCGTGAAGCTGACCCCCCTGTGCGTGACCCTGAACTGCAGCAAGGCC
361   ---------+---------+---------+---------+---------+---------+
      TCGGACTTCGGGACGCACTTCGACTGGGGGGACACGCACTGGGACTTGACGTCGTTCCGG
       S  L  K  P  C  V  K  L  T  P  L  C  V  T  L  N  C  S  K  A

BclI                                     PstI
      AAGAACATCACCGAGGAAGTGATCAAGAACAACACCTACAAAGAGGACATCCGGAACTGC
421   ---------+---------+---------+---------+---------+---------+
      TTCTTGTAGTGGCTCCTTCACTAGTTCTTGTTGTGGATGTTTCTCCTGTAGGCCTTGACG
       K  N  I  T  E  E  V  I  K  N  N  T  Y  K  E  D  I  R  N  C

AGCTTCAACGCCACCACCGAAGTGAAGGACAAGAAACAGAAGGTGCACGCCCTGTTCTAC
481   ---------+---------+---------+---------+---------+---------+
      TCGAAGTTGCGGTGGTGGCTTCACTTCCTGTTCTTTGTCTTCCACGTGCGGGACAAGATG
       S  F  N  A  T  T  E  V  K  D  K  K  Q  K  V  H  A  L  F  Y

CGGCTGGACATCGTGCCCCTGAACAAGCGGAACAGCAGCGAGAGCGAGGAAGAGAACAGC
541   ---------+---------+---------+---------+---------+---------+
      GCCGACCTGTAGCACGGGGACTTGTTCGCCTTGTCGTCGCTCTCGCTCCTTCTCTTGTCG
       R  L  D  I  V  P  L  N  K  R  N  S  S  E  S  E  E  E  N  S

BclI                          StuI
      TCCGGCTACTACCGGCTGATCAACTGCAACACCAGCGCCGTGACCCAGGCCTGCCCCAAA
601   ---------+---------+---------+---------+---------+---------+
      AGGCCGATGATGGCCGACTAGTTGACGTTGTGGTCGCGGCACTGGGTCCGGACGGGGTTT
       S  G  Y  Y  R  L  I  N  C  N  T  S  A  V  T  Q  A  C  P  K
```

```
        GTGACCTTCGACCCCATCCCCATCCACTACTGCACCCCTGCCGGCTACGCCATCCTGAAG
661     ---------+---------+---------+---------+---------+---------+
        CACTGGAAGCTGGGGTAGGGGTAGGTGATGACGTGGGGACGGCCGATGCGGTAGGACTTC
         V  T  F  D  P  I  P  I  H  Y  C  T  P  A  G  Y  A  I  L  K

TGCAACGAGGAAACCTTCAACGGCACCGGCCCCTGCCACAACGTGTCCACCGTGCAGTGC
721     ---------+---------+---------+---------+---------+---------+
        ACGTTGCTCCTTTGGAAGTTGCCGTGGCCGGGGACGGTGTTGCACAGGTGGCACGTCACG
         C  N  E  E  T  F  N  G  T  G  P  C  H  N  V  S  T  V  Q  C

PvuII
        ACCCACGGCATCAAGCCCGTGGTGTCCACCCAGCTGCTGCTGAATGGCAGCCTGGCTGAG
781     ---------+---------+---------+---------+---------+---------+
        TGGGTGCCGTAGTTCGGGCACCACAGGTGGGTCGACGACGACTTACCGTCGGACCGACTC
         T  H  G  I  K  P  V  V  S  T  Q  L  L  L  N  G  S  L  A  E

GGCGAGATCATCATCAGAAGCAAGAACCTGACCGACAACGCCAAGACCATCATTGTGCAC
841     ---------+---------+---------+---------+---------+---------+
        CCGCTCTAGTAGTAGTCTTCGTTCTTGGACTGGCTGTTGCGGTTCTGGTAGTAACACGTG
         G  E  I  I  I  R  S  K  N  L  T  D  N  A  K  T  I  I  V  H

PflMI
        CTGAACCAGAGCGTGGAAATCGTGTGCACCCGGCCCAACGAGAACCGGCGGAAGTCCATC
901     ---------+---------+---------+---------+---------+---------+
        GACTTGGTCTCGCACCTTTAGCACACGTGGGCCGGGTTGCTCTTGGCCGCCTTCAGGTAG
         L  N  Q  S  V  E  I  V  C  T  R  P  N  E  N  R  R  K  S  I

StuI
        CGGATCGGCCCAGGCCAGGCCTTTTACGCCACCGGCGACATCATCGGCGACATCCGGCAG
961     ---------+---------+---------+---------+---------+---------+
        GCCTAGCCGGGTCCGGTCCGGAAAATGCGGTGGCCGCTGTAGTAGCCGCTGTAGGCCGTC
         R  I  G  P  G  Q  A  F  Y  A  T  G  D  I  I  G  D  I  R  Q
```

```
                                              PstI
      GCCCGGTGCAACATCAGCGAAGAGAAGTGGAACGAGACACTGCAGAGAGTGGGCCGGAAG
1021  ---------+---------+---------+---------+---------+---------+
      CGGGCCACGTTGTAGTCGCTTCTCTTCACCTTGCTCTGTGACGTCTCTCACCCGGCCTTC
       A  R  C  N  I  S  E  E  K  W  N  E  T  L  Q  R  V  G  R  K

CTGGCCGAGCACTTCCCCAACAAGACAATCAAGTTCAAGAGCAGCTCTGGCGGCGACCTG
1081  ---------+---------+---------+---------+---------+---------+
      GACCGGCTCGTGAAGGGGTTGTTCTGTTAGTTCAAGTTCTCGTCGAGACCGCCGCTGGAC
       L  A  E  H  F  P  N  K  T  I  K  F  K  S  S  S  G  G  D  L

PstI
      GAAATCACCACCCACAGCTTCAACTGCAGAGGCGAGTTCTTCTACTGCAATACCTCCGGC
1141  ---------+---------+---------+---------+---------+---------+
      CTTTAGTGGTGGGTGTCGAAGTTGACGTCTCCGCTCAAGAAGATGACGTTATGGAGGCCG
       E  I  T  T  H  S  F  N  C  R  G  E  F  F  Y  C  N  T  S  G

CTGTTCAATGGCACCTACATGCCCACCTATATGCCCAACAGCACCAACTCCAACAGCAGC
1201  ---------+---------+---------+---------+---------+---------+
      GACAAGTTACCGTGGATGTACGGGTGGATATACGGGTTGTCGTGGTTGAGGTTGTCGTCG
       L  F  N  G  T  Y  M  P  T  Y  M  P  N  S  T  N  S  N  S  S

AGCAACATCACCATCCCTTGCCGGATCAAACAGGTCATCAATATGTGGCAGGAAGTGGGC
1261  ---------+---------+---------+---------+---------+---------+
      TCGTTGTAGTGGTAGGGAACGGCCTAGTTTGTCCAGTAGTTATACACCGTCCTTCACCCG
       S  N  I  T  I  P  C  R  I  K  Q  V  I  N  M  W  Q  E  V  G

AGAGCTATGTACGCCCCTCCCATCGAGGGGGAGATCACATGCAAGTCCAACATCACCGGC
1321  ---------+---------+---------+---------+---------+---------+
      TCTCGATACATGCGGGGAGGGTAGCTCCCCCTCTAGTGTACGTTCAGGTTGTAGTGGCCG
       R  A  M  Y  A  P  P  I  E  G  E  I  T  C  K  S  N  I  T  G

BglII
      CTGCTGCTCGTCCGCGACGGCGGCAACGGCAACGACACCAACAAGACCGAGATCTTCCGG
1381  ---------+---------+---------+---------+---------+---------+
      GACGACGAGCAGGCGCTGCCGCCGTTGCCGTTGCTGTGGTTGTTCTGGCTCTAGAAGGCC
       L  L  L  V  R  D  G  G  N  G  N  D  T  N  K  T  E  I  F  R
```

```
        CCCGAGGGCGGCGACATGAGAGACAATTGGCGGAGCGAGCTGTACAAGTACAAGGTGGTG
1441    ---------+---------+---------+---------+---------+---------+
        GGGCTCCCGCCGCTGTACTCTCTGTTAACCGCCTCGCTCGACATGTTCATGTTCCACCAC
         P   E   G   G   D   M   R   D   N   W   R   S   E   L   Y   K   Y   K   V   V

GAAATCAAGCCCCTGGGAATCGCCCCCACCGAGGCCAAGCGGAGAGTGGTGGAAAGCGAG
1501    ---------+---------+---------+---------+---------+---------+
        CTTTAGTTCGGGGACCCTTAGCGGGGGTGGCTCCGGTTCGCCTCTCACCACCTTTCGCTC
         E   I   K   P   L   G   I   A   P   T   E   A   K   R   R   V   V   E   S   E

NarI
                                    KasI
        AAGTCCGCCGTGGGCATCGGCGCCGTGATCCTGGGCTTTCTGGGAGCCGCCGGAAGCACA
1561    ---------+---------+---------+---------+---------+---------+
        TTCAGGCGGCACCCGTAGCCGCGGCACTAGGACCCGAAAGACCCTCGGCGGCCTTCGTGT
         K   S   A   V   G   I   G   A   V   I   L   G   F   L   G   A   A   G   S   T

PvuII
        ATGGGCGCTGCCAGCATCACCCTGACCGCCCAGGCTAGACAGCTGCTGAGCGGCATCGTG
1621    ---------+---------+---------+---------+---------+---------+
        TACCCGCGACGGTCGTAGTGGGACTGGCGGGTCCGATCTGTCGACGACTCGCCGTAGCAC
         M   G   A   A   S   I   T   L   T   A   Q   A   R   Q   L   L   S   G   I   V

PvuII
                BspMI                                       PstI
        CAGCAGCAGAGCAACCTGCTGAAGGCCATCGACGCCCAGCAGCATCTGCTGCAGCTGACC
1681    ---------+---------+---------+---------+---------+---------+
        GTCGTCGTCTCGTTGGACGACTTCCGGTAGCTGCGGGTCGTCGTAGACGACGTCGACTGG
         Q   Q   Q   S   N   L   L   K   A   I   D   A   Q   Q   H   L   L   Q   L   T

PvuII
                    PstI    SmaI
        GTGTGGGGCATCAAGCAGCTGCAGGCCCGGGTGCTGGCCGTGGAAAGATACCTGAAGGAC
1741    ---------+---------+---------+---------+---------+---------+
        CACACCCCGTAGTTCGTCGACGTCCGGGCCCACGACCGGCACCTTTCTATGGACTTCCTG
         V   W   G   I   K   Q   L   Q   A   R   V   L   A   V   E   R   Y   L   K   D
```

```
                               PstI
        CAGCAGCTCCTGGGAATCTGGGGCTGCAGCGGCAAGCTGATCTGCCCCACCAACGTGCCC
1801    ---------+---------+---------+---------+---------+---------+
        GTCGTCGAGGACCCTTAGACCCCGACGTCGCCGTTCGACTAGACGGGGTGGTTGCACGGG
         Q  Q  L  L  G  I  W  G  C  S  G  K  L  I  C  P  T  N  V  P

TGGAACAGCTCCTGGTCCAACAAGAGCAAAGAGTATATCTGGAACAACATGACCTGGATG
1861    ---------+---------+---------+---------+---------+---------+
        ACCTTGTCGAGGACCAGGTTGTTCTCGTTTCTCATATAGACCTTGTTGTACTGGACCTAC
         W  N  S  S  W  S  N  K  S  K  E  Y  I  W  N  N  M  T  W  M

CAGTGGGACGGCGAGATCAGCAACTACACCGACATCATCTACGGCCTGCTGGAAGATAGC
1921    ---------+---------+---------+---------+---------+---------+
        GTCACCCTGCCGCTCTAGTCGTTGATGTGGCTGTAGTAGATGCCGGACGACCTTCTATCG
         Q  W  D  G  E  I  S  N  Y  T  D  I  I  Y  G  L  L  E  D  S

BspMI           PvuII
        CAGATCCAGCAGGAAAAGAACGAGAAGGACCTGCTGACCCTGGACAGCTGGAAGAACCTG
1981    ---------+---------+---------+---------+---------+---------+
        GTCTAGGTCGTCCTTTTCTTGCTCTTCCTGGACGACTGGGACCTGTCGACCTTCTTGGAC
         Q  I  Q  Q  E  K  N  E  K  D  L  L  T  L  D  S  W  K  N  L

BglII
        TGGAATTGGTTCGACATCACCAAGTGGCTGTGGTACATCAAGATCTTCATCATGATCGTG
2041    ---------+---------+---------+---------+---------+---------+
        ACCTTAACCAAGCTGTAGTGGTTCACCGACACCATGTAGTTCTAGAAGTAGTACTAGCAC
         W  N  W  F  D  I  T  K  W  L  W  Y  I  K  I  F  I  M  I  V

GGCGGCCTGATCGGCCTGCGGATCATCTTCGCCGTGCTGAGCATCGTGGGAGGCGGAGCC
2101    ---------+---------+---------+---------+---------+---------+
        CCGCCGGACTAGCCGGACGCCTAGTAGAAGCGGCACGACTCGTAGCACCCTCCGCCTCGG
         G  G  L  I  G  L  R  I  I  F  A  V  L  S  I  V  G  G  A

AAGTTCGTGGCCGCCTGGACACTGAAAGCCGCTGCTGGCGGCACCGAGACATCTCAGGTG
2161    ---------+---------+---------+---------+---------+---------+
        TTCAAGCACCGGCGGACCTGTGACTTTCGGCGACGACCGCCGTGGCTCTGTAGAGTCCAC
         K  F  V  A  A  W  T  L  K  A  A  A  G  G  T  E  T  S  Q  V
```

```
             XhoI  XbaI  ApaI   PmeI
       GCCCCTGCCTGACTCGAGTCTAGAGGGCCCGTTTAAACCCGC
2221   ---------+---------+---------+---------+--
       CGGGGACGGACTGAGCTCAGATCTCCCGGGCAAATTTGGGCG
       A   P   A   *
```

FIG. 36

```
                          PacI    HindIII                              PstI
            GAGCGGAAGGCCCATGAGGCCAGTTAATTAAGCTTGCCACCATGCCTATGGGCAGCCTGC
          1 ---------+---------+---------+---------+---------+---------+
            CTCGCCTTCCGGGTACTCCGGTCAATTAATTCGAACGGTGGTACGGATACCCGTCGGACG
                                                       M  P  M  G  S  L  Q BspMI    SphI                            PvuII
            AGCCTCTGGCCACCCTGTACCTGCTGGGCATGCTGGTGGCCTCCGTGCTGGCAGCTGGCA
         61 ---------+---------+---------+---------+---------+---------+
            TCGGAGACCGGTGGGACATGGACGACCCGTACGACCACCGGAGGCACGACCGTCGACCGT
             P  L  A  T  L  Y  L  L  G  M  L  V  A  S  V  L  A  A  G  N ACCTGTGGGTCACAGTGTACTACGGCGTGCCCGTGTGGAAAGAGGCCAAGACCACCCTGT
        121 ---------+---------+---------+---------+---------+---------+
            TGGACACCCAGTGTCACATGATGCCGCACGGGCACACCTTTCTCCGGTTCTGGTGGGACA
             L  W  V  T  V  Y  Y  G  V  P  V  W  K  E  A  K  T  T  L  F StuI
            TCTGCGCCAGCGACGCCAAGGCCTACGAGAAAGAGGTGCACAACGTCTGGGCCACCCACG
        181 ---------+---------+---------+---------+---------+---------+
            AGACGCGGTCGCTGCGGTTCCGGATGCTCTTTCTCCACGTGTTGCAGACCCGGTGGGTGC
             C  A  S  D  A  K  A  Y  E  K  E  V  H  N  V  W  A  T  H  A PflMI
            CCTGCGTGCCCACCGACCCCAACCCCCAGGAAATGGTCCTGGAAAACGTGACCGAGAACT
        241 ---------+---------+---------+---------+---------+---------+
            GGACGCACGGGTGGCTGGGGTTGGGGGTCCTTTACCAGGACCTTTTGCACTGGCTCTTGA
             C  V  P  T  D  P  N  P  Q  E  M  V  L  E  N  V  T  E  N  F
```

```
                                                             BclI
        TCAACATGTGGAAGAACGACATGGTGGAACAGATGCACGAGGACGTGATCAGCCTGTGGG
301     ---------+---------+---------+---------+---------+---------+
        AGTTGTACACCTTCTTGCTGTACCACCTTGTCTACGTGCTCCTGCACTAGTCGGACACCC
         N  M  W  K  N  D  M  V  E  Q  M  H  E  D  V  I  S  L  W  D

ACCAGAGCCTGAAGCCCTGCGTGAAGCTGACCCCCCTGTGCGTGACCCTGGAATGCAGAC
361     ---------+---------+---------+---------+---------+---------+
        TGGTCTCGGACTTCGGGACGCACTTCGACTGGGGGGACACGCACTGGGACCTTACGTCTG
         Q  S  L  K  P  C  V  K  L  T  P  L  C  V  T  L  E  C  R  Q

HincII
        AGGTCAACACCACCAACGCCACCAGCAGCGTGAACGTGACCAACGGCGAGGAAATCAAGA
421     ---------+---------+---------+---------+---------+---------+
        TCCAGTTGTGGTGGTTGCGGTGGTCGTCGCACTTGCACTGGTTGCCGCTCCTTTAGTTCT
         V  N  T  T  N  A  T  S  S  V  N  V  T  N  G  E  E  I  K  N PstI
        ACTGCAGCTTCAATGCCACCACCGAGATCCGGGACAAGAAACAGAAGGTGTACGCCCTGT
481     ---------+---------+---------+---------+---------+---------+
        TGACGTCGAAGTTACGGTGGTGGCTCTAGGCCCTGTTCTTTGTCTTCCACATGCGGGACA
         C  S  F  N  A  T  T  E  I  R  D  K  K  Q  K  V  Y  A  L  F TCTACCGGCTGGACATCGTGCCCCTGGAAGAGGAACGGAAGGGCAACAGCAGCAAGTACC
541     ---------+---------+---------+---------+---------+---------+
        AGATGGCCGACCTGTAGCACGGGGACCTTCTCCTTGCCTTCCCGTTGTCGTCGTTCATGG
         Y  R  L  D  I  V  P  L  E  E  E  R  K  G  N  S  S  K  Y  R BclI                          StuI
        GGCTGATCAACTGCAACACCAGCGCCATCACCCAGGCCTGCCCCAAAGTGACCTTCGACC
601     ---------+---------+---------+---------+---------+---------+
        CCGACTAGTTGACGTTGTGGTCGCGGTAGTGGGTCCGGACGGGGTTTCACTGGAAGCTGG
         L  I  N  C  N  T  S  A  I  T  Q  A  C  P  K  V  T  F  D  P
```

```
       CTATCCCCATCCACTACTGCGCCCCTGCCGGCTACGCCATCCTGAAGTGCAACAACAAGA
  661  ---------+---------+---------+---------+---------+---------+
       GATAGGGGTAGGTGATGACGCGGGGACGGCCGATGCGGTAGGACTTCACGTTGTTGTTCT
        I  P  I  H  Y  C  A  P  A  G  Y  A  I  L  K  C  N  N  K  T

CCTTCAACGGCACCGGCCCCTGCAACAACGTGTCCACCGTGCAGTGCACCCACGGCATCA
  721  ---------+---------+---------+---------+---------+---------+
       GGAAGTTGCCGTGGCCGGGGACGTTGTTGCACAGGTGGCACGTCACGTGGGTGCCGTAGT
        F  N  G  T  G  P  C  N  N  V  S  T  V  Q  C  T  H  G  I  K

PvuII
       AGCCCGTGGTGTCCACCCAGCTGCTGCTGAATGGCAGCCTGGCCGAGGGCGAGATCATCA
  781  ---------+---------+---------+---------+---------+---------+
       TCGGGCACCACAGGTGGGTCGACGACGACTTACCGTCGGACCGGCTCCCGCTCTAGTAGT
        P  V  V  S  T  Q  L  L  L  N  G  S  L  A  E  G  E  I  I  I

TCAGAAGCGAGAACCTGACCAACAACGTGAAAACCATCATCGTGCACCTGAACGAGAGCG
  841  ---------+---------+---------+---------+---------+---------+
       AGTCTTCGCTCTTGGACTGGTTGTTGCACTTTTGGTAGTAGCACGTGGACTTGCTCTCGC
        R  S  E  N  L  T  N  N  V  K  T  I  I  V  H  L  N  E  S  V

TGGAAATCGTGTGCACCCGGCCCAACAACAACACCAGAAAGAGCATCCGGATCGGCCCTG
  901  ---------+---------+---------+---------+---------+---------+
       ACCTTTAGCACACGTGGGCCGGGTTGTTGTTGTGGTCTTTCTCGTAGGCCTAGCCGGGAC
        E  I  V  C  T  R  P  N  N  N  T  R  K  S  I  R  I  G  P  G

StuI
       GCCAGACCTTTTACGCCACCGGCGACATCATCGGCAACATCCGGCAGGCCTACTGCAACA
  961  ---------+---------+---------+---------+---------+---------+
       CGGTCTGGAAAATGCGGTGGCCGCTGTAGTAGCCGTTGTAGGCCGTCCGGATGACGTTGT
        Q  T  F  Y  A  T  G  D  I  I  G  N  I  R  Q  A  Y  C  N  I

BamHI        PstI
       TCAAGAAGGACGACTGGATCCGGACCCTGCAGAGAGTGGGCAAGAAGCTGGCCGAGCACT
 1021  ---------+---------+---------+---------+---------+---------+
       AGTTCTTCCTGCTGACCTAGGCCTGGGACGTCTCTCACCCGTTCTTCGACCGGCTCGTGA
        K  K  D  D  W  I  R  T  L  Q  R  V  G  K  K  L  A  E  H  F
```

```
        TCCCCAGACGGATCATCAACTTCACCAGCCCCGCTGGCGGCGACCTGGAAATCACCACCC
1081    ---------+---------+---------+---------+---------+---------+
        AGGGGTCTGCCTAGTAGTTGAAGTGGTCGGGGCGACCGCCGCTGGACCTTTAGTGGTGGG
         P   R   R   I   N   F   T   S   P   A   G   G   D   L   E   I   T   T   H

PstI
        ACAGCTTCAACTGCAGAGGCGAGTTCTTCTACTGCAATACCAGCAGCCTGTTCAACAGCA
1141    ---------+---------+---------+---------+---------+---------+
        TGTCGAAGTTGACGTCTCCGCTCAAGAAGATGACGTTATGGTCGTCGGACAAGTTGTCGT
         S   F   N   C   R   G   E   F   F   Y   C   N   T   S   S   L   F   N   S   T

CCTACAACCCCAACGACACCAACAGCAACAGCTCCAGCAGCAACTCCAGCCTGGACATCA
1201    ---------+---------+---------+---------+---------+---------+
        GGATGTTGGGGTTGCTGTGGTTGTCGTTGTCGAGGTCGTCGTTGAGGTCGGACCTGTAGT
         Y   N   P   N   D   T   N   S   N   S   S   S   S   N   S   S   L   D   I   T

CCATCCCTTGCCGGATCAAGCAGATCATCAATATGTGGCAGGAAGTGGGCAGGGCTATGT
1261    ---------+---------+---------+---------+---------+---------+
        GGTAGGGAACGGCCTAGTTCGTCTAGTAGTTATACACCGTCCTTCACCCGTCCCGATACA
         I   P   C   R   I   K   Q   I   I   N   M   W   Q   E   V   G   R   A   M   Y

ACGCCCCTCCCATCGAGGGCAACATCACATGCAAGAGCAACATCACCGGCCTGCTCCTGG
1321    ---------+---------+---------+---------+---------+---------+
        TGCGGGGAGGGTAGCTCCCGTTGTAGTGTACGTTCTCGTTGTAGTGGCCGGACGAGGACC
         A   P   P   I   E   G   N   I   T   C   K   S   N   I   T   G   L   L   L   V

BglII
        TCCGCGACGGCGGCGTGGAAAGCAACGAGACAGAGATCTTCAGACCCGGCGGAGGCGACA
1381    ---------+---------+---------+---------+---------+---------+
        AGGCGCTGCCGCCGCACCTTTCGTTGCTCTGTCTCTAGAAGTCTGGGCCGCCTCCGCTGT
         R   D   G   G   V   E   S   N   E   T   E   I   F   R   P   G   G   G   D   M

TGCGGAACAACTGGCGGAGCGAGCTGTACAAGTACAAGGTGGTGGAAATCAAGCCCCTGG
1441    ---------+---------+---------+---------+---------+---------+
        ACGCCTTGTTGACCGCCTCGCTCGACATGTTCATGTTCCACCACCTTTAGTTCGGGGACC
         R   N   N   W   R   S   E   L   Y   K   Y   K   V   V   E   I   K   P   L   G
```

```
                                              NarI
                                              KasI
         GAATCGCCCCCACCGCCGCCAAGCGGAGAGTGGTGGAAGGCGCCCACCACCACCATCACC
    1501 ---------+---------+---------+---------+---------+---------+
         CTTAGCGGGGGTGGCGGCGGTTCGCCTCTCACCACCTTCCGCGGGTGGTGGTGGTAGTGG
            I  A  P  T  A  A  K  R  R  V  V  E  G  A  H  H  H  H  H  H

BssHII  StuI
            XhoI AscI   AvrII
         ACTGACTCGAGGCGCGCCTAGGCCTTGACGGCCTTCCGCCA
    1561 ---------+---------+---------+---------+-
         TGACTGAGCTCCGCGCGGATCCGGAACTGCCGGAAGGCGGT
            *
```

FIG. 37

```
                                   HindIII
          NheI    PmeI    AflII                                    PstI
        CCAAGCTGGCTAGCGTTTAAACTTAAGCTTGCCACCATGCCTATGGGCAGCCTGCAGCCT
     1  ---------+---------+---------+---------+---------+---------+
        GGTTCGACCGATCGCAAATTTGAATTCGAACGGTGGTACGGATACCCGTCGGACGTCGGA
                                         M   P   M   G   S   L   Q   P BspMI      SphI                        PvuII
        CTGGCCACCCTGTACCTGCTGGGCATGCTGGTGGCCTCCGTGCTGGCAGCTGGCAACCTG
    61  ---------+---------+---------+---------+---------+---------+
        GACCGGTGGGACATGGACGACCCGTACGACCACCGGAGGCACGACCGTCGACCGTTGGAC
         L   A   T   L   Y   L   L   G   M   L   V   A   S   V   L   A   A   G   N   L TGGGTCACAGTGTACTACGGCGTGCCCGTGTGGAAAGAGGCCAAGACCACCCTGTTCTGC
   121  ---------+---------+---------+---------+---------+---------+
        ACCCAGTGTCACATGATGCCGCACGGGCACACCTTTCTCCGGTTCTGGTGGGACAAGACG
         W   V   T   V   Y   Y   G   V   P   V   W   K   E   A   K   T   T   L   F   C StuI
        GCCAGCGACGCCAAGGCCTACGAGAAAGAGGTGCACAACGTCTGGGCCACCCACGCCTGC
   181  ---------+---------+---------+---------+---------+---------+
        CGGTCGCTGCGGTTCCGGATGCTCTTTCTCCACGTGTTGCAGACCCGGTGGGTGCGGACG
         A   S   D   A   K   A   Y   E   K   E   V   H   N   V   W   A   T   H   A   C PflMI
        GTGCCCACCGACCCCAACCCCCAGGAAATGGTCCTGGAAAACGTGACCGAGAACTTCAAC
   241  ---------+---------+---------+---------+---------+---------+
        CACGGGTGGCTGGGGTTGGGGGTCCTTTACCAGGACCTTTTGCACTGGCTCTTGAAGTTG
         V   P   T   D   P   N   P   Q   E   M   V   L   E   N   V   T   E   N   F   N
```

```
                                                           BclI
       ATGTGGAAGAACGACATGGTGGAACAGATGCACGAGGACGTGATCAGCCTGTGGGACCAG
301    ---------+---------+---------+---------+---------+---------+
       TACACCTTCTTGCTGTACCACCTTGTCTACGTGCTCCTGCACTAGTCGGACACCCTGGTC
        M  W  K  N  D  M  V  E  Q  M  H  E  D  V  I  S  L  W  D  Q

HincII
       AGCCTGAAGCCCTGCGTGAAGCTGACCCCCCTGTGCGTGACCCTGGAATGCAGACAGGTC
361    ---------+---------+---------+---------+---------+---------+
       TCGGACTTCGGGACGCACTTCGACTGGGGGGACACGCACTGGGACCTTACGTCTGTCCAG
        S  L  K  P  C  V  K  L  T  P  L  C  V  T  L  E  C  R  Q  V PstI
       AACACCACCAACGCCACCAGCAGCGTGAACGTGACCAACGGCGAGGAAATCAAGAACTGC
421    ---------+---------+---------+---------+---------+---------+
       TTGTGGTGGTTGCGGTGGTCGTCGCACTTGCACTGGTTGCCGCTCCTTTAGTTCTTGACG
        N  T  T  N  A  T  S  S  V  N  V  T  N  G  E  E  I  K  N  C AGCTTCAATGCCACCACCGAGATCCGGGACAAGAAACAGAAGGTGTACGCCCTGTTCTAC
481    ---------+---------+---------+---------+---------+---------+
       TCGAAGTTACGGTGGTGGCTCTAGGCCCTGTTCTTTGTCTTCCACATGCGGGACAAGATG
        S  F  N  A  T  T  E  I  R  D  K  K  Q  K  V  Y  A  L  F  Y BclI
       CGGCTGGACATCGTGCCCCTGGAAGAGGAACGGAAGGGCAACAGCAGCAAGTACCGGCTG
541    ---------+---------+---------+---------+---------+---------+
       GCCGACCTGTAGCACGGGGACCTTCTCCTTGCCTTCCCGTTGTCGTCGTTCATGGCCGAC
        R  L  D  I  V  P  L  E  E  E  R  K  G  N  S  S  K  Y  R  L StuI
       ATCAACTGCAACACCAGCGCCATCACCCAGGCCTGCCCCAAAGTGACCTTCGACCCTATC
601    ---------+---------+---------+---------+---------+---------+
       TAGTTGACGTTGTGGTCGCGGTAGTGGGTCCGGACGGGGTTTCACTGGAAGCTGGGATAG
        I  N  C  N  T  S  A  I  T  Q  A  C  P  K  V  T  F  D  P  I
```

```
             CCCATCCACTACTGCGCCCCTGCCGGCTACGCCATCCTGAAGTGCAACAACAAGACCTTC
     661    ---------+---------+---------+---------+---------+---------+
             GGGTAGGTGATGACGCGGGGACGGCCGATGCGGTAGGACTTCACGTTGTTGTTCTGGAAG
              P  I  H  Y  C  A  P  A  G  Y  A  I  L  K  C  N  N  K  T  F

AACGGCACCGGCCCCTGCAACAACGTGTCCACCGTGCAGTGCACCCACGGCATCAAGCCC
     721    ---------+---------+---------+---------+---------+---------+
             TTGCCGTGGCCGGGGACGTTGTTGCACAGGTGGCACGTCACGTGGGTGCCGTAGTTCGGG
              N  G  T  G  P  C  N  N  V  S  T  V  Q  C  T  H  G  I  K  P

PvuII
             GTGGTGTCCACCCAGCTGCTGCTGAATGGCAGCCTGGCCGAGGGCGAGATCATCATCAGA
     781    ---------+---------+---------+---------+---------+---------+
             CACCACAGGTGGGTCGACGACGACTTACCGTCGGACCGGCTCCCGCTCTAGTAGTAGTCT
              V  V  S  T  Q  L  L  L  N  G  S  L  A  E  G  E  I  I  I  R

AGCGAGAACCTGACCAACAACGTGAAAACCATCATCGTGCACCTGAACGAGAGCGTGGAA
     841    ---------+---------+---------+---------+---------+---------+
             TCGCTCTTGGACTGGTTGTTGCACTTTTGGTAGTAGCACGTGGACTTGCTCTCGCACCTT
              S  E  N  L  T  N  N  V  K  T  I  I  V  H  L  N  E  S  V  E

ATCGTGTGCACCCGGCCCAACAACAACACCAGAAAGAGCATCCGGATCGGCCCTGGCCAG
     901    ---------+---------+---------+---------+---------+---------+
             TAGCACACGTGGGCCGGGTTGTTGTTGTGGTCTTTCTCGTAGGCCTAGCCGGGACCGGTC
              I  V  C  T  R  P  N  N  N  T  R  K  S  I  R  I  G  P  G  Q

StuI
             ACCTTTTACGCCACCGGCGACATCATCGGCAACATCCGGCAGGCCTACTGCAACATCAAG
     961    ---------+---------+---------+---------+---------+---------+
             TGGAAAATGCGGTGGCCGCTGTAGTAGCCGTTGTAGGCCGTCCGGATGACGTTGTAGTTC
              T  F  Y  A  T  G  D  I  I  G  N  I  R  Q  A  Y  C  N  I  K

BamHI      PstI
             AAGGACGACTGGATCCGGACCCTGCAGAGAGTGGGCAAGAAGCTGGCCGAGCACTTCCCC
    1021    ---------+---------+---------+---------+---------+---------+
             TTCCTGCTGACCTAGGCCTGGGACGTCTCTCACCCGTTCTTCGACCGGCTCGTGAAGGGG
              K  D  D  W  I  R  T  L  Q  R  V  G  K  K  L  A  E  H  F  P
```

```
        AGACGGATCATCAACTTCACCAGCCCCGCTGGCGGCGACCTGGAAATCACCACCCACAGC
1081    ---------+---------+---------+---------+---------+---------+
        TCTGCCTAGTAGTTGAAGTGGTCGGGGCGACCGCCGCTGGACCTTTAGTGGTGGGTGTCG
         R   R   I   I   N   F   T   S   P   A   G   G   D   L   E   I   T   T   H   S

PstI
        TTCAACTGCAGAGGCGAGTTCTTCTACTGCAATACCAGCAGCCTGTTCAACAGCACCTAC
1141    ---------+---------+---------+---------+---------+---------+
        AAGTTGACGTCTCCGCTCAAGAAGATGACGTTATGGTCGTCGGACAAGTTGTCGTGGATG
         F   N   C   R   G   E   F   F   Y   C   N   T   S   S   L   F   N   S   T   Y

AACCCCAACGACACCAACAGCAACAGCTCCAGCAGCAACTCCAGCCTGGACATCACCATC
1201    ---------+---------+---------+---------+---------+---------+
        TTGGGGTTGCTGTGGTTGTCGTTGTCGAGGTCGTCGTTGAGGTCGGACCTGTAGTGGTAG
         N   P   N   D   T   N   S   N   S   S   S   S   N   S   S   L   D   I   T   I

CCTTGCCGGATCAAGCAGATCATCAATATGTGGCAGGAAGTGGGCAGGGCTATGTACGCC
1261    ---------+---------+---------+---------+---------+---------+
        GGAACGGCCTAGTTCGTCTAGTAGTTATACACCGTCCTTCACCCGTCCCGATACATGCGG
         P   C   R   I   K   Q   I   I   N   M   W   Q   E   V   G   R   A   M   Y   A

CCTCCCATCGAGGGCAACATCACATGCAAGAGCAACATCACCGGCCTGCTCCTGGTCCGC
1321    ---------+---------+---------+---------+---------+---------+
        GGAGGGTAGCTCCCGTTGTAGTGTACGTTCTCGTTGTAGTGGCCGGACGAGGACCAGGCG
         P   P   I   E   G   N   I   T   C   K   S   N   I   T   G   L   L   L   V   R

BglII
        GACGGCGGCGTGGAAAGCAACGAGACAGAGATCTTCAGACCCGGCGGAGGCGACATGCGG
1381    ---------+---------+---------+---------+---------+---------+
        CTGCCGCCGCACCTTTCGTTGCTCTGTCTCTAGAAGTCTGGGCCGCCTCCGCTGTACGCC
         D   G   G   V   E   S   N   E   T   E   I   F   R   P   G   G   G   D   M   R

AACAACTGGCGGAGCGAGCTGTACAAGTACAAGGTGGTGGAAATCAAGCCCCTGGGAATC
1441    ---------+---------+---------+---------+---------+---------+
        TTGTTGACCGCCTCGCTCGACATGTTCATGTTCCACCACCTTTAGTTCGGGGACCCTTAG
         N   N   W   R   S   E   L   Y   K   Y   K   V   V   E   I   K   P   L   G   I
```

```
                                        NarI
                                        KasI
           GCCCCCACCGCCGCCAAGCGGAGAGTGGTGGAAGGCGCCCACCACCACCATCACCACTGC
1501       ---------+---------+---------+---------+---------+---------+
           CGGGGGTGGCGGCGGTTCGCCTCTCACCACCTTCCGCGGGTGGTGGTGGTAGTGGTGACG
           A  P  T  A  A  K  R  R  V  V  E  G  A  H  H  H  H  H  H  C

XhoI  XbaI  ApaI  PmeI
           TGACTCGAGTCTAGAGGGCCCGTTTAAACCCGC
1561       ---------+---------+---------+---
           ACTGAGCTCAGATCTCCCGGGCAAATTTGGGCG
           *
```

FIG. 38

```
                                            PacI       HindIII
      CGAATTGAAGGAAGGCCGTCAAGGCCGCATTTAATTAAGCTTGCCACCATGCCTATGGGC
  1   ---------+---------+---------+---------+---------+---------+
      GCTTAACTTCCTTCCGGCAGTTCCGGCGTAAATTAATTCGAACGGTGGTACGGATACCCG
                                                       M  P  M  G PstI                        BspMI     SphI                  PvuII
      AGCCTGCAGCCTCTGGCCACCCTGTACCTGCTGGGCATGCTGGTGGCCTCCGTGCTGGCA
 61   ---------+---------+---------+---------+---------+---------+
      TCGGACGTCGGAGACCGGTGGGACATGGACGACCCGTACGACCACCGGAGGCACGACCGT
      S  L  Q  P  L  A  T  L  Y  L  L  G  M  L  V  A  S  V  L  A GCTGGCAACCTGTGGGTCACAGTGTACTACGGCGTGCCCGTGTGGAAAGAGGCCAAGACC
121   ---------+---------+---------+---------+---------+---------+
      CGACCGTTGGACACCCAGTGTCACATGATGCCGCACGGGCACACCTTTCTCCGGTTCTGG
      A  G  N  L  W  V  T  V  Y  Y  G  V  P  V  W  K  E  A  K  T StuI
      ACCCTGTTCTGCGCCAGCGACGCCAAGGCCTACGAGAAAGAGGTGCACAACGTCTGGGCC
181   ---------+---------+---------+---------+---------+---------+
      TGGGACAAGACGCGGTCGCTGCGGTTCCGGATGCTCTTTCTCCACGTGTTGCAGACCCGG
      T  L  F  C  A  S  D  A  K  A  Y  E  K  E  V  H  N  V  W  A PflMI
      ACCCACGCCTGCGTGCCCACCGACCCCAACCCCCAGGAAATGGTCCTGGAAAACGTGACC
241   ---------+---------+---------+---------+---------+---------+
      TGGGTGCGGACGCACGGGTGGCTGGGGTTGGGGGTCCTTTACCAGGACCTTTTGCACTGG
      T  H  A  C  V  P  T  D  P  N  P  Q  E  M  V  L  E  N  V  T
```

```
                                                              BclI
      GAGAACTTCAACATGTGGAAGAACGACATGGTGGAACAGATGCACGAGGACGTGATCAGC
301   ---------+---------+---------+---------+---------+---------+
      CTCTTGAAGTTGTACACCTTCTTGCTGTACCACCTTGTCTACGTGCTCCTGCACTAGTCG
       E  N  F  N  M  W  K  N  D  M  V  E  Q  M  H  E  D  V  I  S

CTGTGGGACCAGAGCCTGAAGCCCTGCGTGAAGCTGACCCCCCTGTGCGTGACCCTGGAA
361   ---------+---------+---------+---------+---------+---------+
      GACACCCTGGTCTCGGACTTCGGGACGCACTTCGACTGGGGGGACACGCACTGGGACCTT
       L  W  D  Q  S  L  K  P  C  V  K  L  T  P  L  C  V  T  L  E

HincII
      TGCAGACAGGTCAACACCACCAACGCCACCAGCAGCGTGAACGTGACCAACGGCGAGGAA
421   ---------+---------+---------+---------+---------+---------+
      ACGTCTGTCCAGTTGTGGTGGTTGCGGTGGTCGTCGCACTTGCACTGGTTGCCGCTCCTT
       C  R  Q  V  N  T  T  N  A  T  S  S  V  N  V  T  N  G  E  E PstI
      ATCAAGAACTGCAGCTTCAATGCCACCACCGAGATCCGGGACAAGAAACAGAAGGTGTAC
481   ---------+---------+---------+---------+---------+---------+
      TAGTTCTTGACGTCGAAGTTACGGTGGTGGCTCTAGGCCCTGTTCTTTGTCTTCCACATG
       I  K  N  C  S  F  N  A  T  T  E  I  R  D  K  K  Q  K  V  Y GCCCTGTTCTACCGGCTGGACATCGTGCCCCTGGAAGAGGAACGGAAGGGCAACAGCAGC
541   ---------+---------+---------+---------+---------+---------+
      CGGGACAAGATGGCCGACCTGTAGCACGGGGACCTTCTCCTTGCCTTCCCGTTGTCGTCG
       A  L  F  Y  R  L  D  I  V  P  L  E  E  E  R  K  G  N  S  S BclI                      StuI
      AAGTACCGGCTGATCAACTGCAACACCAGCGCCATCACCCAGGCCTGCCCCAAAGTGACC
601   ---------+---------+---------+---------+---------+---------+
      TTCATGGCCGACTAGTTGACGTTGTGGTCGCGGTAGTGGGTCCGGACGGGGTTTCACTGG
       K  Y  R  L  I  N  C  N  T  S  A  I  T  Q  A  C  P  K  V  T
```

```
     TTCGACCCTATCCCCATCCACTACTGCGCCCCTGCCGGCTACGCCATCCTGAAGTGCAAC
661  ---------+---------+---------+---------+---------+---------+
     AAGCTGGGATAGGGGTAGGTGATGACGCGGGGACGGCCGATGCGGTAGGACTTCACGTTG
      F  D  P  I  P  I  H  Y  C  A  P  A  G  Y  A  I  L  K  C  N

AACAAGACCTTCAACGGCACCGGCCCCTGCAACAACGTGTCCACCGTGCAGTGCACCCAC
721  ---------+---------+---------+---------+---------+---------+
     TTGTTCTGGAAGTTGCCGTGGCCGGGGACGTTGTTGCACAGGTGGCACGTCACGTGGGTG
      N  K  T  F  N  G  T  G  P  C  N  N  V  S  T  V  Q  C  T  H

PvuII
     GGCATCAAGCCCGTGGTGTCCACCCAGCTGCTGCTGAATGGCAGCCTGGCCGAGGGCGAG
781  ---------+---------+---------+---------+---------+---------+
     CCGTAGTTCGGGCACCACAGGTGGGTCGACGACGACTTACCGTCGGACCGGCTCCCGCTC
      G  I  K  P  V  V  S  T  Q  L  L  L  N  G  S  L  A  E  G  E

ATCATCATCAGAAGCGAGAACCTGACCAACAACGTGAAAACCATCATCGTGCACCTGAAC
841  ---------+---------+---------+---------+---------+---------+
     TAGTAGTAGTCTTCGCTCTTGGACTGGTTGTTGCACTTTTGGTAGTAGCACGTGGACTTG
      I  I  I  R  S  E  N  L  T  N  N  V  K  T  I  I  V  H  L  N

GAGAGCGTGGAAATCGTGTGCACCCGGCCCAACAACAACACCAGAAAGAGCATCCGGATC
901  ---------+---------+---------+---------+---------+---------+
     CTCTCGCACCTTTAGCACACGTGGGCCGGGTTGTTGTTGTGGTCTTTCTCGTAGGCCTAG
      E  S  V  E  I  V  C  T  R  P  N  N  N  T  R  K  S  I  R  I

StuI
     GGCCCTGGCCAGACCTTTTACGCCACCGGCGACATCATCGGCAACATCCGGCAGGCCTAC
961  ---------+---------+---------+---------+---------+---------+
     CCGGGACCGGTCTGGAAAATGCGGTGGCCGCTGTAGTAGCCGTTGTAGGCCGTCCGGATG
      G  P  G  Q  T  F  Y  A  T  G  D  I  I  G  N  I  R  Q  A  Y

BamHI       PstI
     TGCAACATCAAGAAGGACGACTGGATCCGGACCCTGCAGAGAGTGGGCAAGAAGCTGGCC
1021 ---------+---------+---------+---------+---------+---------+
     ACGTTGTAGTTCTTCCTGCTGACCTAGGCCTGGGACGTCTCTCACCCGTTCTTCGACCGG
      C  N  I  K  K  D  D  W  I  R  T  L  Q  R  V  G  K  K  L  A
```

```
          GAGCACTTCCCCAGACGGATCATCAACTTCACCAGCCCCGCTGGCGGCGACCTGGAAATC
1081      ---------+---------+---------+---------+---------+---------+
          CTCGTGAAGGGGTCTGCCTAGTAGTTGAAGTGGTCGGGGCGACCGCCGCTGGACCTTTAG
           E  H  F  P  R  R  I  I  N  F  T  S  P  A  G  G  D  L  E  I

PstI
          ACCACCCACAGCTTCAACTGCAGAGGCGAGTTCTTCTACTGCAATACCAGCAGCCTGTTC
1141      ---------+---------+---------+---------+---------+---------+
          TGGTGGGTGTCGAAGTTGACGTCTCCGCTCAAGAAGATGACGTTATGGTCGTCGGACAAG
           T  T  H  S  F  N  C  R  G  E  F  F  Y  C  N  T  S  S  L  F

AACAGCACCTACAACCCCAACGACACCAACAGCAACAGCTCCAGCAGCAACTCCAGCCTG
1201      ---------+---------+---------+---------+---------+---------+
          TTGTCGTGGATGTTGGGGTTGCTGTGGTTGTCGTTGTCGAGGTCGTCGTTGAGGTCGGAC
           N  S  T  Y  N  P  N  D  T  N  S  N  S  S  S  S  N  S  S  L

GACATCACCATCCCTTGCCGGATCAAGCAGATCATCAATATGTGGCAGGAAGTGGGCAGG
1261      ---------+---------+---------+---------+---------+---------+
          CTGTAGTGGTAGGGAACGGCCTAGTTCGTCTAGTAGTTATACACCGTCCTTCACCCGTCC
           D  I  T  I  P  C  R  I  K  Q  I  I  N  M  W  Q  E  V  G  R

GCTATGTACGCCCCTCCCATCGAGGGCAACATCACATGCAAGAGCAACATCACCGGCCTG
1321      ---------+---------+---------+---------+---------+---------+
          CGATACATGCGGGGAGGGTAGCTCCCGTTGTAGTGTACGTTCTCGTTGTAGTGGCCGGAC
           A  M  Y  A  P  P  I  E  G  N  I  T  C  K  S  N  I  T  G  L

BglII
          CTCCTGGTCCGCGACGGCGGCGTGGAAAGCAACGAGACAGAGATCTTCAGACCCGGCGGA
1381      ---------+---------+---------+---------+---------+---------+
          GAGGACCAGGCGCTGCCGCCGCACCTTTCGTTGCTCTGTCTCTAGAAGTCTGGGCCGCCT
           L  L  V  R  D  G  G  V  E  S  N  E  T  E  I  F  R  P  G  G

GGCGACATGCGGAACAACTGGCGGAGCGAGCTGTACAAGTACAAGGTGGTGGAAATCAAG
1441      ---------+---------+---------+---------+---------+---------+
          CCGCTGTACGCCTTGTTGACCGCCTCGCTCGACATGTTCATGTTCCACCACCTTTAGTTC
           G  D  M  R  N  N  W  R  S  E  L  Y  K  Y  K  V  V  E  I  K
```

```
              CCCCTGGGAATCGCCCCCACCGCCGCCAAGCGGAGAGTGGTGGAAAGCGAGAAGTCCGCC
     1501  ---------+---------+---------+---------+---------+---------+
              GGGGACCCTTAGCGGGGGTGGCGGCGGTTCGCCTCTCACCACCTTTCGCTCTTCAGGCGG
              P   L   G   I   A   P   T   A   A   K   R   R   V   V   E   S   E   K   S   A

NarI
                   KasI                                         NcoI
              GTGGGCCTGGGCGCCGTGATCTTCGGCTTTCTGGGAGCCGCCGGAAGCACCATGGGCGCT
     1561  ---------+---------+---------+---------+---------+---------+
              CACCCGGACCCGCGGCACTAGAAGCCGAAAGACCCTCGGCGGCCTTCGTGGTACCCGCGA
              V   G   L   G   A   V   I   F   G   F   L   G   A   A   G   S   T   M   G   A

PvuII
              GCCAGCATCACCCTGACCGTGCAGGCCAGACAGCTGCTGAGCGGCATCGTGCAGCAGCAG
     1621  ---------+---------+---------+---------+---------+---------+
              CGGTCGTAGTGGGACTGGCACGTCCGGTCTGTCGACGACTCGCCGTAGCACGTCGTCGTC
              A   S   I   T   L   T   V   Q   A   R   Q   L   L   S   G   I   V   Q   Q   Q

PvuII
                   BspMI                              PstI
              AGCAACCTGCTGAAGGCCATCGAGGCCCAGCAGCATCTGCTGCAGCTGACCGTGTGGGGC
     1681  ---------+---------+---------+---------+---------+---------+
              TCGTTGGACGACTTCCGGTAGCTCCGGGTCGTCGTAGACGACGTCGACTGGCACACCCCG
              S   N   L   L   K   A   I   E   A   Q   Q   H   L   L   Q   L   T   V   W   G

PvuII
                      PstI    SmaI
              ATCAAGCAGCTGCAGACCCGGGTGCTGGCCATCGAGAGATACCTGAAGGACCAGCAGCTC
     1741  ---------+---------+---------+---------+---------+---------+
              TAGTTCGTCGACGTCTGGGCCCACGACCGGTAGCTCTCTATGGACTTCCTGGTCGTCGAG
              I   K   Q   L   Q   T   R   V   L   A   I   E   R   Y   L   K   D   Q   Q   L

PstI                                            PvuII
              CTGGGAATCTGGGGCTGCAGCGGCAAGCTGATCTGCACCACCGCCGTGCCCTGGAACAGC
     1801  ---------+---------+---------+---------+---------+---------+
              GACCCTTAGACCCCGACGTCGCCGTTCGACTAGACGTGGTGGCGGCACGGGACCTTGTCG
              L   G   I   W   G   C   S   G   K   L   I   C   T   T   A   V   P   W   N   S
```

```
                    BglII
         AGCTGGTCCAACAAGAGCCACGACGAGATCTGGGGCAACATGACCTGGATGCAGTGGGAC
1861     ---------+---------+---------+---------+---------+---------+
         TCGACCAGGTTGTTCTCGGTGCTGCTCTAGACCCCGTTGTACTGGACCTACGTCACCCTG
          S   W   S   N   K   S   H   D   E   I   W   G   N   M   T   W   M   Q   W   D

AGAGAGATCAGCAACTACACCAACACCATCTACCGCCTGCTGGAAGATAGCCAGAACCAG
1921     ---------+---------+---------+---------+---------+---------+
         TCTCTCTAGTCGTTGATGTGGTTGTGGTAGATGGCGGACGACCTTCTATCGGTCTTGGTC
          R   E   I   S   N   Y   T   N   T   I   Y   R   L   L   E   D   S   Q   N   Q

BspMI           PvuII
         CAGGAACAGAACGAGAAGGACCTGCTGGCCCTGGACAGCTGGGAGAACCTGTGGAACTGG
1981     ---------+---------+---------+---------+---------+---------+
         GTCCTTGTCTTGCTCTTCCTGGACGACCGGGACCTGTCGACCCTCTTGGACACCTTGACC
          Q   E   Q   N   E   K   D   L   L   A   L   D   S   W   E   N   L   W   N   W

NarI
                                    KasI
         TTCAGCATCACCAAGTGGCTGTGGTACATCAAGGGCGCCCACCACCACCATCACCACTGA
2041     ---------+---------+---------+---------+---------+---------+
         AAGTCGTAGTGGTTCACCGACACCATGTAGTTCCCGCGGGTGGTGGTGGTAGTGGTGACT
          F   S   I   T   K   W   L   W   Y   I   K   G   A   H   H   H   H   H   H   *

BssHII
         XhoI AscI
         CTCGAGGCGCGCCCTGGGCCTCATGGGCCTTCCTTTCACTGCC
2101     ---------+---------+---------+---------+---
         GAGCTCCGCGCGGGACCCGGAGTACCCGGAAGGAAAGTGACGG
```

FIG. 39

```
                                     HindIII
            NheI    PmeI    AflII                              PstI
        CCAAGCTGGCTAGCGTTTAAACTTAAGCTTGCCACCATGCCTATGGGCAGCCTGCAGCCT
   1    ---------+---------+---------+---------+---------+---------+
        GGTTCGACCGATCGCAAATTTGAATTCGAACGGTGGTACGGATACCCGTCGGACGTCGGA
                                           M  P  M  G  S  L  Q  P BspMI   SphI                        PvuII
        CTGGCCACCCTGTACCTGCTGGGCATGCTGGTGGCCTCCGTGCTGGCAGCTGGCAACCTG
  61    ---------+---------+---------+---------+---------+---------+
        GACCGGTGGGACATGGACGACCCGTACGACCACCGGAGGCACGACCGTCGACCGTTGGAC
         L  A  T  L  Y  L  L  G  M  L  V  A  S  V  L  A  A  G  N  L TGGGTCACAGTGTACTACGGCGTGCCCGTGTGGAAAGAGGCCAAGACCACCCTGTTCTGC
 121    ---------+---------+---------+---------+---------+---------+
        ACCCAGTGTCACATGATGCCGCACGGGCACACCTTTCTCCGGTTCTGGTGGGACAAGACG
         W  V  T  V  Y  Y  G  V  P  V  W  K  E  A  K  T  T  L  F  C StuI
        GCCAGCGACGCCAAGGCCTACGAGAAAGAGGTGCACAACGTCTGGGCCACCCACGCCTGC
 181    ---------+---------+---------+---------+---------+---------+
        CGGTCGCTGCGGTTCCGGATGCTCTTTCTCCACGTGTTGCAGACCCGGTGGGTGCGGACG
         A  S  D  A  K  A  Y  E  K  E  V  H  N  V  W  A  T  H  A  C PflMI
        GTGCCCACCGACCCCAACCCCCAGGAAATGGTCCTGGAAAACGTGACCGAGAACTTCAAC
 241    ---------+---------+---------+---------+---------+---------+
        CACGGGTGGCTGGGGTTGGGGGTCCTTTACCAGGACCTTTTGCACTGGCTCTTGAAGTTG
         V  P  T  D  P  N  P  Q  E  M  V  L  E  N  V  T  E  N  F  N
```

```
                                           BclI
       ATGTGGAAGAACGACATGGTGGAACAGATGCACGAGGACGTGATCAGCCTGTGGGACCAG
301    ---------+---------+---------+---------+---------+---------+
       TACACCTTCTTGCTGTACCACCTTGTCTACGTGCTCCTGCACTAGTCGGACACCCTGGTC
       M  W  K  N  D  M  V  E  Q  M  H  E  D  V  I  S  L  W  D  Q

HincII
       AGCCTGAAGCCCTGCGTGAAGCTGACCCCCCTGTGCGTGACCCTGGAATGCAGACAGGTC
361    ---------+---------+---------+---------+---------+---------+
       TCGGACTTCGGGACGCACTTCGACTGGGGGGACACGCACTGGGACCTTACGTCTGTCCAG
       S  L  K  P  C  V  K  L  T  P  L  C  V  T  L  E  C  R  Q  V PstI
       AACACCACCAACGCCACCAGCAGCGTGAACGTGACCAACGGCGAGGAAATCAAGAACTGC
421    ---------+---------+---------+---------+---------+---------+
       TTGTGGTGGTTGCGGTGGTCGTCGCACTTGCACTGGTTGCCGCTCCTTTAGTTCTTGACG
       N  T  T  N  A  T  S  S  V  N  V  T  N  G  E  E  I  K  N  C AGCTTCAATGCCACCACCGAGATCCGGGACAAGAAACAGAAGGTGTACGCCCTGTTCTAC
481    ---------+---------+---------+---------+---------+---------+
       TCGAAGTTACGGTGGTGGCTCTAGGCCCTGTTCTTTGTCTTCCACATGCGGGACAAGATG
       S  F  N  A  T  T  E  I  R  D  K  K  Q  K  V  Y  A  L  F  Y BclI
       CGGCTGGACATCGTGCCCCTGGAAGAGGAACGGAAGGGCAACAGCAGCAAGTACCGGCTG
541    ---------+---------+---------+---------+---------+---------+
       GCCGACCTGTAGCACGGGGACCTTCTCCTTGCCTTCCCGTTGTCGTCGTTCATGGCCGAC
       R  L  D  I  V  P  L  E  E  E  R  K  G  N  S  S  K  Y  R  L StuI
       ATCAACTGCAACACCAGCGCCATCACCCAGGCCTGCCCCAAAGTGACCTTCGACCCTATC
601    ---------+---------+---------+---------+---------+---------+
       TAGTTGACGTTGTGGTCGCGGTAGTGGGTCCGGACGGGGTTTCACTGGAAGCTGGGATAG
       I  N  C  N  T  S  A  I  T  Q  A  C  P  K  V  T  F  D  P  I
```

```
            CCCATCCACTACTGCGCCCCTGCCGGCTACGCCATCCTGAAGTGCAACAACAAGACCTTC
    661     ---------+---------+---------+---------+---------+---------+
            GGGTAGGTGATGACGCGGGGACGGCCGATGCGGTAGGACTTCACGTTGTTGTTCTGGAAG
             P   I   H   Y   C   A   P   A   G   Y   A   I   L   K   C   N   N   K   T   F

AACGGCACCGGCCCCTGCAACAACGTGTCCACCGTGCAGTGCACCCACGGCATCAAGCCC
    721     ---------+---------+---------+---------+---------+---------+
            TTGCCGTGGCCGGGGACGTTGTTGCACAGGTGGCACGTCACGTGGGTGCCGTAGTTCGGG
             N   G   T   G   P   C   N   N   V   S   T   V   Q   C   T   H   G   I   K   P

PvuII
            GTGGTGTCCACCCAGCTGCTGCTGAATGGCAGCCTGGCCGAGGGCGAGATCATCATCAGA
    781     ---------+---------+---------+---------+---------+---------+
            CACCACAGGTGGGTCGACGACGACTTACCGTCGGACCGGCTCCCGCTCTAGTAGTAGTCT
             V   V   S   T   Q   L   L   L   N   G   S   L   A   E   G   E   I   I   I   R

AGCGAGAACCTGACCAACAACGTGAAAACCATCATCGTGCACCTGAACGAGAGCGTGGAA
    841     ---------+---------+---------+---------+---------+---------+
            TCGCTCTTGGACTGGTTGTTGCACTTTTGGTAGTAGCACGTGGACTTGCTCTCGCACCTT
             S   E   N   L   T   N   N   V   K   T   I   I   V   H   L   N   E   S   V   E

ATCGTGTGCACCCGGCCCAACAACAACACCAGAAAGAGCATCCGGATCGGCCCTGGCCAG
    901     ---------+---------+---------+---------+---------+---------+
            TAGCACACGTGGGCCGGGTTGTTGTTGTGGTCTTTCTCGTAGGCCTAGCCGGGACCGGTC
             I   V   C   T   R   P   N   N   N   T   R   K   S   I   R   I   G   P   G   Q

StuI
            ACCTTTTACGCCACCGGCGACATCATCGGCAACATCCGGCAGGCCTACTGCAACATCAAG
    961     ---------+---------+---------+---------+---------+---------+
            TGGAAAATGCGGTGGCCGCTGTAGTAGCCGTTGTAGGCCGTCCGGATGACGTTGTAGTTC
             T   F   Y   A   T   G   D   I   I   G   N   I   R   Q   A   Y   C   N   I   K

BamHI        PstI
            AAGGACGACTGGATCCGGACCCTGCAGAGAGTGGGCAAGAAGCTGGCCGAGCACTTCCCC
    1021    ---------+---------+---------+---------+---------+---------+
            TTCCTGCTGACCTAGGCCTGGGACGTCTCTCACCCGTTCTTCGACCGGCTCGTGAAGGGG
             K   D   D   W   I   R   T   L   Q   R   V   G   K   K   L   A   E   H   F   P
```

```
           AGACGGATCATCAACTTCACCAGCCCCGCTGGCGGCGACCTGGAAATCACCACCCACAGC
1081       ------------------------------------------------------------
           TCTGCCTAGTAGTTGAAGTGGTCGGGGCGACCGCCGCTGGACCTTTAGTGGTGGGTGTCG
            R  R  I  I  N  F  T  S  P  A  G  G  D  L  E  I  T  T  H  S

PstI
           TTCAACTGCAGAGGCGAGTTCTTCTACTGCAATACCAGCAGCCTGTTCAACAGCACCTAC
1141       ------------------------------------------------------------
           AAGTTGACGTCTCCGCTCAAGAAGATGACGTTATGGTCGTCGGACAAGTTGTCGTGGATG
            F  N  C  R  G  E  F  F  Y  C  N  T  S  S  L  F  N  S  T  Y

AACCCCAACGACACCAACAGCAACAGCTCCAGCAGCAACTCCAGCCTGGACATCACCATC
1201       ------------------------------------------------------------
           TTGGGGTTGCTGTGGTTGTCGTTGTCGAGGTCGTCGTTGAGGTCGGACCTGTAGTGGTAG
            N  P  N  D  T  N  S  N  S  S  S  S  N  S  S  L  D  I  T  I

CCTTGCCGGATCAAGCAGATCATCAATATGTGGCAGGAAGTGGGCAGGGCTATGTACGCC
1261       ------------------------------------------------------------
           GGAACGGCCTAGTTCGTCTAGTAGTTATACACCGTCCTTCACCCGTCCCGATACATGCGG
            P  C  R  I  K  Q  I  I  N  M  W  Q  E  V  G  R  A  M  Y  A

CCTCCCATCGAGGGCAACATCACATGCAAGAGCAACATCACCGGCCTGCTCCTGGTCCGC
1321       ------------------------------------------------------------
           GGAGGGTAGCTCCCGTTGTAGTGTACGTTCTCGTTGTAGTGGCCGGACGAGGACCAGGCG
            P  P  I  E  G  N  I  T  C  K  S  N  I  T  G  L  L  L  V  R

BglII
           GACGGCGGCGTGGAAAGCAACGAGACAGAGATCTTCAGACCCGGCGGAGGCGACATGCGG
1381       ------------------------------------------------------------
           CTGCCGCCGCACCTTTCGTTGCTCTGTCTCTAGAAGTCTGGGCCGCCTCCGCTGTACGCC
            D  G  G  V  E  S  N  E  T  E  I  F  R  P  G  G  G  D  M  R

AACAACTGGCGGAGCGAGCTGTACAAGTACAAGGTGGTGGAAATCAAGCCCCTGGGAATC
1441       ------------------------------------------------------------
           TTGTTGACCGCCTCGCTCGACATGTTCATGTTCCACCACCTTTAGTTCGGGGACCCTTAG
            N  N  W  R  S  E  L  Y  K  Y  K  V  V  E  I  K  P  L  G  I
```

```
                                                          NarI
                                                          KasI
     GCCCCCACCGCCGCCAAGCGGAGAGTGGTGGAAAGCGAGAAGTCCGCCGTGGGCCTGGGC
1501 ---------+---------+---------+---------+---------+---------+
     CGGGGGTGGCGGCGGTTCGCCTCTCACCACCTTTCGCTCTTCAGGCGGCACCCGGACCCG
      A  P  T  A  A  K  R  R  V  V  E  S  E  K  S  A  V  G  L  G

NcoI
     GCCGTGATCTTCGGCTTTCTGGGAGCCGCCGGAAGCACCATGGGCGCTGCCAGCATCACC
1561 ---------+---------+---------+---------+---------+---------+
     CGGCACTAGAAGCCGAAAGACCCTCGGCGGCCTTCGTGGTACCCGCGACGGTCGTAGTGG
      A  V  I  F  G  F  L  G  A  A  G  S  T  M  G  A  A  S  I  T

PvuII                              BspMI
     CTGACCGTGCAGGCCAGACAGCTGCTGAGCGGCATCGTGCAGCAGCAGAGCAACCTGCTG
1621 ---------+---------+---------+---------+---------+---------+
     GACTGGCACGTCCGGTCTGTCGACGACTCGCCGTAGCACGTCGTCGTCTCGTTGGACGAC
      L  T  V  Q  A  R  Q  L  L  S  G  I  V  Q  Q  Q  S  N  L  L

PvuII              PvuII
                           PstI                        PstI
     AAGGCCATCGAGGCCCAGCAGCATCTGCTGCAGCTGACCGTGTGGGGCATCAAGCAGCTG
1681 ---------+---------+---------+---------+---------+---------+
     TTCCGGTAGCTCCGGGTCGTCGTAGACGACGTCGACTGGCACACCCCGTAGTTCGTCGAC
      K  A  I  E  A  Q  Q  H  L  L  Q  L  T  V  W  G  I  K  Q  L

SmaI
     CAGACCCGGGTGCTGGCCATCGAGAGATACCTGAAGGACCAGCAGCTCCTGGGAATCTGG
1741 ---------+---------+---------+---------+---------+---------+
     GTCTGGGCCCACGACCGGTAGCTCTCTATGGACTTCCTGGTCGTCGAGGACCCTTAGACC
      Q  T  R  V  L  A  I  E  R  Y  L  K  D  Q  Q  L  L  G  I  W

PstI                                  PvuII
     GGCTGCAGCGGCAAGCTGATCTGCACCACCGCCGTGCCCTGGAACAGCAGCTGGTCCAAC
1801 ---------+---------+---------+---------+---------+---------+
     CCGACGTCGCCGTTCGACTAGACGTGGTGGCGGCACGGGACCTTGTCGTCGACCAGGTTG
      G  C  S  G  K  L  I  C  T  T  A  V  P  W  N  S  S  W  S  N
```

```
                     BglII
       AAGAGCCACGACGAGATCTGGGGCAACATGACCTGGATGCAGTGGGACAGAGAGATCAGC
1861   ---------+---------+---------+---------+---------+---------+
       TTCTCGGTGCTGCTCTAGACCCCGTTGTACTGGACCTACGTCACCCTGTCTCTCTAGTCG
        K  S  H  D  E  I  W  G  N  M  T  W  M  Q  W  D  R  E  I  S

AACTACACCAACACCATCTACCGCCTGCTGGAAGATAGCCAGAACCAGCAGGAACAGAAC
1921   ---------+---------+---------+---------+---------+---------+
       TTGATGTGGTTGTGGTAGATGGCGGACGACCTTCTATCGGTCTTGGTCGTCCTTGTCTTG
        N  Y  T  N  T  I  Y  R  L  L  E  D  S  Q  N  Q  Q  E  Q  N

BspMI           PvuII
       GAGAAGGACCTGCTGGCCCTGGACAGCTGGGAGAACCTGTGGAACTGGTTCAGCATCACC
1981   ---------+---------+---------+---------+---------+---------+
       CTCTTCCTGGACGACCGGGACCTGTCGACCCTCTTGGACACCTTGACCAAGTCGTAGTGG
        E  K  D  L  L  A  L  D  S  W  E  N  L  W  N  W  F  S  I  T

NarI
                    KasI                              XhoI   XbaI
       AAGTGGCTGTGGTACATCAAGGGCGCCCACCACCACCATCACCACTGCTGACTCGAGTCT
2041   ---------+---------+---------+---------+---------+---------+
       TTCACCGACACCATGTAGTTCCCGCGGGTGGTGGTGGTAGTGGTGACGACTGAGCTCAGA
        K  W  L  W  Y  I  K  G  A  H  H  H  H  H  H  C  *

ApaI  PmeI
       AGAGGGCCCGTTTAAACCCGC
2101   ---------+---------+-
       TCTCCCGGGCAAATTTGGGCG
```

FIG. 40

```
                          HindIII
        NheI  PmeI   AflII                            PstI
        CCAAGCTGGCTAGCGTTTAAACTTAAGCTTGCCACCATGCCTATGGGCAGCCTGCAGCCT
    1   ---------+---------+---------+---------+---------+---------+
        GGTTCGACCGATCGCAAATTTGAATTCGAACGGTGGTACGGATACCCGTCGGACGTCGGA
                                             M   P   M   G   S   L   Q   P BspMI    SphI                       PvuII
        CTGGCCACCCTGTACCTGCTGGGCATGCTGGTGGCCTCCGTGCTGGCAGCTGGCAACCTG
   61   ---------+---------+---------+---------+---------+---------+
        GACCGGTGGGACATGGACGACCCGTACGACCACCGGAGGCACGACCGTCGACCGTTGGAC
         L   A   T   L   Y   L   L   G   M   L   V   A   S   V   L   A   A   G   N   L TGGGTCACAGTGTACTACGGCGTGCCCGTGTGGAAAGAGGCCAAGACCACCCTGTTCTGC
  121   ---------+---------+---------+---------+---------+---------+
        ACCCAGTGTCACATGATGCCGCACGGGCACACCTTTCTCCGGTTCTGGTGGGACAAGACG
         W   V   T   V   Y   Y   G   V   P   V   W   K   E   A   K   T   T   L   F   C StuI
        GCCAGCGACGCCAAGGCCTACGAGAAAGAGGTGCACAACGTCTGGGCCACCCACGCCTGC
  181   ---------+---------+---------+---------+---------+---------+
        CGGTCGCTGCGGTTCCGGATGCTCTTTCTCCACGTGTTGCAGACCCGGTGGGTGCGGACG
         A   S   D   A   K   A   Y   E   K   E   V   H   N   V   W   A   T   H   A   C PflMI
        GTGCCCACCGACCCCAACCCCCAGGAAATGGTCCTGGAAAACGTGACCGAGAACTTCAAC
  241   ---------+---------+---------+---------+---------+---------+
        CACGGGTGGCTGGGGTTGGGGGTCCTTTACCAGGACCTTTTGCACTGGCTCTTGAAGTTG
         V   P   T   D   P   N   P   Q   E   M   V   L   E   N   V   T   E   N   F   N
```

```
                                                        BclI
       ATGTGGAAGAACGACATGGTGGAACAGATGCACGAGGACGTGATCAGCCTGTGGGACCAG
301    ---------+---------+---------+---------+---------+---------+
       TACACCTTCTTGCTGTACCACCTTGTCTACGTGCTCCTGCACTAGTCGGACACCCTGGTC
        M  W  K  N  D  M  V  E  Q  M  H  E  D  V  I  S  L  W  D  Q

HincII
       AGCCTGAAGCCCTGCGTGAAGCTGACCCCCCTGTGCGTGACCCTGGAATGCAGACAGGTC
361    ---------+---------+---------+---------+---------+---------+
       TCGGACTTCGGGACGCACTTCGACTGGGGGGACACGCACTGGGACCTTACGTCTGTCCAG
        S  L  K  P  C  V  K  L  T  P  L  C  V  T  L  E  C  R  Q  V PstI
       AACACCACCAACGCCACCAGCAGCGTGAACGTGACCAACGGCGAGGAAATCAAGAACTGC
421    ---------+---------+---------+---------+---------+---------+
       TTGTGGTGGTTGCGGTGGTCGTCGCACTTGCACTGGTTGCCGCTCCTTTAGTTCTTGACG
        N  T  T  N  A  T  S  S  V  N  V  T  N  G  E  E  I  K  N  C AGCTTCAATGCCACCACCGAGATCCGGGACAAGAAACAGAAGGTGTACGCCCTGTTCTAC
481    ---------+---------+---------+---------+---------+---------+
       TCGAAGTTACGGTGGTGGCTCTAGGCCCTGTTCTTTGTCTTCCACATGCGGGACAAGATG
        S  F  N  A  T  T  E  I  R  D  K  K  Q  K  V  Y  A  L  F  Y BclI
       CGGCTGGACATCGTGCCCCTGGAAGAGGAACGGAAGGGCAACAGCAGCAAGTACCGGCTG
541    ---------+---------+---------+---------+---------+---------+
       GCCGACCTGTAGCACGGGGACCTTCTCCTTGCCTTCCCGTTGTCGTCGTTCATGGCCGAC
        R  L  D  I  V  P  L  E  E  E  R  K  G  N  S  S  K  Y  R  L StuI
       ATCAACTGCAACACCAGCGCCATCACCCAGGCCTGCCCCAAAGTGACCTTCGACCCTATC
601    ---------+---------+---------+---------+---------+---------+
       TAGTTGACGTTGTGGTCGCGGTAGTGGGTCCGGACGGGGTTTCACTGGAAGCTGGGATAG
        I  N  C  N  T  S  A  I  T  Q  A  C  P  K  V  T  F  D  P  I
```

```
           CCCATCCACTACTGCGCCCCTGCCGGCTACGCCATCCTGAAGTGCAACAACAAGACCTTC
 661   ---------+---------+---------+---------+---------+---------+
           GGGTAGGTGATGACGCGGGGACGGCCGATGCGGTAGGACTTCACGTTGTTGTTCTGGAAG
            P  I  H  Y  C  A  P  A  G  Y  A  I  L  K  C  N  N  K  T  F

AACGGCACCGGCCCCTGCAACAACGTGTCCACCGTGCAGTGCACCCACGGCATCAAGCCC
 721   ---------+---------+---------+---------+---------+---------+
           TTGCCGTGGCCGGGGACGTTGTTGCACAGGTGGCACGTCACGTGGGTGCCGTAGTTCGGG
            N  G  T  G  P  C  N  N  V  S  T  V  Q  C  T  H  G  I  K  P

PvuII
           GTGGTGTCCACCCAGCTGCTGCTGAATGGCAGCCTGGCCGAGGGCGAGATCATCATCAGA
 781   ---------+---------+---------+---------+---------+---------+
           CACCACAGGTGGGTCGACGACGACTTACCGTCGGACCGGCTCCCGCTCTAGTAGTAGTCT
            V  V  S  T  Q  L  L  L  N  G  S  L  A  E  G  E  I  I  I  R

AGCGAGAACCTGACCAACAACGTGAAAACCATCATCGTGCACCTGAACGAGAGCGTGGAA
 841   ---------+---------+---------+---------+---------+---------+
           TCGCTCTTGGACTGGTTGTTGCACTTTTGGTAGTAGCACGTGGACTTGCTCTCGCACCTT
            S  E  N  L  T  N  N  V  K  T  I  I  V  H  L  N  E  S  V  E

ATCGTGTGCACCCGGCCCAACAACAACACCAGAAAGAGCATCCGGATCGGCCCTGGCCAG
 901   ---------+---------+---------+---------+---------+---------+
           TAGCACACGTGGGCCGGGTTGTTGTTGTGGTCTTTCTCGTAGGCCTAGCCGGGACCGGTC
            I  V  C  T  R  P  N  N  N  T  R  K  S  I  R  I  G  P  G  Q

StuI
           ACCTTTTACGCCACCGGCGACATCATCGGCAACATCCGGCAGGCCTACTGCAACATCAAG
 961   ---------+---------+---------+---------+---------+---------+
           TGGAAAATGCGGTGGCCGCTGTAGTAGCCGTTGTAGGCCGTCCGGATGACGTTGTAGTTC
            T  F  Y  A  T  G  D  I  I  G  N  I  R  Q  A  Y  C  N  I  K

BamHI      PstI
           AAGGACGACTGGATCCGGACCCTGCAGAGAGTGGGCAAGAAGCTGGCCGAGCACTTCCCC
1021   ---------+---------+---------+---------+---------+---------+
           TTCCTGCTGACCTAGGCCTGGGACGTCTCTCACCCGTTCTTCGACCGGCTCGTGAAGGGG
            K  D  D  W  I  R  T  L  Q  R  V  G  K  K  L  A  E  H  F  P
```

```
             AGACGGATCATCAACTTCACCAGCCCCGCTGGCGGCGACCTGGAAATCACCACCCACAGC
1081         ---------+---------+---------+---------+---------+---------+
             TCTGCCTAGTAGTTGAAGTGGTCGGGGCGACCGCCGCTGGACCTTTAGTGGTGGGTGTCG
              R   R   I   I   N   F   T   S   P   A   G   G   D   L   E   I   T   T   H   S

PstI
             TTCAACTGCAGAGGCGAGTTCTTCTACTGCAATACCAGCAGCCTGTTCAACAGCACCTAC
1141         ---------+---------+---------+---------+---------+---------+
             AAGTTGACGTCTCCGCTCAAGAAGATGACGTTATGGTCGTCGGACAAGTTGTCGTGGATG
              F   N   C   R   G   E   F   F   Y   C   N   T   S   S   L   F   N   S   T   Y

AACCCCAACGACACCAACAGCAACAGCTCCAGCAGCAACTCCAGCCTGGACATCACCATC
1201         ---------+---------+---------+---------+---------+---------+
             TTGGGGTTGCTGTGGTTGTCGTTGTCGAGGTCGTCGTTGAGGTCGGACCTGTAGTGGTAG
              N   P   N   D   T   N   S   N   S   S   S   N   S   S   L   D   I   T   I

CCTTGCCGGATCAAGCAGATCATCAATATGTGGCAGGAAGTGGGCAGGGCTATGTACGCC
1261         ---------+---------+---------+---------+---------+---------+
             GGAACGGCCTAGTTCGTCTAGTAGTTATACACCGTCCTTCACCCGTCCCGATACATGCGG
              P   C   R   I   K   Q   I   I   N   M   W   Q   E   V   G   R   A   M   Y   A

CCTCCCATCGAGGGCAACATCACATGCAAGAGCAACATCACCGGCCTGCTCCTGGTCCGC
1321         ---------+---------+---------+---------+---------+---------+
             GGAGGGTAGCTCCCGTTGTAGTGTACGTTCTCGTTGTAGTGGCCGGACGAGGACCAGGCG
              P   P   I   E   G   N   I   T   C   K   S   N   I   T   G   L   L   L   V   R

BglII
             GACGGCGGCGTGGAAAGCAACGAGACAGAGATCTTCAGACCCGGCGGAGGCGACATGCGG
1381         ---------+---------+---------+---------+---------+---------+
             CTGCCGCCGCACCTTTCGTTGCTCTGTCTCTAGAAGTCTGGGCCGCCTCCGCTGTACGCC
              D   G   G   V   E   S   N   E   T   E   I   F   R   P   G   G   G   D   M   R

AACAACTGGCGGAGCGAGCTGTACAAGTACAAGGTGGTGGAAATCAAGCCCCTGGGAATC
1441         ---------+---------+---------+---------+---------+---------+
             TTGTTGACCGCCTCGCTCGACATGTTCATGTTCCACCACCTTTAGTTCGGGGACCCTTAG
              N   N   W   R   S   E   L   Y   K   Y   K   V   V   E   I   K   P   L   G   I
```

```
                                                                      NarI
                                                                      KasI
       GCCCCCACCGCCGCCAAGCGGAGAGTGGTGGAAAGCGAGAAGTCCGCCGTGGGCCTGGGC
1501   ---------+---------+---------+---------+---------+---------+
       CGGGGGTGGCGGCGGTTCGCCTCTCACCACCTTTCGCTCTTCAGGCGGCACCCGGACCCG
        A  P  T  A  A  K  R  R  V  V  E  S  E  K  S  A  V  G  L  G

NcoI
       GCCGTGATCTTCGGCTTTCTGGGAGCCGCCGGAAGCACCATGGGCGCTGCCAGCATCACC
1561   ---------+---------+---------+---------+---------+---------+
       CGGCACTAGAAGCCGAAAGACCCTCGGCGGCCTTCGTGGTACCCGCGACGGTCGTAGTGG
        A  V  I  F  G  F  L  G  A  A  G  S  T  M  G  A  A  S  I  T

PvuII                                     BspMI
       CTGACCGTGCAGGCCAGACAGCTGCTGAGCGGCATCGTGCAGCAGCAGAGCAACCTGCTG
1621   ---------+---------+---------+---------+---------+---------+
       GACTGGCACGTCCGGTCTGTCGACGACTCGCCGTAGCACGTCGTCGTCTCGTTGGACGAC
        L  T  V  Q  A  R  Q  L  L  S  G  I  V  Q  Q  Q  S  N  L  L

PvuII              PvuII
                                        PstI               PstI
       AAGGCCATCGAGGCCCAGCAGCATCTGCTGCAGCTGACCGTGTGGGGCATCAAGCAGCTG
1681   ---------+---------+---------+---------+---------+---------+
       TTCCGGTAGCTCCGGGTCGTCGTAGACGACGTCGACTGGCACACCCCGTAGTTCGTCGAC
        K  A  I  E  A  Q  Q  H  L  L  Q  L  T  V  W  G  I  K  Q  L

SmaI
       CAGACCCGGGTGCTGGCCATCGAGAGATACCTGAAGGACCAGCAGCTCCTGGGAATCTGG
1741   ---------+---------+---------+---------+---------+---------+
       GTCTGGGCCCACGACCGGTAGCTCTCTATGGACTTCCTGGTCGTCGAGGACCCTTAGACC
        Q  T  R  V  L  A  I  E  R  Y  L  K  D  Q  Q  L  L  G  I  W

PstI                                              PvuII
       GGCTGCAGCGGCAAGCTGATCTGCACCACCGCCGTGCCCTGGAACAGCAGCTGGTCCAAC
1801   ---------+---------+---------+---------+---------+---------+
       CCGACGTCGCCGTTCGACTAGACGTGGTGGCGGCACGGGACCTTGTCGTCGACCAGGTTG
        G  C  S  G  K  L  I  C  T  T  A  V  P  W  N  S  S  W  S  N
```

```
            BglII
     AAGAGCCACGACGAGATCTGGGGCAACATGACCTGGATGCAGTGGGACAGAGAGATCAGC
1861 ---------+---------+---------+---------+---------+---------+
     TTCTCGGTGCTGCTCTAGACCCCGTTGTACTGGACCTACGTCACCCTGTCTCTCTAGTCG
      K  S  H  D  E  I  W  G  N  M  T  W  M  Q  W  D  R  E  I  S

AACTACACCAACACCATCTACCGCCTGCTGGAAGATAGCCAGAACCAGCAGGAACAGAAC
1921 ---------+---------+---------+---------+---------+---------+
     TTGATGTGGTTGTGGTAGATGGCGGACGACCTTCTATCGGTCTTGGTCGTCCTTGTCTTG
      N  Y  T  N  T  I  Y  R  L  L  E  D  S  Q  N  Q  Q  E  Q  N

BspMI             PvuII
     GAGAAGGACCTGCTGGCCCTGGACAGCTGGGAGAACCTGTGGAACTGGTTCAGCATCACC
1981 ---------+---------+---------+---------+---------+---------+
     CTCTTCCTGGACGACCGGGACCTGTCGACCCTCTTGGACACCTTGACCAAGTCGTAGTGG
      E  K  D  L  L  A  L  D  S  W  E  N  L  W  N  W  F  S  I  T

NarI
                     KasI
     AAGTGGCTGTGGTACATCAAGGGCGCCGGAGGCGGAGCCAAGTTTGTGGCCGCCTGGACC
2041 ---------+---------+---------+---------+---------+---------+
     TTCACCGACACCATGTAGTTCCCGCGGCCTCCGCCTCGGTTCAAACACCGGCGGACCTGG
      K  W  L  W  Y  I  K  G  A  G  G  G  A  K  F  V  A  A  W  T

XhoI   XbaI   ApaI
     CTGAAGGCCGCTGCTGGCGGAGGCCACCACCACCATCACCACTGACTCGAGTCTAGAGGG
2101 ---------+---------+---------+---------+---------+---------+
     GACTTCCGGCGACGACCGCCTCCGGTGGTGGTGGTAGTGGTGACTGAGCTCAGATCTCCC
      L  K  A  A  A  G  G  G  H  H  H  H  H  H  *

PmeI
     CCCGTTTAAACCCGC
2161 ---------+-----
     GGGCAAATTTGGGCG
```

FIG. 41

```
                              HindIII
            NheI   PmeI    AflII                              PstI
            CCAAGCTGGCTAGCGTTTAAACTTAAGCTTGCCACCATGCCTATGGGCAGCCTGCAGCCT
    1       ---------+---------+---------+---------+---------+---------+
            GGTTCGACCGATCGCAAATTTGAATTCGAACGGTGGTACGGATACCCGTCGGACGTCGGA
                                              M   P   M   G   S   L   Q   P BspMI    SphI                          PvuII
            CTGGCCACCCTGTACCTGCTGGGCATGCTGGTGGCCTCCGTGCTGGCAGCTGGCAACCTG
    61      ---------+---------+---------+---------+---------+---------+
            GACCGGTGGGACATGGACGACCCGTACGACCACCGGAGGCACGACCGTCGACCGTTGGAC
            L   A   T   L   Y   L   L   G   M   L   V   A   S   V   L   A   A   G   N   L TGGGTCACAGTGTACTACGGCGTGCCCGTGTGGAAAGAGGCCAAGACCACCCTGTTCTGC
    121     ---------+---------+---------+---------+---------+---------+
            ACCCAGTGTCACATGATGCCGCACGGGCACACCTTTCTCCGGTTCTGGTGGGACAAGACG
            W   V   T   V   Y   Y   G   V   P   V   W   K   E   A   K   T   T   L   F   C StuI
            GCCAGCGACGCCAAGGCCTACGAGAAAGAGGTGCACAACGTCTGGGCCACCCACGCCTGC
    181     ---------+---------+---------+---------+---------+---------+
            CGGTCGCTGCGGTTCCGGATGCTCTTTCTCCACGTGTTGCAGACCCGGTGGGTGCGGACG
            A   S   D   A   K   A   Y   E   K   E   V   H   N   V   W   A   T   H   A   C PflMI
            GTGCCCACCGACCCCAACCCCCAGGAAATGGTCCTGGAAAACGTGACCGAGAACTTCAAC
    241     ---------+---------+---------+---------+---------+---------+
            CACGGGTGGCTGGGGTTGGGGGTCCTTTACCAGGACCTTTTGCACTGGCTCTTGAAGTTG
            V   P   T   D   P   N   P   Q   E   M   V   L   E   N   V   T   E   N   F   N
```

```
                                                  BclI
         ATGTGGAAGAACGACATGGTGGAACAGATGCACGAGGACGTGATCAGCCTGTGGGACCAG
301      ---------+---------+---------+---------+---------+---------+
         TACACCTTCTTGCTGTACCACCTTGTCTACGTGCTCCTGCACTAGTCGGACACCCTGGTC
          M  W  K  N  D  M  V  E  Q  M  H  E  D  V  I  S  L  W  D  Q

HincII
         AGCCTGAAGCCCTGCGTGAAGCTGACCCCCCTGTGCGTGACCCTGGAATGCAGACAGGTC
361      ---------+---------+---------+---------+---------+---------+
         TCGGACTTCGGGACGCACTTCGACTGGGGGGACACGCACTGGGACCTTACGTCTGTCCAG
          S  L  K  P  C  V  K  L  T  P  L  C  V  T  L  E  C  R  Q  V PstI
         AACACCACCAACGCCACCAGCAGCGTGAACGTGACCAACGGCGAGGAAATCAAGAACTGC
421      ---------+---------+---------+---------+---------+---------+
         TTGTGGTGGTTGCGGTGGTCGTCGCACTTGCACTGGTTGCCGCTCCTTTAGTTCTTGACG
          N  T  T  N  A  T  S  S  V  N  V  T  N  G  E  E  I  K  N  C AGCTTCAATGCCACCACCGAGATCCGGGACAAGAAACAGAAGGTGTACGCCCTGTTCTAC
481      ---------+---------+---------+---------+---------+---------+
         TCGAAGTTACGGTGGTGGCTCTAGGCCCTGTTCTTTGTCTTCCACATGCGGGACAAGATG
          S  F  N  A  T  T  E  I  R  D  K  K  Q  K  V  Y  A  L  F  Y BclI
         CGGCTGGACATCGTGCCCCTGGAAGAGGAACGGAAGGGCAACAGCAGCAAGTACCGGCTG
541      ---------+---------+---------+---------+---------+---------+
         GCCGACCTGTAGCACGGGGACCTTCTCCTTGCCTTCCCGTTGTCGTCGTTCATGGCCGAC
          R  L  D  I  V  P  L  E  E  E  R  K  G  N  S  S  K  Y  R  L StuI
         ATCAACTGCAACACCAGCGCCATCACCCAGGCCTGCCCCAAAGTGACCTTCGACCCTATC
601      ---------+---------+---------+---------+---------+---------+
         TAGTTGACGTTGTGGTCGCGGTAGTGGGTCCGGACGGGGTTTCACTGGAAGCTGGGATAG
          I  N  C  N  T  S  A  I  T  Q  A  C  P  K  V  T  F  D  P  I
```

```
       CCCATCCACTACTGCGCCCCTGCCGGCTACGCCATCCTGAAGTGCAACAACAAGACCTTC
661    ---------+---------+---------+---------+---------+---------+
       GGGTAGGTGATGACGCGGGGACGGCCGATGCGGTAGGACTTCACGTTGTTGTTCTGGAAG
        P   I   H   Y   C   A   P   A   G   Y   A   I   L   K   C   N   N   K   T   F

AACGGCACCGGCCCCTGCAACAACGTGTCCACCGTGCAGTGCACCCACGGCATCAAGCCC
721    ---------+---------+---------+---------+---------+---------+
       TTGCCGTGGCCGGGGACGTTGTTGCACAGGTGGCACGTCACGTGGGTGCCGTAGTTCGGG
        N   G   T   G   P   C   N   N   V   S   T   V   Q   C   T   H   G   I   K   P

PvuII
       GTGGTGTCCACCCAGCTGCTGCTGAATGGCAGCCTGGCCGAGGGCGAGATCATCATCAGA
781    ---------+---------+---------+---------+---------+---------+
       CACCACAGGTGGGTCGACGACGACTTACCGTCGGACCGGCTCCCGCTCTAGTAGTAGTCT
        V   V   S   T   Q   L   L   L   N   G   S   L   A   E   G   E   I   I   I   R

AGCGAGAACCTGACCAACAACGTGAAAACCATCATCGTGCACCTGAACGAGAGCGTGGAA
841    ---------+---------+---------+---------+---------+---------+
       TCGCTCTTGGACTGGTTGTTGCACTTTTGGTAGTAGCACGTGGACTTGCTCTCGCACCTT
        S   E   N   L   T   N   N   V   K   T   I   I   V   H   L   N   E   S   V   E

ATCGTGTGCACCCGGCCCAACAACAACACCAGAAAGAGCATCCGGATCGGCCCTGGCCAG
901    ---------+---------+---------+---------+---------+---------+
       TAGCACACGTGGGCCGGGTTGTTGTTGTGGTCTTTCTCGTAGGCCTAGCCGGGACCGGTC
        I   V   C   T   R   P   N   N   N   T   R   K   S   I   R   I   G   P   G   Q

StuI
       ACCTTTTACGCCACCGGCGACATCATCGGCAACATCCGGCAGGCCTACTGCAACATCAAG
961    ---------+---------+---------+---------+---------+---------+
       TGGAAAATGCGGTGGCCGCTGTAGTAGCCGTTGTAGGCCGTCCGGATGACGTTGTAGTTC
        T   F   Y   A   T   G   D   I   I   G   N   I   R   Q   A   Y   C   N   I   K

BamHI       PstI
       AAGGACGACTGGATCCGGACCCTGCAGAGAGTGGGCAAGAAGCTGGCCGAGCACTTCCCC
1021   ---------+---------+---------+---------+---------+---------+
       TTCCTGCTGACCTAGGCCTGGGACGTCTCTCACCCGTTCTTCGACCGGCTCGTGAAGGGG
        K   D   D   W   I   R   T   L   Q   R   V   G   K   K   L   A   E   H   F   P
```

```
          AGACGGATCATCAACTTCACCAGCCCCGCTGGCGGCGACCTGGAAATCACCACCCACAGC
1081      ---------+---------+---------+---------+---------+---------+
          TCTGCCTAGTAGTTGAAGTGGTCGGGGCGACCGCCGCTGGACCTTTAGTGGTGGGTGTCG
           R   R   I   I   N   F   T   S   P   A   G   G   D   L   E   I   T   T   H   S

PstI
          TTCAACTGCAGAGGCGAGTTCTTCTACTGCAATACCAGCAGCCTGTTCAACAGCACCTAC
1141      ---------+---------+---------+---------+---------+---------+
          AAGTTGACGTCTCCGCTCAAGAAGATGACGTTATGGTCGTCGGACAAGTTGTCGTGGATG
           F   N   C   R   G   E   F   F   Y   C   N   T   S   S   L   F   N   S   T   Y

AACCCCAACGACACCAACAGCAACAGCTCCAGCAGCAACTCCAGCCTGGACATCACCATC
1201      ---------+---------+---------+---------+---------+---------+
          TTGGGGTTGCTGTGGTTGTCGTTGTCGAGGTCGTCGTTGAGGTCGGACCTGTAGTGGTAG
           N   P   N   D   T   N   S   N   S   S   S   S   N   S   S   L   D   I   T   I

CCTTGCCGGATCAAGCAGATCATCAATATGTGGCAGGAAGTGGGCAGGGCTATGTACGCC
1261      ---------+---------+---------+---------+---------+---------+
          GGAACGGCCTAGTTCGTCTAGTAGTTATACACCGTCCTTCACCCGTCCCGATACATGCGG
           P   C   R   I   K   Q   I   I   N   M   W   Q   E   V   G   R   A   M   Y   A

CCTCCCATCGAGGGCAACATCACATGCAAGAGCAACATCACCGGCCTGCTCCTGGTCCGC
1321      ---------+---------+---------+---------+---------+---------+
          GGAGGGTAGCTCCCGTTGTAGTGTACGTTCTCGTTGTAGTGGCCGGACGAGGACCAGGCG
           P   P   I   E   G   N   I   T   C   K   S   N   I   T   G   L   L   L   V   R

BglII
          GACGGCGGCGTGGAAAGCAACGAGACAGAGATCTTCAGACCCGGCGGAGGCGACATGCGG
1381      ---------+---------+---------+---------+---------+---------+
          CTGCCGCCGCACCTTTCGTTGCTCTGTCTCTAGAAGTCTGGGCCGCCTCCGCTGTACGCC
           D   G   G   V   E   S   N   E   T   E   I   F   R   P   G   G   G   D   M   R

AACAACTGGCGGAGCGAGCTGTACAAGTACAAGGTGGTGGAAATCAAGCCCCTGGGAATC
1441      ---------+---------+---------+---------+---------+---------+
          TTGTTGACCGCCTCGCTCGACATGTTCATGTTCCACCACCTTTAGTTCGGGGACCCTTAG
           N   N   W   R   S   E   L   Y   K   Y   K   V   V   E   I   K   P   L   G   I
```

```
                                                              NarI
                                                              KasI
      GCCCCCACCGCCGCCAAGCGGAGAGTGGTGGAAAGCGAGAAGTCCGCCGTGGGCCTGGGC
1501  ---------+---------+---------+---------+---------+---------+
      CGGGGGTGGCGGCGGTTCGCCTCTCACCACCTTTCGCTCTTCAGGCGGCACCCGGACCCG
       A  P  T  A  A  K  R  R  V  V  E  S  E  K  S  A  V  G  L  G

NcoI
      GCCGTGATCTTCGGCTTTCTGGGAGCCGCCGGAAGCACCATGGGCGCTGCCAGCATCACC
1561  ---------+---------+---------+---------+---------+---------+
      CGGCACTAGAAGCCGAAAGACCCTCGGCGGCCTTCGTGGTACCCGCGACGGTCGTAGTGG
       A  V  I  F  G  F  L  G  A  A  G  S  T  M  G  A  A  S  I  T

PvuII                              BspMI
      CTGACCGTGCAGGCCAGACAGCTGCTGAGCGGCATCGTGCAGCAGCAGAGCAACCTGCTG
1621  ---------+---------+---------+---------+---------+---------+
      GACTGGCACGTCCGGTCTGTCGACGACTCGCCGTAGCACGTCGTCGTCTCGTTGGACGAC
       L  T  V  Q  A  R  Q  L  L  S  G  I  V  Q  Q  Q  S  N  L  L

PvuII                    PvuII
                                     PstI                     PstI
      AAGGCCATCGAGGCCCAGCAGCATCTGCTGCAGCTGACCGTGTGGGGCATCAAGCAGCTG
1681  ---------+---------+---------+---------+---------+---------+
      TTCCGGTAGCTCCGGGTCGTCGTAGACGACGTCGACTGGCACACCCCGTAGTTCGTCGAC
       K  A  I  E  A  Q  Q  H  L  L  Q  L  T  V  W  G  I  K  Q  L

SmaI
      CAGACCCGGGTGCTGGCCATCGAGAGATACCTGAAGGACCAGCAGCTCCTGGGAATCTGG
1741  ---------+---------+---------+---------+---------+---------+
      GTCTGGGCCCACGACCGGTAGCTCTCTATGGACTTCCTGGTCGTCGAGGACCCTTAGACC
       Q  T  R  V  L  A  I  E  R  Y  L  K  D  Q  Q  L  L  G  I  W

PstI                                         PvuII
      GGCTGCAGCGGCAAGCTGATCTGCACCACCGCCGTGCCCTGGAACAGCAGCTGGTCCAAC
1801  ---------+---------+---------+---------+---------+---------+
      CCGACGTCGCCGTTCGACTAGACGTGGTGGCGGCACGGGACCTTGTCGTCGACCAGGTTG
       G  C  S  G  K  L  I  C  T  T  A  V  P  W  N  S  S  W  S  N
```

```
              BglII
         AAGAGCCACGACGAGATCTGGGGCAACATGACCTGGATGCAGTGGGACAGAGAGATCAGC
   1861  ---------+---------+---------+---------+---------+---------+
         TTCTCGGTGCTGCTCTAGACCCCGTTGTACTGGACCTACGTCACCCTGTCTCTCTAGTCG
          K  S  H  D  E  I  W  G  N  M  T  W  M  Q  W  D  R  E  I  S

AACTACACCAACACCATCTACCGCCTGCTGGAAGATAGCCAGAACCAGCAGGAACAGAAC
   1921  ---------+---------+---------+---------+---------+---------+
         TTGATGTGGTTGTGGTAGATGGCGGACGACCTTCTATCGGTCTTGGTCGTCCTTGTCTTG
          N  Y  T  N  T  I  Y  R  L  L  E  D  S  Q  N  Q  Q  E  Q  N

BspMI           PvuII
         GAGAAGGACCTGCTGGCCCTGGACAGCTGGGAGAACCTGTGGAACTGGTTCAGCATCACC
   1981  ---------+---------+---------+---------+---------+---------+
         CTCTTCCTGGACGACCGGGACCTGTCGACCCTCTTGGACACCTTGACCAAGTCGTAGTGG
          E  K  D  L  L  A  L  D  S  W  E  N  L  W  N  W  F  S  I  T

BglII
         AAGTGGCTGTGGTACATCAAGATCTTCATCATGATCGTGGGCGGCCTGATCGGCCTGCGG
   2041  ---------+---------+---------+---------+---------+---------+
         TTCACCGACACCATGTAGTTCTAGAAGTAGTACTAGCACCCGCCGGACTAGCCGGACGCC
          K  W  L  W  Y  I  K  I  F  I  M  I  V  G  G  L  I  G  L  R

ATCATCTTCGCCGTGCTGAGCGTGGTGGGAGGCGGAGCCAAGTTTGTGGCCGCCTGGACC
   2101  ---------+---------+---------+---------+---------+---------+
         TAGTAGAAGCGGCACGACTCGCACCACCCTCCGCCTCGGTTCAAACACCGGCGGACCTGG
          I  I  F  A  V  L  S  V  V  G  G  G  A  K  F  V  A  A  W  T

XhoI  XbaI
         CTGAAAGCCGCTGCCGGCGGAACCGAGACAAGCCAGGTGGCCCCTGCCTGACTCGAGTCT
   2161  ---------+---------+---------+---------+---------+---------+
         GACTTTCGGCGACGGCCGCCTTGGCTCTGTTCGGTCCACCGGGGACGGACTGAGCTCAGA
          L  K  A  A  A  G  T  E  T  S  Q  V  A  P  A  *
```

```
          ApaI   PmeI
       AGAGGGCCCGTTTAAACCCGC
2221   ---------+---------+-
       TCTCCCGGGCAAATTTGGGCG
```

FIG. 42

```
              PacI    HindIII                              PstI
     GAGCGGAAGGCCCATGAGGCCAGTTAATTAAGCTTGCCACCATGCCTATGGGCAGCCTGC
  1  ---------+---------+---------+---------+---------+---------+
     CTCGCCTTCCGGGTACTCCGGTCAATTAATTCGAACGGTGGTACGGATACCCGTCGGACG
                                              M   P   M   G   S   L   Q BspMI    SphI                        PvuII
     AGCCTCTGGCCACCCTGTACCTGCTGGGCATGCTGGTGGCCTCCGTGCTGGCAGCTGGCA
 61  ---------+---------+---------+---------+---------+---------+
     TCGGAGACCGGTGGGACATGGACGACCCGTACGACCACCGGAGGCACGACCGTCGACCGT
      P   L   A   T   L   Y   L   L   G   M   L   V   A   S   V   L   A   A   G   N ACCTGTGGGTCACAGTGTACTACGGCGTGCCCGTGTGGAAAGAGGCCACCACCACCCTGT
121  ---------+---------+---------+---------+---------+---------+
     TGGACACCCAGTGTCACATGATGCCGCACGGGCACACCTTTCTCCGGTGGTGGTGGGACA
      L   W   V   T   V   Y   Y   G   V   P   V   W   K   E   A   T   T   T   L   F StuI
     TCTGCGCCAGCGACGCCAAGGCCTACGACAAAGAGGTGCACAACGTCTGGGCCACCCACG
181  ---------+---------+---------+---------+---------+---------+
     AGACGCGGTCGCTGCGGTTCCGGATGCTGTTTCTCCACGTGTTGCAGACCCGGTGGGTGC
      C   A   S   D   A   K   A   Y   D   K   E   V   H   N   V   W   A   T   H   A PflMI
     CCTGCGTGCCCACCGACCCCAACCCCCAGGAAATGGTCCTGGGCAACGTGACCGAGAACT
241  ---------+---------+---------+---------+---------+---------+
     GGACGCACGGGTGGCTGGGGTTGGGGGTCCTTTACCAGGACCCGTTGCACTGGCTCTTGA
      C   V   P   T   D   P   N   P   Q   E   M   V   L   G   N   V   T   E   N   F
```

```
              HincII                    BclI
       TCAACATGTGGAAGAACGAGATGGTCAACCAGATGCACGAGGACGTGATCAGCCTGTGGG
301    ---------+---------+---------+---------+---------+---------+
       AGTTGTACACCTTCTTGCTCTACCAGTTGGTCTACGTGCTCCTGCACTAGTCGGACACCC
        _N__M__W__K__N__E__M__V__N__Q__M__H__E__D__V__I__S__L__W__D ACCAGAGCCTGAAGCCCTGCGTGAAGCTGACCCCCCTGTGCGTGACCCTGGAATGCTCCA
361    ---------+---------+---------+---------+---------+---------+
       TGGTCTCGGACTTCGGGACGCACTTCGACTGGGGGGACACGCACTGGGACCTTACGAGGT
        _Q__S__L__K__P__C__V__K__L__T__P__L__C__V__T__L__E__C__S__N PstI
       ACGTGACCTACAACGAGAGCATGAAGGAAGTGAAGAACTGCAGCTTCAACCTGACCACCG
421    ---------+---------+---------+---------+---------+---------+
       TGCACTGGATGTTGCTCTCGTACTTCCTTCACTTCTTGACGTCGAAGTTGGACTGGTGGC
        _V__T__Y__N__E__S__M__K__E__V__K__N__C__S__F__N__L__T__T__E AGCTGCGGGACAAGAAACAGAAGGTGCACGCCCTGTTCTACCGGCTGGACATCGTGCCCC
481    ---------+---------+---------+---------+---------+---------+
       TCGACGCCCTGTTCTTTGTCTTCCACGTGCGGGACAAGATGGCCGACCTGTAGCACGGGG
        _L__R__D__K__K__Q__K__V__H__A__L__F__Y__R__L__D__I__V__P__L BclI
       TGAACGACACCGAGAAGAAGAACAGCAGCCGGCCCTACCGGCTGATCAACTGCAACACCA
541    ---------+---------+---------+---------+---------+---------+
       ACTTGCTGTGGCTCTTCTTCTTGTCGTCGGCCGGGATGGCCGACTAGTTGACGTTGTGGT
        _N__D__T__E__K__K__N__S__S__R__P__Y__R__L__I__N__C__N__T__S StuI
       GCGCCATCACCCAGGCCTGCCCCAAAGTGACCTTCGACCCTATCCCCATCCACTACTGCA
601    ---------+---------+---------+---------+---------+---------+
       CGCGGTAGTGGGTCCGGACGGGGTTTCACTGGAAGCTGGGATAGGGGTAGGTGATGACGT
        _A__I__T__Q__A__C__P__K__V__T__F__D__P__I__P__I__H__Y__C__T
```

```
            CCCCTGCCGGCTACGCCATCCTGAAGTGCAACGACAAGAAGTTCAACGGCACCGGCCCCT
    661     ---------+---------+---------+---------+---------+---------+
            GGGGACGGCCGATGCGGTAGGACTTCACGTTGCTGTTCTTCAAGTTGCCGTGGCCGGGGA
             _P__A__G__Y__A__I__L__K__C__N__D__K__K__F__N__G__T__G__P__C

PvuII
            GCCACAAGGTGTCCACCGTGCAGTGCACCCACGGCATCAAGCCCGTGGTGTCCACCCAGC
    721     ---------+---------+---------+---------+---------+---------+
            CGGTGTTCCACAGGTGGCACGTCACGTGGGTGCCGTAGTTCGGGCACCACAGGTGGGTCG
             _H__K__V__S__T__V__Q__C__T__H__G__I__K__P__V__V__S__T__Q__L

TGCTGCTGAATGGCAGCCTGGCCGAGGGCGAGATCATCATCAGAAGCGAGAACCTGACCA
    781     ---------+---------+---------+---------+---------+---------+
            ACGACGACTTACCGTCGGACCGGCTCCCGCTCTAGTAGTAGTCTTCGCTCTTGGACTGGT
             _L__L__N__G__S__L__A__E__G__E__I__I__I__R__S__E__N__L__T__N

PflMI
            ACAACGCCAAGACCATCATTGTGCACCTGAACCAGAGCGTGGAAATCGTGTGCGCCAGAC
    841     ---------+---------+---------+---------+---------+---------+
            TGTTGCGGTTCTGGTAGTAACACGTGGACTTGGTCTCGCACCTTTAGCACACGCGGTCTG
             _N__A__K__T__I__I__V__H__L__N__Q__S__V__E__I__V__C__A__R__P

NarI
                                                                KasI
            CCAGCAACAACACCCGGACCAGCATCCGGATCGGCCCTGGCCAGACCTTCTATGCCACCG
    901     ---------+---------+---------+---------+---------+---------+
            GGTCGTTGTTGTGGGCCTGGTCGTAGGCCTAGCCGGGACCGGTCTGGAAGATACGGTGGC
             _S__N__N__T__R__T__S__I__R__I__G__P__G__Q__T__F__Y__A__T__G

GCGCCATTACCGGCGACATCAGACAGGCCCACTGCAACATCAGCAAGGACAAGTGGAACG
    961     ---------+---------+---------+---------+---------+---------+
            CGCGGTAATGGCCGCTGTAGTCTGTCCGGGTGACGTTGTAGTCGTTCCTGTTCACCTTGC
             _A__I__T__G__D__I__R__Q__A__H__C__N__I__S__K__D__K__W__N__E
```

```
                PstI
         AGACACTGCAGAGAGTCGGCGAGAAGCTGGCCGAGCACTTCCCCAACAAGACAATCAAGT
   1021  ---------+---------+---------+---------+---------+---------+
         TCTGTGACGTCTCTCACCCGCTCTTCGACCGGCTCGTGAAGGGGTTGTTCTGTTAGTTCA
          _T__L__Q__R__V__G__E__K__L__A__E__H__F__P__N__K__T__I__K__F

PstI
         TCAACAGCAGCTCTGGCGGCGACCTGGAAATCACCACCCACAGCTTCAACTGCAGAGGCG
   1081  ---------+---------+---------+---------+---------+---------+
         AGTTGTCGTCGAGACCGCCGCTGGACCTTTAGTGGTGGGTGTCGAAGTTGACGTCTCCGC
          _N__S__S__S__G__D__L__E__I__T__T__H__S__F__N__C__R__G__E

AGTTCTTCTACTGCAATACCTCCGGCCTGTTCAATGGCACCTTTAACGGCACCTACGTGT
   1141  ---------+---------+---------+---------+---------+---------+
         TCAAGAAGATGACGTTATGGAGGCCGGACAAGTTACCGTGGAAATTGCCGTGGATGCACA
          _F__F__Y__C__N__T__S__G__L__F__N__G__T__F__N__G__T__Y__V__S

CCCCCAACAGCACCGACAGCAACAGCTCCAGCATCATCACCATCCCTTGCCGGATCAAGC
   1201  ---------+---------+---------+---------+---------+---------+
         GGGGGTTGTCGTGGCTGTCGTTGTCGAGGTCGTAGTAGTGGTAGGGAACGGCCTAGTTCG
          _P__N__S__T__D__S__N__S__S__S__I__I__T__I__P__C__R__I__K__Q

AGATCATCAATATGTGGCAGGAAGTGGGCAGGGCTATGTACGCCCCTCCTATCGCCGGCA
   1261  ---------+---------+---------+---------+---------+---------+
         TCTAGTAGTTATACACCGTCCTTCACCCGTCCCGATACATGCGGGGAGGATAGCGGCCGT
          _I__I__N__M__W__Q__E__V__G__R__A__M__Y__A__P__P__I__A__G__N

ACATCACATGCAAGAGCAACATCACCGGCCTGCTGCTCGTCCGCGACGGCGGAACAGGCA
   1321  ---------+---------+---------+---------+---------+---------+
         TGTAGTGTACGTTCTCGTTGTAGTGGCCGGACGACGAGCAGGCGCTGCCGCCTTGTCCGT
          _I__T__C__K__S__N__I__T__G__L__L__L__V__R__D__G__G__T__G__S

BglII
         GCGAGAGCAACAAGACCGAGATCTTCAGACCCGGCGGAGGCGACATGCGGGACAATTGGC
   1381  ---------+---------+---------+---------+---------+---------+
         CGCTCTCGTTGTTCTGGCTCTAGAAGTCTGGGCCGCCTCCGCTGTACGCCCTGTTAACCG
          _E__S__N__K__T__E__I__F__R__P__G__G__G__D__M__R__D__N__W__R
```

```
        GGAGCGAGCTGTACAAGTACAAGGTGGTGGAAATCAAGCCCCTGGGCGTGGCCCCCACCA
1441    ---------+---------+---------+---------+---------+---------+
        CCTCGCTCGACATGTTCATGTTCCACCACCTTTAGTTCGGGGACCCGCACCGGGGGTGGT
         S   E   L   Y   K   Y   K   V   V   E   I   K   P   L   G   V   A   P   T   K

NarI                                    BssHII
                                KasI                                    XhoI AscI
        AGGCCAAGCGGAGAGTGGTGGAAGGCGCCCACCACCACCATCACCACTGACTCGAGGCGC
1501    ---------+---------+---------+---------+---------+---------+
        TCCGGTTCGCCTCTCACCACCTTCCGCGGGTGGTGGTGGTAGTGGTGACTGAGCTCCGCG
         A   K   R   R   V   V   E   G   A   H   H   H   H   H   H   *

StuI
         AvrII
        GCCTAGGCCTTGACGGCCTTCCGCCA
1561    ---------+---------+------
        CGGATCCGGAACTGCCGGAAGGCGGT
```

FIG. 43

```
               HindIII
     NheI  PmeI   AflII                              PstI
     CCAAGCTGGCTAGCGTTTAAACTTAAGCTTGCCACCATGCCTATGGGCAGCCTGCAGCCT
  1  ---------+---------+---------+---------+---------+---------+
     GGTTCGACCGATCGCAAATTTGAATTCGAACGGTGGTACGGATACCCGTCGGACGTCGGA
                                        M   P   M   G   S   L   Q   P BspMI      SphI                          PvuII
     CTGGCCACCCTGTACCTGCTGGGCATGCTGGTGGCCTCCGTGCTGGCAGCTGGCAACCTG
 61  ---------+---------+---------+---------+---------+---------+
     GACCGGTGGGACATGGACGACCCGTACGACCACCGGAGGCACGACCGTCGACCGTTGGAC
     L   A   T   L   Y   L   L   G   M   L   V   A   S   V   L   A   A   G   N   L TGGGTCACAGTGTACTACGGCGTGCCCGTGTGGAAAGAGGCCACCACCACCCTGTTCTGC
121  ---------+---------+---------+---------+---------+---------+
     ACCCAGTGTCACATGATGCCGCACGGGCACACCTTTCTCCGGTGGTGGTGGGACAAGACG
     W   V   T   V   Y   Y   G   V   P   V   W   K   E   A   T   T   T   L   F   C StuI
     GCCAGCGACGCCAAGGCCTACGACAAAGAGGTGCACAACGTCTGGGCCACCCACGCCTGC
181  ---------+---------+---------+---------+---------+---------+
     CGGTCGCTGCGGTTCCGGATGCTGTTTCTCCACGTGTTGCAGACCCGGTGGGTGCGGACG
     A   S   D   A   K   A   Y   D   K   E   V   H   N   V   W   A   T   H   A   C PflMI
     GTGCCCACCGACCCCAACCCCCAGGAAATGGTCCTGGGCAACGTGACCGAGAACTTCAAC
241  ---------+---------+---------+---------+---------+---------+
     CACGGGTGGCTGGGGTTGGGGGTCCTTTACCAGGACCCGTTGCACTGGCTCTTGAAGTTG
     V   P   T   D   P   N   P   Q   E   M   V   L   G   N   V   T   E   N   F   N
```

```
              HincII                   BclI
      ATGTGGAAGAACGAGATGGTCAACCAGATGCACGAGGACGTGATCAGCCTGTGGGACCAG
301   ---------+---------+---------+---------+---------+---------+
      TACACCTTCTTGCTCTACCAGTTGGTCTACGTGCTCCTGCACTAGTCGGACACCCTGGTC
       M  W  K  N  E  M  V  N  Q  M  H  E  D  V  I  S  L  W  D  Q AGCCTGAAGCCCTGCGTGAAGCTGACCCCCCTGTGCGTGACCCTGGAATGCTCCAACGTG
361   ---------+---------+---------+---------+---------+---------+
      TCGGACTTCGGGACGCACTTCGACTGGGGGGACACGCACTGGGACCTTACGAGGTTGCAC
       S  L  K  P  C  V  K  L  T  P  L  C  V  T  L  E  C  S  N  V PstI
      ACCTACAACGAGAGCATGAAGGAAGTGAAGAACTGCAGCTTCAACCTGACCACCGAGCTG
421   ---------+---------+---------+---------+---------+---------+
      TGGATGTTGCTCTCGTACTTCCTTCACTTCTTGACGTCGAAGTTGGACTGGTGGCTCGAC
       T  Y  N  E  S  M  K  E  V  K  N  C  S  F  N  L  T  T  E  L CGGGACAAGAAACAGAAGGTGCACGCCCTGTTCTACCGGCTGGACATCGTGCCCCTGAAC
481   ---------+---------+---------+---------+---------+---------+
      GCCCTGTTCTTTGTCTTCCACGTGCGGGACAAGATGGCCGACCTGTAGCACGGGGACTTG
       R  D  K  K  Q  K  V  H  A  L  F  Y  R  L  D  I  V  P  L  N BclI
      GACACCGAGAAGAAGAACAGCAGCCGGCCCTACCGGCTGATCAACTGCAACACCAGCGCC
541   ---------+---------+---------+---------+---------+---------+
      CTGTGGCTCTTCTTCTTGTCGTCGGCCGGGATGGCCGACTAGTTGACGTTGTGGTCGCGG
       D  T  E  K  K  N  S  S  R  P  Y  R  L  I  N  C  N  T  S  A StuI
      ATCACCCAGGCCTGCCCCAAAGTGACCTTCGACCCTATCCCCATCCACTACTGCACCCCT
601   ---------+---------+---------+---------+---------+---------+
      TAGTGGGTCCGGACGGGGTTTCACTGGAAGCTGGGATAGGGGTAGGTGATGACGTGGGGA
       I  T  Q  A  C  P  K  V  T  F  D  P  I  P  I  H  Y  C  T  P
```

```
            GCCGGCTACGCCATCCTGAAGTGCAACGACAAGAAGTTCAACGGCACCGGCCCCTGCCAC
    661     ---------+---------+---------+---------+---------+---------+
            CGGCCGATGCGGTAGGACTTCACGTTGCTGTTCTTCAAGTTGCCGTGGCCGGGGACGGTG
            A  G  Y  A  I  L  K  C  N  D  K  K  F  N  G  T  G  P  C  H

PvuII
            AAGGTGTCCACCGTGCAGTGCACCCACGGCATCAAGCCCGTGGTGTCCACCCAGCTGCTG
    721     ---------+---------+---------+---------+---------+---------+
            TTCCACAGGTGGCACGTCACGTGGGTGCCGTAGTTCGGGCACCACAGGTGGGTCGACGAC
            K  V  S  T  V  Q  C  T  H  G  I  K  P  V  V  S  T  Q  L  L

CTGAATGGCAGCCTGGCCGAGGGCGAGATCATCATCAGAAGCGAGAACCTGACCAACAAC
    781     ---------+---------+---------+---------+---------+---------+
            GACTTACCGTCGGACCGGCTCCCGCTCTAGTAGTAGTCTTCGCTCTTGGACTGGTTGTTG
            L  N  G  S  L  A  E  G  E  I  I  R  S  E  N  L  T  N  N

PflMI
            GCCAAGACCATCATTGTGCACCTGAACCAGAGCGTGGAAATCGTGTGCGCCAGACCCAGC
    841     ---------+---------+---------+---------+---------+---------+
            CGGTTCTGGTAGTAACACGTGGACTTGGTCTCGCACCTTTAGCACACGCGGTCTGGGTCG
            A  K  T  I  I  V  H  L  N  Q  S  V  E  I  V  C  A  R  P  S

NarI
                                                                 KasI
            AACAACACCCGGACCAGCATCCGGATCGGCCCTGGCCAGACCTTCTATGCCACCGGCGCC
    901     ---------+---------+---------+---------+---------+---------+
            TTGTTGTGGGCCTGGTCGTAGGCCTAGCCGGGACCGGTCTGGAAGATACGGTGGCCGCGG
            N  N  T  R  T  S  I  R  I  G  P  G  Q  T  F  Y  A  T  G  A

ATTACCGGCGACATCAGACAGGCCCACTGCAACATCAGCAAGGACAAGTGGAACGAGACA
    961     ---------+---------+---------+---------+---------+---------+
            TAATGGCCGCTGTAGTCTGTCCGGGTGACGTTGTAGTCGTTCCTGTTCACCTTGCTCTGT
            I  T  G  D  I  R  Q  A  H  C  N  I  S  K  D  K  W  N  E  T
```

```
       PstI
       CTGCAGAGAGTGGGCGAGAAGCTGGCCGAGCACTTCCCCAACAAGACAATCAAGTTCAAC
1021   ---------+---------+---------+---------+---------+---------+
       GACGTCTCTCACCCGCTCTTCGACCGGCTCGTGAAGGGGTTGTTCTGTTAGTTCAAGTTG
        L  Q  R  V  G  E  K  L  A  E  H  F  P  N  K  T  I  K  F  N

PstI
       AGCAGCTCTGGCGGCGACCTGGAAATCACCACCCACAGCTTCAACTGCAGAGGCGAGTTC
1081   ---------+---------+---------+---------+---------+---------+
       TCGTCGAGACCGCCGCTGGACCTTTAGTGGTGGGTGTCGAAGTTGACGTCTCCGCTCAAG
        S  S  S  G  G  D  L  E  I  T  T  H  S  F  N  C  R  G  E  F

TTCTACTGCAATACCTCCGGCCTGTTCAATGGCACCTTTAACGGCACCTACGTGTCCCCC
1141   ---------+---------+---------+---------+---------+---------+
       AAGATGACGTTATGGAGGCCGGACAAGTTACCGTGGAAATTGCCGTGGATGCACAGGGGG
        F  Y  C  N  T  S  G  L  F  N  G  T  F  N  G  T  Y  V  S  P

AACAGCACCGACAGCAACAGCTCCAGCATCATCACCATCCCTTGCCGGATCAAGCAGATC
1201   ---------+---------+---------+---------+---------+---------+
       TTGTCGTGGCTGTCGTTGTCGAGGTCGTAGTAGTGGTAGGGAACGGCCTAGTTCGTCTAG
        N  S  T  D  S  N  S  S  S  I  I  T  I  P  C  R  I  K  Q  I

ATCAATATGTGGCAGGAAGTGGGCAGGGCTATGTACGCCCCTCCTATCGCCGGCAACATC
1261   ---------+---------+---------+---------+---------+---------+
       TAGTTATACACCGTCCTTCACCCGTCCCGATACATGCGGGGAGGATAGCGGCCGTTGTAG
        I  N  M  W  Q  E  V  G  R  A  M  Y  A  P  P  I  A  G  N  I

ACATGCAAGAGCAACATCACCGGCCTGCTGCTCGTCCGCGACGGCGGAACAGGCAGCGAG
1321   ---------+---------+---------+---------+---------+---------+
       TGTACGTTCTCGTTGTAGTGGCCGGACGACGAGCAGGCGCTGCCGCCTTGTCCGTCGCTC
        T  C  K  S  N  I  T  G  L  L  L  V  R  D  G  G  T  G  S  E

BglII
       AGCAACAAGACCGAGATCTTCAGACCCGGCGGAGGCGACATGCGGGACAATTGGCGGAGC
1381   ---------+---------+---------+---------+---------+---------+
       TCGTTGTTCTGGCTCTAGAAGTCTGGGCCGCCTCCGCTGTACGCCCTGTTAACCGCCTCG
        S  N  K  T  E  I  F  R  P  G  G  G  D  M  R  D  N  W  R  S
```

```
      GAGCTGTACAAGTACAAGGTGGTGGAAATCAAGCCCCTGGGCGTGGCCCCCACCAAGGCC
1441  ---------+---------+---------+---------+---------+---------+
      CTCGACATGTTCATGTTCCACCACCTTTAGTTCGGGGACCCGCACCGGGGGTGGTTCCGG
       E  L  Y  K  Y  K  V  V  E  I  K  P  L  G  V  A  P  T  K  A

NarI
                                             KasI
      AAGCGGAGAGTGGTGGAAAGCGAGAAGTCCGCCGTGGGAATCGGCGCCGTGTTCCTGGGC
1501  ---------+---------+---------+---------+---------+---------+
      TTCGCCTCTCACCACCTTTCGCTCTTCAGGCGGCACCCTTAGCCGCGGCACAAGGACCCG
       K  R  R  V  V  E  S  E  K  S  A  V  G  I  G  A  V  F  L  G

TTTCTGGGAGCCGCCGGAAGCACAATGGGCGCTGCCAGCATCACCCTGACCGTGCAGGCC
1561  ---------+---------+---------+---------+---------+---------+
      AAAGACCCTCGGCGGCCTTCGTGTTACCCGCGACGGTCGTAGTGGGACTGGCACGTCCGG
       F  L  G  A  A  G  S  T  M  G  A  A  S  I  T  L  T  V  Q  A

PvuII                                BspMI
      AGACAGCTGCTGAGCGGCATCGTGCAGCAGCAGAGCAACCTGCTGAGAGCTATCGAGGCC
1621  ---------+---------+---------+---------+---------+---------+
      TCTGTCGACGACTCGCCGTAGCACGTCGTCGTCTCGTTGGACGACTCTCGATAGCTCCGG
       R  Q  L  L  S  G  I  V  Q  Q  Q  S  N  L  L  R  A  I  E  A

PvuII                      PvuII
              PstI                       PstI    SmaI
      CAGCAGCATCTGCTGCAGCTGACCGTGTGGGGCATCAAGCAGCTGCAGACCCGGGTGCTG
1681  ---------+---------+---------+---------+---------+---------+
      GTCGTCGTAGACGACGTCGACTGGCACACCCCGTAGTTCGTCGACGTCTGGGCCCACGAC
       Q  Q  H  L  L  Q  L  T  V  W  G  I  K  Q  L  Q  T  R  V  L

PstI
      GCCATCGAGAGATACCTGAAGGACCAGCAGCTCCTGGGAATCTGGGGCTGCAGCGGCAAG
1741  ---------+---------+---------+---------+---------+---------+
      CGGTAGCTCTCTATGGACTTCCTGGTCGTCGAGGACCCTTAGACCCCGACGTCGCCGTTC
       A  I  E  R  Y  L  K  D  Q  Q  L  L  G  I  W  G  C  S  G  K
```

```
                                            PvuII
        CTGATCTGCACCACCGCCGTGCCCTGGAACTACAGCTGGTCCAACAGAAGCCAGGACGAC
1801    ---------+---------+---------+---------+---------+---------+
        GACTAGACGTGGTGGCGGCACGGGACCTTGATGTCGACCAGGTTGTCTTCGGTCCTGCTG
         L  I  C  T  T  A  V  P  W  N  Y  S  W  S  N  R  S  Q  D  D

ATCTGGGACAACATGACCTGGATGCAGTGGGACAAAGAGATCAGCAACTACACCAACACC
1861    ---------+---------+---------+---------+---------+---------+
        TAGACCCTGTTGTACTGGACCTACGTCACCCTGTTTCTCTAGTCGTTGATGTGGTTGTGG
         I  W  D  N  M  T  W  M  Q  W  D  K  E  I  S  N  Y  T  N  T

BspMI
        ATCTACAAGCTGCTGGAAGATAGCCAGATCCAGCAGGAAAAGAACGAGAAGGACCTGCTG
1921    ---------+---------+---------+---------+---------+---------+
        TAGATGTTCGACGACCTTCTATCGGTCTAGGTCGTCCTTTTCTTGCTCTTCCTGGACGAC
         I  Y  K  L  L  E  D  S  Q  I  Q  Q  E  K  N  E  K  D  L  L

PvuII
        GCCCTGGACAGCTGGGAGAACCTGTGGAACTGGTTCAACATCACCAACTGGCTGTGGTAC
1981    ---------+---------+---------+---------+---------+---------+
        CGGGACCTGTCGACCCTCTTGGACACCTTGACCAAGTTGTAGTGGTTGACCGACACCATG
         A  L  D  S  W  E  N  L  W  N  W  F  N  I  T  N  W  L  W  Y

BglII
        ATCAAGATCTTCATCATCATCGTGGGCGGCCTGATCGGCCTGCGGATCATCTTCGCCGTG
2041    ---------+---------+---------+---------+---------+---------+
        TAGTTCTAGAAGTAGTAGTAGCACCCGCCGGACTAGCCGGACGCCTAGTAGAAGCGGCAC
         I  K  I  F  I  I  I  V  G  G  L  I  G  L  R  I  I  F  A  V

CTGCCCATCGTGGGAGGCGGAGCCAAGTTTGTGGCCGCCTGGACCCTGAAAGCTGCCGCT
2101    ---------+---------+---------+---------+---------+---------+
        GACGGGTAGCACCCTCCGCCTCGGTTCAAACACCGGCGGACCTGGGACTTTCGACGGCGA
         L  P  I  V  G  G  A  K  F  V  A  A  W  T  L  K  A  A  A
```

```
                                         XhoI   XbaI   ApaI   PmeI
        GGCGGCACCGAGACATCTCAGGTGGCCCCTGCCTGACTCGAGTCTAGAGGGCCCGTTTAA
2161    ---------+---------+---------+---------+---------+---------+
        CCGCCGTGGCTCTGTAGAGTCCACCGGGGACGGACTGAGCTCAGATCTCCCGGGCAAATT
         G  G  T  E  T  S  Q  V  A  P  A  *

ACCCGC
2221    ------
        TGGGCG
```

FIG. 44

```
                PacI  HindIII                              PstI
     GAGCGGAAGGCCCATGAGGCCAGTTAATTAAGCTTGCCACCATGCCTATGGGCAGCCTGC
  1  ---------+---------+---------+---------+---------+---------+
     CTCGCCTTCCGGGTACTCCGGTCAATTAATTCGAACGGTGGTACGGATACCCGTCGGACG
                                         M   P   M   G   S   L   Q BspMI    SphI                       PvuII
     AGCCTCTGGCCACCCTGTACCTGCTGGGCATGCTGGTGGCCTCCGTGCTGGCAGCTGGCA
 61  ---------+---------+---------+---------+---------+---------+
     TCGGAGACCGGTGGGACATGGACGACCCGTACGACCACCGGAGGCACGACCGTCGACCGT
       P   L   A   T   L   Y   L   L   G   M   L   V   A   S   V   L   A   A   G   N ACCTGTGGGTCACAGTGTACTACGGCGTGCCCGTGTGGAAAGAGGCCAAGGCCACACTGT
121  ---------+---------+---------+---------+---------+---------+
     TGGACACCCAGTGTCACATGATGCCGCACGGGCACACCTTTCTCCGGTTCCGGTGTGACA
       L   W   V   T   V   Y   Y   G   V   P   V   W   K   E   A   K   A   T   L   F StuI
     TCTGCGCCAGCGACGCCAAGGCCTACGAGACAGAGGTGCACAACGTCTGGGCCACCCACG
181  ---------+---------+---------+---------+---------+---------+
     AGACGCGGTCGCTGCGGTTCCGGATGCTCTGTCTCCACGTGTTGCAGACCCGGTGGGTGC
       C   A   S   D   A   K   A   Y   E   T   E   V   H   N   V   W   A   T   H   A CCTGCGTGCCCACCGACCCCAACCCCCAGGAAATCGTCCTGGAAAACGTGACCGAGAACT
241  ---------+---------+---------+---------+---------+---------+
     GGACGCACGGGTGGCTGGGGTTGGGGGTCCTTTAGCAGGACCTTTTGCACTGGCTCTTGA
       C   V   P   T   D   P   N   P   Q   E   I   V   L   E   N   V   T   E   N   F
```

```
                        HincII                         BclI
        TCAACATGTGGGAGAACGACATGGTCAACCAGATGCACGAGGACGTGATCAGCCTGTGGG
301     ---------+---------+---------+---------+---------+---------+
        AGTTGTACACCCTCTTGCTGTACCAGTTGGTCTACGTGCTCCTGCACTAGTCGGACACCC
         _N__M__W__E__N__D__M__V__N__Q__M__H__E__D__V__I__S__L__W__D ACCAGAGCCTGAAGCCCTGCGTGAAGCTGACCCCCCTGTGCGTGACCCTGGACTGCGAGA
361     ---------+---------+---------+---------+---------+---------+
        TGGTCTCGGACTTCGGGACGCACTTCGACTGGGGGGACACGCACTGGGACCTGACGCTCT
         _Q__S__L__K__P__C__V__K__L__T__P__L__C__V__T__L__D__C__E__N PstI
        ACGTGGACGGCAACGACACCTACAACGGCACCAACGAGATGAAGAACTGCAGCTTCAACA
421     ---------+---------+---------+---------+---------+---------+
        TGCACCTGCCGTTGCTGTGGATGTTGCCGTGGTTGCTCTACTTCTTGACGTCGAAGTTGT
         _V__D__G__N__D__T__Y__N__G__T__N__E__M__K__N__C__S__F__N__T CCACCACCGAGCTGCGGGACAAGAAACAGAAGGTGTCCGCCCTGTTCTACCGGCTGGACA
481     ---------+---------+---------+---------+---------+---------+
        GGTGGTGGCTCGACGCCCTGTTCTTTGTCTTCCACAGGCGGGACAAGATGGCCGACCTGT
         _T__T__E__L__R__D__K__K__Q__K__V__S__A__L__F__Y__R__L__D__I PvuII
                                                             BclI
        TCGTGCCCCTGAACAGAAGCAGCAGCAGCAACAGCAGCGACTACTACCGGCTGATCAGCT
541     ---------+---------+---------+---------+---------+---------+
        AGCACGGGGACTTGTCTTCGTCGTCGTCGTTGTCGTCGCTGATGATGGCCGACTAGTCGA
         _V__P__L__N__R__S__S__S__N__S__S__D__Y__Y__R__L__I__S__C StuI
        GCAACACCAGCGCCATCACCCAGGCCTGCCCCAAAGTGACCTTCGACCCTATCCCCATCC
601     ---------+---------+---------+---------+---------+---------+
        CGTTGTGGTCGCGGTAGTGGGTCCGGACGGGGTTTCACTGGAAGCTGGGATAGGGGTAGG
         _N__T__S__A__I__T__Q__A__C__P__K__V__T__F__D__P__I__P__I__H
```

```
         ACTACTGCGCCCCTGCCGGCTTCGCCATCCTGAAGTGCAACAACAAGACCTTCAATGGCA
661      ---------+---------+---------+---------+---------+---------+
         TGATGACGCGGGGACGGCCGAAGCGGTAGGACTTCACGTTGTTGTTCTGGAAGTTACCGT
          Y  C  A  P  A  G  F  A  I  L  K  C  N  N  K  T  F  N  G  T

CCGGCCCCTGCCACAACGTGTCCACCGTGCAGTGCACCCACGGCATCAAGCCCGTGGTGT
721      ---------+---------+---------+---------+---------+---------+
         GGCCGGGGACGGTGTTGCACAGGTGGCACGTCACGTGGGTGCCGTAGTTCGGGCACCACA
          G  P  C  H  N  V  S  T  V  Q  C  T  H  G  I  K  P  V  V  S

PvuII
         CCACCCAGCTGCTGCTGAATGGCAGCCTGGCCGAGAAAGAGATCATCATCAGAAGCAAGA
781      ---------+---------+---------+---------+---------+---------+
         GGTGGGTCGACGACGACTTACCGTCGGACCGGCTCTTTCTCTAGTAGTAGTCTTCGTTCT
          T  Q  L  L  L  N  G  S  L  A  E  K  E  I  I  I  R  S  K  N

ACCTGAGCGACAACGTGAAAACCATCATTGTGCACCTGAACGAGAGCGTGGAAATCGTGT
841      ---------+---------+---------+---------+---------+---------+
         TGGACTCGCTGTTGCACTTTTGGTAGTAACACGTGGACTTGCTCTCGCACCTTTAGCACA
          L  S  D  N  V  K  T  I  I  V  H  L  N  E  S  V  E  I  V  C

GCACCCGGCCCAACAACAACACCAGAAAGAGCATCCGGATCGGCCCTGGCCAGACCTTCT
901      ---------+---------+---------+---------+---------+---------+
         CGTGGGCCGGGTTGTTGTTGTGGTCTTTCTCGTAGGCCTAGCCGGGACCGGTCTGGAAGA
          T  R  P  N  N  N  T  R  K  S  I  R  I  G  P  G  Q  T  F  Y

NarI
            KasI
         ACGCCACCGGCGCCATCATCGGCAACATCAGAGAGGCCCACTGCAACATCAGCCGGGACA
961      ---------+---------+---------+---------+---------+---------+
         TGCGGTGGCCGCGGTAGTAGCCGTTGTAGTCTCTCCGGGTGACGTTGTAGTCGGCCCTGT
          A  T  G  A  I  I  G  N  I  R  E  A  H  C  N  I  S  R  D  K
```

```
                       PstI
        AGTGGAACGAGACACTGCAGAGAGTGGGCAAGAAGCTGGAAGAACAGTTCCCTAACAAGA
1021    ---------+---------+---------+---------+---------+---------+
        TCACCTTGCTCTGTGACGTCTCTCACCCGTTCTTCGACCTTCTTGTCAAGGGATTGTTCT
         W  N  E  T  L  Q  R  V  G  K  K  L  E  E  Q  F  P  N  K  T

PstI
        CAATCAACTTCACCTCCAGCTCTGGCGGCGACCTGGAAATCACCACCCACAGCTTCAACT
1081    ---------+---------+---------+---------+---------+---------+
        GTTAGTTGAAGTGGAGGTCGAGACCGCCGCTGGACCTTTAGTGGTGGGTGTCGAAGTTGA
         I  N  F  T  S  S  S  G  G  D  L  E  I  T  T  H  S  F  N  C

GCAGAGGCGAGTTCTTCTACTGCAACACCTCCAAGCTGTTCAACAGCACCTACATCCCCA
1141    ---------+---------+---------+---------+---------+---------+
        CGTCTCCGCTCAAGAAGATGACGTTGTGGAGGTTCGACAAGTTGTCGTGGATGTAGGGGT
         R  G  E  F  F  Y  C  N  T  S  K  L  F  N  S  T  Y  I  P  T

CCTACAGACCCAACAACACCCAGGGCAACAGCTCCAGCACCATCACAATCCCCTTGCCGGA
1201    ---------+---------+---------+---------+---------+---------+
        GGATGTCTGGGTTGTTGTGGGTCCCGTTGTCGAGGTCGTGGTAGTGTTAGGGAACGGCCT
         Y  R  P  N  N  T  Q  G  N  S  S  S  T  I  T  I  P  C  R  I

TCAAGCAGATCATCAATATGTGGCAGGAAGTGGGCAGGGCTATGTACGCCCCTCCTATCG
1261    ---------+---------+---------+---------+---------+---------+
        AGTTCGTCTAGTAGTTATACACCGTCCTTCACCCGTCCCGATACATGCGGGGAGGATAGC
         K  Q  I  I  N  M  W  Q  E  V  G  R  A  M  Y  A  P  P  I  A

BspMI
        CCGGCAACATTACCTGCAAGAGCCACATCACCGGCCTGCTGCTCGTCCGCGACGGCGGCA
1321    ---------+---------+---------+---------+---------+---------+
        GGCCGTTGTAATGGACGTTCTCGGTGTAGTGGCCGGACGACGAGCAGGCGCTGCCGCCGT
         G  N  I  T  C  K  S  H  I  T  G  L  L  L  V  R  D  G  G  T
```

```
       StuI
       CAGGCCTGAACAGCAGCACCGAGACATTCAGACCCGGCGGAGGCGACATGCGGGACAATT
1381   ---------+---------+---------+---------+---------+---------+
       GTCCGGACTTGTCGTCGTGGCTCTGTAAGTCTGGGCCGCCTCCGCTGTACGCCCTGTTAA
        _G__L__N__S__S__T__E__T__F__R__P__G__G__G__D__M__R__D__N__W

GGCGGAGCGAGCTGTACAAGTACAAGGTGGTGGAAATCAAGCCCCTGGGCGTGGCCCCTA
1441   ---------+---------+---------+---------+---------+---------+
       CCGCCTCGCTCGACATGTTCATGTTCCACCACCTTTAGTTCGGGGACCCGCACCGGGGAT
        _R__S__E__L__Y__K__Y__K__V__V__E__I__K__P__L__G__V__A__P__T

NarI                            BssHII
                                  KasI                       XhoI AscI
       CCGCCGCCAAGAGAAGAGTGGTGCAGGGCGCCCACCACCACCATCACCACTGACTCGAGG
1501   ---------+---------+---------+---------+---------+---------+
       GGCGGCGGTTCTCTTCTCACCACGTCCCGCGGGTGGTGGTGGTAGTGGTGACTGAGCTCC
        _A__A__K__R__R__V__V__Q__G__A__H__H__H__H__H__H__*_

StuI
         AvrII
       CGCGCCTAGGCCTTGACGGCCTTCCGCCA
1561   ---------+---------+---------
       GCGCGGATCCGGAACTGCCGGAAGGCGGT
```

FIG. 45

```
LOCUS       0951839_295 and 332 Glycan_16055_gp120        1555 bp   DNA
FEATURES            Location/Qualifiers
     CDS            19..1542
                    /label="EF117268_gp120"
ORIGIN
TTAATTAAGCTTGCCACCATGCCTATGGGCAGCCTGCAGCCTCTGGCCACCCTGTACCTG
CTGGGCATGCTGGTGGCCTCCGTGCTGGCAGCTGGCAACCTGTGGGTCACAGTGTACTAC
GGCGTGCCCGTGTGGAAAGAGGCCAAGACCACCCTGTTCTGCGCCAGCGACGCCAAGGCC
TACGAGAAAGAGGTGCACAACGTCTGGGCCACCCACGCCTGCGTGCCCACCGACCCCAAC
CCCCAGGAAATGGTCCTGGAAAACGTGACCGAGAACTTCAACATGTGGAAGAACGACATG
GTGGAACAGATGCACGAGGACGTGATCAGCCTGTGGGACCAGAGCCTGAAGCCCTGCGTG
AAGCTGACCCCCCTGTGCGTGACCCTGGAATGCAGACAGGTCAACACCACCAACGCCACC
AGCAGCGTGAACGTGACCAACGGCGAGGAAATCAAGAACTGCAGCTTCAATGCCACCACC
GAGATCCGGGACAAGAAACAGAAGGTGTACGCCCTGTTCTACCGGCTGGACATCGTGCCC
CTGGAAGAGGAACGGAAGGGCAACAGCAGCAAGTACCGGCTGATCAACTGCAACACCAGC
GCCATCACCCAGGCCTGCCCCAAAGTGACCTTCGACCCTATCCCCATCCACTACTGCGCC
CCTGCCGGCTACGCCATCCTGAAGTGCAACAACAAGACCTTCAACGGCACCGGCCCCTGC
AACAACGTGTCCACCGTGCAGTGCACCCACGGCATCAAGCCCGTGGTGTCCACCCAGCTG
CTGCTGAATGGCAGCCTGGCCGAGGGCGAGATCATCATCAGAAGCGAGAACCTGACCAAC
AACGTGAAAACCATCATCGTGCACCTGAACGAGAGCGTGGAAATCAACTGCACCCGGCCC
AACAACAACACCAGAAAGAGCATCCGGATCGGCCCTGGCCAGACCTTTTACGCCACCGGC
GACATCATCGGCAACATCCGGCAGGCCTACTGCAACATCAGCAAGGACGACTGGATCCGG
ACCCTGCAGAGAGTGGGCAAGAAGCTGGCCGAGCACTTCCCCAGACGGATCATCAACTTC
ACCAGCCCCGCTGGCGGCGACCTGGAAATCACCACCCACAGCTTCAACTGCAGAGGCGAG
TTCTTCTACTGCAATACCAGCAGCCTGTTCAACAGCACCTACAACCCCAACGACACCAAC
AGCAACAGCTCCAGCAGCAACTCCAGCCTGGACATCACCATCCCCTTGCCGGATCAAGCAG
ATCATCAATATGTGGCAGGAAGTGGGCAGGGCTATGTACGCCCCTCCCATCGAGGGCAAC
ATCACATGCAAGAGCAACATCACCGGCCTGCTCCTGGTCCGCGACGGCGGCGTGGAAAGC
AACGAGACAGAGATCTTCAGACCCGGCGGAGGCGACATGCGGAACAACTGGCGGAGCGAG
CTGTACAAGTACAAGGTGGTGGAAATCAAGCCCCTGGGAATCGCCCCCACCGCCGCCAAG
CGGAGAGTGGTGGAAGGCGCCCACCACCACCATCACCACTGACTCGAGGCGCGCC
//
```

Mutant 295 332 Glycan 16055 gp120 Env protein sequence

MPMGSLQPLATLYLLGMLVASVLAAGNLWVTVYYGVPVWKEAKTTLFCASDAKA
YEKEVHNVWATHACVPTDPNPQEMVLENVTENFNMWKNDMVEQMHEDVISLWDQSLKPCV
KLTPLCVTLECRQVNTTNATSSVNVTNGEEIKNCSFNATTEIRDKKQKVYALFYRLDIVP
LEEERKGNSSKYRLINCNTSAITQACPKVTFDPIPIHYCAPAGYAILKCNNKTFNGTPC
NNVSTVQCTHGIKPVVSTQLLLNGSLAEGEIIIRSENLTNNVKTIIVHLNESVEINCTRP
NNNTRKSIRIGPGQTFYATGDIIGNIRQAYCNISKDDWIRTLQRVGKKLAEHFPRRIINF
TSPAGGDLEITTHSFNCRGEFFYCNTSSLFNSTYNPNDTNSNSSSSNSSLDITIPCRIKQ
IINMWQEVGRAMYAPPIEGNITCKSNITGLLLVRDGGVESNETEIFRPGGGDMRNNWRSE
LYKYKVVEIKPLGIAPTAAKRRVVEGAHHHHHH*

FIG. 46

16936V1-3- 55 gp160 full length Env

MPMGSLQPLATLYLLGMLVASVLAAGNLWVTVYYGVPVWKEAKTTLFCASDAKAYET
EVHNVWATHACVPTDPNPQELVLENVTENFNMWRNDMVDQMHEDVISLWDQSLKPC
VKLTPLCVTLECRQVNTTNATSSVNVTNGEEIKNCSFNATTEIRDKKQKVYALFYRLDIV
PLEEERKGNSSKYRLINCNTSAITQACPKVNFDPIPIHYCTPAGYAILKCNNKTFNGTGP
CSNVSTVQCTHGIKPVVSTQLLLNGSLAEEGIIIRSENLTDNVKTIIVHLEEPVEIVCTRPN
NNTRKSIRIGPGQTFYATGDIIGNIRQAYCNISEAKWNETLQNVTKKLKEHFPNKTIIFNS
SSGGDLEITTHSFNCRGEFFYCNTSKLFNGIYNGTQSNSSNSNSTIIIPCKIKQIVNMWQ
KVGRAMYAPPIAGNITCTSNITGLLLVRDGGPDNVTEIFRPGGGDMRDNWRSELYKYK
VVEIKPLGIAPTGAKRRVVEREKRAVGLGAVFLGFLGAAGSTMGAASITLTVQARQLLS
GIVQQQSNLLRAIEAQQHMLQLTVWGIKQLQTRVLAIERYLKDQQLLGIWGCSGKLICT
TAVPWNASWSNRSHDDIWNNMTWMQWDREISNYTNTIYRLLEESQNQQERNEKDLL
ALDSWGNLWNWFSITNWLWYIKIFIMIVGGLIGLRIIFAVLSIVNRVRQGYSPLSFQTPTP
NPREADRLGGIEEEGGEQDRTRSIRLVNGFLALAWDDLRSLCLFSYHRLRDFILVVARA
VELLGRSLLRGLQKGWEALKYLGGLVQYWGLELKKSAISLLDTTAIAVAEGTDRIIAVIQ
GICRAIRNIPRRIRQGFETILQ*

US 8,586,056 B2

HIV-1 ENVELOPE GLYCOPROTEIN

This application claims priority to U.S. provisional patent application Ser. No. 61/309,685 filed Mar. 2, 2010.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted in ASCII format via EFS-Web and is hereby incorporated by reference in its entirety. Said ASCII copy, created on Apr. 22, 2011, is named 43094992.txt and is 605,771 bytes in size.

FIELD OF THE INVENTION

This application relates to a novel HIV-1 envelope glycoprotein which may be utilized as an HW-1 vaccine immunogen, as native Env trimer mimic, identification of small molecules for use as immunogen that bind specific HIV-1 broad neutralizing antibodies, identification of small molecules for use as anti-viral compound that bind specific HIV-1 envelope glycoprotein monomer and/or trimer, antigens for crystallization and for the identification of broad neutralizing antibodies.

BACKGROUND OF THE INVENTION

AIDS, or Acquired Immunodeficiency Syndrome, is caused by human immunodeficiency virus (HIV) and is characterized by several clinical features including wasting syndromes, central nervous system degeneration and profound immunosuppression that results in opportunistic infections and malignancies. HIV is a member of the lentivirus family of animal retroviruses, which include the visna virus of sheep and the bovine, feline, and simian immunodeficiency viruses (SIV). Two closely related types of HIV, designated HIV-1 and HIV-2, have been identified thus far, of which HIV-1 is by far the most common cause of AIDS. However, HIV-2, which differs in genomic structure and antigenicity, causes a similar clinical syndrome.

An infectious HIV particle consists of two identical strands of RNA, each approximately 9.2 kb long, packaged within a core of viral proteins. This core structure is surrounded by a phospholipid bilayer envelope derived from the host cell membrane that also includes virally-encoded membrane proteins (Abbas et al., Cellular and Molecular Immunology, 4th edition, W.B. Saunders Company, 2000, p. 454). The HIV genome has the characteristic 5'-LTR-Gag-Pol-Env-LTR-3' organization of the retrovirus family. Long terminal repeats (LTRs) at each end of the viral genome serve as binding sites for transcriptional regulatory proteins from the host and regulate viral integration into the host genome, viral gene expression, and viral replication.

The HIV genome encodes several structural proteins. The gag gene encodes structural proteins of the nucleocapsid core and matrix. The pol gene encodes reverse transcriptase (RT), integrase (IN), and viral protease (PR) enzymes required for viral replication. The tat gene encodes a protein that is required for elongation of viral transcripts. The rev gene encodes a protein that promotes the nuclear export of incompletely spliced or unspliced viral RNAs. The vif gene product enhances the infectivity of viral particles. The vpr gene product promotes the nuclear import of viral DNA and regulates G2 cell cycle arrest. The vpu and nef genes encode proteins that down regulate host cell CD4 expression and enhance release of virus from infected cells. The env gene encodes the viral envelope glycoprotein that is translated as a 160-kilodalton (kDa) precursor (gp160) and cleaved by a cellular protease to yield the external 120-kDa envelope glycoprotein (gp120) and the transmembrane 41-kDa envelope glycoprotein (gp41), which are required for the infection of cells (Abbas et al., Cellular and Molecular Immunology, 4th edition, W.B. Saunders Company, 2000, pp. 454-456). gp140 is a modified form of the Env glycoprotein, which contains the external 120-kDa envelope glycoprotein portion and the extracellular part of the gp41 portion of Env and has characteristics of both gp120 and gp41. The nef gene is conserved among primate lentiviruses and is one of the first viral genes that is transcribed following infection. In vitro, several functions have been described, including down-regulation of CD4 and MHC class I surface expression, altered T-cell signaling and activation, and enhanced viral infectivity.

HIV infection initiates with gp120 on the viral particle binding to the CD4 and chemokine receptor molecules (e.g., CXCR4, CCR5) on the cell membrane of target cells such as $CD4^+$ T-cells, macrophages and dendritic cells. The bound virus fuses with the target cell and reverse transcribes the RNA genome. The resulting viral DNA integrates into the cellular genome, where it directs the production of new viral RNA, and thereby viral proteins and new virions. These virions bud from the infected cell membrane and establish productive infections in other cells. This process also kills the originally infected cell. HIV can also kill cells indirectly because the CD4 receptor on uninfected T-cells has a strong affinity for gp120 expressed on the surface of infected cells. In this case, the uninfected cells bind, via the CD4 receptor-gp120 interaction, to infected cells and fuse to form a syncytium, which cannot survive. Destruction of $CD4^+$ T-lymphocytes, which are critical to immune defense, is a major cause of the progressive immune dysfunction that is the hallmark of AIDS disease progression. The loss of $CD4^+$ T cells seriously impairs the body's ability to fight most invaders, but it has a particularly severe impact on the defenses against viruses, fungi, parasites and certain bacteria, including mycobacteria.

Research on the Env glycoprotein has shown that the virus has many effective protective mechanisms with few vulnerabilities (Wyatt & Sodroski, Science. 1998 June 19; 280 (5371):1884-8). For fusion with its target cells, HIV-1 uses a trimeric Env complex containing gp120 and gp41 subunits (Burton et al., Nat Immunol. 2004 March; 5(3):233-6). The fusion potential of the Env complex is triggered by engagement of the CD4 receptor and a coreceptor, usually CCR5 or CXCR4. Neutralizing antibodies seem to work either by binding to the mature trimer on the virion surface and preventing initial receptor engagement events, or by binding after virion attachment and inhibiting the fusion process (Parren & Burton, Adv Immunol. 2001; 77:195-262). In the latter case, neutralizing antibodies may bind to epitopes whose exposure is enhanced or triggered by receptor binding. However, given the potential antiviral effects of neutralizing antibodies, it is not unexpected that HIV-1 has evolved multiple mechanisms to protect it from antibody binding (Johnson & Desrosiers, Annu Rev Med. 2002; 53:499-518).

Most experimental HW-1 vaccines tested in human and/or non-human primate suggests that a successful vaccine will incorporate immunogens that elicit broad neutralizing antibodies (bNabs) and robust cell-mediated immunity. HIV-1 envelope glycoprotein (Env) is the main viral protein involved in the entry of the virus and is also the primary target for neutralizing antibodies, but due to immune evasion strategies and extreme sequence variability of Envs, generation of bNabs has been daunting task (Phogat S, Wyatt R. Curr Pharm Des. 2007; 13:213-27, Phogat S, et al. J Intern Med. 2007 262:26-43, Karlsson Hedestam G B, et al Nat Rev Microbiol. 2008 6:143-55).

The ability to elicit broad and potent neutralizing antibodies is a major challenge in the development of an HIV-1 vaccine. Namely, HIV-1 has evolved an impressive array of strategies to evade antibody-mediated neutralization, bNAbs develop over time in a proportion of HIV-1 infected individuals, and a handful of broad neutralizing monoclonal antibodies have been isolated from clade B infected donors. These antibodies tend to display less breadth and potency against non-clade B viruses, and they recognize epitopes on the virus that so far have failed to elicit broad neutralizing responses when incorporated into a diverse range of immunogens. Presumably, due to the ability of these bNabs to recognize conserved recessed targets on HIV Env which are either inaccessible by elicited antibodies or difficult to precisely redesign and present to the immune system.

Recently using a sensitive high-throughput micro-neutralization screening of supernatants from approximately 30,000 IgG+ memory B cells from a HIV-1 clade A-infected African donor, Applicants identified two new bNabs PG9 and PG16 that are broad and exceptionally potent neutralizing antibodies (Walker L, Phogat S, et al. Science. 2009; 326:285-9. Epub 2009 September 3). These antibodies recognize a new conserved, yet accessible, vaccine target (consisting of conserved elements on the variable loops 2 and 3) on the Env and show preferential binding to HIV Env trimer (Model of PG9 and 16 epitopes on HIV-1 trimer.). When tested for binding, these antibodies did not show binding to many empirically designed soluble (Env gp140) HIV Env trimer thought to be mimics of the native HIV-1 Env spike, suggesting that either these Env designs are either incorrect or they are fixed in a form not recognized by PG9 and PG16.

Citation or identification of any document in this application is not an admission that such document is available as prior art to the present invention.

SUMMARY OF THE INVENTION

Based on the binding property and breadth/potency of the new antibodies to neutralize >75% of the viruses tested, Applicants hypothesize that PG9, PG16 and certain CD4-binding site antibodies recognize a relevant vaccine target on the native HIV-1 Env on the surface of the virus and identification of HIV-1 envelope glycoproteins that present these targets on soluble forms of HIV-1 envelope would be good HIV-1 vaccine candidates to elicit PG9 and PG16 like antibodies and also can be used as reagents for mapping and crystallization studies.

The envelope glycoproteins identified as a part of this invention shows significantly better binding to new identified broad neutralizing antibodies PG9 and/or PG16. These are the only soluble forms of envelope identified that show such remarkable binding to PG9 and PG16. The envelope glycoproteins Envs have value (a) as reagents for screening of broad neutralizing antibodies, such as but not limited to, PG9 and PG16, (b) as reagents for screening of small molecules that compete binding of broad neutralizing antibodies, such as but not limited to, PG9 and PG16, (c) as monomer and native envelope trimer mimic for crystallization studies and (d) as immunogens in different forms to use as HIV-1 vaccine components, for example, to elicit broadly neutralizing antibodies.

In an advantageous embodiment, the soluble envelope glycoproteins of the present invention may be isolated from HIV-1 Clade A virus, HW-1 Clade B virus, HIV-1 Clade C virus, a HIV-1 Clade A pseudo-virus, HIV-1 Clade B pseudo-virus or a HIV-1 Clade C pseudo-virus. In an advantageous embodiment, the soluble envelope glycoproteins of the present invention may be isolated from the 6535 virus, the 13095 virus, the 16055 virus, the 25710 virus, the 25925 virus, the CAAN virus or the Zm109F virus. Sequences of these viruses are available in the NCBI data base and Applicants have used them to generate recombinant Env proteins with unique sequences in which Applicants have modified the leader, added His-tag and terminated the sequence before the cleavage site for gp 120 and before the transmembrane for gp 140. The DNA sequences are unique as they are codon optimized based on mammalian codons for expression in mammalian cells.

In another advantageous embodiment, the soluble envelope glycoproteins have substantially similar sequences to the protein sequences depicted in FIGS. 9A-9J. In another particularly advantageous embodiment, the soluble envelope glycoprotein has a substantially similar consensus sequence to the consensus sequence depicted in FIGS. 9A-9J.

In a particularly advantageous embodiment, the soluble envelope glycoproteins of the present invention have about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% sequence identity to any of the sequences depicted in FIGS. 14-46.

Another advantageous embodiment encompasses a stable soluble HIV-1 envelope glycoprotein trimer mimic.

A further embodiment involves the use of the identified Env monomer gp120 for selection of small molecules that bind to PG9 and antibodies that bind CD4 sites and can be used as immunogens.

Another embodiment encompasses the use of the identified Env monomer gp120 for selection of small molecules that bind to PG9 binding site or the binding site of antibodies that bind to CD4 sites on the monomer and inactivates the HIV-1 virus in a manner similar to the manner in which antibody PG9 and antibodies that bind CD4 sites do.

A further embodiment involves the use of the discovered Env trimer mimic gp140 for selection of small molecules that bind to PG9, PG16 antibodies and antibodies that bind to CD4 binding sites and can be used as immunogen.

In another advantageous embodiment, the identified Env trimer is used for selection of small molecules that bind to PG9, PG16 and CD4 binding sites on the HIV-1 virus Env trimer and inactivates the HIV-1 virus in a manner similar to the antibodies PG9, PG16 and antibodies that bind to CD4 binding sites.

A further embodiment involves the use of the monomer and trimer for mapping of PG9 and PG 16 specificity in human and animal sera.

Another embodiment includes the identification of PG9 and PG16 like antibodies using the identified HIV-1 Env monomer and trimer.

A further embodiment involves the use of the HIV Env monomer and trimer for display on particulate antigens like Qbeta particle.

Another embodiment includes the use of the HIV-1 Env monomer and trimer in replicating and non-replicating vectors as DNA for priming.

Yet another embodiment encompasses a method for identifying novel HIV envelope proteins binding to broad neutralizing antibodies (such as PG9 and PG16 antibodies) by using a combination of bioinformatics approach based on patients Envelope sequences and binding assay of the homologous proteins. The evolutionary proximity of these proteins to the patients' Envelope proteins may improve generation of broadly neutralizing antibodies administered alone or in combination with other PG9 and PG16 binding proteins. The present invention also encompasses proteins identified by this method, such as, for example, gp120 BG505 clade A.

The present invention also encompasses an isolated or non-naturally occurring V1-3 loop which may comprise a conformation of an amino acid sequence of a PG9 binding protein. The isolated or non-naturally occurring V1-3 loop may comprise the amino acid sequences of V1-16055, V2-16055 or V3-16055. An isolated or non-naturally occurring soluble HIV-1 envelope glycoprotein having the V1-3 loop which may have a conformation of an amino acid sequence of a PG9 binding protein, wherein the amino acid sequence may comprise the amino acid sequences of V1-16055, V2-16055 or V3-16055.

The present invention also encompasses an isolated or non-naturally occurring soluble HIV-1 envelope glycoprotein which may comprise the amino acid sequences of V1-16055, V2-16055 or V3-16055. In an advantageous embodiment, the glycoprotein may be a chimeric protein.

The invention also relates to a method for neutralizing tier 1 and tier 2 HIV-1 viruses in patient in need thereof which may comprise administering to the patient a priming dose of a vector containing and expressing gp120 isolated from a 16055 virus and further administering to the patient a protein boost a gp120 protein isolated from a 16055 virus, wherein the sera from the patient neutralizes tier 1 and tier 2 clade B and clade C HIV-1 viruses in the patient. The method may further comprise isolating the sera from the patient and testing the sera in a pseudoneutralization assay to determine if the sera is indeed neutralizing. The HIV-1 virus may be a HIV-1 Clade A virus, HIV-1 Clade B virus, HIV-1 Clade C virus, a HIV-1 Clade A pseudo-virus, HIV-1 Clade B pseudo-virus or a HIV-1 Clade C pseudo-virus.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 depicts the neutralization activity of PG9 and PG16 antibodies against HIV-1 viruses. The IC50 value for neutralization is represented as antibody concentration in ug/ml. The HIV-1 viruses whose envelope glycoprotein in soluble form (gp120/gp140) bind to PG9 and/or PG16 are shown below: a) binders, b) weak or moderate binders, c) non-binders and d) control.

FIG. 2 depicts the neutralization IC50 value of selected Clade C viruses by broad neutralizing b12, PG9, PG16, 4E10 and another CD4 binding site antibody.

FIG. 3C depicts a neutralization activity and shed gp120 binding profile for selected clade A, B and C HIV-1 pseudoviruses by broad neutralizing b12, PG9, PG16 and b12. Interestingly, PG16 binding does not correlate with PG16 neutralization, however, there is a correlation between PG9 binding and PG9 neutralization.

FIG. 5A-5K depict recombinant gp120 and gp140 protein sequences of HIV-1 envelope glycoproteins that show good binding to PG9 antibody a) clade C and b) clade B Envs.

FIG. 6 depicts recombinant HIV-1 envelope glycoprotein gp120 BG505 clade A ELISA binding and phylogeny tree. ELISA showed significant binding of PG9, PG16 and b12 antibodies to BG505 gp 120. The BG505 protein sequence was selected using bioinformatics approach that identified close progenitor sequence to HIV-1 clade A Env from Env protein database. The HIV-1 Env clade A sequences from the donor (V1_011) who gave rise to PG9 and PG16 antibodies were used to search the HIV-1 Env protein data base.

FIGS. 7A and 7B depict the binding of recombinant HIV-1 envelope glycoproteins (gp140) to PG9 and PG16 antibodies. Only 16055 gp140 shows significant binding to PG9, PG16 and b12. B) Stabilization of 16055 gp140 trimer by addition of c-terminus trimerization domain GCN4 does not affect PG9, PG16, b12 and another CD4 binding site antibody.

FIG. 8 binding kinetics of neutralizing and non-neutralizing ligands to 16055 gp 120 determined using Octet binding. Octet analyzes the interference pattern of white light reflected from two surfaces: a layer of immobilized protein on the biosensor tip, and an internal reference layer. Any change in the number of molecules bound to the biosensor tip causes a shift in the interference pattern that can be measured in real-time. 16055 gp120 bound with high affinity to PG9 (45 nM), VRCO1 (61 nM), and CD4IgG2 (19 nM), but binding to F105

(200 nM) and b12 (120 nM) was 3-5 folds lower. Interestingly 16055 did not show any binding to b13 but bound with high affinity to VRC01. In most cases a fast on-rate of antibodies binding to 16055 was observed suggesting that the binding site for these antibodies on 16055 was preformed. In addition, the CD4 inducible antibody 17b bound 16055 gp120 (82 nM) in the absence of CD4. On rates for binding to most antibodies tested on 16055 gp120 were comparable, but the off-rates were different.

Figure 3A:
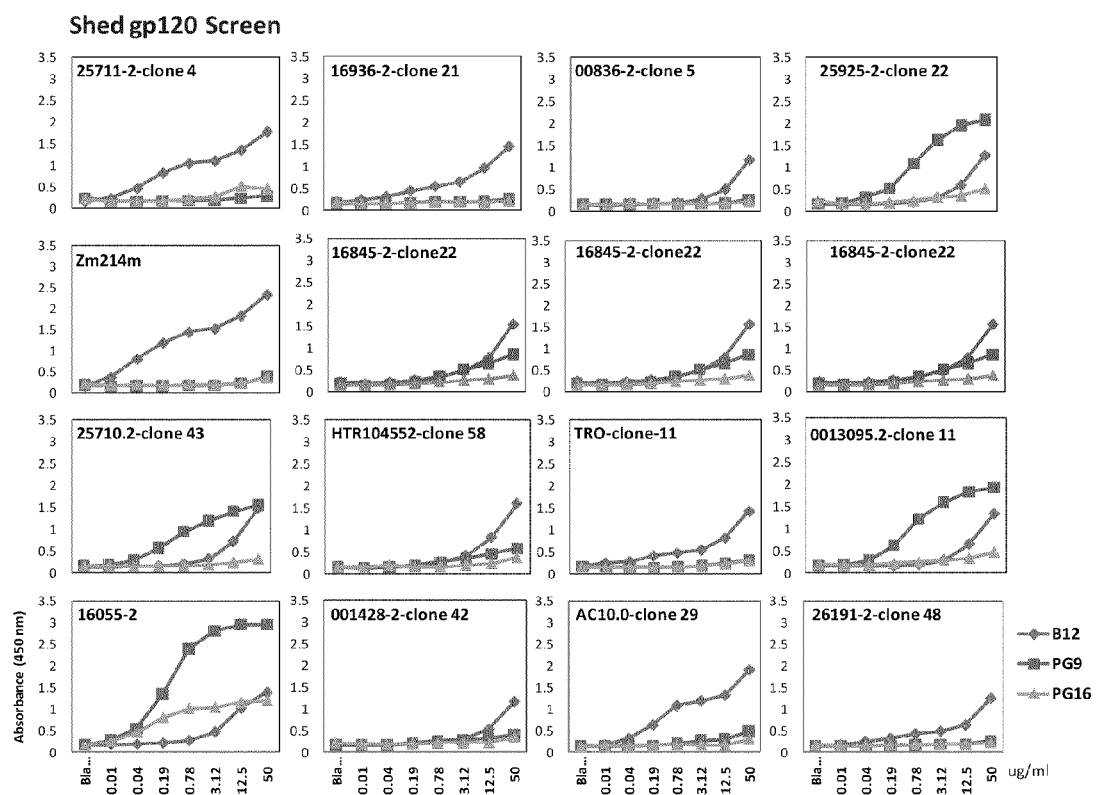
FIG. 3A depicts a shed gp120 screen using HIV-1 clade C pseudo-viruses.
Figure 3B:
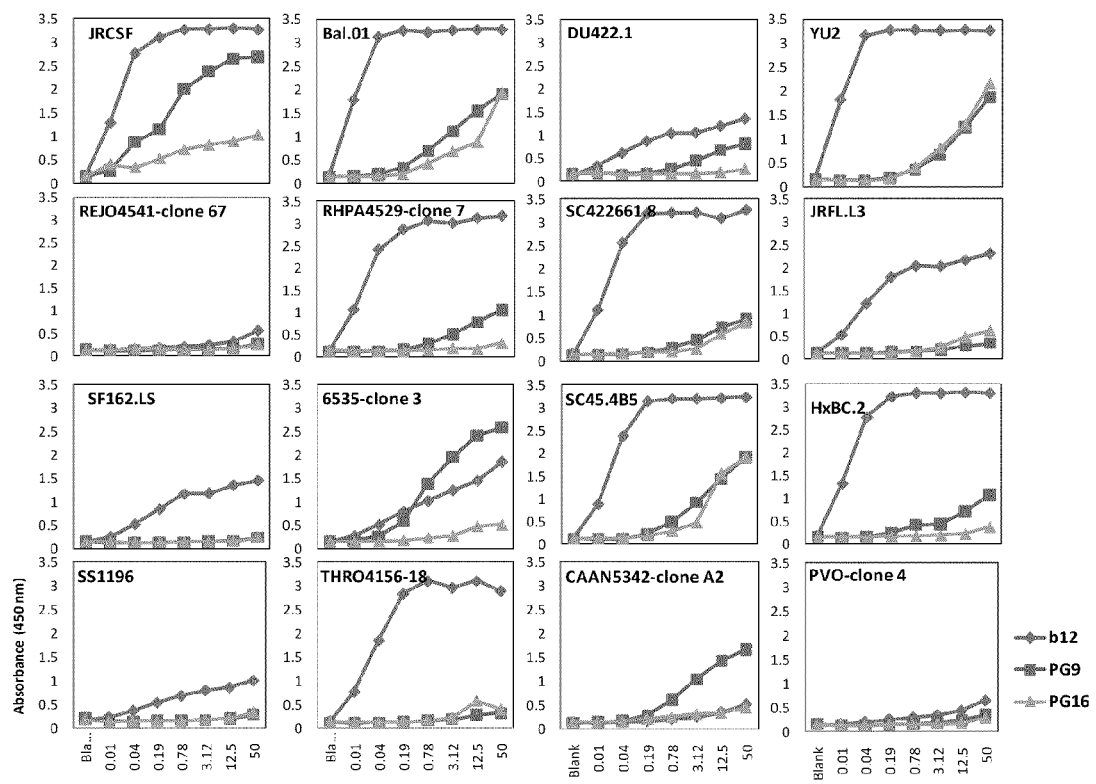
FIG. 3B depicts a shed gp120 screen using HIV-1 clade B pseudo-viruses.
Figure 4A:
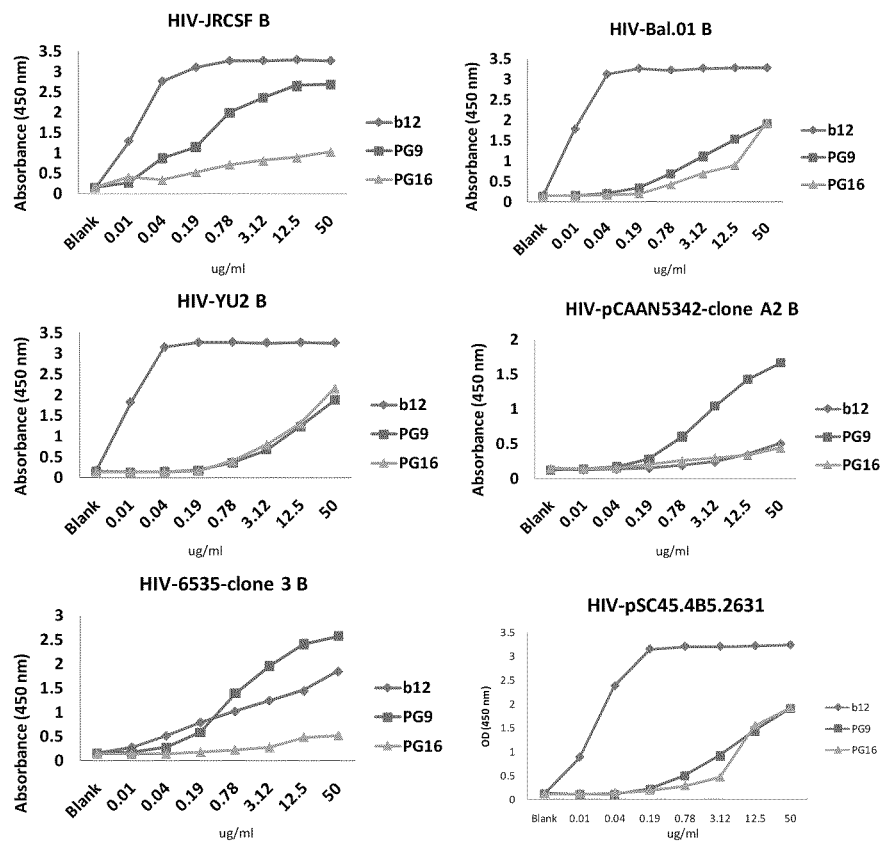
FIGS. 4A-4C depict shed gp120 based screening and selection of HIV-1 Env A) PG9 binders, a) HIV-1 clade B, b) HIV-1 clade C and B) a few PG9 non-binders.
Figure 4B:
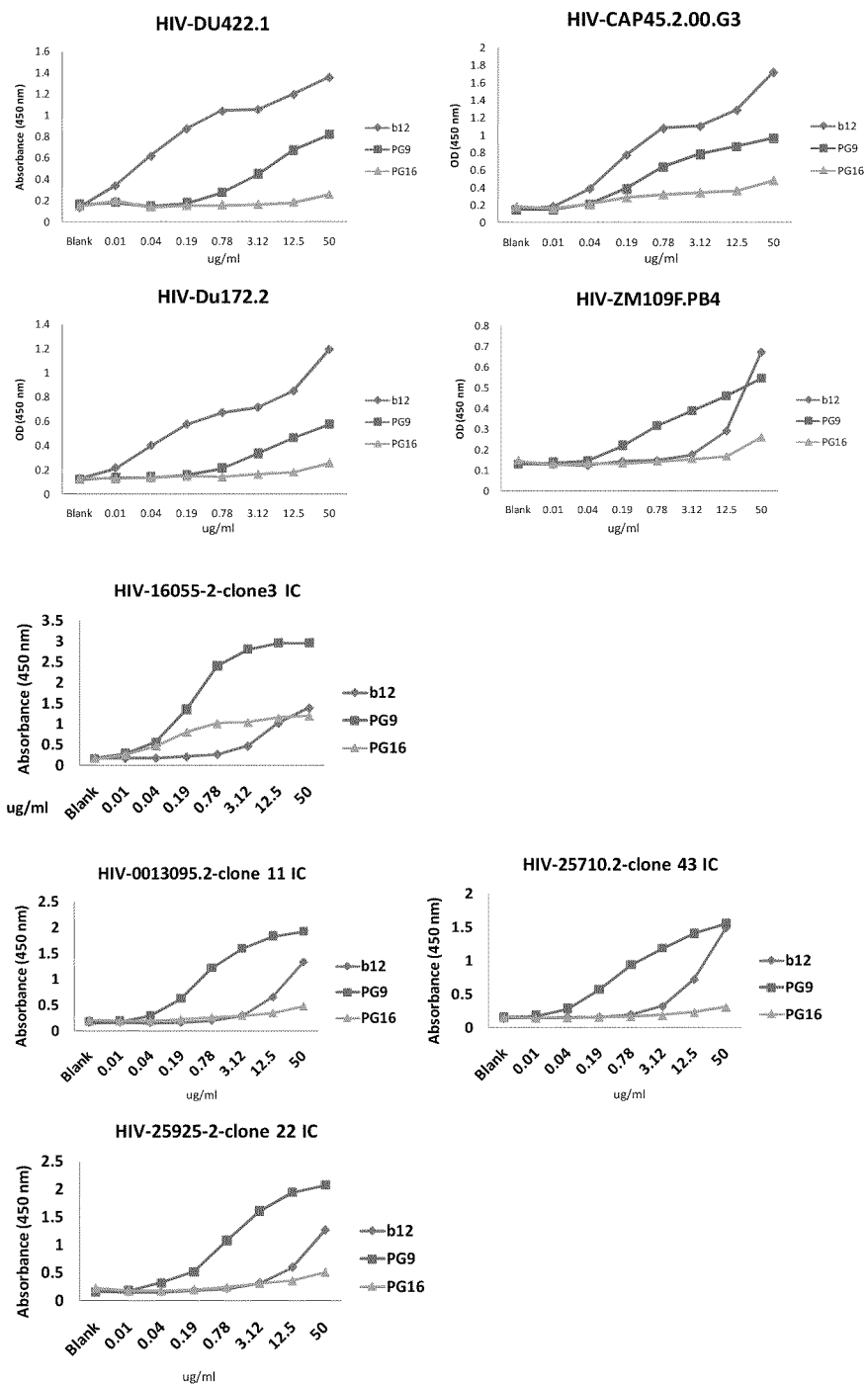
Figure 4C:
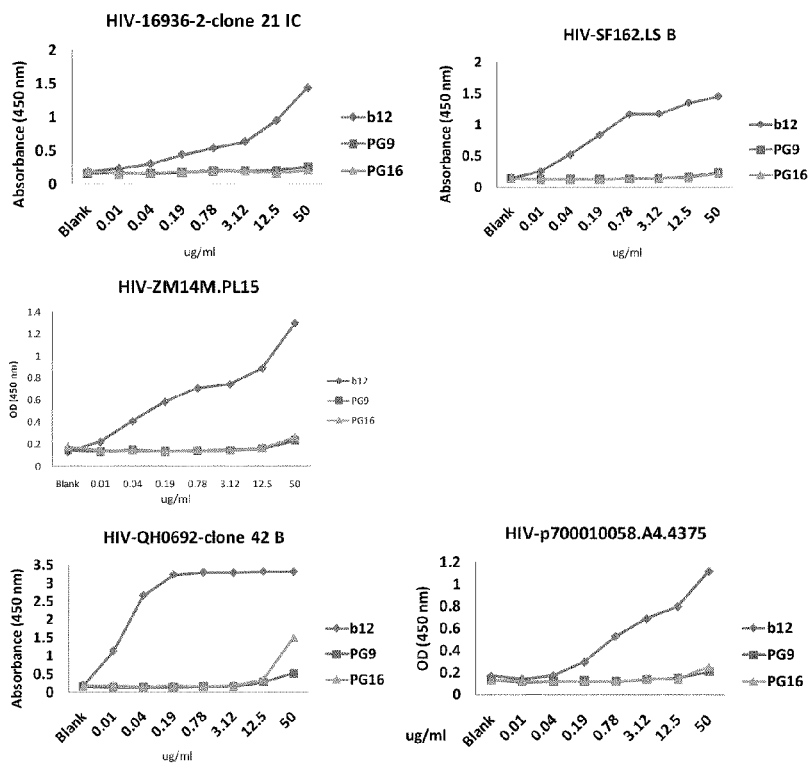
Figure 5G:
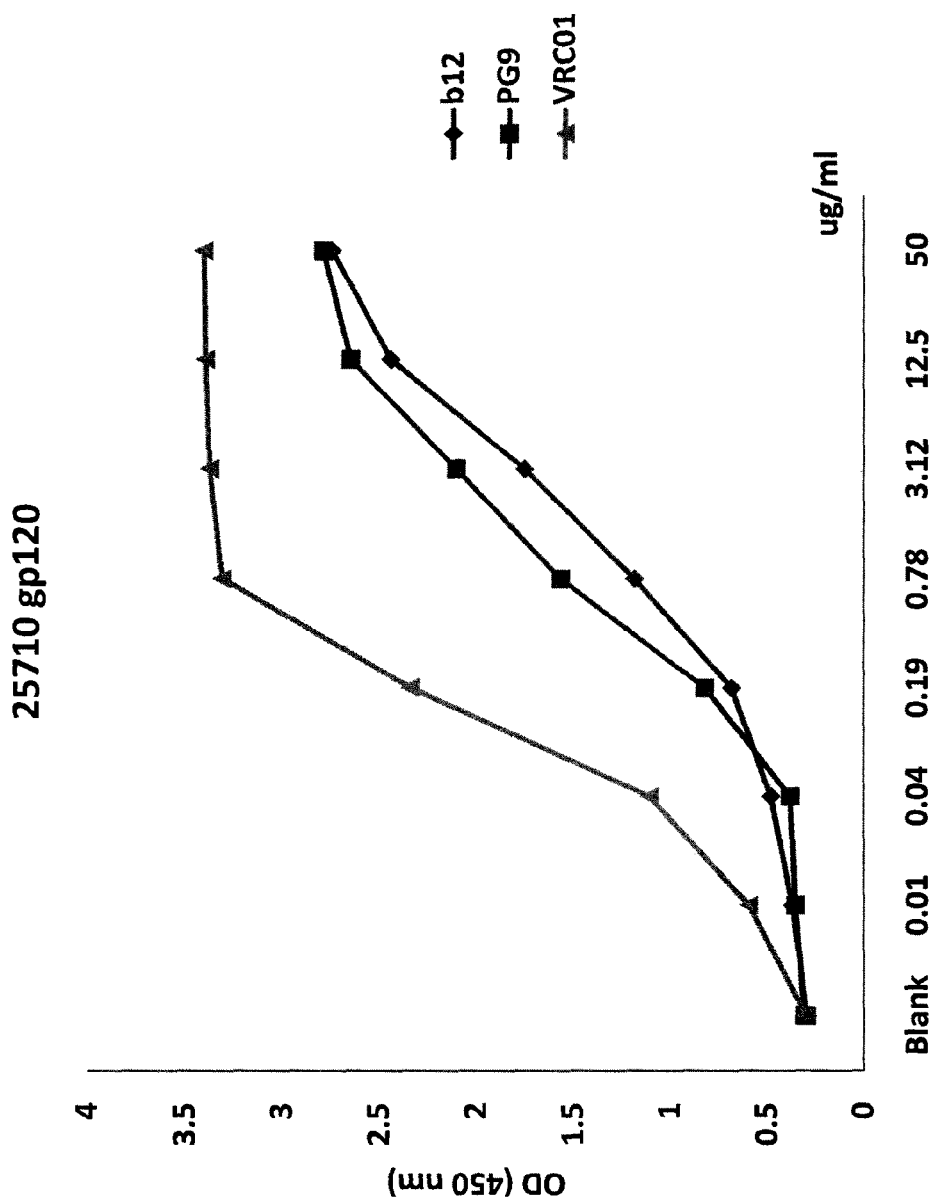
Figure 5H:
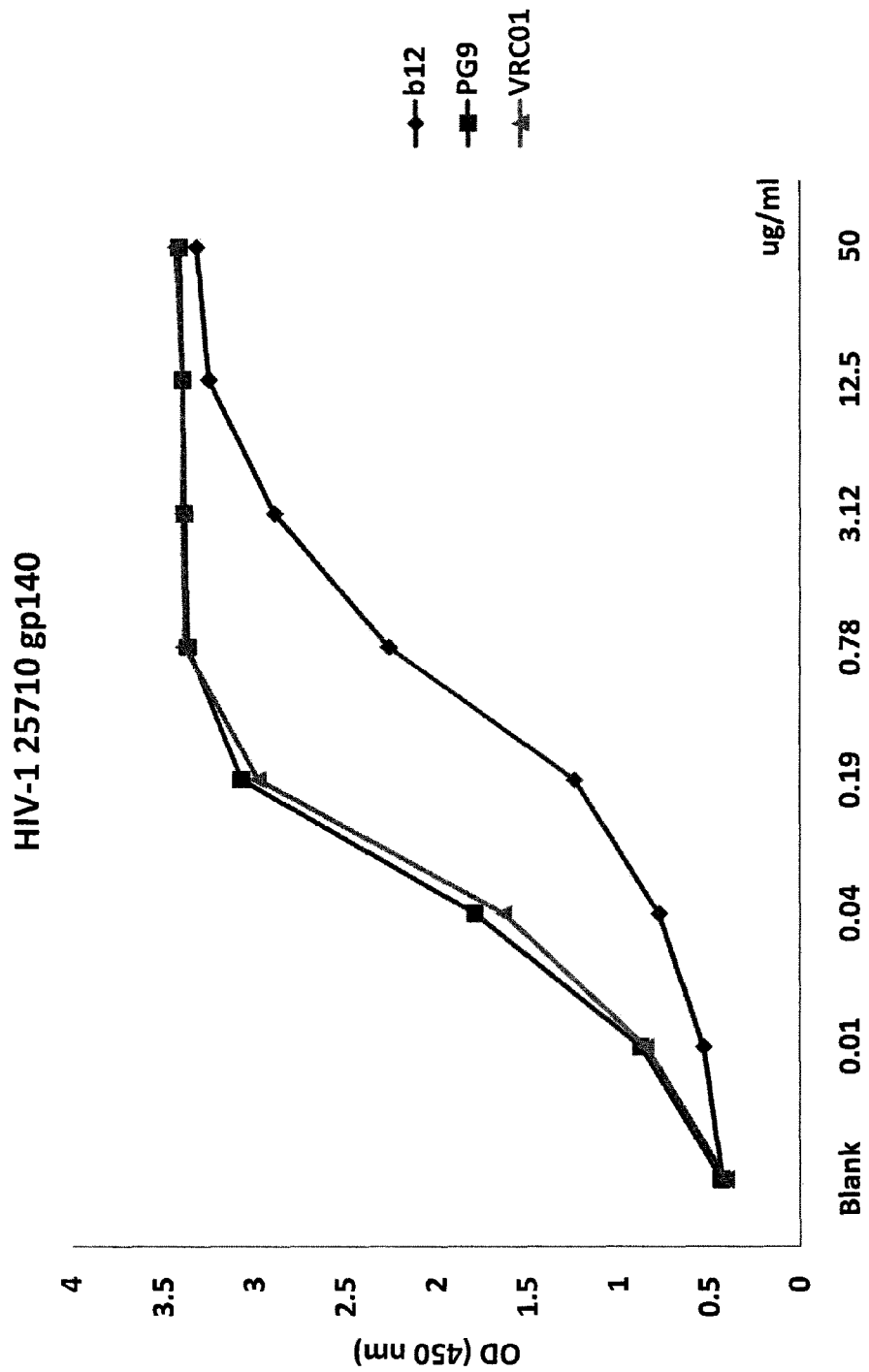
Figure 5I:
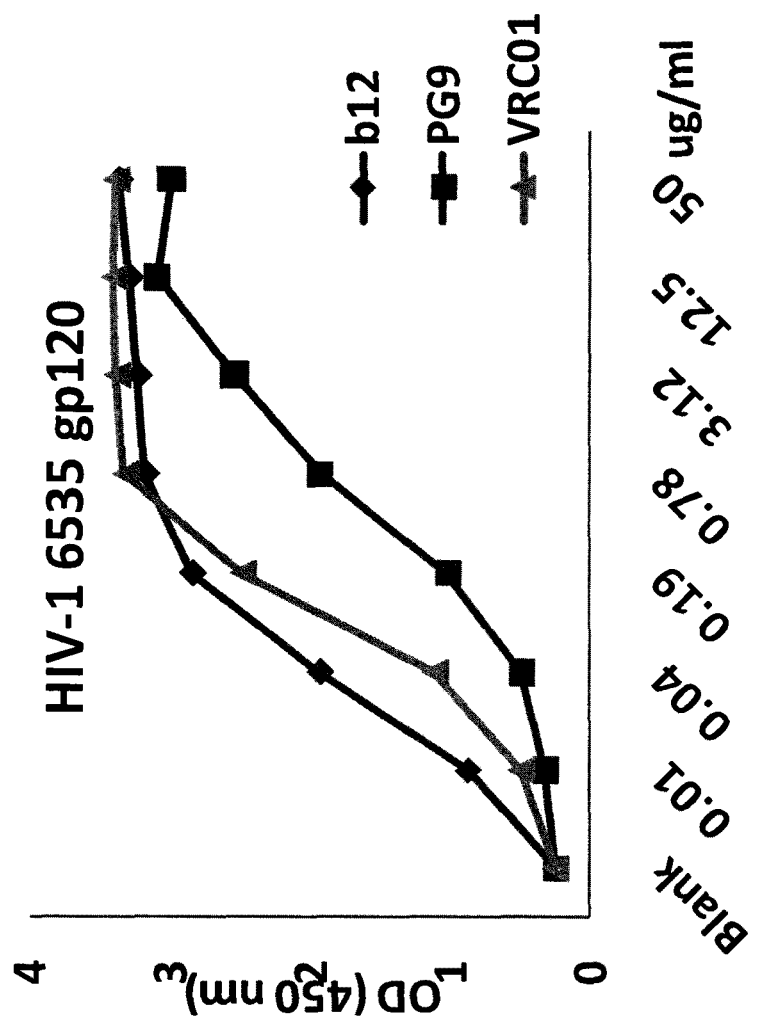
Figure 9J:
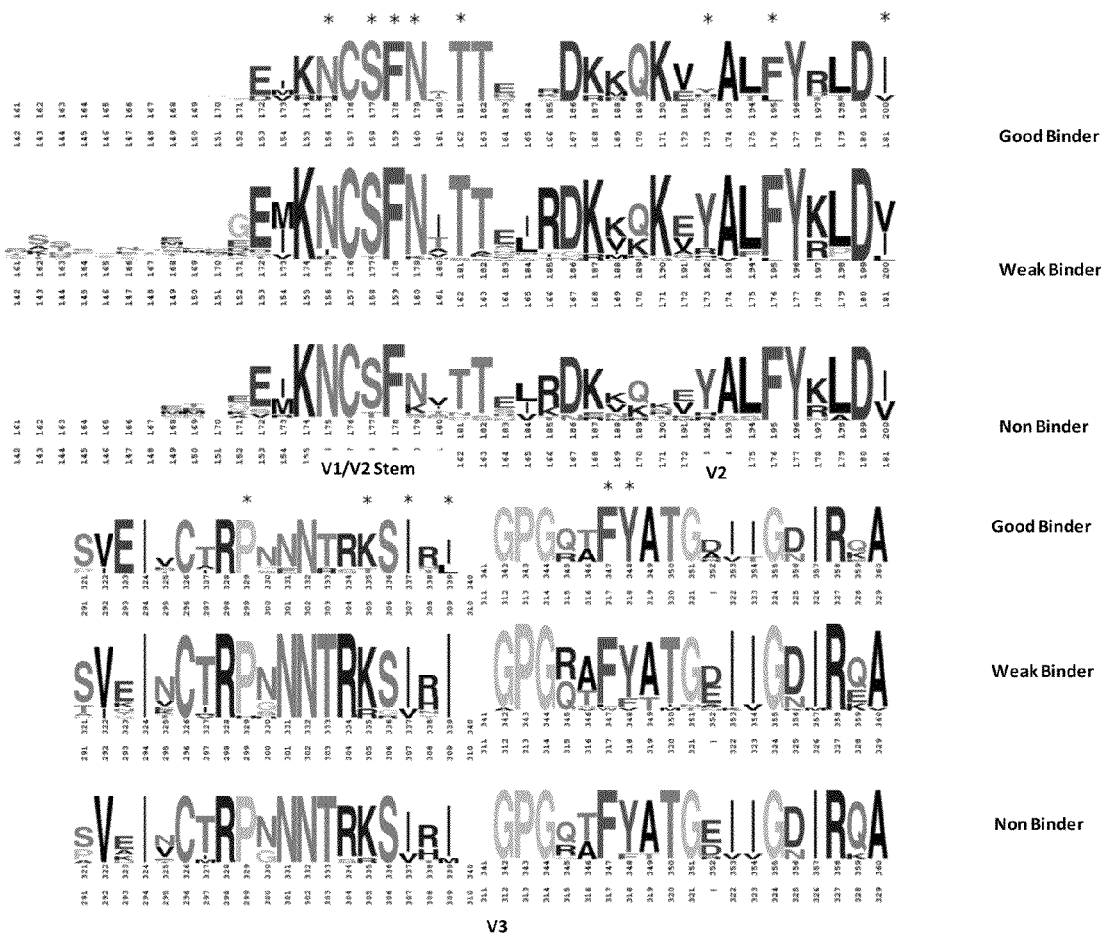

FIGS. 9A-9J depict the alignment of HIV-1 ENV protein gp120 sequences of good (red letters), moderate (green) and non (black)-PG9 binder and subjected to web logo analysis. Residues important for PG9 and PG16 binding are boxed in vertical columns located in the variable loops V1/V2 stem, V2 and V3 loop. Residues (HxBC2 numbering) at positions 156, 158, 159, 160, 162 in V1/V2 stem, 168, 176, 181 in V2 and 299, 305, 307, 309, 317, 318 in V3 loop are highly conserved and are found in all Envs irrespective of their neutralization or binding by PG antibodies. FIG. 9J depicts web logo analysis of the HIV-1 Env sequences in the variable loop 1, 2 and 3 aligned in FIGS. 9A-9I (SEQ ID NOS 1-38, respectively, in order of appearance the size of the residue represents conservation. All residues involved in PG9 and PG16 binding are denoted by "*".

Figure 10:
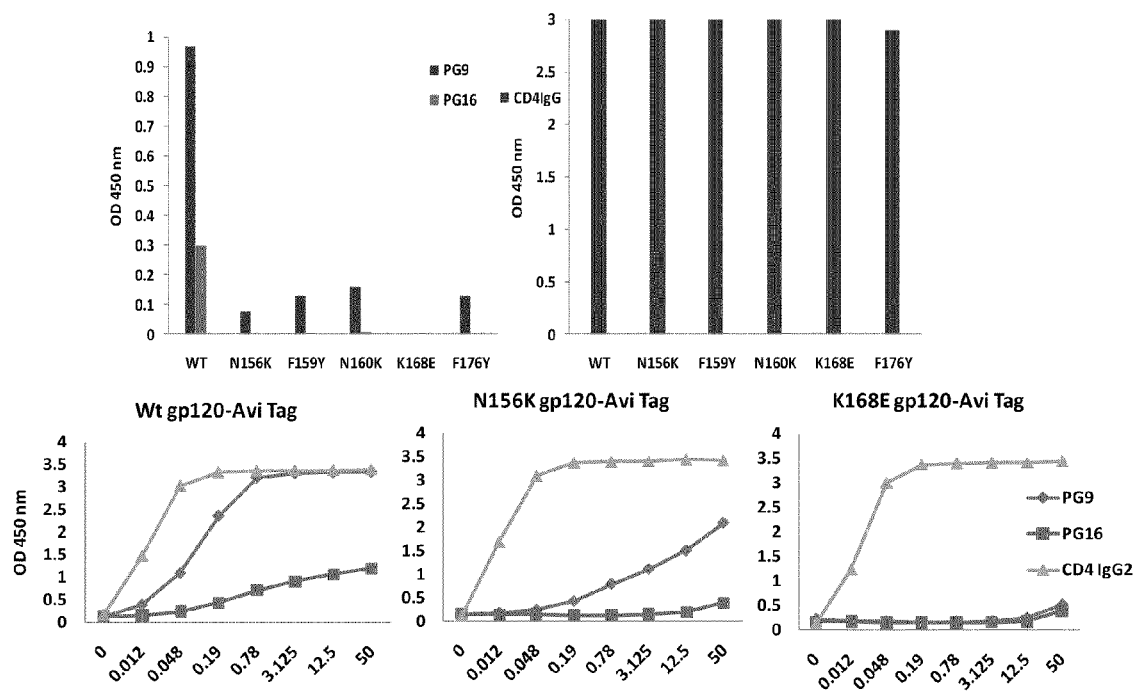

FIG. 10 depicts analysis of amino acid residues on 16055 gp120 Env (HxBC2 numbering) which were shown to be involved in PG9 binding. N-linked glycan site at position 156 and 160 mutated to lysine on 16055 gp120 completely abrogated binding of PG16 antibody and PG9 binding was significantly reduced. Mutants at position 159 and 176 that effect PG antibodies neutralization also affected PG9 binding on soluble 16055 gp120. At position 168, a positive charge was critical. Conversion of K168E abrogated PG9 and PG16 binding to the 16055 gp120. None of the mutations impacted CD4IgG binding.

Figures 11A, 11B:
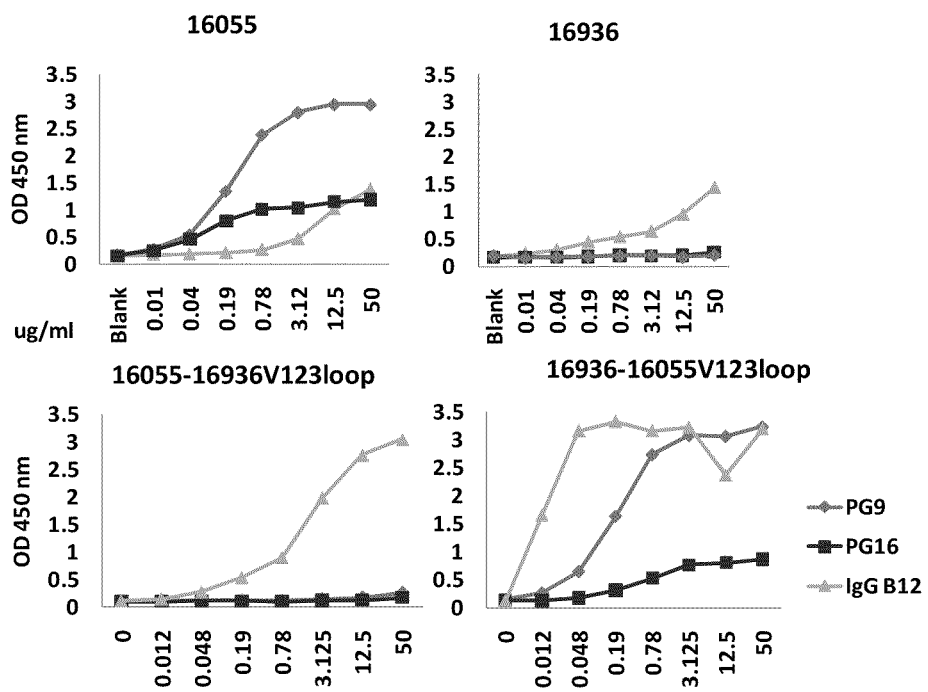

FIGS. 11A-11C depict effects of variable loop swapping from a PG9 and PG16 binding Env to a non-binder and vice versa. (a) represents HIV-1 Env 16936 (SEQ ID NOS 39, 41 and 43, respectively, in order of appearance) and 16055 (SEQ ID NOS 40, 42 and 44, respectively, in order of appearance) sequence alignment of the variable loop 1, 2 and 3. Residues involved in PG9 and PG16 binding are represented by #. (b) ELISA binding shows that swapping 16936 V1-3 loops in 16055 abrogates PG9 and PG16 binding on the contrary swapping 16055 V1-3 loops in 16936 gains PG9, PG16 and improves b12 binding. (c) Full length pseudovirus of chimeric 16936 with V1-3 loops of 16055 is functional and is neutralized by b12, PG9, PG16, 4E10 and another CD4 binding site antibody.

Figure 12:
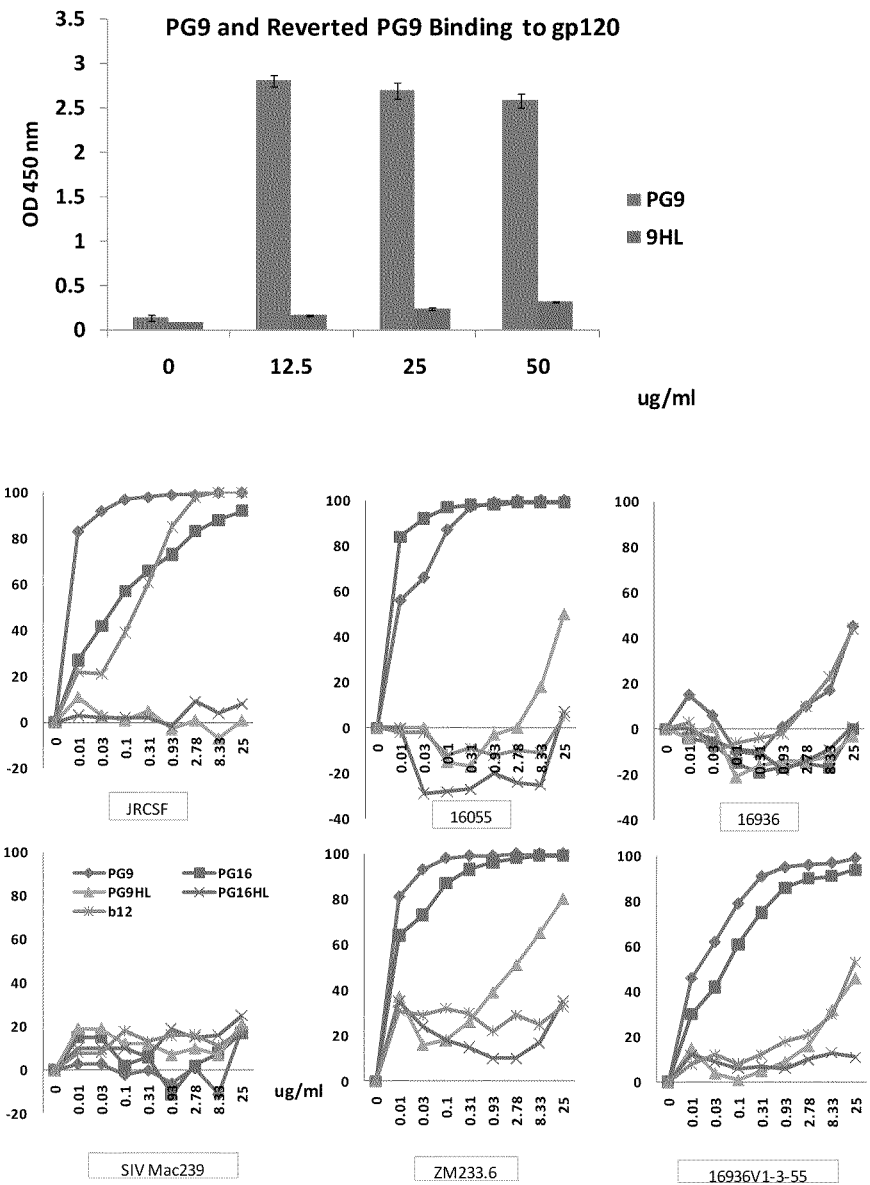
Figure 13A:
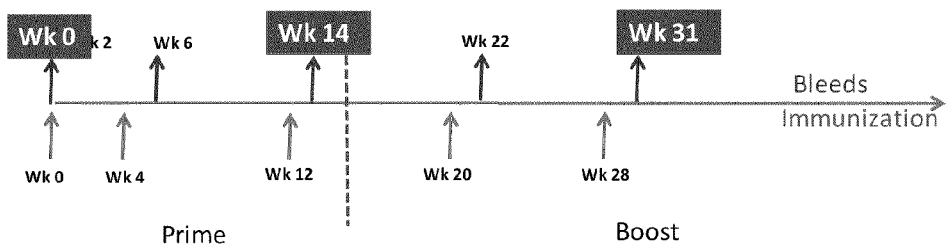
Figure 13B:
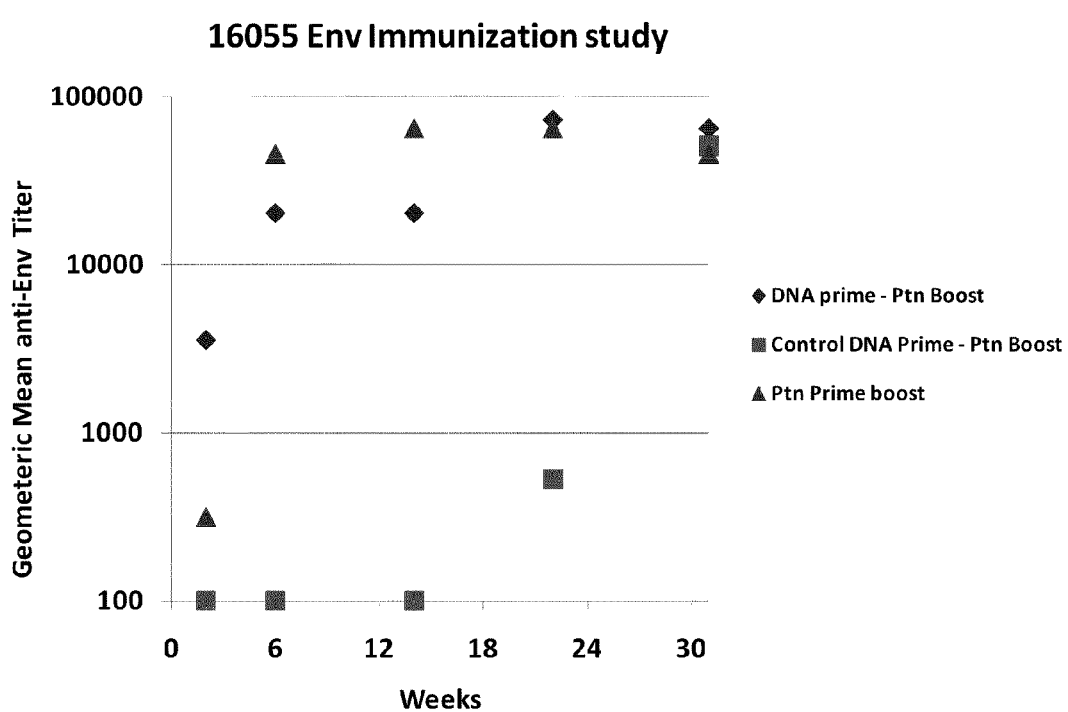

FIG. 12 depicts binding and neutralization by PG9HL antibody, in PG9HL the variable loops H and L chain are reverted to germ line amino acids. PG9HL showed weak binding to 16055. PG9HL showed neutralization of ZM233.6 (reported Pancera et al 2010 J. Virol), 16055 and chimeric 16936 V1-3-16055 loop viruses.

FIGS. 13A-13D depict a 16055 immunogenicity study in rabbits. (a) immunization schedule and dose is presented for six animals immunized by intra muscular route per group at weeks 0, 4, 12, 20 and 28. Sera were collected two weeks post immunization and week 0, 14 and 31 sera were analyzed for binding and neutralization activity. (b) represent anti-Env ELISA titer represented as geometric mean titers and (c) represents IC50 values for neutralization of tier I and tier II clade B and clade C HW-1 viruses, JRCSF N160K and N156K. In group I and II, six rabbits were immunized with pCMVR-16055 gp120 DNA and pCMVR DNA respectively (250 ug/animal/immunization) at week 0, 4 and 12 by electroporation followed by two protein boost (50 ug/animal/immunization) at weeks 20 and 28. Six rabbits in group III were immunized with 16055 gp120 protein at week 0, 4, 12, 20 and 28. All bleeds were collected 2 weeks post immunization except at for the last bleed which was collected 3 weeks post immunization. In group I DNA priming elicited high titer anti-Env antibodies after 1st immunization (~1:5000) which saturated after 2nd DNA EP ($1:2\times10^4$) and did not increase after 3rd DNA EP. Following protein boost the anti-Env titer further increased (~$1:1\times10^5$). In group II no anti-Env antibodies were observed following control DNA EP at week but following protein boost the anti-Env titer of $1:1\times10^5$ was observed. In group III anti-Env titers saturated following three protein immunization. The sera were tested for pseudovirus neutralization assay based on Tzmbl cells containing Tat controlled luciferase expression. The DNA EP-16055 gp120 protein generated sera showed neutralization of homologous 16055 virus for two out of six rabbits, the other groups did not neutralize 16055 virus. Heterologous tier I clade C MW965 virus was potently neutralized by sera generated at week 14 and 31 by all three group. Similarly potent cross clade-neutralization was observed for tier I clade B SF162 and SS1196 viruses. Heterologous tier II clade C IN905 and MGRMO26 were potently neutralized by group I and III sera at week 31. IN905 virus was also neutralized by group I and III sera at week 14. Heterologous cross-clade tier II YU2 virus was resistant to all group sera but JRCSF virus was neutralized weakly by week 14 sera and the neut titers increased at week 31. JRCSF mutant N160K shown to be resistant to PG9 and PG16 antibodies was resistant to all group sera whereas another mutant N156A was globally sensitive and behaved like a tier I virus. Over all anti-Env sera was elicited that showed cross clade neutralization of Tier I and II homologous and heterologous viruses.

FIG. 14 depicts the sequence (coding nucleotide sequence disclosed as SEQ ID NO: 45 and coded peptide sequence disclosed as SEQ ID NO: 46) of HIV-1 clade 25925-2 gp160 ΔCT PADRE-C9 tag.

FIG. 15 depicts the sequence (coding nucleotide sequence disclosed as SEQ ID NO: 47 and coded peptide sequence disclosed as. SEQ ID NO: 48) of AY835452_gp120.

FIG. 16 depicts the sequence (coding nucleotide sequence disclosed as SEQ ID NO: 49 and coded peptide sequence disclosed as SEQ ID NO: 50) of 16055 gp120-TM.

FIG. 17 depicts the sequence (coding nucleotide sequence disclosed as SEQ ID NO: 51 and coded peptide sequence disclosed as SEQ ID NO: 52) of 16055 gp120 AviTag.

FIG. 18 depicts the sequence (coding nucleotide sequence disclosed as SEQ ID NO: 53 and coded peptide sequence disclosed as SEQ ID NO: 54) of 16055gp120N160KAviTag.

FIG. 19 depicts the sequence (coding nucleotide sequence disclosed as SEQ ID NO: 55 and coded peptide sequence disclosed as SEQ ID NO: 56) of 16055gp120N156KAviTag.

FIG. 20 depicts the sequence (coding nucleotide sequence disclosed as SEQ ID NO: 57 and coded peptide sequence disclosed as SEQ ID NO: 58) of 16055gp120F159YAviTag.

FIG. 21 depicts the sequence (coding nucleotide sequence disclosed as SEQ ID NO: 59 and coded peptide sequence disclosed as SEQ ID NO: 60) of 16055gp120K168EAviTag.

FIG. 22 depicts the sequence (coding nucleotide sequence disclosed as SEQ ID NO: 61 and coded peptide sequence disclosed as SEQ ID NO: 62) of 16055gp120F176YAviTag.

FIG. 23 depicts the sequence (coding nucleotide sequence disclosed as SEQ ID NO: 63 and coded peptide sequence disclosed as SEQ ID NO: 64) of 16055_gp140_MF10.

FIG. 24 depicts the sequence (coding nucleotide sequence disclosed as SEQ ID NO: 65 and coded peptide sequence disclosed as SEQ ID NO: 66) of 16055gp140GCN4N160KAv.

FIG. 25 depicts the sequence (coding nucleotide sequence disclosed as SEQ ID NO: 67 and coded peptide sequence disclosed as SEQ ID NO: 68) of gp140-L4GNC4_fragment.

FIG. 26 depicts the sequence (coding nucleotide sequence disclosed as SEQ ID NO: 69 and coded peptide sequence disclosed as SEQ ID NO: 70) of 16936-16055V123loop.

FIG. 27 depicts the sequence (coding nucleotide sequence disclosed as SEQ ID NO: 71 and coded peptide sequence disclosed as SEQ ID NO: 72) of 16055-16936V123loop.

FIG. 28 depicts the sequence (coding nucleotide sequence disclosed as SEQ ID NO: 73 and coded peptide sequence disclosed as SEQ ID NO: 74) of BG505_gp120.

FIG. 29 depicts the sequence (coding nucleotide sequence disclosed as SEQ ID NO: 75 and coded peptide sequence disclosed as SEQ ID NO: 76) of BG505_gp140.

FIG. 30 depicts the sequence (coding nucleotide sequence disclosed as SEQ ID NO: 77 and coded peptide sequence disclosed as SEQ ID NO: 78) of BG505gp140GCN4L4.

FIG. 31 depicts the sequence (coding nucleotide sequence disclosed as SEQ ID NO: 79 and coded peptide sequence disclosed as SEQ ID NO: 80) of BG505gp160ΔCT.

FIG. 32 depicts the sequence (coding nucleotide sequence disclosed as SEQ ID NO: 81 and coded peptide sequence disclosed as SEQ ID NO: 82) of HIV-1 clade B 6535, clone 3 gp120, AY835438_gp120.

FIG. 33 depicts the sequence (coding nucleotide sequence disclosed as SEQ ID NO: 83 and coded peptide sequence disclosed as SEQ ID NO: 84) of HIV-1 clade B CAAN5342 gp120, AY835452_gp120.

FIG. 34 depicts the sequence (coding nucleotide sequence disclosed as SEQ ID NO: 85 and coded peptide sequence disclosed as SEQ ID NO: 86) of HIV-1 clade C 0013095-2 gp120Histag, EF117267_gp120.

FIG. 35 depicts the sequence (coding nucleotide sequence disclosed as SEQ ID NO: 87 and coded peptide sequence disclosed as SEQ ID NO: 88) of HIV-1 clade C 0013095 gp160ΔCT-PADRE-C9tag.

FIG. 36 depicts the sequence (coding nucleotide sequence disclosed as SEQ ID NO: 89 and coded peptide sequence disclosed as SEQ ID NO: 90) of HIV-1 clade C 16055 gp120-Histag, EF117268_gp120.

FIG. 37 depicts the sequence (coding nucleotide sequence disclosed as SEQ ID NO: 91 and coded peptide sequence disclosed as SEQ ID NO: 92) of HIV-1 clade C 16055 gp120-Histag-Cys.

FIG. 38 depicts the sequence (coding nucleotide sequence disclosed as SEQ ID NO: 93 and coded peptide sequence disclosed as SEQ ID NO: 94) of HIV-1 clade C 16055 gp140-Histag, EF117268_gp140.

FIG. 39 depicts the sequence (coding nucleotide sequence disclosed as SEQ ID NO: 95 and coded peptide sequence disclosed as SEQ ID NO: 96) of HIV-1 clade C 16055 gp140-Histag-Cys.

FIG. 40 depicts the sequence (coding nucleotide sequence disclosed as SEQ ID NO: 97 and coded peptide sequence disclosed as SEQ ID NO: 98) of HIV-1 clade C 16055 gp140-PADREHistag.

FIG. 41 depicts the sequence (coding nucleotide sequence disclosed as SEQ ID NO: 99 and coded peptide sequence disclosed as SEQ ID NO: 100) of IV-1 clade C 16055 gp160ΔCT-PADRE-C9tag.

FIG. 42 depicts the sequence (coding nucleotide sequence disclosed as SEQ ID NO: 101 and coded peptide sequence disclosed as SEQ ID NO: 102) of HIV-1 clade C 25710-2 gp120-Histag, EF117271_gp120.

FIG. 43 depicts the sequence (coding nucleotide sequence disclosed as SEQ ID NO: 103 and coded peptide sequence disclosed as SEQ ID NO: 104) of HIV-1 clade C 25710-2 gp160ΔCT-PADRE-C9tag.

FIG. 44 depicts the sequence (coding nucleotide sequence disclosed as SEQ ID NO: 105 and coded peptide sequence disclosed as SEQ ID NO: 106) of HIV-1 clade C 25925-2 gp120-Histag, EF117273_gp120.

FIG. 45 depicts the sequence (nucleotide sequence disclosed as SEQ ID NO: 107 and peptide sequence disclosed as SEQ ID NO: 108) of 16055 gp120 mutants 295 and 332, EF117268_gp120.

FIG. 46 depicts the sequence (SEQ ID NO: 109) of 16936V1-3-55 gp160 full length Env.

DETAILED DESCRIPTION

Broad neutralizing antibodies PG9 and PG16 were used for screening and selecting HIV-1 isolates from a panel consisting of sixty four viral isolates from HIV-1 clade-B and C for their ability to neutralize and to bind soluble form of HIV-1 Envelope glycoprotein. Applicants identified nine HIV-1 envelopes that were neutralized and showed binding by bNab PG9 and/or PG16. Two of the soluble HW-1 Envs—DU422 (clade C) and YU2 (clade B) were already identified and reported (Walker L, Phogat S, et al. Science. 2009; 326:285-9. Epub 2009 September 3). As a part of this invention, Applicants identified three new soluble HIV-1 Envs each from HIV-1 clade B and clade C viral isolates that show binding to bNab PG9. In addition, Applicants identified one soluble Env from HIV-1 clade C that showing binding to both bNab PG9 and PG16. The Envs identified as a part of this invention shows significantly better binding to bNabs PG9 and PG16 compared to DU422 and YU2 envelope. These newly identified Envs are the only soluble forms of Env identified till date that show such remarkable binding to PG9 and/or PG16. In addition to identification of soluble gp120 that shows significant binding to PG9, Applicants identified one native envelope trimer mimic gp140 molecules that shows significant binding to both PG9 and PG16.

These Envs may have the following utilities:
a) Reagents for screening of new broad neutralizing antibodies like PG9 and PG16, mapping of human sera with broad neutralizing serum activity and animal sera following immunization studies
b) For screening of small molecules that competes binding of broad neutralizing antibodies, such as PG9 and PG16. The identified small molecule could be used as immunogen or anti-viral compounds
c) Crystallization studies with Monomer bound PG9 and PG16 to determine the exact molecular surface where PG9 and PG16 bind to design novel HIV-1 immunogens
d) Crystallization studies with trimer bound PG9 and PG16 and any other ligand to determine the exact structure of a native Env trimer
e) Immunogens in different forms to use as HIV-1 vaccine components to elicit bNabs. The different forms of the HIV-1 envelope will be use in a prime, as DNA/vector expressing the protein/protein and as a boost as protein. The envelopes could also be used as particulate immunogen by cross linking to virus particles like Qbeta, cow pea mosaic virus, CRM, HPV, HBsAg etc.

In an advantageous embodiment, the soluble envelope glycoproteins of the present invention may be isolated from HIV-1 Clade A virus, HW-1 Clade B virus, HIV-1 Clade C virus, a HIV-1 Clade A pseudo-virus, HIV-1 Clade B pseudo-virus or a HIV-1 Clade C pseudo-virus In an advantageous embodiment, the soluble envelope glycoproteins of the present invention may be isolated from the 6535 virus, the 13095 virus, the 16055 virus, the 25710 virus, the 25925 virus, the CAAN virus or the Zm109F virus. Applicants have generated recombinant Env proteins with unique sequences in which Applicants have modified the leader, added His-tag and terminated the sequence before the cleavage site for gp 120 and before the transmembrane for gp140. The DNA sequences are unique as they are codon optimized.

In a particularly advantageous embodiment, the envelope glycoproteins of the present invention are isolated from the 16055 virus.

In another advantageous embodiment, the soluble envelope glycoproteins have substantially similar sequences to the protein sequences depicted in FIGS. 9A-9J. In another particularly advantageous embodiment, the soluble envelope glycoprotein has a substantially similar consensus sequence to the consensus sequence depicted in FIGS. 9A-9J.

In a particularly advantageous embodiment, the soluble envelope glycoproteins of the present invention have about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% sequence identity to any of the sequences depicted in FIGS. 14-46.

In one embodiment, the soluble Env of the present invention may be used as reagants to screen for and identify new broadly neutralizing antibodies, such as PG9 and PG16. As used herein, a neutralizing antibody may inhibit the entry of HIV-1 virus with a neutralization index >1.5 or >2.0. Broad and potent neutralizing antibodies may neutralize greater than about 50% of HIV-1 viruses (from diverse clades and different strains within a clade) in a neutralization assay. The inhibitory concentration of the monoclonal antibody may be less than about 25 mg/ml to neutralize about 50% of the input virus in the neutralization assay.

Yet another embodiment encompasses a method for identifying novel HIV envelope proteins binding to PG9 and PG16 antibodies by using a combination of bioinformatics approach based on patients Envelope sequences and binding assay of the homologous proteins. The evolutionary proximity of these proteins to the patients' Envelope proteins may improve generation of broadly neutralizing antibodies administered alone or in combination with other PG9 and PG16 binding proteins. The present invention also encompasses proteins identified by this method, such as, for example, gp120 BG505 clade A.

Essentially the approach will be to generate HIV-1 Env sequence from donor who give rise to any (new or existing) broad neutralizing antibodies. Thus far in all cases Applicants have found that the Env sequence in donor sera escape neutralization by the broad neutralizing antibodies isolated from the donor. As a result the isolated sequence is not good for use as an immunogen. The new approach uses HIV-1 Env sequence isolated from the donor, the sequences are used to identify its close progenitor, sequence alignment is performed with all the Env sequences using programs like clustalW and then phylogenic tree is generated to determine Env sequences that are closely related and have least genetic distances. These closest homolog are then tested for binding to identify novel immunogen that bind broad neutralizing antibodies and are potential candidates to elicit neutralizing response.

In particular, such a method is exemplified in FIG. 6, which depicts a recombinant HIV-1 envelope glycoprotein gp120 BG505 clade A ELISA binding and phylogeny tree. ELISA showed significant binding of PG9, PG16 and b12 antibodies to BG505 gp120. The BG505 protein sequence was selected using bioinformatics approach that identified close progenitor sequence to HIV-1 clade A Env from Env protein database. The HIV-1 Env clade A sequences from the donor (V1_011) who gave rise to PG9 and PG16 antibodies were used to search the HIV-1 Env protein data base.

The present invention also encompasses an isolated or non-naturally occurring V1-3 loop which may comprise a conformation of an amino acid sequence of a PG9 binding protein. The isolated or non-naturally occurring V1-3 loop may comprise the amino acid sequences of V1-16055, V2-16055 or V3-16055. The V1-3 loop sequences of 16055 may be advantageous for conferring binding and/or neutralization activity. The present invention also encompasses an isolated or non-naturally occurring soluble HIV-1 envelope glycoprotein which may comprise the amino acid sequences of V1-16055, V2-16055 or V3-16055. In an advantageous embodiment, the glycoprotein may be a chimeric protein. Without being bound by theory, Applicants surmise that the conformation, and not necessarily the sequence, of the loop confers PG9, PG16 and possibly b12 binding.

The invention also relates to a method for neutralizing tier 1 and tier 2 HIV-1 viruses in patient in need thereof which may comprise administering to the patient a priming dose of a vector containing and expressing gp120 isolated from a 16055 virus and further administering to the patient a protein boost a gp120 protein isolated from a 16055 virus, wherein the sera from the patient neutralizes HIV-1 viruses in the patient. The HIV-1 virus may be HIV-1 Clade A virus, HIV-1 Clade B virus, HIV-1 Clade C virus, a HIV-1 Clade A pseudo-virus, HIV-1 Clade B pseudo-virus or a HIV-1 Clade C pseudo-virus, Advantageously, the HIV-1 viruses are tier 1 and tier 2 clade B and clade C HIV-1 viruses. The method may further comprise isolating the sera from the patient and testing the sera in a pseudoneutralization assay to determine if the sera is indeed neutralizing. Representative tier 1, tier 2 and tier 3 viruses are provided by Seaman et al., Journal of Virology, February 2010, Vol. 84, No. 3, pp. 1439-1452.

FIGS. 13A-13D depict a 16055 immunogenicity study in rabbits. (a) immunization schedule and dose is presented for six animals immunized by intra muscular route per group at weeks 0, 4, 12, 20 and 28. Sera were collected two weeks post immunization and week 0, 14 and 31 sera were analyzed for binding and neutralization activity. (b) represent anti-Env ELISA titer represented as geometric mean titers and (c) represents IC50 values for neutralization of tier I and tier II clade B and clade C HW-1 viruses, JRCSF N160K and N156K. In group I and II, six rabbits were immunized with pCMVR-16055 gp120 DNA and pCMVR DNA respectively (250 ug/animal/immunization) at week 0, 4 and 12 by electroporation followed by two protein boost (50 ug/animal/immunization) at weeks 20 and 28. Six rabbits in group III were immunized with 16055 gp120 protein at week 0, 4, 12, 20 and 28. All bleeds were collected 2 weeks post immunization except at for the last bleed which was collected 3 weeks post immunization. In group I DNA priming elicited high titer anti-Env antibodies after 1st immunization (~1:5000) which saturated after 2nd DNA EP ($1:2\times10^4$) and did not increase after 3rd DNA EP. Following protein boost the anti-Env titer further increased (~$1:1\times10^5$). In group II no anti-Env antibodies were observed following control DNA EP at week but following protein boost the anti-Env titer of $1:1\times10^5$ was observed. In group III anti-Env titers saturated following three protein immunization. The sera were tested for pseudovirus neutralization assay based on Tzmbl cells containing Tat controlled luciferase expression. The DNA EP-16055 gp120 protein generated sera showed neutralization of homologous 16055 virus for two out of six rabbits, the other groups did not neutralize 16055 virus. Heterologous tier I clade C MW965 virus was potently neutralized by sera generated at week 14 and 31 by all three group. Similarly potent cross clade-neutralization was observed for tier I clade B SF162 and SS1196 viruses. Heterologous tier II clade C IN905 and MGRMO26 were potently neutralized by group I and III sera at week 31. IN905 virus was also neutralized by group I and III sera at week 14. Heterologous cross-clade tier II YU2 virus was resistant to all group sera but JRCSF virus was neutralized weakly by week 14 sera and the neut titers increased at week 31. JRCSF mutant N160K shown to be resistant to PG9 and PG16 antibodies was resistant to all group sera whereas another mutant N156A was globally sensitive and behaved like a tier I virus. Over all anti-Env sera was elicited that showed cross clade neutralization of Tier I and II homologous and heterologous viruses.

Assays for screening for neutralizing antibodies are known in the art. A neutralization assay approach has been described previously (Binley J M, et al., (2004). Comprehensive Cross-Clade Neutralization Analysis of a Panel of Anti-Human Immunodeficiency Virus Type 1 Monoclonal Antibodies. *J. Virol.* 78: 13232-13252). Pseudotyped viruses may be generated by co-transfecting cells with at least two plasmids encoding the soluble Env cDNA of the present invention and the rest of the HIV genome separately. In the HIV genome encoding vector, the Env gene may be replaced by the firefly luciferase gene. Transfectant supernatants containing pseudotyped virus may be co-incubated overnight with B cell supernatants derived from activation of an infected donor's primary peripheral blood mononuclear cells (PBMCs). Cells stably transfected with and expressing CD4 plus the CCR5 and CXCR4 coreceptors may be added to the mixture and incubated for 3 days at 37° C. Infected cells may be quantified by luminometry.

The method of U.S. Pat. No. 7,386,232 may also be utilized for the screening of broad neutralizing antibodies. An envelope-enzyme fusion protein may be constructed by attaching an enzyme to the C-terminal end of an envelope protein. Virus particles comprising of the fusion protein and wild type and/or soluble envelope glycoprotein may be generated and used to infect target cells in the presence of a patients' sera. Activities of enzyme measured in such infected cells are measures of virus binding and entry to the target cells that are mediated by the wild type viral envelope protein. Examples of enzymes that can be used to generate the fusion protein include, but are not limited to, luciferase, bacterial or placental alkaline phosphatase, β-galactosidase, and fluorescent proteins such as Green fluorescent protein or toxins. The assay, in general, can also be carried out in 96-well plate. Decreased enzyme activities in the presence of the sera indicate that there are neutralizing antibodies in the sera.

In another embodiment of the present invention, the soluble envelope glycoproteins of the present invention may be crystallized in the combination with PG9 or PG16 or with any other neutralizing antibodies, including those identified by the above methods, to determine the exact molecular surface where the soluble envelope glycoprotein binds with the neutralizing antibody to design novel HIV-1 immunogens.

Crystals of the invention may be obtained by conventional means as are well-known in the art of protein crystallography, including batch, liquid bridge, dialysis, vapor diffusion and hanging drop methods (see, e.g., Johnson et al., Biochemistry.

1982 Sep. 28; 21(20):4839-43; Brayer & McPherson, J Biol Chem. 1982 Apr. 10; 257(7):3359-61; McPherson &Weickmann, J Biomol Struct Dyn. 1990 Apr. 7(5):1053-60; and Koszelak et al., J Mol Biol. 1989 Sep. 20; 209(2):323-5; Weber et al., Acta Crystallogr B. 1991 Feb. 1; 47 (Pt 1):116-27 and Weber, Methods Enzymol. 1991; 202:727-41).

Generally, the crystals of the invention are grown by dissolving a substantially pure neutralizing antibody, such as PG9 or PG16, and soluble envelope glycoprotein in an aqueous buffer containing a precipitant at a concentration just below that necessary to precipitate the protein. Water is removed by controlled evaporation to produce precipitating conditions, which are maintained until crystal growth ceases.

The crystals of the invention, and particularly the atomic structure co-ordinates obtained therefrom, have a wide variety of uses. The crystals and structure co-ordinates are particularly useful for identifying compounds that bind to a neutralizing antibody, such as PG9 or PG16, and thus are useful to elicit anti-HIV antibodies. Such compounds may be useful in eliciting clade B and C anti-HIV antibodies, however variants may be useful in eliciting clade A, D or E anti-HIV antibodies.

The structure co-ordinates may be used as phasing models in determining the crystal structures of a synthetic or mutated neutralizing antibody, such as PG9 or PG16, domains, as well as the structures of co-crystals of such domains with ligands.

The provision of the crystal structure of a neutralizing antibody, such as PG9 or PG16, complexed with a soluble envelope glycoprotein provide the skilled artisan with a detailed insight into the mechanisms of action of a neutralizing antibody, such as PG9 or PG16. This insight provides a means to design compounds that bind to a neutralizing antibody, such as PG9 or PG16, and thus to certain anti-HIV antibodies, and therefore compounds that elicit anti-HIV antibodies, which are useful in diagnosis, treatment, or prevention of HIV in an individual in need thereof.

The provision of the crystal structure of a neutralizing antibody, such as PG9 or PG16, complexed with a soluble envelope glycoprotein allows a novel approach for drug or compound discovery, identification, and design for compounds that bind to a neutralizing antibody, such as PG9 or PG16, and thus to anti-HIV antibodies, and therefore compounds that elicit anti-HIV antibodies, which are useful in diagnosis, treatment, or prevention of HIV in an individual in need thereof. Accordingly, the invention provides a computer-based method of rational drug or compound design or identification which comprises: providing the structure of a neutralizing antibody, such as PG9 or PG16, complex as defined by the co-ordinates or the identifying co-ordinates, providing a structure of a candidate compound; and fitting the structure of the candidate to the structure of a neutralizing antibody, such as PG9 or PG16.

In an alternative aspect, the method may use the co-ordinates of atoms of interest of a neutralizing antibody, such as PG9 or PG16, which are in the vicinity of the active site or binding region in order to model the pocket in which the substrate or ligand binds. These co-ordinates may be used to define a space which is then screened "in silico" against a candidate molecule. Thus, the invention provides a computer-based method of rational drug or compound design or identification which comprises: providing the co-ordinates of at least selected co-ordinates; providing the structure of a candidate compound; and fitting the structure of the candidate to the selected co-ordinates.

In practice, it may be desirable to model a sufficient number of atoms of a neutralizing antibody, such as PG9 or PG16, as defined by its co-ordinates which represent the active site or binding region. Thus, there can be provided the co-ordinates of at least 5, advantageously at least 10, more advantageously at least 50 and even more advantageously at least 100 atoms of the structure.

Accordingly, the methods of the invention can employ a sub-domain of interest of a neutralizing antibody, such as PG9 or PG16, which is in the vicinity of the active site or binding region, and the invention can provide a computer-based method for identifying or rationally designing a compound or drug which comprises: providing the coordinates of at least a sub-domain of; providing the structure of a candidate modulator or inhibitor of a neutralizing antibody, such as PG9 or PG16; and fitting the structure of the candidate to the co-ordinates of the sub-domain provided.

These methods can optionally include synthesizing the candidate and can optionally further include contacting the candidate with a neutralizing antibody, such as PG9 or PG16, to test whether there is binding and/or inhibition and/or administering the compound to an animal capable of eliciting antibodies and testing whether the compound elicits anti-HIV antibodies. Compounds which elicit anti-HIV antibodies are useful for diagnostic purposes, as well as for immunogenic, immunological or even vaccine compositions, as well as pharmaceutical compositions.

"Fitting" can mean determining, by automatic or semi-automatic means, interactions between at least one atom of the candidate and at least one atom of a neutralizing antibody, such as PG9 or PG16, and calculating the extent to which such an interaction is stable. Interactions can include attraction, repulsion, brought about by charge, steric considerations, and the like. A "sub-domain" can mean at least one, e.g., one, two, three, or four, complete element(s) of secondary structure.

The step of providing the structure of a candidate molecule may involve selecting the compound by computationally screening a database of compounds for interaction with the active site. For example, a 3-D descriptor for the potential modulator may be derived, the descriptor including geometric and functional constraints derived from the architecture and chemical nature of the active site. The descriptor may then be used to interrogate the compound database, a potential modulator being a compound that has a good match to the features of the descriptor. In effect, the descriptor can be a type of virtual pharmacophore.

In any event, the determination of the three-dimensional structure of a neutralizing antibody, such as PG9 or PG16, complex provides a basis for the design of new and specific compounds that bind to a neutralizing antibody, such as PG9 or PG16, and are useful for eliciting an immune response. For example, from knowing the three-dimensional structure of a neutralizing antibody, such as PG9 or PG16, complex, computer modelling programs may be used to design or identify different molecules expected to interact with possible or confirmed active sites such as binding sites or other structural or functional features of a neutralizing antibody, such as PG9 or PG16.

More specifically, a compound that potentially binds ("binder") to a neutralizing antibody, such as PG9 or PG16, activity can be examined through the use of computer modeling using a docking program such as GRAM, DOCK or AUTODOCK (see Walters et al. Drug Discovery Today, vol. 3, no. 4 (1998), 160-178, and Dunbrack et al. Folding and Design 2 (1997), 27-42). This procedure can include computer fitting of potential binders to a neutralizing antibody, such as PG9 or PG16, to ascertain how well the shape and the chemical structure of the potential binder will bind to the antibody.

Also, computer-assisted, manual examination of the active site or binding site of a neutralizing antibody, such as PG9 or PG16, may be performed. The use of programs such as GRID (P. Goodford, J. Med. Chem, 1985, 28, 849-57)—program that determines probable interaction sites between molecules with various functional groups and the antibody—may also be used to analyze the active site or binding site to predict partial structures of binding compounds.

Computer programs can be employed to estimate the attraction, repulsion or steric hindrance of the two binding partners, e.g., a neutralizing antibody, such as PG9 or PG16, and a candidate binder. Generally, the tighter the fit, the fewer the steric hindrances, and the greater the attractive forces, the more potent the potential binder, since these properties are consistent with a tighter binding constant. Furthermore, the more specificity in the design of a candidate binder, the more likely it is that it will not interact with other proteins as well.

In a further aspect, the invention provides for a method for determining the structure of a binder of a neutralizing antibody, such as PG9 or PG16, bound to a neutralizing antibody, such as PG9 or PG16, said method comprising, (a) providing a crystal of a neutralizing antibody, such as PG9 or PG16, according to the invention, (b) soaking the crystal or another crystal with said binder; and (c) determining the structure of said a neutralizing antibody-binder complex. Such other crystal may have essentially the same coordinates discussed herein, however due to minor alterations in the polypeptide or sequence, the crystal may form in a different space group.

The invention further involves, in place of or in addition to in silico methods, high throughput screening of compounds to select compounds with binding activity. Those compounds which show binding activity may be selected as possible candidate binders, and further crystallized with a neutralizing antibody, such as PG9 or PG16, e.g., by co-crystallization or by soaking, for X-ray analysis. The resulting X-ray structure may be compared with known coordinates for a variety of purposes. For example, where the contacts made by such compounds overlap with those made by a neutralizing antibody, such as PG9 or PG16, novel molecules comprising residues which contain contacts of a neutralizing antibody, such as PG9 or PG16, and other compounds may be provided.

Having designed, identified, or selected possible binding candidate binders by determining those which have favorable fitting properties, e.g., strong attraction between a candidate and a neutralizing antibody, such as PG9 or PG16, these can then be screened for activity. Consequently, the invention further involves: obtaining or synthesizing the candidate modulator or inhibitor; and contacting the candidate binder with a neutralizing antibody, such as PG9 or PG 16, to determine the ability of the candidate to bind with a neutralizing antibody, such as PG9 or PG16. In the latter step, the candidate is advantageously contacted with a neutralizing antibody, such as PG9 or PG16, under conditions to determine its function. Instead of, or in addition to, performing such an assay, the invention may comprise: obtaining or synthesizing the candidate modulator, forming a complex of a neutralizing antibody, such as PG9 or PG16, and the candidate, and analyzing the complex, e.g., by X-ray diffraction or NMR or other means, to determine the ability of the candidate to interact with a neutralizing antibody, such as PG9 or PG16. Detailed structural information can then be obtained about the binding of the candidate to a neutralizing antibody, such as PG9 or PG16, and in light of this information, adjustments can be made to the structure or functionality of the potential modulator, e.g., to improve its binding to a neutralizing antibody, such as PG9 or PG16. These steps may be repeated and re-repeated as necessary. Alternatively or additionally, potential binders can be administered to an animal capable of eliciting an antibody response, to ascertain whether the potential binder elicits anti-HIV antibodies.

Once the amino acid sequence of the polypeptides with known and unknown structures are aligned, the structures of the conserved amino acids in a computer representation of the polypeptide with known structure are transferred to the corresponding amino acids of the polypeptide whose structure is unknown. For example, a tyrosine in the amino acid sequence of known structure may be replaced by a phenylalanine, the corresponding homologous amino acid in the amino acid sequence of unknown structure. The structures of amino acids located in non-conserved regions may be assigned manually using standard peptide geometries or by molecular simulation techniques, such as molecular dynamics. Refining the entire structure can be by molecular dynamics and/or energy minimization.

The aspects of the invention which employ the neutralizing antibody, such as PG9 or PG16, structure in silico may be equally applied to homologue models of a neutralizing antibody, such as PG9 or PG16, obtained by the above aspect of the invention and this forms yet a further embodiment of the invention. Thus, having determined a conformation of a neutralizing antibody, such as PG9 or PG16, by the methods described herein, such a conformation may be used in a computer-based method of rational drug or compound design or identification as described herein.

The invention further provides a method for determining the structure of a binder of a neutralizing antibody, such as PG9 or PG16, bound to a neutralizing antibody, such as PG9 or PG16, comprising: providing a crystal of a neutralizing antibody, such as PG9 or PG16, e.g., according to the invention, soaking the crystal with the binder, and determining the structure of the neutralizing antibody-binder complex. Alternatively or additionally the neutralizing antibody, such as PG9 or PG16, and the binder may be co-crystallized.

The invention further provides systems, such as computer systems, intended to generate structures and/or perform rational drug or compound design for a neutralizing antibody, such as PG9 or PG16, or complex of neutralizing antibody, such as PG9 or PG16, and a potential binder. The system can contain: atomic co-ordinate data, said data defining the three-dimensional structure of a neutralizing antibody, such as PG9 or PG16, or at least one sub-domain thereof; or structure factor data for neutralizing antibody, such as PG9 or PG16, said structure factor data being derivable from the atomic co-ordinate data. The invention also involves computer readable media with: atomic co-ordinate data by homology modeling, said data defining the three-dimensional structure of a neutralizing antibody, such as PG9 or PG16, or at least one sub-domain thereof; or structure factor data for neutralizing antibody, such as PG9 or PG16, said structure factor data being derivable from the atomic co-ordinate data. "Computer readable media" refers to any media which can be read and accessed directly by a computer, and includes, but is not limited to: magnetic storage media such as floppy discs, hard storage medium and magnetic tape; optical storage media such as optical discs or CD-ROM; electrical storage media such as RAM and ROM; and hybrids of these categories, such as magnetic/optical media. By providing such computer readable media, the atomic co-ordinate data can be routinely accessed to model a neutralizing antibody, such as PG9 or PG16, or a sub-domain thereof. For example RASMOL (Sayle et al., TIBS vol. 20 (1995), 374) is a publicly available software package which allows access and analysis of atomic co-ordinate data for structural determination and/or rational drug design. The invention further comprehends methods of doing business by providing access to such computer readable media and/or computer systems and/or atomic co-ordinate data to users; e.g., the media and/or atomic co-ordinate data can be accessible to a user, for instance on a subscription basis, via the Internet or a global communication/computer network; or, the computer system can be available to a user, on a subscription basis. Structure factor data, which are derivable from atomic co-ordinate data (see, e.g., Blundell et al., in Protein Crystallography, Academic Press, NY, London and San Francisco (1976)), are particularly useful for calculating electron density maps, e.g., difference Fourier electron density maps. Thus, there are additional uses for the computer readable media and/or computer systems and/or atomic co-ordinate data and additional reasons to provide them to users. A "computer system" refers to the hardware means, software means and data storage means used to analyze the atomic co-ordinate data of the present invention. The minimum hardware means of computer-based systems of the invention may comprise a central processing unit (CPU), input means, output means, and data storage means. Desirably, a monitor is provided to visualize structure data. The data storage means may be RAM or other means for accessing computer readable media of the invention. Examples of such systems are microcomputer workstations available from Silicon Graphics Incorporated and Sun Microsystems running Unix based, Linux, Windows NT or IBM OS/2 operating systems.

Accordingly, the invention further comprehends methods of transmitting information obtained in any method or step thereof described herein or any information described herein, e.g., via telecommunications, telephone, mass communications, mass media, presentations, internet, email, etc.

The invention also provides a method of analyzing a complex of a neutralizing antibody, such as PG9 or PG16, and a potential binder comprising: employing X-ray crystallographic diffraction data from the complex and a three-dimensional structure of a neutralizing antibody, such as PG9 or PG16, or at least a sub-domain thereof, to generate a different Fourier electron density map of the complex; advantageously, the three-dimensional structure being as defined by its atomic co-ordinate data.

Such complexes can be crystallized and analyzed using X-ray diffraction methods, e.g., according to the approaches described by Greer et al., 1994, and difference Fourier electron density maps can be calculated based on X-ray diffraction patterns of soaked or co-crystallized neutralizing antibody, such as PG9 or PG16, and the solved structure of an uncomplexed neutralizing antibody, such as PG9 or PG16. These maps can then be used to determine whether and where a particular potential binder binds to a neutralizing antibody, such as PG9 or PG 16, and/or changes the conformation of a neutralizing antibody, such as PG9 or PG16. Electron density maps can be calculated using programs such as those from the CCP4 computer package (Collaborative Computing Project, No. 4. The CCP4 Suite: Programs for Protein Crystallography, Acta Crystallographica, D50, 1994, 760-763). For map visualization and model building programs such as "QUANTA" (1994, San Diego, Calif.: Molecular Simulations, Jones et al., 1991) can be used.

Determination of the 3D structure of a neutralizing antibody, such as PG9 or PG16, provides important information about the likely active/binding site(s) of a neutralizing antibody, such as PG9 or PG16. This information may be used for rational design of neutralizing antibody binders, e.g., by computational techniques that identify possible binding ligands for the active site(s), by enabling linked-fragment approaches to drug design, and by enabling the identification and location of bound ligands using analyses such as X-ray crystallographic analysis.

Greer et al., supra, relates to an iterative approach to ligand design based on repeated sequences of computer modeling, protein-ligand complex formation, and X-ray analysis. Thymidylate synthase inhibitors were designed by Greer; and, Fab neutralizing antibody binders may also be designed in this way. Using, for example, GRID (P. Goodford, 1985) or the solved 3D structure of Fab neutralizing antibody, such as PG9 or PG16, a potential binder of a neutralizing antibody, such as PG9 or PG16, may be designed that complements the functionalities of the neutralizing antibody active site(s). The potential binder can be synthesized, formed into a complex with a neutralizing antibody, such as PG9 or PG16, and the complex then analyzed, e.g., by X-ray crystallography, NMR or a combination thereof, to identify the actual position of the bound compound.

Determination of the position of the potential binder compound in the complex allows determination of the interactions of it with a neutralizing antibody, such as PG9 or PG16. This allows the skilled artisan to analyze the affinity and specificity of the compound for a neutralizing antibody, such as PG9 or PG16, and to propose modifications to the compound to increase or decrease either or both of these properties. Thus, the structure and/or functional groups of the compound can then be adjusted, if necessary or desired, in view of the results from the analysis (e.g., X-ray analysis), and the synthesis and analysis sequence repeated until an optimized compound is obtained. Related approaches to structure-based drug and compound design are also discussed in other documents cited herein, as well as in Bohacek et al., 1996.

As a result of the determination of the neutralizing antibody, such as PG9 or PG16, 3D structure, more purely computational techniques for rational drug and compound design may also be used to design neutralizing antibody, such as PG9 or PG16, binders and hence compounds that elicit anti-HIV antibodies; for example, automated ligand-receptor docking programs (see Jones et al., 1995) which require accurate information on the atomic co-ordinates of target receptors, may be used to design or identify potential neutralizing antibody, such as PG9 or PG 16, binders.

Linked-fragment approaches to drug or compound design also require accurate information on the atomic co-ordinates of a target. Small compounds that have the potential to bind to regions of a neutralizing antibody, such as PG9 or PG16, which in themselves may not be binder compounds may be assembled by chemical linkage to provide potential binders. Thus, the basic idea behind these approaches is to determine the binding locations of more than one, e.g., plural or a plurality of, ligands to a target molecule, and then construct a molecular scaffold to connect the ligands together in such a way that their relative binding positions are preserved. The ligands may be provided computationally and modeled in a computer system, or provided in an experimental setting, wherein crystals according to the invention are provided and more than one, e.g., plural or a plurality of, ligands soaked separately or in mixed pools into the crystal prior to analysis, e.g., X-ray analysis, and determination of their location.

The binding site of two or more ligands are determined and may be connected to thus form a potential lead compound that can be further refined, e.g., the iterative technique of Greer et al. For a virtual linked-fragment approach, see Verlinde et al., 1992; and for NMR and X-ray approaches, see Skuker et al., 1996; and Stout et al., 1998. The use of these or other approaches to design and/or identify neutralizing antibody, such as PG9 or PG16, binders and hence compounds that elicit anti-HIV antibodies (see, e.g., patent documents cited herein such as in the Background Section and documents cited therein, supra) is made possible by the determination of the neutralizing antibody, such as PG9 or PG16, structure.

Many of the techniques and approaches to structure-based described herein employ X-ray analysis to identify the binding position of a potential modulator in a complex with a protein. A common way of doing this is to perform X-ray crystallography on the complex, produce a difference Fourier electron density map, and associate a particular pattern of electron density with the potential modulator. However, to produce a map (See Blundell et al., supra), it is important to know the 3D structure of the protein beforehand (or at least the protein structure factors). Therefore, determination of the neutralizing antibody, such as PG9 or PG16, structure also allows difference Fourier electron density maps of complexes of neutralizing antibody, such as PG9 or PG16, with a potential modulator to be produced, which can greatly assist in the process of rational compound and/or drug design or identification.

The approaches to structure-based drug or compound design or identification described herein involve initial identification of possible compounds for interaction with the target molecule (in this case a neutralizing antibody, such as PG9 or PG16), and thus elicit anti-HIV antibodies. Sometimes these compounds are known, e.g., from research literature. However, when they are not, or when novel compounds are wanted, a first stage of the drug or compound design or identification program may involve computer-based in silico screening of compound databases (such as the Cambridge Structural Database) with the aim of identifying compounds which interact with the active site or sites of the target biomolecule (in this case a neutralizing antibody, such as PG9 or PG16). Screening selection criteria may be based on pharmacokinetic properties such as metabolic stability and toxicity. However, determination of the neutralizing antibody, such as PG9 or PG16, structure allows the architecture and chemical nature of each neutralizing antibody, such as PG9 or PG16, active site to be identified, which in turn allows the geometric and functional constraints of a descriptor for the potential binder to be derived. The descriptor can be, therefore, a type of virtual 3D pharmacophore, which can also be used as selection criteria or filter for database screening.

Compounds which have a chemical structure selected using the invention, wherein said compounds are neutralizing antibody, such as PG9 or PG16, binders, form a further aspect of the invention; and, such compounds may be used in methods of medical treatments, such as for diagnosis, preventing or treating HIV or for eliciting antibodies for diagnosis of HIV, including use in vaccines. Further, such compounds may be used in the preparation of medicaments for such treatments or prevention, or compositions for diagnostic purposes. The compounds may be employed alone or in combination with other treatments, vaccines or preventatives; and, the compounds may be used in the preparation of combination medicaments for such treatments or prevention, or in kits containing the compound and the other treatment or preventative.

In yet another embodiment, the present invention also encompassed the use of the soluble envelope glycoproteins described herein as immunogens, advantageously as HIV-1 vaccine components.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, F(ab')$_2$, Fv and scFv which are capable of binding the epitope determinant. These antibody fragments retain some ability to selectively bind with its antigen or receptor and include, for example:

(i) Fab, the fragment which contains a monovalent antigen-binding fragment of an antibody molecule can be produced by digestion of whole antibody with the enzyme papain to yield an intact light chain and a portion of one heavy chain;
 (ii) Fab', the fragment of an antibody molecule can be obtained by treating whole antibody with pepsin, followed by reduction, to yield an intact light chain and a portion of the heavy chain; two Fab' fragments are obtained per antibody molecule;
 (iii) F(ab')$_2$, the fragment of the antibody that can be obtained by treating whole antibody with the enzyme pepsin without subsequent reduction; F(ab')$_2$ is a dimer of two Fab' fragments held together by two disulfide bonds;
 (iv) scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

A "neutralizing antibody" may inhibit the entry of HIV-1 virus for example SF162 and/or JRCSF with a neutralization index >1.5 or >2.0. Broad and potent neutralizing antibodies may neutralize greater than about 50% of HIV-1 viruses (from diverse clades and different strains within a clade) in a neutralization assay. The inhibitory concentration of the monoclonal antibody may be less than about 25 mg/ml to neutralize about 50% of the input virus in the neutralization assay.

It should be understood that the proteins, including the antibodies and/or antigens of the invention may differ from the exact sequences illustrated and described herein. Thus, the invention contemplates deletions, additions and substitutions to the sequences shown, so long as the sequences function in accordance with the methods of the invention. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may be used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the Gag, Pol, Env, Nef, RT, and Int sequences of the invention may be altered in these ways.

As regards codon optimization, the nucleic acid molecules of the invention have a nucleotide sequence that encodes the antigens of the invention and can be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens can be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Geneart (geneart.com). Thus, the nucleotide sequences of the invention can readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM 120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and antibodies and/or antigens of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antibodies and/or antigens of the present invention may be used in accordance with the present invention. In certain embodiments, the antigens and/or antibodies of the present invention may be used in vitro (such as using cell-free expression systems) and/or in cultured cells grown in vitro in order to produce the encoded HIV-antigens and/or antibodies which may then be used for various applications such as in the production of proteinaceous vaccines. For such applications, any vector that allows expression of the antigens and/or antibodies in vitro and/or in cultured cells may be used.

For applications where it is desired that the antibodies and/or antigens be expressed in vivo, for example when the transgenes of the invention are used in DNA or DNA-containing vaccines, any vector that allows for the expression of the antibodies and/or antigens of the present invention and is safe for use in vivo may be used. In preferred embodiments the vectors used are safe for use in humans, mammals and/or laboratory animals.

For the antibodies and/or antigens of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The present invention relates to a recombinant vector expressing a foreign epitope. Advantageously, the epitope is an HIV epitope. In an advantageous embodiment, the HIV epitope is a soluble envelope glycoprotein, however, the present invention may encompass additional HIV antigens, epitopes or immunogens. Advantageously, the HIV epitope is an HIV antigen, HIV epitope or an HIV immunogen, such as, but not limited to, the HIV antigens, HIV epitopes or HIV immunogens of U.S. Pat. Nos. 7,341,731; 7,335,364; 7,329,807; 7,323,553; 7,320,859; 7,311,920; 7,306,798; 7,285,646; 7,285,289; 7,285,271; 7,282,364; 7,273,695; 7,270,997; 7,262,270; 7,244,819; 7,244,575; 7,232,567; 7,232,566; 7,223,844; 7,223,739; 7,223,534; 7,223,368; 7,220,554; 7,214,530; 7,211,659; 7,211,432; 7,205,159; 7,198,934; 7,195,768; 7,192,555; 7,189,826; 7,189,522; 7,186,507; 7,179,645; 7,175,843; 7,172,761; 7,169,550; 7,157,083; 7,153,509; 7,147,862; 7,141,550; 7,129,219; 7,122,188; 7,118,859; 7,118,855; 7,118,751; 7,118,742; 7,105,655; 7,101,552; 7,097,971; 7,097,842; 7,094,405; 7,091,049; 7,090,648; 7,087,377; 7,083,787; 7,070,787; 7,070,781; 7,060,273; 7,056,521; 7,056,519; 7,049,136; 7,048,929; 7,033,593; 7,030,094; 7,022,326; 7,009,037; 7,008,622; 7,001,759; 6,997,863; 6,995,008; 6,979,535; 6,974,574;

6,972,126; 6,969,609; 6,964,769; 6,964,762; 6,958,158;
6,956,059; 6,953,689; 6,951,648; 6,946,075; 6,927,031;
6,919,319; 6,919,318; 6,919,077; 6,913,752; 6,911,315;
6,908,617; 6,908,612; 6,902,743; 6,900,010; 6,893,869;
6,884,785; 6,884,435; 6,875,435; 6,867,005; 6,861,234;
6,855,539; 6,841,381 6,841,345; 6,838,477; 6,821,955;
6,818,392; 6,818,222; 6,815,217; 6,815,201; 6,812,026;
6,812,025; 6,812,024; 6,808,923; 6,806,055; 6,803,231;
6,800,613; 6,800,288; 6,797,811; 6,780,967; 6,780,598;
6,773,920; 6,764,682; 6,761,893; 6,753,015; 6,750,005;
6,737,239; 6,737,067; 6,730,304; 6,720,310; 6,716,823;
6,713,301; 6,713,070; 6,706,859; 6,699,722; 6,699,656;
6,696,291; 6,692,745; 6,670,181; 6,670,115; 6,664,406;
6,657,055; 6,657,050; 6,656,471; 6,653,066; 6,649,409;
6,649,372; 6,645,732; 6,641,816; 6,635,469; 6,613,530;
6,605,427; 6,602,709; 6,602,705; 6,600,023; 6,596,477;
6,596,172; 6,593,103; 6,593,079; 6,579,673; 6,576,758;
6,573,245; 6,573,040; 6,569,418; 6,569,340; 6,562,800;
6,558,961; 6,551,828; 6,551,824; 6,548,275; 6,544,780;
6,544,752; 6,544,728; 6,534,482; 6,534,312; 6,534,064;
6,531,572; 6,531,313; 6,525,179; 6,525,028; 6,524,582;
6,521,449; 6,518,030; 6,518,015; 6,514,691; 6,514,503;
6,511,845; 6,511,812; 6,511,801; 6,509,313; 6,506,384;
6,503,882; 6,495,676; 6,495,526; 6,495,347; 6,492,123;
6,489,131; 6,489,129; 6,482,614; 6,479,286; 6,479,284;
6,465,634; 6,461,615; 6,458,560; 6,458,527; 6,458,370;
6,451,601; 6,451,592; 6,451,323; 6,436,407; 6,432,633;
6,428,970; 6,428,952; 6,428,790; 6,420,139; 6,416,997;
6,410,318; 6,410,028; 6,410,014; 6,407,221; 6,406,710;
6,403,092; 6,399,295; 6,392,013; 6,391,657; 6,384,198;
6,380,170; 6,376,170; 6,372,426; 6,365,187; 6,358,739;
6,355,248; 6,355,247; 6,348,450; 6,342,372; 6,342,228;
6,338,952; 6,337,179; 6,335,183; 6,335,017; 6,331,404;
6,329,202; 6,329,173; 6,328,976; 6,322,964; 6,319,666;
6,319,665; 6,319,500; 6,319,494; 6,316,205; 6,316,003;
6,309,633; 6,306,625; 6,296,807; 6,294,322; 6,291,239;
6,291,157; 6,287,568; 6,284,456; 6,284,194; 6,274,337;
6,270,956; 6,270,769; 6,268,484; 6,265,562; 6,265,149;
6,262,029; 6,261,762; 6,261,571; 6,261,569; 6,258,599;
6,258,358; 6,248,332; 6,245,331; 6,242,461; 6,241,986;
6,235,526; 6,235,466; 6,232,120; 6,228,361; 6,221,579;
6,214,862; 6,214,804; 6,210,963; 6,210,873; 6,207,185;
6,203,974; 6,197,755; 6,197,531; 6,197,496; 6,194,142;
6,190,871; 6,190,666; 6,168,923; 6,156,302; 6,153,408;
6,153,393; 6,153,392; 6,153,378; 6,153,377; 6,146,635;
6,146,614; 6,143,876 6,140,059; 6,140,043; 6,139,746;
6,132,992; 6,124,306; 6,124,132; 6,121,006; 6,120,990;
6,114,507; 6,114,143; 6,110,466; 6,107,020; 6,103,521;
6,100,234; 6,099,848; 6,099,847; 6,096,291; 6,093,405;
6,090,392; 6,087,476; 6,083,903; 6,080,846; 6,080,725;
6,074,650; 6,074,646; 6,070,126; 6,063,905; 6,063,564;
6,060,256; 6,060,064; 6,048,530; 6,045,788; 6,043,347;
6,043,248; 6,042,831; 6,037,165; 6,033,672; 6,030,772;
6,030,770; 6,030,618; 6,025,141; 6,025,125; 6,020,468;
6,019,979; 6,017,543; 6,017,537; 6,015,694; 6,015,661;
6,013,484; 6,013,432; 6,007,838; 6,004,811; 6,004,807;
6,004,763; 5,998,132; 5,993,819; 5,989,806; 5,985,926;
5,985,641; 5,985,545; 5,981,537; 5,981,505; 5,981,170;
5,976,551; 5,972,339; 5,965,371; 5,962,428; 5,962,318;
5,961,979; 5,961,970; 5,958,765; 5,958,422; 5,955,647;
5,955,342; 5,951,986; 5,951,975; 5,942,237; 5,939,277;
5,939,074; 5,935,580; 5,928,930; 5,928,913; 5,928,644;
5,928,642; 5,925,513; 5,922,550; 5,922,325; 5,919,458;
5,916,806; 5,916,563; 5,914,395; 5,914,109; 5,912,338;
5,912,176; 5,912,170; 5,906,936; 5,895,650; 5,891,623;
5,888,726; 5,885,580 5,885,578; 5,879,685; 5,876,731;
5,876,716; 5,874,226; 5,872,012; 5,871,747; 5,869,058;
5,866,694; 5,866,341; 5,866,320; 5,866,319; 5,866,137;
5,861,290; 5,858,740; 5,858,647; 5,858,646; 5,858,369;
5,858,368; 5,858,366; 5,856,185; 5,854,400; 5,853,736;
5,853,725; 5,853,724; 5,852,186; 5,851,829; 5,851,529;
5,849,475; 5,849,288; 5,843,728; 5,843,723; 5,843,640;
5,843,635; 5,840,480; 5,837,510; 5,837,250; 5,837,242;
5,834,599; 5,834,441; 5,834,429; 5,834,256; 5,830,876;
5,830,641; 5,830,475; 5,830,458; 5,830,457; 5,827,749;
5,827,723; 5,824,497; 5,824,304; 5,821,047; 5,817,767;
5,817,754; 5,817,637; 5,817,470; 5,817,318; 5,814,482;
5,807,707; 5,804,604; 5,804,371; 5,800,822; 5,795,955;
5,795,743; 5,795,572; 5,789,388; 5,780,279; 5,780,038;
5,776,703; 5,773,260; 5,770,572; 5,766,844; 5,766,842;
5,766,625; 5,763,574; 5,763,190; 5,762,965; 5,759,769;
5,756,666; 5,753,258; 5,750,373; 5,747,641; 5,747,526;
5,747,028; 5,736,320; 5,736,146; 5,733,760; 5,731,189;
5,728,385; 5,721,095; 5,716,826; 5,716,637; 5,716,613;
5,714,374; 5,709,879; 5,709,860; 5,709,843; 5,705,331;
5,703,057; 5,702,707 5,698,178; 5,688,914; 5,686,078;
5,681,831; 5,679,784; 5,674,984; 5,672,472; 5,667,964;
5,667,783; 5,665,536; 5,665,355; 5,660,990; 5,658,745;
5,658,569; 5,643,756; 5,641,624; 5,639,854; 5,639,598;
5,637,677; 5,637,455; 5,633,234; 5,629,153; 5,627,025;
5,622,705; 5,614,413; 5,610,035; 5,607,831; 5,606,026;
5,601,819; 5,597,688; 5,593,972; 5,591,829; 5,591,823;
5,589,466; 5,587,285; 5,585,254; 5,585,250; 5,580,773;
5,580,739; 5,580,563; 5,573,916; 5,571,667; 5,569,468;
5,558,865; 5,556,745; 5,550,052; 5,543,328; 5,541,100;
5,541,057; 5,534,406; 5,529,765; 5,523,232; 5,516,895;
5,514,541; 5,510,264; 5,500,161; 5,480,967; 5,480,966;
5,470,701; 5,468,606; 5,462,852; 5,459,127; 5,449,601;
5,447,838; 5,447,837; 5,439,809; 5,439,792; 5,418,136;
5,399,501; 5,397,695; 5,391,479; 5,384,240; 5,374,519;
5,374,518; 5,374,516; 5,364,933; 5,359,046; 5,356,772;
5,354,654; 5,344,755; 5,335,673; 5,332,567; 5,320,940;
5,317,009; 5,312,902; 5,304,466; 5,296,347; 5,286,852;
5,268,265; 5,264,356; 5,264,342; 5,260,308; 5,256,767;
5,256,561; 5,252,556; 5,230,998; 5,230,887; 5,227,159;
5,225,347; 5,221,610 5,217,861; 5,208,321; 5,206,136;
5,198,346; 5,185,147; 5,178,865; 5,173,400; 5,173,399;
5,166,050; 5,156,951; 5,135,864; 5,122,446; 5,120,662;
5,103,836; 5,100,777; 5,100,662; 5,093,230; 5,077,284;
5,070,010; 5,068,174; 5,066,782; 5,055,391; 5,043,262;
5,039,604; 5,039,522; 5,030,718; 5,030,555; 5,030,449;
5,019,387; 5,013,556; 5,008,183; 5,004,697; 4,997,772;
4,983,529; 4,983,387; 4,965,069; 4,945,082; 4,921,787;
4,918,166; 4,900,548; 4,888,290; 4,886,742; 4,885,235;
4,870,003; 4,869,903; 4,861,707; 4,853,326; 4,839,288;
4,833,072 and 4,795,739.

In another embodiment, HIV, or immunogenic fragments thereof, may be utilized as the HIV epitope. For example, the HIV nucleotides of U.S. Pat. Nos. 7,393,949, 7,374,877, 7,306,901, 7,303,754, 7,173,014, 7,122,180, 7,078,516, 7,022,814, 6,974,866, 6,958,211, 6,949,337, 6,946,254, 6,896,900, 6,887,977, 6,870,045, 6,803,187, 6,794,129, 6,773,915, 6,768,004, 6,706,268, 6,696,291, 6,692,955, 6,656,706, 6,649,409, 6,627,442, 6,610,476, 6,602,705, 6,582,920, 6,557,296, 6,531,587, 6,531,137, 6,500,623, 6,448,078, 6,429,306, 6,420,545, 6,410,013, 6,407,077, 6,395,891, 6,355,789, 6,335,158, 6,323,185, 6,316,183, 6,303,293, 6,300,056, 6,277,561, 6,270,975, 6,261,564, 6,225,045, 6,222,024, 6,194,391, 6,194,142, 6,162,631, 6,114,167, 6,114,109, 6,090,392, 6,060,587, 6,057,102, 6,054,565, 6,043,081, 6,037,165, 6,034,233, 6,033,902, 6,030,769, 6,020,123, 6,015,661, 6,010,895, 6,001,555, 5,985,661, 5,980,900, 5,972,596, 5,939,538, 5,912,338, 5,869,339, 5,866,701, 5,866,694, 5,866,320, 5,866,137, 5,864,027, 5,861,242, 5,858,785, 5,858,651, 5,849,475, 5,843,638, 5,840,480, 5,821,046, 5,801,056, 5,786,177, 5,786,145, 5,773,247, 5,770,703, 5,756,674, 5,741,706, 5,705,612, 5,693,752, 5,688,637, 5,688,511, 5,684,147, 5,665,577, 5,585,263, 5,578,715, 5,571,712, 5,567,603, 5,554,528, 5,545,726, 5,527,895, 5,527,894, 5,223,423, 5,204,259, 5,144,019, 5,051,496 and 4,942,122 are useful for the present invention.

Any epitope recognized by an HIV antibody may be used in the present invention. For example, the anti-HIV antibodies of U.S. Pat. Nos. 6,949,337, 6,900,010, 6,821,744, 6,768,004, 6,613,743, 6,534,312, 6,511,830, 6,489,131, 6,242,197, 6,114,143, 6,074,646, 6,063,564, 6,060,254, 5,919,457, 5,916,806, 5,871,732, 5,824,304, 5,773,247, 5,736,320, 5,637,455, 5,587,285, 5,514,541, 5,317,009, 4,983,529, 4,886,742, 4,870,003 and 4,795,739 are useful for the present invention. Furthermore, monoclonal anti-HIV antibodies of U.S. Pat. Nos. 7,074,556, 7,074,554, 7,070,787, 7,060,273, 7,045,130, 7,033,593, RE39,057, 7,008,622, 6,984,721, 6,972,126, 6,949,337, 6,946,465, 6,919,077, 6,916,475, 6,911,315, 6,905,680, 6,900,010, 6,825,217, 6,824,975, 6,818,392, 6,815,201, 6,812,026, 6,812,024, 6,797,811, 6,768,004, 6,703,019, 6,689,118, 6,657,050, 6,608,179, 6,600,023, 6,596,497, 6,589,748, 6,569,143, 6,548,275, 6,525,179, 6,524,582, 6,506,384, 6,498,006, 6,489,131, 6,465,173, 6,461,612, 6,458,933, 6,432,633, 6,410,318, 6,406,701, 6,395,275, 6,391,657, 6,391,635, 6,384,198, 6,376,170, 6,372,217, 6,344,545, 6,337,181, 6,329,202, 6,319,665, 6,319,500, 6,316,003, 6,312,931, 6,309,880, 6,296,807, 6,291,239, 6,261,558, 6,248,514, 6,245,331, 6,242,197, 6,241,986, 6,228,361, 6,221,580, 6,190,871, 6,177,253, 6,146,635, 6,146,627, 6,146,614, 6,143,876, 6,132,992, 6,124,132, RE36,866, 6,114,143, 6,103,238, 6,060,254, 6,039,684, 6,030,772, 6,020,468, 6,013,484, 6,008,044, 5,998,132, 5,994,515, 5,993,812, 5,985,545, 5,981,278, 5,958,765, 5,939,277, 5,928,930, 5,922,325, 5,919,457, 5,916,806, 5,914,109, 5,911,989, 5,906,936, 5,889,158, 5,876,716, 5,874,226, 5,872,012, 5,871,732, 5,866,694, 5,854,400, 5,849,583, 5,849,288, 5,840,480, 5,840,305, 5,834,599, 5,831,034, 5,827,723, 5,821,047, 5,817,767, 5,817,458, 5,804,440, 5,795,572, 5,783,670, 5,776,703, 5,773,225, 5,766,944, 5,753,503, 5,750,373, 5,747,641, 5,736,341, 5,731,189, 5,707,814, 5,702,707, 5,698,178, 5,695,927, 5,665,536, 5,658,745, 5,652,138, 5,645,836, 5,635,345, 5,618,922, 5,610,035, 5,607,847, 5,604,092, 5,601,819, 5,597,896, 5,597,688, 5,591,829, 5,558,865, 5,514,541, 5,510,264, 5,478,753, 5,374,518, 5,374,516, 5,344,755, 5,332,567, 5,300,433, 5,296,347, 5,286,852, 5,264,221, 5,260,308, 5,256,561, 5,254,457, 5,230,998, 5,227,159, 5,223,408, 5,217,895, 5,180,660, 5,173,399, 5,169,752, 5,166,050, 5,156,951, 5,140,105, 5,135,864, 5,120,640, 5,108,904, 5,104,790, 5,049,389, 5,030,718, 5,030,555, 5,004,697, 4,983,529, 4,888,290, 4,886,742 and 4,853,326, are also useful for the present invention.

The vectors used in accordance with the present invention should typically be chosen such that they contain a suitable gene regulatory region, such as a promoter or enhancer, such that the antigens and/or antibodies of the invention can be expressed.

For example, when the aim is to express the antibodies and/or antigens of the invention in vitro, or in cultured cells, or in any prokaryotic or eukaryotic system for the purpose of producing the protein(s) encoded by that antibody and/or antigen, then any suitable vector can be used depending on the application. For example, plasmids, viral vectors, bacterial vectors, protozoal vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the antibodies and/or antigens under the identified circumstances.

When the aim is to express the antibodies and/or antigens of the invention in vivo in a subject, for example in order to generate an immune response against an HW-1 antigen and/or protective immunity against HIV-1, expression vectors that are suitable for expression on that subject, and that are safe for use in vivo, should be chosen. For example, in some embodiments it may be desired to express the antibodies and/or antigens of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA; ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and can be used as gene delivery vectors.

The nucleotide sequences and vectors of the invention can be delivered to cells, for example if aim is to express and the HW-1 antigens in cells in order to produce and isolate the expressed proteins, such as from cells grown in culture. For expressing the antibodies and/or antigens in cells any suitable transfection, transformation, or gene delivery methods can be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies and/or antigens can be carried out in any suitable type of host cells, such as bacterial cells, yeast, insect cells, and mammalian cells. The antibodies and/or antigens of the invention can also be expressed using including in vitro transcription/translation systems. All of such methods are well known by those skilled in the art, and one of skill in the art would readily be able to select a suitable method depending on the nature of the nucleotide sequences, vectors, and cell types used.

In preferred embodiments, the nucleotide sequences, antibodies and/or antigens of the invention are administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. In preferred embodiments the subject is a human, for example a human that is infected with, or is at risk of infection with, HIV-1.

For such in vivo applications the nucleotide sequences, antibodies and/or antigens of the invention are preferably administered as a component of an immunogenic composition comprising the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the antibodies and/or antigens of the invention to a subject, such as a human, such that the antibodies and/or antigens are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

An immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri(caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is commercially available under the name Provax® (IDEC Pharmaceuticals, San Diego, Calif.).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., $AlK(SO_4)_2$, $AlNa(SO_4)_2$, $AlNH(SO_4)_2$, silica, alum, $Al(OH)_3$, $Ca_3(PO_4)_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC31; see Schellack, C. et al (2003) Proceedings of the 34$^{th}$ Annual Meeting of the German Society of Immunology; Lingnau, K. et al (2002) Vaccine 20(29-30): 3498-508), JuvaVax™ (U.S. Pat. No. 6,693,086), certain natural substances (e.g., wax D from *Mycobacterium tuberculosis*, substances found in *Cornyebacterium parvum, Bordetella pertussis*, or members of the genus *Brucella*), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057, 540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689, 338; 5,238,944; Zuber, A. K. et al (2004) 22(13-14): 1791-8), and the CCR5 inhibitor CMPD167 (see Veazey, R. S. et al (2003) J. Exp. Med. 198: 1551-1562).

Aluminum hydroxide or phosphate (alum) are commonly used at 0.05 to 0.1% solution in phosphate buffered saline. Other adjuvants that can be used, especially with DNA vaccines, are cholera toxin, especially CTA 1-DD/ISCOMs (see Mowat, A. M. et al (2001) J. Immunol. 167(6): 3398-405), polyphosphazenes (Allcock, H. R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-α, IFN-β, and IFN-γ (Boyer et al., (2002) J. Liposome Res. 121:137-142; WO01/095919), immunoregulatory proteins such as CD40L (ADX40; see, for example, WO03/063899), and the CD1a ligand of natural killer cells (also known as CRONY or α-galactosyl ceramide; see Green, T. D. et al, (2003) J. Virol. 77(3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which can be administered either as proteins or in the form of DNA, on the same expression vectors as those encoding the antigens of the invention or on separate expression vectors.

In an advantageous embodiment, the adjuvants may be lecithin combined with an acrylic polymer (Adjuplex-LAP), lecithin coated oil droplets in an oil-in-water emulsion (Adjuplex-LE) or lecithin and acrylic polymer in an oil-in-water emulsion (Adjuplex-LAO) (Advanced BioAdjuvants (ABA)).

The immunogenic compositions can be designed to introduce the nucleic acids or expression vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulation can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the nucleic acids and expression vectors of the invention (collectively, the immunogens) in the immunogenic composition of the invention can be readily determined by those of skill in the art. For example, the dosage of the immunogens can vary depending on the route of administration and the size of the subject. Suitable doses can be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of HIV infection, or evidence of HIV infection, or in advance of any symptom due to AIDS, especially in high-risk subjects. The prophylactic administration of the immunogenic compositions can serve to provide protective immunity of a subject against HIV-1 infection or to prevent or attenuate the progression of AIDS in a subject already infected with HIV-1. When provided therapeutically, the immunogenic compositions can serve to ameliorate and treat AIDS symptoms and are advantageously used as soon after infection as possible, preferably before appearance of any symptoms of AIDS but may also be used at (or after) the onset of the disease symptoms.

The immunogenic compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes can be oral, intranasal or by any other suitable route. Delivery also be accomplished via a mucosal surface such as the anal, vaginal or oral mucosa.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens, for example DNA prime-Adenovirus boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

A specific embodiment of the invention provides methods of inducing an immune response against HIV in a subject by administering an immunogenic composition of the invention, preferably comprising an adenovirus vector containing DNA encoding one or more of the epitopes of the invention, one or more times to a subject wherein the epitopes are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. In an advantageous embodiment, the other HIV immunogen is env, preferably the HIV env trimer.

Many other HIV immunogens are known in the art, one such preferred immunogen is HIVA (described in WO 01/47955), which can be administered as a protein, on a plasmid (e.g., pTHr.HIVA) or in a viral vector (e.g., MVA-.HIVA). Another such HIV immunogen is RENTA (described in PCT/US2004/037699), which can also be administered as a protein, on a plasmid (e.g., pTHr.RENTA) or in a viral vector (e.g., MVA.RENTA).

For example, one method of inducing an immune response against HIV in a human subject comprises administering at least one priming dose of an HIV immunogen and at least one boosting dose of an HIV immunogen, wherein the immunogen in each dose can be the same or different, provided that at least one of the immunogens is an epitope of the present invention, a nucleic acid encoding an epitope of the invention or an expression vector, preferably a VSV vector, encoding an epitope of the invention, and wherein the immunogens are administered in an amount or expressed at a level sufficient to induce an HIV-specific immune response in the subject. The HIV-specific immune response can include an HIV-specific T-cell immune response or an HIV-specific B-cell immune response. Such immunizations can be done at intervals, preferably of at least 2-6 or more weeks.

The invention will now be further described by way of the following non-limiting examples.

Example

Identification of soluble HIV-1 Envs with better binding to PG9/PG16

Shed gp120 were screened as follows. More than 50 HIV-1 Envs from Tier II Clade B, C, Indian clade C panel, some tier I clade B and few founder virus envelopes were tested.

The method for screening shed gp120 was as follows:
Transfect 293T cells with NL4-3 back bond and HIV-1 Env plasmids;
Collect supernatant;
Capture shed gp120 on ELISA plate coated with D7324 (anti-CS polyclonal); and
Probe the captured Env for binding to b12, PG9 and PG16.

Applicants have codon optimized gp120 and gp140 versions of all the four Indian Clade C strains that show exceptional binding to PG9. Applicants have tested the Envs by transient transfection and they maintain the property of binding as seen on shed gp120. Applicants may use these Envs for immunogenicity studies, to generate tools for mapping of PG9-like antibodies in sera and/or generate resurfaced gp 120 for better presentation of a PG9 epitope.

The invention is further described by the following numbered paragraphs:
1. An isolated or non-naturally occurring soluble HIV-1 envelope glycoprotein.
2. The glycoprotein of paragraph 1, wherein the glycoprotein is isolated from a HIV-1 Clade A virus, HIV-1 Clade B virus, HIV-1 Clade C virus, a HIV-1 Clade A pseudo-virus, HIV-1 Clade B pseudo-virus or a HIV-1 Clade C pseudo-virus.
3. The glycoprotein of paragraph 1 or 2, wherein the glycoprotein binds a broadly neutralizing antibody.
4. The glycoprotein of paragraph 3, wherein the antibody is PG9 and/or PG16.
5. The glycoprotein of any one of paragraphs 1-4, wherein the soluble envelope glycoproteins of the present invention is isolated from a HIV-1 Clade A virus, HIV-1 Clade B virus, HIV-1 Clade C virus, a HIV-1 Clade A pseudo-virus, HIV-1 Clade B pseudo-virus, a HIV-1 Clade C pseudo-virus, the 6535 virus, the 13095 virus, the 16055 virus, the 25710 virus, the 25925 virus, the CAAN virus or the Zm109F virus.
6. The glycoprotein of any one of paragraphs 1-5, wherein an amino acid sequence of the glycoprotein has a substantially similar consensus sequence to the consensus sequence depicted in FIGS. 9A-9J.
7. The glycoprotein of any one of paragraphs 1-6, wherein an amino acid sequence of the glycoprotein has about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% sequence identity to any of the sequences depicted in FIGS. 14-46.
8. A method for screening broad neutralizing antibodies comprising contacting the glycoprotein of any one of paragraphs 1-6 with an animal or human sera, isolating the glycoprotein complexed to the broad neutralizing antibodies, thereby screening for a broad neutralizing antibody.
9. A method for identifying a binding site of a soluble HIV-1 envelope glycoprotein to a broadly neutralizing antibody comprising contacting the glycoprotein of any one of paragraphs 1-6 with a broadly neutralizing antibody, isolating the glycoprotein complexed to the antibody, and determining the crystal structure of the glycoprotein-antibody complex, wherein the crystal structure identifies the binding site of the glycoprotein and the antibody, thereby identifying a binding site of a soluble HIV-1 envelope glycoprotein to a broadly neutralizing antibody.
10. The method of paragraph 6, wherein the antibody is PG9 and/or PG16.
11. A method of producing an immune response comprising administering to a mammal the glycoprotein of any one of paragraphs 1-6.
12. A method of eliciting an immune response comprising administering to a mammal the vector of any one of paragraphs 1-6.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

SEQUENCE LISTING

<160> NUMBER OF SEQ ID NOS: 109

<210> SEQ ID NO 1
<211> LENGTH: 471
<212> TYPE: PRT
<213> ORGANISM: Human immunodeficiency virus 1

<400> SEQUENCE: 1

Leu Trp Val Thr Val Tyr Tyr Gly Val Pro Val Trp Lys Glu Ala Lys
1               5                   10                  15

Thr Thr Leu Phe Cys Ala Ser Asp Ala Lys Ala Tyr Glu Lys Glu Val
            20                  25                  30

His Asn Val Trp Ala Thr His Ala Cys Val Pro Thr Asp Pro Asn Pro
        35                  40                  45

Gln Glu Met Val Leu Glu Asn Val Thr Glu Asn Phe Asn Met Trp Glu
    50                  55                  60

Asn Asp Val Val Asp Gln Met His Glu Asp Val Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Ser Lys Ala Lys Asn Ile Thr Glu Glu Val Ile Lys Asn Asn
            100                 105                 110

Thr Tyr Lys Glu Asp Ile Arg Asn Cys Ser Phe Asn Ala Thr Thr Glu
        115                 120                 125

Val Lys Asp Lys Lys Gln Lys Val His Ala Leu Phe Tyr Arg Leu Asp
    130                 135                 140

Ile Val Pro Leu Asn Lys Arg Asn Ser Ser Glu Ser Glu Glu Glu Asn
145                 150                 155                 160

Ser Ser Gly Tyr Tyr Arg Leu Ile Asn Cys Asn Thr Ser Ala Val Thr
                165                 170                 175

Gln Ala Cys Pro Lys Val Thr Phe Asp Pro Ile Pro Ile His Tyr Cys
            180                 185                 190

Thr Pro Ala Gly Tyr Ala Ile Leu Lys Cys Asn Glu Glu Thr Phe Asn
        195                 200                 205

Gly Thr Gly Pro Cys His Asn Val Ser Thr Val Gln Cys Thr His Gly
    210                 215                 220

Ile Lys Pro Val Val Ser Thr Gln Leu Leu Leu Asn Gly Ser Leu Ala
225                 230                 235                 240

Glu Gly Glu Ile Ile Ile Arg Ser Lys Asn Leu Thr Asp Asn Ala Lys
                245                 250                 255

Thr Ile Ile Val His Leu Asn Gln Ser Val Glu Ile Val Cys Thr Arg
            260                 265                 270

Pro Asn Glu Asn Arg Arg Lys Ser Ile Arg Ile Gly Pro Gly Gln Ala
        275                 280                 285

Phe Tyr Ala Thr Gly Asp Ile Ile Gly Asp Ile Arg Gln Ala Arg Cys
    290                 295                 300

Asn Ile Ser Glu Glu Lys Trp Asn Glu Thr Leu Gln Arg Val Gly Arg
305                 310                 315                 320

Lys Leu Ala Glu His Phe Pro Asn Lys Thr Ile Lys Phe Lys Ser Ser
                325                 330                 335

Ser Gly Gly Asp Leu Glu Ile Thr Thr His Ser Phe Asn Cys Arg Gly
            340                 345                 350

Glu Phe Phe Tyr Cys Asn Thr Ser Gly Leu Phe Asn Gly Thr Tyr Met
        355                 360                 365

Pro Thr Tyr Met Pro Asn Ser Thr Asn Ser Asn Ser Ser Asn Ile
        370                 375                 380

Thr Ile Pro Cys Arg Ile Lys Gln Val Ile Asn Met Trp Gln Glu Val
385                 390                 395                 400

Gly Arg Ala Met Tyr Ala Pro Pro Ile Glu Gly Glu Ile Thr Cys Lys
            405                 410                 415

Ser Asn Ile Thr Gly Leu Leu Leu Val Arg Asp Gly Gly Asn Gly Asn
        420                 425                 430

Asp Thr Asn Lys Thr Glu Ile Phe Arg Pro Glu Gly Gly Asp Met Arg
        435                 440                 445

Asp Asn Trp Arg Ser Glu Leu Tyr Lys Tyr Lys Val Val Glu Ile Lys
        450                 455                 460

Pro Leu Gly Ile Ala Pro Thr
465                 470

<210> SEQ ID NO 2
<211> LENGTH: 459
<212> TYPE: PRT
<213> ORGANISM: Human immunodeficiency virus 1

<400> SEQUENCE: 2

Leu Trp Val Thr Val Tyr Tyr Gly Val Pro Val Trp Lys Glu Ala Thr
1               5                   10                  15

Thr Thr Leu Phe Cys Ala Ser Asp Ala Lys Ala Tyr Asp Lys Glu Val
            20                  25                  30

His Asn Val Trp Ala Thr His Ala Cys Val Pro Thr Asp Pro Asn Pro
        35                  40                  45

Gln Glu Met Val Leu Gly Asn Val Thr Glu Asn Phe Asn Met Trp Lys
    50                  55                  60

Asn Glu Met Val Asn Gln Met His Glu Asp Val Ile Ser Leu Trp Asp
65                  70                  75                  80

Gln Ser Leu Lys Pro Cys Val Lys Leu Thr Pro Leu Cys Val Thr Leu
                85                  90                  95

Glu Cys Ser Asn Val Thr Tyr Asn Glu Ser Met Lys Glu Val Lys Asn
            100                 105                 110

Cys Ser Phe Asn Leu Thr Thr Glu Leu Arg Asp Lys Lys Gln Lys Val
        115                 120                 125

His Ala Leu Phe Tyr Arg Leu Asp Ile Val Pro Leu Asn Asp Thr Glu
    130                 135                 140

Lys Lys Asn Ser Ser Arg Pro Tyr Arg Leu Ile Asn Cys Asn Thr Ser
145                 150                 155                 160

Ala Ile Thr Gln Ala Cys Pro Lys Val Thr Phe Asp Pro Ile Pro Ile
                165                 170                 175

His Tyr Cys Thr Pro Ala Gly Tyr Ala Ile Leu Lys Cys Asn Asp Lys
            180                 185                 190

Lys Phe Asn Gly Thr Gly Pro Cys His Lys Val Ser Thr Val Gln Cys
        195                 200                 205

Thr His Gly Ile Lys Pro Val Val Ser Thr Gln Leu Leu Leu Asn Gly
    210                 215                 220

Ser Leu Ala Glu Gly Glu Ile Ile Ile Arg Ser Glu Asn Leu Thr Asn
225                 230                 235                 240

Asn Ala Lys Thr Ile Ile Val His Leu Asn Gln Ser Val Glu Ile Val
                245                 250                 255

Cys Ala Arg Pro Ser Asn Asn Thr Arg Thr Ser Ile Arg Ile Gly Pro
            260                 265                 270

-continued

```
Gly Gln Thr Phe Tyr Ala Thr Gly Ala Ile Thr Gly Asp Ile Arg Gln
        275                 280                 285

Ala His Cys Asn Ile Ser Lys Asp Lys Trp Asn Glu Thr Leu Gln Arg
    290                 295                 300

Val Gly Glu Lys Leu Ala Glu His Phe Pro Asn Lys Thr Ile Lys Phe
305                 310                 315                 320

Asn Ser Ser Ser Gly Gly Asp Leu Glu Ile Thr Thr His Ser Phe Asn
                325                 330                 335

Cys Arg Gly Glu Phe Phe Tyr Cys Asn Thr Ser Gly Leu Phe Asn Gly
            340                 345                 350

Thr Phe Asn Gly Thr Tyr Val Ser Pro Asn Ser Thr Asp Ser Asn Ser
        355                 360                 365

Ser Ser Ile Ile Thr Ile Pro Cys Arg Ile Lys Gln Ile Ile Asn Met
    370                 375                 380

Trp Gln Glu Val Gly Arg Ala Met Tyr Ala Pro Pro Ile Ala Gly Asn
385                 390                 395                 400

Ile Thr Cys Lys Ser Asn Ile Thr Gly Leu Leu Leu Val Arg Asp Gly
                405                 410                 415

Gly Thr Gly Ser Glu Ser Asn Lys Thr Glu Ile Phe Arg Pro Gly Gly
            420                 425                 430

Gly Asp Met Arg Asp Asn Trp Arg Ser Glu Leu Tyr Lys Tyr Lys Val
        435                 440                 445

Val Glu Ile Lys Pro Leu Gly Val Ala Pro Thr
    450                 455

<210> SEQ ID NO 3
<211> LENGTH: 472
<212> TYPE: PRT
<213> ORGANISM: Human immunodeficiency virus 1

<400> SEQUENCE: 3

Leu Trp Val Thr Val Tyr Tyr Gly Val Pro Val Trp Lys Glu Ala Lys
1               5                   10                  15

Ala Thr Leu Phe Cys Ala Ser Asp Ala Lys Ala Tyr Glu Thr Glu Val
            20                  25                  30

His Asn Val Trp Ala Thr His Ala Cys Val Pro Thr Asp Pro Asn Pro
        35                  40                  45

Gln Glu Ile Val Leu Glu Asn Val Thr Glu Asn Phe Asn Met Trp Glu
    50                  55                  60

Asn Asp Met Val Asn Gln Met His Glu Asp Val Ile Ser Leu Trp Asp
65                  70                  75                  80

Gln Ser Leu Lys Pro Cys Val Lys Leu Thr Pro Leu Cys Val Thr Leu
                85                  90                  95

Asp Cys Glu Asn Val Asp Gly Asn Asp Thr Tyr Asn Gly Thr Asn Glu
            100                 105                 110

Met Lys Asn Cys Ser Phe Asn Thr Thr Thr Glu Leu Arg Asp Lys Lys
        115                 120                 125

Gln Lys Val Ser Ala Leu Phe Tyr Arg Leu Asp Ile Val Pro Leu Asn
    130                 135                 140

Arg Ser Ser Ser Asn Ser Ser Asp Tyr Tyr Arg Leu Ile Ser Cys
145                 150                 155                 160

Asn Thr Ser Ala Ile Thr Gln Ala Cys Pro Lys Val Thr Phe Asp Pro
                165                 170                 175

Ile Pro Ile His Tyr Cys Ala Pro Ala Gly Phe Ala Ile Leu Lys Cys
            180                 185                 190
```

Asn Asn Lys Thr Phe Asn Gly Thr Gly Pro Cys His Asn Val Ser Thr
            195                 200                 205

Val Gln Cys Thr His Gly Ile Lys Pro Val Val Ser Thr Gln Leu Leu
            210                 215                 220

Leu Asn Gly Ser Leu Ala Glu Lys Glu Ile Ile Ile Arg Ser Lys Asn
225                 230                 235                 240

Leu Ser Asp Asn Val Lys Thr Ile Ile Val His Leu Asn Glu Ser Val
                245                 250                 255

Glu Ile Val Cys Thr Arg Pro Asn Asn Asn Thr Arg Lys Ser Ile Arg
            260                 265                 270

Ile Gly Pro Gly Gln Thr Phe Tyr Ala Thr Gly Ala Ile Ile Gly Asn
            275                 280                 285

Ile Arg Glu Ala His Cys Asn Ile Ser Arg Asp Lys Trp Asn Glu Thr
            290                 295                 300

Leu Gln Arg Val Gly Lys Lys Leu Glu Glu Gln Phe Pro Asn Lys Thr
305                 310                 315                 320

Ile Asn Phe Thr Ser Ser Ser Gly Gly Asp Leu Glu Ile Thr Thr His
                325                 330                 335

Ser Phe Asn Cys Arg Gly Glu Phe Phe Tyr Cys Asn Thr Ser Lys Leu
            340                 345                 350

Phe Asn Ser Thr Tyr Ile Pro Thr Tyr Arg Pro Asn Asn Thr Gln Gly
            355                 360                 365

Asn Ser Ser Ser Thr Ile Thr Ile Pro Cys Arg Ile Lys Gln Ile Ile
370                 375                 380

Asn Met Trp Gln Glu Val Gly Arg Ala Met Tyr Ala Pro Pro Ile Ala
385                 390                 395                 400

Gly Asn Ile Thr Cys Lys Ser His Ile Thr Gly Leu Leu Leu Val Arg
                405                 410                 415

Asp Gly Gly Thr Gly Leu Asn Ser Ser Thr Glu Thr Phe Arg Pro Gly
            420                 425                 430

Gly Gly Asp Met Arg Asp Asn Trp Arg Ser Glu Leu Tyr Lys Tyr Lys
            435                 440                 445

Val Val Glu Ile Lys Pro Leu Gly Val Ala Pro Thr Ala Ala Lys Arg
            450                 455                 460

Arg Val Val Gln Arg Glu Lys Arg
465                 470

<210> SEQ ID NO 4
<211> LENGTH: 456
<212> TYPE: PRT
<213> ORGANISM: Human immunodeficiency virus 1

<400> SEQUENCE: 4

Leu Trp Val Thr Val Tyr Tyr Gly Val Pro Val Trp Lys Glu Ala Lys
1               5                   10                  15

Thr Thr Leu Phe Cys Ala Ser Asp Ala Lys Ala His Glu Arg Glu Val
            20                  25                  30

His Asn Val Trp Ala Thr Tyr Ala Cys Val Pro Thr Asp Pro Asn Pro
            35                  40                  45

Gln Glu Ile Val Leu Lys Asn Val Thr Glu Asn Phe Asn Met Trp Glu
        50                  55                  60

Asn Asp Met Val Asp Gln Met Gln Glu Asp Val Ile Ser Leu Trp Asp
65                  70                  75                  80

Gln Ser Leu Lys Pro Cys Ile Lys Leu Thr Pro Leu Cys Val Thr Leu
                85                  90                  95

```
Glu Cys Thr Asn Val Asn Ile Ile Asn Gly Thr Ile His Asn Glu Thr
            100                 105                 110
Tyr Glu Ser Met Lys Asn Cys Ser Phe Asn Thr Thr Thr Glu Leu Lys
        115                 120                 125
Asp Lys Lys Gln Ser Val Tyr Ala Leu Phe Tyr Arg Leu Asp Ile Val
    130                 135                 140
Pro Leu Asn Asn Ser Asn Glu Tyr Tyr Arg Leu Ile Asn Cys Asn Thr
145                 150                 155                 160
Ser Ala Ile Lys Gln Ala Cys Pro Lys Val Thr Phe Asp Pro Ile Pro
                165                 170                 175
Ile His Tyr Cys Ala Pro Ala Gly Tyr Ala Ile Leu Lys Cys Asn Asp
            180                 185                 190
Lys Thr Phe Ser Gly Thr Gly Pro Cys His Asn Val Ser Thr Val Gln
        195                 200                 205
Cys Thr His Gly Ile Lys Pro Val Val Ser Thr Gln Leu Leu Leu Asn
    210                 215                 220
Gly Ser Leu Ala Glu Gly Glu Ile Ile Arg Ser Lys Lys Leu Asp
225                 230                 235                 240
Asp Asn Ala Asn Thr Ile Ile Val His Leu Asp Glu Pro Val Lys Ile
                245                 250                 255
Glu Cys Thr Arg Pro Asn Asn Asn Thr Arg Lys Ser Ile Arg Ile Gly
            260                 265                 270
Pro Gly Gln Thr Phe Tyr Ala Thr Gly Glu Ile Ile Gly Asn Ile Arg
        275                 280                 285
Gln Ala His Cys Asp Ile Ser Glu Asp Gln Trp Asn Glu Thr Leu Gln
    290                 295                 300
Arg Val Gly Lys Lys Leu Ala Glu Leu Phe Pro Asn Lys Thr Ile Thr
305                 310                 315                 320
Phe Asn Ser Ser Ser Gly Gly Asp Leu Glu Ile Thr Thr His Ser Phe
                325                 330                 335
Asn Cys Arg Gly Glu Phe Phe Tyr Cys Asn Thr Ser Ser Leu Phe Lys
            340                 345                 350
Gly Thr Tyr Arg Pro Asn Gly Thr Ser Asn Ser Thr Ser Gly Ser Ile
        355                 360                 365
Ile Thr Leu Pro Cys Tyr Ile Lys Gln Val Ile Asn Leu Trp Gln Glu
    370                 375                 380
Val Gly Arg Ala Ile Tyr Ala Pro Pro Ile Glu Gly Asn Ile Thr Cys
385                 390                 395                 400
Ile Ser Asn Ile Thr Gly Leu Leu Leu Val Arg Asp Gly Gly Asn His
                405                 410                 415
Glu Glu Ala Asn Thr Thr Glu Thr Phe Arg Pro Gly Gly Gly Asn Met
            420                 425                 430
Arg Asp Asn Trp Arg Ser Glu Leu Tyr Lys Tyr Lys Val Val Glu Ile
        435                 440                 445
Lys Pro Leu Gly Val Ala Pro Thr
    450                 455

<210> SEQ ID NO 5
<211> LENGTH: 464
<212> TYPE: PRT
<213> ORGANISM: Human immunodeficiency virus 1

<400> SEQUENCE: 5

Leu Trp Val Thr Val Tyr Tyr Gly Val Pro Val Trp Lys Glu Ala Lys
1               5                   10                  15
```

-continued

Thr Thr Leu Phe Cys Ala Ser Asp Ala Lys Ala Tyr Glu Lys Glu Val
        20                  25                  30

His Asn Val Trp Ala Thr His Ala Cys Val Pro Thr Asp Pro Asn Pro
            35                  40                  45

Gln Glu Met Val Leu Glu Asn Val Thr Glu Asn Phe Asn Met Trp Lys
50                  55                  60

Asn Asp Met Val Glu Gln Met His Glu Asp Val Ile Ser Leu Trp Asp
65                  70                  75                  80

Gln Ser Leu Lys Pro Cys Val Lys Leu Thr Pro Leu Cys Val Thr Leu
                85                  90                  95

Glu Cys Arg Gln Val Asn Thr Thr Asn Ala Thr Ser Ser Val Asn Val
                100                 105                 110

Thr Asn Gly Glu Glu Ile Lys Asn Cys Ser Phe Asn Ala Thr Thr Glu
            115                 120                 125

Ile Arg Asp Lys Lys Gln Lys Val Tyr Ala Leu Phe Tyr Arg Leu Asp
        130                 135                 140

Ile Val Pro Leu Glu Glu Arg Lys Gly Asn Ser Ser Lys Tyr Arg
145                 150                 155                 160

Leu Ile Asn Cys Asn Thr Ser Ala Ile Thr Gln Ala Cys Pro Lys Val
                165                 170                 175

Thr Phe Asp Pro Ile Pro Ile His Tyr Cys Ala Pro Ala Gly Tyr Ala
            180                 185                 190

Ile Leu Lys Cys Asn Asn Lys Thr Phe Asn Gly Thr Gly Pro Cys Asn
        195                 200                 205

Asn Val Ser Thr Val Gln Cys Thr His Gly Ile Lys Pro Val Val Ser
    210                 215                 220

Thr Gln Leu Leu Leu Asn Gly Ser Leu Ala Glu Gly Glu Ile Ile Ile
225                 230                 235                 240

Arg Ser Glu Asn Leu Thr Asn Asn Val Lys Thr Ile Ile Val His Leu
                245                 250                 255

Asn Glu Ser Val Glu Ile Val Cys Thr Arg Pro Asn Asn Asn Thr Arg
            260                 265                 270

Lys Ser Ile Arg Ile Gly Pro Gly Gln Thr Phe Tyr Ala Thr Gly Asp
        275                 280                 285

Ile Ile Gly Asn Ile Arg Gln Ala Tyr Cys Asn Ile Lys Lys Asp Asp
290                 295                 300

Trp Ile Arg Thr Leu Gln Arg Val Gly Lys Lys Leu Ala Glu His Phe
305                 310                 315                 320

Pro Arg Arg Ile Ile Asn Phe Thr Ser Pro Ala Gly Gly Asp Leu Glu
                325                 330                 335

Ile Thr Thr His Ser Phe Asn Cys Arg Gly Glu Phe Phe Tyr Cys Asn
            340                 345                 350

Thr Ser Ser Leu Phe Asn Ser Thr Tyr Asn Pro Asn Asp Thr Asn Ser
        355                 360                 365

Asn Ser Ser Ser Ser Asn Ser Ser Leu Asp Ile Thr Ile Pro Cys Arg
    370                 375                 380

Ile Lys Gln Ile Ile Asn Met Trp Gln Glu Val Gly Arg Ala Met Tyr
385                 390                 395                 400

Ala Pro Pro Ile Glu Gly Asn Ile Thr Cys Lys Ser Asn Ile Thr Gly
                405                 410                 415

Leu Leu Leu Val Arg Asp Gly Gly Val Glu Ser Asn Glu Thr Glu Ile
            420                 425                 430

Phe Arg Pro Gly Gly Gly Asp Met Arg Asn Asn Trp Arg Ser Glu Leu

```
                   435                 440                 445
Tyr Lys Tyr Lys Val Val Glu Ile Lys Pro Leu Gly Ile Ala Pro Thr
    450                 455                 460

<210> SEQ ID NO 6
<211> LENGTH: 469
<212> TYPE: PRT
<213> ORGANISM: Human immunodeficiency virus 1

<400> SEQUENCE: 6

Leu Trp Val Thr Val Tyr Tyr Gly Val Pro Val Trp Lys Glu Ala Arg
1               5                   10                  15

Thr Thr Leu Phe Cys Ala Ser Asp Ala Lys Ala Tyr Glu Thr Glu Val
            20                  25                  30

His Asn Val Trp Ala Thr His Ala Cys Val Pro Thr Asp Pro Asn Pro
        35                  40                  45

Gln Glu Met Val Leu Gly Asn Val Thr Glu Asn Phe Asn Met Trp Lys
    50                  55                  60

Asn Asp Met Val Asp Gln Met His Glu Asp Val Ile Ser Leu Trp Ala
65                  70                  75                  80

Gln Ser Leu Lys Pro Cys Val Lys Leu Thr Pro Leu Cys Val Thr Leu
                85                  90                  95

Glu Cys Thr Gln Val Asn Ala Thr Gln Gly Asn Thr Thr Gln Val Asn
            100                 105                 110

Val Thr Gln Val Asn Gly Asp Glu Met Lys Asn Cys Ser Phe Asn Thr
        115                 120                 125

Thr Thr Glu Ile Arg Asp Lys Lys Gln Lys Ala Tyr Ala Leu Phe Tyr
    130                 135                 140

Arg Leu Asp Leu Val Pro Leu Glu Arg Glu Asn Arg Gly Asp Ser Asn
145                 150                 155                 160

Ser Ala Ser Lys Tyr Ile Leu Ile Asn Cys Asn Thr Ser Ala Ile Thr
                165                 170                 175

Gln Ala Cys Pro Lys Val Asn Phe Asp Pro Ile Pro Ile His Tyr Cys
            180                 185                 190

Thr Pro Ala Gly Tyr Ala Ile Leu Lys Cys Asn Asn Lys Thr Phe Asn
        195                 200                 205

Gly Thr Gly Ser Cys Asn Asn Val Ser Thr Val Gln Cys Thr His Gly
    210                 215                 220

Ile Lys Pro Val Val Ser Thr Gln Leu Leu Asn Gly Ser Leu Ala
225                 230                 235                 240

Glu Glu Glu Ile Ile Ile Arg Ser Glu Asn Leu Thr Asp Asn Val Lys
                245                 250                 255

Thr Ile Ile Val His Leu Asp Gln Ser Val Glu Ile Val Cys Thr Arg
            260                 265                 270

Pro Asn Asn Asn Thr Arg Lys Ser Ile Arg Ile Gly Pro Gly Gln Thr
        275                 280                 285

Phe Tyr Ala Thr Gly Asp Ile Ile Gly Asn Ile Arg Glu Ala His Cys
    290                 295                 300

Asn Ile Ser Glu Lys Lys Trp His Glu Met Leu Arg Arg Val Ser Glu
305                 310                 315                 320

Lys Leu Ala Glu His Phe Pro Asn Lys Thr Ile Lys Phe Thr Ser Ser
                325                 330                 335

Ser Gly Gly Asp Leu Glu Ile Thr Thr His Ser Phe Asn Cys Arg Gly
            340                 345                 350

Glu Phe Phe Tyr Cys Asn Thr Ser Gly Leu Phe Asn Ser Thr Tyr Met
```

```
                    355                 360                 365
Pro Asn Gly Thr Tyr Met Pro Asn Gly Thr Asn Asn Ser Asn Ser Thr
    370                 375                 380

Ile Ile Leu Pro Cys Arg Ile Lys Gln Ile Ile Asn Met Trp Gln Glu
385                 390                 395                 400

Val Gly Arg Ala Met Tyr Ala Pro Pro Ile Ala Gly Asn Ile Thr Cys
                405                 410                 415

Asn Ser Asn Ile Thr Gly Leu Leu Leu Val Arg Asp Gly Gly Lys Asn
                420                 425                 430

Asn Asn Thr Glu Ile Phe Arg Pro Gly Gly Gly Asp Met Arg Asp Asn
            435                 440                 445

Trp Arg Ser Glu Leu Tyr Lys Tyr Lys Val Val Glu Ile Lys Pro Leu
    450                 455                 460

Gly Val Ala Pro Thr
465

<210> SEQ ID NO 7
<211> LENGTH: 456
<212> TYPE: PRT
<213> ORGANISM: Human immunodeficiency virus 1

<400> SEQUENCE: 7

Leu Trp Val Thr Val Tyr Tyr Gly Val Pro Val Trp Lys Glu Ala Lys
1               5                   10                  15

Thr Thr Leu Phe Cys Ala Ser Asp Ala Lys Ala Tyr Glu Thr Glu Val
            20                  25                  30

His Asn Val Trp Ala Thr His Ala Cys Val Pro Thr Asp Pro Asn Pro
        35                  40                  45

Gln Glu Leu Val Leu Glu Asn Val Thr Glu Asn Phe Asn Met Trp Arg
    50                  55                  60

Asn Asp Met Val Asp Gln Met His Glu Asp Val Ile Ser Leu Trp Asp
65                  70                  75                  80

Gln Ser Leu Lys Pro Cys Val Lys Leu Thr Pro Leu Cys Val Thr Leu
                85                  90                  95

Glu Cys Arg Asn Ala Thr Ser Lys Met Val Asn Asp Thr Arg Asn Val
            100                 105                 110

Glu Glu Met Lys Asn Cys Ser Phe Asn Thr Thr Thr Glu Leu Arg Asp
        115                 120                 125

Arg Lys Gln Thr Val Tyr Ala Ser Phe Tyr Lys Leu Asp Ile Val Pro
    130                 135                 140

Leu Asn Glu Asn Lys Ser Thr Ser Ser Glu Asn Tyr Arg Leu Ile Asn
145                 150                 155                 160

Cys Asn Thr Ser Ala Ile Thr Gln Ala Cys Pro Lys Val Asn Phe Asp
                165                 170                 175

Pro Ile Pro Ile His Tyr Cys Thr Pro Ala Gly Tyr Ala Ile Leu Lys
            180                 185                 190

Cys Asn Asn Lys Thr Phe Asn Gly Thr Gly Pro Cys Ser Asn Val Ser
        195                 200                 205

Thr Val Gln Cys Thr His Gly Ile Lys Pro Val Val Ser Thr Gln Leu
    210                 215                 220

Leu Leu Asn Gly Ser Leu Ala Glu Glu Gly Ile Ile Ile Arg Ser Glu
225                 230                 235                 240

Asn Leu Thr Asp Asn Val Lys Thr Ile Ile Val His Leu Glu Glu Pro
                245                 250                 255

Val Glu Ile Val Cys Thr Arg Pro Asn Asn Asn Thr Arg Lys Ser Val
```

```
                    260                 265                 270
Arg Ile Gly Pro Gly Gln Thr Phe Tyr Ala Thr Gly Glu Ile Ile Gly
                275                 280                 285

Asp Ile Arg Gln Ala His Cys Asn Ile Ser Glu Ala Lys Trp Asn Glu
            290                 295                 300

Thr Leu Gln Asn Val Thr Lys Lys Leu Lys Glu His Phe Pro Asn Lys
305                 310                 315                 320

Thr Ile Ile Phe Asn Ser Ser Gly Gly Asp Leu Glu Ile Thr Thr
                325                 330                 335

His Ser Phe Asn Cys Arg Gly Glu Phe Phe Tyr Cys Asn Thr Ser Lys
            340                 345                 350

Leu Phe Asn Gly Ile Tyr Asn Gly Thr Gln Ser Asn Ser Ser Asn Ser
                355                 360                 365

Asn Ser Thr Ile Ile Ile Pro Cys Lys Ile Lys Gln Ile Val Asn Met
            370                 375                 380

Trp Gln Lys Val Gly Arg Ala Met Tyr Ala Pro Pro Ile Ala Gly Asn
385                 390                 395                 400

Ile Thr Cys Thr Ser Asn Ile Thr Gly Leu Leu Leu Val Arg Asp Gly
                405                 410                 415

Gly Pro Asp Asn Val Thr Glu Ile Phe Arg Pro Gly Gly Gly Asp Met
            420                 425                 430

Arg Asp Asn Trp Arg Ser Glu Leu Tyr Lys Tyr Lys Val Val Glu Ile
                435                 440                 445

Lys Pro Leu Gly Ile Ala Pro Thr
            450                 455

<210> SEQ ID NO 8
<211> LENGTH: 483
<212> TYPE: PRT
<213> ORGANISM: Human immunodeficiency virus 1

<400> SEQUENCE: 8

Leu Trp Val Thr Val Tyr Tyr Gly Val Pro Val Trp Arg Glu Ala Lys
1               5                   10                  15

Thr Thr Leu Phe Cys Ala Ser Asp Ala Lys Ala Tyr Glu Lys Glu Val
                20                  25                  30

His Asn Val Trp Ala Thr His Ala Cys Val Pro Thr Asp Pro Asn Pro
            35                  40                  45

Gln Glu Ile Asp Leu Asn Met Trp Lys Asn Asp Met Val Glu Gln Met
        50                  55                  60

His Glu Asp Val Ile Ser Leu Trp Asp Gln Ser Leu Lys Pro Cys Val
65                  70                  75                  80

Lys Leu Thr Pro Ile Cys Val Thr Leu Glu Cys Thr Asp Ala Asn Ile
                85                  90                  95

Thr Cys Asn Ser Thr Thr Ser Ser Asn Asn Cys Thr Ser Tyr Glu Ile
            100                 105                 110

Asn Lys Glu Asp Met Gly Glu Ile Lys Asn Cys Ser Phe Asn Thr Thr
        115                 120                 125

Thr Glu Leu Ile Asp Lys Gln Lys Lys Val His Ala Leu Phe Tyr Arg
    130                 135                 140

Leu Asp Ile Val Ser Leu Glu Lys Asp Asn Ser Ser Lys Asn Asp
145                 150                 155                 160

Ser Asn Glu Tyr Tyr Arg Leu Ile Asn Cys Asn Thr Ser Ala Ile Thr
                165                 170                 175

Gln Ala Cys Pro Lys Val Thr Phe Asp Pro Ile Pro Ile His Tyr Cys
```

```
Ala Pro Ala Gly Tyr Ala Ile Leu Lys Cys Lys Asn Lys Thr Phe Asn
            180                 185                 190
Gly Thr Gly Pro Cys Asn Asn Val Ser Thr Val Gln Cys Thr His Gly
    195                 200                 205
Ile Lys Pro Val Val Ser Thr Gln Leu Leu Leu Asn Gly Ser Leu Ala
210                 215                 220
Glu Glu Glu Ile Ile Arg Ser Glu Asn Leu Thr Asn Asn Ala Lys
225                 230                 235                 240
Ile Ile Ile Val His Leu Asn Gln Ala Val Glu Ile Val Cys Thr Arg
            245                 250                 255
Pro Gly Asn Asn Thr Arg Lys Ser Ile Arg Ile Gly Pro Gly Gln Thr
    260                 265                 270
Phe Tyr Ala Thr Gly Asp Ile Ile Gly Asp Ile Arg Gln Ala His Cys
    275                 280                 285
Asn Ile Ser Glu Ala Lys Trp Asn Lys Thr Leu Arg Glu Val Ser Lys
290                 295                 300
Lys Leu Ala Glu His Phe Pro Asn Lys Thr Ile Ile Phe Asn Ser Ser
305                 310                 315                 320
Ser Gly Gly Asp Leu Glu Ile Thr Thr His Ser Phe Asn Cys Gly Gly
            325                 330                 335
Glu Phe Phe Tyr Cys Asn Thr Ser Ser Leu Phe Asn Ser Thr Phe Asn
    340                 345                 350
Ser Thr Tyr Met Thr Asn Asp Thr Asp Met Asn Ser Asn Ser Thr Ile
    355                 360                 365
Ser Ile Pro Cys Arg Ile Lys Gln Ile Ile Asn Met Trp Gln Glu Val
370                 375                 380
Gly Arg Ala Met Tyr Ala Pro Pro Ile Ala Gly Asn Ile Thr Cys Lys
385                 390                 395                 400
Ser Asn Ile Thr Gly Leu Leu Leu Val Arg Asp Gly Gly Asn Ser Asn
            405                 410                 415
Asp Thr Asn Glu Pro Glu Ile Phe Arg Pro Gln Gly Gly Asp Met Arg
    420                 425                 430
Asp Asn Trp Arg Ser Glu Leu Tyr Lys Tyr Lys Val Val Glu Ile Lys
    435                 440                 445
Pro Leu Gly Val Ala Pro Thr Ala Ala Lys Arg Arg Val Val Gly Arg
465                 470                 475                 480
Glu Lys Arg

<210> SEQ ID NO 9
<211> LENGTH: 463
<212> TYPE: PRT
<213> ORGANISM: Human immunodeficiency virus 1

<400> SEQUENCE: 9

Leu Trp Val Thr Val Tyr Tyr Gly Val Pro Val Trp Lys Glu Ala Lys
1               5                   10                  15
Thr Thr Leu Phe Cys Ala Ser Asp Ala Lys Ala Tyr Glu Lys Glu Val
            20                  25                  30
His Asn Val Trp Ala Thr His Ala Cys Val Pro Thr Asp Pro Asn Pro
        35                  40                  45
Gln Glu Ile Val Leu Gly Asn Val Thr Glu Asp Phe Asn Met Trp Lys
    50                  55                  60
Asn Asp Met Val Asp Gln Met His Glu Asp Val Ile Ser Leu Trp Asp
65                  70                  75                  80
```

```
Gln Ser Leu Lys Pro Cys Val Lys Leu Thr Pro Leu Cys Val Thr Leu
                 85                  90                  95

Asp Cys Ala Asn Val Thr Ser Asn Ile Thr Asn Gly Glu Glu Ile Lys
            100                 105                 110

Asn Cys Ser Phe Asn Ala Thr Thr Asp Val Arg Asp Lys Lys Lys Thr
            115                 120                 125

Val Tyr Ser Leu Phe Tyr Arg Leu Asp Ile Val Gln Leu Asp Gly Arg
    130                 135                 140

Ser Asn Thr Ser Asn Tyr Arg Leu Ile Asn Cys Asn Thr Ser Thr Ile
145                 150                 155                 160

Thr Gln Ala Cys Pro Lys Val Ser Phe Asp Pro Ile Pro Ile His Tyr
                165                 170                 175

Cys Ala Pro Ala Gly Tyr Ala Ile Leu Lys Cys Asn Asn Lys Thr Phe
            180                 185                 190

Asn Gly Lys Gly Pro Cys His Asn Ile Ser Thr Val Gln Cys Thr His
            195                 200                 205

Gly Ile Lys Pro Val Val Ser Thr Gln Leu Leu Leu Asn Gly Ser Leu
    210                 215                 220

Ala Glu Glu Glu Ile Ile Ile Arg Ser Glu Asn Leu Thr Asn Asn Val
225                 230                 235                 240

Lys Thr Ile Ile Val His Leu Asn Lys Pro Val Lys Ile Val Cys Thr
                245                 250                 255

Arg Pro Gly Asn Asn Thr Arg Lys Ser Ile Arg Ile Gly Pro Gly Gln
            260                 265                 270

Thr Phe Tyr Ala Thr Gly Glu Ile Ile Gly Asn Ile Arg Gln Ala His
    275                 280                 285

Cys Asn Ile Ser Lys Glu Glu Trp Asn Lys Thr Leu Gln Gly Val Gly
290                 295                 300

Glu Lys Leu Ala Glu His Phe Pro Asn Lys Thr Ile Glu Phe Thr Ser
305                 310                 315                 320

Pro Ser Gly Gly Asp Leu Glu Ile Thr Thr His Ser Phe Asn Cys Arg
                325                 330                 335

Gly Glu Phe Phe Tyr Cys Asn Thr Ser Asp Leu Phe Asn Gly Ile Tyr
            340                 345                 350

Asn Gly Thr Tyr Ile Pro Lys Gly Asn Leu Asn Ser Thr Ile Thr Ile
            355                 360                 365

Gln Cys Lys Ile Lys Gln Phe Ile Asn Met Trp Gln Glu Val Gly Arg
    370                 375                 380

Ala Met Tyr Ala Pro Pro Ile Gln Gly Asn Ile Thr Cys Glu Ser Asn
385                 390                 395                 400

Ile Thr Gly Leu Leu Leu Val Arg Asp Gly Gly Asn Ser Asn Ser Thr
                405                 410                 415

Glu Glu Ile Phe Arg Pro Gly Gly Gly Asp Met Arg Asp Asn Trp Arg
            420                 425                 430

Ser Glu Leu Tyr Lys Tyr Lys Val Val Glu Ile Lys Pro Leu Gly Val
            435                 440                 445

Ala Pro Thr Asp Ala Lys Arg Arg Val Val Glu Arg Gly Lys Arg
                450                 455                 460

<210> SEQ ID NO 10
<211> LENGTH: 446
<212> TYPE: PRT
<213> ORGANISM: Human immunodeficiency virus 1

<400> SEQUENCE: 10
```

```
Leu Trp Val Thr Val Tyr Tyr Gly Val Pro Val Trp Arg Glu Ala Lys
1               5                   10                  15

Thr Thr Leu Phe Cys Ala Ser Asp Ala Lys Ala Tyr Glu Arg Glu Val
            20                  25                  30

His Asn Val Trp Ala Thr His Ala Cys Val Pro Thr Asp Pro Asn Pro
                35                  40                  45

Gln Glu Met Val Leu Glu Asn Val Thr Glu Asn Phe Asn Met Trp Lys
        50                  55                  60

Asn Asp Met Val Asp Gln Met Gln Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Ser Lys Leu Asn Asn Ala Thr Asp Gly Glu Met Lys Asn Cys
            100                 105                 110

Ser Phe Asn Ala Thr Thr Glu Leu Arg Asp Lys Lys Gln Val Tyr
        115                 120                 125

Ala Leu Phe Tyr Lys Leu Asp Ile Val Pro Leu Asp Gly Arg Asn Asn
130                 135                 140

Ser Ser Glu Tyr Arg Leu Ile Asn Cys Asn Thr Ser Thr Ile Thr Gln
145                 150                 155                 160

Ala Cys Pro Lys Val Ser Phe Asp Pro Ile Pro Ile His Tyr Cys Ala
                165                 170                 175

Pro Ala Gly Tyr Ala Ile Leu Lys Cys Asn Asn Lys Thr Phe Asn Gly
            180                 185                 190

Thr Gly Pro Cys His Asn Val Ser Thr Val Gln Cys Thr His Gly Ile
        195                 200                 205

Lys Pro Val Ile Ser Thr Gln Leu Leu Leu Asn Gly Ser Thr Ala Glu
210                 215                 220

Glu Asp Ile Ile Ile Arg Ser Glu Asn Leu Thr Asn Asn Ala Lys Thr
225                 230                 235                 240

Ile Ile Val His Leu Asn Glu Ser Ile Glu Ile Glu Cys Thr Arg Pro
                245                 250                 255

Gly Asn Asn Thr Arg Lys Ser Ile Arg Ile Gly Pro Gly Gln Ala Phe
            260                 265                 270

Phe Ala Thr Thr Asn Ile Ile Gly Asp Ile Arg Gln Ala Tyr Cys Ile
        275                 280                 285

Ile Asn Lys Ala Asn Trp Thr Asn Thr Leu His Arg Val Ser Lys Lys
290                 295                 300

Leu Glu Glu His Phe Pro Asn Lys Thr Ile Asn Phe Asn Ser Ser Ser
305                 310                 315                 320

Gly Gly Asp Leu Glu Ile Thr Thr His Ser Phe Asn Cys Gly Gly Glu
                325                 330                 335

Phe Phe Tyr Cys Asn Thr Ser Ser Leu Phe Asn Gly Thr Tyr Asn Asp
            340                 345                 350

Thr Asp Ile Tyr Asn Ser Thr Asp Ile Ile Leu Leu Cys Arg Ile Lys
        355                 360                 365

Gln Ile Ile Asn Met Trp Gln Glu Val Gly Arg Ala Met Tyr Ala Pro
370                 375                 380

Pro Ile Glu Gly Asn Ile Thr Cys Ser Ser Asn Ile Thr Gly Leu Leu
385                 390                 395                 400

Leu Thr Arg Asp Gly Gly Leu Thr Asn Glu Ser Lys Glu Thr Phe Arg
                405                 410                 415

Pro Gly Gly Gly Asp Met Arg Asp Asn Trp Arg Ser Glu Leu Tyr Lys
```

```
                     420                 425                 430
Tyr Lys Val Val Glu Ile Lys Pro Leu Gly Ile Ala Pro Thr
                435                 440                 445

<210> SEQ ID NO 11
<211> LENGTH: 466
<212> TYPE: PRT
<213> ORGANISM: Human immunodeficiency virus 1

<400> SEQUENCE: 11

Leu Trp Val Thr Val Tyr Tyr Gly Val Pro Val Trp Lys Glu Ala Lys
1               5                   10                  15

Thr Thr Leu Phe Cys Ala Ser Asp Ala Lys Gly Tyr Asp Lys Glu Val
                20                  25                  30

His Asn Val Trp Ala Thr His Ala Cys Val Pro Thr Asp Pro Asn Pro
            35                  40                  45

Gln Glu Met Pro Leu Glu Asn Val Thr Glu Asn Phe Asn Met Trp Glu
        50                  55                  60

Asn Asp Met Val Asn Gln Met His Glu Asp Val Ile Ser Leu Trp Asp
65                  70                  75                  80

Glu Ser Leu Lys Pro Cys Val Lys Leu Thr Pro Leu Cys Val Thr Leu
                85                  90                  95

Asn Cys Thr Asp Val Asn Lys Asn Val Ser Ser Ser Thr Asp Asn
                100                 105                 110

Tyr Lys Glu Thr Met Lys Glu Arg Lys Asn Cys Thr Phe Asn Met Thr
            115                 120                 125

Thr Glu Leu Arg Asp Lys Asn Gln Lys Lys Tyr Ala Leu Phe Tyr Lys
        130                 135                 140

Leu Asp Ile Val Pro Leu Asp Asp Asn Asp Asn Ala Ser Tyr Arg Leu
145                 150                 155                 160

Ile Asn Cys Asn Thr Ser Thr Leu Thr Gln Ala Cys Pro Lys Val Ser
                165                 170                 175

Phe Asp Pro Ile Pro Ile His Tyr Cys Ala Pro Ala Gly Tyr Ala Ile
            180                 185                 190

Leu Lys Cys Lys Asn Lys Thr Phe Asn Gly Ile Gly Pro Cys Asn Lys
        195                 200                 205

Val Ser Thr Val Gln Cys Thr His Gly Ile Lys Pro Val Val Ser Thr
210                 215                 220

Gln Leu Leu Leu Asn Gly Ser Leu Ala Glu Glu Asp Ile Val Ile Arg
225                 230                 235                 240

Ser Glu Asn Ile Thr Asp Asn Ala Lys Thr Ile Ile Val His Leu Asn
                245                 250                 255

Glu Ser Val Glu Ile Val Cys Ile Arg Pro Asn Asn Thr Arg Lys
            260                 265                 270

Ser Ile Arg Ile Gly Pro Gly Gln Thr Phe Tyr Ala Thr Gly Asp Ile
        275                 280                 285

Val Gly Asp Ile Arg Gln Ala Tyr Cys Asn Ile Ser Glu Gly Lys Trp
290                 295                 300

Asn Lys Thr Leu Gln Arg Val Ser Glu Lys Leu Ala Glu His Phe Pro
305                 310                 315                 320

Asn Ser Thr Ile Asn Phe Asn Ser Ser Gly Gly Asp Leu Glu Ile
                325                 330                 335

Thr Thr His Ser Phe Asn Cys Gly Gly Glu Phe Phe Tyr Cys Asn Thr
            340                 345                 350

Ser Gly Leu Phe Asn Gly Thr Tyr Met Asn Asn Asp Thr Lys Ser Asn
```

-continued

```
            355                 360                 365
Asp Thr Lys Ser Asn Ser Ser Ile Ile Thr Ile Pro Cys Arg Ile
370                 375                 380

Lys Gln Ile Ile Asn Met Trp Gln Glu Val Gly Arg Ala Val Tyr Ala
385                 390                 395                 400

Pro Pro Ile Ala Gly Asn Ile Thr Cys Lys Ser Asn Ile Thr Gly Ile
                    405                 410                 415

Leu Leu Thr Arg Asp Gly Gly Arg Gly Glu Val Lys Asn Asp Thr
                420                 425                 430

Glu Thr Phe Arg Pro Gly Gly Asn Met Lys Asp Asn Trp Arg Ser
            435                 440                 445

Glu Leu Tyr Lys Tyr Lys Val Val Glu Ile Lys Pro Leu Gly Val Ala
450                 455                 460

Pro Thr
465

<210> SEQ ID NO 12
<211> LENGTH: 472
<212> TYPE: PRT
<213> ORGANISM: Human immunodeficiency virus 1

<400> SEQUENCE: 12

Leu Trp Val Thr Val Tyr Tyr Gly Val Pro Val Trp Lys Glu Ala Lys
1               5                   10                  15

Thr Thr Leu Phe Cys Ala Ser Asp Ala Lys Ala Tyr Asp Lys Glu Val
                20                  25                  30

His Asn Val Trp Ala Thr His Ala Cys Val Pro Thr Asp Pro Asn Pro
            35                  40                  45

Gln Glu Ile Val Leu Glu Asn Val Thr Glu Asn Phe Asn Met Trp Lys
        50                  55                  60

Asn Asp Met Val Asp Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Lys Asn Val Asn Ile Ser Ala Asn Ala Asn Ala Thr Ala Thr
            100                 105                 110

Leu Asn Ser Ser Met Asn Gly Glu Ile Lys Asn Cys Ser Phe Asn Thr
        115                 120                 125

Thr Thr Glu Leu Arg Asp Lys Lys Gln Lys Val Tyr Ala Leu Phe Tyr
130                 135                 140

Lys Pro Asp Val Val Pro Leu Asn Gly Gly His Asn Glu Thr Gly
145                 150                 155                 160

Glu Tyr Ile Leu Ile Asn Cys Asn Ser Ser Thr Ile Thr Gln Ala Cys
                165                 170                 175

Pro Lys Val Ser Phe Asp Pro Ile Pro Ile His Tyr Cys Ala Pro Ala
            180                 185                 190

Gly Tyr Ala Ile Leu Lys Cys Asn Asn Lys Thr Phe Asn Gly Thr Gly
        195                 200                 205

Pro Cys Asn Asn Val Ser Thr Val Gln Cys Thr His Gly Ile Lys Pro
210                 215                 220

Val Val Ser Thr Gln Leu Leu Leu Asn Gly Ser Leu Ala Glu Glu
225                 230                 235                 240

Ile Ile Val Arg Ser Glu Asn Leu Thr Asn Asn Ile Lys Thr Ile Ile
                245                 250                 255

Val His Leu Asn Lys Ser Val Glu Ile Lys Cys Thr Arg Pro Asn Asn
```

-continued

```
                260                 265                 270
Asn Thr Arg Lys Ser Val Arg Ile Gly Pro Gly Gln Thr Phe Tyr Ala
            275                 280                 285

Thr Gly Glu Ile Ile Gly Asp Ile Arg Glu Ala His Cys Asn Ile Ser
        290                 295                 300

Arg Glu Thr Trp Asn Ser Thr Leu Ile Gln Val Lys Glu Lys Leu Arg
305                 310                 315                 320

Glu His Tyr Asn Lys Thr Ile Lys Phe Glu Pro Ser Ser Gly Gly Asp
                325                 330                 335

Leu Glu Val Thr Thr His Ser Phe Asn Cys Arg Gly Glu Phe Phe Tyr
            340                 345                 350

Cys Asp Thr Thr Lys Leu Phe Asn Glu Thr Lys Leu Phe Asn Glu Ser
        355                 360                 365

Glu Tyr Val Asp Asn Lys Thr Ile Ile Leu Pro Cys Arg Ile Lys Gln
    370                 375                 380

Ile Ile Asn Met Trp Gln Glu Val Gly Arg Ala Met Tyr Ala Pro Pro
385                 390                 395                 400

Ile Glu Gly Asn Ile Thr Cys Lys Ser Asn Ile Thr Gly Leu Leu Leu
                405                 410                 415

Thr Trp Asp Gly Gly Glu Asn Ser Thr Glu Gly Val Phe Arg Pro Gly
            420                 425                 430

Gly Gly Asn Met Lys Asp Asn Trp Arg Ser Glu Leu Tyr Lys Tyr Lys
        435                 440                 445

Val Val Glu Ile Lys Pro Leu Gly Val Ala Pro Thr Lys Ser Lys Arg
    450                 455                 460

Lys Val Val Gly Arg Glu Lys Arg
465                 470

<210> SEQ ID NO 13
<211> LENGTH: 448
<212> TYPE: PRT
<213> ORGANISM: Human immunodeficiency virus 1

<400> SEQUENCE: 13

Leu Trp Val Thr Val Tyr Tyr Gly Val Pro Val Trp Lys Glu Ala Lys
1               5                   10                  15

Ala Thr Leu Phe Cys Ala Ser Asp Ala Arg Ala Tyr Glu Lys Glu Val
            20                  25                  30

His Asn Val Trp Ala Thr His Ala Cys Val Pro Thr Asp Pro Asn Pro
        35                  40                  45

Gln Glu Ile Tyr Leu Gly Asn Val Thr Glu Asn Phe Asn Met Trp Lys
    50                  55                  60

Asn Asp Met Val Asp Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Arg Cys Thr Asn Ala Thr Ile Asn Gly Ser Leu Thr Glu Glu Val Lys
            100                 105                 110

Asn Cys Ser Phe Asn Ile Thr Thr Glu Leu Arg Asp Lys Lys Gln Lys
        115                 120                 125

Ala Tyr Ala Leu Phe Tyr Arg Pro Asp Val Val Pro Leu Asn Lys Asn
    130                 135                 140

Ser Pro Ser Gly Asn Ser Ser Glu Tyr Ile Leu Ile Asn Cys Asn Thr
145                 150                 155                 160

Ser Thr Ile Thr Gln Ala Cys Pro Lys Val Ser Phe Asp Pro Ile Pro
```

```
              165                 170                 175
Ile His Tyr Cys Ala Pro Ala Gly Tyr Ala Ile Leu Lys Cys Asn Asn
            180                 185                 190

Lys Thr Phe Asn Gly Thr Gly Pro Cys Asn Asn Val Ser Thr Val Gln
            195                 200                 205

Cys Thr His Gly Ile Lys Pro Val Val Ser Thr Gln Leu Leu Leu Asn
            210                 215                 220

Gly Ser Leu Ala Glu Glu Asp Ile Ile Lys Ser Glu Asn Leu Thr
225                 230                 235                 240

Asn Asn Ile Lys Thr Ile Ile Val His Leu Asn Lys Ser Val Glu Ile
                245                 250                 255

Val Cys Arg Arg Pro Asn Asn Asn Thr Arg Lys Ser Ile Arg Ile Gly
            260                 265                 270

Pro Gly Gln Ala Phe Tyr Ala Thr Asn Asp Ile Ile Gly Asp Ile Arg
            275                 280                 285

Gln Ala His Cys Asn Ile Asn Asn Ser Thr Trp Asn Arg Thr Leu Glu
            290                 295                 300

Gln Ile Lys Lys Lys Leu Arg Glu His Phe Leu Asn Arg Thr Ile Glu
305                 310                 315                 320

Phe Glu Pro Pro Ser Gly Gly Asp Leu Glu Val Thr Thr His Ser Phe
                325                 330                 335

Asn Cys Gly Gly Glu Phe Phe Tyr Cys Asn Thr Thr Arg Leu Phe Lys
            340                 345                 350

Trp Ser Ser Asn Val Thr Asn Asp Thr Ile Thr Ile Pro Cys Arg Ile
            355                 360                 365

Lys Gln Phe Ile Asn Met Trp Gln Gly Ala Gly Arg Ala Met Tyr Ala
            370                 375                 380

Pro Pro Ile Glu Gly Asn Ile Thr Cys Asn Ser Ser Ile Thr Gly Leu
385                 390                 395                 400

Leu Leu Thr Arg Asp Gly Gly Lys Thr Asp Arg Asn Asp Thr Glu Ile
                405                 410                 415

Phe Arg Pro Gly Gly Gly Asn Met Lys Asp Asn Trp Arg Asn Glu Leu
            420                 425                 430

Tyr Lys Tyr Lys Val Val Glu Ile Lys Pro Leu Gly Val Ala Pro Thr
            435                 440                 445

<210> SEQ ID NO 14
<211> LENGTH: 459
<212> TYPE: PRT
<213> ORGANISM: Human immunodeficiency virus 1

<400> SEQUENCE: 14

Leu Trp Val Thr Val Tyr Tyr Gly Val Pro Val Trp Arg Glu Ala Lys
1               5                   10                  15

Thr Thr Leu Phe Cys Ala Ser Asp Ala Lys Ala Tyr Glu Lys Glu Val
            20                  25                  30

His Asn Val Trp Val Thr His Ala Cys Val Pro Thr Asp Pro Asn Pro
            35                  40                  45

Gln Glu Met Asn Leu Glu Asn Val Thr Glu Asn Phe Asn Met Trp Lys
        50                  55                  60

Asn Asp Met Val Asp Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Asn Asn Val Asn Val Thr His Asn Ser Thr Tyr Asn Asn Thr
```

```
                    100                 105                 110
Glu Gly Glu Gln Ile Lys Asn Cys Ser Phe Asn Ile Thr Thr Glu Leu
            115                 120                 125

Arg Asp Lys Lys Gln Lys Val Tyr Ala Leu Phe Tyr Lys Leu Asp Ile
        130                 135                 140

Leu Pro Leu Asn Gly Asn Asn Asp Ser Asn Glu Tyr Arg Leu Ile Asn
145                 150                 155                 160

Cys Asn Thr Ser Ala Ile Thr Gln Ala Cys Pro Lys Val Ser Phe Asp
                165                 170                 175

Pro Ile Pro Ile His Tyr Cys Ala Pro Ala Gly Tyr Ala Ile Leu Lys
            180                 185                 190

Cys Asn Asn Lys Thr Phe Asn Gly Lys Gly Pro Cys Asn Asn Val Ser
        195                 200                 205

Thr Val Gln Cys Thr His Gly Ile Lys Pro Val Val Ser Thr Gln Leu
210                 215                 220

Leu Leu Asn Gly Ser Leu Ala Glu Lys Glu Ile Ile Ile Arg Ser Glu
225                 230                 235                 240

Asn Ile Thr Asp Asn Val Lys Ile Ile Ile Val His Leu Asn Glu Ser
                245                 250                 255

Val Glu Ile Asn Cys Thr Arg Pro Asn Asn Asn Thr Arg Lys Ser Ile
            260                 265                 270

Arg Ile Gly Pro Gly Gln Thr Phe Tyr Ala Thr Gly Glu Ile Ile Gly
        275                 280                 285

Lys Ile Arg Glu Ala His Cys Asn Ile Ser Lys Glu Lys Trp Asn Lys
    290                 295                 300

Thr Leu Leu Arg Val Ala Lys Lys Leu Arg Glu His Phe Pro Gly Lys
305                 310                 315                 320

Ala Ile Lys Phe Glu Pro Ser Ser Gly Gly Asp Leu Glu Ile Thr Thr
                325                 330                 335

His Ser Phe Asn Cys Arg Gly Glu Phe Phe Tyr Cys Thr Thr Ser Lys
            340                 345                 350

Leu Phe Asn Ser Thr Tyr Asn Pro Asn Asp Thr Glu Ser Asn Ser Asn
        355                 360                 365

Asn Ser Asn Glu Thr Leu Thr Leu Thr Cys Lys Ile Lys Gln Ile Ile
    370                 375                 380

Asn Met Trp Gln Gly Val Gly Arg Ala Met Tyr Ala Pro Pro Ile Glu
385                 390                 395                 400

Gly Ser Ile Thr Cys Asn Ser Thr Ile Thr Gly Leu Leu Leu Thr Arg
                405                 410                 415

Asp Gly Gly Ser Lys Asn Asn Thr Glu Glu Ile Phe Arg Pro Gly Gly
            420                 425                 430

Gly Asn Met Lys Asp Asn Trp Arg Ser Glu Leu Tyr Lys Tyr Lys Val
        435                 440                 445

Val Glu Ile Lys Pro Leu Gly Val Ala Pro Thr
    450                 455

<210> SEQ ID NO 15
<211> LENGTH: 478
<212> TYPE: PRT
<213> ORGANISM: Human immunodeficiency virus 1

<400> SEQUENCE: 15

Leu Trp Val Thr Val Tyr Tyr Gly Val Pro Val Trp Arg Glu Ala Lys
1               5                   10                  15

Thr Thr Leu Phe Cys Ala Ser Asp Ala Lys Ala Tyr Glu Lys Glu Val
```

```
                    20                  25                  30
His Asn Val Trp Ala Thr His Ala Cys Val Pro Thr Asp Pro Asn Pro
                35                  40                  45
Gln Glu Leu Val Leu Glu Asn Val Thr Glu Asn Phe Asn Met Trp Lys
50                  55                  60
Asn Asp Met Val Asn Gln Met His Glu Asp Ile Ile Ser Leu Trp Asp
65                  70                  75                  80
Gln Ser Leu Lys Pro Cys Val Lys Leu Thr Pro Leu Cys Val Thr Leu
                85                  90                  95
Asn Cys Ser Asn Val Asn Ile Asn Glu Thr Ser Ile Asp Phe Asn Val
                100                 105                 110
Thr Ser Asn Ile Ser Met Lys Glu Glu Met Lys Asn Cys Ser Phe Lys
            115                 120                 125
Val Asn Ser Glu Leu Arg Asp Lys Asn Arg Arg Glu His Ala Leu Phe
            130                 135                 140
Tyr Lys Leu Asp Ile Val Gln Leu Asn Asp Glu Gly Asn Asp Ser Tyr
145                 150                 155                 160
Ser Tyr Arg Leu Ile Asn Cys Asn Thr Ser Thr Ile Lys Gln Ala Cys
                165                 170                 175
Pro Lys Val Ser Phe Glu Pro Ile Pro Ile His Tyr Cys Ala Pro Ala
                180                 185                 190
Gly Tyr Ala Ile Leu Lys Cys Asn Asn Glu Thr Phe Asn Gly Ser Gly
            195                 200                 205
Pro Cys Asn Asn Val Ser Thr Val Gln Cys Thr His Gly Ile Lys Pro
            210                 215                 220
Val Val Ser Thr Gln Leu Leu Leu Asn Gly Ser Leu Ala Glu Lys Glu
225                 230                 235                 240
Ile Met Ile Arg Ser Glu Asn Leu Thr Asn Asn Ala Lys Thr Ile Ile
                245                 250                 255
Val Gln Leu Thr Glu Ala Val Asn Ile Thr Cys Met Arg Pro Gly Asn
                260                 265                 270
Asn Thr Arg Arg Ser Val Arg Ile Gly Pro Gly Gln Thr Phe Tyr Ala
            275                 280                 285
Thr Gly Glu Ile Ile Gly Asp Ile Arg Gln Ala His Cys Asn Ile Ser
290                 295                 300
Lys Asp Lys Trp Asn Gln Ile Leu Gln Asn Val Arg Ala Lys Leu Gly
305                 310                 315                 320
Glu His Phe His Asp Lys Thr Ile Lys Phe Glu Pro Ser Ser Gly Gly
                325                 330                 335
Asp Leu Glu Ile Thr Thr His Ser Phe Asn Cys Gly Gly Glu Phe Phe
            340                 345                 350
Tyr Cys Asn Thr Thr Asn Leu Phe Ser Arg Thr Tyr Thr Asn Gly Ser
        355                 360                 365
Asn Ser Asn Val Asn Ile Thr Ser Ala Thr Ile Thr Leu Pro Cys Arg
        370                 375                 380
Ile Lys Gln Ile Ile Asn Met Trp Gln Glu Val Gly Arg Ala Met Tyr
385                 390                 395                 400
Ala Pro Pro Ile Ala Gly Asn Ile Thr Cys Ile Ser Asn Ile Thr Gly
                405                 410                 415
Leu Leu Leu Thr Arg Asp Gly Gly Asn Gly Asn Asp Thr Asn Asp Thr
                420                 425                 430
Glu Thr Phe Arg Pro Ala Gly Gly Asp Met Arg Asp Asn Trp Arg Ser
            435                 440                 445
```

```
Glu Leu Tyr Lys Tyr Lys Val Val Glu Ile Lys Pro Leu Gly Ile Ala
        450                 455                 460

Pro Thr Lys Ala Lys Arg Arg Val Val Gly Arg Glu Lys Arg
465                 470                 475
```

<210> SEQ ID NO 16
<211> LENGTH: 446
<212> TYPE: PRT
<213> ORGANISM: Human immunodeficiency virus 1

<400> SEQUENCE: 16

```
Leu Trp Val Thr Val Tyr Tyr Gly Val Pro Val Trp Arg Glu Ala Lys
1               5                   10                  15

Thr Thr Leu Phe Cys Ala Ser Asp Ala Lys Ala Tyr Glu Thr Glu Ala
            20                  25                  30

His Ser Val Trp Ala Thr His Ala Cys Val Pro Thr Asp Pro Asn Pro
        35                  40                  45

Gln Glu Met Val Leu Glu Asn Val Thr Glu Asn Phe Asn Met Trp Lys
    50                  55                  60

Asn Asp Met Val Asp Gln Met His Glu Asp Val Ile Ser Ile Trp Asp
65                  70                  75                  80

Gln Ser Leu Lys Pro Cys Val Lys Leu Thr Pro Leu Cys Val Thr Leu
                85                  90                  95

Asp Cys Ser Thr Tyr Asn Asn Thr His Asn Ile Ser Lys Glu Met Lys
            100                 105                 110

Ile Cys Ser Phe Asn Met Thr Thr Glu Leu Arg Asp Lys Lys Arg Lys
        115                 120                 125

Val Asn Val Leu Phe Tyr Lys Leu Asp Leu Val Pro Leu Thr Asn Ser
    130                 135                 140

Ser Asn Thr Thr Asn Tyr Arg Leu Ile Ser Cys Asn Thr Ser Thr Ile
145                 150                 155                 160

Thr Gln Ala Cys Pro Lys Val Ser Phe Asp Pro Ile Pro Ile His Tyr
                165                 170                 175

Cys Ala Pro Ala Gly Tyr Ala Ile Leu Lys Cys Asn Asn Lys Thr Phe
            180                 185                 190

Asn Gly Thr Gly Pro Cys Asn Asn Val Ser Thr Val Gln Cys Thr His
        195                 200                 205

Gly Ile Lys Pro Val Val Ser Thr Gln Leu Leu Asn Gly Ser Leu
    210                 215                 220

Ala Glu Glu Glu Ile Ile Ile Arg Phe Glu Asn Leu Thr Asp Asn Val
225                 230                 235                 240

Lys Ile Ile Ile Val Gln Leu Asn Glu Thr Ile Asn Ile Thr Cys Thr
                245                 250                 255

Arg Pro Asn Asn Asn Thr Arg Lys Ser Ile Arg Ile Gly Pro Gly Gln
            260                 265                 270

Ser Phe Tyr Ala Thr Gly Glu Ile Val Gly Asn Ile Arg Glu Ala His
        275                 280                 285

Cys Asn Ile Ser Ala Ser Lys Trp Asn Lys Thr Leu Glu Arg Val Arg
    290                 295                 300

Thr Lys Leu Lys Glu His Phe Pro Asn Lys Thr Ile Glu Phe Glu Pro
305                 310                 315                 320

Ser Ser Gly Gly Asp Leu Glu Ile Thr Thr His Ser Phe Asn Cys Gly
                325                 330                 335

Gly Glu Phe Phe Tyr Cys Asn Ser Gly Leu Phe Asn Ser Ala Ile
            340                 345                 350
```

-continued

```
Asn Gly Thr Leu Thr Ser Asn Val Thr Leu Pro Cys Arg Ile Lys Gln
            355                 360                 365

Ile Ile Asn Met Trp Gln Glu Val Gly Arg Ala Met Tyr Ala Pro Pro
    370                 375                 380

Ile Ala Gly Asn Ile Thr Cys Lys Ser Asn Ile Thr Gly Leu Leu Leu
385                 390                 395                 400

Thr Arg Asp Gly Gly Glu Asn Ser Ser Thr Thr Glu Thr Phe Arg
                405                 410                 415

Pro Thr Gly Gly Asp Met Lys Asn Asn Trp Arg Ser Glu Leu Tyr Lys
                420                 425                 430

Tyr Lys Val Val Glu Ile Lys Pro Leu Gly Ile Ala Pro Thr
                435                 440                 445

<210> SEQ ID NO 17
<211> LENGTH: 469
<212> TYPE: PRT
<213> ORGANISM: Human immunodeficiency virus 1

<400> SEQUENCE: 17

Leu Trp Val Thr Val Tyr Tyr Gly Val Pro Val Trp Lys Glu Ala Lys
1               5                   10                  15

Thr Thr Leu Phe Cys Ala Ser Asp Ala Lys Gly Tyr Asp Thr Glu Val
            20                  25                  30

His Asn Val Trp Ala Thr His Ala Cys Val Pro Thr Asp Pro Asn Pro
        35                  40                  45

Gln Glu Ile Val Leu Glu Asn Val Thr Glu Asn Phe Asn Met Trp Lys
    50                  55                  60

Asn Asp Met Val Asp Gln Met His Gln Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Ser Asp Ala Thr Tyr Asn Asn Gly Thr Asn Ser Thr Asp Thr
            100                 105                 110

Met Lys Ile Cys Ser Phe Asn Ala Thr Thr Glu Leu Arg Asp Lys Lys
        115                 120                 125

Lys Lys Glu Tyr Ala Leu Phe Tyr Arg Leu Asp Ile Val Pro Leu Lys
    130                 135                 140

Asn Glu Ser Glu Ser Gln Asn Phe Ser Glu Tyr Ile Leu Ile Asn Cys
145                 150                 155                 160

Asn Thr Ser Thr Ile Ala Gln Ala Cys Pro Lys Val Ser Phe Asp Pro
                165                 170                 175

Ile Pro Ile His Tyr Cys Ala Pro Ala Gly Tyr Ala Ile Leu Lys Cys
            180                 185                 190

Asn Asn Lys Thr Phe Asn Gly Thr Gly Pro Cys Asn Asn Val Ser Thr
        195                 200                 205

Val Gln Cys Thr His Gly Ile Lys Pro Val Val Ser Thr Gln Leu Leu
    210                 215                 220

Leu Asn Gly Ser Leu Ala Glu Glu Val Val Ile Arg Ser Glu Asn
225                 230                 235                 240

Ile Ser Asn Asn Val Lys Thr Ile Ile Val His Leu Asn Glu Ser Val
                245                 250                 255

Asn Ile Thr Cys Ile Arg Pro Gly Asn Asn Thr Arg Arg Ser Ile Arg
            260                 265                 270

Ile Gly Pro Gly Gln Ala Phe Tyr Ala Met Gly Asp Ile Ile Gly Asn
        275                 280                 285
```

```
Ile Arg Glu Ala His Cys Asn Ile Ser Glu Lys Ala Trp Asn Glu Thr
            290                 295                 300

Leu Lys Lys Val Val Glu Lys Leu Val Lys Tyr Phe Pro Asn Lys Thr
305                 310                 315                 320

Ile Glu Phe Ala Pro Pro Val Gly Gly Asp Leu Glu Ile Thr Thr His
                325                 330                 335

Ser Phe Asn Cys Gly Gly Glu Phe Phe Tyr Cys Asn Thr Thr Lys Leu
                340                 345                 350

Phe Asn Ser Thr His Asn Ser Thr Asp Ser Thr Val Asn Ser Thr Asp
                355                 360                 365

Ser Thr Ala Glu Thr Gly Asn Ser Thr Asn Thr Asn Ile Thr Leu Pro
370                 375                 380

Cys Arg Ile Arg Gln Ile Ile Asn Met Trp Gln Glu Val Gly Arg Ala
385                 390                 395                 400

Met Tyr Ala Pro Pro Ser Lys Gly Asn Ile Thr Cys Ile Ser Asn Ile
                405                 410                 415

Thr Gly Leu Leu Leu Thr Arg Asp Gly Gly Glu Asn Lys Thr Glu Asn
                420                 425                 430

Asn Asp Thr Glu Ile Phe Arg Pro Gly Gly Gly Asp Met Lys Asp Asn
                435                 440                 445

Trp Arg Ser Glu Leu Tyr Lys Tyr Lys Val Val Glu Ile Lys Pro Leu
450                 455                 460

Gly Val Ala Pro Thr
465

<210> SEQ ID NO 18
<211> LENGTH: 463
<212> TYPE: PRT
<213> ORGANISM: Human immunodeficiency virus 1

<400> SEQUENCE: 18

Leu Trp Val Thr Val Tyr Tyr Gly Val Pro Val Trp Lys Glu Ala Lys
1               5                   10                  15

Thr Thr Leu Phe Cys Ala Ser Asp Ala Lys Ala His Lys Glu Glu Val
                20                  25                  30

His Asn Ile Trp Ala Thr His Ala Cys Val Pro Thr Asp Pro Asn Pro
            35                  40                  45

Gln Glu Ile Val Leu Lys Asn Val Thr Glu Asn Phe Asn Met Trp Lys
        50                  55                  60

Asn Asp Met Val Asp Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Ser Asp Val Lys Ile Lys Gly Thr Asn Ala Thr Tyr Asn Asn
                100                 105                 110

Ala Thr Tyr Asn Asn Asn Thr Ile Ser Asp Met Lys Asn Cys Ser
            115                 120                 125

Phe Asn Thr Thr Glu Ile Thr Asp Lys Lys Lys Glu Tyr Ala
130                 135                 140

Leu Phe Tyr Lys Leu Asp Val Val Ala Leu Asp Gly Lys Glu Thr Asn
145                 150                 155                 160

Ser Thr Asn Ser Ser Glu Tyr Arg Leu Ile Asn Cys Asn Thr Ser Ala
                165                 170                 175

Val Thr Gln Ala Cys Pro Lys Val Ser Phe Asp Pro Ile Pro Ile His
            180                 185                 190
```

```
Tyr Cys Ala Pro Ala Gly Tyr Ala Ile Leu Lys Cys Asn Asn Lys Thr
        195                 200                 205

Phe Asn Gly Thr Gly Pro Cys Asn Asn Val Ser Thr Val Gln Cys Thr
    210                 215                 220

His Gly Ile Lys Pro Val Val Ser Thr Gln Leu Leu Leu Asn Gly Ser
225                 230                 235                 240

Leu Ala Glu Glu Glu Val Val Ile Arg Phe Glu Asn Leu Thr Asn Asn
                245                 250                 255

Ala Lys Ile Ile Ile Val His Leu Asn Glu Ser Val Glu Ile Asn Cys
            260                 265                 270

Thr Arg Pro Ser Asn Asn Thr Arg Lys Ser Val Arg Ile Gly Pro Gly
        275                 280                 285

Gln Thr Phe Phe Ala Thr Gly Asp Ile Ile Gly Asp Ile Arg Gln Ala
    290                 295                 300

His Cys Asn Ile Ser Arg Lys Lys Trp Asn Thr Thr Leu Gln Arg Val
305                 310                 315                 320

Lys Glu Lys Leu Lys Glu Lys Phe Pro Asn Lys Thr Ile Gln Phe Ala
                325                 330                 335

Pro Ser Ser Gly Gly Asp Leu Glu Ile Thr Thr His Ser Phe Asn Cys
            340                 345                 350

Arg Gly Glu Phe Phe Tyr Cys Tyr Thr Ser Asp Leu Phe Asn Ser Thr
        355                 360                 365

Tyr Met Ser Asn Asn Thr Gly Gly Ala Asn Ile Thr Leu Gln Cys Arg
    370                 375                 380

Ile Lys Gln Ile Ile Arg Met Trp Gln Gly Val Gly Gln Ala Met Tyr
385                 390                 395                 400

Ala Pro Pro Ile Ala Gly Asn Ile Thr Cys Lys Ser Asn Ile Thr Gly
                405                 410                 415

Leu Leu Leu Thr Arg Asp Gly Gly Lys Glu Lys Asn Asp Thr Glu Thr
            420                 425                 430

Phe Arg Pro Gly Gly Gly Asp Met Arg Asp Asn Trp Arg Ser Glu Leu
        435                 440                 445

Tyr Lys Tyr Lys Val Val Glu Ile Lys Pro Leu Gly Ile Ala Pro
    450                 455                 460

<210> SEQ ID NO 19
<211> LENGTH: 494
<212> TYPE: PRT
<213> ORGANISM: Human immunodeficiency virus 1

<400> SEQUENCE: 19

Leu Trp Val Thr Val Tyr Tyr Gly Val Pro Val Trp Lys Glu Ala Lys
1               5                   10                  15

Ala Thr Leu Phe Cys Ala Ser Asp Ala Lys Ala Tyr Glu Lys Glu Val
                20                  25                  30

His Asn Val Trp Ala Thr His Ala Cys Val Pro Thr Asp Pro Asn Pro
            35                  40                  45

Gln Glu Ile Pro Leu Gly Asn Val Thr Glu Asn Phe Asn Met Trp Lys
        50                  55                  60

Asn Asp Met Ala Asp Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Ser Asp Ala Thr Ser Asn Thr Thr Lys Asn Ala Thr Asn Thr
            100                 105                 110
```

```
Asn Thr Thr Ser Thr Asp Asn Arg Asn Ala Thr Ser Asn Asp Thr Glu
            115                 120                 125
Met Lys Gly Glu Ile Lys Asp Cys Thr Phe Asn Ile Thr Thr Glu Val
        130                 135                 140
Arg Asp Arg Lys Thr Lys Gln Arg Ala Leu Phe Tyr Lys Leu Asp Val
145                 150                 155                 160
Val Pro Leu Glu Glu Lys Asn Ser Ser Lys Asn Ser Ser Tyr
                165                 170                 175
Lys Glu Tyr Arg Leu Ile Ser Cys Asn Thr Ser Thr Ile Thr Gln Ala
                180                 185                 190
Cys Pro Lys Val Ser Phe Asp Pro Ile Pro Ile His Tyr Cys Ala Pro
            195                 200                 205
Ala Gly Tyr Ala Ile Leu Lys Cys Asn Asn Lys Thr Phe Asn Gly Thr
        210                 215                 220
Gly Pro Cys His Asn Val Ser Thr Val Gln Cys Thr His Gly Ile Lys
225                 230                 235                 240
Pro Val Val Ser Thr Gln Leu Leu Leu Asn Gly Ser Leu Ala Glu Glu
                245                 250                 255
Glu Ile Ile Ile Arg Ser Glu Asn Leu Thr Asp Asn Thr Lys Thr Ile
            260                 265                 270
Ile Val His Leu Asn Glu Ser Val Glu Ile Glu Cys Val Arg Pro Asn
        275                 280                 285
Asn Asn Thr Arg Lys Ser Val Arg Ile Gly Pro Gly Gln Thr Phe Phe
290                 295                 300
Ala Thr Gly Glu Ile Ile Gly Asp Ile Arg Gln Ala His Cys Asp Leu
305                 310                 315                 320
Ser Lys Ser Asn Trp Thr Thr Thr Leu Lys Arg Ile Glu Lys Lys Leu
                325                 330                 335
Lys Glu His Phe Asn Asn Ala Thr Ile Lys Phe Glu Ser Ser Ala Gly
            340                 345                 350
Gly Asp Leu Glu Ile Thr Thr His Ser Phe Asn Cys Arg Gly Glu Phe
        355                 360                 365
Phe Tyr Cys Asn Thr Ser Gly Leu Phe Asn Ser Ser Leu Leu Asn Asp
        370                 375                 380
Thr Asp Gly Thr Ser Asn Ser Thr Ser Asn Ala Thr Ile Thr Leu Pro
385                 390                 395                 400
Cys Arg Ile Lys Gln Ile Ile Asn Met Trp Gln Glu Val Gly Arg Ala
                405                 410                 415
Met Tyr Ala Ser Pro Ile Ala Gly Ile Ile Thr Cys Lys Ser Asn Ile
            420                 425                 430
Thr Gly Leu Leu Leu Thr Arg Asp Gly Gly Asn Lys Ser Ala Gly Ile
        435                 440                 445
Glu Thr Phe Arg Pro Gly Gly Gly Asn Met Lys Asp Asn Trp Arg Ser
        450                 455                 460
Glu Leu Tyr Lys Tyr Lys Val Val Glu Ile Lys Pro Leu Gly Ile Ala
465                 470                 475                 480
Pro Thr Ser Ala Lys Arg Arg Val Val Glu Arg Glu Lys Arg
                485                 490
```

<210> SEQ ID NO 20
<211> LENGTH: 458
<212> TYPE: PRT
<213> ORGANISM: Human immunodeficiency virus 1

<400> SEQUENCE: 20

```
Leu Trp Val Thr Val Tyr Tyr Gly Val Pro Val Trp Arg Glu Ala Lys
1               5                   10                  15

Thr Thr Leu Phe Cys Ala Ser Asp Ala Lys Ala Tyr Glu Lys Glu Val
            20                  25                  30

His Asn Val Trp Ala Thr His Ala Cys Val Pro Thr Asp Pro Asn Pro
        35                  40                  45

Gln Glu Leu Val Leu Gly Asn Val Thr Glu Asn Phe Asn Met Trp Glu
    50                  55                  60

Asn Asp Met Val Asp Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Glu Cys Lys Asn Ala Thr Arg Ser Asn Gln Thr Thr Tyr Tyr Asp Asn
        100                 105                 110

Met Asp Lys Glu Ile Lys Asn Cys Ser Phe Asn Val Thr Thr Glu Leu
        115                 120                 125

Thr Asp Lys Lys Lys Asn Met Arg Ala Leu Phe Tyr Arg Ala Asp Ile
    130                 135                 140

Glu Pro Leu Asp Gly Asn Ser Asn Glu Ser Ile Asn Ser Ser Glu Gly
145                 150                 155                 160

Asp Lys Tyr Ile Leu Ile Asn Cys Asn Thr Ser Thr Ile Ala Gln Ala
                165                 170                 175

Cys Pro Lys Val Thr Phe Asp Pro Ile Pro Ile His Tyr Cys Ala Pro
        180                 185                 190

Ala Gly Tyr Ala Ile Leu Lys Cys Asn Asn Lys Thr Phe Asn Gly Ile
        195                 200                 205

Gly Pro Cys Lys Asn Val Ser Thr Val Gln Cys Thr His Gly Ile Lys
210                 215                 220

Pro Val Val Ser Thr Gln Leu Leu Asn Gly Ser Leu Ser Glu Glu
225                 230                 235                 240

Gly Ile Ile Ile Arg Ser Lys Asn Leu Thr Asp Asn Thr Lys Thr Ile
                245                 250                 255

Ile Val His Leu Asn Glu Ser Val Ala Ile Val Cys Thr Arg Pro Asn
        260                 265                 270

Asn Asn Thr Arg Lys Ser Ile Arg Ile Gly Pro Gly Gln Thr Phe Tyr
        275                 280                 285

Ala Thr Gly Glu Val Ile Gly Asp Ile Arg Gln Ala His Cys Asn Ile
    290                 295                 300

Ser Gly Glu Gln Trp Asn Arg Thr Leu Glu Arg Ile Lys Asp Lys Leu
305                 310                 315                 320

Thr Glu Tyr Phe Pro Asp Lys Ile Ile Lys Phe Asn His Ser Ser Gly
                325                 330                 335

Gly Asp Leu Glu Ile Thr Thr His Thr Phe Asn Cys Arg Gly Glu Phe
        340                 345                 350

Phe Tyr Cys Asn Thr Ser Ile Leu Phe Thr Glu Asn Glu Asn Ser Ser
        355                 360                 365

Asp Asn Ile Thr Leu Pro Cys Arg Ile Lys Gln Phe Val Asn Met Trp
    370                 375                 380

Gln Glu Val Gly Arg Ala Met Tyr Ala Pro Pro Ile Ala Gly Asn Ile
385                 390                 395                 400

Thr Cys Asn Ser Ser Ile Thr Gly Leu Leu Leu Thr Arg Asp Gly Gly
                405                 410                 415

Leu Asn Asn Lys Glu Asn Gly Thr Glu Thr Phe Arg Pro Gln Gly Gly
        420                 425                 430
```

```
Asp Met Arg Asp Asn Trp Arg Ser Glu Leu Tyr Lys Tyr Lys Val Val
        435                 440                 445

Glu Ile Arg Pro Leu Gly Val Ala Pro Thr
        450                 455

<210> SEQ ID NO 21
<211> LENGTH: 457
<212> TYPE: PRT
<213> ORGANISM: Human immunodeficiency virus 1

<400> SEQUENCE: 21

Leu Trp Val Thr Val Tyr Tyr Gly Val Pro Val Trp Lys Glu Ala Lys
1               5                   10                  15

Thr Thr Leu Phe Cys Ala Ser Asp Ala Lys Ser Tyr Glu Arg Glu Val
            20                  25                  30

His Asn Val Trp Ala Thr His Ala Cys Val Pro Thr Asp Pro Asp Pro
        35                  40                  45

Gln Glu Leu Val Met Ala Asn Val Thr Glu Asn Phe Asn Met Trp Lys
    50                  55                  60

Asn Asp Met Val Asp Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Thr Ser Pro Ala Ala His Asn Glu Ser Glu Thr Arg Val Lys
            100                 105                 110

His Cys Ser Phe Asn Ile Thr Thr Asp Val Lys Asp Arg Lys Gln Lys
        115                 120                 125

Val Asn Ala Thr Phe Tyr Asp Leu Asp Ile Val Pro Leu Ser Ser Ser
    130                 135                 140

Asp Asn Ser Ser Asn Ser Ser Leu Tyr Arg Leu Ile Ser Cys Asn Thr
145                 150                 155                 160

Ser Thr Ile Thr Gln Ala Cys Pro Lys Val Ser Phe Asp Pro Ile Pro
                165                 170                 175

Ile His Tyr Cys Ala Pro Ala Gly Tyr Ala Ile Leu Lys Cys Asn Asn
            180                 185                 190

Lys Thr Phe Ser Gly Lys Gly Pro Cys Ser Asn Val Ser Thr Val Gln
        195                 200                 205

Cys Thr His Gly Ile Arg Pro Val Val Ser Thr Gln Leu Leu Leu Asn
    210                 215                 220

Gly Ser Leu Ala Glu Glu Ile Val Ile Arg Ser Glu Asn Leu Thr
225                 230                 235                 240

Asp Asn Ala Lys Thr Ile Ile Val His Leu Asn Lys Ser Val Glu Ile
                245                 250                 255

Glu Cys Ile Arg Pro Gly Asn Asn Thr Arg Lys Ser Ile Arg Leu Gly
            260                 265                 270

Pro Gly Gln Thr Phe Tyr Ala Thr Gly Asp Val Ile Gly Asp Ile Arg
        275                 280                 285

Lys Ala Tyr Cys Lys Ile Asn Gly Ser Glu Trp Asn Gly Thr Leu Thr
    290                 295                 300

Lys Val Ser Glu Lys Leu Lys Glu Tyr Phe Asn Lys Thr Ile Arg Phe
305                 310                 315                 320

Ala Gln His Ser Gly Gly Asp Leu Glu Val Thr Thr His Ser Phe Asn
                325                 330                 335

Cys Arg Gly Glu Phe Phe Tyr Cys Asn Thr Ser Glu Leu Phe Asn Ser
            340                 345                 350
```

```
Asn Ala Thr Glu Ser Asn Ile Thr Leu Pro Cys Arg Ile Lys Gln Ile
            355                 360                 365

Ile Asn Met Trp Gln Gly Val Gly Arg Ala Met Tyr Ala Pro Pro Ile
            370                 375                 380

Arg Gly Glu Ile Lys Cys Thr Ser Asn Ile Thr Gly Leu Leu Leu Thr
385                 390                 395                 400

Arg Asp Gly Gly Asn Asn Asn Ser Thr Glu Glu Ile Phe Arg Pro
            405                 410                 415

Glu Gly Gly Asn Met Arg Asp Asn Trp Arg Ser Glu Leu Tyr Lys Tyr
            420                 425                 430

Lys Val Val Glu Ile Lys Pro Leu Gly Ile Ala Pro Thr Glu Ala Lys
            435                 440                 445

Arg Arg Val Val Gln Arg Glu Lys Arg
450                 455
```

<210> SEQ ID NO 22
<211> LENGTH: 477
<212> TYPE: PRT
<213> ORGANISM: Human immunodeficiency virus 1

<400> SEQUENCE: 22

```
Leu Trp Val Thr Val Tyr Tyr Gly Val Pro Val Trp Lys Glu Ala Thr
1               5                   10                  15

Thr Thr Leu Phe Cys Ala Ser Glu Ala Lys Ala Tyr Asp Thr Glu Val
            20                  25                  30

His Asn Val Trp Ala Thr His Ala Cys Val Pro Thr Asp Pro Asn Pro
            35                  40                  45

Gln Glu Val Glu Leu Gly Asn Val Thr Glu Asn Phe Asn Met Trp Lys
            50                  55                  60

Asn Asp Met Val Glu Gln Met His Glu Asp Ile Ile Ser Leu Trp Asp
65                  70                  75                  80

Gln Ser Leu Lys Pro Cys Val Arg Leu Thr Pro Leu Cys Val Thr Leu
            85                  90                  95

Asp Cys Thr Asp Leu Asn Asn Thr Thr Asn Thr Asn Asn Thr Thr Asn
            100                 105                 110

Thr Asn Ser Ser Lys Ile Glu Gly Gly Glu Met Lys Asn Cys Ser Phe
            115                 120                 125

Asn Ile Thr Thr Asn Arg Gly Asp Lys Arg Gln Lys Glu Tyr Ala Leu
            130                 135                 140

Leu Tyr Arg Thr Asp Ile Val Ser Ile Glu Asn Thr Ser Ser Ser Tyr
145                 150                 155                 160

Arg Leu Ile Ser Cys Asn Thr Ser Val Ile Thr Gln Ala Cys Pro Lys
            165                 170                 175

Val Thr Phe Glu Pro Ile Pro Ile His Tyr Cys Ala Pro Ala Gly Phe
            180                 185                 190

Ala Ile Leu Lys Cys Asn Glu Asp Lys Phe Asn Gly Thr Gly Pro Cys
            195                 200                 205

Lys Asn Val Ser Thr Val Gln Cys Thr His Gly Ile Arg Pro Thr Val
            210                 215                 220

Ser Thr Gln Leu Leu Leu Asn Gly Ser Leu Ala Lys Glu Glu Val Ile
225                 230                 235                 240

Ile Arg Ser Ala Asn Leu Ser Asp Asn Ala Lys Ile Ile Ile Val Gln
            245                 250                 255

Leu Lys Asp Pro Val Glu Ile Asn Cys Thr Arg Pro Asn Asn Asn Thr
            260                 265                 270
```

```
Arg Lys Ser Ile Asn Leu Gly Pro Gly Arg Ala Phe Tyr Ala Thr Gly
            275                 280                 285

Asp Ile Ile Gly Asp Ile Arg Gln Ala His Cys Asn Ile Ser Arg Ala
        290                 295                 300

Lys Trp Asn Asp Thr Leu Arg Glu Ile Ala Lys Leu Ala Glu Gln
305                 310                 315                 320

Phe Asn Asn Arg Thr Ile Val Phe Asn Gln Ser Ser Gly Gly Asp Pro
                325                 330                 335

Glu Ile Val Met His Ser Phe Asn Cys Ala Gly Glu Phe Phe Tyr Cys
                340                 345                 350

Asp Thr Ser Gln Leu Phe Asn Ser Thr Trp Asn Ser Asn Ser Thr Trp
            355                 360                 365

Asn Asp Thr Asn Asn Asn Ser Thr Glu Lys Ile Ile Leu Ser Cys
        370                 375                 380

Arg Ile Arg Gln Ile Ile Asn Arg Trp Gln Glu Val Gly Lys Ala Met
385                 390                 395                 400

Tyr Ala Pro Pro Ile Ser Gly Pro Ile Lys Cys Ser Ser Asn Ile Thr
                405                 410                 415

Gly Leu Leu Leu Ala Arg Asp Gly Gly Asn Glu Thr Asn Val Thr Glu
                420                 425                 430

Thr Phe Arg Pro Ala Gly Gly Asp Met Arg Asp Asn Trp Arg Ser Glu
            435                 440                 445

Leu Tyr Lys Tyr Lys Val Val Gln Ile Glu Pro Leu Gly Ile Ala Pro
        450                 455                 460

Thr Lys Ala Lys Arg Arg Val Val Gln Arg Glu Lys Arg
465                 470                 475

<210> SEQ ID NO 23
<211> LENGTH: 477
<212> TYPE: PRT
<213> ORGANISM: Human immunodeficiency virus 1

<400> SEQUENCE: 23

Leu Trp Val Thr Val Tyr Tyr Gly Val Pro Val Trp Lys Glu Ala Thr
1               5                   10                  15

Thr Thr Leu Phe Cys Ala Ser Asp Ala Lys Ala Tyr Glu Thr Glu Val
            20                  25                  30

His Asn Val Trp Ala Thr His Ala Cys Val Pro Thr Asp Pro Asn Pro
        35                  40                  45

Gln Glu Leu Val Leu Glu Asn Val Thr Glu Tyr Phe Asp Met Trp Lys
    50                  55                  60

Asn Asn Met Val Glu Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Thr Asp Trp Thr Asn Gly Thr Asp Trp Asn Thr Thr Asn Ser
            100                 105                 110

Asn Asn Thr Thr Ile Ser Lys Glu Glu Thr Ile Glu Gly Gly Glu Met
        115                 120                 125

Lys Asn Cys Ser Phe Asn Ile Thr Thr Ala Thr Gly Asp Lys Lys Lys
    130                 135                 140

Glu Arg Ala Phe Phe Tyr Lys Leu Asp Val Ala Pro Ile Asp Asn Ser
145                 150                 155                 160

Asn Thr Ser Tyr Arg Leu Ile Ser Cys Asn Thr Ser Val Ile Thr Gln
                165                 170                 175
```

Ala Cys Pro Lys Ile Ser Phe Glu Pro Ile Pro Ile His Tyr Cys Ala
            180                 185                 190

Pro Ala Gly Phe Ala Ile Leu Lys Cys Asn Asp Lys Lys Phe Asn Gly
            195                 200                 205

Thr Gly Ser Cys Thr Asn Val Ser Thr Val Gln Cys Thr His Gly Ile
210                 215                 220

Arg Pro Val Val Ser Thr Gln Leu Leu Leu Asn Gly Ser Leu Ala Glu
225                 230                 235                 240

Glu Val Val Ile Arg Ser Lys Asn Phe Ser Asp Asn Ala Lys Ile
            245                 250                 255

Ile Ile Val Gln Leu Asn Glu Ser Val Pro Ile Asn Cys Thr Arg Pro
            260                 265                 270

His Asn Asn Thr Arg Lys Ser Ile His Ile Gly Pro Gly Arg Ala Trp
            275                 280                 285

Tyr Ala Thr Gly Asp Ile Ile Gly Asp Ile Arg Lys Ala Tyr Cys Asn
            290                 295                 300

Ile Ser Glu Ala Lys Trp Asn Asn Thr Leu Lys Gln Ile Thr Glu Lys
305                 310                 315                 320

Leu Lys Glu Gln Phe Asn Lys Thr Ile Ile Val Phe Asn Gln Pro Ser
            325                 330                 335

Gly Gly Asp Pro Glu Val Thr Met His Ser Phe Asn Cys Gly Gly Glu
            340                 345                 350

Phe Phe Tyr Cys Asn Thr Ser Lys Leu Phe Asn Gly Thr Trp Asn Ser
            355                 360                 365

Thr Lys Arg Ala Asn Asn Thr Glu Gly Ile Ile Ile Leu Gln Cys Arg
            370                 375                 380

Ile Lys Gln Ile Ile Asn Arg Trp Gln Glu Val Gly Lys Ala Met Tyr
385                 390                 395                 400

Ala Pro Pro Ile Glu Gly Gln Ile Lys Cys Ser Ser Asn Ile Thr Gly
            405                 410                 415

Leu Leu Leu Thr Arg Asp Gly Gly Lys Thr Ala Asn Asn Thr Thr Glu
            420                 425                 430

Phe Phe Arg Pro Gly Gly Gly Asn Met Lys Asp Asn Trp Arg Ser Glu
            435                 440                 445

Leu Tyr Lys Tyr Lys Val Val Arg Ile Glu Pro Leu Gly Val Ala Pro
450                 455                 460

Thr Lys Ala Lys Arg Arg Val Val Gln Arg Glu Lys Arg
465                 470                 475

<210> SEQ ID NO 24
<211> LENGTH: 478
<212> TYPE: PRT
<213> ORGANISM: Human immunodeficiency virus 1

<400> SEQUENCE: 24

Leu Trp Val Thr Val Tyr Tyr Gly Val Pro Val Trp Lys Glu Ala Thr
1               5                   10                  15

Thr Thr Leu Phe Cys Ala Ser Asp Ala Lys Ala Tyr Asp Gln Glu Ile
            20                  25                  30

His Asn Ile Trp Ala Thr His Ala Cys Val Pro Thr Asp Pro Asn Pro
            35                  40                  45

Gln Glu Val Glu Leu Lys Asn Val Thr Glu Asn Phe Asn Met Trp Lys
        50                  55                  60

Ser Asn Met Val Glu Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                    85                  90                  95

Lys Cys Thr Asp Leu Asn Val Thr Asn Ser Asn Ser Thr Asp His Ser
                100                 105                 110

Thr Asn Ser Ser Leu Glu Ala Lys Gly Glu Ile Lys Asn Cys Ser Phe
            115                 120                 125

Asn Ile Thr Thr Thr Pro Arg Asp Lys Ile Gln Lys Glu Tyr Ala Ile
        130                 135                 140

Phe Tyr Lys Gln Asp Val Val Pro Ile Lys Asn Asp Asn Ile Ser Tyr
145                 150                 155                 160

Arg Leu Ile Ser Cys Asn Thr Ser Val Ile Thr Gln Ala Cys Pro Lys
                165                 170                 175

Val Thr Phe Glu Pro Ile Pro Ile His Tyr Cys Ala Pro Ala Gly Phe
                180                 185                 190

Ala Ile Leu Lys Cys Asn Asp Lys Gly Phe Asn Gly Thr Gly Pro Cys
            195                 200                 205

Thr Asn Val Ser Thr Val Gln Cys Thr His Gly Ile Arg Pro Ala Ile
        210                 215                 220

Ser Thr Gln Leu Leu Leu Asn Gly Ser Leu Ala Glu Asp Lys Val Val
225                 230                 235                 240

Ile Arg Ser Glu Asn Phe Thr Asp Asn Ala Lys Ile Ile Val His
                245                 250                 255

Leu Asn Glu Thr Val Lys Ile Asn Cys Thr Arg Pro Asn Asn Asn Thr
                260                 265                 270

Arg Lys Ser Ile His Ile Ala Pro Gly Arg Ala Phe Tyr Ala Thr Gly
            275                 280                 285

Glu Ile Ile Gly Asp Ile Arg Lys Ala Tyr Cys Thr Ile Asn Glu Ser
        290                 295                 300

Glu Trp Asn Asn Thr Leu Gln Lys Ile Val Thr Leu Arg Glu Gln
305                 310                 315                 320

Phe Arg Asn Lys Thr Ile Val Phe Asn Gln Ser Ser Gly Gly Asp Pro
                325                 330                 335

Glu Val Thr Met His Thr Phe Asn Cys Gly Gly Glu Phe Phe Tyr Cys
                340                 345                 350

Asn Thr Ala Gln Leu Phe Asn Ser Ser Trp Asp Thr Asn Thr Asn Gly
            355                 360                 365

Asn Asp Thr Gln Gly Pro Ser Glu Asn Asn Thr Ile Ile Leu Pro Cys
        370                 375                 380

Arg Ile Lys Gln Ile Ile Asn Met Trp Gln Arg Val Gly Lys Ala Ile
385                 390                 395                 400

Tyr Ala Pro Pro Ile Ser Gly Gln Ile Arg Cys Leu Ser Asn Ile Thr
                405                 410                 415

Gly Leu Ile Leu Thr Arg Asp Gly Gly Asn Ser Ser Leu Ser Ser Pro
                420                 425                 430

Glu Ile Phe Arg Pro Gly Gly Gly Asp Met Arg Asp Asn Trp Arg Ser
            435                 440                 445

Glu Leu Tyr Lys Tyr Lys Val Val Gln Ile Glu Pro Leu Gly Ile Ala
        450                 455                 460

Pro Thr Arg Ala Lys Arg Arg Ala Val Gln Arg Glu Lys Arg
465                 470                 475

<210> SEQ ID NO 25
<211> LENGTH: 484
<212> TYPE: PRT

<213> ORGANISM: Human immunodeficiency virus 1

<400> SEQUENCE: 25

| | | | | | | | | | | | | | | |
|---|---|---|---|---|---|---|---|---|---|---|---|---|---|---|
| Leu | Trp | Val | Thr | Val | Tyr | Tyr | Gly | Val | Pro | Val | Trp | Lys | Asp | Ala | Ser |
| 1 | | | | 5 | | | | | 10 | | | | | 15 |
| Thr | Thr | Leu | Phe | Cys | Ala | Ser | Asp | Ala | Lys | Ala | Tyr | Asp | Thr | Glu | Val |
| | | | 20 | | | | | 25 | | | | | 30 | |
| His | Asn | Val | Trp | Ala | Thr | His | Ala | Cys | Val | Pro | Thr | Asp | Pro | Asn | Pro |
| | | 35 | | | | | 40 | | | | | 45 | | |
| Gln | Glu | Val | Val | Leu | Gly | Asn | Val | Thr | Glu | Asn | Phe | Asn | Met | Trp | Lys |
| | 50 | | | | | 55 | | | | | 60 | | | | |
| Asn | Asn | Met | Val | Asp | Gln | Met | His | Glu | Asp | Ile | Ile | Ser | Leu | Trp | Asp |
| 65 | | | | | 70 | | | | | 75 | | | | | 80 |
| Gln | Ser | Leu | Lys | Pro | Cys | Val | Lys | Leu | Thr | Pro | Leu | Cys | Val | Thr | Leu |
| | | | | 85 | | | | | 90 | | | | | 95 | |
| Asn | Cys | Thr | Asp | Asn | Ile | Thr | Asn | Thr | Asn | Ser | Ser | Lys | Asn |
| | | | 100 | | | | | 105 | | | | | 110 |
| Ser | Ser | Thr | His | Ser | Tyr | Asn | Asn | Ser | Leu | Glu | Gly | Glu | Met | Lys | Asn |
| | | | 115 | | | | | 120 | | | | | 125 | | |
| Cys | Ser | Phe | Asn | Ile | Thr | Ala | Gly | Ile | Arg | Asp | Lys | Val | Lys | Lys | Glu |
| 130 | | | | | 135 | | | | | 140 | | | | | |
| Tyr | Ala | Leu | Phe | Tyr | Lys | Leu | Asp | Val | Val | Pro | Ile | Glu | Glu | Asp | Lys |
| 145 | | | | | 150 | | | | | 155 | | | | | 160 |
| Asp | Thr | Asn | Lys | Thr | Thr | Tyr | Arg | Leu | Arg | Ser | Cys | Asn | Thr | Ser | Val |
| | | | | 165 | | | | | 170 | | | | | 175 | |
| Ile | Thr | Gln | Ala | Cys | Pro | Lys | Val | Thr | Phe | Glu | Pro | Ile | Pro | Ile | His |
| | | | 180 | | | | | 185 | | | | | 190 | | |
| Tyr | Cys | Ala | Pro | Ala | Gly | Phe | Ala | Ile | Leu | Lys | Cys | Asn | Asp | Lys | Lys |
| | | 195 | | | | | 200 | | | | | 205 | | | |
| Phe | Asn | Gly | Thr | Gly | Pro | Cys | Thr | Asn | Val | Ser | Thr | Val | Gln | Cys | Thr |
| | 210 | | | | | 215 | | | | | 220 | | | | |
| His | Gly | Ile | Arg | Pro | Val | Val | Ser | Thr | Gln | Leu | Leu | Leu | Asn | Gly | Ser |
| 225 | | | | | 230 | | | | | 235 | | | | | 240 |
| Leu | Ala | Glu | Glu | Glu | Val | Val | Ile | Arg | Ser | Glu | Asn | Phe | Thr | Asn | Asn |
| | | | | 245 | | | | | 250 | | | | | 255 | |
| Ala | Lys | Thr | Ile | Ile | Val | Gln | Leu | Asn | Glu | Ser | Ile | Ala | Ile | Asn | Cys |
| | | | 260 | | | | | 265 | | | | | 270 | | |
| Thr | Arg | Pro | Asn | Asn | Asn | Thr | Arg | Arg | Ser | Ile | His | Ile | Gly | Pro | Gly |
| | | 275 | | | | | 280 | | | | | 285 | | | |
| Arg | Ala | Phe | Tyr | Ala | Thr | Gly | Asp | Ile | Ile | Gly | Asp | Ile | Arg | Gln | Ala |
| | 290 | | | | | 295 | | | | | 300 | | | | |
| His | Cys | Asn | Ile | Ser | Arg | Thr | Glu | Trp | Asn | Ser | Thr | Leu | Arg | Gln | Ile |
| 305 | | | | | 310 | | | | | 315 | | | | | 320 |
| Val | Thr | Lys | Leu | Arg | Glu | Gln | Leu | Gly | Asp | Pro | Asn | Lys | Thr | Ile | Ile |
| | | | | 325 | | | | | 330 | | | | | 335 | |
| Phe | Asn | Gln | Ser | Ser | Gly | Gly | Asp | Thr | Glu | Ile | Thr | Met | His | Ser | Phe |
| | | | 340 | | | | | 345 | | | | | 350 | | |
| Asn | Cys | Gly | Gly | Glu | Phe | Phe | Tyr | Cys | Asn | Thr | Thr | Lys | Leu | Phe | Asn |
| | | 355 | | | | | 360 | | | | | 365 | | | |
| Ser | Thr | Trp | Asn | Gly | Asn | Asn | Thr | Thr | Glu | Ser | Asp | Ser | Thr | Gly | Glu |
| | 370 | | | | | 375 | | | | | 380 | | | | |
| Asn | Ile | Thr | Leu | Pro | Cys | Arg | Ile | Lys | Gln | Ile | Ile | Asn | Leu | Trp | Gln |
| 385 | | | | | 390 | | | | | 395 | | | | | 400 |
| Glu | Val | Gly | Lys | Ala | Met | Tyr | Ala | Pro | Pro | Ile | Lys | Gly | Gln | Ile | Ser |

```
                405                 410                 415
Cys Ser Ser Asn Ile Thr Gly Leu Leu Leu Thr Arg Asp Gly Gly Asn
            420                 425                 430

Asn Asn Ser Ser Gly Pro Glu Thr Phe Arg Pro Gly Gly Asn Met
        435                 440                 445

Lys Asp Asn Trp Arg Ser Glu Leu Tyr Lys Tyr Lys Val Ile Lys Ile
    450                 455                 460

Glu Pro Leu Gly Val Ala Pro Thr Arg Ala Lys Arg Val Val Gln
465                 470                 475                 480

Arg Glu Lys Arg

<210> SEQ ID NO 26
<211> LENGTH: 477
<212> TYPE: PRT
<213> ORGANISM: Human immunodeficiency virus 1

<400> SEQUENCE: 26

Leu Trp Val Thr Val Tyr Tyr Gly Val Pro Val Trp Lys Glu Ala Asn
1               5                   10                  15

Thr Thr Leu Phe Cys Ala Ser Asp Ala Lys Ala Tyr Asp Thr Glu Ala
            20                  25                  30

His Asn Val Trp Ala Thr His Ala Cys Val Pro Thr Asp Pro Asn Pro
        35                  40                  45

Gln Glu Val Val Leu Glu Asn Val Thr Glu Asn Phe Asn Met Trp Lys
    50                  55                  60

Asn His Met Val Glu Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Thr Asp Leu Val Asn Ser Asn Ile Thr Arg Val Asp Asn Thr
            100                 105                 110

Thr Glu Lys Glu Met Lys Asn Cys Ser Phe Asn Val Thr Ser Gly Ile
        115                 120                 125

Arg Asp Lys Val Gln Lys Glu Tyr Ala Leu Leu Tyr Lys Leu Asp Ile
    130                 135                 140

Val Gln Ile Asp Asn Asp Asn Thr Ser His Arg Asp Asn Thr Ser Tyr
145                 150                 155                 160

Arg Leu Ile Ser Cys Asn Thr Ser Val Ile Thr Gln Ala Cys Pro Lys
                165                 170                 175

Ile Ser Phe Glu Pro Ile Pro Ile His Phe Cys Ala Pro Ala Gly Phe
            180                 185                 190

Ala Ile Leu Lys Cys Asn Asp Lys Lys Phe Asn Gly Thr Gly Pro Cys
        195                 200                 205

Thr Asn Val Ser Thr Val Gln Cys Thr His Gly Ile Arg Pro Val Val
    210                 215                 220

Ser Thr Gln Leu Leu Leu Asn Gly Ser Leu Ala Glu Glu Val Val
225                 230                 235                 240

Ile Arg Ser Glu Asn Phe Thr Asn Asn Val Lys Asn Ile Ile Val Gln
                245                 250                 255

Leu Asn Glu Ser Val Gln Ile Asn Cys Thr Arg His Asn Asn Thr
            260                 265                 270

Arg Lys Ser Ile Asn Ile Gly Pro Gly Arg Ala Phe Tyr Ala Thr Gly
        275                 280                 285

Lys Ile Ile Gly Asp Ile Arg Gln Ala His Cys Asn Ile Ser Arg Glu
    290                 295                 300
```

-continued

```
Lys Trp Gln Asn Thr Leu Lys Gln Ile Val Lys Leu Arg Glu Gln
305                 310                 315                 320

Phe Lys Asn Lys Thr Ile Ala Phe Ala Pro Ser Ser Gly Gly Asp Pro
            325                 330                 335

Glu Ile Val Met His Ser Phe Asn Cys Asn Gly Glu Phe Phe Tyr Cys
            340                 345                 350

Asn Thr Thr Lys Leu Phe Thr Ser Thr Trp Asn Ser Thr Trp Asn Ser
            355                 360                 365

Thr Trp Asn Asn Thr Glu Gly Ser Asn Ser Thr Val Ile Thr Leu Pro
            370                 375                 380

Cys Arg Ile Arg Gln Ile Ile Asn Met Trp Gln Glu Val Gly Lys Ala
385                 390                 395                 400

Met Tyr Ala Pro Pro Ile Gln Gly Gln Ile Lys Cys Ser Ser Asn Ile
            405                 410                 415

Thr Gly Leu Leu Leu Thr Arg Asp Gly Gly Val Asp Thr Thr Lys Glu
            420                 425                 430

Thr Phe Arg Pro Gly Gly Gly Asn Met Lys Asp Asn Trp Arg Ser Glu
            435                 440                 445

Leu Tyr Lys Tyr Lys Val Val Arg Ile Glu Pro Leu Gly Val Ala Pro
            450                 455                 460

Thr Lys Ala Lys Arg Arg Val Val Gln Arg Glu Lys Arg
465                 470                 475

<210> SEQ ID NO 27
<211> LENGTH: 472
<212> TYPE: PRT
<213> ORGANISM: Human immunodeficiency virus 1

<400> SEQUENCE: 27

Leu Trp Val Thr Val Tyr Tyr Gly Val Pro Val Trp Arg Glu Ala Asn
1               5                   10                  15

Thr Thr Leu Phe Cys Ala Ser Asp Ala Lys Ala Tyr Asp Thr Glu Val
            20                  25                  30

His Asn Val Trp Ala Thr His Ala Cys Val Pro Thr Asp Pro Asn Pro
        35                  40                  45

Gln Glu Val Val Met Gly Asn Val Thr Glu Asp Phe Asn Met Trp Lys
    50                  55                  60

Asn Asn Met Val Glu Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

His Cys Thr Asn Val Thr Ile Ser Ser Thr Asn Gly Ser Thr Ala Asn
            100                 105                 110

Val Thr Met Arg Glu Glu Met Lys Asn Cys Ser Phe Asn Thr Thr Thr
        115                 120                 125

Val Ile Arg Asp Lys Ile Gln Lys Glu Tyr Ala Leu Phe Tyr Lys Leu
    130                 135                 140

Asp Ile Val Pro Ile Glu Gly Lys Asn Thr Asn Thr Gly Tyr Arg Leu
145                 150                 155                 160

Ile Asn Cys Asn Thr Ser Val Ile Thr Gln Ala Cys Pro Lys Val Ser
                165                 170                 175

Phe Glu Pro Ile Pro Ile His Tyr Cys Ala Pro Ala Gly Phe Ala Ile
            180                 185                 190

Leu Lys Cys Asn Asn Lys Thr Phe Asn Gly Lys Gly Pro Cys Arg Asn
        195                 200                 205
```

```
Val Ser Thr Val Gln Cys Thr His Gly Ile Lys Pro Val Val Ser Thr
    210                 215                 220

Gln Leu Leu Asn Gly Ser Leu Ala Glu Glu Asp Ile Ile Arg
225                 230                 235                 240

Ser Glu Asn Phe Thr Asn Asn Gly Lys Asn Ile Ile Val Gln Leu Lys
                245                 250                 255

Glu Pro Val Lys Ile Asn Cys Thr Arg Pro Gly Asn Asn Thr Arg Arg
                260                 265                 270

Ser Ile Asn Ile Gly Pro Gly Arg Ala Phe Tyr Ala Thr Gly Ala Ile
                275                 280                 285

Ile Gly Asp Ile Arg Lys Ala His Cys Asn Ile Ser Thr Glu Gln Trp
    290                 295                 300

Asn Asn Thr Leu Thr Gln Ile Val Asp Lys Leu Arg Glu Gln Phe Gly
305                 310                 315                 320

Asn Lys Thr Ile Ile Phe Asn Gln Ser Ser Gly Gly Asp Pro Glu Val
                325                 330                 335

Val Met His Thr Phe Asn Cys Gly Gly Glu Phe Phe Tyr Cys Asn Ser
                340                 345                 350

Thr Gln Leu Phe Asn Ser Thr Trp Phe Asn Asn Gly Thr Ser Thr Trp
                355                 360                 365

Asn Ser Thr Ala Asp Asn Ile Thr Leu Pro Cys Arg Ile Lys Gln Val
    370                 375                 380

Ile Asn Met Trp Gln Glu Val Gly Lys Ala Met Tyr Ala Pro Pro Ile
385                 390                 395                 400

Arg Gly Gln Ile Asp Cys Ser Ser Asn Ile Thr Gly Leu Ile Leu Thr
                405                 410                 415

Arg Asp Gly Gly Ser Asn Ser Ser Gln Asn Glu Thr Phe Arg Pro Gly
                420                 425                 430

Gly Gly Asn Met Lys Asp Asn Trp Arg Ser Glu Leu Tyr Lys Tyr Lys
                435                 440                 445

Val Val Lys Ile Glu Pro Leu Gly Ile Ala Pro Thr Arg Ala Lys Arg
    450                 455                 460

Arg Val Val Gln Arg Glu Lys Arg
465                 470

<210> SEQ ID NO 28
<211> LENGTH: 476
<212> TYPE: PRT
<213> ORGANISM: Human immunodeficiency virus 1

<400> SEQUENCE: 28

Leu Trp Val Thr Val Tyr Tyr Gly Val Pro Val Trp Lys Glu Ala Thr
1               5                   10                  15

Thr Thr Leu Phe Cys Ala Ser Asp Ala Lys Ala Tyr Glu Thr Glu Lys
                20                  25                  30

His Asn Val Trp Ala Thr His Ala Cys Val Pro Thr Asp Pro Asn Pro
            35                  40                  45

Gln Glu Val Val Leu Gly Asn Val Thr Glu Asn Phe Asn Met Trp Lys
    50                  55                  60

Asn Asn Met Val Glu Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Thr Asp Glu Leu Arg Asn Gly Thr Tyr Ala Asn Val Thr Val
                100                 105                 110
```

```
Thr Glu Lys Gly Glu Ile Lys Asn Cys Ser Phe Asn Ile Thr Thr Ala
            115                 120                 125

Ile Arg Asp Lys Val Gln Lys Thr Tyr Ala Leu Phe Tyr Arg Leu Asp
        130                 135                 140

Val Val Pro Ile Asp Asn Asn His Gly Asn Ser Ser Asn Tyr Ser
145                 150                 155                 160

Asn Tyr Arg Leu Ile Asn Cys Asn Thr Ser Val Ile Thr Gln Ala Cys
                165                 170                 175

Pro Lys Val Ser Phe Glu Pro Ile Pro Ile His Tyr Cys Ala Pro Ala
                180                 185                 190

Gly Phe Ala Ile Leu Lys Cys Asn Asn Lys Lys Phe Asn Gly Thr Gly
            195                 200                 205

Pro Cys Lys Asn Val Ser Thr Val Gln Cys Thr His Gly Ile Arg Pro
        210                 215                 220

Val Val Ser Thr Gln Leu Leu Leu Asn Gly Ser Leu Ala Glu Glu Glu
225                 230                 235                 240

Val Val Ile Arg Ser Glu Asn Phe Thr Asp Asn Ala Lys Thr Ile Ile
                245                 250                 255

Val Gln Leu Asn Asp Ser Val Ile Ile Asn Cys Thr Arg Pro Asn Asn
                260                 265                 270

Asn Thr Arg Lys Gly Ile Thr Ile Gly Pro Gly Arg Val Phe Tyr Thr
            275                 280                 285

Gly Glu Ile Val Gly Asp Ile Arg Gln Val His Cys Asn Leu Ser Ser
        290                 295                 300

Ala Lys Trp Asn Ser Thr Leu Lys Gln Val Val Thr Lys Leu Arg Glu
305                 310                 315                 320

Gln Phe Gly Asn Lys Thr Ile Val Phe Asn Gln Ser Ser Gly Gly Asp
                325                 330                 335

Pro Glu Ile Val Met His Ser Phe Asn Cys Gly Gly Glu Phe Phe Phe
            340                 345                 350

Cys Asn Thr Thr Gln Leu Phe Asn Ser Thr Trp Asn Ile Asn Gly Thr
        355                 360                 365

Trp His Gly Thr Thr Val Ser Asn Lys Thr Ile Ile Leu Pro Cys Arg
        370                 375                 380

Ile Lys Gln Ile Ile Asn Met Trp Gln Glu Val Gly Lys Ala Met Tyr
385                 390                 395                 400

Ala Pro Pro Ile Arg Gly Gln Ile Arg Cys Ser Ser Asn Ile Thr Gly
                405                 410                 415

Leu Leu Leu Thr Arg Asp Gly Gly Asn Asn Asn Ser Thr Thr Glu Ile
            420                 425                 430

Phe Arg Pro Gly Gly Asp Met Arg Asp Asn Trp Arg Ser Glu Leu
        435                 440                 445

Tyr Lys Tyr Lys Val Val Lys Ile Glu Pro Leu Gly Ile Ala Pro Thr
450                 455                 460

Lys Ala Arg Arg Arg Val Val Gln Arg Glu Lys Arg
465                 470                 475

<210> SEQ ID NO 29
<211> LENGTH: 490
<212> TYPE: PRT
<213> ORGANISM: Human immunodeficiency virus 1

<400> SEQUENCE: 29

Leu Trp Val Thr Val Tyr Tyr Gly Val Pro Val Trp Lys Glu Ala Thr
1               5                   10                  15
```

-continued

Thr Thr Leu Phe Cys Ala Ser Asp Ala Lys Ala Tyr Glu Thr Glu Lys
            20                  25                  30

His Asn Val Trp Ala Thr His Ala Cys Val Pro Thr Asp Pro Asn Pro
        35                  40                  45

Gln Glu Val Val Leu Gly Asn Val Thr Glu Asn Phe Asn Met Trp Lys
50                  55                  60

Asn Asn Met Val Glu Gln Met His Glu Asp Ile Ile Ser Leu Trp Asp
65                  70                  75                  80

Glu Ser Leu Lys Pro Cys Val Lys Leu Thr Pro Leu Cys Val Thr Leu
                85                  90                  95

Asn Cys Thr Asp Glu Val Lys Thr Ser Tyr Ala Asn Lys Thr Ser Asn
                100                 105                 110

Glu Thr Tyr Lys Thr Ser Asn Glu Thr Phe Gly Glu Ile Lys Asn Cys
            115                 120                 125

Ser Phe Ser Val Pro Thr Gly Ile Lys Asp Lys Val Gln Asn Val Tyr
130                 135                 140

Ala Leu Phe Tyr Lys Leu Asp Val Ile Pro Ile Asp Asp Asn Asn Asn
145                 150                 155                 160

Ser Ser Lys Asn Asn Gly Ser Tyr Ser Tyr Arg Leu Ile Asn
                165                 170                 175

Cys Asn Thr Ser Val Ile Thr Gln Ala Cys Pro Lys Val Ser Phe Glu
            180                 185                 190

Pro Ile Pro Ile His Tyr Cys Ala Pro Ala Gly Phe Ala Ile Leu Lys
            195                 200                 205

Cys Asn Asn Lys Thr Phe Asn Gly Thr Gly Pro Cys Thr Asn Val Ser
210                 215                 220

Thr Val Gln Cys Thr His Gly Ile Arg Pro Val Val Ser Thr Gln Leu
225                 230                 235                 240

Leu Leu Asn Gly Ser Leu Ala Glu Glu Val Val Ile Arg Ser Glu
                245                 250                 255

Asn Phe Thr Asn Asn Ala Lys Thr Ile Ile Val His Leu Lys Lys Ser
            260                 265                 270

Val Glu Ile Asn Cys Thr Arg Pro Gly Asn Asn Thr Arg Lys Ser Ile
            275                 280                 285

His Ile Gly Pro Gly Arg Ala Phe Tyr Ala Thr Gly Asp Ile Ile Gly
290                 295                 300

Asp Ile Arg Gln Ala His Cys Asn Leu Ser Ser Val Gln Trp Asn Asp
305                 310                 315                 320

Thr Leu Lys Gln Ile Val Ile Lys Leu Gly Glu Gln Phe Gly Thr Asn
            325                 330                 335

Lys Thr Ile Ala Phe Asn Gln Ser Ser Gly Gly Asp Pro Glu Ile Val
                340                 345                 350

Met His Ser Phe Asn Cys Gly Gly Glu Phe Phe Tyr Cys Asn Thr Thr
            355                 360                 365

Gln Leu Phe Asn Ser Thr Trp Glu Phe His Gly Asn Trp Thr Arg Ser
    370                 375                 380

Asn Phe Thr Glu Ser Asn Ser Thr Thr Ile Thr Leu Pro Cys Arg Ile
385                 390                 395                 400

Lys Gln Ile Val Asn Met Trp Gln Glu Val Gly Lys Ala Met Tyr Ala
                405                 410                 415

Pro Pro Ile Arg Gly Gln Ile Arg Cys Ser Ser Asn Ile Thr Gly Leu
            420                 425                 430

Leu Leu Thr Arg Asp Gly Gly Val Asn Gly Thr Arg Glu Thr Phe Arg

```
                          435                 440                 445
Pro Gly Gly Gly Asp Met Arg Asp Asn Trp Arg Ser Glu Leu Tyr Lys
450                 455                 460

Tyr Lys Val Val Lys Ile Glu Pro Leu Gly Val Ala Pro Thr Lys Ala
465                 470                 475                 480

Lys Arg Arg Val Val Gln Arg Glu Lys Arg
                    485                 490

<210> SEQ ID NO 30
<211> LENGTH: 471
<212> TYPE: PRT
<213> ORGANISM: Human immunodeficiency virus 1

<400> SEQUENCE: 30

Leu Trp Val Thr Val Tyr Tyr Gly Val Pro Val Trp Lys Glu Thr Thr
1               5                   10                  15

Thr Thr Leu Phe Cys Ala Ser Asp Ala Lys Ala Tyr Asp Thr Glu Val
                20                  25                  30

His Asn Val Trp Ala Thr His Ala Cys Val Pro Thr Asp Pro Asn Pro
            35                  40                  45

Gln Glu Val Val Leu Glu Asn Val Thr Glu Asp Phe Asn Met Trp Lys
50                  55                  60

Asn Asn Met Val Glu Gln Met Gln Glu Asp Val Ile Asn Leu Trp Asp
65                  70                  75                  80

Gln Ser Leu Lys Pro Cys Val Lys Leu Thr Pro Leu Cys Val Thr Leu
                85                  90                  95

Asn Cys Lys Asp Val Asn Ala Thr Asn Thr Thr Ser Ser Ser Glu Gly
            100                 105                 110

Met Met Glu Arg Gly Glu Ile Lys Asn Cys Ser Phe Asn Ile Thr Lys
            115                 120                 125

Ser Ile Arg Asp Lys Val Gln Lys Glu Tyr Ala Leu Phe Tyr Lys Leu
            130                 135                 140

Asp Val Val Pro Ile Asp Asn Lys Asn Asn Thr Lys Tyr Arg Leu Ile
145                 150                 155                 160

Ser Cys Asn Thr Ser Val Ile Thr Gln Ala Cys Pro Lys Val Ser Phe
                165                 170                 175

Glu Pro Ile Pro Ile His Tyr Cys Ala Pro Ala Gly Phe Ala Ile Leu
            180                 185                 190

Lys Cys Asn Asn Lys Thr Phe Asn Gly Lys Gly Gln Cys Lys Asn Val
            195                 200                 205

Ser Thr Val Gln Cys Thr His Gly Ile Arg Pro Val Val Ser Thr Gln
210                 215                 220

Leu Leu Leu Asn Gly Ser Leu Ala Glu Glu Lys Val Val Ile Arg Ser
225                 230                 235                 240

Asp Asn Phe Thr Asp Asn Ala Lys Thr Ile Ile Val Gln Leu Asn Glu
                245                 250                 255

Ser Val Lys Ile Asn Cys Thr Arg Pro Ser Asn Asn Thr Arg Lys Ser
            260                 265                 270

Ile His Ile Gly Pro Gly Arg Ala Phe Tyr Thr Thr Gly Glu Ile Ile
            275                 280                 285

Gly Asp Ile Arg Gln Ala His Cys Asn Ile Ser Arg Ala Gln Trp Asn
            290                 295                 300

Asn Thr Leu Lys Gln Ile Val Glu Lys Leu Arg Glu Gln Phe Asn Asn
305                 310                 315                 320

Lys Thr Ile Val Phe Thr His Ser Ser Gly Gly Asp Pro Glu Ile Val
```

```
                        325                 330                 335
Met His Ser Phe Asn Cys Gly Gly Glu Phe Phe Tyr Cys Asn Ser Thr
            340                 345                 350

Gln Leu Phe Asn Ser Thr Trp Asn Asp Thr Glu Lys Ser Ser Gly Thr
            355                 360                 365

Glu Gly Asn Asp Thr Ile Ile Leu Pro Cys Arg Ile Lys Gln Ile Ile
            370                 375                 380

Asn Met Trp Gln Glu Val Gly Lys Ala Met Tyr Ala Pro Pro Ile Lys
385                 390                 395                 400

Gly Gln Ile Arg Cys Ser Ser Asn Ile Thr Gly Leu Leu Leu Thr Arg
                405                 410                 415

Asp Gly Gly Lys Asn Glu Ser Glu Ile Glu Ile Phe Arg Pro Gly Gly
                420                 425                 430

Gly Asp Met Arg Asp Asn Trp Arg Ser Glu Leu Tyr Lys Tyr Lys Val
                435                 440                 445

Val Lys Ile Glu Pro Leu Gly Val Ala Pro Thr Lys Ala Lys Arg Arg
                450                 455                 460

Val Val Gln Arg Glu Lys Arg
465                 470

<210> SEQ ID NO 31
<211> LENGTH: 470
<212> TYPE: PRT
<213> ORGANISM: Human immunodeficiency virus 1

<400> SEQUENCE: 31

Leu Trp Val Thr Val Tyr Tyr Gly Val Pro Val Trp Lys Glu Ala Thr
1               5                   10                  15

Thr Thr Leu Phe Cys Ala Ser Asp Ala Lys Ala Tyr Asp Thr Glu Val
                20                  25                  30

His Asn Val Trp Ala Thr His Ala Cys Val Pro Thr Asp Pro Asn Pro
            35                  40                  45

Gln Glu Val Val Leu Glu Asn Val Thr Glu His Phe Asn Met Trp Lys
        50                  55                  60

Asn Asn Met Val Glu Gln Met Gln Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Lys Asp Val Asn Ala Thr Asn Thr Thr Asn Asp Ser Glu Gly
            100                 105                 110

Thr Met Glu Arg Gly Glu Ile Lys Asn Cys Ser Phe Asn Ile Thr Thr
        115                 120                 125

Ser Ile Arg Asp Glu Val Gln Lys Glu Tyr Ala Leu Phe Tyr Lys Leu
    130                 135                 140

Asp Val Val Pro Ile Asp Asn Asn Asn Thr Ser Tyr Arg Leu Ile Ser
145                 150                 155                 160

Cys Asp Thr Ser Val Ile Thr Gln Ala Cys Pro Lys Ile Ser Phe Glu
                165                 170                 175

Pro Ile Pro Ile His Tyr Cys Ala Pro Ala Gly Phe Ala Ile Leu Lys
            180                 185                 190

Cys Asn Asp Lys Thr Phe Asn Gly Lys Gly Pro Cys Lys Asn Val Ser
        195                 200                 205

Thr Val Gln Cys Thr His Gly Ile Arg Pro Val Val Ser Thr Gln Leu
    210                 215                 220

Leu Leu Asn Gly Ser Leu Ala Glu Glu Glu Val Val Ile Arg Ser Asp
```

```
                 225                 230                 235                 240
Asn Phe Thr Asn Asn Ala Lys Thr Ile Ile Val Gln Leu Lys Glu Ser
                245                 250                 255

Val Glu Ile Asn Cys Thr Arg Pro Asn Asn Asn Thr Arg Lys Ser Ile
                260                 265                 270

His Ile Gly Pro Gly Arg Ala Phe Tyr Thr Thr Gly Glu Ile Ile Gly
                275                 280                 285

Asp Ile Arg Gln Ala His Cys Asn Ile Ser Arg Ala Lys Trp Asn Asp
                290                 295                 300

Thr Leu Lys Gln Ile Val Ile Lys Leu Arg Glu Gln Phe Glu Asn Lys
305                 310                 315                 320

Thr Ile Val Phe Asn His Ser Ser Gly Gly Asp Pro Glu Ile Val Met
                325                 330                 335

His Ser Phe Asn Cys Gly Gly Glu Phe Phe Tyr Cys Asn Ser Thr Gln
                340                 345                 350

Leu Phe Asn Ser Thr Trp Asn Asn Asn Thr Glu Gly Ser Asn Asn Thr
                355                 360                 365

Glu Gly Asn Thr Ile Thr Leu Pro Cys Arg Ile Lys Gln Ile Ile Asn
370                 375                 380

Met Trp Gln Glu Val Gly Lys Ala Met Tyr Ala Pro Pro Ile Arg Gly
385                 390                 395                 400

Gln Ile Arg Cys Ser Ser Asn Ile Thr Gly Leu Leu Leu Thr Arg Asp
                405                 410                 415

Gly Gly Ile Asn Glu Asn Gly Thr Glu Ile Phe Arg Pro Gly Gly Gly
                420                 425                 430

Asp Met Arg Asp Asn Trp Arg Ser Glu Leu Tyr Lys Tyr Lys Val Val
                435                 440                 445

Lys Ile Glu Pro Leu Gly Val Ala Pro Thr Lys Ala Lys Arg Arg Val
                450                 455                 460

Val Gln Arg Glu Lys Arg
465                 470

<210> SEQ ID NO 32
<211> LENGTH: 476
<212> TYPE: PRT
<213> ORGANISM: Human immunodeficiency virus 1

<400> SEQUENCE: 32

Leu Trp Val Thr Val Tyr Tyr Gly Val Pro Val Trp Lys Glu Ala Thr
1               5                   10                  15

Thr Thr Leu Phe Cys Ala Ser Asp Ala Lys Ala Tyr Asp Thr Glu Val
                20                  25                  30

His Asn Val Trp Ala Thr His Ala Cys Val Pro Thr Asp Pro Asn Pro
                35                  40                  45

Gln Glu Val Lys Met Glu Asn Val Thr Glu Asn Phe Asn Met Trp Lys
                50                  55                  60

Asn Asn Met Val Glu Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Thr Asp Leu Arg Asn Ala Thr Ser Arg Asn Val Thr Asn Thr
                100                 105                 110

Thr Ser Ser Ser Arg Gly Met Val Gly Gly Gly Glu Met Lys Asn Cys
                115                 120                 125

Ser Phe Asn Ile Thr Thr Gly Ile Arg Gly Lys Val Gln Lys Glu Tyr
```

```
                130                 135                 140
Ala Leu Phe Tyr Glu Leu Asp Ile Val Pro Ile Asp Asn Lys Ile Asp
145                 150                 155                 160

Arg Tyr Arg Leu Ile Ser Cys Asn Thr Ser Val Ile Thr Gln Ala Cys
                165                 170                 175

Pro Lys Val Ser Phe Glu Pro Ile Pro Ile His Tyr Cys Ala Pro Ala
            180                 185                 190

Gly Phe Ala Ile Leu Lys Cys Lys Asp Lys Lys Phe Asn Gly Lys Gly
        195                 200                 205

Pro Cys Thr Asn Val Ser Thr Val Gln Cys Thr His Gly Ile Arg Pro
210                 215                 220

Val Val Ser Thr Gln Leu Leu Leu Asn Gly Ser Leu Ala Glu Glu Glu
225                 230                 235                 240

Val Val Ile Arg Ser Glu Asn Phe Thr Asn Asn Ala Lys Ile Ile Ile
                245                 250                 255

Val Gln Leu Asn Glu Ser Val Glu Ile Asn Cys Thr Arg Pro Asn Asn
            260                 265                 270

Asn Thr Arg Lys Ser Ile His Ile Gly Pro Gly Arg Ala Phe Tyr Thr
        275                 280                 285

Thr Gly Glu Ile Ile Gly Asp Ile Arg Gln Ala His Cys Asn Leu Ser
290                 295                 300

Arg Ala Lys Trp Asn Asp Thr Leu Asn Lys Ile Val Ile Lys Leu Arg
305                 310                 315                 320

Glu Gln Phe Gly Asn Lys Thr Ile Val Phe Lys His Ser Ser Gly Gly
                325                 330                 335

Asp Pro Glu Ile Val Thr His Ser Phe Asn Cys Gly Gly Glu Phe Phe
            340                 345                 350

Tyr Cys Asn Ser Thr Gln Leu Phe Asn Ser Thr Trp Asn Val Thr Glu
        355                 360                 365

Glu Ser Asn Asn Thr Val Glu Asn Asn Thr Ile Thr Leu Pro Cys Arg
370                 375                 380

Ile Lys Gln Ile Ile Asn Met Trp Gln Glu Val Gly Arg Ala Met Tyr
385                 390                 395                 400

Ala Pro Pro Ile Arg Gly Gln Ile Arg Cys Ser Ser Asn Ile Thr Gly
                405                 410                 415

Leu Leu Leu Thr Arg Asp Gly Gly Pro Glu Asp Asn Lys Thr Glu Val
            420                 425                 430

Phe Arg Pro Gly Gly Gly Asp Met Arg Asp Asn Trp Arg Ser Glu Leu
        435                 440                 445

Tyr Lys Tyr Lys Val Val Lys Ile Glu Pro Leu Gly Val Ala Pro Thr
450                 455                 460

Lys Ala Lys Arg Arg Val Val Gln Arg Glu Lys Arg
465                 470                 475

<210> SEQ ID NO 33
<211> LENGTH: 478
<212> TYPE: PRT
<213> ORGANISM: Human immunodeficiency virus 1

<400> SEQUENCE: 33

Leu Trp Val Thr Val Tyr Tyr Gly Val Pro Val Trp Lys Glu Ala Thr
1               5                   10                  15

Thr Thr Leu Phe Cys Ala Ser Asp Ala Lys Ala Tyr Asp Thr Glu Val
            20                  25                  30

His Asn Val Trp Ala Thr His Ala Cys Val Pro Thr Asp Pro Asn Pro
```

-continued

```
                35                  40                  45
Gln Glu Val Val Leu Val Asn Val Thr Glu Asn Phe Asn Met Trp Lys
 50                  55                  60
Asn Asp Met Val Glu Gln Met His Glu Asp Ile Ile Ser Leu Trp Asp
 65                  70                  75                  80
Gln Ser Leu Lys Pro Cys Val Lys Leu Thr Pro Leu Cys Val Ser Leu
                 85                  90                  95
Lys Cys Thr Asp Leu Lys Asn Asp Thr Asn Thr Asn Ser Ser Ser Gly
                100                 105                 110
Arg Met Ile Met Glu Lys Gly Glu Ile Lys Asn Cys Ser Phe Asn Ile
                115                 120                 125
Ser Thr Ser Ile Arg Gly Lys Val Gln Lys Glu Tyr Ala Phe Phe Tyr
            130                 135                 140
Lys Leu Asp Ile Ile Pro Ile Asp Asn Asp Thr Thr Ser Tyr Lys Leu
145                 150                 155                 160
Thr Ser Cys Asn Thr Ser Val Ile Thr Gln Ala Cys Pro Lys Val Ser
                165                 170                 175
Phe Glu Pro Ile Pro Ile His Tyr Cys Ala Pro Ala Gly Phe Ala Ile
                180                 185                 190
Leu Lys Cys Asn Asn Lys Thr Phe Asn Gly Thr Gly Pro Cys Thr Asn
            195                 200                 205
Val Ser Thr Val Gln Cys Thr His Gly Ile Arg Pro Val Val Ser Thr
        210                 215                 220
Gln Leu Leu Leu Asn Gly Ser Leu Ala Glu Glu Val Val Ile Arg
225                 230                 235                 240
Ser Val Asn Phe Thr Asp Asn Ala Lys Thr Ile Ile Val Gln Leu Asn
                245                 250                 255
Thr Ser Val Glu Ile Asn Cys Thr Arg Pro Asn Asn Asn Thr Arg Lys
                260                 265                 270
Arg Ile Arg Ile Gln Arg Gly Pro Gly Arg Ala Phe Val Thr Ile Gly
            275                 280                 285
Lys Ile Gly Asn Met Arg Gln Ala His Cys Asn Ile Ser Arg Ala Lys
290                 295                 300
Trp Asn Asn Thr Leu Lys Gln Ile Ala Ser Lys Leu Arg Glu Gln Phe
305                 310                 315                 320
Gly Asn Asn Lys Thr Ile Ile Phe Lys Gln Ser Ser Gly Gly Asp Pro
                325                 330                 335
Glu Ile Val Thr His Ser Phe Asn Cys Gly Gly Glu Phe Phe Tyr Cys
            340                 345                 350
Asn Ser Thr Gln Leu Phe Asn Ser Thr Trp Phe Asn Ser Thr Trp Ser
            355                 360                 365
Thr Glu Gly Ser Asn Asn Thr Glu Gly Ser Asp Thr Ile Thr Leu Pro
        370                 375                 380
Cys Arg Ile Lys Gln Ile Ile Asn Met Trp Gln Lys Val Gly Lys Ala
385                 390                 395                 400
Met Tyr Ala Pro Pro Ile Ser Gly Gln Ile Arg Cys Ser Ser Asn Ile
                405                 410                 415
Thr Gly Leu Leu Leu Thr Arg Asp Gly Gly Asn Ser Asn Asn Glu Ser
            420                 425                 430
Glu Ile Phe Arg Pro Gly Gly Gly Asp Met Arg Asp Asn Trp Arg Ser
            435                 440                 445
Glu Leu Tyr Lys Tyr Lys Val Val Lys Ile Glu Pro Leu Gly Val Ala
        450                 455                 460
```

```
Pro Thr Lys Ala Lys Arg Arg Val Gln Arg Glu Lys Arg
465                 470                 475
```

```
<210> SEQ ID NO 34
<211> LENGTH: 470
<212> TYPE: PRT
<213> ORGANISM: Human immunodeficiency virus 1

<400> SEQUENCE: 34

Leu Trp Val Thr Val Tyr Tyr Gly Val Pro Val Trp Lys Glu Ala Thr
1               5                   10                  15

Thr Thr Leu Phe Cys Ala Ser Asp Ala Lys Ala Tyr Asp Thr Glu Val
                20                  25                  30

His Asn Val Trp Ala Thr His Ala Cys Val Pro Thr Asp Pro Asn Pro
            35                  40                  45

Gln Glu Ile Val Leu Glu Asn Val Thr Glu Asn Phe Asn Met Trp Lys
        50                  55                  60

Asn Asn Met Val Glu Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

His Cys Thr Asn Leu Lys Asn Ala Thr Asn Thr Lys Ser Ser Asn Trp
            100                 105                 110

Lys Glu Met Asp Arg Gly Glu Ile Lys Asn Cys Ser Phe Lys Val Thr
        115                 120                 125

Thr Ser Ile Arg Asn Lys Met Gln Lys Glu Tyr Ala Leu Phe His Lys
130                 135                 140

Leu Asp Val Val Pro Ile Asp Asn Asp Asn Thr Ser Tyr Lys Leu Ile
145                 150                 155                 160

Asn Cys Asn Thr Ser Val Ile Thr Gln Ala Cys Pro Lys Val Ser Phe
                165                 170                 175

Glu Pro Ile Pro Ile His Tyr Cys Ala Pro Ala Gly Phe Ala Ile Leu
            180                 185                 190

Lys Cys Asn Asp Lys Lys Phe Asn Gly Ser Gly Pro Cys Thr Asn Val
        195                 200                 205

Ser Thr Val Gln Cys Thr His Gly Ile Arg Pro Val Val Ser Thr Gln
210                 215                 220

Leu Leu Leu Asn Gly Ser Leu Ala Glu Glu Gly Val Val Ile Arg Ser
225                 230                 235                 240

Glu Asn Phe Thr Asp Asn Ala Lys Thr Ile Ile Val Gln Leu Lys Glu
                245                 250                 255

Ser Val Glu Ile Asn Cys Thr Arg Pro Asn Asn Asn Thr Arg Lys Ser
            260                 265                 270

Ile Thr Ile Gly Pro Gly Arg Ala Phe Tyr Ala Thr Gly Asp Ile Ile
        275                 280                 285

Gly Asp Ile Arg Gln Ala His Cys Asn Ile Ser Gly Glu Lys Trp Asn
290                 295                 300

Asn Thr Leu Lys Gln Ile Val Thr Lys Leu Gln Ala Gln Phe Gly Asn
305                 310                 315                 320

Lys Thr Ile Val Phe Lys Gln Ser Ser Gly Gly Asp Pro Glu Ile Val
                325                 330                 335

Met His Ser Phe Asn Cys Gly Gly Glu Phe Phe Tyr Cys Asn Ser Thr
            340                 345                 350

Gln Leu Phe Asn Ser Thr Trp Asn Asn Thr Ile Gly Pro Asn Asn Thr
        355                 360                 365
```

```
Asn Gly Thr Ile Thr Leu Pro Cys Arg Ile Lys Gln Ile Ile Asn Arg
        370                 375                 380

Trp Gln Glu Val Gly Lys Ala Met Tyr Ala Pro Pro Ile Arg Gly Gln
385                 390                 395                 400

Ile Arg Cys Ser Ser Asn Ile Thr Gly Leu Leu Leu Thr Arg Asp Gly
                405                 410                 415

Gly Lys Glu Ile Ser Asn Thr Thr Glu Ile Phe Arg Pro Gly Gly Gly
            420                 425                 430

Asp Met Arg Asp Asn Trp Arg Ser Glu Leu Tyr Lys Tyr Lys Val Val
        435                 440                 445

Lys Ile Glu Pro Leu Gly Val Ala Pro Thr Lys Ala Lys Arg Arg Val
    450                 455                 460

Val Gln Arg Glu Lys Arg
465                 470

<210> SEQ ID NO 35
<211> LENGTH: 481
<212> TYPE: PRT
<213> ORGANISM: Human immunodeficiency virus 1

<400> SEQUENCE: 35

Trp Val Thr Val Tyr Tyr Gly Val Pro Val Trp Lys Glu Ala Asn Thr
1               5                   10                  15

Thr Leu Phe Cys Ala Ser Asp Ala Lys Ala Tyr Asn Thr Glu Val His
                20                  25                  30

Asn Val Trp Ala Thr His Ala Cys Val Pro Thr Asp Pro Asn Pro Gln
            35                  40                  45

Glu Val Glu Leu Glu Asn Val Thr Glu Asn Phe Asn Met Trp Lys Asn
        50                  55                  60

Asn Met Val Asp Gln Met His Glu Asp Ile Ile Ser Leu Trp Asp Gln
65                  70                  75                  80

Ser Leu Lys Pro Cys Val Lys Leu Thr Pro Leu Cys Val Thr Leu Ser
                85                  90                  95

Cys Thr Asp Asn Val Gly Asn Asp Thr Ser Thr Asn Asn Ser Arg Trp
                100                 105                 110

Asp Lys Met Glu Lys Gly Glu Ile Lys Asn Cys Ser Phe Asn Ile Thr
            115                 120                 125

Thr Asn Met Arg Asp Lys Met Gln Lys Gln Tyr Ala Leu Phe Tyr Lys
130                 135                 140

Leu Asp Val Val Pro Ile Glu Glu Gly Lys Asn Asn Asn Ser Ser Phe
145                 150                 155                 160

Thr Asp Tyr Arg Leu Ile Ser Cys Asn Thr Ser Val Ile Thr Gln Ala
                165                 170                 175

Cys Pro Lys Val Thr Phe Glu Pro Ile Pro Ile His Tyr Cys Ala Pro
                180                 185                 190

Ala Gly Phe Ala Leu Leu Lys Cys Lys Asp Lys Lys Phe Asn Gly Thr
            195                 200                 205

Gly Pro Cys Lys Asn Val Ser Thr Val Gln Cys Thr His Gly Ile Lys
        210                 215                 220

Pro Val Val Ser Thr Gln Leu Leu Leu Asn Gly Ser Leu Ala Glu Glu
225                 230                 235                 240

Glu Val Val Ile Arg Ser Glu Asn Phe Ser Asn Asn Ala Arg Thr Ile
                245                 250                 255

Ile Val Gln Leu Asn Thr Ser Val Glu Ile Lys Cys Ile Arg Pro Asn
                260                 265                 270
```

-continued

```
Asn Asn Thr Arg Lys Gly Ile His Ile Gly Pro Gly Arg Ala Phe Tyr
            275                 280                 285

Thr Thr Gly Asp Ile Ile Gly Asp Ile Arg Gln Ala His Cys Asn Ile
        290                 295                 300

Ser Arg Gln Asn Trp Asn Asn Thr Leu Lys Gln Ile Ala Glu Lys Leu
305                 310                 315                 320

Arg Glu Gln Phe Gly Asn Lys Thr Ile Val Phe Arg Asn Ser Ser Gly
                325                 330                 335

Gly Asp Pro Glu Ile Val Met His Thr Phe Asn Cys Ala Gly Glu Phe
            340                 345                 350

Phe Tyr Cys Asn Thr Ala Glu Leu Phe Asn Ser Thr Trp Tyr Ala Asn
        355                 360                 365

Gly Thr Ile Ser Ile Gly Gly Asn Lys Thr Asn Ile Ile Leu Pro
370                 375                 380

Cys Arg Ile Lys Gln Phe Ile Asn Met Trp Gln Glu Val Gly Lys Ala
385                 390                 395                 400

Met Tyr Ala Pro Pro Ile Ser Gly Gln Ile Arg Cys Ser Ser Asn Ile
                405                 410                 415

Thr Gly Leu Leu Leu Thr Arg Asp Gly Gly Arg Gly Asn Gln Thr Asp
            420                 425                 430

Asn Gln Thr Glu Ile Phe Arg Pro Val Gly Gly Asp Met Lys Asn Asn
        435                 440                 445

Trp Arg Ser Glu Leu Tyr Lys Tyr Lys Val Val Arg Ile Glu Pro Leu
450                 455                 460

Gly Ile Ala Pro Thr Arg Ala Lys Arg Arg Val Val Gln Arg Glu Lys
465                 470                 475                 480

Arg

<210> SEQ ID NO 36
<211> LENGTH: 496
<212> TYPE: PRT
<213> ORGANISM: Human immunodeficiency virus 1

<400> SEQUENCE: 36

Leu Trp Val Thr Val Tyr Tyr Gly Val Pro Val Trp Lys Glu Ala Val
1               5                   10                  15

Thr Thr Leu Phe Cys Ala Ser Asp Ala Lys Ala Tyr Asp Thr Glu Val
            20                  25                  30

His Asn Val Trp Ala Thr His Ala Cys Val Pro Thr Asp Pro Asp Pro
        35                  40                  45

Gln Glu Val Val Leu Glu Asn Val Thr Glu Asn Phe Asn Met Trp Lys
    50                  55                  60

Asn Asn Met Val Glu Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Thr Asp Tyr Asn Asn Thr Ala Thr Asn Thr Ser Ser Ala
            100                 105                 110

Thr Thr Thr Ala Ser Ser Ala Asn Lys Thr Ala Lys Glu Glu Ala Val
        115                 120                 125

Met Lys Asn Cys Ser Phe Asn Ile Thr Thr Asn Val Arg Asp Lys Val
    130                 135                 140

Lys Arg Glu Tyr Ala Leu Phe Tyr Asn Leu Asp Val Val Lys Leu Glu
145                 150                 155                 160

Glu Gly Glu Thr Ser Tyr Arg Leu Val Ser Cys Asn Thr Ser Val Val
```

```
                    165                 170                 175
Thr Gln Ala Cys Pro Lys Ile Thr Phe Glu Pro Ile Pro Ile His Tyr
            180                 185                 190

Cys Ala Pro Ala Gly Phe Ala Ile Leu Lys Cys Asn Asn Lys Thr Phe
        195                 200                 205

Asn Gly Thr Gly Pro Cys Thr Asn Val Ser Thr Val Gln Cys Thr His
    210                 215                 220

Gly Ile Lys Pro Val Val Ser Thr Gln Leu Leu Leu Asn Gly Ser Leu
225                 230                 235                 240

Ala Glu Gly Gly Glu Val Met Ile Arg Ser Ala Asn Phe Thr Asn Asn
                245                 250                 255

Ala Lys Thr Ile Ile Val Gln Leu Ser Lys Ser Val Ala Ile Asn Cys
            260                 265                 270

Thr Arg Pro Asn Asn Asn Thr Ser Lys Ser Ile His Met Gly Pro Gly
        275                 280                 285

Gly Ala Phe Phe Ala Thr Gly Arg Ile Ile Gly Asp Ile Arg Lys Ala
    290                 295                 300

Tyr Cys Thr Val Asn Gly Thr Glu Trp Asn Thr Thr Leu Arg Gln Ile
305                 310                 315                 320

Val Glu Lys Phe Lys Lys Gln Phe Gly Glu Asn Lys Thr Ile Val Phe
                325                 330                 335

Lys Pro Ser Ala Gly Gly Asp Pro Glu Ile Val Thr His Ser Phe Asn
            340                 345                 350

Cys Gly Gly Glu Phe Phe Tyr Cys Asn Thr Thr Asn Leu Phe Asn Ser
        355                 360                 365

Ser Ser Thr Glu Leu Asn Ser Thr Trp Ser Gly Asn Ser Asn Asp Thr
    370                 375                 380

Gly Lys Asn Asp Thr Ile Thr Leu Pro Cys Arg Ile Lys Gln Ile Ile
385                 390                 395                 400

Asn Met Trp Gln Gln Val Gly Lys Ala Met Tyr Ala Pro Pro Ile Ser
                405                 410                 415

Gly Lys Ile Asn Cys Leu Ser Asn Ile Thr Gly Leu Leu Leu Thr Arg
            420                 425                 430

Asp Gly Gly Ser Asp Gly Gly Ser Lys Asn Ser Ser Lys Asn Glu Thr
        435                 440                 445

Gly Thr Glu Ile Phe Arg Pro Gly Gly Gly Asp Met Arg Asp Asn Trp
    450                 455                 460

Arg Ser Glu Leu Tyr Lys Tyr Lys Val Val Arg Ile Glu Pro Leu Gly
465                 470                 475                 480

Val Ala Pro Thr Lys Ala Lys Arg Arg Ala Val Gln Arg Glu Lys Arg
                485                 490                 495

<210> SEQ ID NO 37
<211> LENGTH: 475
<212> TYPE: PRT
<213> ORGANISM: Human immunodeficiency virus 1

<400> SEQUENCE: 37

Leu Trp Val Thr Val Tyr Tyr Gly Val Pro Val Trp Lys Glu Ala Thr
1               5                   10                  15

Thr Thr Leu Phe Cys Ala Ser Asp Ala Lys Gly Tyr Glu Lys Glu Val
            20                  25                  30

His Asn Val Trp Ala Thr His Ala Cys Val Pro Thr Asp Pro Asn Pro
        35                  40                  45

Gln Glu Val Val Leu Glu Asn Val Thr Glu Asn Phe Asn Met Trp Lys
```

```
            50                  55                  60
Asn Asn Met Val Glu Gln Met His Glu Asp Ile Ile Ser Leu Trp Asp
 65                  70                  75                  80

Gln Ser Leu Lys Pro Cys Val Lys Leu Thr Pro Leu Cys Val Thr Leu
                 85                  90                  95

Asn Cys Ser Asp Val Asn Thr Thr Ser Val Asn Thr Thr Ala Ser Ser
                100                 105                 110

Met Glu Gly Gly Glu Ile Lys Asn Cys Ser Phe Asn Thr Thr Thr Ser
            115                 120                 125

Met Ser Asp Lys Met Gln Lys Glu Tyr Ala Leu Phe Tyr Thr Leu Asp
        130                 135                 140

Val Val Pro Ile Val Lys Glu Asn Asn Thr Tyr Arg Leu Ile Ser Cys
145                 150                 155                 160

Asn Thr Ser Val Ile Thr Gln Ala Cys Pro Lys Val Ser Phe Glu Pro
                165                 170                 175

Ile Pro Ile His Tyr Cys Ala Pro Ala Gly Phe Ala Ile Leu Met Cys
            180                 185                 190

Asn Asn Lys Thr Phe Asp Gly Lys Gly Pro Cys Asn Asn Val Ser Thr
        195                 200                 205

Val Gln Cys Thr His Gly Ile Lys Pro Val Val Ser Thr Gln Leu Leu
210                 215                 220

Leu Asn Gly Ser Leu Ala Glu Glu Val Val Ile Arg Ser Asp Asn
225                 230                 235                 240

Phe Thr Asp Asn Ala Lys Thr Ile Ile Val His Leu Asn Glu Ser Ile
                245                 250                 255

Glu Ile Thr Cys Thr Arg Pro Asn Asn Asn Thr Ser Lys Ser Ile Thr
            260                 265                 270

Ile Gly Pro Gly Arg Ala Phe Tyr Ala Thr Gly Arg Ile Ile Gly Asp
        275                 280                 285

Ile Arg Lys Ala His Cys Asn Ile Ser Gly Glu Lys Trp His Asn Ala
290                 295                 300

Leu Glu Gln Ile Val Lys Lys Leu Gly Glu Lys Phe Glu Asn Ala Thr
305                 310                 315                 320

Thr Ile Arg Phe Asn Gln Ser Ser Gly Gly Asp Gln Glu Ile Val Met
                325                 330                 335

His Thr Phe Asn Cys Gly Gly Glu Phe Phe Tyr Cys Asn Ser Thr Gln
            340                 345                 350

Leu Phe Asn Ser Thr Trp Trp Pro Asn Gly Thr Thr Thr Glu Trp Ser
        355                 360                 365

Asn Glu Thr Ser Asn Gly Thr Ile Thr Leu Pro Cys Arg Ile Lys Gln
370                 375                 380

Ile Ile Asn Met Trp Gln Glu Val Gly Lys Ala Met Tyr Ala Pro Pro
385                 390                 395                 400

Ile Ser Gly Pro Ile Ser Cys Ser Ser Asn Ile Thr Gly Leu Leu Leu
                405                 410                 415

Val Arg Asp Gly Gly Asn Asp Asn Glu Thr Asn Gly Thr Glu Thr Phe
            420                 425                 430

Arg Pro Gly Gly Gly Asp Met Arg Asp Asn Trp Arg Ser Glu Leu Tyr
        435                 440                 445

Lys Tyr Lys Val Val Lys Ile Glu Pro Leu Gly Val Ala Pro Thr Lys
        450                 455                 460

Ala Lys Arg Arg Val Val Gln Arg Glu Lys Arg
465                 470                 475
```

```
<210> SEQ ID NO 38
<211> LENGTH: 473
<212> TYPE: PRT
<213> ORGANISM: Human immunodeficiency virus 1

<400> SEQUENCE: 38

Leu Trp Val Thr Val Tyr Tyr Gly Val Pro Val Trp Lys Glu Ala Thr
 1               5                  10                  15

Thr Thr Leu Phe Cys Ala Ser Asp Ala Lys Ala Tyr Asn Thr Glu Val
            20                  25                  30

His Asn Val Trp Ala Thr His Ala Cys Val Pro Thr Asp Pro Asn Pro
        35                  40                  45

Gln Glu Val Gly Leu Glu Asn Val Thr Glu Asn Phe Asn Met Trp Lys
    50                  55                  60

Asn Asn Met Val Glu Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Ser Asp Leu Arg Asn Ala Thr Asn Thr Thr Asn Pro Thr Val
            100                 105                 110

Ser Ser Arg Val Ile Lys Lys Glu Met Met Gly Glu Val Lys Asn Cys
        115                 120                 125

Ser Phe Asn Val Thr Thr Asp Ile Arg Asp Arg Met Gln Lys Val Tyr
    130                 135                 140

Ala Leu Phe Tyr Arg Pro Asp Val Val Pro Ile Gln Asp His Thr Ile
145                 150                 155                 160

Glu Asn Asn Asn Thr Ile Glu Asn Asn Thr Thr Tyr Arg Leu Ile Ser
                165                 170                 175

Cys Asn Thr Ser Val Ile Thr Gln Ala Cys Pro Lys Ile Ser Phe Glu
            180                 185                 190

Pro Ile Pro Ile His Tyr Cys Thr Pro Ala Gly Phe Ala Ile Leu Lys
        195                 200                 205

Cys Asn Asp Lys Lys Phe Asn Gly Ser Gly Pro Cys Thr Asn Val Ser
    210                 215                 220

Thr Val Gln Cys Thr His Gly Ile Arg Pro Val Val Ser Thr Gln Leu
225                 230                 235                 240

Leu Leu Asn Gly Ser Arg Ala Glu Glu Val Ile Ile Arg Ser Glu
                245                 250                 255

Asn Phe Thr Asn Asn Ala Lys Thr Ile Ile Val Gln Leu Asn Lys Thr
            260                 265                 270

Val Glu Ile Asn Cys Thr Arg Pro Asn Asn Asn Thr Arg Lys Ser Ile
        275                 280                 285

Ser Ile Gly Pro Gly Arg Ala Phe Tyr Ala Thr Gly Asp Ile Ile Gly
    290                 295                 300

Asp Ile Arg Gln Ala His Cys Asn Leu Ser Arg Ala Glu Trp Asn Lys
305                 310                 315                 320

Thr Leu Lys Tyr Ile Ser Thr Lys Leu Arg Glu Gln Phe Gly Asn Lys
                325                 330                 335

Thr Ile Ile Phe Asn Gly Ser Ser Gly Gly Asp Pro Glu Ile Val Thr
            340                 345                 350

His Ser Phe Asn Cys Gly Gly Glu Phe Phe Tyr Cys Asn Thr Thr Lys
        355                 360                 365

Leu Phe Asn Ser Thr Trp Asp Ala Asn Gly Asn Cys Thr Gly Cys Asp
    370                 375                 380
```

```
Glu Ser Asp Gly Asn Asn Thr Ile Thr Leu Pro Cys Arg Ile Lys Gln
385                 390                 395                 400

Ile Val Asn Met Trp Gln Glu Val Gly Lys Ala Met Tyr Ala Pro Pro
                405                 410                 415

Ile Lys Gly Leu Ile Lys Cys Thr Ser Asn Ile Thr Gly Leu Leu Leu
            420                 425                 430

Thr Arg Asp Gly Gly Ala Asn Asn Thr Asn Glu Thr Phe Arg Pro Gly
        435                 440                 445

Gly Gly Asp Met Arg Asp Asn Trp Arg Ser Glu Leu Tyr Lys Tyr Lys
    450                 455                 460

Val Val Gln Ile Glu Pro Leu Gly Ile
465                 470

<210> SEQ ID NO 39
<211> LENGTH: 21
<212> TYPE: PRT
<213> ORGANISM: Human immunodeficiency virus 1

<400> SEQUENCE: 39

Cys Arg Asn Ala Thr Ser Lys Met Val Asn Asp Thr Arg Asn Val Glu
1               5                   10                  15

Glu Met Lys Asn Cys
            20

<210> SEQ ID NO 40
<211> LENGTH: 24
<212> TYPE: PRT
<213> ORGANISM: Human immunodeficiency virus 1

<400> SEQUENCE: 40

Cys Arg Gln Val Asn Thr Thr Asn Ala Thr Ser Ser Val Asn Val Thr
1               5                   10                  15

Asn Gly Glu Glu Ile Lys Asn Cys
            20

<210> SEQ ID NO 41
<211> LENGTH: 43
<212> TYPE: PRT
<213> ORGANISM: Human immunodeficiency virus 1

<400> SEQUENCE: 41

Ser Phe Asn Thr Thr Thr Glu Leu Arg Asp Arg Lys Gln Thr Val Tyr
1               5                   10                  15

Ala Ser Phe Tyr Lys Leu Asp Ile Val Pro Leu Asn Glu Asn Lys Ser
            20                  25                  30

Thr Ser Ser Glu Asn Tyr Arg Leu Ile Asn Cys
        35                  40

<210> SEQ ID NO 42
<211> LENGTH: 43
<212> TYPE: PRT
<213> ORGANISM: Human immunodeficiency virus 1

<400> SEQUENCE: 42

Ser Phe Asn Ala Thr Thr Glu Ile Arg Asp Lys Lys Gln Lys Val Tyr
1               5                   10                  15

Ala Leu Phe Tyr Arg Leu Asp Ile Val Pro Leu Glu Glu Glu Arg Lys
            20                  25                  30

Gly Asn Ser Ser Lys Tyr Arg Leu Ile Asn Cys
        35                  40
```

```
<210> SEQ ID NO 43
<211> LENGTH: 35
<212> TYPE: PRT
<213> ORGANISM: Human immunodeficiency virus 1

<400> SEQUENCE: 43

Cys Thr Arg Pro Asn Asn Thr Arg Lys Ser Val Arg Ile Gly Pro
1               5                   10                  15

Gly Gln Thr Phe Tyr Ala Thr Gly Glu Ile Ile Gly Asp Ile Arg Gln
            20                  25                  30

Ala His Cys
        35

<210> SEQ ID NO 44
<211> LENGTH: 35
<212> TYPE: PRT
<213> ORGANISM: Human immunodeficiency virus 1

<400> SEQUENCE: 44

Cys Thr Arg Pro Asn Asn Asn Thr Arg Lys Ser Ile Arg Ile Gly Pro
1               5                   10                  15

Gly Gln Thr Phe Tyr Ala Thr Gly Asp Ile Ile Gly Asn Ile Arg Gln
            20                  25                  30

Ala Tyr Cys
        35

<210> SEQ ID NO 45
<211> LENGTH: 2229
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (37)..(2196)

<400> SEQUENCE: 45
ccaagctggc tagcgtttaa acttaagctt gccacc atg cct atg ggc agc ctg      54
                                       Met Pro Met Gly Ser Leu
                                         1               5 cag cct ctg gcc acc ctg tac ctg ctg ggc atg ctg gtg gcc tcc gtg     102
Gln Pro Leu Ala Thr Leu Tyr Leu Leu Gly Met Leu Val Ala Ser Val
            10                  15                  20 ctg gca gct ggc aac ctg tgg gtc aca gtg tac tac ggc gtg ccc gtg     150
Leu Ala Ala Gly Asn Leu Trp Val Thr Val Tyr Tyr Gly Val Pro Val
            25                  30                  35 tgg aaa gag gcc aag gcc aca ctg ttc tgc gcc agc gac gcc aag gcc     198
Trp Lys Glu Ala Lys Ala Thr Leu Phe Cys Ala Ser Asp Ala Lys Ala
    40                  45                  50 tac gag aca gag gtg cac aac gtc tgg gcc acc cac gcc tgc gtg ccc     246
Tyr Glu Thr Glu Val His Asn Val Trp Ala Thr His Ala Cys Val Pro
55                  60                  65                  70 acc gac ccc aac ccc cag gaa atc gtc ctg gaa aac gtg acc gag aac     294
Thr Asp Pro Asn Pro Gln Glu Ile Val Leu Glu Asn Val Thr Glu Asn
                75                  80                  85 ttc aac atg tgg gag aac gac atg gtc aac cag atg cac gag gac gtg     342
Phe Asn Met Trp Glu Asn Asp Met Val Asn Gln Met His Glu Asp Val
            90                  95                  100 atc agc ctg tgg gac cag agc ctg aag ccc tgc gtg aag ctg acc ccc     390
Ile Ser Leu Trp Asp Gln Ser Leu Lys Pro Cys Val Lys Leu Thr Pro
            105                 110                 115
```

```
                                                        -continued ctg tgc gtg acc ctg gac tgc gag aac gtg gac ggc aac gac acc tac      438
Leu Cys Val Thr Leu Asp Cys Glu Asn Val Asp Gly Asn Asp Thr Tyr
    120             125                 130 aac ggc acc aac gag atg aag aac tgc agc ttc aac acc acc gag          486
Asn Gly Thr Asn Glu Met Lys Asn Cys Ser Phe Asn Thr Thr Thr Glu
135             140                 145                 150 ctg cgg gac aag aaa cag aag gtg tcc gcc ctg ttc tac cgg ctg gac      534
Leu Arg Asp Lys Lys Gln Lys Val Ser Ala Leu Phe Tyr Arg Leu Asp
            155                 160                 165 atc gtg ccc ctg aac aga agc agc agc aac agc agc gac tac tac          582
Ile Val Pro Leu Asn Arg Ser Ser Ser Asn Ser Ser Asp Tyr Tyr
                170                 175                 180 cgg ctg atc agc tgc aac acc agc gcc atc acc cag gcc tgc ccc aaa      630
Arg Leu Ile Ser Cys Asn Thr Ser Ala Ile Thr Gln Ala Cys Pro Lys
            185                 190                 195 gtg acc ttc gac cct atc ccc atc cac tac tgc gcc cct gcc ggc ttc      678
Val Thr Phe Asp Pro Ile Pro Ile His Tyr Cys Ala Pro Ala Gly Phe
                200                 205                 210 gcc atc ctg aag tgc aac aac aag acc ttc aat ggc acc ggc ccc tgc      726
Ala Ile Leu Lys Cys Asn Asn Lys Thr Phe Asn Gly Thr Gly Pro Cys
215             220                 225                 230 cac aac gtg tcc acc gtg cag tgc acc cac ggc atc aag ccc gtg gtg      774
His Asn Val Ser Thr Val Gln Cys Thr His Gly Ile Lys Pro Val Val
            235                 240                 245 tcc acc cag ctg ctg aat ggc agc ctg gcc gag aaa gag atc atc          822
Ser Thr Gln Leu Leu Asn Gly Ser Leu Ala Glu Lys Glu Ile Ile
                250                 255                 260 atc aga agc aag aac ctg agc gac aac gtg aaa acc atc att gtg cac      870
Ile Arg Ser Lys Asn Leu Ser Asp Asn Val Lys Thr Ile Ile Val His
            265                 270                 275 ctg aac gag agc gtg gaa atc gtg tgc acc cgg ccc aac aac aac acc      918
Leu Asn Glu Ser Val Glu Ile Val Cys Thr Arg Pro Asn Asn Asn Thr
280             285                 290 aga aag agc atc cgg atc ggc cct ggc cag acc ttc tac gcc acc ggc      966
Arg Lys Ser Ile Arg Ile Gly Pro Gly Gln Thr Phe Tyr Ala Thr Gly
295             300                 305                 310 gcc atc atc ggc aac atc aga gag gcc cac tgc aac atc agc cgg gac     1014
Ala Ile Ile Gly Asn Ile Arg Glu Ala His Cys Asn Ile Ser Arg Asp
            315                 320                 325 aag tgg aac gag aca ctg cag aga gtg ggc aag aag ctg gaa gaa cag     1062
Lys Trp Asn Glu Thr Leu Gln Arg Val Gly Lys Lys Leu Glu Glu Gln
                330                 335                 340 ttc cct aac aag aca atc aac ttc acc tcc agc tct ggc ggc gac ctg     1110
Phe Pro Asn Lys Thr Ile Asn Phe Thr Ser Ser Ser Gly Gly Asp Leu
            345                 350                 355 gaa atc acc acc cac agc ttc aac tgc aga ggc gag ttc ttc tac tgc     1158
Glu Ile Thr Thr His Ser Phe Asn Cys Arg Gly Glu Phe Phe Tyr Cys
360             365                 370 aac acc tcc aag ctg ttc aac agc acc tac atc ccc acc tac aga ccc     1206
Asn Thr Ser Lys Leu Phe Asn Ser Thr Tyr Ile Pro Thr Tyr Arg Pro
375             380                 385                 390 aac aac acc cag ggc aac agc tcc agc acc atc aca atc cct tgc cgg     1254
Asn Asn Thr Gln Gly Asn Ser Ser Ser Thr Ile Thr Ile Pro Cys Arg
            395                 400                 405 atc aag cag atc atc aat atg tgg cag gaa gtg ggc agg gct atg tac     1302
Ile Lys Gln Ile Ile Asn Met Trp Gln Glu Val Gly Arg Ala Met Tyr
                410                 415                 420 gcc cct cct atc gcc ggc aac att acc tgc aag agc cac atc acc ggc     1350
Ala Pro Pro Ile Ala Gly Asn Ile Thr Cys Lys Ser His Ile Thr Gly
            425                 430                 435
```

```
ctg ctg ctc gtc cgc gac gga ggc aca ggc ctg aac agc agc acc gag    1398
Leu Leu Leu Val Arg Asp Gly Gly Thr Gly Leu Asn Ser Ser Thr Glu
    440             445                 450 aca ttc aga ccc ggg gga ggc gac atg cgg gac aat tgg cgg agc gag    1446
Thr Phe Arg Pro Gly Gly Gly Asp Met Arg Asp Asn Trp Arg Ser Glu
455                 460                 465                 470 ctg tac aag tac aag gtg gtg gaa atc aag ccc ctg ggc gtg gcc cct    1494
Leu Tyr Lys Tyr Lys Val Val Glu Ile Lys Pro Leu Gly Val Ala Pro
            475                 480                 485 acc gcc gcc aag aga aga gtg gtg cag agc gag aag tcc gcc gtg gga    1542
Thr Ala Ala Lys Arg Arg Val Val Gln Ser Glu Lys Ser Ala Val Gly
        490                 495                 500 ctg ggc gcc gtg ttc ctg ggc ttt ctg gga gcc gcc gga agc aca atg    1590
Leu Gly Ala Val Phe Leu Gly Phe Leu Gly Ala Ala Gly Ser Thr Met
    505                 510                 515 ggc gct gcc agc atc acc ctg acc gtg cag gcc aga cag ctg ctg agc    1638
Gly Ala Ala Ser Ile Thr Leu Thr Val Gln Ala Arg Gln Leu Leu Ser
520                 525                 530 ggc atc gtg cag cag cag agc aac ctg ctg aga gct atc gag gcc cag    1686
Gly Ile Val Gln Gln Gln Ser Asn Leu Leu Arg Ala Ile Glu Ala Gln
535                 540                 545                 550 cag cac atg ctg cag ctg acc gtg tgg ggc atc aag cag ctg cag acc    1734
Gln His Met Leu Gln Leu Thr Val Trp Gly Ile Lys Gln Leu Gln Thr
            555                 560                 565 cgg gtg ctg gcc atc gag aga tac ctg aag gac cag cag ctc ctg gga    1782
Arg Val Leu Ala Ile Glu Arg Tyr Leu Lys Asp Gln Gln Leu Leu Gly
        570                 575                 580 atc tgg ggc tgc agc ggc aag ctg atc tgc acc acc gcc gtg ccc tgg    1830
Ile Trp Gly Cys Ser Gly Lys Leu Ile Cys Thr Thr Ala Val Pro Trp
    585                 590                 595 aac acc agc tgg tcc aac aga agc cag gcc gac atc tgg ggc aac atg    1878
Asn Thr Ser Trp Ser Asn Arg Ser Gln Ala Asp Ile Trp Gly Asn Met
600                 605                 610 acc tgg atg cag tgg gac aga gag atc agc aac tac acc aac acc atc    1926
Thr Trp Met Gln Trp Asp Arg Glu Ile Ser Asn Tyr Thr Asn Thr Ile
615                 620                 625                 630 ttc cgg ctg ctc gaa gat agc cag atc cag cag gaa agc aac gag aag    1974
Phe Arg Leu Leu Glu Asp Ser Gln Ile Gln Gln Glu Ser Asn Glu Lys
            635                 640                 645 gac ctg ctg gcc ctg gac agc tgg aag aac ctg tgg tcc tgg ttt gac    2022
Asp Leu Leu Ala Leu Asp Ser Trp Lys Asn Leu Trp Ser Trp Phe Asp
        650                 655                 660 atc acc aac tgg ctg tgg tac atc aag atc ttc atc atg atc gtg ggc    2070
Ile Thr Asn Trp Leu Trp Tyr Ile Lys Ile Phe Ile Met Ile Val Gly
    665                 670                 675 ggc ctg atc ggc ctg cgg atc atc ttc gcc gtg ctg agc atc gtg gga    2118
Gly Leu Ile Gly Leu Arg Ile Ile Phe Ala Val Leu Ser Ile Val Gly
680                 685                 690 ggc gga gcc aag ttc gtg gcc gcc tgg aca ctg aaa gcc gct gct ggc    2166
Gly Gly Ala Lys Phe Val Ala Ala Trp Thr Leu Lys Ala Ala Ala Gly
695                 700                 705                 710 ggc acc gaa acc tct cag gtg gcc cct gcc tgactcgagt ctagagggcc      2216
Gly Thr Glu Thr Ser Gln Val Ala Pro Ala
            715                 720 cgtttaaacc cgc                                                     2229

<210> SEQ ID NO 46
<211> LENGTH: 720
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 46

```
Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
            20                  25                  30

Tyr Tyr Gly Val Pro Val Trp Lys Glu Ala Lys Ala Thr Leu Phe Cys
        35                  40                  45

Ala Ser Asp Ala Lys Ala Tyr Glu Thr Glu Val His Asn Val Trp Ala
    50                  55                  60

Thr His Ala Cys Val Pro Thr Asp Pro Asn Pro Gln Glu Ile Val Leu
65                  70                  75                  80

Glu Asn Val Thr Glu Asn Phe Asn Met Trp Glu Asn Asp Met Val Asn
                85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu Asp Cys Glu Asn Val
        115                 120                 125

Asp Gly Asn Asp Thr Tyr Asn Gly Thr Asn Glu Met Lys Asn Cys Ser
    130                 135                 140

Phe Asn Thr Thr Thr Glu Leu Arg Asp Lys Lys Gln Lys Val Ser Ala
145                 150                 155                 160

Leu Phe Tyr Arg Leu Asp Ile Val Pro Leu Asn Arg Ser Ser Ser Ser
                165                 170                 175

Asn Ser Ser Asp Tyr Tyr Arg Leu Ile Ser Cys Asn Thr Ser Ala Ile
            180                 185                 190

Thr Gln Ala Cys Pro Lys Val Thr Phe Asp Pro Ile Pro Ile His Tyr
        195                 200                 205

Cys Ala Pro Ala Gly Phe Ala Ile Leu Lys Cys Asn Asn Lys Thr Phe
    210                 215                 220

Asn Gly Thr Gly Pro Cys His Asn Val Ser Thr Val Gln Cys Thr His
225                 230                 235                 240

Gly Ile Lys Pro Val Val Ser Thr Gln Leu Leu Leu Asn Gly Ser Leu
                245                 250                 255

Ala Glu Lys Glu Ile Ile Ile Arg Ser Lys Asn Leu Ser Asp Asn Val
            260                 265                 270

Lys Thr Ile Ile Val His Leu Asn Glu Ser Val Glu Ile Val Cys Thr
        275                 280                 285

Arg Pro Asn Asn Asn Thr Arg Lys Ser Ile Arg Ile Gly Pro Gly Gln
    290                 295                 300

Thr Phe Tyr Ala Thr Gly Ala Ile Ile Gly Asn Ile Arg Glu Ala His
305                 310                 315                 320

Cys Asn Ile Ser Arg Asp Lys Trp Asn Glu Thr Leu Gln Arg Val Gly
                325                 330                 335

Lys Lys Leu Glu Glu Gln Phe Pro Asn Lys Thr Ile Asn Phe Thr Ser
            340                 345                 350

Ser Ser Gly Gly Asp Leu Glu Ile Thr Thr His Ser Phe Asn Cys Arg
        355                 360                 365

Gly Glu Phe Phe Tyr Cys Asn Thr Ser Lys Leu Phe Asn Ser Thr Tyr
    370                 375                 380

Ile Pro Thr Tyr Arg Pro Asn Asn Thr Gln Gly Asn Ser Ser Ser Thr
385                 390                 395                 400
```

```
Ile Thr Ile Pro Cys Arg Ile Lys Gln Ile Ile Asn Met Trp Gln Glu
            405                 410                 415

Val Gly Arg Ala Met Tyr Ala Pro Pro Ile Ala Gly Asn Ile Thr Cys
        420                 425                 430

Lys Ser His Ile Thr Gly Leu Leu Leu Val Arg Asp Gly Gly Thr Gly
    435                 440                 445

Leu Asn Ser Ser Thr Glu Thr Phe Arg Pro Gly Gly Gly Asp Met Arg
450                 455                 460

Asp Asn Trp Arg Ser Glu Leu Tyr Lys Tyr Lys Val Val Glu Ile Lys
465                 470                 475                 480

Pro Leu Gly Val Ala Pro Thr Ala Lys Arg Arg Val Val Gln Ser
                485                 490                 495

Glu Lys Ser Ala Val Gly Leu Gly Ala Val Phe Leu Gly Phe Leu Gly
            500                 505                 510

Ala Ala Gly Ser Thr Met Gly Ala Ala Ser Ile Thr Leu Thr Val Gln
        515                 520                 525

Ala Arg Gln Leu Leu Ser Gly Ile Val Gln Gln Ser Asn Leu Leu
    530                 535                 540

Arg Ala Ile Glu Ala Gln Gln His Met Leu Gln Leu Thr Val Trp Gly
545                 550                 555                 560

Ile Lys Gln Leu Gln Thr Arg Val Leu Ala Ile Glu Arg Tyr Leu Lys
                565                 570                 575

Asp Gln Gln Leu Leu Gly Ile Trp Gly Cys Ser Gly Lys Leu Ile Cys
            580                 585                 590

Thr Thr Ala Val Pro Trp Asn Thr Ser Trp Ser Asn Arg Ser Gln Ala
        595                 600                 605

Asp Ile Trp Gly Asn Met Thr Trp Met Gln Trp Asp Arg Glu Ile Ser
610                 615                 620

Asn Tyr Thr Asn Thr Ile Phe Arg Leu Leu Glu Asp Ser Gln Ile Gln
625                 630                 635                 640

Gln Glu Ser Asn Glu Lys Asp Leu Leu Ala Leu Asp Ser Trp Lys Asn
                645                 650                 655

Leu Trp Ser Trp Phe Asp Ile Thr Asn Trp Leu Trp Tyr Ile Lys Ile
            660                 665                 670

Phe Ile Met Ile Val Gly Gly Leu Ile Gly Leu Arg Ile Ile Phe Ala
        675                 680                 685

Val Leu Ser Ile Val Gly Gly Ala Lys Phe Val Ala Ala Trp Thr
    690                 695                 700

Leu Lys Ala Ala Ala Gly Gly Thr Glu Thr Ser Gln Val Ala Pro Ala
705                 710                 715                 720

<210> SEQ ID NO 47
<211> LENGTH: 1590
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (37)..(1557)

<400> SEQUENCE: 47
ccaagctggc tagcgtttaa acttaagctt gccacc atg cct atg ggc agc ctg        54
                                        Met Pro Met Gly Ser Leu
                                        1               5 cag cct ctg gcc acc ctg tac ctg ctg ggc atg ctg gtg gcc tcc gtg       102
Gln Pro Leu Ala Thr Leu Tyr Leu Leu Gly Met Leu Val Ala Ser Val
```

```
                  10               15                20
ctg gct gcc acc gag aac ctg tgg gtc aca gtg tac tac ggc gtg ccc    150
Leu Ala Ala Thr Glu Asn Leu Trp Val Thr Val Tyr Tyr Gly Val Pro
         25                  30                  35 gtg tgg aaa gag gcc acc acc acc ctg ttc tgc gcc tct gac gcc aag    198
Val Trp Lys Glu Ala Thr Thr Thr Leu Phe Cys Ala Ser Asp Ala Lys
 40                  45                  50 ggc tac gag aaa gag gtg cac aac gtc tgg gcc acc cac gcc tgc gtg    246
Gly Tyr Glu Lys Glu Val His Asn Val Trp Ala Thr His Ala Cys Val
 55                  60                  65                  70 ccc acc gac ccc aac cct cag gaa gtg gtc ctg gaa aac gtg acc gag    294
Pro Thr Asp Pro Asn Pro Gln Glu Val Val Leu Glu Asn Val Thr Glu
                 75                  80                  85 aac ttc aac atg tgg aag aac aac atg gtg gaa cag atg cac gag gac    342
Asn Phe Asn Met Trp Lys Asn Asn Met Val Glu Gln Met His Glu Asp
             90                  95                 100 atc atc agc ctg tgg gac cag agc ctg aag ccc tgc gtg aag ctg acc    390
Ile Ile Ser Leu Trp Asp Gln Ser Leu Lys Pro Cys Val Lys Leu Thr
        105                 110                 115 ccc ctg tgc gtg acc ctg aac tgc agc gac gtg aac acc acc tcc gtg    438
Pro Leu Cys Val Thr Leu Asn Cys Ser Asp Val Asn Thr Thr Ser Val
120                 125                 130 aat acc acc gcc agc agc atg gaa ggc ggc gag atc aag aac tgc agc    486
Asn Thr Thr Ala Ser Ser Met Glu Gly Gly Glu Ile Lys Asn Cys Ser
135                 140                 145                 150 ttc aac acc acc acc agc atg agc gac aag atg cag aaa gag tac gcc    534
Phe Asn Thr Thr Thr Ser Met Ser Asp Lys Met Gln Lys Glu Tyr Ala
                155                 160                 165 ctg ttc tac acc ctg gac gtg gtg ccc atc gtg aaa gag aac aac acc    582
Leu Phe Tyr Thr Leu Asp Val Val Pro Ile Val Lys Glu Asn Asn Thr
            170                 175                 180 tac cgg ctg atc agc tgc aac acc agc gtg atc acc cag gcc tgc ccc    630
Tyr Arg Leu Ile Ser Cys Asn Thr Ser Val Ile Thr Gln Ala Cys Pro
        185                 190                 195 aag gtg tcc ttc gag ccc atc ccc atc cac tac tgc gcc cct gcc ggc    678
Lys Val Ser Phe Glu Pro Ile Pro Ile His Tyr Cys Ala Pro Ala Gly
200                 205                 210 ttc gcc atc ctg atg tgc aac aac aag acc ttc gac ggc aag ggc ccc    726
Phe Ala Ile Leu Met Cys Asn Asn Lys Thr Phe Asp Gly Lys Gly Pro
215                 220                 225                 230 tgc aac aac gtg tcc acc gtg cag tgc acc cac ggc atc aag ccc gtg    774
Cys Asn Asn Val Ser Thr Val Gln Cys Thr His Gly Ile Lys Pro Val
                235                 240                 245 gtg tcc acc cag ctg ctg ctg aat ggc agc ctg gcc gaa gag gaa gtg    822
Val Ser Thr Gln Leu Leu Leu Asn Gly Ser Leu Ala Glu Glu Glu Val
            250                 255                 260 gtc atc aga agc gac aac ttc acc gac aac gcc aag acc atc atc gtg    870
Val Ile Arg Ser Asp Asn Phe Thr Asp Asn Ala Lys Thr Ile Ile Val
        265                 270                 275 cac ctg aac gag agc atc gag atc acc tgt acc cgg ccc aac aac aac    918
His Leu Asn Glu Ser Ile Glu Ile Thr Cys Thr Arg Pro Asn Asn Asn
    280                 285                 290 acc agc aag agc atc acc atc ggc cct ggc aga gcc ttc tac gcc acc    966
Thr Ser Lys Ser Ile Thr Ile Gly Pro Gly Arg Ala Phe Tyr Ala Thr
295                 300                 305                 310 ggc cgg atc atc ggc gac atc aga aag gcc cac tgc aac atc agc ggc   1014
Gly Arg Ile Ile Gly Asp Ile Arg Lys Ala His Cys Asn Ile Ser Gly
                315                 320                 325 gag aag tgg cac aac gcc ctg gaa cag atc gtg aag aag ctg ggc gag   1062
Glu Lys Trp His Asn Ala Leu Glu Gln Ile Val Lys Lys Leu Gly Glu
```

```
                    330                 335                 340
aag ttc gag aac gcc acc acc atc cgg ttc aac cag agc agc gga ggc       1110
Lys Phe Glu Asn Ala Thr Thr Ile Arg Phe Asn Gln Ser Ser Gly Gly
        345                 350                 355 gac cag gaa atc gtg atg cac acc ttc aac tgt ggc ggc gag ttc ttc       1158
Asp Gln Glu Ile Val Met His Thr Phe Asn Cys Gly Gly Glu Phe Phe
360                 365                 370 tac tgc aac agc acc cag ctg ttc aac agc acc tgg tgg ccc aac ggc       1206
Tyr Cys Asn Ser Thr Gln Leu Phe Asn Ser Thr Trp Trp Pro Asn Gly
375                 380                 385                 390 acc acc acc gag tgg tcc aac gag aca agc aat ggc acc atc acc ctg       1254
Thr Thr Thr Glu Trp Ser Asn Glu Thr Ser Asn Gly Thr Ile Thr Leu
                395                 400                 405 ccc tgc cgg atc aag cag atc atc aat atg tgg cag gaa gtg ggc aag       1302
Pro Cys Arg Ile Lys Gln Ile Ile Asn Met Trp Gln Glu Val Gly Lys
            410                 415                 420 gct atg tac gcc cct ccc atc agc ggc ccc atc agc tgc tcc agc aac       1350
Ala Met Tyr Ala Pro Pro Ile Ser Gly Pro Ile Ser Cys Ser Ser Asn
                425                 430                 435 atc acc ggc ctg ctc ctc gtc cgc gac ggc ggc aac gac aac gag act       1398
Ile Thr Gly Leu Leu Leu Val Arg Asp Gly Gly Asn Asp Asn Glu Thr
440                 445                 450 aac ggc acc gag aca ttc aga ccc gga gga ggc gat atg cgg gac aac       1446
Asn Gly Thr Glu Thr Phe Arg Pro Gly Gly Gly Asp Met Arg Asp Asn
455                 460                 465                 470 tgg cgg agc gag ctg tac aag tac aag gtg gtc aaa atc gag ccc ctg       1494
Trp Arg Ser Glu Leu Tyr Lys Tyr Lys Val Val Lys Ile Glu Pro Leu
                475                 480                 485 ggc gtg gcc ccc acc aag gcc aag aga aga gtg gtg cag ggc gcc cac       1542
Gly Val Ala Pro Thr Lys Ala Lys Arg Arg Val Val Gln Gly Ala His
                490                 495                 500 cac cac cat cac cac tgactcgagt ctagagggcc cgtttaaacc cgc              1590
His His His His His
        505

<210> SEQ ID NO 48
<211> LENGTH: 507
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Pro Met Gly Ser Leu Gln Pro Leu Ala Thr Leu Tyr Leu Leu Gly
1               5                   10                  15

Met Leu Val Ala Ser Val Leu Ala Ala Thr Glu Asn Leu Trp Val Thr
            20                  25                  30

Val Tyr Tyr Gly Val Pro Val Trp Lys Glu Ala Thr Thr Thr Leu Phe
        35                  40                  45

Cys Ala Ser Asp Ala Lys Gly Tyr Glu Lys Glu Val His Asn Val Trp
    50                  55                  60

Ala Thr His Ala Cys Val Pro Thr Asp Pro Asn Pro Gln Glu Val Val
65                  70                  75                  80

Leu Glu Asn Val Thr Glu Asn Phe Asn Met Trp Lys Asn Asn Met Val
                85                  90                  95

Glu Gln Met His Glu Asp Ile Ile Ser Leu Trp Asp Gln Ser Leu Lys
            100                 105                 110

Pro Cys Val Lys Leu Thr Pro Leu Cys Val Thr Leu Asn Cys Ser Asp
        115                 120                 125
```

Val Asn Thr Thr Ser Val Asn Thr Thr Ala Ser Ser Met Glu Gly Gly
            130                 135                 140

Glu Ile Lys Asn Cys Ser Phe Asn Thr Thr Thr Ser Met Ser Asp Lys
145                 150                 155                 160

Met Gln Lys Glu Tyr Ala Leu Phe Tyr Thr Leu Asp Val Val Pro Ile
                165                 170                 175

Val Lys Glu Asn Asn Thr Tyr Arg Leu Ile Ser Cys Asn Thr Ser Val
            180                 185                 190

Ile Thr Gln Ala Cys Pro Lys Val Ser Phe Glu Pro Ile Pro Ile His
        195                 200                 205

Tyr Cys Ala Pro Ala Gly Phe Ala Ile Leu Met Cys Asn Asn Lys Thr
        210                 215                 220

Phe Asp Gly Lys Gly Pro Cys Asn Asn Val Ser Thr Val Gln Cys Thr
225                 230                 235                 240

His Gly Ile Lys Pro Val Val Ser Thr Gln Leu Leu Leu Asn Gly Ser
                245                 250                 255

Leu Ala Glu Glu Glu Val Val Ile Arg Ser Asp Asn Phe Thr Asp Asn
            260                 265                 270

Ala Lys Thr Ile Ile Val His Leu Asn Glu Ser Ile Glu Ile Thr Cys
        275                 280                 285

Thr Arg Pro Asn Asn Asn Thr Ser Lys Ser Ile Thr Ile Gly Pro Gly
        290                 295                 300

Arg Ala Phe Tyr Ala Thr Gly Arg Ile Ile Gly Asp Ile Arg Lys Ala
305                 310                 315                 320

His Cys Asn Ile Ser Gly Glu Lys Trp His Asn Ala Leu Glu Gln Ile
                325                 330                 335

Val Lys Lys Leu Gly Glu Lys Phe Glu Asn Ala Thr Thr Ile Arg Phe
            340                 345                 350

Asn Gln Ser Ser Gly Gly Asp Gln Glu Ile Val Met His Thr Phe Asn
        355                 360                 365

Cys Gly Gly Glu Phe Phe Tyr Cys Asn Ser Thr Gln Leu Phe Asn Ser
        370                 375                 380

Thr Trp Trp Pro Asn Gly Thr Thr Thr Glu Trp Ser Asn Glu Thr Ser
385                 390                 395                 400

Asn Gly Thr Ile Thr Leu Pro Cys Arg Ile Lys Gln Ile Ile Asn Met
                405                 410                 415

Trp Gln Glu Val Gly Lys Ala Met Tyr Ala Pro Pro Ile Ser Gly Pro
            420                 425                 430

Ile Ser Cys Ser Ser Asn Ile Thr Gly Leu Leu Leu Val Arg Asp Gly
        435                 440                 445

Gly Asn Asp Asn Glu Thr Asn Gly Thr Glu Thr Phe Arg Pro Gly Gly
        450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Lys Ala Lys Arg Arg
                485                 490                 495

Val Val Gln Gly Ala His His His His His
            500                 505

<210> SEQ ID NO 49
<211> LENGTH: 1799
<212> TYPE: DNA
<213> ORGANISM: Artificial Sequence
<220> FEATURE:
<223> OTHER INFORMATION: Description of Artificial Sequence: Synthetic

```
        polynucleotide
<220> FEATURE:
<221> NAME/KEY: CDS
<222> LOCATION: (53)..(1750)

<400> SEQUENCE: 49
ctcactatag ggagacccaa gctggctagc gtttaaactt aagcttgcca cc atg cct       58
                                                          Met Pro
                                                           1 atg ggc agc ctg cag cct ctg gcc acc ctg tac ctg ctg ggc atg ctg        106
Met Gly Ser Leu Gln Pro Leu Ala Thr Leu Tyr Leu Leu Gly Met Leu
         5                  10                  15 gtg gcc tcc gtg ctg gca gct ggc aac ctg tgg gtc aca gtg tac tac        154
Val Ala Ser Val Leu Ala Ala Gly Asn Leu Trp Val Thr Val Tyr Tyr
     20                  25                  30 ggc gtg ccc gtg tgg aaa gag gcc aag acc acc ctg ttc tgc gcc agc        202
Gly Val Pro Val Trp Lys Glu Ala Lys Thr Thr Leu Phe Cys Ala Ser
 35                  40                  45                  50 gac gcc aag gcc tac gag aaa gag gtg cac aac gtc tgg gcc acc cac        250
Asp Ala Lys Ala Tyr Glu Lys Glu Val His Asn Val Trp Ala Thr His
                 55                  60                  65 gcc tgc gtg ccc acc gac ccc aac ccc cag gaa atg gtc ctg gaa aac        298
Ala Cys Val Pro Thr Asp Pro Asn Pro Gln Glu Met Val Leu Glu Asn
             70                  75                  80 gtg acc gag aac ttc aac atg tgg aag aac gac atg gtg gaa cag atg        346
Val Thr Glu Asn Phe Asn Met Trp Lys Asn Asp Met Val Glu Gln Met
         85                  90                  95 cac gag gac gtg atc agc ctg tgg gac cag agc ctg aag ccc tgc gtg        394
His Glu Asp Val Ile Ser Leu Trp Asp Gln Ser Leu Lys Pro Cys Val
    100                 105                 110 aag ctg acc ccc ctg tgc gtg acc ctg gaa tgc aga cag gtc aac acc        442
Lys Leu Thr Pro Leu Cys Val Thr Leu Glu Cys Arg Gln Val Asn Thr
115                 120                 125                 130 acc aac gcc acc agc agc gtg aac gtg acc aac ggc gag gaa atc aag        490
Thr Asn Ala Thr Ser Ser Val Asn Val Thr Asn Gly Glu Glu Ile Lys
                135                 140                 145 aac tgc agc ttc aat gcc acc acc gag atc cgg gac aag aaa cag aag        538
Asn Cys Ser Phe Asn Ala Thr Thr Glu Ile Arg Asp Lys Lys Gln Lys
            150                 155                 160 gtg tac gcc ctg ttc tac cgg ctg gac atc gtg ccc ctg gaa gag gaa        586
Val Tyr Ala Leu Phe Tyr Arg Leu Asp Ile Val Pro Leu Glu Glu Glu
        165                 170                 175 cgg aag ggc aac agc agc aag tac cgg ctg atc aac tgc aac acc agc        634
Arg Lys Gly Asn Ser Ser Lys Tyr Arg Leu Ile Asn Cys Asn Thr Ser
    180                 185                 190 gcc atc acc cag gcc tgc ccc aaa gtg acc ttc gac cct atc ccc atc        682
Ala Ile Thr Gln Ala Cys Pro Lys Val Thr Phe Asp Pro Ile Pro Ile
195                 200                 205                 210 cac tac tgc gcc cct gcc ggc tac gcc atc ctg aag tgc aac aac aag        730
His Tyr Cys Ala Pro Ala Gly Tyr Ala Ile Leu Lys Cys Asn Asn Lys
                215                 220                 225 acc ttc aac ggc acc ggc ccc tgc aac aac gtg tcc acc gtg cag tgc        778
Thr Phe Asn Gly Thr Gly Pro Cys Asn Asn Val Ser Thr Val Gln Cys
            230                 235                 240 acc cac ggc atc aag ccc gtg gtg tcc acc cag ctg ctg aat ggc              826
Thr His Gly Ile Lys Pro Val Val Ser Thr Gln Leu Leu Leu Asn Gly
        245                 250                 255 agc ctg gcc gag ggc gag atc atc atc aga agc gag aac ctg acc aac        874
Ser Leu Ala Glu Gly Glu Ile Ile Ile Arg Ser Glu Asn Leu Thr Asn
    260                 265                 270 aac gtg aaa acc atc atc gtg cac ctg aac gag agc gtg gaa atc gtg        922
```

```
Asn Val Lys Thr Ile Ile Val His Leu Asn Glu Ser Val Glu Ile Val
275                 280                 285                 290 tgc acc cgg ccc aac aac aac acc aga aag agc atc cgg atc ggc cct      970
Cys Thr Arg Pro Asn Asn Asn Thr Arg Lys Ser Ile Arg Ile Gly Pro
                    295                 300                 305 ggc cag acc ttt tac gcc acc ggc gac atc atc ggc aac atc cgg cag     1018
Gly Gln Thr Phe Tyr Ala Thr Gly Asp Ile Ile Gly Asn Ile Arg Gln
            310                 315                 320 gcc tac tgc aac atc aag aag gac gac tgg atc cgg acc ctg cag aga     1066
Ala Tyr Cys Asn Ile Lys Lys Asp Asp Trp Ile Arg Thr Leu Gln Arg
        325                 330                 335 gtg ggc aag aag ctg gcc gag cac ttc ccc aga cgg atc atc aac ttc     1114
Val Gly Lys Lys Leu Ala Glu His Phe Pro Arg Arg Ile Ile Asn Phe
    340                 345                 350 acc agc ccc gct ggc ggc gac ctg gaa atc acc acc cac agc ttc aac     1162
Thr Ser Pro Ala Gly Gly Asp Leu Glu Ile Thr Thr His Ser Phe Asn
355                 360                 365                 370 tgc aga ggc gag ttc ttc tac tgc aat acc agc agc ctg ttc aac agc     1210
Cys Arg Gly Glu Phe Phe Tyr Cys Asn Thr Ser Ser Leu Phe Asn Ser
                375                 380                 385 acc tac aac ccc aac gac acc aac agc aac agc tcc agc agc aac tcc     1258
Thr Tyr Asn Pro Asn Asp Thr Asn Ser Asn Ser Ser Ser Ser Asn Ser
            390                 395                 400 agc ctg gac atc acc atc cct tgc cgg atc aag cag atc atc aat atg     1306
Ser Leu Asp Ile Thr Ile Pro Cys Arg Ile Lys Gln Ile Ile Asn Met
        405                 410                 415 tgg cag gaa gtg ggc agg gct atg tac gcc cct ccc atc gag ggc aac     1354
Trp Gln Glu Val Gly Arg Ala Met Tyr Ala Pro Pro Ile Glu Gly Asn
    420                 425                 430 atc aca tgc aag agc aac atc acc ggc ctg ctc ctg gtc cgc gac ggc     1402
Ile Thr Cys Lys Ser Asn Ile Thr Gly Leu Leu Leu Val Arg Asp Gly
435                 440                 445                 450 ggc gtg gaa agc aac gag aca gag atc ttc aga ccc ggc gga ggc gac     1450
Gly Val Glu Ser Asn Glu Thr Glu Ile Phe Arg Pro Gly Gly Gly Asp
                455                 460                 465 atg cgg aac aac tgg cgg agc gag ctg tac aag tac aag gtg gtg gaa     1498
Met Arg Asn Asn Trp Arg Ser Glu Leu Tyr Lys Tyr Lys Val Val Glu
            470                 475                 480 atc aag ccc ctg gga atc gcc ccc acc gcc gcc aag cgg aga gtg gtg     1546
Ile Lys Pro Leu Gly Ile Ala Pro Thr Ala Ala Lys Arg Arg Val Val
        485                 490                 495 gaa ggc ggc gaa cag aac gag aag gac ctg ctg gcc ctg gac agc tgg     1594
Glu Gly Gly Glu Gln Asn Glu Lys Asp Leu Leu Ala Leu Asp Ser Trp
    500                 505                 510 gag aac ctg tgg aac tgg ttc agc atc acc aag tgg ctg tgg tac atc     1642
Glu Asn Leu Trp Asn Trp Phe Ser Ile Thr Lys Trp Leu Trp Tyr Ile
515                 520                 525                 530 aag atc ttc atc atg atc gtg ggc ggc ctg atc ggc ctg cgg atc atc     1690
Lys Ile Phe Ile Met Ile Val Gly Gly Leu Ile Gly Leu Arg Ile Ile
                535                 540                 545 ttc gcc gtg ctg agc gtg gtg aac aga gtg cgg cag ggc gcc cac cac     1738
Phe Ala Val Leu Ser Val Val Asn Arg Val Arg Gln Gly Ala His His
            550                 555                 560 cac cat cac cac tgactcgagt ctagagggcc cgtttaaacc cgctgatcag         1790
His His His His
        565 cctcgactg                                                           1799

<210> SEQ ID NO 50
<211> LENGTH: 566
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

```
Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
            20                  25                  30

Tyr Tyr Gly Val Pro Val Trp Lys Glu Ala Lys Thr Thr Leu Phe Cys
        35                  40                  45

Ala Ser Asp Ala Lys Ala Tyr Glu Lys Glu Val His Asn Val Trp Ala
    50                  55                  60

Thr His Ala Cys Val Pro Thr Asp Pro Asn Pro Gln Glu Met Val Leu
65                  70                  75                  80

Glu Asn Val Thr Glu Asn Phe Asn Met Trp Lys Asn Asp Met Val Glu
                85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu Glu Cys Arg Gln Val
        115                 120                 125

Asn Thr Thr Asn Ala Thr Ser Ser Val Asn Val Thr Asn Gly Glu Glu
    130                 135                 140

Ile Lys Asn Cys Ser Phe Asn Ala Thr Thr Glu Ile Arg Asp Lys Lys
145                 150                 155                 160

Gln Lys Val Tyr Ala Leu Phe Tyr Arg Leu Asp Ile Val Pro Leu Glu
                165                 170                 175

Glu Glu Arg Lys Gly Asn Ser Ser Lys Tyr Arg Leu Ile Asn Cys Asn
            180                 185                 190

Thr Ser Ala Ile Thr Gln Ala Cys Pro Lys Val Thr Phe Asp Pro Ile
        195                 200                 205

Pro Ile His Tyr Cys Ala Pro Ala Gly Tyr Ala Ile Leu Lys Cys Asn
    210                 215                 220

Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Gly Glu Ile Ile Arg Ser Glu Asn Leu
            260                 265                 270

Thr Asn Asn Val Lys Thr Ile Ile Val His Leu Asn Glu Ser Val Glu
        275                 280                 285

Ile Val Cys Thr Arg Pro Asn Asn Asn Thr Arg Lys Ser Ile Arg Ile
    290                 295                 300

Gly Pro Gly Gln Thr Phe Tyr Ala Thr Gly Asp Ile Ile Gly Asn Ile
305                 310                 315                 320

Arg Gln Ala Tyr Cys Asn Ile Lys Lys Asp Asp Trp Ile Arg Thr Leu
                325                 330                 335

Gln Arg Val Gly Lys Lys Leu Ala Glu His Phe Pro Arg Arg Ile Ile
            340                 345                 350

Asn Phe Thr Ser Pro Ala Gly Gly Asp Leu Glu Ile Thr Thr His Ser
        355                 360                 365

Phe Asn Cys Arg Gly Glu Phe Phe Tyr Cys Asn Thr Ser Ser Leu Phe
    370                 375                 380
```

```
Asn Ser Thr Tyr Asn Pro Asn Asp Thr Asn Ser Asn Ser Ser Ser Ser
385                 390                 395                 400

Asn Ser Ser Leu Asp Ile Thr Ile Pro Cys Arg Ile Lys Gln Ile Ile
            405                 410                 415

Asn Met Trp Gln Glu Val Gly Arg Ala Met Tyr Ala Pro Pro Ile Glu
        420                 425                 430

Gly Asn Ile Thr Cys Lys Ser Asn Ile Thr Gly Leu Leu Leu Val Arg
            435                 440                 445

Asp Gly Gly Val Glu Ser Asn Glu Thr Glu Ile Phe Arg Pro Gly Gly
        450                 455                 460

Gly Asp Met Arg Asn Asn Trp Arg Ser Glu Leu Tyr Lys Tyr Lys Val
465                 470                 475                 480

Val Glu Ile Lys Pro Leu Gly Ile Ala Pro Thr Ala Ala Lys Arg Arg
                485                 490                 495

Val Val Glu Gly Gly Glu Gln Asn Glu Lys Asp Leu Leu Ala Leu Asp
            500                 505                 510

Ser Trp Glu Asn Leu Trp Asn Trp Phe Ser Ile Thr Lys Trp Leu Trp
        515                 520                 525

Tyr Ile Lys Ile Phe Ile Met Ile Val Gly Gly Leu Ile Gly Leu Arg
            530                 535                 540

Ile Ile Phe Ala Val Leu Ser Val Val Asn Arg Val Arg Gln Gly Ala
545                 550                 555                 560

His His His His His His
                565

<210> SEQ ID NO 51
<211> LENGTH: 1667
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (53)..(1618)

<400> SEQUENCE: 51
ctcactatag ggagacccaa gctggctagc gtttaaactt aagcttgcca cc atg cct         58
                                                          Met Pro
                                                           1 atg ggc agc ctg cag cct ctg gcc acc ctg tac ctg ctg ggc atg ctg        106
Met Gly Ser Leu Gln Pro Leu Ala Thr Leu Tyr Leu Leu Gly Met Leu
         5                  10                  15 gtg gcc tcc gtg ctg gca gct ggc aac ctg tgg gtc aca gtg tac tac        154
Val Ala Ser Val Leu Ala Ala Gly Asn Leu Trp Val Thr Val Tyr Tyr
     20                  25                  30 ggc gtg ccc gtg tgg aaa gag gcc aag acc acc ctg ttc tgc gcc agc        202
Gly Val Pro Val Trp Lys Glu Ala Lys Thr Thr Leu Phe Cys Ala Ser
 35                  40                  45                  50 gac gcc aag gcc tac gag aaa gag gtg cac aac gtc tgg gcc acc cac        250
Asp Ala Lys Ala Tyr Glu Lys Glu Val His Asn Val Trp Ala Thr His
                 55                  60                  65 gcc tgc gtg ccc acc gac ccc aac ccc cag gaa atg gtc ctg gaa aac        298
Ala Cys Val Pro Thr Asp Pro Asn Pro Gln Glu Met Val Leu Glu Asn
             70                  75                  80 gtg acc gag aac ttc aac atg tgg aag aac gac atg gtg gaa cag atg        346
Val Thr Glu Asn Phe Asn Met Trp Lys Asn Asp Met Val Glu Gln Met
         85                  90                  95 cac gag gac gtg atc agc ctg tgg gac cag agc ctg aag ccc tgc gtg        394
His Glu Asp Val Ile Ser Leu Trp Asp Gln Ser Leu Lys Pro Cys Val
```

-continued

```
                100                 105                 110
aag ctg acc ccc ctg tgc gtg acc ctg gaa tgc aga cag gtc aac acc      442
Lys Leu Thr Pro Leu Cys Val Thr Leu Glu Cys Arg Gln Val Asn Thr
115                 120                 125                 130 acc aac gcc acc agc agc gtg aac gtg acc aac ggc gag gaa atc aag      490
Thr Asn Ala Thr Ser Ser Val Asn Val Thr Asn Gly Glu Glu Ile Lys
                135                 140                 145 aac tgc agc ttc aat gcc acc acc gag atc cgg gac aag aaa cag aag      538
Asn Cys Ser Phe Asn Ala Thr Thr Glu Ile Arg Asp Lys Lys Gln Lys
            150                 155                 160 gtg tac gcc ctg ttc tac cgg ctg gac atc gtg ccc ctg gaa gag gaa      586
Val Tyr Ala Leu Phe Tyr Arg Leu Asp Ile Val Pro Leu Glu Glu Glu
        165                 170                 175 cgg aag ggc aac agc agc aag tac cgg ctg atc aac tgc aac acc agc      634
Arg Lys Gly Asn Ser Ser Lys Tyr Arg Leu Ile Asn Cys Asn Thr Ser
    180                 185                 190 gcc atc acc cag gcc tgc ccc aaa gtg acc ttc gac cct atc ccc atc      682
Ala Ile Thr Gln Ala Cys Pro Lys Val Thr Phe Asp Pro Ile Pro Ile
195                 200                 205                 210 cac tac tgc gcc cct gcc ggc tac gcc atc ctg aag tgc aac aac aag      730
His Tyr Cys Ala Pro Ala Gly Tyr Ala Ile Leu Lys Cys Asn Asn Lys
                215                 220                 225 acc ttc aac ggc acc ggc ccc tgc aac aac gtg tcc acc gtg cag tgc      778
Thr Phe Asn Gly Thr Gly Pro Cys Asn Asn Val Ser Thr Val Gln Cys
            230                 235                 240 acc cac ggc atc aag ccc gtg gtg tcc acc cag ctg ctg ctg aat ggc      826
Thr His Gly Ile Lys Pro Val Val Ser Thr Gln Leu Leu Leu Asn Gly
        245                 250                 255 agc ctg gcc gag ggc gag atc atc atc aga agc gag aac ctg acc aac      874
Ser Leu Ala Glu Gly Glu Ile Ile Ile Arg Ser Glu Asn Leu Thr Asn
    260                 265                 270 aac gtg aaa acc atc atc gtg cac ctg aac gag agc gtg gaa atc gtg      922
Asn Val Lys Thr Ile Ile Val His Leu Asn Glu Ser Val Glu Ile Val
275                 280                 285                 290 tgc acc cgg ccc aac aac aac acc aga aag agc atc cgg atc ggc cct      970
Cys Thr Arg Pro Asn Asn Asn Thr Arg Lys Ser Ile Arg Ile Gly Pro
                295                 300                 305 ggc cag acc ttt tac gcc acc ggc gac atc atc ggc aac atc cgg cag     1018
Gly Gln Thr Phe Tyr Ala Thr Gly Asp Ile Ile Gly Asn Ile Arg Gln
            310                 315                 320 gcc tac tgc aac atc aag aag gac gac tgg atc cgg acc ctg cag aga     1066
Ala Tyr Cys Asn Ile Lys Lys Asp Asp Trp Ile Arg Thr Leu Gln Arg
        325                 330                 335 gtg ggc aag aag ctg gcc gag cac ttc ccc aga cgg atc atc aac ttc     1114
Val Gly Lys Lys Leu Ala Glu His Phe Pro Arg Arg Ile Ile Asn Phe
    340                 345                 350 acc agc ccc gct ggc ggc gac ctg gaa atc acc acc cac agc ttc aac     1162
Thr Ser Pro Ala Gly Gly Asp Leu Glu Ile Thr Thr His Ser Phe Asn
355                 360                 365                 370 tgc aga ggc gag ttc ttc tac tgc aat acc agc agc ctg ttc aac agc     1210
Cys Arg Gly Glu Phe Phe Tyr Cys Asn Thr Ser Ser Leu Phe Asn Ser
                375                 380                 385 acc tac aac ccc aac gac acc aac agc aac agc tcc agc agc aac tcc     1258
Thr Tyr Asn Pro Asn Asp Thr Asn Ser Asn Ser Ser Ser Ser Asn Ser
            390                 395                 400 agc ctg gac atc acc atc cct tgc cgg atc aag cag atc atc aat atg     1306
Ser Leu Asp Ile Thr Ile Pro Cys Arg Ile Lys Gln Ile Ile Asn Met
        405                 410                 415 tgg cag gaa gtg ggc agg gct atg tac gcc cct ccc atc gag ggc aac     1354
Trp Gln Glu Val Gly Arg Ala Met Tyr Ala Pro Pro Ile Glu Gly Asn
```

```
                420                 425                 430
atc aca tgc aag agc aac atc acc ggc ctg ctc ctg gtc cgc gac ggc      1402
Ile Thr Cys Lys Ser Asn Ile Thr Gly Leu Leu Leu Val Arg Asp Gly
435                 440                 445                 450 ggc gtg gaa agc aac gag aca gag atc ttc aga ccc gga ggc gac          1450
Gly Val Glu Ser Asn Glu Thr Glu Ile Phe Arg Pro Gly Gly Gly Asp
                455                 460                 465 atg cgg aac aac tgg cgg agc gag ctg tac aag tac aag gtg gtg gaa      1498
Met Arg Asn Asn Trp Arg Ser Glu Leu Tyr Lys Tyr Lys Val Val Glu
                470                 475                 480 atc aag ccc ctg gga atc gcc ccc acc gcc gcc aag cgg aga gtg gtg      1546
Ile Lys Pro Leu Gly Ile Ala Pro Thr Ala Ala Lys Arg Arg Val Val
                485                 490                 495 gaa ggc gct cac cac cac cat cac cac ggc ctg aac gac atc ttc gag      1594
Glu Gly Ala His His His His His His Gly Leu Asn Asp Ile Phe Glu
500                 505                 510 gcc cag aaa atc gag tgg cac gag tgactcgagt ctagagggcc cgtttaaacc     1648
Ala Gln Lys Ile Glu Trp His Glu
515                 520 cgctgatcag cctcgactg                                                 1667

<210> SEQ ID NO 52
<211> LENGTH: 522
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
                20                  25                  30

Tyr Tyr Gly Val Pro Val Trp Lys Glu Ala Lys Thr Thr Leu Phe Cys
            35                  40                  45

Ala Ser Asp Ala Lys Ala Tyr Glu Lys Glu Val His Asn Val Trp Ala
        50                  55                  60

Thr His Ala Cys Val Pro Thr Asp Pro Asn Pro Gln Glu Met Val Leu
65                  70                  75                  80

Glu Asn Val Thr Glu Asn Phe Asn Met Trp Lys Asn Asp Met Val Glu
                85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu Glu Cys Arg Gln Val
        115                 120                 125

Asn Thr Thr Asn Ala Thr Ser Ser Val Asn Val Thr Asn Gly Glu Glu
130                 135                 140

Ile Lys Asn Cys Ser Phe Asn Ala Thr Thr Glu Ile Arg Asp Lys Lys
145                 150                 155                 160

Gln Lys Val Tyr Ala Leu Phe Tyr Arg Leu Asp Ile Val Pro Leu Glu
                165                 170                 175

Glu Glu Arg Lys Gly Asn Ser Ser Lys Tyr Arg Leu Ile Asn Cys Asn
            180                 185                 190

Thr Ser Ala Ile Thr Gln Ala Cys Pro Lys Val Thr Phe Asp Pro Ile
        195                 200                 205

Pro Ile His Tyr Cys Ala Pro Ala Gly Tyr Ala Ile Leu Lys Cys Asn
210                 215                 220
```

```
Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu Leu
            245                 250                 255

Asn Gly Ser Leu Ala Glu Gly Glu Ile Ile Arg Ser Glu Asn Leu
        260                 265                 270

Thr Asn Asn Val Lys Thr Ile Ile Val His Leu Asn Glu Ser Val Glu
            275                 280                 285

Ile Val Cys Thr Arg Pro Asn Asn Asn Thr Arg Lys Ser Ile Arg Ile
290                 295                 300

Gly Pro Gly Gln Thr Phe Tyr Ala Thr Gly Asp Ile Ile Gly Asn Ile
305                 310                 315                 320

Arg Gln Ala Tyr Cys Asn Ile Lys Lys Asp Asp Trp Ile Arg Thr Leu
                325                 330                 335

Gln Arg Val Gly Lys Lys Leu Ala Glu His Phe Pro Arg Arg Ile Ile
            340                 345                 350

Asn Phe Thr Ser Pro Ala Gly Gly Asp Leu Glu Ile Thr Thr His Ser
        355                 360                 365

Phe Asn Cys Arg Gly Glu Phe Phe Tyr Cys Asn Thr Ser Ser Leu Phe
370                 375                 380

Asn Ser Thr Tyr Asn Pro Asn Asp Thr Asn Ser Asn Ser Ser Ser Ser
385                 390                 395                 400

Asn Ser Ser Leu Asp Ile Thr Ile Pro Cys Arg Ile Lys Gln Ile Ile
                405                 410                 415

Asn Met Trp Gln Glu Val Gly Arg Ala Met Tyr Ala Pro Pro Ile Glu
            420                 425                 430

Gly Asn Ile Thr Cys Lys Ser Asn Ile Thr Gly Leu Leu Leu Val Arg
        435                 440                 445

Asp Gly Gly Val Glu Ser Asn Glu Thr Glu Ile Phe Arg Pro Gly Gly
450                 455                 460

Gly Asp Met Arg Asn Asn Trp Arg Ser Glu Leu Tyr Lys Tyr Lys Val
465                 470                 475                 480

Val Glu Ile Lys Pro Leu Gly Ile Ala Pro Thr Ala Ala Lys Arg Arg
                485                 490                 495

Val Val Glu Gly Ala His His His His His His Gly Leu Asn Asp Ile
            500                 505                 510

Phe Glu Ala Gln Lys Ile Glu Trp His Glu
        515                 520

<210> SEQ ID NO 53
<211> LENGTH: 1667
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (53)..(1618)

<400> SEQUENCE: 53
ctcactatag ggagacccaa gctggctagc gtttaaactt aagcttgcca cc atg cct      58
                                                          Met Pro
                                                          1 atg ggc agc ctg cag cct ctg gcc acc ctg tac ctg ctg ggc atg ctg      106
Met Gly Ser Leu Gln Pro Leu Ala Thr Leu Tyr Leu Leu Gly Met Leu
        5                  10                  15
```

-continued

| | | |
|---|---|---|
| gtg gcc tcc gtg ctg gca gct ggc aac ctg tgg gtc aca gtg tac tac<br>Val Ala Ser Val Leu Ala Ala Gly Asn Leu Trp Val Thr Val Tyr Tyr<br>20                                    25                              30 | | 154 |
| ggc gtg ccc gtg tgg aaa gag gcc aag acc acc ctg ttc tgc gcc agc<br>Gly Val Pro Val Trp Lys Glu Ala Lys Thr Thr Leu Phe Cys Ala Ser<br>35                                     40                        45                        50 | | 202 |
| gac gcc aag gcc tac gag aaa gag gtg cac aac gtc tgg gcc acc cac<br>Asp Ala Lys Ala Tyr Glu Lys Glu Val His Asn Val Trp Ala Thr His<br>                          55                        60                        65 | | 250 |
| gcc tgc gtg ccc acc gac ccc aac ccc cag gaa atg gtc ctg gaa aac<br>Ala Cys Val Pro Thr Asp Pro Asn Pro Gln Glu Met Val Leu Glu Asn<br>                  70                        75                                  80 | | 298 |
| gtg acc gag aac ttc aac atg tgg aag aac gac atg gtg gaa cag atg<br>Val Thr Glu Asn Phe Asn Met Trp Lys Asn Asp Met Val Glu Gln Met<br>                85                        90                        95 | | 346 |
| cac gag gac gtg atc agc ctg tgg gac cag agc ctg aag ccc tgc gtg<br>His Glu Asp Val Ile Ser Leu Trp Asp Gln Ser Leu Lys Pro Cys Val<br>100                               105                        110 | | 394 |
| aag ctg acc ccc ctg tgc gtg acc ctg gaa tgc aga cag gtc aac acc<br>Lys Leu Thr Pro Leu Cys Val Thr Leu Glu Cys Arg Gln Val Asn Thr<br>115                               120                        125                        130 | | 442 |
| acc aac gcc acc agc agc gtg aac gtg acc aac ggc gag gaa atc aag<br>Thr Asn Ala Thr Ser Ser Val Asn Val Thr Asn Gly Glu Glu Ile Lys<br>                              135                        140                        145 | | 490 |
| aac tgc agc ttc aag gcc acc acc gag atc cgg gac aag aaa cag aag<br>Asn Cys Ser Phe Lys Ala Thr Thr Glu Ile Arg Asp Lys Lys Gln Lys<br>                              150                        155                        160 | | 538 |
| gtg tac gcc ctg ttc tac cgg ctg gac atc gtg ccc ctg gaa gag gaa<br>Val Tyr Ala Leu Phe Tyr Arg Leu Asp Ile Val Pro Leu Glu Glu Glu<br>165                               170                        175 | | 586 |
| cgg aag ggc aac agc agc aag tac cgg ctg atc aac tgc aac acc agc<br>Arg Lys Gly Asn Ser Ser Lys Tyr Arg Leu Ile Asn Cys Asn Thr Ser<br>180                               185                        190 | | 634 |
| gcc atc acc cag gcc tgc ccc aaa gtg acc ttc gac cct atc ccc atc<br>Ala Ile Thr Gln Ala Cys Pro Lys Val Thr Phe Asp Pro Ile Pro Ile<br>195                               200                        205                        210 | | 682 |
| cac tac tgc gcc cct gcc ggc tac gcc atc ctg aag tgc aac aac aag<br>His Tyr Cys Ala Pro Ala Gly Tyr Ala Ile Leu Lys Cys Asn Asn Lys<br>                              215                        220                        225 | | 730 |
| acc ttc aac ggc acc ggc ccc tgc aac aac gtg tcc acc gtg cag tgc<br>Thr Phe Asn Gly Thr Gly Pro Cys Asn Asn Val Ser Thr Val Gln Cys<br>                              230                        235                        240 | | 778 |
| acc cac ggc atc aag ccc gtg gtg tcc acc cag ctg ctg ctg aat ggc<br>Thr His Gly Ile Lys Pro Val Val Ser Thr Gln Leu Leu Leu Asn Gly<br>245                               250                        255 | | 826 |
| agc ctg gcc gag ggc gag atc atc atc aga agc gag aac ctg acc aac<br>Ser Leu Ala Glu Gly Glu Ile Ile Ile Arg Ser Glu Asn Leu Thr Asn<br>260                               265                        270 | | 874 |
| aac gtg aaa acc atc atc gtg cac ctg aac gag agc gtg gaa atc gtg<br>Asn Val Lys Thr Ile Ile Val His Leu Asn Glu Ser Val Glu Ile Val<br>275                               280                        285                        290 | | 922 |
| tgc acc cgg ccc aac aac aac acc aga aag agc atc cgg atc ggc cct<br>Cys Thr Arg Pro Asn Asn Asn Thr Arg Lys Ser Ile Arg Ile Gly Pro<br>                              295                        300                        305 | | 970 |
| ggc cag acc ttt tac gcc acc ggc gac atc atc ggc aac atc cgg cag<br>Gly Gln Thr Phe Tyr Ala Thr Gly Asp Ile Ile Gly Asn Ile Arg Gln<br>                              310                        315                        320 | | 1018 |
| gcc tac tgc aac atc aag aag gac gac tgg atc cgg acc ctg cag aga<br>Ala Tyr Cys Asn Ile Lys Lys Asp Asp Trp Ile Arg Thr Leu Gln Arg<br>325                               330                        335 | | 1066 |

| | | | | | | | | | | | | | | | | |
|---|---|---|---|---|---|---|---|---|---|---|---|---|---|---|---|---|
| gtg | ggc | aag | aag | ctg | gcc | gag | cac | ttc | ccc | aga | cgg | atc | atc | aac | ttc | 1114 |
| Val | Gly | Lys | Lys | Leu | Ala | Glu | His | Phe | Pro | Arg | Arg | Ile | Ile | Asn | Phe | |
| | 340 | | | | 345 | | | | 350 | | | | | | | |
| acc | agc | ccc | gct | ggc | ggc | gac | ctg | gaa | atc | acc | acc | cac | agc | ttc | aac | 1162 |
| Thr | Ser | Pro | Ala | Gly | Gly | Asp | Leu | Glu | Ile | Thr | Thr | His | Ser | Phe | Asn | |
| 355 | | | | | 360 | | | | | 365 | | | | | 370 | |
| tgc | aga | ggc | gag | ttc | ttc | tac | tgc | aat | acc | agc | agc | ctg | ttc | aac | agc | 1210 |
| Cys | Arg | Gly | Glu | Phe | Phe | Tyr | Cys | Asn | Thr | Ser | Ser | Leu | Phe | Asn | Ser | |
| | | | | 375 | | | | | 380 | | | | | 385 | | |
| acc | tac | aac | ccc | aac | gac | acc | aac | agc | aac | agc | tcc | agc | agc | aac | tcc | 1258 |
| Thr | Tyr | Asn | Pro | Asn | Asp | Thr | Asn | Ser | Asn | Ser | Ser | Ser | Ser | Asn | Ser | |
| | | | | 390 | | | | | 395 | | | | | 400 | | |
| agc | ctg | gac | atc | acc | atc | cct | tgc | cgg | atc | aag | cag | atc | atc | aat | atg | 1306 |
| Ser | Leu | Asp | Ile | Thr | Ile | Pro | Cys | Arg | Ile | Lys | Gln | Ile | Ile | Asn | Met | |
| | | 405 | | | | | 410 | | | | | 415 | | | | |
| tgg | cag | gaa | gtg | ggc | agg | gct | atg | tac | gcc | cct | ccc | atc | gag | ggc | aac | 1354 |
| Trp | Gln | Glu | Val | Gly | Arg | Ala | Met | Tyr | Ala | Pro | Pro | Ile | Glu | Gly | Asn | |
| | 420 | | | | 425 | | | | 430 | | | | | | | |
| atc | aca | tgc | aag | agc | aac | atc | acc | ggc | ctc | ctc | ctg | gtc | cgc | gac | ggc | 1402 |
| Ile | Thr | Cys | Lys | Ser | Asn | Ile | Thr | Gly | Leu | Leu | Leu | Val | Arg | Asp | Gly | |
| 435 | | | | | 440 | | | | | 445 | | | | | 450 | |
| ggc | gtg | gaa | agc | aac | gag | aca | gag | atc | ttc | aga | ccc | ggc | gga | ggc | gac | 1450 |
| Gly | Val | Glu | Ser | Asn | Glu | Thr | Glu | Ile | Phe | Arg | Pro | Gly | Gly | Gly | Asp | |
| | | | | 455 | | | | | 460 | | | | | 465 | | |
| atg | cgg | aac | aac | tgg | cgg | agc | gag | ctg | tac | aag | tac | aag | gtg | gtg | gaa | 1498 |
| Met | Arg | Asn | Asn | Trp | Arg | Ser | Glu | Leu | Tyr | Lys | Tyr | Lys | Val | Val | Glu | |
| | | 470 | | | | | 475 | | | | | 480 | | | | |
| atc | aag | ccc | ctg | gga | atc | gcc | ccc | acc | gcc | gcc | aag | cgg | aga | gtg | gtg | 1546 |
| Ile | Lys | Pro | Leu | Gly | Ile | Ala | Pro | Thr | Ala | Ala | Lys | Arg | Arg | Val | Val | |
| | 485 | | | | 490 | | | | | 495 | | | | | | |
| gaa | ggc | gct | cac | cac | cac | cat | cac | cac | ggc | ctg | aac | gac | atc | ttc | gag | 1594 |
| Glu | Gly | Ala | His | His | His | His | His | His | Gly | Leu | Asn | Asp | Ile | Phe | Glu | |
| 500 | | | | | 505 | | | | | 510 | | | | | | |
| gcc | cag | aaa | atc | gag | tgg | cac | gag | tgactcgagt | | ctagagggcc | | cgtttaaacc | | | | 1648 |
| Ala | Gln | Lys | Ile | Glu | Trp | His | Glu | | | | | | | | | |
| 515 | | | | 520 | | | | | | | | | | | | |
| cgctgatcag | | cctcgactg | | | | | | | | | | | | | | 1667 |

<210> SEQ ID NO 54
<211> LENGTH: 522
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
            20                  25                  30

Tyr Tyr Gly Val Pro Val Trp Lys Glu Ala Lys Thr Thr Leu Phe Cys
        35                  40                  45

Ala Ser Asp Ala Lys Ala Tyr Glu Lys Glu Val His Asn Val Trp Ala
    50                  55                  60

Thr His Ala Cys Val Pro Thr Asp Pro Asn Pro Gln Glu Met Val Leu
65                  70                  75                  80

Glu Asn Val Thr Glu Asn Phe Asn Met Trp Lys Asn Asp Met Val Glu
                85                  90                  95

Gln Met His Glu Asp Val Ile Ser Leu Trp Asp Gln Ser Leu Lys Pro

```
                    100                 105                 110
Cys Val Lys Leu Thr Pro Leu Cys Val Thr Leu Glu Cys Arg Gln Val
            115                 120                 125
Asn Thr Thr Asn Ala Thr Ser Ser Val Asn Val Thr Asn Gly Glu Glu
        130                 135                 140
Ile Lys Asn Cys Ser Phe Lys Ala Thr Thr Glu Ile Arg Asp Lys Lys
145                 150                 155                 160
Gln Lys Val Tyr Ala Leu Phe Tyr Arg Leu Asp Ile Val Pro Leu Glu
                165                 170                 175
Glu Glu Arg Lys Gly Asn Ser Ser Lys Tyr Arg Leu Ile Asn Cys Asn
            180                 185                 190
Thr Ser Ala Ile Thr Gln Ala Cys Pro Lys Val Thr Phe Asp Pro Ile
        195                 200                 205
Pro Ile His Tyr Cys Ala Pro Ala Gly Tyr Ala Ile Leu Lys Cys Asn
    210                 215                 220
Asn Lys Thr Phe Asn Gly Thr Gly Pro Cys Asn Asn Val Ser Thr Val
225                 230                 235                 240
Gln Cys Thr His Gly Ile Lys Pro Val Val Ser Thr Gln Leu Leu Leu
                245                 250                 255
Asn Gly Ser Leu Ala Glu Gly Glu Ile Ile Ile Arg Ser Glu Asn Leu
            260                 265                 270
Thr Asn Asn Val Lys Thr Ile Ile Val His Leu Asn Glu Ser Val Glu
        275                 280                 285
Ile Val Cys Thr Arg Pro Asn Asn Asn Thr Arg Lys Ser Ile Arg Ile
    290                 295                 300
Gly Pro Gly Gln Thr Phe Tyr Ala Thr Gly Asp Ile Ile Gly Asn Ile
305                 310                 315                 320
Arg Gln Ala Tyr Cys Asn Ile Lys Lys Asp Asp Trp Ile Arg Thr Leu
                325                 330                 335
Gln Arg Val Gly Lys Lys Leu Ala Glu His Phe Pro Arg Ile Ile
            340                 345                 350
Asn Phe Thr Ser Pro Ala Gly Gly Asp Leu Glu Ile Thr Thr His Ser
        355                 360                 365
Phe Asn Cys Arg Gly Glu Phe Phe Tyr Cys Asn Thr Ser Ser Leu Phe
    370                 375                 380
Asn Ser Thr Tyr Asn Pro Asn Asp Thr Asn Ser Ser Ser Ser Ser
385                 390                 395                 400
Asn Ser Ser Leu Asp Ile Thr Ile Pro Cys Arg Ile Lys Gln Ile Ile
                405                 410                 415
Asn Met Trp Gln Glu Val Gly Arg Ala Met Tyr Ala Pro Pro Ile Glu
            420                 425                 430
Gly Asn Ile Thr Cys Lys Ser Asn Ile Thr Gly Leu Leu Leu Val Arg
        435                 440                 445
Asp Gly Gly Val Glu Ser Asn Gly Thr Glu Ile Phe Arg Pro Gly Gly
    450                 455                 460
Gly Asp Met Arg Asn Asn Trp Arg Ser Glu Leu Tyr Lys Tyr Lys Val
465                 470                 475                 480
Val Glu Ile Lys Pro Leu Gly Ile Ala Pro Thr Ala Ala Lys Arg Arg
                485                 490                 495
Val Val Glu Gly Ala His His His His His His Gly Leu Asn Asp Ile
            500                 505                 510
Phe Glu Ala Gln Lys Ile Glu Trp His Glu
        515                 520
```

<210> SEQ ID NO 55
<211> LENGTH: 1667
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (53)..(1618)

<400> SEQUENCE: 55

```
ctcactatag ggagacccaa gctggctagc gtttaaactt aagcttgcca cc atg cct      58
                                                          Met Pro
                                                          1 atg ggc agc ctg cag cct ctg gcc acc ctg tac ctg ctg ggc atg ctg      106
Met Gly Ser Leu Gln Pro Leu Ala Thr Leu Tyr Leu Leu Gly Met Leu
          5                  10                  15 gtg gcc tcc gtg ctg gca gct ggc aac ctg tgg gtc aca gtg tac tac      154
Val Ala Ser Val Leu Ala Ala Gly Asn Leu Trp Val Thr Val Tyr Tyr
     20                  25                  30 ggc gtg ccc gtg tgg aaa gag gcc aag acc acc ctg ttc tgc gcc agc      202
Gly Val Pro Val Trp Lys Glu Ala Lys Thr Thr Leu Phe Cys Ala Ser
 35                  40                  45                  50 gac gcc aag gcc tac gag aaa gag gtg cac aac gtc tgg gcc acc cac      250
Asp Ala Lys Ala Tyr Glu Lys Glu Val His Asn Val Trp Ala Thr His
                 55                  60                  65 gcc tgc gtg ccc acc gac ccc aac ccc cag gaa atg gtc ctg gaa aac      298
Ala Cys Val Pro Thr Asp Pro Asn Pro Gln Glu Met Val Leu Glu Asn
             70                  75                  80 gtg acc gag aac ttc aac atg tgg aag aac gac atg gtg gaa cag atg      346
Val Thr Glu Asn Phe Asn Met Trp Lys Asn Asp Met Val Glu Gln Met
         85                  90                  95 cac gag gac gtg atc agc ctg tgg gac cag agc ctg aag ccc tgc gtg      394
His Glu Asp Val Ile Ser Leu Trp Asp Gln Ser Leu Lys Pro Cys Val
    100                 105                 110 aag ctg acc ccc ctg tgc gtg acc ctg gaa tgc aga cag gtc aac acc      442
Lys Leu Thr Pro Leu Cys Val Thr Leu Glu Cys Arg Gln Val Asn Thr
115                 120                 125                 130 acc aac gcc acc agc agc gtg aac gtg acc aac ggc gag gaa atc aag      490
Thr Asn Ala Thr Ser Ser Val Asn Val Thr Asn Gly Glu Glu Ile Lys
                135                 140                 145 aaa tgc agc ttc aat gcc acc acc gag atc cgg gac aag aaa cag aag      538
Lys Cys Ser Phe Asn Ala Thr Thr Glu Ile Arg Asp Lys Lys Gln Lys
            150                 155                 160 gtg tac gcc ctg ttc tac cgg ctg gac atc gtg ccc ctg gaa gag gaa      586
Val Tyr Ala Leu Phe Tyr Arg Leu Asp Ile Val Pro Leu Glu Glu Glu
        165                 170                 175 cgg aag ggc aac agc agc aag tac cgg ctg atc aac tgc aac acc agc      634
Arg Lys Gly Asn Ser Ser Lys Tyr Arg Leu Ile Asn Cys Asn Thr Ser
    180                 185                 190 gcc atc acc cag gcc tgc ccc aaa gtg acc ttc gac cct atc ccc atc      682
Ala Ile Thr Gln Ala Cys Pro Lys Val Thr Phe Asp Pro Ile Pro Ile
195                 200                 205                 210 cac tac tgc gcc cct gcc ggc tac gcc atc ctg aag tgc aac aac aag      730
His Tyr Cys Ala Pro Ala Gly Tyr Ala Ile Leu Lys Cys Asn Asn Lys
                215                 220                 225 acc ttc aac ggc acc ggc ccc tgc aac aac gtg tcc acc gtg cag tgc      778
Thr Phe Asn Gly Thr Gly Pro Cys Asn Asn Val Ser Thr Val Gln Cys
            230                 235                 240 acc cac ggc atc aag ccc gtg gtg tcc acc cag ctg ctg ctg aat ggc      826
Thr His Gly Ile Lys Pro Val Val Ser Thr Gln Leu Leu Leu Asn Gly
```

|  |  |
|---|---|
| agc ctg gcc gag ggc gag atc atc atc aga agc gag aac ctg acc aac<br>Ser Leu Ala Glu Gly Glu Ile Ile Ile Arg Ser Glu Asn Leu Thr Asn<br>260               265               270 | 874 |
| aac gtg aaa acc atc atc gtg cac ctg aac gag agc gtg gaa atc gtg<br>Asn Val Lys Thr Ile Ile Val His Leu Asn Glu Ser Val Glu Ile Val<br>275               280               285               290 | 922 |
| tgc acc cgg ccc aac aac aac acc aga aag agc atc cgg atc ggc cct<br>Cys Thr Arg Pro Asn Asn Asn Thr Arg Lys Ser Ile Arg Ile Gly Pro<br>               295               300               305 | 970 |
| ggc cag acc ttt tac gcc acc ggc gac atc atc ggc aac atc cgg cag<br>Gly Gln Thr Phe Tyr Ala Thr Gly Asp Ile Ile Gly Asn Ile Arg Gln<br>310               315               320 | 1018 |
| gcc tac tgc aac atc aag aag gac gac tgg atc cgg acc ctg cag aga<br>Ala Tyr Cys Asn Ile Lys Lys Asp Asp Trp Ile Arg Thr Leu Gln Arg<br>325               330               335 | 1066 |
| gtg ggc aag aag ctg gcc gag cac ttc ccc aga cgg atc atc aac ttc<br>Val Gly Lys Lys Leu Ala Glu His Phe Pro Arg Arg Ile Ile Asn Phe<br>340               345               350 | 1114 |
| acc agc ccc gct ggc ggc gac ctg gaa atc acc acc cac agc ttc aac<br>Thr Ser Pro Ala Gly Gly Asp Leu Glu Ile Thr Thr His Ser Phe Asn<br>355               360               365               370 | 1162 |
| tgc aga ggc gag ttc ttc tac tgc aat acc agc agc ctg ttc aac agc<br>Cys Arg Gly Glu Phe Phe Tyr Cys Asn Thr Ser Ser Leu Phe Asn Ser<br>               375               380               385 | 1210 |
| acc tac aac ccc aac gac acc aac agc aac agc tcc agc agc aac tcc<br>Thr Tyr Asn Pro Asn Asp Thr Asn Ser Asn Ser Ser Ser Ser Asn Ser<br>390               395               400 | 1258 |
| agc ctg gac atc acc atc cct tgc cgg atc aag cag atc atc aat atg<br>Ser Leu Asp Ile Thr Ile Pro Cys Arg Ile Lys Gln Ile Ile Asn Met<br>405               410               415 | 1306 |
| tgg cag gaa gtg ggc agg gct atg tac gcc cct ccc atc gag ggc aac<br>Trp Gln Glu Val Gly Arg Ala Met Tyr Ala Pro Pro Ile Glu Gly Asn<br>420               425               430 | 1354 |
| atc aca tgc aag agc aac atc acc ggc ctg ctc ctg gtc cgc gac ggc<br>Ile Thr Cys Lys Ser Asn Ile Thr Gly Leu Leu Leu Val Arg Asp Gly<br>435               440               445               450 | 1402 |
| ggc gtg gaa agc aac gag aca gag atc ttc aga ccc ggc gga ggc gac<br>Gly Val Glu Ser Asn Glu Thr Glu Ile Phe Arg Pro Gly Gly Gly Asp<br>               455               460               465 | 1450 |
| atg cgg aac aac tgg cgg agc gag ctg tac aag tac aag gtg gtg gaa<br>Met Arg Asn Asn Trp Arg Ser Glu Leu Tyr Lys Tyr Lys Val Val Glu<br>470               475               480 | 1498 |
| atc aag ccc ctg gga atc gcc ccc acc gcc gcc aag cgg aga gtg gtg<br>Ile Lys Pro Leu Gly Ile Ala Pro Thr Ala Ala Lys Arg Arg Val Val<br>485               490               495 | 1546 |
| gaa ggc gct cac cac cac cat cac cac ggc ctg aac gac atc ttc gag<br>Glu Gly Ala His His His His His His Gly Leu Asn Asp Ile Phe Glu<br>500               505               510 | 1594 |
| gcc cag aaa atc gag tgg cac gag tgactcgagt ctagagggcc cgtttaaacc<br>Ala Gln Lys Ile Glu Trp His Glu<br>515               520 | 1648 |
| cgctgatcag cctcgactg | 1667 |

<210> SEQ ID NO 56
<211> LENGTH: 522
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 56

```
Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
            20                  25                  30

Tyr Tyr Gly Val Pro Val Trp Lys Glu Ala Lys Thr Thr Leu Phe Cys
        35                  40                  45

Ala Ser Asp Ala Lys Ala Tyr Glu Lys Glu Val His Asn Val Trp Ala
    50                  55                  60

Thr His Ala Cys Val Pro Thr Asp Pro Asn Pro Gln Glu Met Val Leu
65                  70                  75                  80

Glu Asn Val Thr Glu Asn Phe Asn Met Trp Lys Asn Asp Met Val Glu
                85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu Glu Cys Arg Gln Val
        115                 120                 125

Asn Thr Thr Asn Ala Thr Ser Ser Val Asn Val Thr Asn Gly Glu Glu
    130                 135                 140

Ile Lys Lys Cys Ser Phe Asn Ala Thr Thr Glu Ile Arg Asp Lys Lys
145                 150                 155                 160

Gln Lys Val Tyr Ala Leu Phe Tyr Arg Leu Asp Ile Val Pro Leu Glu
                165                 170                 175

Glu Glu Arg Lys Gly Asn Ser Ser Lys Tyr Arg Leu Ile Asn Cys Asn
            180                 185                 190

Thr Ser Ala Ile Thr Gln Ala Cys Pro Lys Val Thr Phe Asp Pro Ile
        195                 200                 205

Pro Ile His Tyr Cys Ala Pro Ala Gly Tyr Ala Ile Leu Lys Cys Asn
    210                 215                 220

Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Gly Glu Ile Ile Ile Arg Ser Glu Asn Leu
            260                 265                 270

Thr Asn Asn Val Lys Thr Ile Ile Val His Leu Asn Glu Ser Val Glu
        275                 280                 285

Ile Val Cys Thr Arg Pro Asn Asn Asn Thr Arg Lys Ser Ile Arg Ile
    290                 295                 300

Gly Pro Gly Gln Thr Phe Tyr Ala Thr Gly Asp Ile Ile Gly Asn Ile
305                 310                 315                 320

Arg Gln Ala Tyr Cys Asn Ile Lys Lys Asp Asp Trp Ile Arg Thr Leu
                325                 330                 335

Gln Arg Val Gly Lys Lys Leu Ala Glu His Phe Pro Arg Arg Ile Ile
            340                 345                 350

Asn Phe Thr Ser Pro Ala Gly Gly Asp Leu Glu Ile Thr Thr His Ser
        355                 360                 365

Phe Asn Cys Arg Gly Glu Phe Phe Tyr Cys Asn Thr Ser Ser Leu Phe
    370                 375                 380

Asn Ser Thr Tyr Asn Pro Asn Asp Thr Asn Ser Asn Ser Ser Ser
385                 390                 395                 400

Asn Ser Ser Leu Asp Ile Thr Ile Pro Cys Arg Ile Lys Gln Ile Ile
                405                 410                 415
```

```
Asn Met Trp Gln Glu Val Gly Arg Ala Met Tyr Ala Pro Pro Ile Glu
            420                 425                 430
Gly Asn Ile Thr Cys Lys Ser Asn Ile Thr Gly Leu Leu Leu Val Arg
        435                 440                 445
Asp Gly Gly Val Glu Ser Asn Glu Thr Glu Ile Phe Arg Pro Gly Gly
    450                 455                 460
Gly Asp Met Arg Asn Asn Trp Arg Ser Glu Leu Tyr Lys Tyr Lys Val
465                 470                 475                 480
Val Glu Ile Lys Pro Leu Gly Ile Ala Pro Thr Ala Ala Lys Arg Arg
                485                 490                 495
Val Val Glu Gly Ala His His His His His Gly Leu Asn Asp Ile
            500                 505                 510
Phe Glu Ala Gln Lys Ile Glu Trp His Glu
            515                 520

<210> SEQ ID NO 57
<211> LENGTH: 1667
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (53)..(1618)

<400> SEQUENCE: 57
ctcactatag ggagacccaa gctggctagc gtttaaactt aagcttgcca cc atg cct         58
                                                          Met Pro
                                                            1 atg ggc agc ctg cag cct ctg gcc acc ctg tac ctg ctg ggc atg ctg        106
Met Gly Ser Leu Gln Pro Leu Ala Thr Leu Tyr Leu Leu Gly Met Leu
        5                   10                  15 gtg gcc tcc gtg ctg gca gct ggc aac ctg tgg gtc aca gtg tac tac        154
Val Ala Ser Val Leu Ala Ala Gly Asn Leu Trp Val Thr Val Tyr Tyr
 20                  25                  30 ggc gtg ccc gtg tgg aaa gag gcc aag acc acc ctg ttc tgc gcc agc        202
Gly Val Pro Val Trp Lys Glu Ala Lys Thr Thr Leu Phe Cys Ala Ser
35                  40                  45                  50 gac gcc aag gcc tac gag aaa gag gtg cac aac gtc tgg gcc acc cac        250
Asp Ala Lys Ala Tyr Glu Lys Glu Val His Asn Val Trp Ala Thr His
                55                  60                  65 gcc tgc gtg ccc acc gac ccc aac ccc cag gaa atg gtc ctg gaa aac        298
Ala Cys Val Pro Thr Asp Pro Asn Pro Gln Glu Met Val Leu Glu Asn
            70                  75                  80 gtg acc gag aac ttc aac atg tgg aag aac gac atg gtg gaa cag atg        346
Val Thr Glu Asn Phe Asn Met Trp Lys Asn Asp Met Val Glu Gln Met
        85                  90                  95 cac gag gac gtg atc agc ctg tgg gac cag agc ctg aag ccc tgc gtg        394
His Glu Asp Val Ile Ser Leu Trp Asp Gln Ser Leu Lys Pro Cys Val
    100                 105                 110 aag ctg acc ccc ctg tgc gtg acc ctg gaa tgc aga cag gtc aac acc        442
Lys Leu Thr Pro Leu Cys Val Thr Leu Glu Cys Arg Gln Val Asn Thr
115                 120                 125                 130 acc aac gcc acc agc agc gtg aac gtg acc aac ggc gag gaa atc aag        490
Thr Asn Ala Thr Ser Ser Val Asn Val Thr Asn Gly Glu Glu Ile Lys
                135                 140                 145 aac tgc agc tac aat gcc acc acc gag atc cgg gac aag aaa cag aag        538
Asn Cys Ser Tyr Asn Ala Thr Thr Glu Ile Arg Asp Lys Lys Gln Lys
            150                 155                 160
```

```
gtg tac gcc ctg ttc tac cgg ctg gac atc gtg ccc ctg gaa gag gaa    586
Val Tyr Ala Leu Phe Tyr Arg Leu Asp Ile Val Pro Leu Glu Glu Glu
        165                 170                 175 cgg aag ggc aac agc agc aag tac cgg ctg atc aac tgc aac acc agc    634
Arg Lys Gly Asn Ser Ser Lys Tyr Arg Leu Ile Asn Cys Asn Thr Ser
    180                 185                 190 gcc atc acc cag gcc tgc ccc aaa gtg acc ttc gac cct atc ccc atc    682
Ala Ile Thr Gln Ala Cys Pro Lys Val Thr Phe Asp Pro Ile Pro Ile
195                 200                 205                 210 cac tac tgc gcc cct gcc ggc tac gcc atc ctg aag tgc aac aac aag    730
His Tyr Cys Ala Pro Ala Gly Tyr Ala Ile Leu Lys Cys Asn Asn Lys
                215                 220                 225 acc ttc aac ggc acc ggc ccc tgc aac aac gtg tcc acc gtg cag tgc    778
Thr Phe Asn Gly Thr Gly Pro Cys Asn Asn Val Ser Thr Val Gln Cys
        230                 235                 240 acc cac ggc atc aag ccc gtg gtg tcc acc cag ctg ctg ctg aat ggc    826
Thr His Gly Ile Lys Pro Val Val Ser Thr Gln Leu Leu Leu Asn Gly
            245                 250                 255 agc ctg gcc gag ggc gag atc atc atc aga agc gag aac ctg acc aac    874
Ser Leu Ala Glu Gly Glu Ile Ile Ile Arg Ser Glu Asn Leu Thr Asn
    260                 265                 270 aac gtg aaa acc atc atc gtg cac ctg aac gag agc gtg gaa atc gtg    922
Asn Val Lys Thr Ile Ile Val His Leu Asn Glu Ser Val Glu Ile Val
275                 280                 285                 290 tgc acc cgg ccc aac aac aac acc aga aag agc atc cgg atc ggc cct    970
Cys Thr Arg Pro Asn Asn Asn Thr Arg Lys Ser Ile Arg Ile Gly Pro
                295                 300                 305 ggc cag acc ttt tac gcc acc ggc gac atc atc ggc aac atc cgg cag    1018
Gly Gln Thr Phe Tyr Ala Thr Gly Asp Ile Ile Gly Asn Ile Arg Gln
        310                 315                 320 gcc tac tgc aac atc aag aag gac gac tgg atc cgg acc ctg cag aga    1066
Ala Tyr Cys Asn Ile Lys Lys Asp Asp Trp Ile Arg Thr Leu Gln Arg
            325                 330                 335 gtg ggc aag aag ctg gcc gag cac ttc ccc aga cgg atc atc aac ttc    1114
Val Gly Lys Lys Leu Ala Glu His Phe Pro Arg Arg Ile Ile Asn Phe
    340                 345                 350 acc agc ccc gct ggc ggc gac ctg gaa atc acc acc cac agc ttc aac    1162
Thr Ser Pro Ala Gly Gly Asp Leu Glu Ile Thr Thr His Ser Phe Asn
355                 360                 365                 370 tgc aga ggc gag ttc ttc tac tgc aat acc agc agc ctg ttc aac agc    1210
Cys Arg Gly Glu Phe Phe Tyr Cys Asn Thr Ser Ser Leu Phe Asn Ser
                375                 380                 385 acc tac aac ccc aac gac acc aac agc aac agc tcc agc agc aac tcc    1258
Thr Tyr Asn Pro Asn Asp Thr Asn Ser Asn Ser Ser Ser Ser Asn Ser
        390                 395                 400 agc ctg gac atc acc atc cct tgc cgg atc aag cag atc atc aat atg    1306
Ser Leu Asp Ile Thr Ile Pro Cys Arg Ile Lys Gln Ile Ile Asn Met
            405                 410                 415 tgg cag gaa gtg ggc agg gct atg tac gcc cct ccc atc gag ggc aac    1354
Trp Gln Glu Val Gly Arg Ala Met Tyr Ala Pro Pro Ile Glu Gly Asn
    420                 425                 430 atc aca tgc aag agc aac atc acc ggc ctg ctc ctg gtc cgc gac ggc    1402
Ile Thr Cys Lys Ser Asn Ile Thr Gly Leu Leu Leu Val Arg Asp Gly
435                 440                 445                 450 ggc gtg gaa agc aac gag aca gag atc ttc aga ccc ggc gga ggc gac    1450
Gly Val Glu Ser Asn Glu Thr Glu Ile Phe Arg Pro Gly Gly Gly Asp
                455                 460                 465 atg cgg aac aac tgg cgg agc gag ctg tac aag tac aag gtg gtg gaa    1498
Met Arg Asn Asn Trp Arg Ser Glu Leu Tyr Lys Tyr Lys Val Val Glu
        470                 475                 480
```

```
atc aag ccc ctg gga atc gcc ccc acc gcc gcc aag cgg aga gtg gtg    1546
Ile Lys Pro Leu Gly Ile Ala Pro Thr Ala Ala Lys Arg Arg Val Val
        485                 490                 495 gaa ggc gct cac cac cac cat cac cac ggc ctg aac gac atc ttc gag    1594
Glu Gly Ala His His His His His His Gly Leu Asn Asp Ile Phe Glu
500                 505                 510 gcc cag aaa atc gag tgg cac gag tgactcgagt ctagagggcc cgtttaaacc   1648
Ala Gln Lys Ile Glu Trp His Glu
515                 520 cgctgatcag cctcgactg                                               1667

<210> SEQ ID NO 58
<211> LENGTH: 522
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Thr Val
            20                  25                  30

Tyr Tyr Gly Val Pro Val Trp Lys Glu Ala Lys Thr Thr Leu Phe Cys
        35                  40                  45

Ala Ser Asp Ala Lys Ala Tyr Glu Lys Glu Val His Asn Val Trp Ala
    50                  55                  60

Thr His Ala Cys Val Pro Thr Asp Pro Asn Pro Gln Glu Met Val Leu
65                  70                  75                  80

Glu Asn Val Thr Glu Asn Phe Asn Met Trp Lys Asn Asp Met Val Glu
                85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu Glu Cys Arg Gln Val
        115                 120                 125

Asn Thr Thr Asn Ala Thr Ser Ser Val Asn Val Thr Asn Gly Glu Glu
    130                 135                 140

Ile Lys Asn Cys Ser Tyr Asn Ala Thr Thr Glu Ile Arg Asp Lys Lys
145                 150                 155                 160

Gln Lys Val Tyr Ala Leu Phe Tyr Arg Leu Asp Ile Val Pro Leu Glu
                165                 170                 175

Glu Glu Arg Lys Gly Asn Ser Ser Lys Tyr Arg Leu Ile Asn Cys Asn
            180                 185                 190

Thr Ser Ala Ile Thr Gln Ala Cys Pro Lys Val Thr Phe Asp Pro Ile
        195                 200                 205

Pro Ile His Tyr Cys Ala Pro Ala Gly Tyr Ala Ile Leu Lys Cys Asn
    210                 215                 220

Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Gly Glu Ile Ile Ile Arg Ser Glu Asn Leu
            260                 265                 270

Thr Asn Asn Val Lys Thr Ile Ile Val His Leu Asn Glu Ser Val Glu
        275                 280                 285

Ile Val Cys Thr Arg Pro Asn Asn Asn Thr Arg Lys Ser Ile Arg Ile
```

```
                 290                 295                 300
Gly Pro Gly Gln Thr Phe Tyr Ala Thr Gly Asp Ile Ile Gly Asn Ile
305                 310                 315                 320

Arg Gln Ala Tyr Cys Asn Ile Lys Lys Asp Asp Trp Ile Arg Thr Leu
                325                 330                 335

Gln Arg Val Gly Lys Lys Leu Ala Glu His Phe Pro Arg Arg Ile Ile
            340                 345                 350

Asn Phe Thr Ser Pro Ala Gly Gly Asp Leu Glu Ile Thr Thr His Ser
        355                 360                 365

Phe Asn Cys Arg Gly Glu Phe Phe Tyr Cys Asn Thr Ser Ser Leu Phe
370                 375                 380

Asn Ser Thr Tyr Asn Pro Asn Asp Thr Asn Ser Asn Ser Ser Ser
385                 390                 395                 400

Asn Ser Ser Leu Asp Ile Thr Ile Pro Cys Arg Ile Lys Gln Ile Ile
                405                 410                 415

Asn Met Trp Gln Glu Val Gly Arg Ala Met Tyr Ala Pro Pro Ile Glu
            420                 425                 430

Gly Asn Ile Thr Cys Lys Ser Asn Ile Thr Gly Leu Leu Leu Val Arg
        435                 440                 445

Asp Gly Gly Val Glu Ser Asn Glu Thr Glu Ile Phe Arg Pro Gly Gly
    450                 455                 460

Gly Asp Met Arg Asn Asn Trp Arg Ser Glu Leu Tyr Lys Tyr Lys Val
465                 470                 475                 480

Val Glu Ile Lys Pro Leu Gly Ile Ala Pro Thr Ala Ala Lys Arg Arg
                485                 490                 495

Val Val Glu Gly Ala His His His His His His Gly Leu Asn Asp Ile
            500                 505                 510

Phe Glu Ala Gln Lys Ile Glu Trp His Glu
        515                 520

<210> SEQ ID NO 59
<211> LENGTH: 1667
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (53)..(1618)

<400> SEQUENCE: 59
ctcactatag ggagaccccaa gctggctagc gtttaaactt aagcttgcca cc atg cct      58
                                                           Met Pro
                                                             1 atg ggc agc ctg cag cct ctg gcc acc ctg tac ctg ctg ggc atg ctg        106
Met Gly Ser Leu Gln Pro Leu Ala Thr Leu Tyr Leu Leu Gly Met Leu
          5                  10                  15 gtg gcc tcc gtg ctg gca gct ggc aac ctg tgg gtc aca gtg tac tac        154
Val Ala Ser Val Leu Ala Ala Gly Asn Leu Trp Val Thr Val Tyr Tyr
     20                  25                  30 ggc gtg ccc gtg tgg aaa gag gcc aag acc acc ctg ttc tgc gcc agc        202
Gly Val Pro Val Trp Lys Glu Ala Lys Thr Thr Leu Phe Cys Ala Ser
35                  40                  45                  50 gac gcc aag gcc tac gag aaa gag gtg cac aac gtc tgg gcc acc cac        250
Asp Ala Lys Ala Tyr Glu Lys Glu Val His Asn Val Trp Ala Thr His
                 55                  60                  65 gcc tgc gtg ccc acc gac ccc aac ccc cag gaa atg gtc ctg gaa aac        298
Ala Cys Val Pro Thr Asp Pro Asn Pro Gln Glu Met Val Leu Glu Asn
```

-continued

|  | 70 | 75 | 80 |  |
|---|---|---|---|---|

```
gtg acc gag aac ttc aac atg tgg aag aac gac atg gtg gaa cag atg      346
Val Thr Glu Asn Phe Asn Met Trp Lys Asn Asp Met Val Glu Gln Met
        85                  90                  95 cac gag gac gtg atc agc ctg tgg gac cag agc ctg aag ccc tgc gtg      394
His Glu Asp Val Ile Ser Leu Trp Asp Gln Ser Leu Lys Pro Cys Val
100                 105                 110 aag ctg acc ccc ctg tgc gtg acc ctg gaa tgc aga cag gtc aac acc      442
Lys Leu Thr Pro Leu Cys Val Thr Leu Glu Cys Arg Gln Val Asn Thr
    115                 120                 125                 130 acc aac gcc acc agc agc gtg aac gtg acc aac ggc gag gaa atc aag      490
Thr Asn Ala Thr Ser Ser Val Asn Val Thr Asn Gly Glu Glu Ile Lys
                135                 140                 145 aac tgc agc ttc aag gcc acc acc gag atc cgg gac gag aaa cag aag      538
Asn Cys Ser Phe Lys Ala Thr Thr Glu Ile Arg Asp Glu Lys Gln Lys
            150                 155                 160 gtg tac gcc ctg ttc tac cgg ctg gac atc gtg ccc ctg gaa gag gaa      586
Val Tyr Ala Leu Phe Tyr Arg Leu Asp Ile Val Pro Leu Glu Glu Glu
        165                 170                 175 cgg aag ggc aac agc agc aag tac cgg ctg atc aac tgc aac acc agc      634
Arg Lys Gly Asn Ser Ser Lys Tyr Arg Leu Ile Asn Cys Asn Thr Ser
180                 185                 190 gcc atc acc cag gcc tgc ccc aaa gtg acc ttc gac cct atc ccc atc      682
Ala Ile Thr Gln Ala Cys Pro Lys Val Thr Phe Asp Pro Ile Pro Ile
195                 200                 205                 210 cac tac tgc gcc cct gcc ggc tac gcc atc ctg aag tgc aac aac aag      730
His Tyr Cys Ala Pro Ala Gly Tyr Ala Ile Leu Lys Cys Asn Asn Lys
                215                 220                 225 acc ttc aac ggc acc ggc ccc tgc aac aac gtg tcc acc gtg cag tgc      778
Thr Phe Asn Gly Thr Gly Pro Cys Asn Asn Val Ser Thr Val Gln Cys
            230                 235                 240 acc cac ggc atc aag ccc gtg gtg tcc acc cag ctg ctg aat ggc          826
Thr His Gly Ile Lys Pro Val Val Ser Thr Gln Leu Leu Asn Gly
        245                 250                 255 agc ctg gcc gag ggc gag atc atc atc aga agc gag aac ctg acc aac      874
Ser Leu Ala Glu Gly Glu Ile Ile Ile Arg Ser Glu Asn Leu Thr Asn
260                 265                 270 aac gtg aaa acc atc atc gtg cac ctg aac gag agc gtg gaa atc gtg      922
Asn Val Lys Thr Ile Ile Val His Leu Asn Glu Ser Val Glu Ile Val
275                 280                 285                 290 tgc acc cgg ccc aac aac aac acc aga aag agc atc cgg atc ggc cct      970
Cys Thr Arg Pro Asn Asn Asn Thr Arg Lys Ser Ile Arg Ile Gly Pro
                295                 300                 305 ggc cag acc ttt tac gcc acc ggc gac atc atc ggc aac atc cgg cag     1018
Gly Gln Thr Phe Tyr Ala Thr Gly Asp Ile Ile Gly Asn Ile Arg Gln
            310                 315                 320 gcc tac tgc aac atc aag aag gac gac tgg atc cgg acc ctg cag aga     1066
Ala Tyr Cys Asn Ile Lys Lys Asp Asp Trp Ile Arg Thr Leu Gln Arg
        325                 330                 335 gtg ggc aag aag ctg gcc gag cac ttc ccc aga cgg atc atc aac ttc     1114
Val Gly Lys Lys Leu Ala Glu His Phe Pro Arg Arg Ile Ile Asn Phe
340                 345                 350 acc agc ccc gct ggc ggc gac ctg gaa atc acc acc cac agc ttc aac     1162
Thr Ser Pro Ala Gly Gly Asp Leu Glu Ile Thr Thr His Ser Phe Asn
355                 360                 365                 370 tgc aga ggc gag ttc ttc tac tgc aat acc agc agc ctg ttc aac agc     1210
Cys Arg Gly Glu Phe Phe Tyr Cys Asn Thr Ser Ser Leu Phe Asn Ser
            375                 380                 385 acc tac aac ccc aac gac acc aac agc aac agc tcc agc agc aac tcc     1258
Thr Tyr Asn Pro Asn Asp Thr Asn Ser Asn Ser Ser Ser Ser Asn Ser
```

-continued

```
                390                 395                 400
agc ctg gac atc acc atc cct tgc cgg atc aag cag atc atc aat atg    1306
Ser Leu Asp Ile Thr Ile Pro Cys Arg Ile Lys Gln Ile Ile Asn Met
            405                 410                 415 tgg cag gaa gtg ggc agg gct atg tac gcc cct ccc atc gag ggc aac    1354
Trp Gln Glu Val Gly Arg Ala Met Tyr Ala Pro Pro Ile Glu Gly Asn
420                 425                 430 atc aca tgc aag agc aac atc acc ggc ctg ctc ctg gtc cgc gac ggc    1402
Ile Thr Cys Lys Ser Asn Ile Thr Gly Leu Leu Leu Val Arg Asp Gly
435                 440                 445                 450 ggc gtg gaa agc aac gag aca gag atc ttc aga ccc gga ggc gac        1450
Gly Val Glu Ser Asn Glu Thr Glu Ile Phe Arg Pro Gly Gly Gly Asp
            455                 460                 465 atg cgg aac aac tgg cgg agc gag ctg tac aag tac aag gtg gtg gaa    1498
Met Arg Asn Asn Trp Arg Ser Glu Leu Tyr Lys Tyr Lys Val Val Glu
            470                 475                 480 atc aag ccc ctg gga atc gcc ccc acc gcc gcc aag cgg aga gtg gtg    1546
Ile Lys Pro Leu Gly Ile Ala Pro Thr Ala Ala Lys Arg Arg Val Val
485                 490                 495 gaa ggc gct cac cac cac cat cac cac ggc ctg aac gac atc ttc gag    1594
Glu Gly Ala His His His His His His Gly Leu Asn Asp Ile Phe Glu
500                 505                 510 gcc cag aaa atc gag tgg cac gag tgactcgagt ctagagggcc cgtttaaacc    1648
Ala Gln Lys Ile Glu Trp His Glu
515                 520 cgctgatcag cctcgactg                                                1667
```

<210> SEQ ID NO 60
<211> LENGTH: 522
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
            20                  25                  30

Tyr Tyr Gly Val Pro Val Trp Lys Glu Ala Lys Thr Thr Leu Phe Cys
        35                  40                  45

Ala Ser Asp Ala Lys Ala Tyr Glu Lys Glu Val His Asn Val Trp Ala
    50                  55                  60

Thr His Ala Cys Val Pro Thr Asp Pro Asn Pro Gln Glu Met Val Leu
65                  70                  75                  80

Glu Asn Val Thr Glu Asn Phe Asn Met Trp Lys Asn Asp Met Val Glu
                85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu Glu Cys Arg Gln Val
        115                 120                 125

Asn Thr Thr Asn Ala Thr Ser Ser Val Asn Val Thr Asn Gly Glu Glu
    130                 135                 140

Ile Lys Asn Cys Ser Phe Lys Ala Thr Thr Glu Ile Arg Asp Glu Lys
145                 150                 155                 160

Gln Lys Val Tyr Ala Leu Phe Tyr Arg Leu Asp Ile Val Pro Leu Glu
                165                 170                 175
```

Glu Glu Arg Lys Gly Asn Ser Ser Lys Tyr Arg Leu Ile Asn Cys Asn
            180                 185                 190

Thr Ser Ala Ile Thr Gln Ala Cys Pro Lys Val Thr Phe Asp Pro Ile
        195                 200                 205

Pro Ile His Tyr Cys Ala Pro Ala Gly Tyr Ala Ile Leu Lys Cys Asn
    210                 215                 220

Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Gly Glu Ile Ile Ile Arg Ser Glu Asn Leu
            260                 265                 270

Thr Asn Asn Val Lys Thr Ile Ile Val His Leu Asn Glu Ser Val Glu
        275                 280                 285

Ile Val Cys Thr Arg Pro Asn Asn Asn Thr Arg Lys Ser Ile Arg Ile
    290                 295                 300

Gly Pro Gly Gln Thr Phe Tyr Ala Thr Gly Asp Ile Ile Gly Asn Ile
305                 310                 315                 320

Arg Gln Ala Tyr Cys Asn Ile Lys Lys Asp Asp Trp Ile Arg Thr Leu
                325                 330                 335

Gln Arg Val Gly Lys Lys Leu Ala Glu His Phe Pro Arg Arg Ile Ile
            340                 345                 350

Asn Phe Thr Ser Pro Ala Gly Gly Asp Leu Glu Ile Thr Thr His Ser
        355                 360                 365

Phe Asn Cys Arg Gly Glu Phe Phe Tyr Cys Asn Thr Ser Ser Leu Phe
    370                 375                 380

Asn Ser Thr Tyr Asn Pro Asn Asp Thr Asn Ser Asn Ser Ser Ser Ser
385                 390                 395                 400

Asn Ser Ser Leu Asp Ile Thr Ile Pro Cys Arg Ile Lys Gln Ile Ile
                405                 410                 415

Asn Met Trp Gln Glu Val Gly Arg Ala Met Tyr Ala Pro Pro Ile Glu
            420                 425                 430

Gly Asn Ile Thr Cys Lys Ser Asn Ile Thr Gly Leu Leu Leu Val Arg
        435                 440                 445

Asp Gly Gly Val Glu Ser Asn Glu Thr Glu Ile Phe Arg Pro Gly Gly
    450                 455                 460

Gly Asp Met Arg Asn Asn Trp Arg Ser Glu Leu Tyr Lys Tyr Lys Val
465                 470                 475                 480

Val Glu Ile Lys Pro Leu Gly Ile Ala Pro Thr Ala Ala Lys Arg Arg
                485                 490                 495

Val Val Glu Gly Ala His His His His His His Gly Leu Asn Asp Ile
            500                 505                 510

Phe Glu Ala Gln Lys Ile Glu Trp His Glu
            515                 520

<210> SEQ ID NO 61
<211> LENGTH: 1667
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (53)..(1618)

<400> SEQUENCE: 61

```
ctcactatag ggagacccaa gctggctagc gtttaaactt aagcttgcca cc atg cct      58
                                                         Met Pro
                                                         1 atg ggc agc ctg cag cct ctg gcc acc ctg tac ctg ctg ggc atg ctg       106
Met Gly Ser Leu Gln Pro Leu Ala Thr Leu Tyr Leu Leu Gly Met Leu
    5                  10                  15 gtg gcc tcc gtg ctg gca gct ggc aac ctg tgg gtc aca gtg tac tac       154
Val Ala Ser Val Leu Ala Ala Gly Asn Leu Trp Val Thr Val Tyr Tyr
 20                  25                  30 ggc gtg ccc gtg tgg aaa gag gcc aag acc acc ctg ttc tgc gcc agc       202
Gly Val Pro Val Trp Lys Glu Ala Lys Thr Thr Leu Phe Cys Ala Ser
 35                  40                  45                  50 gac gcc aag gcc tac gag aaa gag gtg cac aac gtc tgg gcc acc cac       250
Asp Ala Lys Ala Tyr Glu Lys Glu Val His Asn Val Trp Ala Thr His
                 55                  60                  65 gcc tgc gtg ccc acc gac ccc aac ccc cag gaa atg gtc ctg gaa aac       298
Ala Cys Val Pro Thr Asp Pro Asn Pro Gln Glu Met Val Leu Glu Asn
                 70                  75                  80 gtg acc gag aac ttc aac atg tgg aag aac gac atg gtg gaa cag atg       346
Val Thr Glu Asn Phe Asn Met Trp Lys Asn Asp Met Val Glu Gln Met
                 85                  90                  95 cac gag gac gtg atc agc ctg tgg gac cag agc ctg aag ccc tgc gtg       394
His Glu Asp Val Ile Ser Leu Trp Asp Gln Ser Leu Lys Pro Cys Val
            100                 105                 110 aag ctg acc ccc ctg tgc gtg acc ctg gaa tgc aga cag gtc aac acc       442
Lys Leu Thr Pro Leu Cys Val Thr Leu Glu Cys Arg Gln Val Asn Thr
115                 120                 125                 130 acc aac gcc acc agc agc gtg aac gtg acc aac ggc gag gaa atc aag       490
Thr Asn Ala Thr Ser Ser Val Asn Val Thr Asn Gly Glu Glu Ile Lys
                135                 140                 145 aac tgc agc ttc aat gcc acc acc gag atc cgg gac aag aaa cag aag       538
Asn Cys Ser Phe Asn Ala Thr Thr Glu Ile Arg Asp Lys Lys Gln Lys
            150                 155                 160 gtg tac gcc ctg tac tac cgg ctg gac atc gtg ccc ctg gaa gag gaa       586
Val Tyr Ala Leu Tyr Tyr Arg Leu Asp Ile Val Pro Leu Glu Glu Glu
            165                 170                 175 cgg aag ggc aac agc agc aag tac cgg ctg atc aac tgc aac acc agc       634
Arg Lys Gly Asn Ser Ser Lys Tyr Arg Leu Ile Asn Cys Asn Thr Ser
        180                 185                 190 gcc atc acc cag gcc tgc ccc aaa gtg acc ttc gac cct atc ccc atc       682
Ala Ile Thr Gln Ala Cys Pro Lys Val Thr Phe Asp Pro Ile Pro Ile
195                 200                 205                 210 cac tac tgc gcc cct gcc ggc tac gcc atc ctg aag tgc aac aac aag       730
His Tyr Cys Ala Pro Ala Gly Tyr Ala Ile Leu Lys Cys Asn Asn Lys
            215                 220                 225 acc ttc aac ggc acc ggc ccc tgc aac aac gtg tcc acc gtg cag tgc       778
Thr Phe Asn Gly Thr Gly Pro Cys Asn Asn Val Ser Thr Val Gln Cys
            230                 235                 240 acc cac ggc atc aag ccc gtg gtg tcc acc cag ctg ctg ctg aat ggc       826
Thr His Gly Ile Lys Pro Val Val Ser Thr Gln Leu Leu Leu Asn Gly
            245                 250                 255 agc ctg gcc gag ggc gag atc atc atc aga agc gag aac ctg acc aac       874
Ser Leu Ala Glu Gly Glu Ile Ile Ile Arg Ser Glu Asn Leu Thr Asn
260                 265                 270 aac gtg aaa acc atc atc gtg cac ctg aac gag agc gtg gaa atc gtg       922
Asn Val Lys Thr Ile Ile Val His Leu Asn Glu Ser Val Glu Ile Val
275                 280                 285                 290 tgc acc cgg ccc aac aac aac acc aga aag agc atc cgg atc ggc cct       970
Cys Thr Arg Pro Asn Asn Asn Thr Arg Lys Ser Ile Arg Ile Gly Pro
                295                 300                 305
```

```
ggc cag acc ttt tac gcc acc ggc gac atc atc ggc aac atc cgg cag    1018
Gly Gln Thr Phe Tyr Ala Thr Gly Asp Ile Ile Gly Asn Ile Arg Gln
        310                 315                 320 gcc tac tgc aac atc aag aag gac gac tgg atc cgg acc ctg cag aga    1066
Ala Tyr Cys Asn Ile Lys Lys Asp Asp Trp Ile Arg Thr Leu Gln Arg
325                 330                 335 gtg ggc aag aag ctg gcc gag cac ttc ccc aga cgg atc atc aac ttc    1114
Val Gly Lys Lys Leu Ala Glu His Phe Pro Arg Arg Ile Ile Asn Phe
    340                 345                 350 acc agc ccc gct ggc ggc gac ctg gaa atc acc acc cac agc ttc aac    1162
Thr Ser Pro Ala Gly Gly Asp Leu Glu Ile Thr Thr His Ser Phe Asn
355                 360                 365                 370 tgc aga ggc gag ttc ttc tac tgc aat acc agc agc ctg ttc aac agc    1210
Cys Arg Gly Glu Phe Phe Tyr Cys Asn Thr Ser Ser Leu Phe Asn Ser
                375                 380                 385 acc tac aac ccc aac gac acc aac agc aac agc tcc agc agc aac tcc    1258
Thr Tyr Asn Pro Asn Asp Thr Asn Ser Asn Ser Ser Ser Ser Asn Ser
            390                 395                 400 agc ctg gac atc acc atc cct tgc cgg atc aag cag atc atc aat atg    1306
Ser Leu Asp Ile Thr Ile Pro Cys Arg Ile Lys Gln Ile Ile Asn Met
        405                 410                 415 tgg cag gaa gtg ggc agg gct atg tac gcc cct ccc atc gag ggc aac    1354
Trp Gln Glu Val Gly Arg Ala Met Tyr Ala Pro Pro Ile Glu Gly Asn
    420                 425                 430 atc aca tgc aag agc aac atc acc ggc ctc ctc ctg gtc cgc gac ggc    1402
Ile Thr Cys Lys Ser Asn Ile Thr Gly Leu Leu Leu Val Arg Asp Gly
435                 440                 445                 450 ggc gtg gaa agc aac gag aca gag atc ttc aga ccc ggc gga ggc gac    1450
Gly Val Glu Ser Asn Glu Thr Glu Ile Phe Arg Pro Gly Gly Gly Asp
                455                 460                 465 atg cgg aac aac tgg cgg agc gag ctg tac aag tac aag gtg gtg gaa    1498
Met Arg Asn Asn Trp Arg Ser Glu Leu Tyr Lys Tyr Lys Val Val Glu
            470                 475                 480 atc aag ccc ctg gga atc gcc ccc acc gcc gcc aag cgg aga gtg gtg    1546
Ile Lys Pro Leu Gly Ile Ala Pro Thr Ala Ala Lys Arg Arg Val Val
        485                 490                 495 gaa ggc gct cac cac cac cat cac cac ggc ctg aac gac atc ttc gag    1594
Glu Gly Ala His His His His His His Gly Leu Asn Asp Ile Phe Glu
    500                 505                 510 gcc cag aaa atc gag tgg cac gag tgactcgagt ctagagggcc cgtttaaacc    1648
Ala Gln Lys Ile Glu Trp His Glu
515                 520 cgctgatcag cctcgactg                                                 1667

<210> SEQ ID NO 62
<211> LENGTH: 522
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
            20                  25                  30

Tyr Tyr Gly Val Pro Val Trp Lys Glu Ala Lys Thr Thr Leu Phe Cys
        35                  40                  45

Ala Ser Asp Ala Lys Ala Tyr Glu Lys Glu Val His Asn Val Trp Ala
    50                  55                  60
```

-continued

```
Thr His Ala Cys Val Pro Thr Asp Pro Asn Pro Gln Glu Met Val Leu
 65                  70                  75                  80

Glu Asn Val Thr Glu Asn Phe Asn Met Trp Lys Asn Asp Met Val Glu
                 85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu Glu Cys Arg Gln Val
        115                 120                 125

Asn Thr Thr Asn Ala Thr Ser Ser Val Asn Val Thr Asn Gly Glu Glu
    130                 135                 140

Ile Lys Asn Cys Ser Phe Asn Ala Thr Thr Glu Ile Arg Asp Lys Lys
145                 150                 155                 160

Gln Lys Val Tyr Ala Leu Tyr Tyr Arg Leu Asp Ile Val Pro Leu Glu
                165                 170                 175

Glu Glu Arg Lys Gly Asn Ser Ser Lys Tyr Arg Leu Ile Asn Cys Asn
            180                 185                 190

Thr Ser Ala Ile Thr Gln Ala Cys Pro Lys Val Thr Phe Asp Pro Ile
        195                 200                 205

Pro Ile His Tyr Cys Ala Pro Ala Gly Tyr Ala Ile Leu Lys Cys Asn
    210                 215                 220

Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Gly Glu Ile Ile Ile Arg Ser Glu Asn Leu
            260                 265                 270

Thr Asn Asn Val Lys Thr Ile Ile Val His Leu Asn Glu Ser Val Glu
        275                 280                 285

Ile Val Cys Thr Arg Pro Asn Asn Asn Thr Arg Lys Ser Ile Arg Ile
290                 295                 300

Gly Pro Gly Gln Thr Phe Tyr Ala Thr Gly Asp Ile Ile Gly Asn Ile
305                 310                 315                 320

Arg Gln Ala Tyr Cys Asn Ile Lys Lys Asp Asp Trp Ile Arg Thr Leu
                325                 330                 335

Gln Arg Val Gly Lys Lys Leu Ala Glu His Phe Pro Arg Ile Ile
            340                 345                 350

Asn Phe Thr Ser Pro Ala Gly Gly Asp Leu Glu Ile Thr Thr His Ser
        355                 360                 365

Phe Asn Cys Arg Gly Glu Phe Phe Tyr Cys Asn Thr Ser Ser Leu Phe
370                 375                 380

Asn Ser Thr Tyr Asn Pro Asn Asp Thr Asn Ser Asn Ser Ser Ser
385                 390                 395                 400

Asn Ser Ser Leu Asp Ile Thr Ile Pro Cys Arg Ile Lys Gln Ile Ile
                405                 410                 415

Asn Met Trp Gln Glu Val Gly Arg Ala Met Tyr Ala Pro Pro Ile Glu
            420                 425                 430

Gly Asn Ile Thr Cys Lys Ser Asn Ile Thr Gly Leu Leu Leu Val Arg
        435                 440                 445

Asp Gly Gly Val Glu Ser Asn Gly Thr Glu Ile Phe Arg Pro Gly Gly
    450                 455                 460

Gly Asp Met Arg Asn Asn Trp Arg Ser Glu Leu Tyr Lys Tyr Lys Val
465                 470                 475                 480

Val Glu Ile Lys Pro Leu Gly Ile Ala Pro Thr Ala Ala Lys Arg Arg
```

```
                          485                 490                 495
         Val Val Glu Gly Ala His His His His His Gly Leu Asn Asp Ile
                         500                 505                 510

Phe Glu Ala Gln Lys Ile Glu Trp His Glu
                 515                 520

<210> SEQ ID NO 63
<211> LENGTH: 2479
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (42)..(2441)

<400> SEQUENCE: 63
gagacccaag ctggctagcg tttaaactta agcttgccac c atg cct atg ggc agc      56
                                              Met Pro Met Gly Ser
                                                1               5 ctg cag cct ctg gcc acc ctg tac ctg ctg ggc atg ctg gtg gcc tcc      104
Leu Gln Pro Leu Ala Thr Leu Tyr Leu Leu Gly Met Leu Val Ala Ser
             10                  15                  20 gtg ctg gca gct ggc aac ctg tgg gtc aca gtg tac tac ggc gtg ccc      152
Val Leu Ala Ala Gly Asn Leu Trp Val Thr Val Tyr Tyr Gly Val Pro
         25                  30                  35 gtg tgg aaa gag gcc aag acc acc ctg ttc tgc gcc agc gac gcc aag      200
Val Trp Lys Glu Ala Lys Thr Thr Leu Phe Cys Ala Ser Asp Ala Lys
 40                  45                  50 gcc tac gag aaa gag gtg cac aac gtc tgg gcc acc cac gcc tgc gtg      248
Ala Tyr Glu Lys Glu Val His Asn Val Trp Ala Thr His Ala Cys Val
     55                  60                  65 ccc acc gac ccc aac ccc cag gaa atg gtc ctg gaa aac gtg acc gag      296
Pro Thr Asp Pro Asn Pro Gln Glu Met Val Leu Glu Asn Val Thr Glu
 70                  75                  80                  85 aac ttc aac atg tgg aag aac gac atg gtg gaa cag atg cac gag gac      344
Asn Phe Asn Met Trp Lys Asn Asp Met Val Glu Gln Met His Glu Asp
                 90                  95                 100 gtg atc agc ctg tgg gac cag agc ctg aag ccc tgc gtg aag ctg acc      392
Val Ile Ser Leu Trp Asp Gln Ser Leu Lys Pro Cys Val Lys Leu Thr
            105                 110                 115 ccc ctg tgc gtg acc ctg gaa tgc aga cag gtc aac acc acc aac gcc      440
Pro Leu Cys Val Thr Leu Glu Cys Arg Gln Val Asn Thr Thr Asn Ala
        120                 125                 130 acc agc agc gtg aac gtg acc aac ggc gag gaa atc aag aac tgc agc      488
Thr Ser Ser Val Asn Val Thr Asn Gly Glu Glu Ile Lys Asn Cys Ser
    135                 140                 145 ttc aat gcc acc acc gag atc cgg gac aag aaa cag aag gtg tac gcc      536
Phe Asn Ala Thr Thr Glu Ile Arg Asp Lys Lys Gln Lys Val Tyr Ala
150                 155                 160                 165 ctg ttc tac cgg ctg gac atc gtg ccc ctg gaa gag gaa cgg aag ggc      584
Leu Phe Tyr Arg Leu Asp Ile Val Pro Leu Glu Glu Glu Arg Lys Gly
                170                 175                 180 aac agc agc aag tac cgg ctg atc aac tgc aac acc agc gcc atc acc      632
Asn Ser Ser Lys Tyr Arg Leu Ile Asn Cys Asn Thr Ser Ala Ile Thr
            185                 190                 195 cag gcc tgc ccc aaa gtg acc ttc gac cct atc ccc atc cac tac tgc      680
Gln Ala Cys Pro Lys Val Thr Phe Asp Pro Ile Pro Ile His Tyr Cys
        200                 205                 210 gcc cct gcc ggc tac gcc atc ctg aag tgc aac aac aag acc ttc aac      728
Ala Pro Ala Gly Tyr Ala Ile Leu Lys Cys Asn Asn Lys Thr Phe Asn
```

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     | 215 |     |     |     | 220 |     |     |     | 225 |     |     |     |     |     |     |      |
| ggc | acc | ggc | ccc | tgc | aac | aac | gtg | tcc | acc | gtg | cag | tgc | acc | cac | ggc | 776  |
| Gly | Thr | Gly | Pro | Cys | Asn | Asn | Val | Ser | Thr | Val | Gln | Cys | Thr | His | Gly |      |
| 230 |     |     |     |     | 235 |     |     |     |     | 240 |     |     |     |     | 245 |      |
| atc | aag | ccc | gtg | gtg | tcc | acc | cag | ctg | ctg | ctg | aat | ggc | agc | ctg | gcc | 824  |
| Ile | Lys | Pro | Val | Val | Ser | Thr | Gln | Leu | Leu | Leu | Asn | Gly | Ser | Leu | Ala |      |
|     |     |     |     |     | 250 |     |     |     |     | 255 |     |     |     |     | 260 |      |
| gag | ggc | gag | atc | atc | atc | aga | agc | gag | aac | ctg | acc | aac | aac | gtg | aaa | 872  |
| Glu | Gly | Glu | Ile | Ile | Ile | Arg | Ser | Glu | Asn | Leu | Thr | Asn | Asn | Val | Lys |      |
|     |     |     |     | 265 |     |     |     |     | 270 |     |     |     |     | 275 |     |      |
| acc | atc | atc | gtg | cac | ctg | aac | gag | agc | gtg | gaa | atc | gtg | tgc | acc | cgg | 920  |
| Thr | Ile | Ile | Val | His | Leu | Asn | Glu | Ser | Val | Glu | Ile | Val | Cys | Thr | Arg |      |
|     |     |     |     | 280 |     |     |     |     | 285 |     |     |     |     | 290 |     |      |
| ccc | aac | aac | aac | acc | aga | aag | agc | atc | cgg | atc | ggc | cct | ggc | cag | acc | 968  |
| Pro | Asn | Asn | Asn | Thr | Arg | Lys | Ser | Ile | Arg | Ile | Gly | Pro | Gly | Gln | Thr |      |
|     |     |     |     | 295 |     |     |     |     | 300 |     |     |     |     | 305 |     |      |
| ttt | tac | gcc | acc | ggc | gac | atc | atc | ggc | aac | atc | cgg | cag | gcc | tac | tgc | 1016 |
| Phe | Tyr | Ala | Thr | Gly | Asp | Ile | Ile | Gly | Asn | Ile | Arg | Gln | Ala | Tyr | Cys |      |
| 310 |     |     |     |     | 315 |     |     |     |     | 320 |     |     |     |     | 325 |      |
| aac | atc | aag | aag | gac | gac | tgg | atc | cgg | acc | ctg | cag | aga | gtg | ggc | aag | 1064 |
| Asn | Ile | Lys | Lys | Asp | Asp | Trp | Ile | Arg | Thr | Leu | Gln | Arg | Val | Gly | Lys |      |
|     |     |     |     |     | 330 |     |     |     |     | 335 |     |     |     |     | 340 |      |
| aag | ctg | gcc | gag | cac | ttc | ccc | aga | cgg | atc | atc | aac | ttc | acc | agc | ccc | 1112 |
| Lys | Leu | Ala | Glu | His | Phe | Pro | Arg | Arg | Ile | Ile | Asn | Phe | Thr | Ser | Pro |      |
|     |     |     |     | 345 |     |     |     |     | 350 |     |     |     |     | 355 |     |      |
| gct | ggc | ggc | gac | ctg | gaa | atc | acc | acc | cac | agc | ttc | aac | tgc | aga | ggc | 1160 |
| Ala | Gly | Gly | Asp | Leu | Glu | Ile | Thr | Thr | His | Ser | Phe | Asn | Cys | Arg | Gly |      |
|     |     |     |     | 360 |     |     |     |     | 365 |     |     |     |     | 370 |     |      |
| gag | ttc | ttc | tac | tgc | aat | acc | agc | agc | ctg | ttc | aac | agc | acc | tac | aac | 1208 |
| Glu | Phe | Phe | Tyr | Cys | Asn | Thr | Ser | Ser | Leu | Phe | Asn | Ser | Thr | Tyr | Asn |      |
|     | 375 |     |     |     |     | 380 |     |     |     |     | 385 |     |     |     |     |      |
| ccc | aac | gac | acc | aac | agc | aac | agc | tcc | agc | agc | aac | tcc | agc | ctg | gac | 1256 |
| Pro | Asn | Asp | Thr | Asn | Ser | Asn | Ser | Ser | Ser | Ser | Asn | Ser | Ser | Leu | Asp |      |
| 390 |     |     |     |     | 395 |     |     |     |     | 400 |     |     |     |     | 405 |      |
| atc | acc | atc | cct | tgc | cgg | atc | aag | cag | atc | atc | aat | atg | tgg | cag | gaa | 1304 |
| Ile | Thr | Ile | Pro | Cys | Arg | Ile | Lys | Gln | Ile | Ile | Asn | Met | Trp | Gln | Glu |      |
|     |     |     |     |     | 410 |     |     |     |     | 415 |     |     |     |     | 420 |      |
| gtg | ggc | agg | gct | atg | tac | gcc | cct | ccc | atc | gag | ggc | aac | atc | aca | tgc | 1352 |
| Val | Gly | Arg | Ala | Met | Tyr | Ala | Pro | Pro | Ile | Glu | Gly | Asn | Ile | Thr | Cys |      |
|     |     |     |     | 425 |     |     |     |     | 430 |     |     |     |     | 435 |     |      |
| aag | agc | aac | atc | acc | ggc | ctg | ctc | ctg | gtc | cgc | gac | ggc | ggc | gtg | gaa | 1400 |
| Lys | Ser | Asn | Ile | Thr | Gly | Leu | Leu | Leu | Val | Arg | Asp | Gly | Gly | Val | Glu |      |
|     |     |     |     | 440 |     |     |     |     | 445 |     |     |     |     | 450 |     |      |
| agc | aac | gag | aca | gag | atc | ttc | aga | ccc | ggc | gga | ggc | gac | atg | cgg | aac | 1448 |
| Ser | Asn | Glu | Thr | Glu | Ile | Phe | Arg | Pro | Gly | Gly | Gly | Asp | Met | Arg | Asn |      |
|     | 455 |     |     |     |     | 460 |     |     |     |     | 465 |     |     |     |     |      |
| aac | tgg | cgg | agc | gag | ctg | tac | aag | tac | aag | gtg | gtg | gaa | atc | aag | ccc | 1496 |
| Asn | Trp | Arg | Ser | Glu | Leu | Tyr | Lys | Tyr | Lys | Val | Val | Glu | Ile | Lys | Pro |      |
| 470 |     |     |     |     | 475 |     |     |     |     | 480 |     |     |     |     | 485 |      |
| ctg | gga | atc | gcc | ccc | acc | gcc | gcc | aag | cgg | aga | gtg | gtg | gaa | agc | gag | 1544 |
| Leu | Gly | Ile | Ala | Pro | Thr | Ala | Ala | Lys | Arg | Arg | Val | Val | Glu | Ser | Glu |      |
|     |     |     |     | 490 |     |     |     |     | 495 |     |     |     |     | 500 |     |      |
| aag | tcc | gcc | gtg | ggc | ctg | ggc | gcc | gtg | atc | ttc | ggc | ttt | ctg | gga | gcc | 1592 |
| Lys | Ser | Ala | Val | Gly | Leu | Gly | Ala | Val | Ile | Phe | Gly | Phe | Leu | Gly | Ala |      |
|     |     |     |     | 505 |     |     |     |     | 510 |     |     |     |     | 515 |     |      |
| gcc | gga | agc | acc | atg | ggc | gct | gcc | agc | atc | acc | ctg | acc | gtg | cag | gcc | 1640 |
| Ala | Gly | Ser | Thr | Met | Gly | Ala | Ala | Ser | Ile | Thr | Leu | Thr | Val | Gln | Ala |      |
|     |     |     |     | 520 |     |     |     |     | 525 |     |     |     |     | 530 |     |      |
| aga | cag | ctg | ctg | agc | ggc | atc | gtg | cag | cag | cag | agc | aac | ctg | ctg | aag | 1688 |
| Arg | Gln | Leu | Leu | Ser | Gly | Ile | Val | Gln | Gln | Gln | Ser | Asn | Leu | Leu | Lys |      |

```
gcc atc gag gcc cag cag cat ctg ctg cag ctg acc gtg tgg ggc atc    1736
Ala Ile Glu Ala Gln Gln His Leu Leu Gln Leu Thr Val Trp Gly Ile
550             555                 560                 565 aag cag ctg cag acc cgg gtg ctg gcc atc gag aga tac ctg aag gac    1784
Lys Gln Leu Gln Thr Arg Val Leu Ala Ile Glu Arg Tyr Leu Lys Asp
                570                 575                 580 cag cag ctc ctg gga atc tgg ggc tgc agc ggc aag ctg atc tgc acc    1832
Gln Gln Leu Leu Gly Ile Trp Gly Cys Ser Gly Lys Leu Ile Cys Thr
            585                 590                 595 acc gcc gtg ccc tgg aac agc agc tgg tcc aac aag agc cac gac gag    1880
Thr Ala Val Pro Trp Asn Ser Ser Trp Ser Asn Lys Ser His Asp Glu
        600                 605                 610 atc tgg ggc aac atg acc tgg atg cag tgg gac aga gag atc agc aac    1928
Ile Trp Gly Asn Met Thr Trp Met Gln Trp Asp Arg Glu Ile Ser Asn
    615                 620                 625 tac acc aac acc atc tac cgc ctg ctg gaa gat agc cag aac cag cag    1976
Tyr Thr Asn Thr Ile Tyr Arg Leu Leu Glu Asp Ser Gln Asn Gln Gln
630                 635                 640                 645 gaa cag aac gag aag gac ctg ctg gcc ctg gac agc tgg gag aac ctg    2024
Glu Gln Asn Glu Lys Asp Leu Leu Ala Leu Asp Ser Trp Glu Asn Leu
                650                 655                 660 tgg aac tgg ttc agc atc acc aag tgg ctg tgg tac atc aag ggc agc    2072
Trp Asn Trp Phe Ser Ile Thr Lys Trp Leu Trp Tyr Ile Lys Gly Ser
            665                 670                 675 ggc atg gtc cga ggc atc aga ggc gcc atc acc gtg gaa gag gac acc    2120
Gly Met Val Arg Gly Ile Arg Gly Ala Ile Thr Val Glu Glu Asp Thr
        680                 685                 690 ccc gag gcc atc cac cag gcc acc aga gaa ctg ctc ctc aag atg ctg    2168
Pro Glu Ala Ile His Gln Ala Thr Arg Glu Leu Leu Leu Lys Met Leu
    695                 700                 705 gaa gcc aac ggc atc cag agc tac gag gaa ctg gcc gcc gtg atc ttc    2216
Glu Ala Asn Gly Ile Gln Ser Tyr Glu Glu Leu Ala Ala Val Ile Phe
710                 715                 720                 725 acc gtg aca gag gac ctg acc ttc gcc ttc ccc gcc gaa gcc gcc aga    2264
Thr Val Thr Glu Asp Leu Thr Phe Ala Phe Pro Ala Glu Ala Ala Arg
                730                 735                 740 cag atc ggc atg cac cgg gtg ccc ctg ctg agc gcc aga gaa gtg cct    2312
Gln Ile Gly Met His Arg Val Pro Leu Leu Ser Ala Arg Glu Val Pro
            745                 750                 755 gtg ccc ggc agc ctg ccc aga gtg atc aga gtg ctg gcc ctg tgg aac    2360
Val Pro Gly Ser Leu Pro Arg Val Ile Arg Val Leu Ala Leu Trp Asn
        760                 765                 770 acc gcc acc ccc cag gat aga gtg cgg cac gtg tac ctg cgc gag gct    2408
Thr Ala Thr Pro Gln Asp Arg Val Arg His Val Tyr Leu Arg Glu Ala
    775                 780                 785 gtc aga ctg agg cct cac cac cac cat cac cac tgactcgagt ctagagggcc    2461
Val Arg Leu Arg Pro His His His His His His
790                 795                 800 cgtttaaacc cgctgatc                                                 2479

<210> SEQ ID NO 64
<211> LENGTH: 800
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Pro Met Gly Ser Leu Gln Pro Leu Ala Thr Leu Tyr Leu Leu Gly
```

-continued

```
1               5               10              15
Met Leu Val Ala Ser Val Leu Ala Ala Gly Asn Leu Trp Val Thr Val
                20              25              30
Tyr Tyr Gly Val Pro Val Trp Lys Glu Ala Lys Thr Thr Leu Phe Cys
                35              40              45
Ala Ser Asp Ala Lys Ala Tyr Glu Lys Glu Val His Asn Val Trp Ala
 50              55              60
Thr His Ala Cys Val Pro Thr Asp Pro Asn Pro Gln Glu Met Val Leu
 65              70              75              80
Glu Asn Val Thr Glu Asn Phe Asn Met Trp Lys Asn Asp Met Val Glu
                85              90              95
Gln Met His Glu Asp Val Ile Ser Leu Trp Asp Gln Ser Leu Lys Pro
                100             105             110
Cys Val Lys Leu Thr Pro Leu Cys Val Thr Leu Glu Cys Arg Gln Val
                115             120             125
Asn Thr Thr Asn Ala Thr Ser Ser Val Asn Val Thr Asn Gly Glu Glu
                130             135             140
Ile Lys Asn Cys Ser Phe Asn Ala Thr Thr Glu Ile Arg Asp Lys Lys
145             150             155             160
Gln Lys Val Tyr Ala Leu Phe Tyr Arg Leu Asp Ile Val Pro Leu Glu
                165             170             175
Glu Glu Arg Lys Gly Asn Ser Ser Lys Tyr Arg Leu Ile Asn Cys Asn
                180             185             190
Thr Ser Ala Ile Thr Gln Ala Cys Pro Lys Val Thr Phe Asp Pro Ile
                195             200             205
Pro Ile His Tyr Cys Ala Pro Ala Gly Tyr Ala Ile Leu Lys Cys Asn
                210             215             220
Asn Lys Thr Phe Asn Gly Thr Gly Pro Cys Asn Asn Val Ser Thr Val
225             230             235             240
Gln Cys Thr His Gly Ile Lys Pro Val Val Ser Thr Gln Leu Leu Leu
                245             250             255
Asn Gly Ser Leu Ala Glu Gly Glu Ile Ile Ile Arg Ser Glu Asn Leu
                260             265             270
Thr Asn Asn Val Lys Thr Ile Ile Val His Leu Asn Glu Ser Val Glu
                275             280             285
Ile Val Cys Thr Arg Pro Asn Asn Thr Arg Lys Ser Ile Arg Ile
                290             295             300
Gly Pro Gly Gln Thr Phe Tyr Ala Thr Gly Asp Ile Ile Gly Asn Ile
305             310             315             320
Arg Gln Ala Tyr Cys Asn Ile Lys Lys Asp Asp Trp Ile Arg Thr Leu
                325             330             335
Gln Arg Val Gly Lys Lys Leu Ala Glu His Phe Pro Arg Arg Ile Ile
                340             345             350
Asn Phe Thr Ser Pro Ala Gly Gly Asp Leu Glu Ile Thr Thr His Ser
                355             360             365
Phe Asn Cys Arg Gly Glu Phe Phe Tyr Cys Asn Thr Ser Ser Leu Phe
                370             375             380
Asn Ser Thr Tyr Asn Pro Asn Asp Thr Asn Ser Asn Ser Ser Ser
385             390             395             400
Asn Ser Ser Leu Asp Ile Thr Ile Pro Cys Arg Ile Lys Gln Ile Ile
                405             410             415
Asn Met Trp Gln Glu Val Gly Arg Ala Met Tyr Ala Pro Pro Ile Glu
                420             425             430
```

```
Gly Asn Ile Thr Cys Lys Ser Asn Ile Thr Gly Leu Leu Leu Val Arg
        435                 440                 445

Asp Gly Gly Val Glu Ser Asn Glu Thr Glu Ile Phe Arg Pro Gly Gly
    450                 455                 460

Gly Asp Met Arg Asn Asn Trp Arg Ser Glu Leu Tyr Lys Tyr Lys Val
465                 470                 475                 480

Val Glu Ile Lys Pro Leu Gly Ile Ala Pro Thr Ala Ala Lys Arg Arg
                485                 490                 495

Val Val Glu Ser Glu Lys Ser Ala Val Gly Leu Gly Ala Val Ile Phe
            500                 505                 510

Gly Phe Leu Gly Ala Ala Gly Ser Thr Met Gly Ala Ala Ser Ile Thr
        515                 520                 525

Leu Thr Val Gln Ala Arg Gln Leu Leu Ser Gly Ile Val Gln Gln Gln
    530                 535                 540

Ser Asn Leu Leu Lys Ala Ile Glu Ala Gln Gln His Leu Leu Gln Leu
545                 550                 555                 560

Thr Val Trp Gly Ile Lys Gln Leu Gln Thr Arg Val Leu Ala Ile Glu
                565                 570                 575

Arg Tyr Leu Lys Asp Gln Gln Leu Leu Gly Ile Trp Gly Cys Ser Gly
            580                 585                 590

Lys Leu Ile Cys Thr Thr Ala Val Pro Trp Asn Ser Ser Trp Ser Asn
        595                 600                 605

Lys Ser His Asp Glu Ile Trp Gly Asn Met Thr Trp Met Gln Trp Asp
    610                 615                 620

Arg Glu Ile Ser Asn Tyr Thr Asn Thr Ile Tyr Arg Leu Leu Glu Asp
625                 630                 635                 640

Ser Gln Asn Gln Gln Glu Gln Asn Glu Lys Asp Leu Leu Ala Leu Asp
                645                 650                 655

Ser Trp Glu Asn Leu Trp Asn Trp Phe Ser Ile Thr Lys Trp Leu Trp
            660                 665                 670

Tyr Ile Lys Gly Ser Gly Met Val Arg Gly Ile Arg Gly Ala Ile Thr
        675                 680                 685

Val Glu Glu Asp Thr Pro Glu Ala Ile His Gln Ala Thr Arg Glu Leu
    690                 695                 700

Leu Leu Lys Met Leu Glu Ala Asn Gly Ile Gln Ser Tyr Glu Glu Leu
705                 710                 715                 720

Ala Ala Val Ile Phe Thr Val Thr Glu Asp Leu Thr Phe Ala Phe Pro
                725                 730                 735

Ala Glu Ala Ala Arg Gln Ile Gly Met His Arg Val Pro Leu Leu Ser
            740                 745                 750

Ala Arg Glu Val Pro Val Pro Gly Ser Leu Pro Arg Val Ile Arg Val
        755                 760                 765

Leu Ala Leu Trp Asn Thr Ala Thr Pro Gln Asp Arg Val Arg His Val
    770                 775                 780

Tyr Leu Arg Glu Ala Val Arg Leu Arg Pro His His His His His His
785                 790                 795                 800

<210> SEQ ID NO 65
<211> LENGTH: 2275
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (42)..(2237)
```

<400> SEQUENCE: 65

```
gagacccaag ctggctagcg tttaaactta agcttgccac c atg cct atg ggc agc          56
                                              Met Pro Met Gly Ser
                                              1               5 ctg cag cct ctg gcc acc ctg tac ctg ctg ggc atg ctg gtg gcc tcc          104
Leu Gln Pro Leu Ala Thr Leu Tyr Leu Leu Gly Met Leu Val Ala Ser
            10                  15                  20 gtg ctg gca gct ggc aac ctg tgg gtc aca gtg tac tac ggc gtg ccc          152
Val Leu Ala Ala Gly Asn Leu Trp Val Thr Val Tyr Tyr Gly Val Pro
                25                  30                  35 gtg tgg aaa gag gcc aag acc acc ctg ttc tgc gcc agc gac gcc aag          200
Val Trp Lys Glu Ala Lys Thr Thr Leu Phe Cys Ala Ser Asp Ala Lys
        40                  45                  50 gcc tac gag aaa gag gtg cac aac gtc tgg gcc acc cac gcc tgc gtg          248
Ala Tyr Glu Lys Glu Val His Asn Val Trp Ala Thr His Ala Cys Val
    55                  60                  65 ccc acc gac ccc aac ccc cag gaa atg gtc ctg gaa aac gtg acc gag          296
Pro Thr Asp Pro Asn Pro Gln Glu Met Val Leu Glu Asn Val Thr Glu
70                  75                  80                  85 aac ttc aac atg tgg aag aac gac atg gtg gaa cag atg cac gag gac          344
Asn Phe Asn Met Trp Lys Asn Asp Met Val Glu Gln Met His Glu Asp
                90                  95                  100 gtg atc agc ctg tgg gac cag agc ctg aag ccc tgc gtg aag ctg acc          392
Val Ile Ser Leu Trp Asp Gln Ser Leu Lys Pro Cys Val Lys Leu Thr
                105                 110                 115 ccc ctg tgc gtg acc ctg gaa tgc aga cag gtc aac acc acc aac gcc          440
Pro Leu Cys Val Thr Leu Glu Cys Arg Gln Val Asn Thr Thr Asn Ala
            120                 125                 130 acc agc agc gtg aac gtg acc aac ggc gag gaa atc aag aac tgc agc          488
Thr Ser Ser Val Asn Val Thr Asn Gly Glu Glu Ile Lys Asn Cys Ser
        135                 140                 145 ttc aag gcc acc acc gag atc cgg gac aag aaa cag aag gtg tac gcc          536
Phe Lys Ala Thr Thr Glu Ile Arg Asp Lys Lys Gln Lys Val Tyr Ala
150                 155                 160                 165 ctg ttc tac cgg ctg gac atc gtg ccc ctg gaa gag gaa cgg aag ggc          584
Leu Phe Tyr Arg Leu Asp Ile Val Pro Leu Glu Glu Glu Arg Lys Gly
                170                 175                 180 aac agc agc aag tac cgg ctg atc aac tgc aac acc agc gcc atc acc          632
Asn Ser Ser Lys Tyr Arg Leu Ile Asn Cys Asn Thr Ser Ala Ile Thr
                185                 190                 195 cag gcc tgc ccc aaa gtg acc ttc gac cct atc ccc atc cac tac tgc          680
Gln Ala Cys Pro Lys Val Thr Phe Asp Pro Ile Pro Ile His Tyr Cys
            200                 205                 210 gcc cct gcc ggc tac gcc atc ctg aag tgc aac aac aag acc ttc aac          728
Ala Pro Ala Gly Tyr Ala Ile Leu Lys Cys Asn Asn Lys Thr Phe Asn
        215                 220                 225 ggc acc ggc ccc tgc aac aac gtg tcc acc gtg cag tgc acc cac ggc          776
Gly Thr Gly Pro Cys Asn Asn Val Ser Thr Val Gln Cys Thr His Gly
230                 235                 240                 245 atc aag ccc gtg gtg tcc acc cag ctg ctg ctg aat ggc agc ctg gcc          824
Ile Lys Pro Val Val Ser Thr Gln Leu Leu Leu Asn Gly Ser Leu Ala
                250                 255                 260 gag ggc gag atc atc atc aga agc gag aac ctg acc aac aac gtg aaa          872
Glu Gly Glu Ile Ile Ile Arg Ser Glu Asn Leu Thr Asn Asn Val Lys
                265                 270                 275 acc atc atc gtg cac ctg aac gag agc gtg gaa atc gtg tgc acc cgg          920
Thr Ile Ile Val His Leu Asn Glu Ser Val Glu Ile Val Cys Thr Arg
            280                 285                 290 ccc aac aac aac acc aga aag agc atc cgg atc ggc cct ggc cag acc          968
Pro Asn Asn Asn Thr Arg Lys Ser Ile Arg Ile Gly Pro Gly Gln Thr
```

-continued

```
        Pro Asn Asn Thr Arg Lys Ser Ile Arg Ile Gly Pro Gly Gln Thr
            295                 300                 305 ttt tac gcc acc ggc gac atc atc ggc aac atc cgg cag gcc tac tgc       1016
Phe Tyr Ala Thr Gly Asp Ile Ile Gly Asn Ile Arg Gln Ala Tyr Cys
310                 315                 320                 325 aac atc aag aag gac gac tgg atc cgg acc ctg cag aga gtg ggc aag       1064
Asn Ile Lys Lys Asp Asp Trp Ile Arg Thr Leu Gln Arg Val Gly Lys
                330                 335                 340 aag ctg gcc gag cac ttc ccc aga cgg atc atc aac ttc acc agc ccc       1112
Lys Leu Ala Glu His Phe Pro Arg Arg Ile Ile Asn Phe Thr Ser Pro
            345                 350                 355 gct ggc ggc gac ctg gaa atc acc acc cac agc ttc aac tgc aga ggc       1160
Ala Gly Gly Asp Leu Glu Ile Thr Thr His Ser Phe Asn Cys Arg Gly
        360                 365                 370 gag ttc ttc tac tgc aat acc agc agc ctg ttc aac agc acc tac aac       1208
Glu Phe Phe Tyr Cys Asn Thr Ser Ser Leu Phe Asn Ser Thr Tyr Asn
375                 380                 385 ccc aac gac acc aac agc aac agc tcc agc agc aac tcc agc ctg gac       1256
Pro Asn Asp Thr Asn Ser Asn Ser Ser Ser Asn Ser Ser Leu Asp
390                 395                 400                 405 atc acc atc cct tgc cgg atc aag cag atc atc aat atg tgg cag gaa       1304
Ile Thr Ile Pro Cys Arg Ile Lys Gln Ile Ile Asn Met Trp Gln Glu
                410                 415                 420 gtg ggc agg gct atg tac gcc cct ccc atc gag ggc aac atc aca tgc       1352
Val Gly Arg Ala Met Tyr Ala Pro Pro Ile Glu Gly Asn Ile Thr Cys
            425                 430                 435 aag agc aac atc acc ggc ctg ctc ctg gtc cgc gac ggc ggc gtg gaa       1400
Lys Ser Asn Ile Thr Gly Leu Leu Leu Val Arg Asp Gly Gly Val Glu
        440                 445                 450 agc aac gag aca gag atc ttc aga ccc ggc gga ggc gac atg cgg aac       1448
Ser Asn Glu Thr Glu Ile Phe Arg Pro Gly Gly Gly Asp Met Arg Asn
455                 460                 465 aac tgg cgg agc gag ctg tac aag tac aag gtg gtg gaa atc aag ccc       1496
Asn Trp Arg Ser Glu Leu Tyr Lys Tyr Lys Val Val Glu Ile Lys Pro
470                 475                 480                 485 ctg gga atc gcc ccc acc gcc gcc aag cgg aga gtg gtg gaa agc gag       1544
Leu Gly Ile Ala Pro Thr Ala Ala Lys Arg Arg Val Val Glu Ser Glu
                490                 495                 500 aag tcc gcc gtg ggc ctg ggc gcc gtg atc ttc ggc ttt ctg gga gcc       1592
Lys Ser Ala Val Gly Leu Gly Ala Val Ile Phe Gly Phe Leu Gly Ala
            505                 510                 515 gcc gga agc acc atg ggc gct gcc agc atc acc ctg acc gtg cag gcc       1640
Ala Gly Ser Thr Met Gly Ala Ala Ser Ile Thr Leu Thr Val Gln Ala
        520                 525                 530 aga cag ctg ctg agc ggc atc gtg cag cag cag agc aac ctg ctg aag       1688
Arg Gln Leu Leu Ser Gly Ile Val Gln Gln Gln Ser Asn Leu Leu Lys
535                 540                 545 gcc atc gag gcc cag cag cat ctg ctg cag ctg acc gtg tgg ggc atc       1736
Ala Ile Glu Ala Gln Gln His Leu Leu Gln Leu Thr Val Trp Gly Ile
550                 555                 560                 565 aag cag ctg cag acc cgg gtg ctg gcc atc gag aga tac ctg aag gac       1784
Lys Gln Leu Gln Thr Arg Val Leu Ala Ile Glu Arg Tyr Leu Lys Asp
                570                 575                 580 cag cag ctc ctg gga atc tgg ggc tgc agc ggc aag ctg atc tgc acc       1832
Gln Gln Leu Leu Gly Ile Trp Gly Cys Ser Gly Lys Leu Ile Cys Thr
            585                 590                 595 acc gcc gtg ccc tgg aac agc agc tgg tcc aac aag agc cac gac gag       1880
Thr Ala Val Pro Trp Asn Ser Ser Trp Ser Asn Lys Ser His Asp Glu
        600                 605                 610 atc tgg ggc aac atg acc tgg atg cag tgg gac aga gag atc agc aac       1928
Ile Trp Gly Asn Met Thr Trp Met Gln Trp Asp Arg Glu Ile Ser Asn
```

```
Ile Trp Gly Asn Met Thr Trp Met Gln Trp Asp Arg Glu Ile Ser Asn
615                 620                 625 tac acc aac acc atc tac cgc ctg ctg gaa gat agc cag aac cag cag       1976
Tyr Thr Asn Thr Ile Tyr Arg Leu Leu Glu Asp Ser Gln Asn Gln Gln
630                 635                 640                 645 gaa cag aac gag aag gac ctg ctg gcc ctg gac agc tgg gag aac ctg       2024
Glu Gln Asn Glu Lys Asp Leu Leu Ala Leu Asp Ser Trp Glu Asn Leu
                650                 655                 660 tgg aac tgg ttc agc atc acc aag tgg ctg tgg tac atc aag ggc agc       2072
Trp Asn Trp Phe Ser Ile Thr Lys Trp Leu Trp Tyr Ile Lys Gly Ser
            665                 670                 675 ggc atg aag cag atc gag gac aag atc gag gaa atc gag agc aag atc       2120
Gly Met Lys Gln Ile Glu Asp Lys Ile Glu Glu Ile Glu Ser Lys Ile
        680                 685                 690 aag aag atc gag aac gag atc gcc cgg atc aag aag ctg atc ggc gag       2168
Lys Lys Ile Glu Asn Glu Ile Ala Arg Ile Lys Lys Leu Ile Gly Glu
    695                 700                 705 agc ggc cac cac cac cat cac cac ggc ctg aac gac atc ttc gag gcc       2216
Ser Gly His His His His His His Gly Leu Asn Asp Ile Phe Glu Ala
710                 715                 720                 725 cag aaa atc gag tgg cac gag tgactcgagt ctagagggcc cgtttaaacc          2267
Gln Lys Ile Glu Trp His Glu
                730 cgctgatc                                                              2275

<210> SEQ ID NO 66
<211> LENGTH: 732
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
                20                  25                  30

Tyr Tyr Gly Val Pro Val Trp Lys Glu Ala Lys Thr Thr Leu Phe Cys
            35                  40                  45

Ala Ser Asp Ala Lys Ala Tyr Glu Lys Glu Val His Asn Val Trp Ala
        50                  55                  60

Thr His Ala Cys Val Pro Thr Asp Pro Asn Pro Gln Glu Met Val Leu
65                  70                  75                  80

Glu Asn Val Thr Glu Asn Phe Asn Met Trp Lys Asn Asp Met Val Glu
                85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu Glu Cys Arg Gln Val
        115                 120                 125

Asn Thr Thr Asn Ala Thr Ser Ser Val Asn Val Thr Asn Gly Glu Glu
    130                 135                 140

Ile Lys Asn Cys Ser Phe Lys Ala Thr Thr Glu Ile Arg Asp Lys Lys
145                 150                 155                 160

Gln Lys Val Tyr Ala Leu Phe Tyr Arg Leu Asp Ile Val Pro Leu Glu
                165                 170                 175

Glu Glu Arg Lys Gly Asn Ser Ser Lys Tyr Arg Leu Ile Asn Cys Asn
            180                 185                 190
```

-continued

```
Thr Ser Ala Ile Thr Gln Ala Cys Pro Lys Val Thr Phe Asp Pro Ile
        195                 200                 205

Pro Ile His Tyr Cys Ala Pro Ala Gly Tyr Ala Ile Leu Lys Cys Asn
        210                 215                 220

Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Gly Glu Ile Ile Arg Ser Glu Asn Leu
        260                 265                 270

Thr Asn Asn Val Lys Thr Ile Ile Val His Leu Asn Glu Ser Val Glu
        275                 280                 285

Ile Val Cys Thr Arg Pro Asn Asn Asn Thr Arg Lys Ser Ile Arg Ile
        290                 295                 300

Gly Pro Gly Gln Thr Phe Tyr Ala Thr Gly Asp Ile Ile Gly Asn Ile
305                 310                 315                 320

Arg Gln Ala Tyr Cys Asn Ile Lys Lys Asp Trp Ile Arg Thr Leu
                325                 330                 335

Gln Arg Val Gly Lys Lys Leu Ala Glu His Phe Pro Arg Arg Ile Ile
        340                 345                 350

Asn Phe Thr Ser Pro Ala Gly Gly Asp Leu Glu Ile Thr Thr His Ser
        355                 360                 365

Phe Asn Cys Arg Gly Glu Phe Phe Tyr Cys Asn Thr Ser Ser Leu Phe
        370                 375                 380

Asn Ser Thr Tyr Asn Pro Asn Asp Thr Asn Ser Asn Ser Ser Ser
385                 390                 395                 400

Asn Ser Ser Leu Asp Ile Thr Ile Pro Cys Arg Ile Lys Gln Ile Ile
                405                 410                 415

Asn Met Trp Gln Glu Val Gly Arg Ala Met Tyr Ala Pro Pro Ile Glu
        420                 425                 430

Gly Asn Ile Thr Cys Lys Ser Asn Ile Thr Gly Leu Leu Leu Val Arg
        435                 440                 445

Asp Gly Gly Val Glu Ser Asn Glu Thr Glu Ile Phe Arg Pro Gly Gly
450                 455                 460

Gly Asp Met Arg Asn Asn Trp Arg Ser Glu Leu Tyr Lys Tyr Lys Val
465                 470                 475                 480

Val Glu Ile Lys Pro Leu Gly Ile Ala Pro Thr Ala Ala Lys Arg Arg
                485                 490                 495

Val Val Glu Ser Glu Lys Ser Ala Val Gly Leu Gly Ala Val Ile Phe
        500                 505                 510

Gly Phe Leu Gly Ala Ala Gly Ser Thr Met Gly Ala Ala Ser Ile Thr
        515                 520                 525

Leu Thr Val Gln Ala Arg Gln Leu Leu Ser Gly Ile Val Gln Gln Gln
        530                 535                 540

Ser Asn Leu Leu Lys Ala Ile Glu Ala Gln Gln His Leu Leu Gln Leu
545                 550                 555                 560

Thr Val Trp Gly Ile Lys Gln Leu Gln Thr Arg Val Leu Ala Ile Glu
                565                 570                 575

Arg Tyr Leu Lys Asp Gln Gln Leu Leu Gly Ile Trp Gly Cys Ser Gly
        580                 585                 590

Lys Leu Ile Cys Thr Thr Ala Val Pro Trp Asn Ser Ser Trp Ser Asn
        595                 600                 605

Lys Ser His Asp Glu Ile Trp Gly Asn Met Thr Trp Met Gln Trp Asp
        610                 615                 620
```

```
Arg Glu Ile Ser Asn Tyr Thr Asn Thr Ile Tyr Arg Leu Leu Glu Asp
625                 630                 635                 640

Ser Gln Asn Gln Gln Glu Gln Asn Glu Lys Asp Leu Leu Ala Leu Asp
                645                 650                 655

Ser Trp Glu Asn Leu Trp Asn Trp Phe Ser Ile Thr Lys Trp Leu Trp
            660                 665                 670

Tyr Ile Lys Gly Ser Gly Met Lys Gln Ile Glu Asp Lys Ile Glu Glu
        675                 680                 685

Ile Glu Ser Lys Ile Lys Lys Ile Glu Asn Glu Ile Ala Arg Ile Lys
    690                 695                 700

Lys Leu Ile Gly Glu Ser Gly His His His His His His Gly Leu Asn
705                 710                 715                 720

Asp Ile Phe Glu Ala Gln Lys Ile Glu Trp His Glu
                725                 730
```

<210> SEQ ID NO 67
<211> LENGTH: 612
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (50)..(556)

<400> SEQUENCE: 67

```
actggaaagc gggcagtgaa aggaaggccc atgaggccag ttaattaag gcc atc gag       58
                                                        Ala Ile Glu
                                                        1 gcc cag cag cat ctg ctg cag ctg acc gtg tgg ggc atc aag cag ctg       106
Ala Gln Gln His Leu Leu Gln Leu Thr Val Trp Gly Ile Lys Gln Leu
    5                  10                  15 cag acc cgg gtg ctg gcc atc gag aga tac ctg aag gac cag cag ctc       154
Gln Thr Arg Val Leu Ala Ile Glu Arg Tyr Leu Lys Asp Gln Gln Leu
20                  25                  30                  35 ctg gga atc tgg ggc tgc agc ggc aag ctg atc tgc acc acc gcc gtg       202
Leu Gly Ile Trp Gly Cys Ser Gly Lys Leu Ile Cys Thr Thr Ala Val
                40                  45                  50 ccc tgg aac agc agc tgg tcc aac aag agc cac gac gag atc tgg ggc       250
Pro Trp Asn Ser Ser Trp Ser Asn Lys Ser His Asp Glu Ile Trp Gly
            55                  60                  65 aac atg acc tgg atg cag tgg gac aga gag atc agc aac tac acc aac       298
Asn Met Thr Trp Met Gln Trp Asp Arg Glu Ile Ser Asn Tyr Thr Asn
        70                  75                  80 acc atc tac cgc ctg ctg gaa gat agc cag aac cag cag gaa cag aac       346
Thr Ile Tyr Arg Leu Leu Glu Asp Ser Gln Asn Gln Gln Glu Gln Asn
    85                  90                  95 gag aag gac ctg ctg gcc ctg gac agc tgg gag aac ctc tgg aac tgg       394
Glu Lys Asp Leu Leu Ala Leu Asp Ser Trp Glu Asn Leu Trp Asn Trp
100                 105                 110                 115 ttc agc atc acc aag tgg ctg tgg tac atc aag ggc agc ggc ggc atg       442
Phe Ser Ile Thr Lys Trp Leu Trp Tyr Ile Lys Gly Ser Gly Gly Met
                120                 125                 130 aag cag atc gag gac aag atc gag gaa atc gag agc aag atc aag aag       490
Lys Gln Ile Glu Asp Lys Ile Glu Glu Ile Glu Ser Lys Ile Lys Lys
            135                 140                 145 atc gag aac gag atc gcc cgg atc aag aag ctg atc ggc gag agc ggc       538
Ile Glu Asn Glu Ile Ala Arg Ile Lys Lys Leu Ile Gly Glu Ser Gly
        150                 155                 160
```

```
cac cac cac cat cac cac tgactcgagg cgcgcctagg ccttgacggc      586
His His His His His His
          165 cttccttcaa ttcgccctat agtgag                                   612
```

<210> SEQ ID NO 68
<211> LENGTH: 169
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Ala Ile Glu Ala Gln Gln His Leu Leu Gln Leu Thr Val Trp Gly Ile
1               5                   10                  15

Lys Gln Leu Gln Thr Arg Val Leu Ala Ile Glu Arg Tyr Leu Lys Asp
            20                  25                  30

Gln Gln Leu Leu Gly Ile Trp Gly Cys Ser Gly Lys Leu Ile Cys Thr
        35                  40                  45

Thr Ala Val Pro Trp Asn Ser Ser Trp Ser Asn Lys Ser His Asp Glu
50                  55                  60

Ile Trp Gly Asn Met Thr Trp Met Gln Trp Asp Arg Glu Ile Ser Asn
65                  70                  75                  80

Tyr Thr Asn Thr Ile Tyr Arg Leu Leu Glu Asp Ser Gln Asn Gln Gln
                85                  90                  95

Glu Gln Asn Glu Lys Asp Leu Leu Ala Leu Asp Ser Trp Glu Asn Leu
            100                 105                 110

Trp Asn Trp Phe Ser Ile Thr Lys Trp Leu Trp Tyr Ile Lys Gly Ser
        115                 120                 125

Gly Gly Met Lys Gln Ile Glu Asp Lys Ile Glu Glu Ile Glu Ser Lys
    130                 135                 140

Ile Lys Lys Ile Glu Asn Glu Ile Ala Arg Ile Lys Lys Leu Ile Gly
145                 150                 155                 160

Glu Ser Gly His His His His His His
                165
```

<210> SEQ ID NO 69
<211> LENGTH: 1585
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (42)..(1547)

<400> SEQUENCE: 69

```
gagacccaag ctggctagcg tttaaactta agcttgccac c atg ccc atg gga tcc    56
                                             Met Pro Met Gly Ser
                                              1               5 ctg cag cct ctg gcc aca ctg tat ctg ctg ggc atg ctg gtg gcc tct    104
Leu Gln Pro Leu Ala Thr Leu Tyr Leu Leu Gly Met Leu Val Ala Ser
                10                  15                  20 gtg ctg gcc gct ggc aat ctg tgg gtc acc gtg tac tac ggc gtg ccc    152
Val Leu Ala Ala Gly Asn Leu Trp Val Thr Val Tyr Tyr Gly Val Pro
            25                  30                  35 gtg tgg aaa gag gcc aag acc acc ctg ttc tgc gcc tct gac gcc aag    200
Val Trp Lys Glu Ala Lys Thr Thr Leu Phe Cys Ala Ser Asp Ala Lys
40                  45                  50
```

-continued

| | |
|---|---|
| gcc tac gag aca gag gtg cac aac gtg tgg gcc acc cac gcc tgt gtg<br>Ala Tyr Glu Thr Glu Val His Asn Val Trp Ala Thr His Ala Cys Val<br>55                   60                   65 | 248 |
| ccc acc gat ccc aac cct cag gaa ctg gtc ctg gaa aac gtg acc gag<br>Pro Thr Asp Pro Asn Pro Gln Glu Leu Val Leu Glu Asn Val Thr Glu<br>70                 75                  80                85 | 296 |
| aac ttc aac atg tgg cgg aac gac atg gtg gac cag atg cac gag gac<br>Asn Phe Asn Met Trp Arg Asn Asp Met Val Asp Gln Met His Glu Asp<br>                90                    95                  100 | 344 |
| gtg atc agc ctg tgg gac cag agc ctg aag ccc tgc gtg aag ctg acc<br>Val Ile Ser Leu Trp Asp Gln Ser Leu Lys Pro Cys Val Lys Leu Thr<br>                105                    110                 115 | 392 |
| cct ctg tgc gtg acc ctg gaa tgc cgg cag gtc aac acc acc aac gcc<br>Pro Leu Cys Val Thr Leu Glu Cys Arg Gln Val Asn Thr Thr Asn Ala<br>120                  125                    130 | 440 |
| acc agc agc gtg aac gtg acc aac ggc gag gaa atc aag aac tgc agc<br>Thr Ser Ser Val Asn Val Thr Asn Gly Glu Glu Ile Lys Asn Cys Ser<br>    135                    140                    145 | 488 |
| ttc aat gcc acc acc gag atc cgg gac aag aaa cag aag gtg tac gcc<br>Phe Asn Ala Thr Thr Glu Ile Arg Asp Lys Lys Gln Lys Val Tyr Ala<br>150                  155                    160                165 | 536 |
| ctg ttc tac cgg ctg gac atc gtg ccc ctg gaa gag gaa cgg aag ggc<br>Leu Phe Tyr Arg Leu Asp Ile Val Pro Leu Glu Glu Glu Arg Lys Gly<br>                170                    175                 180 | 584 |
| aac agc agc aag tac cgg ctg atc aac tgc aac acc agc gcc atc acc<br>Asn Ser Ser Lys Tyr Arg Leu Ile Asn Cys Asn Thr Ser Ala Ile Thr<br>                185                    190                 195 | 632 |
| cag gcc tgc ccc aaa gtg aac ttc gac ccc atc ccc atc cac tac tgc<br>Gln Ala Cys Pro Lys Val Asn Phe Asp Pro Ile Pro Ile His Tyr Cys<br>200                  205                    210 | 680 |
| acc cct gcc ggc tac gcc atc ctg aag tgc aac aac aag acc ttc aac<br>Thr Pro Ala Gly Tyr Ala Ile Leu Lys Cys Asn Asn Lys Thr Phe Asn<br>    215                    220                    225 | 728 |
| ggc acc ggc ccc tgc agc aat gtg tcc acc gtg cag tgc acc cac ggc<br>Gly Thr Gly Pro Cys Ser Asn Val Ser Thr Val Gln Cys Thr His Gly<br>230                  235                    240                245 | 776 |
| atc aag cct gtg gtg tcc acc cag ctg ctg ctg aat ggc agc ctg gcc<br>Ile Lys Pro Val Val Ser Thr Gln Leu Leu Leu Asn Gly Ser Leu Ala<br>                250                    255                 260 | 824 |
| gag gaa ggc atc atc atc aga agc gag aac ctg acc gac aac gtc aag<br>Glu Glu Gly Ile Ile Ile Arg Ser Glu Asn Leu Thr Asp Asn Val Lys<br>                265                    270                 275 | 872 |
| acc atc att gtg cac ctg gaa gaa ccc gtg gaa atc gtg tgc acc cgg<br>Thr Ile Ile Val His Leu Glu Glu Pro Val Glu Ile Val Cys Thr Arg<br>280                  285                    290 | 920 |
| ccc aac aac aac acc aga aag agc atc cgg atc ggc cct ggc cag acc<br>Pro Asn Asn Asn Thr Arg Lys Ser Ile Arg Ile Gly Pro Gly Gln Thr<br>    295                    300                    305 | 968 |
| ttt tac gcc acc ggc gac atc atc ggc aac atc aga cag gcc tac tgc<br>Phe Tyr Ala Thr Gly Asp Ile Ile Gly Asn Ile Arg Gln Ala Tyr Cys<br>310                  315                    320                325 | 1016 |
| aac atc tcc gag gcc aag tgg aac gag aca ctg cag aat gtg acc aag<br>Asn Ile Ser Glu Ala Lys Trp Asn Glu Thr Leu Gln Asn Val Thr Lys<br>                330                    335                 340 | 1064 |
| aag ctg aaa gag cac ttc ccc aac aag aca atc atc ttc aac agc agc<br>Lys Leu Lys Glu His Phe Pro Asn Lys Thr Ile Ile Phe Asn Ser Ser<br>                345                    350                 355 | 1112 |
| tct ggc ggc gac ctg gaa atc acc acc cac agc ttc aac tgc aga ggc<br>Ser Gly Gly Asp Leu Glu Ile Thr Thr His Ser Phe Asn Cys Arg Gly<br>360                  365                    370 | 1160 |

-continued

```
gag ttc ttc tac tgc aat acc agc aag ctg ttc aac ggc atc tac aac      1208
Glu Phe Phe Tyr Cys Asn Thr Ser Lys Leu Phe Asn Gly Ile Tyr Asn
375                 380                 385 ggc acc cag agc aac agc tcc aac agc aac agc acc atc atc atc cct      1256
Gly Thr Gln Ser Asn Ser Ser Asn Ser Asn Ser Thr Ile Ile Ile Pro
390                 395                 400                 405 tgc aag atc aag cag atc gtg aac atg tgg cag aaa gtg ggc aga gct      1304
Cys Lys Ile Lys Gln Ile Val Asn Met Trp Gln Lys Val Gly Arg Ala
            410                 415                 420 atg tac gcc cct cct atc gcc ggc aac att acc tgc acc agc aac atc      1352
Met Tyr Ala Pro Pro Ile Ala Gly Asn Ile Thr Cys Thr Ser Asn Ile
                425                 430                 435 acc ggc ctg ctg ctc gtg cga gat ggc ggc cct gac aat gtg acc gag      1400
Thr Gly Leu Leu Leu Val Arg Asp Gly Gly Pro Asp Asn Val Thr Glu
        440                 445                 450 atc ttt aga ccc ggc gga ggc gac atg cgg gac aat tgg aga agc gag      1448
Ile Phe Arg Pro Gly Gly Gly Asp Met Arg Asp Asn Trp Arg Ser Glu
455                 460                 465 ctg tac aag tac aag gtg gtg gaa atc aag ccc ctg gga atc gcc cct      1496
Leu Tyr Lys Tyr Lys Val Val Glu Ile Lys Pro Leu Gly Ile Ala Pro
470                 475                 480                 485 acc ggc gcc aaa aga aga gtg gtc gaa ggc gcc cac cac cac cat cac      1544
Thr Gly Ala Lys Arg Arg Val Val Glu Gly Ala His His His His His
                490                 495                 500 cac tgactcgagt ctagagggcc cgtttaaacc cgctgatc                         1585
His
```

<210> SEQ ID NO 70
<211> LENGTH: 502
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
                20                  25                  30

Tyr Tyr Gly Val Pro Val Trp Lys Glu Ala Lys Thr Thr Leu Phe Cys
            35                  40                  45

Ala Ser Asp Ala Lys Ala Tyr Glu Thr Glu Val His Asn Val Trp Ala
        50                  55                  60

Thr His Ala Cys Val Pro Thr Asp Pro Asn Pro Gln Glu Leu Val Leu
65                  70                  75                  80

Glu Asn Val Thr Glu Asn Phe Asn Met Trp Arg Asn Asp Met Val Asp
                85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu Glu Cys Arg Gln Val
        115                 120                 125

Asn Thr Thr Asn Ala Thr Ser Ser Val Asn Val Thr Asn Gly Glu Glu
    130                 135                 140

Ile Lys Asn Cys Ser Phe Asn Ala Thr Thr Glu Ile Arg Asp Lys Lys
145                 150                 155                 160

Gln Lys Val Tyr Ala Leu Phe Tyr Arg Leu Asp Ile Val Pro Leu Glu
                165                 170                 175

Glu Glu Arg Lys Gly Asn Ser Ser Lys Tyr Arg Leu Ile Asn Cys Asn
```

```
                    180             185              190
Thr Ser Ala Ile Thr Gln Ala Cys Pro Lys Val Asn Phe Asp Pro Ile
        195                 200                 205
Pro Ile His Tyr Cys Thr Pro Ala Gly Tyr Ala Ile Leu Lys Cys Asn
        210                 215                 220
Asn Lys Thr Phe Asn Gly Thr Gly Pro Cys Ser Asn Val Ser Thr Val
225                 230                 235                 240
Gln Cys Thr His Gly Ile Lys Pro Val Val Ser Thr Gln Leu Leu Leu
                245                 250                 255
Asn Gly Ser Leu Ala Glu Glu Gly Ile Ile Arg Ser Glu Asn Leu
        260                 265                 270
Thr Asp Asn Val Lys Thr Ile Ile Val His Leu Glu Glu Pro Val Glu
        275                 280                 285
Ile Val Cys Thr Arg Pro Asn Asn Asn Thr Arg Lys Ser Ile Arg Ile
        290                 295                 300
Gly Pro Gly Gln Thr Phe Tyr Ala Thr Gly Asp Ile Ile Gly Asn Ile
305                 310                 315                 320
Arg Gln Ala Tyr Cys Asn Ile Ser Glu Ala Lys Trp Asn Glu Thr Leu
                325                 330                 335
Gln Asn Val Thr Lys Lys Leu Lys Glu His Phe Pro Asn Lys Thr Ile
                340                 345                 350
Ile Phe Asn Ser Ser Ser Gly Gly Asp Leu Glu Ile Thr Thr His Ser
                355                 360                 365
Phe Asn Cys Arg Gly Glu Phe Phe Tyr Cys Asn Thr Ser Lys Leu Phe
        370                 375                 380
Asn Gly Ile Tyr Asn Gly Thr Gln Ser Asn Ser Ser Asn Ser Asn Ser
385                 390                 395                 400
Thr Ile Ile Ile Pro Cys Lys Ile Lys Gln Ile Val Asn Met Trp Gln
                405                 410                 415
Lys Val Gly Arg Ala Met Tyr Ala Pro Pro Ile Ala Gly Asn Ile Thr
                420                 425                 430
Cys Thr Ser Asn Ile Thr Gly Leu Leu Leu Val Arg Asp Gly Gly Pro
        435                 440                 445
Asp Asn Val Thr Glu Ile Phe Arg Pro Gly Gly Gly Asp Met Arg Asp
450                 455                 460
Asn Trp Arg Ser Glu Leu Tyr Lys Tyr Lys Val Val Glu Ile Lys Pro
465                 470                 475                 480
Leu Gly Ile Ala Pro Thr Gly Ala Lys Arg Arg Val Val Glu Gly Ala
                485                 490                 495
His His His His His His
        500

<210> SEQ ID NO 71
<211> LENGTH: 1591
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (42)..(1553)

<400> SEQUENCE: 71
gagacccaag ctggctagcg tttaaactta agcttgccac c atg ccc atg gga tcc    56
                                             Met Pro Met Gly Ser
                                             1               5
```

-continued

| | |
|---|---|
| ctg cag cct ctg gcc aca ctg tat ctg ctg ggc atg ctg gtg gcc tct<br>Leu Gln Pro Leu Ala Thr Leu Tyr Leu Leu Gly Met Leu Val Ala Ser<br>10 15 20 | 104 |
| gtg ctg gcc gct ggc aat ctg tgg gtc acc gtg tac tac ggc gtg ccc<br>Val Leu Ala Ala Gly Asn Leu Trp Val Thr Val Tyr Tyr Gly Val Pro<br>25 30 35 | 152 |
| gtg tgg aaa gag gcc aag acc acc ctg ttc tgc gcc tct gac gcc aag<br>Val Trp Lys Glu Ala Lys Thr Thr Leu Phe Cys Ala Ser Asp Ala Lys<br>40 45 50 | 200 |
| gcc tac gag aaa gag gtg cac aac gtc tgg gcc acc cac gcc tgt gtg<br>Ala Tyr Glu Lys Glu Val His Asn Val Trp Ala Thr His Ala Cys Val<br>55 60 65 | 248 |
| ccc acc gat ccc aac ccc cag gaa atg gtc ctg gaa aac gtg acc gag<br>Pro Thr Asp Pro Asn Pro Gln Glu Met Val Leu Glu Asn Val Thr Glu<br>70 75 80 85 | 296 |
| aac ttc aac atg tgg aag aac gac atg gtc gag cag atg cac gag gac<br>Asn Phe Asn Met Trp Lys Asn Asp Met Val Glu Gln Met His Glu Asp<br>90 95 100 | 344 |
| gtg atc agc ctg tgg gac cag agc ctg aag ccc tgc gtg aag ctg acc<br>Val Ile Ser Leu Trp Asp Gln Ser Leu Lys Pro Cys Val Lys Leu Thr<br>105 110 115 | 392 |
| cct ctg tgc gtg acc ctg gaa tgc aga aac gcc acc agc aag atg gtc<br>Pro Leu Cys Val Thr Leu Glu Cys Arg Asn Ala Thr Ser Lys Met Val<br>120 125 130 | 440 |
| aac gac acc cgg aac gtg gaa gag atg aag aac tgc agc ttc aac acc<br>Asn Asp Thr Arg Asn Val Glu Glu Met Lys Asn Cys Ser Phe Asn Thr<br>135 140 145 | 488 |
| acc acc gag ctg cgg gac cgg aag cag aca gtg tac gcc agc ttc tac<br>Thr Thr Glu Leu Arg Asp Arg Lys Gln Thr Val Tyr Ala Ser Phe Tyr<br>150 155 160 165 | 536 |
| aag ctg gac atc gtg ccc ctg aac gag aac aag agc acc agc agc gag<br>Lys Leu Asp Ile Val Pro Leu Asn Glu Asn Lys Ser Thr Ser Ser Glu<br>170 175 180 | 584 |
| aac tac cgg ctg atc aac tgc aac acc agc gcc atc acc cag gcc tgc<br>Asn Tyr Arg Leu Ile Asn Cys Asn Thr Ser Ala Ile Thr Gln Ala Cys<br>185 190 195 | 632 |
| ccc aaa gtg acc ttc gac ccc atc ccc atc cac tac tgt gcc cct gcc<br>Pro Lys Val Thr Phe Asp Pro Ile Pro Ile His Tyr Cys Ala Pro Ala<br>200 205 210 | 680 |
| ggc tac gcc atc ctg aag tgc aac aac aag acc ttc aac ggc acc ggc<br>Gly Tyr Ala Ile Leu Lys Cys Asn Asn Lys Thr Phe Asn Gly Thr Gly<br>215 220 225 | 728 |
| ccc tgc aac aac gtg tcc acc gtg cag tgc acc cac ggc atc aag cct<br>Pro Cys Asn Asn Val Ser Thr Val Gln Cys Thr His Gly Ile Lys Pro<br>230 235 240 245 | 776 |
| gtg gtg tcc acc cag ctg ctg ctg aat ggc tct ctg gcc gag ggc gag<br>Val Val Ser Thr Gln Leu Leu Leu Asn Gly Ser Leu Ala Glu Gly Glu<br>250 255 260 | 824 |
| atc atc atc aga agc gag aac ctg acc aac aac gtc aag acc atc atc<br>Ile Ile Ile Arg Ser Glu Asn Leu Thr Asn Asn Val Lys Thr Ile Ile<br>265 270 275 | 872 |
| gtc cac ctg aat gag agc gtg gaa atc gtg tgc acc cgg ccc aac aac<br>Val His Leu Asn Glu Ser Val Glu Ile Val Cys Thr Arg Pro Asn Asn<br>280 285 290 | 920 |
| aac acc aga aag agc gtg cgg atc ggc cct ggc cag acc ttt tat gcc<br>Asn Thr Arg Lys Ser Val Arg Ile Gly Pro Gly Gln Thr Phe Tyr Ala<br>295 300 305 | 968 |
| acc ggg gag atc atc ggc gac atc aga cag gcc cac tgc aac atc aag<br>Thr Gly Glu Ile Ile Gly Asp Ile Arg Gln Ala His Cys Asn Ile Lys<br>310 315 320 325 | 1016 |

```
aag gac gac tgg atc cgg acc ctg cag aga gtg ggc aag aag ctg gcc    1064
Lys Asp Asp Trp Ile Arg Thr Leu Gln Arg Val Gly Lys Lys Leu Ala
                330                 335                 340 gag cac ttc ccc aga cgg atc atc aac ttc acc agc ccc gct ggc ggc    1112
Glu His Phe Pro Arg Arg Ile Ile Asn Phe Thr Ser Pro Ala Gly Gly
            345                 350                 355 gac ctg gaa atc acc acc cac agc ttc aac tgc aga ggc gag ttc ttc    1160
Asp Leu Glu Ile Thr Thr His Ser Phe Asn Cys Arg Gly Glu Phe Phe
        360                 365                 370 tac tgc aat acc agc agc ctg ttc aac agc acc tac aac ccc aac gac    1208
Tyr Cys Asn Thr Ser Ser Leu Phe Asn Ser Thr Tyr Asn Pro Asn Asp
    375                 380                 385 acc aac agc aac agc agc agc tcc aac agc agc ctg gac atc acc atc    1256
Thr Asn Ser Asn Ser Ser Ser Asn Ser Ser Leu Asp Ile Thr Ile
390                 395                 400                 405 cct tgc cgg atc aag cag atc atc aat atg tgg cag gaa gtg ggc agg    1304
Pro Cys Arg Ile Lys Gln Ile Ile Asn Met Trp Gln Glu Val Gly Arg
                410                 415                 420 gct atg tac gcc cct ccc atc gag ggc aac atc aca tgc aag agc aac    1352
Ala Met Tyr Ala Pro Pro Ile Glu Gly Asn Ile Thr Cys Lys Ser Asn
            425                 430                 435 atc acc ggc ctg ctc gtg cga gat ggc ggc gtg gaa agc aac gag        1400
Ile Thr Gly Leu Leu Leu Val Arg Asp Gly Gly Val Glu Ser Asn Glu
        440                 445                 450 aca gag atc ttc aga ccc gga ggc gac atg cgg aac aat tgg cgg        1448
Thr Glu Ile Phe Arg Pro Gly Gly Asp Met Arg Asn Asn Trp Arg
    455                 460                 465 agc gag ctg tac aag tac aag gtg gtg gaa atc aag ccc ctg gga atc    1496
Ser Glu Leu Tyr Lys Tyr Lys Val Val Glu Ile Lys Pro Leu Gly Ile
470                 475                 480                 485 gcc cct acc gcc gcc aaa aga aga gtg gtc gaa ggc gcc cac cac cac    1544
Ala Pro Thr Ala Ala Lys Arg Arg Val Val Glu Gly Ala His His His
                490                 495                 500 cat cac cac tgactcgagt ctagagggcc cgtttaaacc cgctgatc             1591
His His His
```

<210> SEQ ID NO 72
<211> LENGTH: 504
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

```
Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
                20                  25                  30

Tyr Tyr Gly Val Pro Val Trp Lys Glu Ala Lys Thr Thr Leu Phe Cys
            35                  40                  45

Ala Ser Asp Ala Lys Ala Tyr Glu Lys Glu Val His Asn Val Trp Ala
        50                  55                  60

Thr His Ala Cys Val Pro Thr Asp Pro Asn Pro Gln Glu Met Val Leu
65                  70                  75                  80

Glu Asn Val Thr Glu Asn Phe Asn Met Trp Lys Asn Asp Met Val Glu
                85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu Glu Cys Arg Asn Ala
```

```
                    115                 120                 125
Thr Ser Lys Met Val Asn Asp Thr Arg Asn Val Glu Glu Met Lys Asn
130                 135                 140
Cys Ser Phe Asn Thr Thr Thr Glu Leu Arg Asp Arg Lys Gln Thr Val
145                 150                 155                 160
Tyr Ala Ser Phe Tyr Lys Leu Asp Ile Val Pro Leu Asn Glu Asn Lys
                    165                 170                 175
Ser Thr Ser Ser Glu Asn Tyr Arg Leu Ile Asn Cys Asn Thr Ser Ala
                    180                 185                 190
Ile Thr Gln Ala Cys Pro Lys Val Thr Phe Asp Pro Ile Pro Ile His
                    195                 200                 205
Tyr Cys Ala Pro Ala Gly Tyr Ala Ile Leu Lys Cys Asn Asn Lys Thr
                    210                 215                 220
Phe Asn Gly Thr Gly Pro Cys Asn Asn Val Ser Thr Val Gln Cys Thr
225                 230                 235                 240
His Gly Ile Lys Pro Val Val Ser Thr Gln Leu Leu Leu Asn Gly Ser
                    245                 250                 255
Leu Ala Glu Gly Glu Ile Ile Ile Arg Ser Glu Asn Leu Thr Asn Asn
                    260                 265                 270
Val Lys Thr Ile Ile Val His Leu Asn Glu Ser Val Glu Ile Val Cys
                    275                 280                 285
Thr Arg Pro Asn Asn Asn Thr Arg Lys Ser Val Arg Ile Gly Pro Gly
290                 295                 300
Gln Thr Phe Tyr Ala Thr Gly Glu Ile Ile Gly Asp Ile Arg Gln Ala
305                 310                 315                 320
His Cys Asn Ile Lys Lys Asp Asp Trp Ile Arg Thr Leu Gln Arg Val
                    325                 330                 335
Gly Lys Lys Leu Ala Glu His Phe Pro Arg Arg Ile Ile Asn Phe Thr
                    340                 345                 350
Ser Pro Ala Gly Gly Asp Leu Glu Ile Thr Thr His Ser Phe Asn Cys
                    355                 360                 365
Arg Gly Glu Phe Phe Tyr Cys Asn Thr Ser Ser Leu Phe Asn Ser Thr
370                 375                 380
Tyr Asn Pro Asn Asp Thr Asn Ser Asn Ser Ser Ser Asn Ser Ser
385                 390                 395                 400
Leu Asp Ile Thr Ile Pro Cys Arg Ile Lys Gln Ile Ile Asn Met Trp
                    405                 410                 415
Gln Glu Val Gly Arg Ala Met Tyr Ala Pro Pro Ile Glu Gly Asn Ile
                    420                 425                 430
Thr Cys Lys Ser Asn Ile Thr Gly Leu Leu Leu Val Arg Asp Gly Gly
                    435                 440                 445
Val Glu Ser Asn Glu Thr Glu Ile Phe Arg Pro Gly Gly Gly Asp Met
450                 455                 460
Arg Asn Asn Trp Arg Ser Glu Leu Tyr Lys Tyr Lys Val Val Glu Ile
465                 470                 475                 480
Lys Pro Leu Gly Ile Ala Pro Thr Ala Ala Lys Arg Arg Val Val Glu
                    485                 490                 495
Gly Ala His His His His His His
                    500

<210> SEQ ID NO 73
<211> LENGTH: 1569
<212> TYPE: DNA
<213> ORGANISM: Artificial Sequence
<220> FEATURE:
```

-continued

```
<223> OTHER INFORMATION: Description of Artificial Sequence: Synthetic
      polynucleotide
<220> FEATURE:
<221> NAME/KEY: CDS
<222> LOCATION: (21)..(1550)

<400> SEQUENCE: 73
```

| | | | | | | | | | | | |
|---|---|---|---|---|---|---|---|---|---|---|---|
| ggcgcgccga attcgccacc | atg cct atg ggc agc ctg cag cct ctg gcc aca | | | | | | | | | | 53 |
| | Met Pro Met Gly Ser Leu Gln Pro Leu Ala Thr | | | | | | | | | | |
| | 1 | | | 5 | | | | | 10 | | |

```
ctg tac ctg ctg ggc atg ctg gtg gcc tct gtg ctg gcc gcc gag aac      101
Leu Tyr Leu Leu Gly Met Leu Val Ala Ser Val Leu Ala Ala Glu Asn
     15                  20                  25 ctg tgg gtg aca gtg tac tac ggc gtg ccc gtg tgg aag gac gcc gag      149
Leu Trp Val Thr Val Tyr Tyr Gly Val Pro Val Trp Lys Asp Ala Glu
 30                  35                  40 aca acc ctg ttc tgc gcc agc gac gcc aag gcc tac gag aca gag aag      197
Thr Thr Leu Phe Cys Ala Ser Asp Ala Lys Ala Tyr Glu Thr Glu Lys
         45                  50                  55 cac aac gtg tgg gcc acc cac gcc tgc gtg cca acc gac cct aac ccc      245
His Asn Val Trp Ala Thr His Ala Cys Val Pro Thr Asp Pro Asn Pro
 60                  65                  70                  75 cag gaa atc cac ctg gaa aac gtg acc gaa gag ttc aac atg tgg aag      293
Gln Glu Ile His Leu Glu Asn Val Thr Glu Glu Phe Asn Met Trp Lys
                 80                  85                  90 aac aac atg gtg gaa cag atg cac acc gac atc atc agc ctg tgg gac      341
Asn Asn Met Val Glu Gln Met His Thr Asp Ile Ile Ser Leu Trp Asp
             95                 100                 105 cag agc ctg aag ccc tgc gtg aag ctg acc ccc ctg tgc gtg acc ctg      389
Gln Ser Leu Lys Pro Cys Val Lys Leu Thr Pro Leu Cys Val Thr Leu
         110                 115                 120 cag tgc acc aac gtg acc aac aac atc acc gac gac atg cgg ggc gag      437
Gln Cys Thr Asn Val Thr Asn Asn Ile Thr Asp Asp Met Arg Gly Glu
 125                 130                 135 ctg aag aac tgc agc ttc aac atg acc acc gag ctg cgg gac aag aaa      485
Leu Lys Asn Cys Ser Phe Asn Met Thr Thr Glu Leu Arg Asp Lys Lys
140                 145                 150                 155 cag aag gtg tac agc ctg ttc tac cgg ctg gac gtg gtg cag atc aac      533
Gln Lys Val Tyr Ser Leu Phe Tyr Arg Leu Asp Val Val Gln Ile Asn
                 160                 165                 170 gag aac cag ggc aac aga agc aac aac agc aac aaa gag tac cgg ctg      581
Glu Asn Gln Gly Asn Arg Ser Asn Asn Ser Asn Lys Glu Tyr Arg Leu
             175                 180                 185 atc aac tgc aac acc agc gcc atc acc cag gcc tgc ccc aag gtg tcc      629
Ile Asn Cys Asn Thr Ser Ala Ile Thr Gln Ala Cys Pro Lys Val Ser
         190                 195                 200 ttc gag ccc atc ccc atc cac tac tgc gcc cct gcc ggc ttc gcc atc      677
Phe Glu Pro Ile Pro Ile His Tyr Cys Ala Pro Ala Gly Phe Ala Ile
 205                 210                 215 ctg aag tgc aag gac aag aag ttc aac ggc acc ggc ccc tgc ccc agc      725
Leu Lys Cys Lys Asp Lys Lys Phe Asn Gly Thr Gly Pro Cys Pro Ser
220                 225                 230                 235 gtg tcc aca gtg cag tgt acc cac ggc atc aag ccc gtg gtg tcc acc      773
Val Ser Thr Val Gln Cys Thr His Gly Ile Lys Pro Val Val Ser Thr
                 240                 245                 250 cag ctg ctg ctg aac ggc agc ctg gcc gaa gag gaa gtg atg atc aga      821
Gln Leu Leu Leu Asn Gly Ser Leu Ala Glu Glu Glu Val Met Ile Arg
             255                 260                 265 agc gag aac atc acc aac aac gcc aag aac atc ctg gtg cag ttc aac      869
Ser Glu Asn Ile Thr Asn Asn Ala Lys Asn Ile Leu Val Gln Phe Asn
         270                 275                 280
```

```
acc ccc gtg cag att aac tgc acc cgg ccc aac aac aac acc aga aag      917
Thr Pro Val Gln Ile Asn Cys Thr Arg Pro Asn Asn Asn Thr Arg Lys
    285                 290                 295 agc atc cgg atc ggc cca ggc cag gcc ttc tac gcc acc ggc gac atc      965
Ser Ile Arg Ile Gly Pro Gly Gln Ala Phe Tyr Ala Thr Gly Asp Ile
300                 305                 310                 315 atc ggc gac atc cgg cag gcc cac tgc acc gtg tcc aag gcc acc tgg     1013
Ile Gly Asp Ile Arg Gln Ala His Cys Thr Val Ser Lys Ala Thr Trp
                320                 325                 330 aac gag aca ctg ggc aag gtg gtg aaa cag ctg cgg aag cac ttc ggg     1061
Asn Glu Thr Leu Gly Lys Val Val Lys Gln Leu Arg Lys His Phe Gly
            335                 340                 345 aac aac acc atc atc cgc ttc gcc aac agc tct ggc ggc gac ctg gaa     1109
Asn Asn Thr Ile Ile Arg Phe Ala Asn Ser Ser Gly Gly Asp Leu Glu
        350                 355                 360 gtg acc acc cac agc ttc aac tgt ggc ggc gag ttc ttc tac tgc aat     1157
Val Thr Thr His Ser Phe Asn Cys Gly Gly Glu Phe Phe Tyr Cys Asn
    365                 370                 375 acc tcc ggc ctg ttc aac agc acc tgg atc agc aat acc agc gtg cag     1205
Thr Ser Gly Leu Phe Asn Ser Thr Trp Ile Ser Asn Thr Ser Val Gln
380                 385                 390                 395 ggc agc aac agc acc ggc agc aac gac agc atc acc ctg ccc tgc cgg     1253
Gly Ser Asn Ser Thr Gly Ser Asn Asp Ser Ile Thr Leu Pro Cys Arg
                400                 405                 410 atc aag cag atc atc aat atg tgg cag cgg att ggc cag gct atg tac     1301
Ile Lys Gln Ile Ile Asn Met Trp Gln Arg Ile Gly Gln Ala Met Tyr
            415                 420                 425 gcc cca ccc atc cag ggc gtg atc aga tgc gtg tcc aat atc acc ggc     1349
Ala Pro Pro Ile Gln Gly Val Ile Arg Cys Val Ser Asn Ile Thr Gly
        430                 435                 440 ctg atc ctg acc cgg gac ggc ggc tct acc aac agc acc acc gaa acc     1397
Leu Ile Leu Thr Arg Asp Gly Gly Ser Thr Asn Ser Thr Thr Glu Thr
    445                 450                 455 ttc aga ccc ggc gga ggc gac atg aga gac aac tgg cgg agc gag ctg     1445
Phe Arg Pro Gly Gly Gly Asp Met Arg Asp Asn Trp Arg Ser Glu Leu
460                 465                 470                 475 tac aag tac aaa gtg gtg aaa atc gag ccc ctg ggc gtg gcc ccc acc     1493
Tyr Lys Tyr Lys Val Val Lys Ile Glu Pro Leu Gly Val Ala Pro Thr
                480                 485                 490 aga gcc aag aga aga gtg gtc gga agc gag aag tcc ggc cac cac cac     1541
Arg Ala Lys Arg Arg Val Val Gly Ser Glu Lys Ser Gly His His His
            495                 500                 505 cat cac cac tgagcggccg cttaattaa                                    1569
His His His
        510

<210> SEQ ID NO 74
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
                20                  25                  30

Tyr Tyr Gly Val Pro Val Trp Lys Asp Ala Glu Thr Thr Leu Phe Cys
            35                  40                  45
```

```
Ala Ser Asp Ala Lys Ala Tyr Glu Thr Glu Lys His Asn Val Trp Ala
     50                  55                  60

Thr His Ala Cys Val Pro Thr Asp Pro Asn Pro Gln Glu Ile His Leu
 65              70                  75                      80

Glu Asn Val Thr Glu Glu Phe Asn Met Trp Lys Asn Asn Met Val Glu
                 85                  90                  95

Gln Met His Thr Asp Ile Ile Ser Leu Trp Asp Gln Ser Leu Lys Pro
             100                 105                 110

Cys Val Lys Leu Thr Pro Leu Cys Val Thr Leu Gln Cys Thr Asn Val
             115                 120                 125

Thr Asn Asn Ile Thr Asp Met Arg Gly Glu Leu Lys Asn Cys Ser
             130                 135                 140

Phe Asn Met Thr Thr Glu Leu Arg Asp Lys Lys Gln Lys Val Tyr Ser
145                 150                 155                 160

Leu Phe Tyr Arg Leu Asp Val Val Gln Ile Asn Glu Asn Gln Gly Asn
             165                 170                 175

Arg Ser Asn Asn Ser Asn Lys Glu Tyr Arg Leu Ile Asn Cys Asn Thr
             180                 185                 190

Ser Ala Ile Thr Gln Ala Cys Pro Lys Val Ser Phe Glu Pro Ile Pro
             195                 200                 205

Ile His Tyr Cys Ala Pro Ala Gly Phe Ala Ile Leu Lys Cys Lys Asp
             210                 215                 220

Lys Lys Phe Asn Gly Thr Gly Pro Cys Pro Ser Val Ser Thr Val Gln
225                 230                 235                 240

Cys Thr His Gly Ile Lys Pro Val Val Ser Thr Gln Leu Leu Leu Asn
             245                 250                 255

Gly Ser Leu Ala Glu Glu Val Met Ile Arg Ser Glu Asn Ile Thr
             260                 265                 270

Asn Asn Ala Lys Asn Ile Leu Val Gln Phe Asn Thr Pro Val Gln Ile
             275                 280                 285

Asn Cys Thr Arg Pro Asn Asn Asn Thr Arg Lys Ser Ile Arg Ile Gly
             290                 295                 300

Pro Gly Gln Ala Phe Tyr Ala Thr Gly Asp Ile Ile Gly Asp Ile Arg
305                 310                 315                 320

Gln Ala His Cys Thr Val Ser Lys Ala Thr Trp Asn Glu Thr Leu Gly
             325                 330                 335

Lys Val Val Lys Gln Leu Arg Lys His Phe Gly Asn Asn Thr Ile Ile
             340                 345                 350

Arg Phe Ala Asn Ser Ser Gly Gly Asp Leu Glu Val Thr Thr His Ser
             355                 360                 365

Phe Asn Cys Gly Gly Glu Phe Phe Tyr Cys Asn Thr Ser Gly Leu Phe
370                 375                 380

Asn Ser Thr Trp Ile Ser Asn Thr Ser Val Gln Gly Ser Asn Ser Thr
385                 390                 395                 400

Gly Ser Asn Asp Ser Ile Thr Leu Pro Cys Arg Ile Lys Gln Ile Ile
                 405                 410                 415

Asn Met Trp Gln Arg Ile Gly Gln Ala Met Tyr Ala Pro Pro Ile Gln
             420                 425                 430

Gly Val Ile Arg Cys Val Ser Asn Ile Thr Gly Leu Ile Leu Thr Arg
             435                 440                 445

Asp Gly Gly Ser Thr Asn Ser Thr Thr Glu Thr Phe Arg Pro Gly Gly
             450                 455                 460

Gly Asp Met Arg Asp Asn Trp Arg Ser Glu Leu Tyr Lys Tyr Lys Val
465                 470                 475                 480
```

-continued

```
Val Lys Ile Glu Pro Leu Gly Val Ala Pro Thr Arg Ala Lys Arg Arg
            485                 490                 495

Val Val Gly Ser Glu Lys Ser Gly His His His His His His
        500                 505                 510

<210> SEQ ID NO 75
<211> LENGTH: 2091
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (21)..(2072)

<400> SEQUENCE: 75
ggcgcgccga attcgccacc atg cct atg ggc agc ctg cag cct ctg gcc aca        53
                     Met Pro Met Gly Ser Leu Gln Pro Leu Ala Thr
                      1               5                      10 ctg tac ctg ctg ggc atg ctg gtg gcc tct gtg ctg gcc gcc gag aac         101
Leu Tyr Leu Leu Gly Met Leu Val Ala Ser Val Leu Ala Ala Glu Asn
             15                  20                  25 ctg tgg gtg aca gtg tac tac ggc gtg ccc gtg tgg aag gac gcc gag         149
Leu Trp Val Thr Val Tyr Tyr Gly Val Pro Val Trp Lys Asp Ala Glu
         30                  35                  40 aca acc ctg ttc tgc gcc agc gac gcc aag gcc tac gag aca gag aag         197
Thr Thr Leu Phe Cys Ala Ser Asp Ala Lys Ala Tyr Glu Thr Glu Lys
     45                  50                  55 cac aac gtg tgg gcc acc cac gcc tgc gtg cca acc gac cct aac ccc         245
His Asn Val Trp Ala Thr His Ala Cys Val Pro Thr Asp Pro Asn Pro
 60                  65                  70                  75 cag gaa atc cac ctg gaa aac gtg acc gaa gag ttc aac atg tgg aag         293
Gln Glu Ile His Leu Glu Asn Val Thr Glu Glu Phe Asn Met Trp Lys
                 80                  85                  90 aac aac atg gtg gaa cag atg cac acc gac atc atc agc ctg tgg gac         341
Asn Asn Met Val Glu Gln Met His Thr Asp Ile Ile Ser Leu Trp Asp
             95                 100                 105 cag agc ctg aag ccc tgc gtg aag ctg acc ccc ctg tgc gtg acc ctg         389
Gln Ser Leu Lys Pro Cys Val Lys Leu Thr Pro Leu Cys Val Thr Leu
        110                 115                 120 cag tgc acc aac gtg acc aac aac atc acc gac gac atg cgg ggc gag         437
Gln Cys Thr Asn Val Thr Asn Asn Ile Thr Asp Asp Met Arg Gly Glu
    125                 130                 135 ctg aag aac tgc agc ttc aac atg acc acc gag ctg cgg gac aag aaa         485
Leu Lys Asn Cys Ser Phe Asn Met Thr Thr Glu Leu Arg Asp Lys Lys
140                 145                 150                 155 cag aag gtg tac agc ctg ttc tac cgg ctg gac gtg gtg cag atc aac         533
Gln Lys Val Tyr Ser Leu Phe Tyr Arg Leu Asp Val Val Gln Ile Asn
                160                 165                 170 gag aac cag ggc aac aga agc aac aac agc aac aaa gag tac cgg ctg         581
Glu Asn Gln Gly Asn Arg Ser Asn Asn Ser Asn Lys Glu Tyr Arg Leu
            175                 180                 185 atc aac tgc aac acc agc gcc atc acc cag gcc tgc ccc aag gtg tcc         629
Ile Asn Cys Asn Thr Ser Ala Ile Thr Gln Ala Cys Pro Lys Val Ser
        190                 195                 200 ttc gag ccc atc ccc atc cac tac tgc gcc cct gcc ggc ttc gcc atc         677
Phe Glu Pro Ile Pro Ile His Tyr Cys Ala Pro Ala Gly Phe Ala Ile
    205                 210                 215 ctg aag tgc aag gac aag aag ttc aac ggc acc ggc ccc tgc ccc agc         725
Leu Lys Cys Lys Asp Lys Lys Phe Asn Gly Thr Gly Pro Cys Pro Ser
220                 225                 230                 235
```

```
gtg tcc aca gtg cag tgt acc cac ggc atc aag ccc gtg gtc tcc acc      773
Val Ser Thr Val Gln Cys Thr His Gly Ile Lys Pro Val Val Ser Thr
            240                 245                 250 cag ctg ctg ctg aac ggc agc ctg gcc gaa gag gaa gtg atg atc aga      821
Gln Leu Leu Leu Asn Gly Ser Leu Ala Glu Glu Glu Val Met Ile Arg
        255                 260                 265 agc gag aac atc acc aac aac gcc aag aac atc ctg gtg cag ttc aac      869
Ser Glu Asn Ile Thr Asn Asn Ala Lys Asn Ile Leu Val Gln Phe Asn
    270                 275                 280 acc ccc gtg cag att aac tgc acc cgg ccc aac aac aac acc aga aag      917
Thr Pro Val Gln Ile Asn Cys Thr Arg Pro Asn Asn Asn Thr Arg Lys
285                 290                 295 agc atc cgg atc ggc cca ggc cag gcc ttc tac gcc acc ggc gac atc      965
Ser Ile Arg Ile Gly Pro Gly Gln Ala Phe Tyr Ala Thr Gly Asp Ile
300                 305                 310                 315 atc ggc gac atc cgg cag gcc cac tgc acc gtg tcc aag gcc acc tgg     1013
Ile Gly Asp Ile Arg Gln Ala His Cys Thr Val Ser Lys Ala Thr Trp
            320                 325                 330 aac gag aca ctg ggc aag gtg gtg aaa cag ctg cgg aag cac ttc ggg     1061
Asn Glu Thr Leu Gly Lys Val Val Lys Gln Leu Arg Lys His Phe Gly
        335                 340                 345 aac aac acc atc atc cgc ttc gcc aac agc tct ggc ggc gac ctg gaa     1109
Asn Asn Thr Ile Ile Arg Phe Ala Asn Ser Ser Gly Gly Asp Leu Glu
    350                 355                 360 gtg acc acc cac agc ttc aac tgt ggc ggc gag ttc ttc tac tgc aat     1157
Val Thr Thr His Ser Phe Asn Cys Gly Gly Glu Phe Phe Tyr Cys Asn
365                 370                 375 acc tcc ggc ctg ttc aac agc acc tgg atc agc aat acc agc gtg cag     1205
Thr Ser Gly Leu Phe Asn Ser Thr Trp Ile Ser Asn Thr Ser Val Gln
380                 385                 390                 395 ggc agc aac agc acc ggc agc aac gac agc atc acc ctg ccc tgc cgg     1253
Gly Ser Asn Ser Thr Gly Ser Asn Asp Ser Ile Thr Leu Pro Cys Arg
            400                 405                 410 atc aag cag atc atc aat atg tgg cag cgg att ggc cag gct atg tac     1301
Ile Lys Gln Ile Ile Asn Met Trp Gln Arg Ile Gly Gln Ala Met Tyr
        415                 420                 425 gcc cca ccc atc cag ggc gtg atc aga tgc gtg tcc aat atc acc ggc     1349
Ala Pro Pro Ile Gln Gly Val Ile Arg Cys Val Ser Asn Ile Thr Gly
    430                 435                 440 ctg atc ctg acc cgg gac ggc ggc tct acc aac agc acc acc gaa acc     1397
Leu Ile Leu Thr Arg Asp Gly Gly Ser Thr Asn Ser Thr Thr Glu Thr
445                 450                 455 ttc aga ccc ggc gga ggc gac atg aga gac aac tgg cgg agc gag ctg     1445
Phe Arg Pro Gly Gly Gly Asp Met Arg Asp Asn Trp Arg Ser Glu Leu
460                 465                 470                 475 tac aag tac aaa gtg gtg aaa atc gag ccc ctg ggc gtg gcc ccc acc     1493
Tyr Lys Tyr Lys Val Val Lys Ile Glu Pro Leu Gly Val Ala Pro Thr
            480                 485                 490 aga gcc aag aga aga gtg gtc gga agc gag aag tcc gcc gtg ggc atc     1541
Arg Ala Lys Arg Arg Val Val Gly Ser Glu Lys Ser Ala Val Gly Ile
        495                 500                 505 ggc gcc gtg ttt ctg gga ttc ctg ggc gct gcc ggc tct aca atg gga     1589
Gly Ala Val Phe Leu Gly Phe Leu Gly Ala Ala Gly Ser Thr Met Gly
    510                 515                 520 gcc gcc agc atg aca ctg acc gtg cag gcc aga aac ctg ctg tcc ggc     1637
Ala Ala Ser Met Thr Leu Thr Val Gln Ala Arg Asn Leu Leu Ser Gly
525                 530                 535 atc gtg cag cag cag agc aac ctg ctg aga gcc atc gag gcc cag cag     1685
Ile Val Gln Gln Gln Ser Asn Leu Leu Arg Ala Ile Glu Ala Gln Gln
540                 545                 550                 555
```

```
cat ctc ctc aaa ctc aca gtc tgg ggc atc aag cag ctg cag gcc agg      1733
His Leu Leu Lys Leu Thr Val Trp Gly Ile Lys Gln Leu Gln Ala Arg
            560                 565                 570 gtg ctg gcc gtg gag aga tac ctg cgg gat cag cag ctc ctc ggc atc      1781
Val Leu Ala Val Glu Arg Tyr Leu Arg Asp Gln Gln Leu Leu Gly Ile
        575                 580                 585 tgg ggc tgc agc ggc aag ctg atc tgc acc acc aac gtg ccc tgg aac      1829
Trp Gly Cys Ser Gly Lys Leu Ile Cys Thr Thr Asn Val Pro Trp Asn
    590                 595                 600 tcc agc tgg tcc aac cgg aac ctg agc gag atc tgg gac aac atg acc      1877
Ser Ser Trp Ser Asn Arg Asn Leu Ser Glu Ile Trp Asp Asn Met Thr
605                 610                 615 tgg ctg cag tgg gac aaa gag atc agc aac tac acc cag atc atc tac      1925
Trp Leu Gln Trp Asp Lys Glu Ile Ser Asn Tyr Thr Gln Ile Ile Tyr
620                 625                 630                 635 ggc ctg ctg gaa gag agc cag aac cag cag gaa aag aac gaa cag gat      1973
Gly Leu Leu Glu Glu Ser Gln Asn Gln Gln Glu Lys Asn Glu Gln Asp
            640                 645                 650 ctc ctg gct ctc gat aag tgg gcc agc ctg tgg aat tgg ttc gac atc      2021
Leu Leu Ala Leu Asp Lys Trp Ala Ser Leu Trp Asn Trp Phe Asp Ile
        655                 660                 665 agc aac tgg ctg tgg tac atc aag ggc agc ggc cac cac cac cat cac      2069
Ser Asn Trp Leu Trp Tyr Ile Lys Gly Ser Gly His His His His His
    670                 675                 680 cac tgagcggccg cttaattaa                                             2091
His

<210> SEQ ID NO 76
<211> LENGTH: 684
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Glu Thr Glu Lys His Asn Val Trp Ala
    50                  55                  60

Thr His Ala Cys Val Pro Thr Asp Pro Asn Pro Gln Glu Ile His Leu
65                  70                  75                  80

Glu Asn Val Thr Glu Glu Phe Asn Met Trp Lys Asn Asn Met Val Glu
                85                  90                  95

Gln Met His Thr Asp Ile Ile Ser Leu Trp Asp Gln Ser Leu Lys Pro
            100                 105                 110

Cys Val Lys Leu Thr Pro Leu Cys Val Thr Leu Gln Cys Thr Asn Val
        115                 120                 125

Thr Asn Asn Ile Thr Asp Asp Met Arg Gly Glu Leu Lys Asn Cys Ser
    130                 135                 140

Phe Asn Met Thr Thr Glu Leu Arg Asp Lys Lys Gln Lys Val Tyr Ser
145                 150                 155                 160

Leu Phe Tyr Arg Leu Asp Val Val Gln Ile Asn Glu Asn Gln Gly Asn
                165                 170                 175
```

```
Arg Ser Asn Asn Ser Asn Lys Glu Tyr Arg Leu Ile Asn Cys Asn Thr
            180                 185                 190

Ser Ala Ile Thr Gln Ala Cys Pro Lys Val Ser Phe Glu Pro Ile Pro
            195                 200                 205

Ile His Tyr Cys Ala Pro Ala Gly Phe Ala Ile Leu Lys Cys Lys Asp
            210                 215                 220

Lys Lys Phe Asn Gly Thr Gly Pro Cys Pro Ser Val Ser Thr Val Gln
225                 230                 235                 240

Cys Thr His Gly Ile Lys Pro Val Val Ser Thr Gln Leu Leu Leu Asn
                    245                 250                 255

Gly Ser Leu Ala Glu Glu Glu Val Met Ile Arg Ser Glu Asn Ile Thr
                260                 265                 270

Asn Asn Ala Lys Asn Ile Leu Val Gln Phe Asn Thr Pro Val Gln Ile
            275                 280                 285

Asn Cys Thr Arg Pro Asn Asn Asn Thr Arg Lys Ser Ile Arg Ile Gly
            290                 295                 300

Pro Gly Gln Ala Phe Tyr Ala Thr Gly Asp Ile Ile Gly Asp Ile Arg
305                 310                 315                 320

Gln Ala His Cys Thr Val Ser Lys Ala Thr Trp Asn Glu Thr Leu Gly
                    325                 330                 335

Lys Val Val Lys Gln Leu Arg Lys His Phe Gly Asn Asn Thr Ile Ile
                340                 345                 350

Arg Phe Ala Asn Ser Ser Gly Gly Asp Leu Glu Val Thr Thr His Ser
            355                 360                 365

Phe Asn Cys Gly Gly Glu Phe Phe Tyr Cys Asn Thr Ser Gly Leu Phe
            370                 375                 380

Asn Ser Thr Trp Ile Ser Asn Thr Ser Val Gln Gly Ser Asn Ser Thr
385                 390                 395                 400

Gly Ser Asn Asp Ser Ile Thr Leu Pro Cys Arg Ile Lys Gln Ile Ile
                    405                 410                 415

Asn Met Trp Gln Arg Ile Gly Gln Ala Met Tyr Ala Pro Pro Ile Gln
                420                 425                 430

Gly Val Ile Arg Cys Val Ser Asn Ile Thr Gly Leu Ile Leu Thr Arg
            435                 440                 445

Asp Gly Gly Ser Thr Asn Ser Thr Thr Glu Thr Phe Arg Pro Gly Gly
450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Arg Ala Lys Arg Arg
                    485                 490                 495

Val Val Gly Ser Glu Lys Ser Ala Val Gly Ile Gly Ala Val Phe Leu
                500                 505                 510

Gly Phe Leu Gly Ala Ala Gly Ser Thr Met Gly Ala Ala Ser Met Thr
            515                 520                 525

Leu Thr Val Gln Ala Arg Asn Leu Leu Ser Gly Ile Val Gln Gln Gln
            530                 535                 540

Ser Asn Leu Leu Arg Ala Ile Glu Ala Gln Gln His Leu Leu Lys Leu
545                 550                 555                 560

Thr Val Trp Gly Ile Lys Gln Leu Gln Ala Arg Val Leu Ala Val Glu
                    565                 570                 575

Arg Tyr Leu Arg Asp Gln Gln Leu Leu Gly Ile Trp Gly Cys Ser Gly
                580                 585                 590

Lys Leu Ile Cys Thr Thr Asn Val Pro Trp Asn Ser Ser Trp Ser Asn
            595                 600                 605
```

Arg Asn Leu Ser Glu Ile Trp Asp Asn Met Thr Trp Leu Gln Trp Asp
                                        610                 615                 620

Lys Glu Ile Ser Asn Tyr Thr Gln Ile Ile Tyr Gly Leu Leu Glu Glu
625                 630                 635                 640

Ser Gln Asn Gln Gln Lys Asn Glu Gln Asp Leu Leu Ala Leu Asp
                    645                 650                 655

Lys Trp Ala Ser Leu Trp Asn Trp Phe Asp Ile Ser Asn Trp Leu Trp
                660                 665                 670

Tyr Ile Lys Gly Ser Gly His His His His His His
        675                 680

<210> SEQ ID NO 77
<211> LENGTH: 2193
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (21)..(2174)

<400> SEQUENCE: 77

```
ggcgcgccga attcgccacc atg ccc atg gga tcc ctg cag cct ctg gcc aca         53
                     Met Pro Met Gly Ser Leu Gln Pro Leu Ala Thr
                      1               5                  10 ctg tat ctg ctg ggc atg ctg gtg gcc tct gtg ctg gcc gct ggc aat         101
Leu Tyr Leu Leu Gly Met Leu Val Ala Ser Val Leu Ala Ala Gly Asn
            15                  20                  25 ctg tgg gtc acc gtg tac tac ggc gtg ccc gtg tgg aag gac gcc gag         149
Leu Trp Val Thr Val Tyr Tyr Gly Val Pro Val Trp Lys Asp Ala Glu
        30                  35                  40 aca acc ctg ttc tgc gcc agc gac gcc aag gcc tac gag aca gag aag         197
Thr Thr Leu Phe Cys Ala Ser Asp Ala Lys Ala Tyr Glu Thr Glu Lys
    45                  50                  55 cac aac gtg tgg gcc acc cac gcc tgc gtg cca acc gac cct aac ccc         245
His Asn Val Trp Ala Thr His Ala Cys Val Pro Thr Asp Pro Asn Pro
60                  65                  70                  75 cag gaa atc cac ctg gaa aac gtg acc gaa gag ttc aac atg tgg aag         293
Gln Glu Ile His Leu Glu Asn Val Thr Glu Glu Phe Asn Met Trp Lys
                80                  85                  90 aac aac atg gtg gaa cag atg cac acc gac atc atc agc ctg tgg gac         341
Asn Asn Met Val Glu Gln Met His Thr Asp Ile Ile Ser Leu Trp Asp
            95                  100                 105 cag agc ctg aag ccc tgc gtg aag ctg acc ccc ctg tgc gtg acc ctg         389
Gln Ser Leu Lys Pro Cys Val Lys Leu Thr Pro Leu Cys Val Thr Leu
        110                 115                 120 cag tgc acc aac gtg acc aac aac atc acc gac gac atg cgg ggc gag         437
Gln Cys Thr Asn Val Thr Asn Asn Ile Thr Asp Asp Met Arg Gly Glu
    125                 130                 135 ctg aag aac tgc agc ttc aac atg acc acc gag ctg cgg gac aag aaa         485
Leu Lys Asn Cys Ser Phe Asn Met Thr Thr Glu Leu Arg Asp Lys Lys
140                 145                 150                 155 cag aag gtg tac agc ctg ttc tac cgg ctg gac gtg gtg cag atc aac         533
Gln Lys Val Tyr Ser Leu Phe Tyr Arg Leu Asp Val Val Gln Ile Asn
                160                 165                 170 gag aac cag ggc aac aga agc aac aac agc aac aaa gag tac cgg ctg         581
Glu Asn Gln Gly Asn Arg Ser Asn Asn Ser Asn Lys Glu Tyr Arg Leu
            175                 180                 185 atc aac tgc aac acc agc gcc atc acc cag gcc tgc ccc aag gtg tcc         629
Ile Asn Cys Asn Thr Ser Ala Ile Thr Gln Ala Cys Pro Lys Val Ser
```

```
                190                 195                 200
ttc gag ccc atc ccc atc cac tac tgc gcc cct gcc ggc ttc gcc atc       677
Phe Glu Pro Ile Pro Ile His Tyr Cys Ala Pro Ala Gly Phe Ala Ile
205                 210                 215 ctg aag tgc aag gac aag aag ttc aac ggc acc ggc ccc tgc ccc agc       725
Leu Lys Cys Lys Asp Lys Lys Phe Asn Gly Thr Gly Pro Cys Pro Ser
220                 225                 230                 235 gtg tcc aca gtg cag tgt acc cac ggc atc aag ccc gtg gtc tcc acc       773
Val Ser Thr Val Gln Cys Thr His Gly Ile Lys Pro Val Val Ser Thr
                240                 245                 250 cag ctg ctg ctg aac ggc agc ctg gcc gaa gag gaa gtg atg atc aga       821
Gln Leu Leu Leu Asn Gly Ser Leu Ala Glu Glu Glu Val Met Ile Arg
                255                 260                 265 agc gag aac atc acc aac aac gcc aag aac atc ctg gtg cag ttc aac       869
Ser Glu Asn Ile Thr Asn Asn Ala Lys Asn Ile Leu Val Gln Phe Asn
        270                 275                 280 acc ccc gtg cag att aac tgc acc cgg ccc aac aac aac acc aga aag       917
Thr Pro Val Gln Ile Asn Cys Thr Arg Pro Asn Asn Asn Thr Arg Lys
285                 290                 295 agc atc cgg atc ggc cca ggc cag gcc ttc tac gcc acc ggc gac atc       965
Ser Ile Arg Ile Gly Pro Gly Gln Ala Phe Tyr Ala Thr Gly Asp Ile
300                 305                 310                 315 atc ggc gac atc cgg cag gcc cac tgc acc gtg tcc aag gcc acc tgg      1013
Ile Gly Asp Ile Arg Gln Ala His Cys Thr Val Ser Lys Ala Thr Trp
                320                 325                 330 aac gag aca ctg ggc aag gtg gtg aaa cag ctg cgg aag cac ttc ggg      1061
Asn Glu Thr Leu Gly Lys Val Val Lys Gln Leu Arg Lys His Phe Gly
                335                 340                 345 aac aac acc atc atc cgc ttc gcc aac agc tct ggc ggc gac ctg gaa      1109
Asn Asn Thr Ile Ile Arg Phe Ala Asn Ser Ser Gly Gly Asp Leu Glu
        350                 355                 360 gtg acc acc cac agc ttc aac tgt ggc ggc gag ttc ttc tac tgc aat      1157
Val Thr Thr His Ser Phe Asn Cys Gly Gly Glu Phe Phe Tyr Cys Asn
365                 370                 375 acc tcc ggc ctg ttc aac agc acc tgg atc agc aat acc agc gtg cag      1205
Thr Ser Gly Leu Phe Asn Ser Thr Trp Ile Ser Asn Thr Ser Val Gln
380                 385                 390                 395 ggc agc aac agc acc ggc agc aac gac agc atc acc ctg ccc tgc cgg      1253
Gly Ser Asn Ser Thr Gly Ser Asn Asp Ser Ile Thr Leu Pro Cys Arg
                400                 405                 410 atc aag cag atc atc aat atg tgg cag cgg att ggc cag gct atg tac      1301
Ile Lys Gln Ile Ile Asn Met Trp Gln Arg Ile Gly Gln Ala Met Tyr
                415                 420                 425 gcc cca ccc atc cag ggc gtg atc aga tgc gtg tcc aat atc acc ggc      1349
Ala Pro Pro Ile Gln Gly Val Ile Arg Cys Val Ser Asn Ile Thr Gly
        430                 435                 440 ctg atc ctg acc cgg gac ggc ggc tct acc aac agc acc acc gaa acc      1397
Leu Ile Leu Thr Arg Asp Gly Gly Ser Thr Asn Ser Thr Thr Glu Thr
445                 450                 455 ttc aga ccc ggc gga ggc gac atg aga gac aac tgg cgg agc gag ctg      1445
Phe Arg Pro Gly Gly Gly Asp Met Arg Asp Asn Trp Arg Ser Glu Leu
460                 465                 470                 475 tac aag tac aaa gtg gtg aaa atc gag ccc ctg ggc gtg gcc ccc acc      1493
Tyr Lys Tyr Lys Val Val Lys Ile Glu Pro Leu Gly Val Ala Pro Thr
                480                 485                 490 aga gcc aag aga aga gtg gtc gga agc gag aag tcc gcc gtg gga atc      1541
Arg Ala Lys Arg Arg Val Val Gly Ser Glu Lys Ser Ala Val Gly Ile
                495                 500                 505 ggc gcc gtg ttt ctg gga ttc ctg ggc gct gcc ggc tct aca atg gga      1589
Gly Ala Val Phe Leu Gly Phe Leu Gly Ala Ala Gly Ser Thr Met Gly
```

```
                510                 515                 520
gcc gcc agc atg aca ctg acc gtg cag gcc aga aac ctg ctg tcc ggc      1637
Ala Ala Ser Met Thr Leu Thr Val Gln Ala Arg Asn Leu Leu Ser Gly
525                 530                 535 atc gtg cag cag cag agc aac ctg ctg aga gcc atc gag gcc cag cag      1685
Ile Val Gln Gln Gln Ser Asn Leu Leu Arg Ala Ile Glu Ala Gln Gln
540                 545                 550                 555 cat ctc ctc aaa ctc aca gtc tgg ggc atc aag cag ctg cag gcc agg      1733
His Leu Leu Lys Leu Thr Val Trp Gly Ile Lys Gln Leu Gln Ala Arg
                560                 565                 570 gtg ctg gcc gtg gag aga tac ctg cgg gat cag cag ctc ctc ggc atc      1781
Val Leu Ala Val Glu Arg Tyr Leu Arg Asp Gln Gln Leu Leu Gly Ile
            575                 580                 585 tgg ggc tgc agc ggc aag ctg atc tgc acc acc aac gtg ccc tgg aac      1829
Trp Gly Cys Ser Gly Lys Leu Ile Cys Thr Thr Asn Val Pro Trp Asn
        590                 595                 600 tcc agc tgg tcc aac cgg aac ctg agc gag atc tgg gac aat atg acc      1877
Ser Ser Trp Ser Asn Arg Asn Leu Ser Glu Ile Trp Asp Asn Met Thr
    605                 610                 615 tgg ctg cag tgg gac aaa gag atc agc aac tac acc cag atc atc tac      1925
Trp Leu Gln Trp Asp Lys Glu Ile Ser Asn Tyr Thr Gln Ile Ile Tyr
620                 625                 630                 635 ggc ctg ctg gaa gag agc cag aac cag cag gaa aag aac gag cag gac      1973
Gly Leu Leu Glu Glu Ser Gln Asn Gln Gln Glu Lys Asn Glu Gln Asp
                640                 645                 650 ctg ctg gcc ctg gac aag tgg gcc tcc ctg tgg aat tgg ttc gac atc      2021
Leu Leu Ala Leu Asp Lys Trp Ala Ser Leu Trp Asn Trp Phe Asp Ile
            655                 660                 665 tcc aac tgg ctg tgg tac atc aag ggc agc ggc ggc atg aag cag atc      2069
Ser Asn Trp Leu Trp Tyr Ile Lys Gly Ser Gly Gly Met Lys Gln Ile
        670                 675                 680 gag gac aag atc gaa gag atc gag tct aag atc aag aag att gag aac      2117
Glu Asp Lys Ile Glu Glu Ile Glu Ser Lys Ile Lys Lys Ile Glu Asn
    685                 690                 695 gag atc gcc cgc atc aag aaa ctg atc ggc gag agc ggc cac cac cac      2165
Glu Ile Ala Arg Ile Lys Lys Leu Ile Gly Glu Ser Gly His His His
700                 705                 710                 715 cat cac cat tgagcggccg cttaattaa                                     2193
His His His
```

```
<210> SEQ ID NO 78
<211> LENGTH: 718
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
                20                  25                  30

Tyr Tyr Gly Val Pro Val Trp Lys Asp Ala Glu Thr Thr Leu Phe Cys
            35                  40                  45

Ala Ser Asp Ala Lys Ala Tyr Glu Thr Glu Lys His Asn Val Trp Ala
        50                  55                  60

Thr His Ala Cys Val Pro Thr Asp Pro Asn Pro Gln Glu Ile His Leu
65                  70                  75                  80

Glu Asn Val Thr Glu Glu Phe Asn Met Trp Lys Asn Asn Met Val Glu
```

-continued

```
                85                  90                  95
Gln Met His Thr Asp Ile Ile Ser Leu Trp Asp Gln Ser Leu Lys Pro
            100                 105                 110
Cys Val Lys Leu Thr Pro Leu Cys Val Thr Leu Gln Cys Thr Asn Val
            115                 120                 125
Thr Asn Asn Ile Thr Asp Asp Met Arg Gly Glu Leu Lys Asn Cys Ser
        130                 135                 140
Phe Asn Met Thr Thr Glu Leu Arg Asp Lys Gln Lys Val Tyr Ser
145                 150                 155                 160
Leu Phe Tyr Arg Leu Asp Val Val Gln Ile Asn Glu Asn Gln Gly Asn
                165                 170                 175
Arg Ser Asn Asn Ser Asn Lys Glu Tyr Arg Leu Ile Asn Cys Asn Thr
                180                 185                 190
Ser Ala Ile Thr Gln Ala Cys Pro Lys Val Ser Phe Glu Pro Ile Pro
            195                 200                 205
Ile His Tyr Cys Ala Pro Ala Gly Phe Ala Ile Leu Lys Cys Lys Asp
            210                 215                 220
Lys Lys Phe Asn Gly Thr Gly Pro Cys Pro Ser Val Ser Thr Val Gln
225                 230                 235                 240
Cys Thr His Gly Ile Lys Pro Val Val Ser Thr Gln Leu Leu Leu Asn
                245                 250                 255
Gly Ser Leu Ala Glu Glu Glu Val Met Ile Arg Ser Glu Asn Ile Thr
                260                 265                 270
Asn Asn Ala Lys Asn Ile Leu Val Gln Phe Asn Thr Pro Val Gln Ile
                275                 280                 285
Asn Cys Thr Arg Pro Asn Asn Asn Thr Arg Lys Ser Ile Arg Ile Gly
            290                 295                 300
Pro Gly Gln Ala Phe Tyr Ala Thr Gly Asp Ile Ile Gly Asp Ile Arg
305                 310                 315                 320
Gln Ala His Cys Thr Val Ser Lys Ala Thr Trp Asn Glu Thr Leu Gly
                325                 330                 335
Lys Val Val Lys Gln Leu Arg Lys His Phe Gly Asn Asn Thr Ile Ile
                340                 345                 350
Arg Phe Ala Asn Ser Ser Gly Gly Asp Leu Glu Val Thr Thr His Ser
            355                 360                 365
Phe Asn Cys Gly Gly Glu Phe Phe Tyr Cys Asn Thr Ser Gly Leu Phe
            370                 375                 380
Asn Ser Thr Trp Ile Ser Asn Thr Ser Val Gln Gly Ser Asn Ser Thr
385                 390                 395                 400
Gly Ser Asn Asp Ser Ile Thr Leu Pro Cys Arg Ile Lys Gln Ile Ile
                405                 410                 415
Asn Met Trp Gln Arg Ile Gly Gln Ala Met Tyr Ala Pro Pro Ile Gln
                420                 425                 430
Gly Val Ile Arg Cys Val Ser Asn Ile Thr Gly Leu Ile Leu Thr Arg
            435                 440                 445
Asp Gly Gly Ser Thr Asn Ser Thr Thr Glu Thr Phe Arg Pro Gly Gly
450                 455                 460
Gly Asp Met Arg Asp Asn Trp Arg Ser Glu Leu Tyr Lys Tyr Lys Val
465                 470                 475                 480
Val Lys Ile Glu Pro Leu Gly Val Ala Pro Thr Arg Ala Lys Arg Arg
                485                 490                 495
Val Val Gly Ser Glu Lys Ser Ala Val Gly Ile Gly Ala Val Phe Leu
                500                 505                 510
```

```
Gly Phe Leu Gly Ala Ala Gly Ser Thr Met Gly Ala Ala Ser Met Thr
            515                 520                 525

Leu Thr Val Gln Ala Arg Asn Leu Leu Ser Gly Ile Val Gln Gln Gln
530                 535                 540

Ser Asn Leu Leu Arg Ala Ile Glu Ala Gln Gln His Leu Leu Lys Leu
545                 550                 555                 560

Thr Val Trp Gly Ile Lys Gln Leu Gln Ala Arg Val Leu Ala Val Glu
                565                 570                 575

Arg Tyr Leu Arg Asp Gln Gln Leu Leu Gly Ile Trp Gly Cys Ser Gly
            580                 585                 590

Lys Leu Ile Cys Thr Thr Asn Val Pro Trp Asn Ser Ser Trp Ser Asn
        595                 600                 605

Arg Asn Leu Ser Glu Ile Trp Asp Asn Met Thr Trp Leu Gln Trp Asp
610                 615                 620

Lys Glu Ile Ser Asn Tyr Thr Gln Ile Ile Tyr Gly Leu Leu Glu Glu
625                 630                 635                 640

Ser Gln Asn Gln Gln Glu Lys Asn Glu Gln Asp Leu Leu Ala Leu Asp
                645                 650                 655

Lys Trp Ala Ser Leu Trp Asn Trp Phe Asp Ile Ser Asn Trp Leu Trp
            660                 665                 670

Tyr Ile Lys Gly Ser Gly Gly Met Lys Gln Ile Glu Asp Lys Ile Glu
        675                 680                 685

Glu Ile Glu Ser Lys Ile Lys Lys Ile Glu Asn Glu Ile Ala Arg Ile
690                 695                 700

Lys Lys Leu Ile Gly Glu Ser Gly His His His His His
705                 710                 715

<210> SEQ ID NO 79
<211> LENGTH: 2154
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (21)..(2135)

<400> SEQUENCE: 79
ggcgcgccga attcgccacc atg ccc atg gga tcc ctg cag cct ctg gcc aca      53
                      Met Pro Met Gly Ser Leu Gln Pro Leu Ala Thr
                       1               5                  10 ctg tat ctg ctg ggc atg ctg gtg gcc tct gtg ctg gcc gct ggc aat       101
Leu Tyr Leu Leu Gly Met Leu Val Ala Ser Val Leu Ala Ala Gly Asn
            15                  20                  25 ctg tgg gtc acc gtg tac tac ggc gtg ccc gtg tgg aag gac gcc gag       149
Leu Trp Val Thr Val Tyr Tyr Gly Val Pro Val Trp Lys Asp Ala Glu
        30                  35                  40 aca acc ctg ttc tgc gcc agc gac gcc aag gcc tac gag aca gag aag       197
Thr Thr Leu Phe Cys Ala Ser Asp Ala Lys Ala Tyr Glu Thr Glu Lys
    45                  50                  55 cac aac gtg tgg gcc acc cac gcc tgc gtg cca acc gac cct aac ccc       245
His Asn Val Trp Ala Thr His Ala Cys Val Pro Thr Asp Pro Asn Pro
60                  65                  70                  75 cag gaa atc cac ctg gaa aac gtg acc gaa gag ttc aac atg tgg aag       293
Gln Glu Ile His Leu Glu Asn Val Thr Glu Glu Phe Asn Met Trp Lys
                80                  85                  90 aac aac atg gtg gaa cag atg cac acc gac atc atc agc ctg tgg gac       341
Asn Asn Met Val Glu Gln Met His Thr Asp Ile Ile Ser Leu Trp Asp
            95                 100                 105
```

| | |
|---|---|
| cag agc ctg aag ccc tgc gtg aag ctg acc ccc ctg tgc gtg acc ctg<br>Gln Ser Leu Lys Pro Cys Val Lys Leu Thr Pro Leu Cys Val Thr Leu<br>110               115                   120 | 389 |
| cag tgc acc aac gtg acc aac aac atc acc gac gac atg cgg ggc gag<br>Gln Cys Thr Asn Val Thr Asn Asn Ile Thr Asp Asp Met Arg Gly Glu<br>125               130                   135 | 437 |
| ctg aag aac tgc agc ttc aac atg acc acc gag ctg cgg gac aag aaa<br>Leu Lys Asn Cys Ser Phe Asn Met Thr Thr Glu Leu Arg Asp Lys Lys<br>140               145              150               155 | 485 |
| cag aag gtg tac agc ctg ttc tac cgg ctg gac gtg gtg cag atc aac<br>Gln Lys Val Tyr Ser Leu Phe Tyr Arg Leu Asp Val Val Gln Ile Asn<br>                   160               165              170 | 533 |
| gag aac cag ggc aac aga agc aac aac agc aac aaa gag tac cgg ctg<br>Glu Asn Gln Gly Asn Arg Ser Asn Asn Ser Asn Lys Glu Tyr Arg Leu<br>175               180                   185 | 581 |
| atc aac tgc aac acc agc gcc atc acc cag gcc tgc ccc aag gtg tcc<br>Ile Asn Cys Asn Thr Ser Ala Ile Thr Gln Ala Cys Pro Lys Val Ser<br>                   190              195              200 | 629 |
| ttc gag ccc atc ccc atc cac tac tgc gcc cct gcc ggc ttc gcc atc<br>Phe Glu Pro Ile Pro Ile His Tyr Cys Ala Pro Ala Gly Phe Ala Ile<br>205               210                   215 | 677 |
| ctg aag tgc aag gac aag aag ttc aac ggc acc ggc ccc tgc ccc agc<br>Leu Lys Cys Lys Asp Lys Lys Phe Asn Gly Thr Gly Pro Cys Pro Ser<br>220               225              230               235 | 725 |
| gtg tcc aca gtg cag tgt acc cac ggc atc aag ccc gtg gtg tcc acc<br>Val Ser Thr Val Gln Cys Thr His Gly Ile Lys Pro Val Val Ser Thr<br>                   240               245              250 | 773 |
| cag ctg ctg ctg aac ggc agc ctg gcc gaa gag gaa gtg atg atc aga<br>Gln Leu Leu Leu Asn Gly Ser Leu Ala Glu Glu Glu Val Met Ile Arg<br>255               260                   265 | 821 |
| agc gag aac atc acc aac aac gcc aag aac atc ctg gtg cag ttc aac<br>Ser Glu Asn Ile Thr Asn Asn Ala Lys Asn Ile Leu Val Gln Phe Asn<br>270               275              280 | 869 |
| acc ccc gtg cag att aac tgc acc cgg ccc aac aac aac acc aga aag<br>Thr Pro Val Gln Ile Asn Cys Thr Arg Pro Asn Asn Asn Thr Arg Lys<br>285               290                   295 | 917 |
| agc atc cgg atc ggc cca ggc cag gcc ttc tac gcc acc ggc gac atc<br>Ser Ile Arg Ile Gly Pro Gly Gln Ala Phe Tyr Ala Thr Gly Asp Ile<br>300               305              310               315 | 965 |
| atc ggc gac atc cgg cag gcc cac tgc acc gtg tcc aag gcc acc tgg<br>Ile Gly Asp Ile Arg Gln Ala His Cys Thr Val Ser Lys Ala Thr Trp<br>                   320               325              330 | 1013 |
| aac gag aca ctg ggc aag gtg gtg aaa cag ctg cgg aag cac ttc ggg<br>Asn Glu Thr Leu Gly Lys Val Val Lys Gln Leu Arg Lys His Phe Gly<br>335               340              345 | 1061 |
| aac aac acc atc atc cgc ttc gcc aac agc tct ggc ggc gac ctg gaa<br>Asn Asn Thr Ile Ile Arg Phe Ala Asn Ser Ser Gly Gly Asp Leu Glu<br>               350              355               360 | 1109 |
| gtg acc acc cac agc ttc aac tgt ggc ggc gag ttc ttc tac tgc aat<br>Val Thr Thr His Ser Phe Asn Cys Gly Gly Glu Phe Phe Tyr Cys Asn<br>365               370                   375 | 1157 |
| acc tcc ggc ctg ttc aac agc acc tgg atc agc aat acc agc gtg cag<br>Thr Ser Gly Leu Phe Asn Ser Thr Trp Ile Ser Asn Thr Ser Val Gln<br>380               385              390               395 | 1205 |
| ggc agc aac agc acc ggc agc aac gac agc atc acc ctg ccc tgc cgg<br>Gly Ser Asn Ser Thr Gly Ser Asn Asp Ser Ile Thr Leu Pro Cys Arg<br>                   400               405              410 | 1253 |
| atc aag cag atc atc aat atg tgg cag cgg att ggc cag gct atg tac<br>Ile Lys Gln Ile Ile Asn Met Trp Gln Arg Ile Gly Gln Ala Met Tyr<br>415               420                   425 | 1301 |

```
gcc cca ccc atc cag ggc gtg atc aga tgc gtg tcc aat atc acc ggc    1349
Ala Pro Pro Ile Gln Gly Val Ile Arg Cys Val Ser Asn Ile Thr Gly
        430                 435                 440 ctg atc ctg acc cgg gac ggc ggc tct acc aac agc acc acc gaa acc    1397
Leu Ile Leu Thr Arg Asp Gly Gly Ser Thr Asn Ser Thr Thr Glu Thr
445                 450                 455 ttc aga ccc ggc gga ggc gac atg aga gac aac tgg cgg agc gag ctg    1445
Phe Arg Pro Gly Gly Gly Asp Met Arg Asp Asn Trp Arg Ser Glu Leu
460                 465                 470                 475 tac aag tac aaa gtg gtg aaa atc gag ccc ctg ggc gtg gcc ccc acc    1493
Tyr Lys Tyr Lys Val Val Lys Ile Glu Pro Leu Gly Val Ala Pro Thr
            480                 485                 490 aga gcc aag aga aga gtg gtc gga cgc gag aag cgg gcc gtg gga att    1541
Arg Ala Lys Arg Arg Val Val Gly Arg Glu Lys Arg Ala Val Gly Ile
        495                 500                 505 gga gcc gtg ttt ctg gga ttc ctg ggc gct gcc ggc tct aca atg gga    1589
Gly Ala Val Phe Leu Gly Phe Leu Gly Ala Ala Gly Ser Thr Met Gly
    510                 515                 520 gcc gcc agc atg aca ctg acc gtg cag gcc aga aac ctg ctg tcc ggc    1637
Ala Ala Ser Met Thr Leu Thr Val Gln Ala Arg Asn Leu Leu Ser Gly
525                 530                 535 atc gtg cag cag cag agc aac ctg ctg aga gcc atc gag gcc cag cag    1685
Ile Val Gln Gln Gln Ser Asn Leu Leu Arg Ala Ile Glu Ala Gln Gln
540                 545                 550                 555 cat ctc ctc aaa ctc aca gtc tgg ggc atc aag cag ctg cag gcc agg    1733
His Leu Leu Lys Leu Thr Val Trp Gly Ile Lys Gln Leu Gln Ala Arg
            560                 565                 570 gtg ctg gcc gtg gag aga tac ctg cgg gat cag cag ctc ctc ggc atc    1781
Val Leu Ala Val Glu Arg Tyr Leu Arg Asp Gln Gln Leu Leu Gly Ile
        575                 580                 585 tgg ggc tgc agc ggc aag ctg atc tgc acc acc aac gtg ccc tgg aac    1829
Trp Gly Cys Ser Gly Lys Leu Ile Cys Thr Thr Asn Val Pro Trp Asn
    590                 595                 600 tcc agc tgg tcc aac cgg aac ctg agc gag atc tgg gac aat atg acc    1877
Ser Ser Trp Ser Asn Arg Asn Leu Ser Glu Ile Trp Asp Asn Met Thr
605                 610                 615 tgg ctg cag tgg gac aaa gag atc agc aac tac acc cag atc atc tac    1925
Trp Leu Gln Trp Asp Lys Glu Ile Ser Asn Tyr Thr Gln Ile Ile Tyr
620                 625                 630                 635 ggc ctg ctg gaa gag agc cag aac cag cag gaa aag aac gag cag gac    1973
Gly Leu Leu Glu Glu Ser Gln Asn Gln Gln Glu Lys Asn Glu Gln Asp
            640                 645                 650 ctg ctg gcc ctg gac aag tgg gcc tcc ctg tgg aat tgg ttc gac atc    2021
Leu Leu Ala Leu Asp Lys Trp Ala Ser Leu Trp Asn Trp Phe Asp Ile
        655                 660                 665 tcc aac tgg ctg tgg tac atc aag atc ttc atc atg atc gtg ggc gga    2069
Ser Asn Trp Leu Trp Tyr Ile Lys Ile Phe Ile Met Ile Val Gly Gly
    670                 675                 680 ctg atc ggc ctg cgg atc gtg ttt gcc gtg ctg agc gtg atc tcc ggc    2117
Leu Ile Gly Leu Arg Ile Val Phe Ala Val Leu Ser Val Ile Ser Gly
685                 690                 695 cac cac cac cat cac cac tgagcggccg cttaattaa                       2154
His His His His His His
700                 705

<210> SEQ ID NO 80
<211> LENGTH: 705
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 80

```
Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Glu Thr Glu Lys His Asn Val Trp Ala
    50                  55                  60

Thr His Ala Cys Val Pro Thr Asp Pro Asn Pro Gln Glu Ile His Leu
65                  70                  75                  80

Glu Asn Val Thr Glu Glu Phe Asn Met Trp Lys Asn Asn Met Val Glu
                85                  90                  95

Gln Met His Thr Asp Ile Ile Ser Leu Trp Asp Gln Ser Leu Lys Pro
            100                 105                 110

Cys Val Lys Leu Thr Pro Leu Cys Val Thr Leu Gln Cys Thr Asn Val
        115                 120                 125

Thr Asn Asn Ile Thr Asp Asp Met Arg Gly Glu Leu Lys Asn Cys Ser
    130                 135                 140

Phe Asn Met Thr Thr Glu Leu Arg Asp Lys Lys Gln Lys Val Tyr Ser
145                 150                 155                 160

Leu Phe Tyr Arg Leu Asp Val Val Gln Ile Asn Glu Asn Gln Gly Asn
                165                 170                 175

Arg Ser Asn Asn Ser Asn Lys Glu Tyr Arg Leu Ile Asn Cys Asn Thr
            180                 185                 190

Ser Ala Ile Thr Gln Ala Cys Pro Lys Val Ser Phe Glu Pro Ile Pro
        195                 200                 205

Ile His Tyr Cys Ala Pro Ala Gly Phe Ala Ile Leu Lys Cys Lys Asp
    210                 215                 220

Lys Lys Phe Asn Gly Thr Gly Pro Cys Pro Ser Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Glu Val Met Ile Arg Ser Glu Asn Ile Thr
            260                 265                 270

Asn Asn Ala Lys Asn Ile Leu Val Gln Phe Asn Thr Pro Val Gln Ile
        275                 280                 285

Asn Cys Thr Arg Pro Asn Asn Asn Thr Arg Lys Ser Ile Arg Ile Gly
    290                 295                 300

Pro Gly Gln Ala Phe Tyr Ala Thr Gly Asp Ile Ile Gly Asp Ile Arg
305                 310                 315                 320

Gln Ala His Cys Thr Val Ser Lys Ala Thr Trp Asn Glu Thr Leu Gly
                325                 330                 335

Lys Val Val Lys Gln Leu Arg Lys His Phe Gly Asn Asn Thr Ile Ile
            340                 345                 350

Arg Phe Ala Asn Ser Ser Gly Gly Asp Leu Glu Val Thr Thr His Ser
        355                 360                 365

Phe Asn Cys Gly Gly Glu Phe Phe Tyr Cys Asn Thr Ser Gly Leu Phe
    370                 375                 380

Asn Ser Thr Trp Ile Ser Asn Thr Ser Val Gln Gly Ser Asn Ser Thr
385                 390                 395                 400

Gly Ser Asn Asp Ser Ile Thr Leu Pro Cys Arg Ile Lys Gln Ile Ile
```

405                 410                 415
Asn Met Trp Gln Arg Ile Gly Gln Ala Met Tyr Ala Pro Pro Ile Gln
            420                 425                 430

Gly Val Ile Arg Cys Val Ser Asn Ile Thr Gly Leu Ile Leu Thr Arg
        435                 440                 445

Asp Gly Gly Ser Thr Asn Ser Thr Thr Glu Thr Phe Arg Pro Gly Gly
    450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Arg Ala Lys Arg Arg
                485                 490                 495

Val Val Gly Arg Glu Lys Arg Ala Val Gly Ile Gly Ala Val Phe Leu
            500                 505                 510

Gly Phe Leu Gly Ala Ala Gly Ser Thr Met Gly Ala Ala Ser Met Thr
        515                 520                 525

Leu Thr Val Gln Ala Arg Asn Leu Leu Ser Gly Ile Val Gln Gln Gln
    530                 535                 540

Ser Asn Leu Leu Arg Ala Ile Glu Ala Gln Gln His Leu Leu Lys Leu
545                 550                 555                 560

Thr Val Trp Gly Ile Lys Gln Leu Gln Ala Arg Val Leu Ala Val Glu
                565                 570                 575

Arg Tyr Leu Arg Asp Gln Gln Leu Leu Gly Ile Trp Gly Cys Ser Gly
            580                 585                 590

Lys Leu Ile Cys Thr Thr Asn Val Pro Trp Asn Ser Ser Trp Ser Asn
        595                 600                 605

Arg Asn Leu Ser Glu Ile Trp Asp Asn Met Thr Trp Leu Gln Trp Asp
    610                 615                 620

Lys Glu Ile Ser Asn Tyr Thr Gln Ile Ile Tyr Gly Leu Leu Glu Glu
625                 630                 635                 640

Ser Gln Asn Gln Gln Glu Lys Asn Glu Gln Asp Leu Leu Ala Leu Asp
                645                 650                 655

Lys Trp Ala Ser Leu Trp Asn Trp Phe Asp Ile Ser Asn Trp Leu Trp
            660                 665                 670

Tyr Ile Lys Ile Phe Ile Met Ile Val Gly Gly Leu Ile Gly Leu Arg
        675                 680                 685

Ile Val Phe Ala Val Leu Ser Val Ile Ser Gly His His His His His
    690                 695                 700

His
705

<210> SEQ ID NO 81
<211> LENGTH: 1596
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (37)..(1563)

<400> SEQUENCE: 81
ccaagctggc tagcgtttaa acttaagctt gccacc atg cct atg ggc agc ctg        54
                                        Met Pro Met Gly Ser Leu
                                         1               5 cag cct ctg gcc acc ctg tac ctg ctg ggc atg ctg gtg gcc tcc gtg     102
Gln Pro Leu Ala Thr Leu Tyr Leu Leu Gly Met Leu Val Ala Ser Val
         10                  15                  20

```
ctg gct gcc acc gag aag ctg tgg gtc aca gtg tac tac ggc gtg ccc      150
Leu Ala Ala Thr Glu Lys Leu Trp Val Thr Val Tyr Tyr Gly Val Pro
        25                  30                  35 gtg tgg aaa gag gcc acc acc acc ctg ttc tgc gcc tct gag gcc aag      198
Val Trp Lys Glu Ala Thr Thr Thr Leu Phe Cys Ala Ser Glu Ala Lys
 40                  45                  50 gcc tac gac acc gag gtg cac aac gtg tgg gcc acc cac gcc tgc gtg      246
Ala Tyr Asp Thr Glu Val His Asn Val Trp Ala Thr His Ala Cys Val
55                  60                  65                  70 cca acc gac ccc aac ccc cag gaa gtg gaa ctg ggc aac gtg acc gag      294
Pro Thr Asp Pro Asn Pro Gln Glu Val Glu Leu Gly Asn Val Thr Glu
                75                  80                  85 aac ttc aac atg tgg aag aac gac atg gtg gaa cag atg cac gag gac      342
Asn Phe Asn Met Trp Lys Asn Asp Met Val Glu Gln Met His Glu Asp
            90                  95                  100 atc atc agc ctg tgg gac cag agc ctg aag ccc tgc gtg cgg ctg acc      390
Ile Ile Ser Leu Trp Asp Gln Ser Leu Lys Pro Cys Val Arg Leu Thr
        105                 110                 115 cct ctg tgc gtg acc ctg gac tgc acc gac ctg aac aac acc acc aac      438
Pro Leu Cys Val Thr Leu Asp Cys Thr Asp Leu Asn Asn Thr Thr Asn
120                 125                 130 acc aac aat acc aca aac act aac agc agc aag atc gag ggc ggc gag      486
Thr Asn Asn Thr Thr Asn Thr Asn Ser Ser Lys Ile Glu Gly Gly Glu
135                 140                 145                 150 atg aag aac tgc agc ttc aac atc acc acc aat cgg ggc gac aag cgg      534
Met Lys Asn Cys Ser Phe Asn Ile Thr Thr Asn Arg Gly Asp Lys Arg
                155                 160                 165 cag aaa gag tac gcc ctg ctg tac cgg acc gac atc gtg tcc atc gag      582
Gln Lys Glu Tyr Ala Leu Leu Tyr Arg Thr Asp Ile Val Ser Ile Glu
            170                 175                 180 aac acc agc agc agc tac cgg ctg atc agc tgc aac acc agc gtg atc      630
Asn Thr Ser Ser Ser Tyr Arg Leu Ile Ser Cys Asn Thr Ser Val Ile
        185                 190                 195 acc cag gcc tgc ccc aaa gtg acc ttc gag ccc atc ccc atc cac tac      678
Thr Gln Ala Cys Pro Lys Val Thr Phe Glu Pro Ile Pro Ile His Tyr
200                 205                 210 tgc gcc cct gcc ggc ttc gcc atc ctg aag tgc aac gag gac aag ttc      726
Cys Ala Pro Ala Gly Phe Ala Ile Leu Lys Cys Asn Glu Asp Lys Phe
215                 220                 225                 230 aac ggc aca ggc ccc tgc aag aac gtg tcc acc gtg cag tgc acc cac      774
Asn Gly Thr Gly Pro Cys Lys Asn Val Ser Thr Val Gln Cys Thr His
                235                 240                 245 ggc atc aga ccc acc gtg tcc acc cag ctg ctg aat ggc agc ctg          822
Gly Ile Arg Pro Thr Val Ser Thr Gln Leu Leu Leu Asn Gly Ser Leu
            250                 255                 260 gcc aaa gaa gaa gtg atc atc aga agc gcc aac ctg agc gac aac gcc      870
Ala Lys Glu Glu Val Ile Ile Arg Ser Ala Asn Leu Ser Asp Asn Ala
        265                 270                 275 aag atc atc atc gtg cag ctg aag gac ccc gtg gaa atc aac tgc acc      918
Lys Ile Ile Ile Val Gln Leu Lys Asp Pro Val Glu Ile Asn Cys Thr
280                 285                 290 cgg ccc aac aac aac acc aga aag agc atc aac ctg ggc cct ggc aga      966
Arg Pro Asn Asn Asn Thr Arg Lys Ser Ile Asn Leu Gly Pro Gly Arg
295                 300                 305                 310 gcc ttc tac gcc acc ggc gac atc atc ggc gac atc cgg cag gcc cac     1014
Ala Phe Tyr Ala Thr Gly Asp Ile Ile Gly Asp Ile Arg Gln Ala His
                315                 320                 325 tgc aac atc agc cgg gcc aag tgg aac gac acc ctg aga gag atc gcc     1062
Cys Asn Ile Ser Arg Ala Lys Trp Asn Asp Thr Leu Arg Glu Ile Ala
            330                 335                 340
```

```
aag aag ctg gcc gag cag ttc aac aat cgg acc atc gtg ttc aac cag      1110
Lys Lys Leu Ala Glu Gln Phe Asn Asn Arg Thr Ile Val Phe Asn Gln
        345                 350                 355 agc agc gga ggc gac ccc gag atc gtg atg cac agc ttc aac tgt gcc      1158
Ser Ser Gly Gly Asp Pro Glu Ile Val Met His Ser Phe Asn Cys Ala
360                 365                 370 ggc gag ttc ttc tac tgc gac acc agc cag ctg ttc aac agc acc tgg      1206
Gly Glu Phe Phe Tyr Cys Asp Thr Ser Gln Leu Phe Asn Ser Thr Trp
375                 380                 385                 390 aac agc aac tcc acc tgg aac gat aca aac aac aat agc acc gag          1254
Asn Ser Asn Ser Thr Trp Asn Asp Thr Asn Asn Asn Ser Thr Glu
                395                 400                 405 aag atc atc ctg agc tgt cgg atc cgg cag atc atc aac cgg tgg cag      1302
Lys Ile Ile Leu Ser Cys Arg Ile Arg Gln Ile Ile Asn Arg Trp Gln
            410                 415                 420 gaa gtg ggc aag gct atg tac gcc cct ccc atc agc ggc ccc atc aag      1350
Glu Val Gly Lys Ala Met Tyr Ala Pro Pro Ile Ser Gly Pro Ile Lys
                425                 430                 435 tgc agc agc aac atc acc ggc ctg ctg ctg gcc agg gac ggc ggc aac      1398
Cys Ser Ser Asn Ile Thr Gly Leu Leu Leu Ala Arg Asp Gly Gly Asn
440                 445                 450 gag aca aat gtg acc gag aca ttc cgg cct gcc ggc gga gac atg cgg      1446
Glu Thr Asn Val Thr Glu Thr Phe Arg Pro Ala Gly Gly Asp Met Arg
455                 460                 465                 470 gac aat tgg cgg agc gag ctg tac aag tac aag gtc gtg cag atc gag      1494
Asp Asn Trp Arg Ser Glu Leu Tyr Lys Tyr Lys Val Val Gln Ile Glu
                475                 480                 485 ccc ctg gga atc gcc ccc acc aag gcc aag cgg aga gtg gtg cag ggc      1542
Pro Leu Gly Ile Ala Pro Thr Lys Ala Lys Arg Arg Val Val Gln Gly
            490                 495                 500 gcc cac cac cac cat cac cac tgactcgagt ctagagggcc cgtttaaacc cgc     1596
Ala His His His His His His
            505

<210> SEQ ID NO 82
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Met Pro Met Gly Ser Leu Gln Pro Leu Ala Thr Leu Tyr Leu Leu Gly
1               5                   10                  15

Met Leu Val Ala Ser Val Leu Ala Ala Thr Glu Lys Leu Trp Val Thr
            20                  25                  30

Val Tyr Tyr Gly Val Pro Val Trp Lys Glu Ala Thr Thr Thr Leu Phe
        35                  40                  45

Cys Ala Ser Glu Ala Lys Ala Tyr Asp Thr Glu Val His Asn Val Trp
    50                  55                  60

Ala Thr His Ala Cys Val Pro Thr Asp Pro Asn Pro Gln Glu Val Glu
65                  70                  75                  80

Leu Gly Asn Val Thr Glu Asn Phe Asn Met Trp Lys Asn Asp Met Val
                85                  90                  95

Glu Gln Met His Glu Asp Ile Ile Ser Leu Trp Asp Gln Ser Leu Lys
            100                 105                 110

Pro Cys Val Arg Leu Thr Pro Leu Cys Val Thr Leu Asp Cys Thr Asp
        115                 120                 125
```

```
Leu Asn Asn Thr Thr Asn Thr Asn Asn Thr Thr Asn Thr Asn Ser Ser
        130                 135                 140

Lys Ile Glu Gly Gly Glu Met Lys Asn Cys Ser Phe Asn Ile Thr Thr
145                 150                 155                 160

Asn Arg Gly Asp Lys Arg Gln Lys Glu Tyr Ala Leu Leu Tyr Arg Thr
                165                 170                 175

Asp Ile Val Ser Ile Glu Asn Thr Ser Ser Ser Tyr Arg Leu Ile Ser
            180                 185                 190

Cys Asn Thr Ser Val Ile Thr Gln Ala Cys Pro Lys Val Thr Phe Glu
        195                 200                 205

Pro Ile Pro Ile His Tyr Cys Ala Pro Ala Gly Phe Ala Ile Leu Lys
210                 215                 220

Cys Asn Glu Asp Lys Phe Asn Gly Thr Gly Pro Cys Lys Asn Val Ser
225                 230                 235                 240

Thr Val Gln Cys Thr His Gly Ile Arg Pro Thr Val Ser Thr Gln Leu
                245                 250                 255

Leu Leu Asn Gly Ser Leu Ala Lys Glu Val Ile Ile Arg Ser Ala
            260                 265                 270

Asn Leu Ser Asp Asn Ala Lys Ile Ile Val Gln Leu Lys Asp Pro
        275                 280                 285

Val Glu Ile Asn Cys Thr Arg Pro Asn Asn Thr Arg Lys Ser Ile
290                 295                 300

Asn Leu Gly Pro Gly Arg Ala Phe Tyr Ala Thr Gly Asp Ile Ile Gly
305                 310                 315                 320

Asp Ile Arg Gln Ala His Cys Asn Ile Ser Arg Ala Lys Trp Asn Asp
                325                 330                 335

Thr Leu Arg Glu Ile Ala Lys Lys Leu Ala Glu Gln Phe Asn Asn Arg
            340                 345                 350

Thr Ile Val Phe Asn Gln Ser Ser Gly Gly Asp Pro Glu Ile Val Met
        355                 360                 365

His Ser Phe Asn Cys Ala Gly Glu Phe Phe Tyr Cys Asp Thr Ser Gln
370                 375                 380

Leu Phe Asn Ser Thr Trp Asn Ser Asn Ser Thr Trp Asn Asp Thr Asn
385                 390                 395                 400

Asn Asn Asn Ser Thr Glu Lys Ile Ile Leu Ser Cys Arg Ile Arg Gln
                405                 410                 415

Ile Ile Asn Arg Trp Gln Glu Val Gly Lys Ala Met Tyr Ala Pro Pro
            420                 425                 430

Ile Ser Gly Pro Ile Lys Cys Ser Ser Asn Ile Thr Gly Leu Leu Leu
        435                 440                 445

Ala Arg Asp Gly Gly Asn Glu Thr Asn Val Thr Glu Thr Phe Arg Pro
450                 455                 460

Ala Gly Gly Asp Met Arg Asp Asn Trp Arg Ser Glu Leu Tyr Lys Tyr
465                 470                 475                 480

Lys Val Val Gln Ile Glu Pro Leu Gly Ile Ala Pro Thr Lys Ala Lys
                485                 490                 495

Arg Arg Val Val Gln Gly Ala His His His His His His
            500                 505
```

<210> SEQ ID NO 83
<211> LENGTH: 1590
<212> TYPE: DNA
<213> ORGANISM: Artificial Sequence
<220> FEATURE:
<223> OTHER INFORMATION: Description of Artificial Sequence: Synthetic polynucleotide

```
<220> FEATURE:
<221> NAME/KEY: CDS
<222> LOCATION: (37)..(1557)

<400> SEQUENCE: 83
ccaagctggc tagcgtttaa acttaagctt gccacc atg cct atg ggc agc ctg         54
                                       Met Pro Met Gly Ser Leu
                                        1               5 cag cct ctg gcc acc ctg tac ctg ctg ggc atg ctg gtg gcc tcc gtg        102
Gln Pro Leu Ala Thr Leu Tyr Leu Leu Gly Met Leu Val Ala Ser Val
             10                  15                  20 ctg gct gcc acc gag aac ctg tgg gtc aca gtg tac tac ggc gtg ccc        150
Leu Ala Ala Thr Glu Asn Leu Trp Val Thr Val Tyr Tyr Gly Val Pro
         25                  30                  35 gtg tgg aaa gag gcc acc acc acc ctg ttc tgc gcc tct gac gcc aag        198
Val Trp Lys Glu Ala Thr Thr Thr Leu Phe Cys Ala Ser Asp Ala Lys
     40                  45                  50 ggc tac gag aaa gag gtg cac aac gtc tgg gcc acc cac gcc tgc gtg        246
Gly Tyr Glu Lys Glu Val His Asn Val Trp Ala Thr His Ala Cys Val
 55                  60                  65                  70 ccc acc gac ccc aac cct cag gaa gtg gtc ctg gaa aac gtg acc gag        294
Pro Thr Asp Pro Asn Pro Gln Glu Val Val Leu Glu Asn Val Thr Glu
                 75                  80                  85 aac ttc aac atg tgg aag aac aac atg gtg gaa cag atg cac gag gac        342
Asn Phe Asn Met Trp Lys Asn Asn Met Val Glu Gln Met His Glu Asp
             90                  95                 100 atc atc agc ctg tgg gac cag agc ctg aag ccc tgc gtg aag ctg acc        390
Ile Ile Ser Leu Trp Asp Gln Ser Leu Lys Pro Cys Val Lys Leu Thr
         105                 110                 115 ccc ctg tgc gtg acc ctg aac tgc agc gac gtg aac acc acc tcc gtg        438
Pro Leu Cys Val Thr Leu Asn Cys Ser Asp Val Asn Thr Thr Ser Val
     120                 125                 130 aat acc acc gcc agc agc atg gaa ggc ggc gag atc aag aac tgc agc        486
Asn Thr Thr Ala Ser Ser Met Glu Gly Gly Glu Ile Lys Asn Cys Ser
135                 140                 145                 150 ttc aac acc acc acc agc atg agc gac aag atg cag aaa gag tac gcc        534
Phe Asn Thr Thr Thr Ser Met Ser Asp Lys Met Gln Lys Glu Tyr Ala
                 155                 160                 165 ctg ttc tac acc ctg gac gtg gtg ccc atc gtg aaa gag aac aac acc        582
Leu Phe Tyr Thr Leu Asp Val Val Pro Ile Val Lys Glu Asn Asn Thr
             170                 175                 180 tac cgg ctg atc agc tgc aac acc agc gtg atc acc cag gcc tgc ccc        630
Tyr Arg Leu Ile Ser Cys Asn Thr Ser Val Ile Thr Gln Ala Cys Pro
         185                 190                 195 aag gtg tcc ttc gag ccc atc ccc atc cac tac tgc gcc cct gcc ggc        678
Lys Val Ser Phe Glu Pro Ile Pro Ile His Tyr Cys Ala Pro Ala Gly
     200                 205                 210 ttc gcc atc ctg atg tgc aac aac aag acc ttc gac ggc aag ggc ccc        726
Phe Ala Ile Leu Met Cys Asn Asn Lys Thr Phe Asp Gly Lys Gly Pro
215                 220                 225                 230 tgc aac aac gtg tcc acc gtg cag tgc acc cac ggc atc aag ccc gtg        774
Cys Asn Asn Val Ser Thr Val Gln Cys Thr His Gly Ile Lys Pro Val
                 235                 240                 245 gtg tcc acc cag ctg ctg ctg aat ggc agc ctg gcc gaa gag gaa gtg        822
Val Ser Thr Gln Leu Leu Leu Asn Gly Ser Leu Ala Glu Glu Glu Val
             250                 255                 260 gtc atc aga agc gac aac ttc acc gac aac gcc aag acc atc atc gtg        870
Val Ile Arg Ser Asp Asn Phe Thr Asp Asn Ala Lys Thr Ile Ile Val
         265                 270                 275 cac ctg aac gag agc atc gag atc acc tgt acc cgg ccc aac aac aac        918
His Leu Asn Glu Ser Ile Glu Ile Thr Cys Thr Arg Pro Asn Asn Asn
```

```
                    280                 285                 290
acc agc aag agc atc acc atc ggc cct ggc aga gcc ttc tac gcc acc       966
Thr Ser Lys Ser Ile Thr Ile Gly Pro Gly Arg Ala Phe Tyr Ala Thr
295                 300                 305                 310 ggc cgg atc atc ggc gac atc aga aag gcc cac tgc aac atc agc ggc      1014
Gly Arg Ile Ile Gly Asp Ile Arg Lys Ala His Cys Asn Ile Ser Gly
                315                 320                 325 gag aag tgg cac aac gcc ctg gaa cag atc gtg aag aag ctg ggc gag      1062
Glu Lys Trp His Asn Ala Leu Glu Gln Ile Val Lys Lys Leu Gly Glu
            330                 335                 340 aag ttc gag aac gcc acc acc atc cgg ttc aac cag agc agc gga ggc      1110
Lys Phe Glu Asn Ala Thr Thr Ile Arg Phe Asn Gln Ser Ser Gly Gly
        345                 350                 355 gac cag gaa atc gtg atg cac acc ttc aac tgt ggc ggc gag ttc ttc      1158
Asp Gln Glu Ile Val Met His Thr Phe Asn Cys Gly Gly Glu Phe Phe
360                 365                 370 tac tgc aac agc acc cag ctg ttc aac agc acc tgg tgg ccc aac ggc      1206
Tyr Cys Asn Ser Thr Gln Leu Phe Asn Ser Thr Trp Trp Pro Asn Gly
375                 380                 385                 390 acc acc acc gag tgg tcc aac gag aca agc aat ggc acc atc acc ctg      1254
Thr Thr Thr Glu Trp Ser Asn Glu Thr Ser Asn Gly Thr Ile Thr Leu
                395                 400                 405 ccc tgc cgg atc aag cag atc atc aat atg tgg cag gaa gtg ggc aag      1302
Pro Cys Arg Ile Lys Gln Ile Ile Asn Met Trp Gln Glu Val Gly Lys
            410                 415                 420 gct atg tac gcc cct ccc atc agc ggc ccc atc agc tgc tcc agc aac      1350
Ala Met Tyr Ala Pro Pro Ile Ser Gly Pro Ile Ser Cys Ser Ser Asn
        425                 430                 435 atc acc ggc ctg ctg ctc gtc cgc gac ggc ggc aac gac aac gag act      1398
Ile Thr Gly Leu Leu Leu Val Arg Asp Gly Gly Asn Asp Asn Glu Thr
440                 445                 450 aac ggc acc gag aca ttc aga ccc ggc gga ggc gat atg cgg gac aac      1446
Asn Gly Thr Glu Thr Phe Arg Pro Gly Gly Gly Asp Met Arg Asp Asn
455                 460                 465                 470 tgg cgg agc gag ctg tac aag tac aag gtg gtc aaa atc gag ccc ctg      1494
Trp Arg Ser Glu Leu Tyr Lys Tyr Lys Val Val Lys Ile Glu Pro Leu
                475                 480                 485 ggc gtg gcc ccc acc aag gcc aag aga aga gtg gtg cag ggc gcc cac      1542
Gly Val Ala Pro Thr Lys Ala Lys Arg Arg Val Val Gln Gly Ala His
            490                 495                 500 cac cac cat cac cac tgactcgagt ctagagggcc cgtttaaacc cgc             1590
His His His His His
        505
```

<210> SEQ ID NO 84
<211> LENGTH: 507
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

```
Met Pro Met Gly Ser Leu Gln Pro Leu Ala Thr Leu Tyr Leu Leu Gly
1               5                   10                  15

Met Leu Val Ala Ser Val Leu Ala Ala Thr Glu Asn Leu Trp Val Thr
            20                  25                  30

Val Tyr Tyr Gly Val Pro Val Trp Lys Glu Ala Thr Thr Thr Leu Phe
        35                  40                  45

Cys Ala Ser Asp Ala Lys Gly Tyr Glu Lys Glu Val His Asn Val Trp
    50                  55                  60
```

-continued

```
Ala Thr His Ala Cys Val Pro Thr Asp Pro Asn Pro Gln Glu Val Val
 65                  70                  75                  80

Leu Glu Asn Val Thr Glu Asn Phe Asn Met Trp Lys Asn Asn Met Val
                 85                  90                  95

Glu Gln Met His Glu Asp Ile Ile Ser Leu Trp Asp Gln Ser Leu Lys
            100                 105                 110

Pro Cys Val Lys Leu Thr Pro Leu Cys Val Thr Leu Asn Cys Ser Asp
        115                 120                 125

Val Asn Thr Thr Ser Val Asn Thr Thr Ala Ser Ser Met Glu Gly Gly
    130                 135                 140

Glu Ile Lys Asn Cys Ser Phe Asn Thr Thr Thr Ser Met Ser Asp Lys
145                 150                 155                 160

Met Gln Lys Glu Tyr Ala Leu Phe Tyr Thr Leu Asp Val Val Pro Ile
                165                 170                 175

Val Lys Glu Asn Asn Thr Tyr Arg Leu Ile Ser Cys Asn Thr Ser Val
            180                 185                 190

Ile Thr Gln Ala Cys Pro Lys Val Ser Phe Glu Pro Ile Pro Ile His
        195                 200                 205

Tyr Cys Ala Pro Ala Gly Phe Ala Ile Leu Met Cys Asn Asn Lys Thr
    210                 215                 220

Phe Asp Gly Lys Gly Pro Cys Asn Asn Val Ser Thr Val Gln Cys Thr
225                 230                 235                 240

His Gly Ile Lys Pro Val Val Ser Thr Gln Leu Leu Leu Asn Gly Ser
                245                 250                 255

Leu Ala Glu Glu Glu Val Val Ile Arg Ser Asp Asn Phe Thr Asp Asn
            260                 265                 270

Ala Lys Thr Ile Ile Val His Leu Asn Glu Ser Ile Glu Ile Thr Cys
        275                 280                 285

Thr Arg Pro Asn Asn Asn Thr Ser Lys Ser Ile Thr Ile Gly Pro Gly
    290                 295                 300

Arg Ala Phe Tyr Ala Thr Gly Arg Ile Ile Gly Asp Ile Arg Lys Ala
305                 310                 315                 320

His Cys Asn Ile Ser Gly Glu Lys Trp His Asn Ala Leu Glu Gln Ile
                325                 330                 335

Val Lys Lys Leu Gly Glu Lys Phe Glu Asn Ala Thr Thr Ile Arg Phe
            340                 345                 350

Asn Gln Ser Ser Gly Gly Asp Gln Glu Ile Val Met His Thr Phe Asn
        355                 360                 365

Cys Gly Gly Glu Phe Phe Tyr Cys Asn Ser Thr Gln Leu Phe Asn Ser
    370                 375                 380

Thr Trp Trp Pro Asn Gly Thr Thr Thr Glu Trp Ser Asn Glu Thr Ser
385                 390                 395                 400

Asn Gly Thr Ile Thr Leu Pro Cys Arg Ile Lys Gln Ile Ile Asn Met
                405                 410                 415

Trp Gln Glu Val Gly Lys Ala Met Tyr Ala Pro Pro Ile Ser Gly Pro
            420                 425                 430

Ile Ser Cys Ser Ser Asn Ile Thr Gly Leu Leu Leu Val Arg Asp Gly
        435                 440                 445

Gly Asn Asp Asn Glu Thr Asn Gly Thr Glu Thr Phe Arg Pro Gly Gly
    450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Lys Ala Lys Arg Arg
```

|  |  |  | 485 |  |  |  | 490 |  |  |  | 495 |  |
|---|---|---|---|---|---|---|---|---|---|---|---|---|
| Val | Val | Gln | Gly | Ala | His | His | His | His | His |  |  |  |
|  |  |  | 500 |  |  |  | 505 |  |  |  |  |  |

<210> SEQ ID NO 85
<211> LENGTH: 1622
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: CDS
<222> LOCATION: (42)..(1583)

<400> SEQUENCE: 85

| gagcggaagg | cccatgaggc | cagttaatta | agcttgccac | c atg cct atg ggc agc |  | 56 |
|---|---|---|---|---|---|---|
|  |  |  |  | Met Pro Met Gly Ser |  |  |
|  |  |  |  | 1 | 5 |  |

| ctg | cag | cct | ctg | gcc | acc | ctg | tac | ctg | ctg | ggc | atg | ctg | gtg | gcc | tcc | 104 |
|---|---|---|---|---|---|---|---|---|---|---|---|---|---|---|---|---|
| Leu | Gln | Pro | Leu | Ala | Thr | Leu | Tyr | Leu | Leu | Gly | Met | Leu | Val | Ala | Ser |  |
|  |  | 10 |  |  |  | 15 |  |  |  |  | 20 |  |  |  |  |  |

| gtg | ctg | gca | gct | ggc | aac | ctg | tgg | gtc | aca | gtg | tac | tac | ggc | gtg | ccc | 152 |
|---|---|---|---|---|---|---|---|---|---|---|---|---|---|---|---|---|
| Val | Leu | Ala | Ala | Gly | Asn | Leu | Trp | Val | Thr | Val | Tyr | Tyr | Gly | Val | Pro |  |
| 25 |  |  |  |  | 30 |  |  |  |  | 35 |  |  |  |  |  |  |

| gtg | tgg | aaa | gag | gcc | aag | acc | acc | ctg | ttc | tgc | gcc | agc | gac | gcc | aag | 200 |
|---|---|---|---|---|---|---|---|---|---|---|---|---|---|---|---|---|
| Val | Trp | Lys | Glu | Ala | Lys | Thr | Thr | Leu | Phe | Cys | Ala | Ser | Asp | Ala | Lys |  |
| 40 |  |  |  | 45 |  |  |  |  | 50 |  |  |  |  |  |  |  |

| gcc | tac | gag | aaa | gag | gtg | cac | aac | gtc | tgg | gcc | acc | cac | gcc | tgc | gtg | 248 |
|---|---|---|---|---|---|---|---|---|---|---|---|---|---|---|---|---|
| Ala | Tyr | Glu | Lys | Glu | Val | His | Asn | Val | Trp | Ala | Thr | His | Ala | Cys | Val |  |
| 55 |  |  |  |  | 60 |  |  |  |  | 65 |  |  |  |  |  |  |

| ccc | acc | gac | ccc | aac | ccc | cag | gaa | atg | gtc | ctg | gaa | aac | gtg | acc | gag | 296 |
|---|---|---|---|---|---|---|---|---|---|---|---|---|---|---|---|---|
| Pro | Thr | Asp | Pro | Asn | Pro | Gln | Glu | Met | Val | Leu | Glu | Asn | Val | Thr | Glu |  |
| 70 |  |  |  | 75 |  |  |  |  | 80 |  |  |  |  | 85 |  |  |

| aac | ttc | aac | atg | tgg | gag | aac | gac | gtg | gtg | gac | cag | atg | cac | gag | gac | 344 |
|---|---|---|---|---|---|---|---|---|---|---|---|---|---|---|---|---|
| Asn | Phe | Asn | Met | Trp | Glu | Asn | Asp | Val | Val | Asp | Gln | Met | His | Glu | Asp |  |
|  |  | 90 |  |  |  |  | 95 |  |  |  |  | 100 |  |  |  |  |

| gtg | atc | agc | ctg | tgg | gac | cag | agc | ctg | aag | ccc | tgc | gtg | aag | ctg | acc | 392 |
|---|---|---|---|---|---|---|---|---|---|---|---|---|---|---|---|---|
| Val | Ile | Ser | Leu | Trp | Asp | Gln | Ser | Leu | Lys | Pro | Cys | Val | Lys | Leu | Thr |  |
|  |  | 105 |  |  |  |  | 110 |  |  |  |  | 115 |  |  |  |  |

| ccc | ctg | tgc | gtg | acc | ctg | aac | tgc | agc | aag | gcc | aag | aac | atc | acc | gag | 440 |
|---|---|---|---|---|---|---|---|---|---|---|---|---|---|---|---|---|
| Pro | Leu | Cys | Val | Thr | Leu | Asn | Cys | Ser | Lys | Ala | Lys | Asn | Ile | Thr | Glu |  |
|  | 120 |  |  |  |  | 125 |  |  |  |  | 130 |  |  |  |  |  |

| gaa | gtg | atc | aag | aac | aac | acc | tac | aaa | gag | gac | atc | cgg | aac | tgc | agc | 488 |
|---|---|---|---|---|---|---|---|---|---|---|---|---|---|---|---|---|
| Glu | Val | Ile | Lys | Asn | Asn | Thr | Tyr | Lys | Glu | Asp | Ile | Arg | Asn | Cys | Ser |  |
| 135 |  |  |  |  | 140 |  |  |  |  | 145 |  |  |  |  |  |  |

| ttc | aac | gcc | acc | acc | gaa | gtg | aag | gac | aag | aaa | cag | aag | gtg | cac | gcc | 536 |
|---|---|---|---|---|---|---|---|---|---|---|---|---|---|---|---|---|
| Phe | Asn | Ala | Thr | Thr | Glu | Val | Lys | Asp | Lys | Lys | Gln | Lys | Val | His | Ala |  |
| 150 |  |  |  | 155 |  |  |  |  | 160 |  |  |  |  | 165 |  |  |

| ctg | ttc | tac | cgg | ctg | gac | atc | gtg | ccc | ctg | aac | aag | cgg | aac | agc | agc | 584 |
|---|---|---|---|---|---|---|---|---|---|---|---|---|---|---|---|---|
| Leu | Phe | Tyr | Arg | Leu | Asp | Ile | Val | Pro | Leu | Asn | Lys | Arg | Asn | Ser | Ser |  |
|  |  | 170 |  |  |  |  | 175 |  |  |  |  | 180 |  |  |  |  |

| gag | agc | gag | gaa | gag | aac | agc | tcc | ggc | tac | tac | cgg | ctg | atc | aac | tgc | 632 |
|---|---|---|---|---|---|---|---|---|---|---|---|---|---|---|---|---|
| Glu | Ser | Glu | Glu | Glu | Asn | Ser | Ser | Gly | Tyr | Tyr | Arg | Leu | Ile | Asn | Cys |  |
|  |  | 185 |  |  |  |  | 190 |  |  |  |  | 195 |  |  |  |  |

| aac | acc | agc | gcc | gtg | acc | cag | gcc | tgc | ccc | aaa | gtg | acc | ttc | gac | ccc | 680 |
|---|---|---|---|---|---|---|---|---|---|---|---|---|---|---|---|---|
| Asn | Thr | Ser | Ala | Val | Thr | Gln | Ala | Cys | Pro | Lys | Val | Thr | Phe | Asp | Pro |  |
|  |  | 200 |  |  |  |  | 205 |  |  |  |  | 210 |  |  |  |  |

| atc | ccc | atc | cac | tac | tgc | acc | cct | gcc | ggc | tac | gcc | atc | ctg | aag | tgc | 728 |
|---|---|---|---|---|---|---|---|---|---|---|---|---|---|---|---|---|
| Ile | Pro | Ile | His | Tyr | Cys | Thr | Pro | Ala | Gly | Tyr | Ala | Ile | Leu | Lys | Cys |  |
|  | 215 |  |  |  |  | 220 |  |  |  |  | 225 |  |  |  |  |  |

| aac | gag | gaa | acc | ttc | aac | ggc | acc | ggc | ccc | tgc | cac | aac | gtg | tcc | acc | 776 |
|---|---|---|---|---|---|---|---|---|---|---|---|---|---|---|---|---|

```
Asn Glu Glu Thr Phe Asn Gly Thr Gly Pro Cys His Asn Val Ser Thr
230                 235                 240                 245 gtg cag tgc acc cac ggc atc aag ccc gtg gtg tcc acc cag ctg ctg      824
Val Gln Cys Thr His Gly Ile Lys Pro Val Val Ser Thr Gln Leu Leu
                250                 255                 260 ctg aat ggc agc ctg gct gag ggc gag atc atc atc aga agc aag aac      872
Leu Asn Gly Ser Leu Ala Glu Gly Glu Ile Ile Ile Arg Ser Lys Asn
            265                 270                 275 ctg acc gac aac gcc aag acc atc att gtg cac ctg aac cag agc gtg      920
Leu Thr Asp Asn Ala Lys Thr Ile Ile Val His Leu Asn Gln Ser Val
        280                 285                 290 gaa atc gtg tgc acc cgg ccc aac gag aac cgg cgg aag tcc atc cgg      968
Glu Ile Val Cys Thr Arg Pro Asn Glu Asn Arg Arg Lys Ser Ile Arg
    295                 300                 305 atc ggc cca ggc cag gcc ttt tac gcc acc ggc gac atc atc ggc gac     1016
Ile Gly Pro Gly Gln Ala Phe Tyr Ala Thr Gly Asp Ile Ile Gly Asp
310                 315                 320                 325 atc cgg cag gcc cgg tgc aac atc agc gaa gag aag tgg aac gag aca     1064
Ile Arg Gln Ala Arg Cys Asn Ile Ser Glu Glu Lys Trp Asn Glu Thr
                330                 335                 340 ctg cag aga gtg ggc cgg aag ctg gcc gag cac ttc ccc aac aag aca     1112
Leu Gln Arg Val Gly Arg Lys Leu Ala Glu His Phe Pro Asn Lys Thr
            345                 350                 355 atc aag ttc aag agc agc tct ggc ggc gac ctg gaa atc acc acc cac     1160
Ile Lys Phe Lys Ser Ser Ser Gly Gly Asp Leu Glu Ile Thr Thr His
        360                 365                 370 agc ttc aac tgc aga ggc gag ttc ttc tac tgc aat acc tcc ggc ctg     1208
Ser Phe Asn Cys Arg Gly Glu Phe Phe Tyr Cys Asn Thr Ser Gly Leu
    375                 380                 385 ttc aat ggc acc tac atg ccc acc tat atg ccc aac agc acc aac tcc     1256
Phe Asn Gly Thr Tyr Met Pro Thr Tyr Met Pro Asn Ser Thr Asn Ser
390                 395                 400                 405 aac agc agc agc aac atc acc atc cct tgc cgg atc aaa cag gtc atc     1304
Asn Ser Ser Ser Asn Ile Thr Ile Pro Cys Arg Ile Lys Gln Val Ile
                410                 415                 420 aat atg tgg cag gaa gtg ggc aga gct atg tac gcc cct ccc atc gag     1352
Asn Met Trp Gln Glu Val Gly Arg Ala Met Tyr Ala Pro Pro Ile Glu
            425                 430                 435 ggg gag atc aca tgc aag tcc aac atc acc ggc ctg ctc ctc gtc cgc     1400
Gly Glu Ile Thr Cys Lys Ser Asn Ile Thr Gly Leu Leu Leu Val Arg
        440                 445                 450 gac ggc ggc aac ggc aac gac acc aac aag acc gag atc ttc cgg ccc     1448
Asp Gly Gly Asn Gly Asn Asp Thr Asn Lys Thr Glu Ile Phe Arg Pro
    455                 460                 465 gag ggc ggc gac atg aga gac aat tgg cgg agc gag ctg tac aag tac     1496
Glu Gly Gly Asp Met Arg Asp Asn Trp Arg Ser Glu Leu Tyr Lys Tyr
470                 475                 480                 485 aag gtg gtg gaa atc aag ccc ctg gga atc gcc ccc acc gag gcc aag     1544
Lys Val Val Glu Ile Lys Pro Leu Gly Ile Ala Pro Thr Glu Ala Lys
                490                 495                 500 cgg aga gtg gtg gaa ggc gcc cac cac cac cat cac cac tgactcgagg      1593
Arg Arg Val Val Glu Gly Ala His His His His His His
            505                 510 cgcgcctagg ccttgacggc cttccgcca                                     1622

<210> SEQ ID NO 86
<211> LENGTH: 514
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 86

```
Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
            20                  25                  30

Tyr Tyr Gly Val Pro Val Trp Lys Glu Ala Lys Thr Thr Leu Phe Cys
        35                  40                  45

Ala Ser Asp Ala Lys Ala Tyr Glu Lys Glu Val His Asn Val Trp Ala
    50                  55                  60

Thr His Ala Cys Val Pro Thr Asp Pro Asn Pro Gln Glu Met Val Leu
65                  70                  75                  80

Glu Asn Val Thr Glu Asn Phe Asn Met Trp Glu Asn Asp Val Val Asp
                85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu Asn Cys Ser Lys Ala
        115                 120                 125

Lys Asn Ile Thr Glu Glu Val Ile Lys Asn Asn Thr Tyr Lys Glu Asp
    130                 135                 140

Ile Arg Asn Cys Ser Phe Asn Ala Thr Thr Glu Val Lys Asp Lys Lys
145                 150                 155                 160

Gln Lys Val His Ala Leu Phe Tyr Arg Leu Asp Ile Val Pro Leu Asn
                165                 170                 175

Lys Arg Asn Ser Ser Glu Ser Glu Glu Asn Ser Ser Gly Tyr Tyr
            180                 185                 190

Arg Leu Ile Asn Cys Asn Thr Ser Ala Val Thr Gln Ala Cys Pro Lys
        195                 200                 205

Val Thr Phe Asp Pro Ile Pro Ile His Tyr Cys Thr Pro Ala Gly Tyr
    210                 215                 220

Ala Ile Leu Lys Cys Asn Glu Glu Thr Phe Asn Gly Thr Gly Pro Cys
225                 230                 235                 240

His Asn Val Ser Thr Val Gln Cys Thr His Gly Ile Lys Pro Val Val
                245                 250                 255

Ser Thr Gln Leu Leu Leu Asn Gly Ser Leu Ala Glu Gly Glu Ile Ile
            260                 265                 270

Ile Arg Ser Lys Asn Leu Thr Asp Asn Ala Lys Thr Ile Ile Val His
        275                 280                 285

Leu Asn Gln Ser Val Glu Ile Val Cys Thr Arg Pro Asn Glu Asn Arg
    290                 295                 300

Arg Lys Ser Ile Arg Ile Gly Pro Gly Gln Ala Phe Tyr Ala Thr Gly
305                 310                 315                 320

Asp Ile Ile Gly Asp Ile Arg Gln Ala Arg Cys Asn Ile Ser Glu Glu
                325                 330                 335

Lys Trp Asn Glu Thr Leu Gln Arg Val Gly Arg Lys Leu Ala Glu His
            340                 345                 350

Phe Pro Asn Lys Thr Ile Lys Phe Lys Ser Ser Ser Gly Gly Asp Leu
        355                 360                 365

Glu Ile Thr Thr His Ser Phe Asn Cys Arg Gly Glu Phe Phe Tyr Cys
    370                 375                 380

Asn Thr Ser Gly Leu Phe Asn Gly Thr Tyr Met Pro Thr Tyr Met Pro
385                 390                 395                 400

Asn Ser Thr Asn Ser Asn Ser Ser Ser Asn Ile Thr Ile Pro Cys Arg
```

```
                        405                 410                 415
Ile Lys Gln Val Ile Asn Met Trp Gln Glu Val Gly Arg Ala Met Tyr
            420                 425                 430

Ala Pro Pro Ile Glu Gly Glu Ile Thr Cys Lys Ser Asn Ile Thr Gly
        435                 440                 445

Leu Leu Leu Val Arg Asp Gly Gly Asn Gly Asn Asp Thr Asn Lys Thr
    450                 455                 460

Glu Ile Phe Arg Pro Glu Gly Gly Asp Met Arg Asp Asn Trp Arg Ser
465                 470                 475                 480

Glu Leu Tyr Lys Tyr Lys Val Val Glu Ile Lys Pro Leu Gly Ile Ala
                485                 490                 495

Pro Thr Glu Ala Lys Arg Arg Val Val Glu Gly Ala His His His His
            500                 505                 510

His His

<210> SEQ ID NO 87
<211> LENGTH: 2262
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (37)..(2229)

<400> SEQUENCE: 87
ccaagctggc tagcgtttaa acttaagctt gccacc atg cct atg ggc agc ctg        54
                                       Met Pro Met Gly Ser Leu
                                        1               5 cag cct ctg gcc acc ctg tac ctg ctg ggc atg ctg gtg gcc tcc gtg       102
Gln Pro Leu Ala Thr Leu Tyr Leu Leu Gly Met Leu Val Ala Ser Val
         10                  15                  20 ctg gca gct ggc aac ctg tgg gtc aca gtg tac tac ggc gtg ccc gtg       150
Leu Ala Ala Gly Asn Leu Trp Val Thr Val Tyr Tyr Gly Val Pro Val
             25                  30                  35 tgg aaa gag gcc aag acc acc ctg ttc tgc gcc agc gac gcc aag gcc       198
Trp Lys Glu Ala Lys Thr Thr Leu Phe Cys Ala Ser Asp Ala Lys Ala
 40                  45                  50 tac gag aaa gag gtg cac aac gtc tgg gcc acc cac gcc tgc gtg ccc       246
Tyr Glu Lys Glu Val His Asn Val Trp Ala Thr His Ala Cys Val Pro
 55                  60                  65                  70 acc gac ccc aac ccc cag gaa atg gtc ctg gaa aac gtg acc gag aac       294
Thr Asp Pro Asn Pro Gln Glu Met Val Leu Glu Asn Val Thr Glu Asn
                 75                  80                  85 ttc aac atg tgg gag aac gac gtg gtg gac cag atg cac gag gac gtg       342
Phe Asn Met Trp Glu Asn Asp Val Val Asp Gln Met His Glu Asp Val
             90                  95                 100 atc agc ctg tgg gac cag agc ctg aag ccc tgc gtg aag ctg acc ccc       390
Ile Ser Leu Trp Asp Gln Ser Leu Lys Pro Cys Val Lys Leu Thr Pro
        105                 110                 115 ctg tgc gtg acc ctg aac tgc agc aag gcc aag aac atc acc gag gaa       438
Leu Cys Val Thr Leu Asn Cys Ser Lys Ala Lys Asn Ile Thr Glu Glu
    120                 125                 130 gtg atc aag aac aac acc tac aaa gag gac atc cgg aac tgc agc ttc       486
Val Ile Lys Asn Asn Thr Tyr Lys Glu Asp Ile Arg Asn Cys Ser Phe
135                 140                 145                 150 aac gcc acc acc gaa gtg aag gac aag aaa cag aag gtg cac gcc ctg       534
Asn Ala Thr Thr Glu Val Lys Asp Lys Lys Gln Lys Val His Ala Leu
                155                 160                 165
```

| | |
|---|---:|
| ttc tac cgg ctg gac atc gtg ccc ctg aac aag cgg aac agc agc gag<br>Phe Tyr Arg Leu Asp Ile Val Pro Leu Asn Lys Arg Asn Ser Ser Glu<br>          170                  175                  180 | 582 |
| agc gag gaa gag aac agc tcc ggc tac tac cgg ctg atc aac tgc aac<br>Ser Glu Glu Glu Asn Ser Ser Gly Tyr Tyr Arg Leu Ile Asn Cys Asn<br>        185                  190                  195 | 630 |
| acc agc gcc gtg acc cag gcc tgc ccc aaa gtg acc ttc gac ccc atc<br>Thr Ser Ala Val Thr Gln Ala Cys Pro Lys Val Thr Phe Asp Pro Ile<br>200                  205                  210 | 678 |
| ccc atc cac tac tgc acc cct gcc ggc tac gcc atc ctg aag tgc aac<br>Pro Ile His Tyr Cys Thr Pro Ala Gly Tyr Ala Ile Leu Lys Cys Asn<br>215                  220                  225              230 | 726 |
| gag gaa acc ttc aac ggc acc ggc ccc tgc cac aac gtg tcc acc gtg<br>Glu Glu Thr Phe Asn Gly Thr Gly Pro Cys His Asn Val Ser Thr Val<br>                  235                  240              245 | 774 |
| cag tgc acc cac ggc atc aag ccc gtg gtg tcc acc cag ctg ctg ctg<br>Gln Cys Thr His Gly Ile Lys Pro Val Val Ser Thr Gln Leu Leu Leu<br>                  250                  255              260 | 822 |
| aat ggc agc ctg gct gag ggc gag atc atc atc aga agc aag aac ctg<br>Asn Gly Ser Leu Ala Glu Gly Glu Ile Ile Ile Arg Ser Lys Asn Leu<br>                  265                  270              275 | 870 |
| acc gac aac gcc aag acc atc att gtg cac ctg aac cag agc gtg gaa<br>Thr Asp Asn Ala Lys Thr Ile Ile Val His Leu Asn Gln Ser Val Glu<br>280                  285                  290 | 918 |
| atc gtg tgc acc cgg ccc aac gag aac cgg aag tcc atc cgg atc<br>Ile Val Cys Thr Arg Pro Asn Glu Asn Arg Lys Ser Ile Arg Ile<br>295                  300                  305              310 | 966 |
| ggc cca ggc cag gcc ttt tac gcc acc ggc gac atc atc ggc gac atc<br>Gly Pro Gly Gln Ala Phe Tyr Ala Thr Gly Asp Ile Ile Gly Asp Ile<br>                  315                  320              325 | 1014 |
| cgg cag gcc cgg tgc aac atc agc gaa gag aag tgg aac gag aca ctg<br>Arg Gln Ala Arg Cys Asn Ile Ser Glu Glu Lys Trp Asn Glu Thr Leu<br>                  330                  335              340 | 1062 |
| cag aga gtg ggc cgg aag ctg gcc gag cac ttc ccc aac aag aca atc<br>Gln Arg Val Gly Arg Lys Leu Ala Glu His Phe Pro Asn Lys Thr Ile<br>                345                  350              355 | 1110 |
| aag ttc aag agc agc tct ggc ggc gac ctg gaa atc acc acc cac agc<br>Lys Phe Lys Ser Ser Ser Gly Gly Asp Leu Glu Ile Thr Thr His Ser<br>360                  365                  370 | 1158 |
| ttc aac tgc aga ggc gag ttc ttc tac tgc aat acc tcc ggc ctg ttc<br>Phe Asn Cys Arg Gly Glu Phe Phe Tyr Cys Asn Thr Ser Gly Leu Phe<br>375                  380                  385              390 | 1206 |
| aat ggc acc tac atg ccc acc tat atg ccc aac agc acc aac tcc aac<br>Asn Gly Thr Tyr Met Pro Thr Tyr Met Pro Asn Ser Thr Asn Ser Asn<br>                  395                  400              405 | 1254 |
| agc agc agc aac atc acc atc cct tgc cgg atc aaa cag gtc atc aat<br>Ser Ser Ser Asn Ile Thr Ile Pro Cys Arg Ile Lys Gln Val Ile Asn<br>                  410                  415              420 | 1302 |
| atg tgg cag gaa gtg ggc aga gct atg tac gcc cct ccc atc gag ggg<br>Met Trp Gln Glu Val Gly Arg Ala Met Tyr Ala Pro Pro Ile Glu Gly<br>                  425                  430              435 | 1350 |
| gag atc aca tgc aag tcc aac atc acc ggc ctg ctc ctc gtc cgc gac<br>Glu Ile Thr Cys Lys Ser Asn Ile Thr Gly Leu Leu Leu Val Arg Asp<br>                440                  445              450 | 1398 |
| ggc ggc aac ggc aac gac acc aac aag acc gag atc ttc cgg ccc gag<br>Gly Gly Asn Gly Asn Asp Thr Asn Lys Thr Glu Ile Phe Arg Pro Glu<br>455                  460                  465              470 | 1446 |
| ggc ggc gac atg aga gac aat tgg cgg agc gag ctg tac aag tac aag<br>Gly Gly Asp Met Arg Asp Asn Trp Arg Ser Glu Leu Tyr Lys Tyr Lys<br>                  475                  480              485 | 1494 |

```
gtg gtg gaa atc aag ccc ctg gga atc gcc ccc acc gag gcc aag cgg    1542
Val Val Glu Ile Lys Pro Leu Gly Ile Ala Pro Thr Glu Ala Lys Arg
            490                 495                 500 aga gtg gtg gaa agc gag aag tcc gcc gtg ggc atc ggc gcc gtg atc    1590
Arg Val Val Glu Ser Glu Lys Ser Ala Val Gly Ile Gly Ala Val Ile
        505                 510                 515 ctg ggc ttt ctg gga gcc gcc gga agc aca atg ggc gct gcc agc atc    1638
Leu Gly Phe Leu Gly Ala Ala Gly Ser Thr Met Gly Ala Ala Ser Ile
    520                 525                 530 acc ctg acc gcc cag gct aga cag ctg ctg agc ggc atc gtg cag cag    1686
Thr Leu Thr Ala Gln Ala Arg Gln Leu Leu Ser Gly Ile Val Gln Gln
535                 540                 545                 550 cag agc aac ctg ctg aag gcc atc gac gcc cag cag cat ctg ctg cag    1734
Gln Ser Asn Leu Leu Lys Ala Ile Asp Ala Gln Gln His Leu Leu Gln
                555                 560                 565 ctg acc gtg tgg ggc atc aag cag ctg cag gcc cgg gtg ctg gcc gtg    1782
Leu Thr Val Trp Gly Ile Lys Gln Leu Gln Ala Arg Val Leu Ala Val
            570                 575                 580 gaa aga tac ctg aag gac cag cag ctc ctg gga atc tgg ggc tgc agc    1830
Glu Arg Tyr Leu Lys Asp Gln Gln Leu Leu Gly Ile Trp Gly Cys Ser
        585                 590                 595 ggc aag ctg atc tgc ccc acc aac gtg ccc tgg aac agc tcc tgg tcc    1878
Gly Lys Leu Ile Cys Pro Thr Asn Val Pro Trp Asn Ser Ser Trp Ser
    600                 605                 610 aac aag agc aaa gag tat atc tgg aac aac atg acc tgg atg cag tgg    1926
Asn Lys Ser Lys Glu Tyr Ile Trp Asn Asn Met Thr Trp Met Gln Trp
615                 620                 625                 630 gac ggc gag atc agc aac tac acc gac atc atc tac ggc ctg ctg gaa    1974
Asp Gly Glu Ile Ser Asn Tyr Thr Asp Ile Ile Tyr Gly Leu Leu Glu
                635                 640                 645 gat agc cag atc cag cag gaa aag aac gag aag gac ctg ctg acc ctg    2022
Asp Ser Gln Ile Gln Gln Glu Lys Asn Glu Lys Asp Leu Leu Thr Leu
            650                 655                 660 gac agc tgg aag aac ctg tgg aat tgg ttc gac atc acc aag tgg ctg    2070
Asp Ser Trp Lys Asn Leu Trp Asn Trp Phe Asp Ile Thr Lys Trp Leu
        665                 670                 675 tgg tac atc aag atc ttc atc atg atc gtg ggc ggc ctg atc ggc ctg    2118
Trp Tyr Ile Lys Ile Phe Ile Met Ile Val Gly Gly Leu Ile Gly Leu
    680                 685                 690 cgg atc atc ttc gcc gtg ctg agc atc gtg gga ggc gga gcc aag ttc    2166
Arg Ile Ile Phe Ala Val Leu Ser Ile Val Gly Gly Gly Ala Lys Phe
695                 700                 705                 710 gtg gcc gcc tgg aca ctg aaa gcc gct gct ggc ggc acc gag aca tct    2214
Val Ala Ala Trp Thr Leu Lys Ala Ala Ala Gly Gly Thr Glu Thr Ser
                715                 720                 725 cag gtg gcc cct gcc tgactcgagt ctagagggcc cgtttaaacc cgc           2262
Gln Val Ala Pro Ala
            730

<210> SEQ ID NO 88
<211> LENGTH: 731
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
            20                  25                  30
```

Tyr Tyr Gly Val Pro Val Trp Lys Glu Ala Lys Thr Thr Leu Phe Cys
         35                  40                  45

Ala Ser Asp Ala Lys Ala Tyr Glu Lys Glu Val His Asn Val Trp Ala
 50                  55                  60

Thr His Ala Cys Val Pro Thr Asp Pro Asn Pro Gln Glu Met Val Leu
 65                  70                  75                  80

Glu Asn Val Thr Glu Asn Phe Asn Met Trp Glu Asn Asp Val Val Asp
                 85                  90                  95

Gln Met His Glu Asp Val Ile Ser Leu Trp Asp Gln Ser Leu Lys Pro
             100                 105                 110

Cys Val Lys Leu Thr Pro Leu Cys Val Thr Leu Asn Cys Ser Lys Ala
             115                 120                 125

Lys Asn Ile Thr Glu Glu Val Ile Lys Asn Asn Thr Tyr Lys Glu Asp
130                 135                 140

Ile Arg Asn Cys Ser Phe Asn Ala Thr Thr Glu Val Lys Asp Lys Lys
145                 150                 155                 160

Gln Lys Val His Ala Leu Phe Tyr Arg Leu Asp Ile Val Pro Leu Asn
             165                 170                 175

Lys Arg Asn Ser Ser Glu Ser Glu Glu Asn Ser Ser Gly Tyr Tyr
             180                 185                 190

Arg Leu Ile Asn Cys Asn Thr Ser Ala Val Thr Gln Ala Cys Pro Lys
             195                 200                 205

Val Thr Phe Asp Pro Ile Pro Ile His Tyr Cys Thr Pro Ala Gly Tyr
             210                 215                 220

Ala Ile Leu Lys Cys Asn Glu Glu Thr Phe Asn Gly Thr Gly Pro Cys
225                 230                 235                 240

His Asn Val Ser Thr Val Gln Cys Thr His Gly Ile Lys Pro Val Val
             245                 250                 255

Ser Thr Gln Leu Leu Leu Asn Gly Ser Leu Ala Glu Gly Glu Ile Ile
             260                 265                 270

Ile Arg Ser Lys Asn Leu Thr Asp Asn Ala Lys Thr Ile Ile Val His
             275                 280                 285

Leu Asn Gln Ser Val Glu Ile Val Cys Thr Arg Pro Asn Glu Asn Arg
             290                 295                 300

Arg Lys Ser Ile Arg Ile Gly Pro Gly Gln Ala Phe Tyr Ala Thr Gly
305                 310                 315                 320

Asp Ile Ile Gly Asp Ile Arg Gln Ala Arg Cys Asn Ile Ser Glu Glu
             325                 330                 335

Lys Trp Asn Glu Thr Leu Gln Arg Val Gly Arg Lys Leu Ala Glu His
             340                 345                 350

Phe Pro Asn Lys Thr Ile Lys Phe Lys Ser Ser Gly Gly Asp Leu
             355                 360                 365

Glu Ile Thr Thr His Ser Phe Asn Cys Arg Gly Glu Phe Phe Tyr Cys
             370                 375                 380

Asn Thr Ser Gly Leu Phe Asn Gly Thr Tyr Met Pro Thr Tyr Met Pro
385                 390                 395                 400

Asn Ser Thr Asn Ser Asn Ser Ser Asn Ile Thr Ile Pro Cys Arg
             405                 410                 415

Ile Lys Gln Val Ile Asn Met Trp Gln Glu Val Gly Arg Ala Met Tyr
             420                 425                 430

Ala Pro Pro Ile Glu Gly Glu Ile Thr Cys Lys Ser Asn Ile Thr Gly
             435                 440                 445

Leu Leu Leu Val Arg Asp Gly Gly Asn Gly Asn Asp Thr Asn Lys Thr

```
                  450                 455                 460
Glu Ile Phe Arg Pro Glu Gly Gly Asp Met Arg Asp Asn Trp Arg Ser
465                 470                 475                 480

Glu Leu Tyr Lys Tyr Lys Val Val Glu Ile Lys Pro Leu Gly Ile Ala
                485                 490                 495

Pro Thr Glu Ala Lys Arg Arg Val Val Glu Ser Glu Lys Ser Ala Val
                500                 505                 510

Gly Ile Gly Ala Val Ile Leu Gly Phe Leu Gly Ala Ala Gly Ser Thr
                515                 520                 525

Met Gly Ala Ala Ser Ile Thr Leu Thr Ala Gln Ala Arg Gln Leu Leu
530                 535                 540

Ser Gly Ile Val Gln Gln Gln Ser Asn Leu Leu Lys Ala Ile Asp Ala
545                 550                 555                 560

Gln Gln His Leu Leu Gln Leu Thr Val Trp Gly Ile Lys Gln Leu Gln
                565                 570                 575

Ala Arg Val Leu Ala Val Glu Arg Tyr Leu Lys Asp Gln Gln Leu Leu
                580                 585                 590

Gly Ile Trp Gly Cys Ser Gly Lys Leu Ile Cys Pro Thr Asn Val Pro
                595                 600                 605

Trp Asn Ser Ser Trp Ser Asn Lys Ser Lys Glu Tyr Ile Trp Asn Asn
                610                 615                 620

Met Thr Trp Met Gln Trp Asp Gly Glu Ile Ser Asn Tyr Thr Asp Ile
625                 630                 635                 640

Ile Tyr Gly Leu Leu Glu Asp Ser Gln Ile Gln Gln Glu Lys Asn Glu
                645                 650                 655

Lys Asp Leu Leu Thr Leu Asp Ser Trp Lys Asn Leu Trp Asn Trp Phe
                660                 665                 670

Asp Ile Thr Lys Trp Leu Trp Tyr Ile Lys Ile Phe Ile Met Ile Val
                675                 680                 685

Gly Gly Leu Ile Gly Leu Arg Ile Ile Phe Ala Val Leu Ser Ile Val
                690                 695                 700

Gly Gly Gly Ala Lys Phe Val Ala Ala Trp Thr Leu Lys Ala Ala Ala
705                 710                 715                 720

Gly Gly Thr Glu Thr Ser Gln Val Ala Pro Ala
                725                 730

<210> SEQ ID NO 89
<211> LENGTH: 1601
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (42)..(1562)

<400> SEQUENCE: 89
gagcggaagg cccatgaggc cagttaatta agcttgccac c atg cct atg ggc agc      56
                                              Met Pro Met Gly Ser
                                              1               5 ctg cag cct ctg gcc acc ctg tac ctg ctg ggc atg ctg gtg gcc tcc     104
Leu Gln Pro Leu Ala Thr Leu Tyr Leu Leu Gly Met Leu Val Ala Ser
            10                  15                  20 gtg ctg gca gct ggc aac ctg tgg gtc aca gtg tac tac ggc gtg ccc     152
Val Leu Ala Ala Gly Asn Leu Trp Val Thr Val Tyr Tyr Gly Val Pro
        25                  30                  35 gtg tgg aaa gag gcc aag acc acc ctg ttc tgc gcc agc gac gcc aag     200
```

-continued

| | | | | | | | | | | | | | | | |
|---|---|---|---|---|---|---|---|---|---|---|---|---|---|---|---|
| Val | Trp | Lys | Glu | Ala | Lys | Thr | Thr | Leu | Phe | Cys | Ala | Ser | Asp | Ala | Lys |
| | | 40 | | | | 45 | | | | 50 | | | | | |

```
gcc tac gag aaa gag gtg cac aac gtc tgg gcc acc cac gcc tgc gtg        248
Ala Tyr Glu Lys Glu Val His Asn Val Trp Ala Thr His Ala Cys Val
 55                  60                  65 ccc acc gac ccc aac ccc cag gaa atg gtc ctg gaa aac gtg acc gag        296
Pro Thr Asp Pro Asn Pro Gln Glu Met Val Leu Glu Asn Val Thr Glu
 70                  75                  80                  85 aac ttc aac atg tgg aag aac gac atg gtg gaa cag atg cac gag gac        344
Asn Phe Asn Met Trp Lys Asn Asp Met Val Glu Gln Met His Glu Asp
                     90                  95                 100 gtg atc agc ctg tgg gac cag agc ctg aag ccc tgc gtg aag ctg acc        392
Val Ile Ser Leu Trp Asp Gln Ser Leu Lys Pro Cys Val Lys Leu Thr
                105                 110                 115 ccc ctg tgc gtg acc ctg gaa tgc aga cag gtc aac acc acc aac gcc        440
Pro Leu Cys Val Thr Leu Glu Cys Arg Gln Val Asn Thr Thr Asn Ala
                120                 125                 130 acc agc agc gtg aac gtg acc aac ggc gag gaa atc aag aac tgc agc        488
Thr Ser Ser Val Asn Val Thr Asn Gly Glu Glu Ile Lys Asn Cys Ser
                135                 140                 145 ttc aat gcc acc acc gag atc cgg gac aag aaa cag aag gtg tac gcc        536
Phe Asn Ala Thr Thr Glu Ile Arg Asp Lys Lys Gln Lys Val Tyr Ala
150                 155                 160                 165 ctg ttc tac cgg ctg gac atc gtg ccc ctg gaa gag gaa cgg aag ggc        584
Leu Phe Tyr Arg Leu Asp Ile Val Pro Leu Glu Glu Glu Arg Lys Gly
                170                 175                 180 aac agc agc aag tac cgg ctg atc aac tgc aac acc agc gcc atc acc        632
Asn Ser Ser Lys Tyr Arg Leu Ile Asn Cys Asn Thr Ser Ala Ile Thr
                185                 190                 195 cag gcc tgc ccc aaa gtg acc ttc gac cct atc ccc atc cac tac tgc        680
Gln Ala Cys Pro Lys Val Thr Phe Asp Pro Ile Pro Ile His Tyr Cys
                200                 205                 210 gcc cct gcc ggc tac gcc atc ctg aag tgc aac aac aag acc ttc aac        728
Ala Pro Ala Gly Tyr Ala Ile Leu Lys Cys Asn Asn Lys Thr Phe Asn
                215                 220                 225 ggc acc ggc ccc tgc aac aac gtg tcc acc gtg cag tgc acc cac ggc        776
Gly Thr Gly Pro Cys Asn Asn Val Ser Thr Val Gln Cys Thr His Gly
230                 235                 240                 245 atc aag ccc gtg gtg tcc acc cag ctg ctg ctg aat ggc agc ctg gcc        824
Ile Lys Pro Val Val Ser Thr Gln Leu Leu Leu Asn Gly Ser Leu Ala
                250                 255                 260 gag ggc gag atc atc atc aga agc gag aac ctg acc aac aac gtg aaa        872
Glu Gly Glu Ile Ile Ile Arg Ser Glu Asn Leu Thr Asn Asn Val Lys
                265                 270                 275 acc atc atc gtg cac ctg aac gag agc gtg gaa atc gtg tgc acc cgg        920
Thr Ile Ile Val His Leu Asn Glu Ser Val Glu Ile Val Cys Thr Arg
                280                 285                 290 ccc aac aac aac acc aga aag agc atc cgg atc ggc cct ggc cag acc        968
Pro Asn Asn Asn Thr Arg Lys Ser Ile Arg Ile Gly Pro Gly Gln Thr
295                 300                 305 ttt tac gcc acc ggc gac atc atc ggc aac atc cgg cag gcc tac tgc       1016
Phe Tyr Ala Thr Gly Asp Ile Ile Gly Asn Ile Arg Gln Ala Tyr Cys
310                 315                 320                 325 aac atc aag aag gac gac tgg atc cgg acc ctg cag aga gtg ggc aag       1064
Asn Ile Lys Lys Asp Asp Trp Ile Arg Thr Leu Gln Arg Val Gly Lys
                330                 335                 340 aag ctg gcc gag cac ttc ccc aga cgg atc atc aac ttc acc agc ccc       1112
Lys Leu Ala Glu His Phe Pro Arg Arg Ile Ile Asn Phe Thr Ser Pro
                345                 350                 355 gct ggc ggc gac ctg gaa atc acc acc cac agc ttc aac tgc aga ggc       1160
Ala Gly Gly Asp Leu Glu Ile Thr Thr His Ser Phe Asn Cys Arg Gly
```

```

Ala Gly Gly Asp Leu Glu Ile Thr Thr His Ser Phe Asn Cys Arg Gly
        360                 365                 370 gag ttc ttc tac tgc aat acc agc agc ctg ttc aac agc acc tac aac      1208
Glu Phe Phe Tyr Cys Asn Thr Ser Ser Leu Phe Asn Ser Thr Tyr Asn
375                 380                 385 ccc aac gac acc aac agc aac agc tcc agc agc aac tcc agc ctg gac      1256
Pro Asn Asp Thr Asn Ser Asn Ser Ser Ser Ser Asn Ser Ser Leu Asp
390                 395                 400                 405 atc acc atc cct tgc cgg atc aag cag atc atc aat atg tgg cag gaa      1304
Ile Thr Ile Pro Cys Arg Ile Lys Gln Ile Ile Asn Met Trp Gln Glu
                410                 415                 420 gtg ggc agg gct atg tac gcc cct ccc atc gag ggc aac atc aca tgc      1352
Val Gly Arg Ala Met Tyr Ala Pro Pro Ile Glu Gly Asn Ile Thr Cys
            425                 430                 435 aag agc aac atc acc ggc ctc ctc ctg gtc cgc gac ggc ggc gtg gaa      1400
Lys Ser Asn Ile Thr Gly Leu Leu Leu Val Arg Asp Gly Gly Val Glu
        440                 445                 450 agc aac gag aca gag atc ttc aga ccc ggc gga ggc gac atg cgg aac      1448
Ser Asn Glu Thr Glu Ile Phe Arg Pro Gly Gly Gly Asp Met Arg Asn
    455                 460                 465 aac tgg cgg agc gag ctg tac aag tac aag gtg gtg gaa atc aag ccc      1496
Asn Trp Arg Ser Glu Leu Tyr Lys Tyr Lys Val Val Glu Ile Lys Pro
470                 475                 480                 485 ctg gga atc gcc ccc acc gcc gcc aag cgg aga gtg gtg gaa ggc gcc      1544
Leu Gly Ile Ala Pro Thr Ala Ala Lys Arg Arg Val Val Glu Gly Ala
                490                 495                 500 cac cac cac cat cac cac tgactcgagg cgcgcctagg ccttgacggc             1592
His His His His His His
                505 cttccgcca                                                             1601

<210> SEQ ID NO 90
<211> LENGTH: 507
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
                20                  25                  30

Tyr Tyr Gly Val Pro Val Trp Lys Glu Ala Lys Thr Thr Leu Phe Cys
            35                  40                  45

Ala Ser Asp Ala Lys Ala Tyr Glu Lys Glu Val His Asn Val Trp Ala
        50                  55                  60

Thr His Ala Cys Val Pro Thr Asp Pro Asn Pro Gln Glu Met Val Leu
65                  70                  75                  80

Glu Asn Val Thr Glu Asn Phe Asn Met Trp Lys Asn Asp Met Val Glu
                85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu Glu Cys Arg Gln Val
        115                 120                 125

Asn Thr Thr Asn Ala Thr Ser Ser Val Asn Val Thr Asn Gly Glu Glu
    130                 135                 140

Ile Lys Asn Cys Ser Phe Asn Ala Thr Thr Glu Ile Arg Asp Lys Lys
```

```
                145                 150                 155                 160
Gln Lys Val Tyr Ala Leu Phe Tyr Arg Leu Asp Ile Val Pro Leu Glu
                165                 170                 175
Glu Glu Arg Lys Gly Asn Ser Ser Lys Tyr Arg Leu Ile Asn Cys Asn
            180                 185                 190
Thr Ser Ala Ile Thr Gln Ala Cys Pro Lys Val Thr Phe Asp Pro Ile
        195                 200                 205
Pro Ile His Tyr Cys Ala Pro Ala Gly Tyr Ala Ile Leu Lys Cys Asn
    210                 215                 220
Asn Lys Thr Phe Asn Gly Thr Gly Pro Cys Asn Asn Val Ser Thr Val
225                 230                 235                 240
Gln Cys Thr His Gly Ile Lys Pro Val Val Ser Thr Gln Leu Leu Leu
                245                 250                 255
Asn Gly Ser Leu Ala Glu Gly Glu Ile Ile Ile Arg Ser Glu Asn Leu
            260                 265                 270
Thr Asn Asn Val Lys Thr Ile Ile Val His Leu Asn Glu Ser Val Glu
        275                 280                 285
Ile Val Cys Thr Arg Pro Asn Asn Asn Thr Arg Lys Ser Ile Arg Ile
    290                 295                 300
Gly Pro Gly Gln Thr Phe Tyr Ala Thr Gly Asp Ile Ile Gly Asn Ile
305                 310                 315                 320
Arg Gln Ala Tyr Cys Asn Ile Lys Lys Asp Asp Trp Ile Arg Thr Leu
                325                 330                 335
Gln Arg Val Gly Lys Lys Leu Ala Glu His Phe Pro Arg Arg Ile Ile
            340                 345                 350
Asn Phe Thr Ser Pro Ala Gly Gly Asp Leu Glu Ile Thr Thr His Ser
        355                 360                 365
Phe Asn Cys Arg Gly Glu Phe Phe Tyr Cys Asn Thr Ser Ser Leu Phe
    370                 375                 380
Asn Ser Thr Tyr Asn Pro Asn Asp Thr Asn Ser Asn Ser Ser Ser Ser
385                 390                 395                 400
Asn Ser Ser Leu Asp Ile Thr Ile Pro Cys Arg Ile Lys Gln Ile Ile
                405                 410                 415
Asn Met Trp Gln Glu Val Gly Arg Ala Met Tyr Ala Pro Pro Ile Glu
            420                 425                 430
Gly Asn Ile Thr Cys Lys Ser Asn Ile Thr Gly Leu Leu Leu Val Arg
        435                 440                 445
Asp Gly Gly Val Glu Ser Asn Glu Thr Glu Ile Phe Arg Pro Gly Gly
    450                 455                 460
Gly Asp Met Arg Asn Asn Trp Arg Ser Glu Leu Tyr Lys Tyr Lys Val
465                 470                 475                 480
Val Glu Ile Lys Pro Leu Gly Ile Ala Pro Thr Ala Ala Lys Arg Arg
                485                 490                 495
Val Val Glu Gly Ala His His His His His
            500                 505

<210> SEQ ID NO 91
<211> LENGTH: 1593
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (37)..(1560)
```

<400> SEQUENCE: 91

```
ccaagctggc tagcgtttaa acttaagctt gccacc atg cct atg ggc agc ctg        54
                                      Met Pro Met Gly Ser Leu
                                      1               5 cag cct ctg gcc acc ctg tac ctg ctg ggc atg ctg gtg gcc tcc gtg       102
Gln Pro Leu Ala Thr Leu Tyr Leu Leu Gly Met Leu Val Ala Ser Val
        10                  15                  20 ctg gca gct ggc aac ctg tgg gtc aca gtg tac tac ggc gtg ccc gtg       150
Leu Ala Ala Gly Asn Leu Trp Val Thr Val Tyr Tyr Gly Val Pro Val
25                  30                  35 tgg aaa gag gcc aag acc acc ctg ttc tgc gcc agc gac gcc aag gcc       198
Trp Lys Glu Ala Lys Thr Thr Leu Phe Cys Ala Ser Asp Ala Lys Ala
    40                  45                  50 tac gag aaa gag gtg cac aac gtc tgg gcc acc cac gcc tgc gtg ccc       246
Tyr Glu Lys Glu Val His Asn Val Trp Ala Thr His Ala Cys Val Pro
55                  60                  65                  70 acc gac ccc aac ccc cag gaa atg gtc ctg gaa aac gtg acc gag aac       294
Thr Asp Pro Asn Pro Gln Glu Met Val Leu Glu Asn Val Thr Glu Asn
                75                  80                  85 ttc aac atg tgg aag aac gac atg gtg gaa cag atg cac gag gac gtg       342
Phe Asn Met Trp Lys Asn Asp Met Val Glu Gln Met His Glu Asp Val
            90                  95                 100 atc agc ctg tgg gac cag agc ctg aag ccc tgc gtg aag ctg acc ccc       390
Ile Ser Leu Trp Asp Gln Ser Leu Lys Pro Cys Val Lys Leu Thr Pro
       105                 110                 115 ctg tgc gtg acc ctg gaa tgc aga cag gtc aac acc acc aac gcc acc       438
Leu Cys Val Thr Leu Glu Cys Arg Gln Val Asn Thr Thr Asn Ala Thr
   120                 125                 130 agc agc gtg aac gtg acc aac ggc gag gaa atc aag aac tgc agc ttc       486
Ser Ser Val Asn Val Thr Asn Gly Glu Glu Ile Lys Asn Cys Ser Phe
135                 140                 145                 150 aat gcc acc acc gag atc cgg gac aag aaa cag aag gtg tac gcc ctg       534
Asn Ala Thr Thr Glu Ile Arg Asp Lys Lys Gln Lys Val Tyr Ala Leu
                155                 160                 165 ttc tac cgg ctg gac atc gtg ccc ctg gaa gag gaa cgg aag ggc aac       582
Phe Tyr Arg Leu Asp Ile Val Pro Leu Glu Glu Glu Arg Lys Gly Asn
            170                 175                 180 agc agc aag tac cgg ctg atc aac tgc aac acc agc gcc atc acc cag       630
Ser Ser Lys Tyr Arg Leu Ile Asn Cys Asn Thr Ser Ala Ile Thr Gln
        185                 190                 195 gcc tgc ccc aaa gtg acc ttc gac cct atc ccc atc cac tac tgc gcc       678
Ala Cys Pro Lys Val Thr Phe Asp Pro Ile Pro Ile His Tyr Cys Ala
    200                 205                 210 cct gcc ggc tac gcc atc ctg aag tgc aac aac aag acc ttc aac ggc       726
Pro Ala Gly Tyr Ala Ile Leu Lys Cys Asn Asn Lys Thr Phe Asn Gly
215                 220                 225                 230 acc ggc ccc tgc aac aac gtg tcc acc gtg cag tgc acc cac ggc atc       774
Thr Gly Pro Cys Asn Asn Val Ser Thr Val Gln Cys Thr His Gly Ile
                235                 240                 245 aag ccc gtg gtg tcc acc cag ctg ctg ctg aat ggc agc ctg gcc gag       822
Lys Pro Val Val Ser Thr Gln Leu Leu Leu Asn Gly Ser Leu Ala Glu
            250                 255                 260 ggc gag atc atc atc aga agc gag aac ctg acc aac aac gtg aaa acc       870
Gly Glu Ile Ile Ile Arg Ser Glu Asn Leu Thr Asn Asn Val Lys Thr
        265                 270                 275 atc atc gtg cac ctg aac gag agc gtg gaa atc gtg tgc acc cgg ccc       918
Ile Ile Val His Leu Asn Glu Ser Val Glu Ile Val Cys Thr Arg Pro
    280                 285                 290 aac aac aac acc aga aag agc atc cgg atc ggc cct ggc cag acc ttt       966
Asn Asn Asn Thr Arg Lys Ser Ile Arg Ile Gly Pro Gly Gln Thr Phe
```

```
                    295                 300                 305                 310
tac gcc acc ggc gac atc atc ggc aac atc cgg cag gcc tac tgc aac        1014
Tyr Ala Thr Gly Asp Ile Ile Gly Asn Ile Arg Gln Ala Tyr Cys Asn
                315                 320                 325 atc aag aag gac gac tgg atc cgg acc ctg cag aga gtg ggc aag aag        1062
Ile Lys Lys Asp Asp Trp Ile Arg Thr Leu Gln Arg Val Gly Lys Lys
                330                 335                 340 ctg gcc gag cac ttc ccc aga cgg atc atc aac ttc acc agc ccc gct        1110
Leu Ala Glu His Phe Pro Arg Arg Ile Ile Asn Phe Thr Ser Pro Ala
                345                 350                 355 ggc ggc gac ctg gaa atc acc acc cac agc ttc aac tgc aga ggc gag        1158
Gly Gly Asp Leu Glu Ile Thr Thr His Ser Phe Asn Cys Arg Gly Glu
                360                 365                 370 ttc ttc tac tgc aat acc agc agc ctg ttc aac agc acc tac aac ccc        1206
Phe Phe Tyr Cys Asn Thr Ser Ser Leu Phe Asn Ser Thr Tyr Asn Pro
375                 380                 385                 390 aac gac acc aac agc aac agc tcc agc agc aac tcc agc ctg gac atc        1254
Asn Asp Thr Asn Ser Asn Ser Ser Ser Ser Asn Ser Ser Leu Asp Ile
                395                 400                 405 acc atc cct tgc cgg atc aag cag atc atc aat atg tgg cag gaa gtg        1302
Thr Ile Pro Cys Arg Ile Lys Gln Ile Ile Asn Met Trp Gln Glu Val
                410                 415                 420 ggc agg gct atg tac gcc cct ccc atc gag ggc aac atc aca tgc aag        1350
Gly Arg Ala Met Tyr Ala Pro Pro Ile Glu Gly Asn Ile Thr Cys Lys
                425                 430                 435 agc aac atc acc ggc ctg ctc ctg gtc cgc gac ggc ggc gtg gaa agc        1398
Ser Asn Ile Thr Gly Leu Leu Leu Val Arg Asp Gly Gly Val Glu Ser
                440                 445                 450 aac gag aca gag atc ttc aga ccc gga ggc gac atg cgg aac aac        1446
Asn Glu Thr Glu Ile Phe Arg Pro Gly Gly Gly Asp Met Arg Asn Asn
455                 460                 465                 470 tgg cgg agc gag ctg tac aag tac aag gtg gtg gaa atc aag ccc ctg        1494
Trp Arg Ser Glu Leu Tyr Lys Tyr Lys Val Val Glu Ile Lys Pro Leu
                475                 480                 485 gga atc gcc ccc acc gcc gcc aag cgg aga gtg gtg gaa ggc gcc cac        1542
Gly Ile Ala Pro Thr Ala Ala Lys Arg Arg Val Val Glu Gly Ala His
                490                 495                 500 cac cac cat cac cac tgc tgactcgagt ctagagggcc cgtttaaacc cgc          1593
His His His His His Cys
        505
```

<210> SEQ ID NO 92
<211> LENGTH: 508
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

```
Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
                20                  25                  30

Tyr Tyr Gly Val Pro Val Trp Lys Glu Ala Lys Thr Thr Leu Phe Cys
            35                  40                  45

Ala Ser Asp Ala Lys Ala Tyr Glu Lys Glu Val His Asn Val Trp Ala
        50                  55                  60

Thr His Ala Cys Val Pro Thr Asp Pro Asn Pro Gln Glu Met Val Leu
65                  70                  75                  80
```

-continued

```
Glu Asn Val Thr Glu Asn Phe Asn Met Trp Lys Asn Asp Met Val Glu
             85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu Glu Cys Arg Gln Val
            115                 120                 125

Asn Thr Thr Asn Ala Thr Ser Ser Val Asn Val Thr Asn Gly Glu Glu
            130                 135                 140

Ile Lys Asn Cys Ser Phe Asn Ala Thr Thr Glu Ile Arg Asp Lys Lys
145                 150                 155                 160

Gln Lys Val Tyr Ala Leu Phe Tyr Arg Leu Asp Ile Val Pro Leu Glu
                165                 170                 175

Glu Glu Arg Lys Gly Asn Ser Ser Lys Tyr Arg Leu Ile Asn Cys Asn
            180                 185                 190

Thr Ser Ala Ile Thr Gln Ala Cys Pro Lys Val Thr Phe Asp Pro Ile
            195                 200                 205

Pro Ile His Tyr Cys Ala Pro Ala Gly Tyr Ala Ile Leu Lys Cys Asn
            210                 215                 220

Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Gly Glu Ile Ile Ile Arg Ser Glu Asn Leu
            260                 265                 270

Thr Asn Asn Val Lys Thr Ile Ile Val His Leu Asn Glu Ser Val Glu
            275                 280                 285

Ile Val Cys Thr Arg Pro Asn Asn Asn Thr Arg Lys Ser Ile Arg Ile
290                 295                 300

Gly Pro Gly Gln Thr Phe Tyr Ala Thr Gly Asp Ile Ile Gly Asn Ile
305                 310                 315                 320

Arg Gln Ala Tyr Cys Asn Ile Lys Lys Asp Asp Trp Ile Arg Thr Leu
                325                 330                 335

Gln Arg Val Gly Lys Lys Leu Ala Glu His Phe Pro Arg Ile Ile
            340                 345                 350

Asn Phe Thr Ser Pro Ala Gly Gly Asp Leu Glu Ile Thr Thr His Ser
            355                 360                 365

Phe Asn Cys Arg Gly Glu Phe Phe Tyr Cys Asn Thr Ser Ser Leu Phe
            370                 375                 380

Asn Ser Thr Tyr Asn Pro Asn Asp Thr Asn Ser Ser Ser Ser Ser
385                 390                 395                 400

Asn Ser Ser Leu Asp Ile Thr Ile Pro Cys Arg Ile Lys Gln Ile Ile
                405                 410                 415

Asn Met Trp Gln Glu Val Gly Arg Ala Met Tyr Ala Pro Pro Ile Glu
            420                 425                 430

Gly Asn Ile Thr Cys Lys Ser Asn Ile Thr Gly Leu Leu Leu Val Arg
                435                 440                 445

Asp Gly Gly Val Glu Ser Asn Glu Thr Glu Ile Phe Arg Pro Gly Gly
            450                 455                 460

Gly Asp Met Arg Asn Asn Trp Arg Ser Glu Leu Tyr Lys Tyr Lys Val
465                 470                 475                 480

Val Glu Ile Lys Pro Leu Gly Ile Ala Pro Thr Ala Ala Lys Arg Arg
                485                 490                 495

Val Val Glu Gly Ala His His His His His Cys
            500                 505
```

-continued

<210> SEQ ID NO 93
<211> LENGTH: 2143
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (49)..(2097)

<400> SEQUENCE: 93

```
cgaattgaag gaaggccgtc aaggccgcat ttaattaagc ttgccacc atg cct atg          57
                                                    Met Pro Met
                                                    1 ggc agc ctg cag cct ctg gcc acc ctg tac ctg ctg ggc atg ctg gtg         105
Gly Ser Leu Gln Pro Leu Ala Thr Leu Tyr Leu Leu Gly Met Leu Val
        5                  10                  15 gcc tcc gtg ctg gca gct ggc aac ctg tgg gtc aca gtg tac tac ggc         153
Ala Ser Val Leu Ala Ala Gly Asn Leu Trp Val Thr Val Tyr Tyr Gly
 20                  25                  30                  35 gtg ccc gtg tgg aaa gag gcc aag acc acc ctg ttc tgc gcc agc gac         201
Val Pro Val Trp Lys Glu Ala Lys Thr Thr Leu Phe Cys Ala Ser Asp
                 40                  45                  50 gcc aag gcc tac gag aaa gag gtg cac aac gtc tgg gcc acc cac gcc         249
Ala Lys Ala Tyr Glu Lys Glu Val His Asn Val Trp Ala Thr His Ala
             55                  60                  65 tgc gtg ccc acc gac ccc aac ccc cag gaa atg gtc ctg gaa aac gtg         297
Cys Val Pro Thr Asp Pro Asn Pro Gln Glu Met Val Leu Glu Asn Val
         70                  75                  80 acc gag aac ttc aac atg tgg aag aac gac atg gtg gaa cag atg cac         345
Thr Glu Asn Phe Asn Met Trp Lys Asn Asp Met Val Glu Gln Met His
     85                  90                  95 gag gac gtg atc agc ctg tgg gac cag agc ctg aag ccc tgc gtg aag         393
Glu Asp Val Ile Ser Leu Trp Asp Gln Ser Leu Lys Pro Cys Val Lys
100                 105                 110                 115 ctg acc ccc ctg tgc gtg acc ctg gaa tgc aga cag gtc aac acc acc         441
Leu Thr Pro Leu Cys Val Thr Leu Glu Cys Arg Gln Val Asn Thr Thr
                 120                 125                 130 aac gcc acc agc agc gtg aac gtg acc aac ggc gag gaa atc aag aac         489
Asn Ala Thr Ser Ser Val Asn Val Thr Asn Gly Glu Glu Ile Lys Asn
             135                 140                 145 tgc agc ttc aat gcc acc acc gag atc cgg gac aag aaa cag aag gtg         537
Cys Ser Phe Asn Ala Thr Thr Glu Ile Arg Asp Lys Lys Gln Lys Val
         150                 155                 160 tac gcc ctg ttc tac cgg ctg gac atc gtg ccc ctg gaa gag gaa cgg         585
Tyr Ala Leu Phe Tyr Arg Leu Asp Ile Val Pro Leu Glu Glu Glu Arg
     165                 170                 175 aag ggc aac agc agc aag tac cgg ctg atc aac tgc aac acc agc gcc         633
Lys Gly Asn Ser Ser Lys Tyr Arg Leu Ile Asn Cys Asn Thr Ser Ala
180                 185                 190                 195 atc acc cag gcc tgc ccc aaa gtg acc ttc gac cct atc ccc atc cac         681
Ile Thr Gln Ala Cys Pro Lys Val Thr Phe Asp Pro Ile Pro Ile His
                 200                 205                 210 tac tgc gcc cct gcc ggc tac gcc atc ctg aag tgc aac aac aag acc         729
Tyr Cys Ala Pro Ala Gly Tyr Ala Ile Leu Lys Cys Asn Asn Lys Thr
             215                 220                 225 ttc aac ggc acc ggc ccc tgc aac aac gtg tcc acc gtg cag tgc acc         777
Phe Asn Gly Thr Gly Pro Cys Asn Asn Val Ser Thr Val Gln Cys Thr
         230                 235                 240 cac ggc atc aag ccc gtg gtg tcc acc cag ctg ctg ctg aat ggc agc         825
```

```
                His Gly Ile Lys Pro Val Val Ser Thr Gln Leu Leu Leu Asn Gly Ser
                245                 250                 255 ctg gcc gag ggc gag atc atc atc aga agc gag aac ctg acc aac aac       873
Leu Ala Glu Gly Glu Ile Ile Ile Arg Ser Glu Asn Leu Thr Asn Asn
260                 265                 270                 275 gtg aaa acc atc atc gtg cac ctg aac gag agc gtg gaa atc gtg tgc       921
Val Lys Thr Ile Ile Val His Leu Asn Glu Ser Val Glu Ile Val Cys
                280                 285                 290 acc cgg ccc aac aac aac acc aga aag agc atc cgg atc ggc cct ggc       969
Thr Arg Pro Asn Asn Asn Thr Arg Lys Ser Ile Arg Ile Gly Pro Gly
                295                 300                 305 cag acc ttt tac gcc acc ggc gac atc atc ggc aac atc cgg cag gcc      1017
Gln Thr Phe Tyr Ala Thr Gly Asp Ile Ile Gly Asn Ile Arg Gln Ala
            310                 315                 320 tac tgc aac atc aag aag gac gac tgg atc cgg acc ctg cag aga gtg      1065
Tyr Cys Asn Ile Lys Lys Asp Asp Trp Ile Arg Thr Leu Gln Arg Val
325                 330                 335 ggc aag aag ctg gcc gag cac ttc ccc aga cgg atc atc aac ttc acc      1113
Gly Lys Lys Leu Ala Glu His Phe Pro Arg Arg Ile Ile Asn Phe Thr
340                 345                 350                 355 agc ccc gct ggc ggc gac ctg gaa atc acc acc cac agc ttc aac tgc      1161
Ser Pro Ala Gly Gly Asp Leu Glu Ile Thr Thr His Ser Phe Asn Cys
                360                 365                 370 aga ggc gag ttc ttc tac tgc aat acc agc agc ctg ttc aac agc acc      1209
Arg Gly Glu Phe Phe Tyr Cys Asn Thr Ser Ser Leu Phe Asn Ser Thr
            375                 380                 385 tac aac ccc aac gac acc aac agc aac agc tcc agc agc aac tcc agc      1257
Tyr Asn Pro Asn Asp Thr Asn Ser Asn Ser Ser Ser Asn Ser Ser
            390                 395                 400 ctg gac atc acc atc cct tgc cgg atc aag cag atc atc aat atg tgg      1305
Leu Asp Ile Thr Ile Pro Cys Arg Ile Lys Gln Ile Ile Asn Met Trp
405                 410                 415 cag gaa gtg ggc agg gct atg tac gcc cct ccc atc gag ggc aac atc      1353
Gln Glu Val Gly Arg Ala Met Tyr Ala Pro Pro Ile Glu Gly Asn Ile
420                 425                 430                 435 aca tgc aag agc aac atc acc ggc ctg ctc ctg gtc cgc gac ggc ggc      1401
Thr Cys Lys Ser Asn Ile Thr Gly Leu Leu Leu Val Arg Asp Gly Gly
                440                 445                 450 gtg gaa agc aac gag aca gag atc ttc aga ccc ggc gga ggc gac atg      1449
Val Glu Ser Asn Glu Thr Glu Ile Phe Arg Pro Gly Gly Gly Asp Met
            455                 460                 465 cgg aac aac tgg cgg agc gag ctg tac aag tac aag gtg gtg gaa atc      1497
Arg Asn Asn Trp Arg Ser Glu Leu Tyr Lys Tyr Lys Val Val Glu Ile
            470                 475                 480 aag ccc ctg gga atc gcc ccc acc gcc gcc aag cgg aga gtg gtg gaa      1545
Lys Pro Leu Gly Ile Ala Pro Thr Ala Ala Lys Arg Arg Val Val Glu
485                 490                 495 agc gag aag tcc gcc gtg ggc ctg ggc gcc gtg atc ttc ggc ttt ctg      1593
Ser Glu Lys Ser Ala Val Gly Leu Gly Ala Val Ile Phe Gly Phe Leu
500                 505                 510                 515 gga gcc gcc gga agc acc atg ggc gct gcc agc atc acc ctg acc gtg      1641
Gly Ala Ala Gly Ser Thr Met Gly Ala Ala Ser Ile Thr Leu Thr Val
                520                 525                 530 cag gcc aga cag ctg ctg agc ggc atc gtg cag cag cag agc aac ctg      1689
Gln Ala Arg Gln Leu Leu Ser Gly Ile Val Gln Gln Gln Ser Asn Leu
            535                 540                 545 ctg aag gcc atc gag gcc cag cag cat ctg ctg cag ctg acc gtg tgg      1737
Leu Lys Ala Ile Glu Ala Gln Gln His Leu Leu Gln Leu Thr Val Trp
            550                 555                 560 ggc atc aag cag ctg cag acc cgg gtg ctg gcc atc gag aga tac ctg      1785
```

-continued

```
Gly Ile Lys Gln Leu Gln Thr Arg Val Leu Ala Ile Glu Arg Tyr Leu
            565                 570                 575 aag gac cag cag ctc ctg gga atc tgg ggc tgc agc ggc aag ctg atc    1833
Lys Asp Gln Gln Leu Leu Gly Ile Trp Gly Cys Ser Gly Lys Leu Ile
580                 585                 590                 595 tgc acc acc gcc gtg ccc tgg aac agc agc tgg tcc aac aag agc cac    1881
Cys Thr Thr Ala Val Pro Trp Asn Ser Ser Trp Ser Asn Lys Ser His
            600                 605                 610 gac gag atc tgg ggc aac atg acc tgg atg cag tgg gac aga gag atc    1929
Asp Glu Ile Trp Gly Asn Met Thr Trp Met Gln Trp Asp Arg Glu Ile
            615                 620                 625 agc aac tac acc aac acc atc tac cgc ctg ctg gaa gat agc cag aac    1977
Ser Asn Tyr Thr Asn Thr Ile Tyr Arg Leu Leu Glu Asp Ser Gln Asn
            630                 635                 640 cag cag gaa cag aac gag aag gac ctg ctg gcc ctg gac agc tgg gag    2025
Gln Gln Glu Gln Asn Glu Lys Asp Leu Leu Ala Leu Asp Ser Trp Glu
        645                 650                 655 aac ctg tgg aac tgg ttc agc atc acc aag tgg ctg tgg tac atc aag    2073
Asn Leu Trp Asn Trp Phe Ser Ile Thr Lys Trp Leu Trp Tyr Ile Lys
660                 665                 670                 675 ggc gcc cac cac cac cat cac cac tgactcgagg cgcgccctgg gcctcatggg    2127
Gly Ala His His His His His His
                    680 ccttcctttc actgcc                                                   2143

<210> SEQ ID NO 94
<211> LENGTH: 683
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
            20                  25                  30

Tyr Tyr Gly Val Pro Val Trp Lys Glu Ala Lys Thr Thr Leu Phe Cys
        35                  40                  45

Ala Ser Asp Ala Lys Ala Tyr Glu Lys Glu Val His Asn Val Trp Ala
    50                  55                  60

Thr His Ala Cys Val Pro Thr Asp Pro Asn Pro Gln Glu Met Val Leu
65                  70                  75                  80

Glu Asn Val Thr Glu Asn Phe Asn Met Trp Lys Asn Asp Met Val Glu
                85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu Glu Cys Arg Gln Val
        115                 120                 125

Asn Thr Thr Asn Ala Thr Ser Ser Val Asn Val Thr Asn Gly Glu Glu
    130                 135                 140

Ile Lys Asn Cys Ser Phe Asn Ala Thr Thr Glu Ile Arg Asp Lys Lys
145                 150                 155                 160

Gln Lys Val Tyr Ala Leu Phe Tyr Arg Leu Asp Ile Val Pro Leu Glu
                165                 170                 175

Glu Glu Arg Lys Gly Asn Ser Ser Lys Tyr Arg Leu Ile Asn Cys Asn
            180                 185                 190
```

-continued

```
Thr Ser Ala Ile Thr Gln Ala Cys Pro Lys Val Thr Phe Asp Pro Ile
    195                 200                 205

Pro Ile His Tyr Cys Ala Pro Ala Gly Tyr Ala Ile Leu Lys Cys Asn
210                 215                 220

Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Gly Glu Ile Ile Arg Ser Glu Asn Leu
            260                 265                 270

Thr Asn Asn Val Lys Thr Ile Ile Val His Leu Asn Glu Ser Val Glu
    275                 280                 285

Ile Val Cys Thr Arg Pro Asn Asn Asn Thr Arg Lys Ser Ile Arg Ile
290                 295                 300

Gly Pro Gly Gln Thr Phe Tyr Ala Thr Gly Asp Ile Ile Gly Asn Ile
305                 310                 315                 320

Arg Gln Ala Tyr Cys Asn Ile Lys Lys Asp Asp Trp Ile Arg Thr Leu
                325                 330                 335

Gln Arg Val Gly Lys Lys Leu Ala Glu His Phe Pro Arg Arg Ile Ile
            340                 345                 350

Asn Phe Thr Ser Pro Ala Gly Gly Asp Leu Glu Ile Thr Thr His Ser
    355                 360                 365

Phe Asn Cys Arg Gly Glu Phe Phe Tyr Cys Asn Thr Ser Ser Leu Phe
370                 375                 380

Asn Ser Thr Tyr Asn Pro Asn Asp Thr Asn Ser Asn Ser Ser Ser Ser
385                 390                 395                 400

Asn Ser Ser Leu Asp Ile Thr Ile Pro Cys Arg Ile Lys Gln Ile Ile
                405                 410                 415

Asn Met Trp Gln Glu Val Gly Arg Ala Met Tyr Ala Pro Pro Ile Glu
            420                 425                 430

Gly Asn Ile Thr Cys Lys Ser Asn Ile Thr Gly Leu Leu Leu Val Arg
    435                 440                 445

Asp Gly Gly Val Glu Ser Asn Glu Thr Glu Ile Phe Arg Pro Gly Gly
450                 455                 460

Gly Asp Met Arg Asn Asn Trp Arg Ser Glu Leu Tyr Lys Tyr Lys Val
465                 470                 475                 480

Val Glu Ile Lys Pro Leu Gly Ile Ala Pro Thr Ala Ala Lys Arg Arg
                485                 490                 495

Val Val Glu Ser Glu Lys Ser Ala Val Gly Leu Gly Ala Val Ile Phe
            500                 505                 510

Gly Phe Leu Gly Ala Ala Gly Ser Thr Met Gly Ala Ala Ser Ile Thr
    515                 520                 525

Leu Thr Val Gln Ala Arg Gln Leu Leu Ser Gly Ile Val Gln Gln Gln
530                 535                 540

Ser Asn Leu Leu Lys Ala Ile Glu Ala Gln Gln His Leu Leu Gln Leu
545                 550                 555                 560

Thr Val Trp Gly Ile Lys Gln Leu Gln Thr Arg Val Leu Ala Ile Glu
                565                 570                 575

Arg Tyr Leu Lys Asp Gln Gln Leu Leu Gly Ile Trp Gly Cys Ser Gly
            580                 585                 590

Lys Leu Ile Cys Thr Thr Ala Val Pro Trp Asn Ser Ser Trp Ser Asn
    595                 600                 605

Lys Ser His Asp Glu Ile Trp Gly Asn Met Thr Trp Met Gln Trp Asp
610                 615                 620
```

```
Arg Glu Ile Ser Asn Tyr Thr Asn Thr Ile Tyr Arg Leu Leu Glu Asp
625                 630                 635                 640

Ser Gln Asn Gln Gln Glu Gln Asn Glu Lys Asp Leu Leu Ala Leu Asp
            645                 650                 655

Ser Trp Glu Asn Leu Trp Asn Trp Phe Ser Ile Thr Lys Trp Leu Trp
            660                 665                 670

Tyr Ile Lys Gly Ala His His His His His His
            675                 680

<210> SEQ ID NO 95
<211> LENGTH: 2121
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (37)..(2088)

<400> SEQUENCE: 95
ccaagctggc tagcgtttaa acttaagctt gccacc atg cct atg ggc agc ctg       54
                                       Met Pro Met Gly Ser Leu
                                       1               5 cag cct ctg gcc acc ctg tac ctg ctg ggc atg ctg gtg gcc tcc gtg     102
Gln Pro Leu Ala Thr Leu Tyr Leu Leu Gly Met Leu Val Ala Ser Val
            10                  15                  20 ctg gca gct ggc aac ctg tgg gtc aca gtg tac tac ggc gtg ccc gtg     150
Leu Ala Ala Gly Asn Leu Trp Val Thr Val Tyr Tyr Gly Val Pro Val
        25                  30                  35 tgg aaa gag gcc aag acc acc ctg ttc tgc gcc agc gac gcc aag gcc     198
Trp Lys Glu Ala Lys Thr Thr Leu Phe Cys Ala Ser Asp Ala Lys Ala
40                  45                  50 tac gag aaa gag gtg cac aac gtc tgg gcc acc cac gcc tgc gtg ccc     246
Tyr Glu Lys Glu Val His Asn Val Trp Ala Thr His Ala Cys Val Pro
55                  60                  65                  70 acc gac ccc aac ccc cag gaa atg gtc ctg gaa aac gtg acc gag aac     294
Thr Asp Pro Asn Pro Gln Glu Met Val Leu Glu Asn Val Thr Glu Asn
                75                  80                  85 ttc aac atg tgg aag aac gac atg gtg gaa cag atg cac gag gac gtg     342
Phe Asn Met Trp Lys Asn Asp Met Val Glu Gln Met His Glu Asp Val
            90                  95                  100 atc agc ctg tgg gac cag agc ctg aag ccc tgc gtg aag ctg acc ccc     390
Ile Ser Leu Trp Asp Gln Ser Leu Lys Pro Cys Val Lys Leu Thr Pro
        105                 110                 115 ctg tgc gtg acc ctg gaa tgc aga cag gtc aac acc acc aac gcc acc     438
Leu Cys Val Thr Leu Glu Cys Arg Gln Val Asn Thr Thr Asn Ala Thr
    120                 125                 130 agc agc gtg aac gtg acc aac ggc gag gaa atc aag aac tgc agc ttc     486
Ser Ser Val Asn Val Thr Asn Gly Glu Glu Ile Lys Asn Cys Ser Phe
135                 140                 145                 150 aat gcc acc acc gag atc cgg gac aag aaa cag aag gtg tac gcc ctg     534
Asn Ala Thr Thr Glu Ile Arg Asp Lys Lys Gln Lys Val Tyr Ala Leu
                155                 160                 165 ttc tac cgg ctg gac atc gtg ccc ctg gaa gag gaa cgg aag ggc aac     582
Phe Tyr Arg Leu Asp Ile Val Pro Leu Glu Glu Glu Arg Lys Gly Asn
            170                 175                 180 agc agc aag tac cgg ctg atc aac tgc aac acc agc gcc atc acc cag     630
Ser Ser Lys Tyr Arg Leu Ile Asn Cys Asn Thr Ser Ala Ile Thr Gln
        185                 190                 195 gcc tgc ccc aaa gtg acc ttc gac cct atc ccc atc cac tac tgc gcc     678
```

-continued

```
                Ala Cys Pro Lys Val Thr Phe Asp Pro Ile Pro Ile His Tyr Cys Ala
                    200                 205                 210 cct gcc ggc tac gcc atc ctg aag tgc aac aac aag acc ttc aac ggc        726
Pro Ala Gly Tyr Ala Ile Leu Lys Cys Asn Asn Lys Thr Phe Asn Gly
215                 220                 225                 230 acc ggc ccc tgc aac aac gtg tcc acc gtg cag tgc acc cac ggc atc        774
Thr Gly Pro Cys Asn Asn Val Ser Thr Val Gln Cys Thr His Gly Ile
                235                 240                 245 aag ccc gtg gtg tcc acc cag ctg ctg ctg aat ggc agc ctg gcc gag        822
Lys Pro Val Val Ser Thr Gln Leu Leu Leu Asn Gly Ser Leu Ala Glu
            250                 255                 260 ggc gag atc atc atc aga agc gag aac ctg acc aac aac gtg aaa acc        870
Gly Glu Ile Ile Ile Arg Ser Glu Asn Leu Thr Asn Asn Val Lys Thr
        265                 270                 275 atc atc gtg cac ctg aac gag agc gtg gaa atc gtg tgc acc cgg ccc        918
Ile Ile Val His Leu Asn Glu Ser Val Glu Ile Val Cys Thr Arg Pro
    280                 285                 290 aac aac aac acc aga aag agc atc cgg atc ggc cct ggc cag acc ttt        966
Asn Asn Asn Thr Arg Lys Ser Ile Arg Ile Gly Pro Gly Gln Thr Phe
295                 300                 305                 310 tac gcc acc ggc gac atc atc ggc aac atc cgg cag gcc tac tgc aac       1014
Tyr Ala Thr Gly Asp Ile Ile Gly Asn Ile Arg Gln Ala Tyr Cys Asn
                315                 320                 325 atc aag aag gac gac tgg atc cgg acc ctg cag aga gtg ggc aag aag       1062
Ile Lys Lys Asp Asp Trp Ile Arg Thr Leu Gln Arg Val Gly Lys Lys
                330                 335                 340 ctg gcc gag cac ttc ccc aga cgg atc atc aac ttc acc agc ccc gct       1110
Leu Ala Glu His Phe Pro Arg Arg Ile Ile Asn Phe Thr Ser Pro Ala
            345                 350                 355 ggc ggc gac ctg gaa atc acc acc cac agc ttc aac tgc aga ggc gag       1158
Gly Gly Asp Leu Glu Ile Thr Thr His Ser Phe Asn Cys Arg Gly Glu
        360                 365                 370 ttc ttc tac tgc aat acc agc agc ctg ttc aac agc acc tac aac ccc       1206
Phe Phe Tyr Cys Asn Thr Ser Ser Leu Phe Asn Ser Thr Tyr Asn Pro
375                 380                 385                 390 aac gac acc aac agc aac agc tcc agc agc aac tcc agc ctg gac atc       1254
Asn Asp Thr Asn Ser Asn Ser Ser Ser Ser Asn Ser Ser Leu Asp Ile
                395                 400                 405 acc atc cct tgc cgg atc aag cag atc atc aat atg tgg cag gaa gtg       1302
Thr Ile Pro Cys Arg Ile Lys Gln Ile Ile Asn Met Trp Gln Glu Val
                410                 415                 420 ggc agg gct atg tac gcc cct ccc atc gag ggc aac atc aca tgc aag       1350
Gly Arg Ala Met Tyr Ala Pro Pro Ile Glu Gly Asn Ile Thr Cys Lys
            425                 430                 435 agc aac atc acc ggc ctg ctc ctg gtc cgc gac ggc ggc gtg gaa agc       1398
Ser Asn Ile Thr Gly Leu Leu Leu Val Arg Asp Gly Gly Val Glu Ser
        440                 445                 450 aac gag aca gag atc ttc aga ccc ggc gga ggc gac atg cgg aac aac       1446
Asn Glu Thr Glu Ile Phe Arg Pro Gly Gly Gly Asp Met Arg Asn Asn
455                 460                 465                 470 tgg cgg agc gag ctg tac aag tac aag gtg gtg gaa atc aag ccc ctg       1494
Trp Arg Ser Glu Leu Tyr Lys Tyr Lys Val Val Glu Ile Lys Pro Leu
                475                 480                 485 gga atc gcc ccc acc gcc gcc aag cgg aga gtg gtg gaa agc gag aag       1542
Gly Ile Ala Pro Thr Ala Ala Lys Arg Arg Val Val Glu Ser Glu Lys
                490                 495                 500 tcc gcc gtg ggc ctg ggc gcc gtg atc ttc ggc ttt ctg gga gcc gcc       1590
Ser Ala Val Gly Leu Gly Ala Val Ile Phe Gly Phe Leu Gly Ala Ala
            505                 510                 515 gga agc acc atg ggc gct gcc agc atc acc ctg acc gtg cag gcc aga       1638
```

```
Gly Ser Thr Met Gly Ala Ala Ser Ile Thr Leu Thr Val Gln Ala Arg
        520                 525                 530 cag ctg ctg agc ggc atc gtg cag cag cag agc aac ctg ctg aag gcc    1686
Gln Leu Leu Ser Gly Ile Val Gln Gln Gln Ser Asn Leu Leu Lys Ala
535                 540                 545                 550 atc gag gcc cag cag cat ctg ctg cag ctg acc gtg tgg ggc atc aag    1734
Ile Glu Ala Gln Gln His Leu Leu Gln Leu Thr Val Trp Gly Ile Lys
                555                 560                 565 cag ctg cag acc cgg gtg ctg gcc atc gag aga tac ctg aag gac cag    1782
Gln Leu Gln Thr Arg Val Leu Ala Ile Glu Arg Tyr Leu Lys Asp Gln
            570                 575                 580 cag ctc ctg gga atc tgg ggc tgc agc ggc aag ctg atc tgc acc acc    1830
Gln Leu Leu Gly Ile Trp Gly Cys Ser Gly Lys Leu Ile Cys Thr Thr
        585                 590                 595 gcc gtg ccc tgg aac agc agc tgg tcc aac aag agc cac gac gag atc    1878
Ala Val Pro Trp Asn Ser Ser Trp Ser Asn Lys Ser His Asp Glu Ile
    600                 605                 610 tgg ggc aac atg acc tgg atg cag tgg gac aga gag atc agc aac tac    1926
Trp Gly Asn Met Thr Trp Met Gln Trp Asp Arg Glu Ile Ser Asn Tyr
615                 620                 625                 630 acc aac acc atc tac cgc ctg ctg gaa gat agc cag aac cag cag gaa    1974
Thr Asn Thr Ile Tyr Arg Leu Leu Glu Asp Ser Gln Asn Gln Gln Glu
                635                 640                 645 cag aac gag aag gac ctg ctg gcc ctg gac agc tgg gag aac ctg tgg    2022
Gln Asn Glu Lys Asp Leu Leu Ala Leu Asp Ser Trp Glu Asn Leu Trp
            650                 655                 660 aac tgg ttc agc atc acc aag tgg ctg tgg tac atc aag ggc gcc cac    2070
Asn Trp Phe Ser Ile Thr Lys Trp Leu Trp Tyr Ile Lys Gly Ala His
        665                 670                 675 cac cac cat cac cac tgc tgactcgagt ctagagggcc cgtttaaacc cgc       2121
His His His His His Cys
            680

<210> SEQ ID NO 96
<211> LENGTH: 684
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
                20                  25                  30

Tyr Tyr Gly Val Pro Val Trp Lys Glu Ala Lys Thr Thr Leu Phe Cys
            35                  40                  45

Ala Ser Asp Ala Lys Ala Tyr Glu Lys Glu Val His Asn Val Trp Ala
        50                  55                  60

Thr His Ala Cys Val Pro Thr Asp Pro Asn Pro Gln Glu Met Val Leu
65                  70                  75                  80

Glu Asn Val Thr Glu Asn Phe Asn Met Trp Lys Asn Asp Met Val Glu
                85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu Glu Cys Arg Gln Val
        115                 120                 125

Asn Thr Thr Asn Ala Thr Ser Ser Val Asn Val Thr Asn Gly Glu Glu
130                 135                 140
```

```
Ile Lys Asn Cys Ser Phe Asn Ala Thr Thr Glu Ile Arg Asp Lys Lys
145                 150                 155                 160

Gln Lys Val Tyr Ala Leu Phe Tyr Arg Leu Asp Ile Val Pro Leu Glu
                165                 170                 175

Glu Glu Arg Lys Gly Asn Ser Ser Lys Tyr Arg Leu Ile Asn Cys Asn
            180                 185                 190

Thr Ser Ala Ile Thr Gln Ala Cys Pro Lys Val Thr Phe Asp Pro Ile
        195                 200                 205

Pro Ile His Tyr Cys Ala Pro Ala Gly Tyr Ala Ile Leu Lys Cys Asn
    210                 215                 220

Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu
                245                 250                 255

Asn Gly Ser Leu Ala Glu Gly Glu Ile Ile Ile Arg Ser Glu Asn Leu
            260                 265                 270

Thr Asn Asn Val Lys Thr Ile Ile Val His Leu Asn Glu Ser Val Glu
        275                 280                 285

Ile Val Cys Thr Arg Pro Asn Asn Thr Arg Lys Ser Ile Arg Ile
    290                 295                 300

Gly Pro Gly Gln Thr Phe Tyr Ala Thr Gly Asp Ile Ile Gly Asn Ile
305                 310                 315                 320

Arg Gln Ala Tyr Cys Asn Ile Lys Lys Asp Asp Trp Ile Arg Thr Leu
                325                 330                 335

Gln Arg Val Gly Lys Lys Leu Ala Glu His Phe Pro Arg Ile Ile
            340                 345                 350

Asn Phe Thr Ser Pro Ala Gly Gly Asp Leu Glu Ile Thr Thr His Ser
        355                 360                 365

Phe Asn Cys Arg Gly Glu Phe Phe Tyr Cys Asn Thr Ser Ser Leu Phe
    370                 375                 380

Asn Ser Thr Tyr Asn Pro Asn Asp Thr Asn Ser Asn Ser Ser Ser
385                 390                 395                 400

Asn Ser Ser Leu Asp Ile Thr Ile Pro Cys Arg Ile Lys Gln Ile Ile
                405                 410                 415

Asn Met Trp Gln Glu Val Gly Arg Ala Met Tyr Ala Pro Pro Ile Glu
            420                 425                 430

Gly Asn Ile Thr Cys Lys Ser Asn Ile Thr Gly Leu Leu Leu Val Arg
        435                 440                 445

Asp Gly Gly Val Glu Ser Asn Glu Thr Glu Ile Phe Arg Pro Gly Gly
    450                 455                 460

Gly Asp Met Arg Asn Asn Trp Arg Ser Glu Leu Tyr Lys Tyr Lys Val
465                 470                 475                 480

Val Glu Ile Lys Pro Leu Gly Ile Ala Pro Thr Ala Ala Lys Arg Arg
                485                 490                 495

Val Val Glu Ser Glu Lys Ser Ala Val Gly Leu Gly Ala Val Ile Phe
            500                 505                 510

Gly Phe Leu Gly Ala Ala Gly Ser Thr Met Gly Ala Ala Ser Ile Thr
        515                 520                 525

Leu Thr Val Gln Ala Arg Gln Leu Leu Ser Gly Ile Val Gln Gln Gln
    530                 535                 540

Ser Asn Leu Leu Lys Ala Ile Glu Ala Gln Gln His Leu Leu Gln Leu
545                 550                 555                 560

Thr Val Trp Gly Ile Lys Gln Leu Gln Thr Arg Val Leu Ala Ile Glu
```

```
                  565                 570                 575
Arg Tyr Leu Lys Asp Gln Gln Leu Leu Gly Ile Trp Gly Cys Ser Gly
            580                 585                 590

Lys Leu Ile Cys Thr Thr Ala Val Pro Trp Asn Ser Ser Trp Ser Asn
            595                 600                 605

Lys Ser His Asp Glu Ile Trp Gly Asn Met Thr Trp Met Gln Trp Asp
            610                 615                 620

Arg Glu Ile Ser Asn Tyr Thr Asn Thr Ile Tyr Arg Leu Leu Glu Asp
625                 630                 635                 640

Ser Gln Asn Gln Gln Glu Gln Asn Glu Lys Asp Leu Leu Ala Leu Asp
                645                 650                 655

Ser Trp Glu Asn Leu Trp Asn Trp Phe Ser Ile Thr Lys Trp Leu Trp
            660                 665                 670

Tyr Ile Lys Gly Ala His His His His His His Cys
            675                 680

<210> SEQ ID NO 97
<211> LENGTH: 2175
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (37)..(2142)

<400> SEQUENCE: 97
ccaagctggc tagcgtttaa acttaagctt gccacc atg cct atg ggc agc ctg          54
                                      Met Pro Met Gly Ser Leu
                                      1               5 cag cct ctg gcc acc ctg tac ctg ctg ggc atg ctg gtg gcc tcc gtg         102
Gln Pro Leu Ala Thr Leu Tyr Leu Leu Gly Met Leu Val Ala Ser Val
        10                  15                  20 ctg gca gct ggc aac ctg tgg gtc aca gtg tac tac ggc gtg ccc gtg         150
Leu Ala Ala Gly Asn Leu Trp Val Thr Val Tyr Tyr Gly Val Pro Val
            25                  30                  35 tgg aaa gag gcc aag acc acc ctg ttc tgc gcc agc gac gcc aag gcc         198
Trp Lys Glu Ala Lys Thr Thr Leu Phe Cys Ala Ser Asp Ala Lys Ala
40                  45                  50 tac gag aaa gag gtg cac aac gtc tgg gcc acc cac gcc tgc gtg ccc         246
Tyr Glu Lys Glu Val His Asn Val Trp Ala Thr His Ala Cys Val Pro
55                  60                  65                  70 acc gac ccc aac ccc cag gaa atg gtc ctg gaa aac gtg acc gag aac         294
Thr Asp Pro Asn Pro Gln Glu Met Val Leu Glu Asn Val Thr Glu Asn
                75                  80                  85 ttc aac atg tgg aag aac gac atg gtg gaa cag atg cac gag gac gtg         342
Phe Asn Met Trp Lys Asn Asp Met Val Glu Gln Met His Glu Asp Val
            90                  95                  100 atc agc ctg tgg gac cag agc ctg aag ccc tgc gtg aag ctg acc ccc         390
Ile Ser Leu Trp Asp Gln Ser Leu Lys Pro Cys Val Lys Leu Thr Pro
        105                 110                 115 ctg tgc gtg acc ctg gaa tgc aga cag gtc aac acc acc aac gcc acc         438
Leu Cys Val Thr Leu Glu Cys Arg Gln Val Asn Thr Thr Asn Ala Thr
120                 125                 130 agc agc gtg aac gtg acc aac ggc gag gaa atc aag aac tgc agc ttc         486
Ser Ser Val Asn Val Thr Asn Gly Glu Glu Ile Lys Asn Cys Ser Phe
135                 140                 145                 150 aat gcc acc acc gag atc cgg gac aag aaa cag aag gtg tac gcc ctg         534
Asn Ala Thr Thr Glu Ile Arg Asp Lys Lys Gln Lys Val Tyr Ala Leu
                155                 160                 165
```

-continued

| | |
|---|---|
| ttc tac cgg ctg gac atc gtg ccc ctg gaa gag gaa cgg aag ggc aac<br>Phe Tyr Arg Leu Asp Ile Val Pro Leu Glu Glu Glu Arg Lys Gly Asn<br>170                            175                          180 | 582 |
| agc agc aag tac cgg ctg atc aac tgc aac acc agc gcc atc acc cag<br>Ser Ser Lys Tyr Arg Leu Ile Asn Cys Asn Thr Ser Ala Ile Thr Gln<br>              185                          190                          195 | 630 |
| gcc tgc ccc aaa gtg acc ttc gac cct atc ccc atc cac tac tgc gcc<br>Ala Cys Pro Lys Val Thr Phe Asp Pro Ile Pro Ile His Tyr Cys Ala<br>200                            205                            210 | 678 |
| cct gcc ggc tac gcc atc ctg aag tgc aac aac aag acc ttc aac ggc<br>Pro Ala Gly Tyr Ala Ile Leu Lys Cys Asn Asn Lys Thr Phe Asn Gly<br>215                            220                          225                          230 | 726 |
| acc ggc ccc tgc aac aac gtg tcc acc gtg cag tgc acc cac ggc atc<br>Thr Gly Pro Cys Asn Asn Val Ser Thr Val Gln Cys Thr His Gly Ile<br>                          235                          240                          245 | 774 |
| aag ccc gtg gtg tcc acc cag ctg ctg ctg aat ggc agc ctg gcc gag<br>Lys Pro Val Val Ser Thr Gln Leu Leu Leu Asn Gly Ser Leu Ala Glu<br>                          250                            255                            260 | 822 |
| ggc gag atc atc atc aga agc gag aac ctg acc aac aac gtg aaa acc<br>Gly Glu Ile Ile Ile Arg Ser Glu Asn Leu Thr Asn Asn Val Lys Thr<br>              265                          270                          275 | 870 |
| atc atc gtg cac ctg aac gag agc gtg gaa atc gtg tgc acc cgg ccc<br>Ile Ile Val His Leu Asn Glu Ser Val Glu Ile Val Cys Thr Arg Pro<br>280                            285                            290 | 918 |
| aac aac aac acc aga aag agc atc cgg atc ggc cct ggc cag acc ttt<br>Asn Asn Asn Thr Arg Lys Ser Ile Arg Ile Gly Pro Gly Gln Thr Phe<br>295                            300                            305                          310 | 966 |
| tac gcc acc ggc gac atc atc ggc aac atc cgg cag gcc tac tgc aac<br>Tyr Ala Thr Gly Asp Ile Ile Gly Asn Ile Arg Gln Ala Tyr Cys Asn<br>                          315                            320                          325 | 1014 |
| atc aag aag gac gac tgg atc cgg acc ctg cag aga gtg ggc aag aag<br>Ile Lys Lys Asp Asp Trp Ile Arg Thr Leu Gln Arg Val Gly Lys Lys<br>              330                          335                          340 | 1062 |
| ctg gcc gag cac ttc ccc aga cgg atc atc aac ttc acc agc ccc gct<br>Leu Ala Glu His Phe Pro Arg Arg Ile Ile Asn Phe Thr Ser Pro Ala<br>                          345                            350                          355 | 1110 |
| ggc ggc gac ctg gaa atc acc acc cac agc ttc aac tgc aga ggc gag<br>Gly Gly Asp Leu Glu Ile Thr Thr His Ser Phe Asn Cys Arg Gly Glu<br>360                            365                            370 | 1158 |
| ttc ttc tac tgc aat acc agc agc ctg ttc aac agc acc tac aac ccc<br>Phe Phe Tyr Cys Asn Thr Ser Ser Leu Phe Asn Ser Thr Tyr Asn Pro<br>375                            380                            385                          390 | 1206 |
| aac gac acc aac agc aac agc tcc agc agc aac tcc agc ctg gac atc<br>Asn Asp Thr Asn Ser Asn Ser Ser Ser Ser Asn Ser Ser Leu Asp Ile<br>                          395                            400                          405 | 1254 |
| acc atc cct tgc cgg atc aag cag atc atc aat atg tgg cag gaa gtg<br>Thr Ile Pro Cys Arg Ile Lys Gln Ile Ile Asn Met Trp Gln Glu Val<br>                          410                            415                          420 | 1302 |
| ggc agg gct atg tac gcc cct ccc atc gag ggc aac atc aca tgc aag<br>Gly Arg Ala Met Tyr Ala Pro Pro Ile Glu Gly Asn Ile Thr Cys Lys<br>                        425                            430                          435 | 1350 |
| agc aac atc acc ggc ctc ctg ctg gtc cgc gac ggc ggc gtg gaa agc<br>Ser Asn Ile Thr Gly Leu Leu Leu Val Arg Asp Gly Gly Val Glu Ser<br>440                            445                            450 | 1398 |
| aac gag aca gag atc ttc aga ccc gga gga ggc gac atg cgg aac aac<br>Asn Glu Thr Glu Ile Phe Arg Pro Gly Gly Gly Asp Met Arg Asn Asn<br>455                            460                            465                          470 | 1446 |
| tgg cgg agc gag ctg tac aag tac aag gtg gtg gaa atc aag ccc ctg<br>Trp Arg Ser Glu Leu Tyr Lys Tyr Lys Val Val Glu Ile Lys Pro Leu<br>                          475                            480                          485 | 1494 |

| | | | | | | | | | | | | | | |
|---|---|---|---|---|---|---|---|---|---|---|---|---|---|---|
| gga | atc | gcc | ccc | acc | gcc | gcc | aag | cgg | aga | gtg | gtg | gaa | agc | gag | aag | 1542 |
| Gly | Ile | Ala | Pro | Thr | Ala | Ala | Lys | Arg | Arg | Val | Val | Glu | Ser | Glu | Lys | |
| | | | 490 | | | | 495 | | | | | 500 | | | | |

```
gga atc gcc ccc acc gcc gcc aag cgg aga gtg gtg gaa agc gag aag    1542
Gly Ile Ala Pro Thr Ala Ala Lys Arg Arg Val Val Glu Ser Glu Lys
            490                 495                 500 tcc gcc gtg ggc ctg ggc gcc gtg atc ttc ggc ttt ctg gga gcc gcc    1590
Ser Ala Val Gly Leu Gly Ala Val Ile Phe Gly Phe Leu Gly Ala Ala
                505                 510                 515 gga agc acc atg ggc gct gcc agc atc acc ctg acc gtg cag gcc aga    1638
Gly Ser Thr Met Gly Ala Ala Ser Ile Thr Leu Thr Val Gln Ala Arg
        520                 525                 530 cag ctg ctg agc ggc atc gtg cag cag cag agc aac ctg ctg aag gcc    1686
Gln Leu Leu Ser Gly Ile Val Gln Gln Gln Ser Asn Leu Leu Lys Ala
535                 540                 545                 550 atc gag gcc cag cag cat ctg ctg cag ctg acc gtg tgg ggc atc aag    1734
Ile Glu Ala Gln Gln His Leu Leu Gln Leu Thr Val Trp Gly Ile Lys
                555                 560                 565 cag ctg cag acc cgg gtg ctg gcc atc gag aga tac ctg aag gac cag    1782
Gln Leu Gln Thr Arg Val Leu Ala Ile Glu Arg Tyr Leu Lys Asp Gln
            570                 575                 580 cag ctc ctg gga atc tgg ggc tgc agc ggc aag ctg atc tgc acc acc    1830
Gln Leu Leu Gly Ile Trp Gly Cys Ser Gly Lys Leu Ile Cys Thr Thr
        585                 590                 595 gcc gtg ccc tgg aac agc agc tgg tcc aac aag agc cac gac gag atc    1878
Ala Val Pro Trp Asn Ser Ser Trp Ser Asn Lys Ser His Asp Glu Ile
600                 605                 610 tgg ggc aac atg acc tgg atg cag tgg gac aga gag atc agc aac tac    1926
Trp Gly Asn Met Thr Trp Met Gln Trp Asp Arg Glu Ile Ser Asn Tyr
615                 620                 625                 630 acc aac acc atc tac cgc ctg ctg gaa gat agc cag aac cag cag gaa    1974
Thr Asn Thr Ile Tyr Arg Leu Leu Glu Asp Ser Gln Asn Gln Gln Glu
                635                 640                 645 cag aac gag aag gac ctg ctg gcc ctg gac agc tgg gag aac ctg tgg    2022
Gln Asn Glu Lys Asp Leu Leu Ala Leu Asp Ser Trp Glu Asn Leu Trp
            650                 655                 660 aac tgg ttc agc atc acc aag tgg ctg tgg tac atc aag ggc gcc gga    2070
Asn Trp Phe Ser Ile Thr Lys Trp Leu Trp Tyr Ile Lys Gly Ala Gly
        665                 670                 675 ggc gga gcc aag ttt gtg gcc gcc tgg acc ctg aag gcc gct gct ggc    2118
Gly Gly Ala Lys Phe Val Ala Ala Trp Thr Leu Lys Ala Ala Ala Gly
    680                 685                 690 gga ggc cac cac cac cat cac cac tgactcgagt ctagagggcc cgtttaaacc   2172
Gly Gly His His His His His His
695                 700 cgc                                                                 2175

<210> SEQ ID NO 98
<211> LENGTH: 702
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
                20                  25                  30

Tyr Tyr Gly Val Pro Val Trp Lys Glu Ala Lys Thr Thr Leu Phe Cys
            35                  40                  45

Ala Ser Asp Ala Lys Ala Tyr Glu Lys Glu Val His Asn Val Trp Ala
```

-continued

```
                50                  55                  60
Thr His Ala Cys Val Pro Thr Asp Pro Asn Pro Gln Glu Met Val Leu
65                  70                  75                  80

Glu Asn Val Thr Glu Asn Phe Asn Met Trp Lys Asn Asp Met Val Glu
                85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu Glu Cys Arg Gln Val
            115                 120                 125

Asn Thr Thr Asn Ala Thr Ser Ser Val Asn Val Thr Asn Gly Glu Glu
        130                 135                 140

Ile Lys Asn Cys Ser Phe Asn Ala Thr Thr Glu Ile Arg Asp Lys Lys
145                 150                 155                 160

Gln Lys Val Tyr Ala Leu Phe Tyr Arg Leu Asp Ile Val Pro Leu Glu
                165                 170                 175

Glu Glu Arg Lys Gly Asn Ser Ser Lys Tyr Arg Leu Ile Asn Cys Asn
            180                 185                 190

Thr Ser Ala Ile Thr Gln Ala Cys Pro Lys Val Thr Phe Asp Pro Ile
            195                 200                 205

Pro Ile His Tyr Cys Ala Pro Ala Gly Tyr Ala Ile Leu Lys Cys Asn
        210                 215                 220

Asn Lys Thr Phe Asn Gly Thr Gly Pro Cys Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Gly Glu Ile Ile Ile Arg Ser Glu Asn Leu
            260                 265                 270

Thr Asn Asn Val Lys Thr Ile Ile Val His Leu Asn Glu Ser Val Glu
        275                 280                 285

Ile Val Cys Thr Arg Pro Asn Asn Asn Thr Arg Lys Ser Ile Arg Ile
290                 295                 300

Gly Pro Gly Gln Thr Phe Tyr Ala Thr Gly Asp Ile Ile Gly Asn Ile
305                 310                 315                 320

Arg Gln Ala Tyr Cys Asn Ile Lys Lys Asp Asp Trp Ile Arg Thr Leu
                325                 330                 335

Gln Arg Val Gly Lys Lys Leu Ala Glu His Phe Pro Arg Arg Ile Ile
            340                 345                 350

Asn Phe Thr Ser Pro Ala Gly Gly Asp Leu Glu Ile Thr Thr His Ser
        355                 360                 365

Phe Asn Cys Arg Gly Glu Phe Phe Tyr Cys Asn Thr Ser Ser Leu Phe
370                 375                 380

Asn Ser Thr Tyr Asn Pro Asn Asp Thr Asn Ser Asn Ser Ser Ser
385                 390                 395                 400

Asn Ser Ser Leu Asp Ile Thr Ile Pro Cys Arg Ile Lys Gln Ile Ile
                405                 410                 415

Asn Met Trp Gln Glu Val Gly Arg Ala Met Tyr Ala Pro Pro Ile Glu
            420                 425                 430

Gly Asn Ile Thr Cys Lys Ser Asn Ile Thr Gly Leu Leu Leu Val Arg
        435                 440                 445

Asp Gly Gly Val Glu Ser Asn Glu Thr Glu Ile Phe Arg Pro Gly Gly
        450                 455                 460

Gly Asp Met Arg Asn Asn Trp Arg Ser Glu Leu Tyr Lys Tyr Lys Val
465                 470                 475                 480
```

```
Val Glu Ile Lys Pro Leu Gly Ile Ala Pro Thr Ala Ala Lys Arg Arg
            485                 490                 495

Val Val Glu Ser Glu Lys Ser Ala Val Gly Leu Gly Ala Val Ile Phe
            500                 505                 510

Gly Phe Leu Gly Ala Ala Gly Ser Thr Met Gly Ala Ala Ser Ile Thr
            515                 520                 525

Leu Thr Val Gln Ala Arg Gln Leu Leu Ser Gly Ile Val Gln Gln Gln
            530                 535                 540

Ser Asn Leu Leu Lys Ala Ile Glu Ala Gln Gln His Leu Leu Gln Leu
545                 550                 555                 560

Thr Val Trp Gly Ile Lys Gln Leu Gln Thr Arg Val Leu Ala Ile Glu
            565                 570                 575

Arg Tyr Leu Lys Asp Gln Gln Leu Leu Gly Ile Trp Gly Cys Ser Gly
            580                 585                 590

Lys Leu Ile Cys Thr Thr Ala Val Pro Trp Asn Ser Ser Trp Ser Asn
            595                 600                 605

Lys Ser His Asp Glu Ile Trp Gly Asn Met Thr Trp Met Gln Trp Asp
            610                 615                 620

Arg Glu Ile Ser Asn Tyr Thr Asn Thr Ile Tyr Arg Leu Leu Glu Asp
625                 630                 635                 640

Ser Gln Asn Gln Gln Glu Gln Asn Glu Lys Asp Leu Leu Ala Leu Asp
            645                 650                 655

Ser Trp Glu Asn Leu Trp Asn Trp Phe Ser Ile Thr Lys Trp Leu Trp
            660                 665                 670

Tyr Ile Lys Gly Ala Gly Gly Gly Ala Lys Phe Val Ala Ala Trp Thr
            675                 680                 685

Leu Lys Ala Ala Ala Gly Gly Gly His His His His His His
            690                 695                 700

<210> SEQ ID NO 99
<211> LENGTH: 2241
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (37)..(2208)

<400> SEQUENCE: 99
ccaagctggc tagcgtttaa acttaagctt gccacc atg cct atg ggc agc ctg          54
                                       Met Pro Met Gly Ser Leu
                                       1               5 cag cct ctg gcc acc ctg tac ctg ctg ggc atg ctg gtg gcc tcc gtg         102
Gln Pro Leu Ala Thr Leu Tyr Leu Leu Gly Met Leu Val Ala Ser Val
            10                  15                  20 ctg gca gct ggc aac ctg tgg gtc aca gtg tac tac ggc gtg ccc gtg         150
Leu Ala Ala Gly Asn Leu Trp Val Thr Val Tyr Tyr Gly Val Pro Val
        25                  30                  35 tgg aaa gag gcc aag acc acc ctg ttc tgc gcc agc gac gcc aag gcc         198
Trp Lys Glu Ala Lys Thr Thr Leu Phe Cys Ala Ser Asp Ala Lys Ala
40                  45                  50 tac gag aaa gag gtg cac aac gtc tgg gcc acc cac gcc tgc gtg ccc         246
Tyr Glu Lys Glu Val His Asn Val Trp Ala Thr His Ala Cys Val Pro
55                  60                  65                  70 acc gac ccc aac ccc cag gaa atg gtc ctg gaa aac gtg acc gag aac         294
Thr Asp Pro Asn Pro Gln Glu Met Val Leu Glu Asn Val Thr Glu Asn
            75                  80                  85
```

| | | |
|---|---|---|
| ttc aac atg tgg aag aac gac atg gtg gaa cag atg cac gag gac gtg<br>Phe Asn Met Trp Lys Asn Asp Met Val Glu Gln Met His Glu Asp Val<br>90 95 100 | 342 | |
| atc agc ctg tgg gac cag agc ctg aag ccc tgc gtg aag ctg acc ccc<br>Ile Ser Leu Trp Asp Gln Ser Leu Lys Pro Cys Val Lys Leu Thr Pro<br>105 110 115 | 390 | |
| ctg tgc gtg acc ctg gaa tgc aga cag gtc aac acc aac gcc acc<br>Leu Cys Val Thr Leu Glu Cys Arg Gln Val Asn Thr Thr Asn Ala Thr<br>120 125 130 | 438 | |
| agc agc gtg aac gtg acc aac ggc gag gaa atc aag aac tgc agc ttc<br>Ser Ser Val Asn Val Thr Asn Gly Glu Glu Ile Lys Asn Cys Ser Phe<br>135 140 145 150 | 486 | |
| aat gcc acc acc gag atc cgg gac aag aaa cag aag gtg tac gcc ctg<br>Asn Ala Thr Thr Glu Ile Arg Asp Lys Lys Gln Lys Val Tyr Ala Leu<br>155 160 165 | 534 | |
| ttc tac cgg ctg gac atc gtg ccc ctg gaa gag gaa cgg aag ggc aac<br>Phe Tyr Arg Leu Asp Ile Val Pro Leu Glu Glu Glu Arg Lys Gly Asn<br>170 175 180 | 582 | |
| agc agc aag tac cgg ctg atc aac tgc aac acc agc gcc atc acc cag<br>Ser Ser Lys Tyr Arg Leu Ile Asn Cys Asn Thr Ser Ala Ile Thr Gln<br>185 190 195 | 630 | |
| gcc tgc ccc aaa gtg acc ttc gac cct atc ccc atc cac tac tgc gcc<br>Ala Cys Pro Lys Val Thr Phe Asp Pro Ile Pro Ile His Tyr Cys Ala<br>200 205 210 | 678 | |
| cct gcc ggc tac gcc atc ctg aag tgc aac aac aag acc ttc aac ggc<br>Pro Ala Gly Tyr Ala Ile Leu Lys Cys Asn Asn Lys Thr Phe Asn Gly<br>215 220 225 230 | 726 | |
| acc ggc ccc tgc aac aac gtg tcc acc gtg cag tgc acc cac ggc atc<br>Thr Gly Pro Cys Asn Asn Val Ser Thr Val Gln Cys Thr His Gly Ile<br>235 240 245 | 774 | |
| aag ccc gtg gtg tcc acc cag ctg ctg ctg aat ggc agc ctg gcc gag<br>Lys Pro Val Val Ser Thr Gln Leu Leu Leu Asn Gly Ser Leu Ala Glu<br>250 255 260 | 822 | |
| ggc gag atc atc atc aga agc gag aac ctg acc aac aac gtg aaa acc<br>Gly Glu Ile Ile Ile Arg Ser Glu Asn Leu Thr Asn Asn Val Lys Thr<br>265 270 275 | 870 | |
| atc atc gtg cac ctg aac gag agc gtg gaa atc gtg tgc acc cgg ccc<br>Ile Ile Val His Leu Asn Glu Ser Val Glu Ile Val Cys Thr Arg Pro<br>280 285 290 | 918 | |
| aac aac aac acc aga aag agc atc cgg atc ggc cct ggc cag acc ttt<br>Asn Asn Asn Thr Arg Lys Ser Ile Arg Ile Gly Pro Gly Gln Thr Phe<br>295 300 305 310 | 966 | |
| tac gcc acc ggc gac atc atc ggc aac atc cgg cag gcc tac tgc aac<br>Tyr Ala Thr Gly Asp Ile Ile Gly Asn Ile Arg Gln Ala Tyr Cys Asn<br>315 320 325 | 1014 | |
| atc aag aag gac gac tgg atc cgg acc ctg cag aga gtg ggc aag aag<br>Ile Lys Lys Asp Asp Trp Ile Arg Thr Leu Gln Arg Val Gly Lys Lys<br>330 335 340 | 1062 | |
| ctg gcc gag cac ttc ccc aga cgg atc atc aac ttc acc agc ccc gct<br>Leu Ala Glu His Phe Pro Arg Arg Ile Ile Asn Phe Thr Ser Pro Ala<br>345 350 355 | 1110 | |
| ggc ggc gac ctg gaa atc acc acc cac agc ttc aac tgc aga ggc gag<br>Gly Gly Asp Leu Glu Ile Thr Thr His Ser Phe Asn Cys Arg Gly Glu<br>360 365 370 | 1158 | |
| ttc ttc tac tgc aat acc agc agc ctg ttc aac agc acc tac aac ccc<br>Phe Phe Tyr Cys Asn Thr Ser Ser Leu Phe Asn Ser Thr Tyr Asn Pro<br>375 380 385 390 | 1206 | |
| aac gac acc aac agc aac agc tcc agc agc aac tcc agc ctg gac atc<br>Asn Asp Thr Asn Ser Asn Ser Ser Ser Ser Asn Ser Ser Leu Asp Ile<br>395 400 405 | 1254 | |

```
acc atc cct tgc cgg atc aag cag atc atc aat atg tgg cag gaa gtg   1302
Thr Ile Pro Cys Arg Ile Lys Gln Ile Ile Asn Met Trp Gln Glu Val
        410                 415                 420 ggc agg gct atg tac gcc cct ccc atc gag ggc aac atc aca tgc aag   1350
Gly Arg Ala Met Tyr Ala Pro Pro Ile Glu Gly Asn Ile Thr Cys Lys
            425                 430                 435 agc aac atc acc ggc ctg ctc ctg gtc cgc gac ggc ggc gtg gaa agc   1398
Ser Asn Ile Thr Gly Leu Leu Leu Val Arg Asp Gly Gly Val Glu Ser
440                 445                 450 aac gag aca gag atc ttc aga ccc ggc gga ggc gac atg cgg aac aac   1446
Asn Glu Thr Glu Ile Phe Arg Pro Gly Gly Gly Asp Met Arg Asn Asn
455                 460                 465                 470 tgg cgg agc gag ctg tac aag tac aag gtg gtg gaa atc aag ccc ctg   1494
Trp Arg Ser Glu Leu Tyr Lys Tyr Lys Val Val Glu Ile Lys Pro Leu
                475                 480                 485 gga atc gcc ccc acc gcc gcc aag cgg aga gtg gtg gaa agc gag aag   1542
Gly Ile Ala Pro Thr Ala Ala Lys Arg Arg Val Val Glu Ser Glu Lys
            490                 495                 500 tcc gcc gtg ggc ctg ggc gcc gtg atc ttc ggc ttt ctg gga gcc gcc   1590
Ser Ala Val Gly Leu Gly Ala Val Ile Phe Gly Phe Leu Gly Ala Ala
        505                 510                 515 gga agc acc atg ggc gct gcc agc atc acc ctg acc gtg cag gcc aga   1638
Gly Ser Thr Met Gly Ala Ala Ser Ile Thr Leu Thr Val Gln Ala Arg
    520                 525                 530 cag ctg ctg agc ggc atc gtg cag cag cag agc aac ctg ctg aag gcc   1686
Gln Leu Leu Ser Gly Ile Val Gln Gln Gln Ser Asn Leu Leu Lys Ala
535                 540                 545                 550 atc gag gcc cag cag cat ctg ctg cag ctg acc gtg tgg ggc atc aag   1734
Ile Glu Ala Gln Gln His Leu Leu Gln Leu Thr Val Trp Gly Ile Lys
                555                 560                 565 cag ctg cag acc cgg gtg ctg gcc atc gag aga tac ctg aag gac cag   1782
Gln Leu Gln Thr Arg Val Leu Ala Ile Glu Arg Tyr Leu Lys Asp Gln
            570                 575                 580 cag ctc ctg gga atc tgg ggc tgc agc ggc aag ctg atc tgc acc acc   1830
Gln Leu Leu Gly Ile Trp Gly Cys Ser Gly Lys Leu Ile Cys Thr Thr
        585                 590                 595 gcc gtg ccc tgg aac agc agc tgg tcc aac aag agc cac gac gag atc   1878
Ala Val Pro Trp Asn Ser Ser Trp Ser Asn Lys Ser His Asp Glu Ile
    600                 605                 610 tgg ggc aac atg acc tgg atg cag tgg gac aga gag atc agc aac tac   1926
Trp Gly Asn Met Thr Trp Met Gln Trp Asp Arg Glu Ile Ser Asn Tyr
615                 620                 625                 630 acc aac acc atc tac cgc ctg ctg gaa gat agc cag aac cag cag gaa   1974
Thr Asn Thr Ile Tyr Arg Leu Leu Glu Asp Ser Gln Asn Gln Gln Glu
                635                 640                 645 cag aac gag aag gac ctg ctg gcc ctg gac agc tgg gag aac ctg tgg   2022
Gln Asn Glu Lys Asp Leu Leu Ala Leu Asp Ser Trp Glu Asn Leu Trp
            650                 655                 660 aac tgg ttc agc atc acc aag tgg ctg tgg tac atc aag atc ttc atc   2070
Asn Trp Phe Ser Ile Thr Lys Trp Leu Trp Tyr Ile Lys Ile Phe Ile
        665                 670                 675 atg atc gtg ggc ggc ctg atc ggc ctg cgg atc atc ttc gcc gtg ctg   2118
Met Ile Val Gly Gly Leu Ile Gly Leu Arg Ile Ile Phe Ala Val Leu
    680                 685                 690 agc gtg gtg gga ggc gga gcc aag ttt gtg gcc gcc tgg acc ctg aaa   2166
Ser Val Val Gly Gly Gly Ala Lys Phe Val Ala Ala Trp Thr Leu Lys
695                 700                 705                 710 gcc gct gcc ggc gga acc gag aca agc cag gtg gcc cct gcc            2208
Ala Ala Ala Gly Gly Thr Glu Thr Ser Gln Val Ala Pro Ala
                715                 720
```
tgactcgagt ctagagggcc cgtttaaacc cgc					2241

<210> SEQ ID NO 100
<211> LENGTH: 724
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 100

```
Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
            20                  25                  30

Tyr Tyr Gly Val Pro Val Trp Lys Glu Ala Lys Thr Thr Leu Phe Cys
        35                  40                  45

Ala Ser Asp Ala Lys Ala Tyr Glu Lys Glu Val His Asn Val Trp Ala
    50                  55                  60

Thr His Ala Cys Val Pro Thr Asp Pro Asn Pro Gln Glu Met Val Leu
65                  70                  75                  80

Glu Asn Val Thr Glu Asn Phe Asn Met Trp Lys Asn Asp Met Val Glu
                85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu Glu Cys Arg Gln Val
        115                 120                 125

Asn Thr Thr Asn Ala Thr Ser Ser Val Asn Val Thr Asn Gly Glu Glu
    130                 135                 140

Ile Lys Asn Cys Ser Phe Asn Ala Thr Thr Glu Ile Arg Asp Lys Lys
145                 150                 155                 160

Gln Lys Val Tyr Ala Leu Phe Tyr Arg Leu Asp Ile Val Pro Leu Glu
                165                 170                 175

Glu Glu Arg Lys Gly Asn Ser Ser Lys Tyr Arg Leu Ile Asn Cys Asn
            180                 185                 190

Thr Ser Ala Ile Thr Gln Ala Cys Pro Lys Val Thr Phe Asp Pro Ile
        195                 200                 205

Pro Ile His Tyr Cys Ala Pro Ala Gly Tyr Ala Ile Leu Lys Cys Asn
    210                 215                 220

Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Gly Glu Ile Ile Arg Ser Glu Asn Leu
            260                 265                 270

Thr Asn Asn Val Lys Thr Ile Ile Val His Leu Asn Glu Ser Val Glu
        275                 280                 285

Ile Val Cys Thr Arg Pro Asn Asn Asn Thr Arg Lys Ser Ile Arg Ile
    290                 295                 300

Gly Pro Gly Gln Thr Phe Tyr Ala Thr Gly Asp Ile Ile Gly Asn Ile
305                 310                 315                 320

Arg Gln Ala Tyr Cys Asn Ile Lys Lys Asp Asp Trp Ile Arg Thr Leu
                325                 330                 335

Gln Arg Val Gly Lys Lys Leu Ala Glu His Phe Pro Arg Arg Ile Ile
            340                 345                 350

Asn Phe Thr Ser Pro Ala Gly Gly Asp Leu Glu Ile Thr Thr His Ser
```

```
                355                 360                 365
Phe Asn Cys Arg Gly Glu Phe Phe Tyr Cys Asn Thr Ser Ser Leu Phe
370                 375                 380

Asn Ser Thr Tyr Asn Pro Asn Asp Thr Asn Ser Asn Ser Ser Ser
385                 390                 395                 400

Asn Ser Ser Leu Asp Ile Thr Ile Pro Cys Arg Ile Lys Gln Ile Ile
            405                 410                 415

Asn Met Trp Gln Glu Val Gly Arg Ala Met Tyr Ala Pro Pro Ile Glu
            420                 425                 430

Gly Asn Ile Thr Cys Lys Ser Asn Ile Thr Gly Leu Leu Leu Val Arg
            435                 440                 445

Asp Gly Gly Val Glu Ser Asn Glu Thr Glu Ile Phe Arg Pro Gly Gly
            450                 455                 460

Gly Asp Met Arg Asn Asn Trp Arg Ser Glu Leu Tyr Lys Tyr Lys Val
465                 470                 475                 480

Val Glu Ile Lys Pro Leu Gly Ile Ala Pro Thr Ala Ala Lys Arg Arg
                485                 490                 495

Val Val Glu Ser Glu Lys Ser Ala Val Gly Leu Gly Ala Val Ile Phe
            500                 505                 510

Gly Phe Leu Gly Ala Ala Gly Ser Thr Met Gly Ala Ala Ser Ile Thr
        515                 520                 525

Leu Thr Val Gln Ala Arg Gln Leu Leu Ser Gly Ile Val Gln Gln Gln
530                 535                 540

Ser Asn Leu Leu Lys Ala Ile Glu Ala Gln Gln His Leu Leu Gln Leu
545                 550                 555                 560

Thr Val Trp Gly Ile Lys Gln Leu Gln Thr Arg Val Leu Ala Ile Glu
                565                 570                 575

Arg Tyr Leu Lys Asp Gln Gln Leu Leu Gly Ile Trp Gly Cys Ser Gly
            580                 585                 590

Lys Leu Ile Cys Thr Thr Ala Val Pro Trp Asn Ser Ser Trp Ser Asn
            595                 600                 605

Lys Ser His Asp Glu Ile Trp Gly Asn Met Thr Trp Met Gln Trp Asp
610                 615                 620

Arg Glu Ile Ser Asn Tyr Thr Asn Thr Ile Tyr Arg Leu Leu Glu Asp
625                 630                 635                 640

Ser Gln Asn Gln Gln Glu Gln Asn Glu Lys Asp Leu Leu Ala Leu Asp
                645                 650                 655

Ser Trp Glu Asn Leu Trp Asn Trp Phe Ser Ile Thr Lys Trp Leu Trp
            660                 665                 670

Tyr Ile Lys Ile Phe Ile Met Ile Val Gly Gly Leu Ile Gly Leu Arg
            675                 680                 685

Ile Ile Phe Ala Val Leu Ser Val Val Gly Gly Ala Lys Phe Val
690                 695                 700

Ala Ala Trp Thr Leu Lys Ala Ala Ala Gly Gly Thr Glu Thr Ser Gln
705                 710                 715                 720

Val Ala Pro Ala

<210> SEQ ID NO 101
<211> LENGTH: 1586
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
```

<222> LOCATION: (42)..(1547)

<400> SEQUENCE: 101

```
gagcggaagg cccatgaggc cagttaatta agcttgccac c atg cct atg ggc agc        56
                                             Met Pro Met Gly Ser
                                              1               5 ctg cag cct ctg gcc acc ctg tac ctg ctg ggc atg ctg gtg gcc tcc         104
Leu Gln Pro Leu Ala Thr Leu Tyr Leu Leu Gly Met Leu Val Ala Ser
             10                  15                  20 gtg ctg gca gct ggc aac ctg tgg gtc aca gtg tac tac ggc gtg ccc         152
Val Leu Ala Ala Gly Asn Leu Trp Val Thr Val Tyr Tyr Gly Val Pro
         25                  30                  35 gtg tgg aaa gag gcc acc acc acc ctg ttc tgc gcc agc gac gcc aag         200
Val Trp Lys Glu Ala Thr Thr Thr Leu Phe Cys Ala Ser Asp Ala Lys
     40                  45                  50 gcc tac gac aaa gag gtg cac aac gtc tgg gcc acc cac gcc tgc gtg         248
Ala Tyr Asp Lys Glu Val His Asn Val Trp Ala Thr His Ala Cys Val
 55                  60                  65 ccc acc gac ccc aac ccc cag gaa atg gtc ctg ggc aac gtg acc gag         296
Pro Thr Asp Pro Asn Pro Gln Glu Met Val Leu Gly Asn Val Thr Glu
 70                  75                  80                  85 aac ttc aac atg tgg aag aac gag atg gtc aac cag atg cac gag gac         344
Asn Phe Asn Met Trp Lys Asn Glu Met Val Asn Gln Met His Glu Asp
                 90                  95                 100 gtg atc agc ctg tgg gac cag agc ctg aag ccc tgc gtg aag ctg acc         392
Val Ile Ser Leu Trp Asp Gln Ser Leu Lys Pro Cys Val Lys Leu Thr
            105                 110                 115 ccc ctg tgc gtg acc ctg gaa tgc tcc aac gtg acc tac aac gag agc         440
Pro Leu Cys Val Thr Leu Glu Cys Ser Asn Val Thr Tyr Asn Glu Ser
        120                 125                 130 atg aag gaa gtg aag aac tgc agc ttc aac ctg acc acc gag ctg cgg         488
Met Lys Glu Val Lys Asn Cys Ser Phe Asn Leu Thr Thr Glu Leu Arg
    135                 140                 145 gac aag aaa cag aag gtg cac gcc ctg ttc tac cgg ctg gac atc gtg         536
Asp Lys Lys Gln Lys Val His Ala Leu Phe Tyr Arg Leu Asp Ile Val
150                 155                 160                 165 ccc ctg aac gac acc gag aag aag aac agc agc cgg ccc tac cgg ctg         584
Pro Leu Asn Asp Thr Glu Lys Lys Asn Ser Ser Arg Pro Tyr Arg Leu
                170                 175                 180 atc aac tgc aac acc agc gcc atc acc cag gcc tgc ccc aaa gtg acc         632
Ile Asn Cys Asn Thr Ser Ala Ile Thr Gln Ala Cys Pro Lys Val Thr
            185                 190                 195 ttc gac cct atc ccc atc cac tac tgc acc cct gcc ggc tac gcc atc         680
Phe Asp Pro Ile Pro Ile His Tyr Cys Thr Pro Ala Gly Tyr Ala Ile
        200                 205                 210 ctg aag tgc aac gac aag aag ttc aac ggc acc ggc ccc tgc cac aag         728
Leu Lys Cys Asn Asp Lys Lys Phe Asn Gly Thr Gly Pro Cys His Lys
    215                 220                 225 gtg tcc acc gtg cag tgc acc cac ggc atc aag ccc gtg gtg tcc acc         776
Val Ser Thr Val Gln Cys Thr His Gly Ile Lys Pro Val Val Ser Thr
230                 235                 240                 245 cag ctg ctg ctg aat ggc agc ctg gcc gag ggc gag atc atc atc aga         824
Gln Leu Leu Leu Asn Gly Ser Leu Ala Glu Gly Glu Ile Ile Ile Arg
                250                 255                 260 agc gag aac ctg acc aac aac gcc aag acc atc att gtg cac ctg aac         872
Ser Glu Asn Leu Thr Asn Asn Ala Lys Thr Ile Ile Val His Leu Asn
            265                 270                 275 cag agc gtg gaa atc gtg tgc gcc aga ccc agc aac aac acc cgg acc         920
Gln Ser Val Glu Ile Val Cys Ala Arg Pro Ser Asn Asn Thr Arg Thr
        280                 285                 290
```

```
agc atc cgg atc ggc cct ggc cag acc ttc tat gcc acc ggc gcc att      968
Ser Ile Arg Ile Gly Pro Gly Gln Thr Phe Tyr Ala Thr Gly Ala Ile
    295                 300                 305 acc ggc gac atc aga cag gcc cac tgc aac atc agc aag gac aag tgg     1016
Thr Gly Asp Ile Arg Gln Ala His Cys Asn Ile Ser Lys Asp Lys Trp
310                 315                 320                 325 aac gag aca ctg cag aga gtg ggc gag aag ctg gcc gag cac ttc ccc     1064
Asn Glu Thr Leu Gln Arg Val Gly Glu Lys Leu Ala Glu His Phe Pro
                330                 335                 340 aac aag aca atc aag ttc aac agc agc tct ggc ggc gac ctg gaa atc     1112
Asn Lys Thr Ile Lys Phe Asn Ser Ser Ser Gly Gly Asp Leu Glu Ile
            345                 350                 355 acc acc cac agc ttc aac tgc aga ggc gag ttc ttc tac tgc aat acc     1160
Thr Thr His Ser Phe Asn Cys Arg Gly Glu Phe Phe Tyr Cys Asn Thr
        360                 365                 370 tcc ggc ctg ttc aat ggc acc ttt aac ggc acc tac gtg tcc ccc aac     1208
Ser Gly Leu Phe Asn Gly Thr Phe Asn Gly Thr Tyr Val Ser Pro Asn
    375                 380                 385 agc acc gac agc aac agc tcc agc atc atc acc atc cct tgc cgg atc     1256
Ser Thr Asp Ser Asn Ser Ser Ser Ile Ile Thr Ile Pro Cys Arg Ile
390                 395                 400                 405 aag cag atc atc aat atg tgg cag gaa gtg ggc agg gct atg tac gcc     1304
Lys Gln Ile Ile Asn Met Trp Gln Glu Val Gly Arg Ala Met Tyr Ala
                410                 415                 420 cct cct atc gcc ggc aac atc aca tgc aag agc aac atc acc ggc ctg     1352
Pro Pro Ile Ala Gly Asn Ile Thr Cys Lys Ser Asn Ile Thr Gly Leu
            425                 430                 435 ctg ctc gtc cgc gac ggc gga aca ggc agc gag agc aac aag acc gag     1400
Leu Leu Val Arg Asp Gly Gly Thr Gly Ser Glu Ser Asn Lys Thr Glu
        440                 445                 450 atc ttc aga ccc ggc gga ggc gac atg cgg gac aat tgg cgg agc gag     1448
Ile Phe Arg Pro Gly Gly Gly Asp Met Arg Asp Asn Trp Arg Ser Glu
    455                 460                 465 ctg tac aag tac aag gtg gtg gaa atc aag ccc ctg ggc gtg gcc ccc     1496
Leu Tyr Lys Tyr Lys Val Val Glu Ile Lys Pro Leu Gly Val Ala Pro
470                 475                 480                 485 acc aag gcc aag cgg aga gtg gtg gaa ggc gcc cac cac cac cat cac     1544
Thr Lys Ala Lys Arg Arg Val Val Glu Gly Ala His His His His His
                490                 495                 500 cac tgactcgagg cgcgcctagg ccttgacggc cttccgcca                      1586
His
```

<210> SEQ ID NO 102
<211> LENGTH: 502
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

```
Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
            20                  25                  30

Tyr Tyr Gly Val Pro Val Trp Lys Glu Ala Thr Thr Thr Leu Phe Cys
        35                  40                  45

Ala Ser Asp Ala Lys Ala Tyr Asp Lys Glu Val His Asn Val Trp Ala
    50                  55                  60

Thr His Ala Cys Val Pro Thr Asp Pro Asn Pro Gln Glu Met Val Leu
65                  70                  75                  80
```

```
Gly Asn Val Thr Glu Asn Phe Asn Met Trp Lys Asn Glu Met Val Asn
            85                  90                  95
Gln Met His Glu Asp Val Ile Ser Leu Trp Asp Gln Ser Leu Lys Pro
           100                 105                 110
Cys Val Lys Leu Thr Pro Leu Cys Val Thr Leu Glu Cys Ser Asn Val
           115                 120                 125
Thr Tyr Asn Glu Ser Met Lys Glu Val Lys Asn Cys Ser Phe Asn Leu
130                 135                 140
Thr Thr Glu Leu Arg Asp Lys Lys Gln Lys Val His Ala Leu Phe Tyr
145                 150                 155                 160
Arg Leu Asp Ile Val Pro Leu Asn Asp Thr Glu Lys Lys Asn Ser Ser
                165                 170                 175
Arg Pro Tyr Arg Leu Ile Asn Cys Asn Thr Ser Ala Ile Thr Gln Ala
            180                 185                 190
Cys Pro Lys Val Thr Phe Asp Pro Ile Pro Ile His Tyr Cys Thr Pro
            195                 200                 205
Ala Gly Tyr Ala Ile Leu Lys Cys Asn Asp Lys Lys Phe Asn Gly Thr
210                 215                 220
Gly Pro Cys His Lys Val Ser Thr Val Gln Cys Thr His Gly Ile Lys
225                 230                 235                 240
Pro Val Val Ser Thr Gln Leu Leu Leu Asn Gly Ser Leu Ala Glu Gly
                245                 250                 255
Glu Ile Ile Ile Arg Ser Glu Asn Leu Thr Asn Asn Ala Lys Thr Ile
                260                 265                 270
Ile Val His Leu Asn Gln Ser Val Glu Ile Val Cys Ala Arg Pro Ser
            275                 280                 285
Asn Asn Thr Arg Thr Ser Ile Arg Ile Gly Pro Gly Gln Thr Phe Tyr
            290                 295                 300
Ala Thr Gly Ala Ile Thr Gly Asp Ile Arg Gln Ala His Cys Asn Ile
305                 310                 315                 320
Ser Lys Asp Lys Trp Asn Glu Thr Leu Gln Arg Val Gly Glu Lys Leu
                325                 330                 335
Ala Glu His Phe Pro Asn Lys Thr Ile Lys Phe Asn Ser Ser Ser Gly
            340                 345                 350
Gly Asp Leu Glu Ile Thr Thr His Ser Phe Asn Cys Arg Gly Glu Phe
            355                 360                 365
Phe Tyr Cys Asn Thr Ser Gly Leu Phe Asn Gly Thr Phe Asn Gly Thr
            370                 375                 380
Tyr Val Ser Pro Asn Ser Thr Asp Ser Asn Ser Ser Ser Ile Ile Thr
385                 390                 395                 400
Ile Pro Cys Arg Ile Lys Gln Ile Ile Asn Met Trp Gln Glu Val Gly
                405                 410                 415
Arg Ala Met Tyr Ala Pro Pro Ile Ala Gly Asn Ile Thr Cys Lys Ser
            420                 425                 430
Asn Ile Thr Gly Leu Leu Leu Val Arg Asp Gly Gly Thr Gly Ser Glu
            435                 440                 445
Ser Asn Lys Thr Glu Ile Phe Arg Pro Gly Gly Gly Asp Met Arg Asp
450                 455                 460
Asn Trp Arg Ser Glu Leu Tyr Lys Tyr Lys Val Val Glu Ile Lys Pro
465                 470                 475                 480
Leu Gly Val Ala Pro Thr Lys Ala Lys Arg Arg Val Val Glu Gly Ala
                485                 490                 495
His His His His His His
```

<210> SEQ ID NO 103
<211> LENGTH: 2226
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (37)..(2193)

<400> SEQUENCE: 103

```
ccaagctggc tagcgtttaa acttaagctt gccacc atg cct atg ggc agc ctg        54
                                       Met Pro Met Gly Ser Leu
                                       1               5 cag cct ctg gcc acc ctg tac ctg ctg ggc atg ctg gtg gcc tcc gtg       102
Gln Pro Leu Ala Thr Leu Tyr Leu Leu Gly Met Leu Val Ala Ser Val
             10                  15                  20 ctg gca gct ggc aac ctg tgg gtc aca gtg tac tac ggc gtg ccc gtg       150
Leu Ala Ala Gly Asn Leu Trp Val Thr Val Tyr Tyr Gly Val Pro Val
         25                  30                  35 tgg aaa gag gcc acc acc acc ctg ttc tgc gcc agc gac gcc aag gcc       198
Trp Lys Glu Ala Thr Thr Thr Leu Phe Cys Ala Ser Asp Ala Lys Ala
 40                  45                  50 tac gac aaa gag gtg cac aac gtc tgg gcc acc cac gcc tgc gtg ccc       246
Tyr Asp Lys Glu Val His Asn Val Trp Ala Thr His Ala Cys Val Pro
 55                  60                  65                  70 acc gac ccc aac ccc cag gaa atg gtc ctg ggc aac gtg acc gag aac       294
Thr Asp Pro Asn Pro Gln Glu Met Val Leu Gly Asn Val Thr Glu Asn
                 75                  80                  85 ttc aac atg tgg aag aac gag atg gtc aac cag atg cac gag gac gtg       342
Phe Asn Met Trp Lys Asn Glu Met Val Asn Gln Met His Glu Asp Val
             90                  95                 100 atc agc ctg tgg gac cag agc ctg aag ccc tgc gtg aag ctg acc ccc       390
Ile Ser Leu Trp Asp Gln Ser Leu Lys Pro Cys Val Lys Leu Thr Pro
        105                 110                 115 ctg tgc gtg acc ctg gaa tgc tcc aac gtg acc tac aac gag agc atg       438
Leu Cys Val Thr Leu Glu Cys Ser Asn Val Thr Tyr Asn Glu Ser Met
    120                 125                 130 aag gaa gtg aag aac tgc agc ttc aac ctg acc acc gag ctg cgg gac       486
Lys Glu Val Lys Asn Cys Ser Phe Asn Leu Thr Thr Glu Leu Arg Asp
135                 140                 145                 150 aag aaa cag aag gtg cac gcc ctg ttc tac cgg ctg gac atc gtg ccc       534
Lys Lys Gln Lys Val His Ala Leu Phe Tyr Arg Leu Asp Ile Val Pro
                155                 160                 165 ctg aac gac acc gag aag aag aac agc agc cgg ccc tac cgg ctg atc       582
Leu Asn Asp Thr Glu Lys Lys Asn Ser Ser Arg Pro Tyr Arg Leu Ile
            170                 175                 180 aac tgc aac acc agc gcc atc acc cag gcc tgc ccc aaa gtg acc ttc       630
Asn Cys Asn Thr Ser Ala Ile Thr Gln Ala Cys Pro Lys Val Thr Phe
        185                 190                 195 gac cct atc ccc atc cac tac tgc acc cct gcc ggc tac gcc atc ctg       678
Asp Pro Ile Pro Ile His Tyr Cys Thr Pro Ala Gly Tyr Ala Ile Leu
    200                 205                 210 aag tgc aac gac aag aag ttc aac ggc acc ggc ccc tgc cac aag gtg       726
Lys Cys Asn Asp Lys Lys Phe Asn Gly Thr Gly Pro Cys His Lys Val
215                 220                 225                 230 tcc acc gtg cag tgc acc cac ggc atc aag ccc gtg gtg tcc acc cag       774
Ser Thr Val Gln Cys Thr His Gly Ile Lys Pro Val Val Ser Thr Gln
                235                 240                 245
```

```
ctg ctg ctg aat ggc agc ctg gcc gag ggc gag atc atc atc aga agc      822
Leu Leu Leu Asn Gly Ser Leu Ala Glu Gly Glu Ile Ile Ile Arg Ser
        250                 255                 260 gag aac ctg acc aac aac gcc aag acc atc att gtg cac ctg aac cag      870
Glu Asn Leu Thr Asn Asn Ala Lys Thr Ile Ile Val His Leu Asn Gln
    265                 270                 275 agc gtg gaa atc gtg tgc gcc aga ccc agc aac aac acc cgg acc agc      918
Ser Val Glu Ile Val Cys Ala Arg Pro Ser Asn Asn Thr Arg Thr Ser
280                 285                 290 atc cgg atc ggc cct ggc cag acc ttc tat gcc acc ggc gcc att acc      966
Ile Arg Ile Gly Pro Gly Gln Thr Phe Tyr Ala Thr Gly Ala Ile Thr
295                 300                 305                 310 ggc gac atc aga cag gcc cac tgc aac atc agc aag gac aag tgg aac     1014
Gly Asp Ile Arg Gln Ala His Cys Asn Ile Ser Lys Asp Lys Trp Asn
            315                 320                 325 gag aca ctg cag aga gtg ggc gag aag ctg gcc gag cac ttc ccc aac     1062
Glu Thr Leu Gln Arg Val Gly Glu Lys Leu Ala Glu His Phe Pro Asn
        330                 335                 340 aag aca atc aag ttc aac agc agc tct ggc ggc gac ctg gaa atc acc     1110
Lys Thr Ile Lys Phe Asn Ser Ser Ser Gly Gly Asp Leu Glu Ile Thr
    345                 350                 355 acc cac agc ttc aac tgc aga ggc gag ttc ttc tac tgc aat acc tcc     1158
Thr His Ser Phe Asn Cys Arg Gly Glu Phe Phe Tyr Cys Asn Thr Ser
360                 365                 370 ggc ctg ttc aat ggc acc ttt aac ggc acc tac gtg tcc ccc aac agc     1206
Gly Leu Phe Asn Gly Thr Phe Asn Gly Thr Tyr Val Ser Pro Asn Ser
375                 380                 385                 390 acc gac agc aac agc tcc agc atc atc acc atc cct tgc cgg atc aag     1254
Thr Asp Ser Asn Ser Ser Ser Ile Ile Thr Ile Pro Cys Arg Ile Lys
            395                 400                 405 cag atc atc aat atg tgg cag gaa gtg ggc agg gct atg tac gcc cct     1302
Gln Ile Ile Asn Met Trp Gln Glu Val Gly Arg Ala Met Tyr Ala Pro
        410                 415                 420 cct atc gcc ggc aac atc aca tgc aag agc aac atc acc ggc ctg ctg     1350
Pro Ile Ala Gly Asn Ile Thr Cys Lys Ser Asn Ile Thr Gly Leu Leu
    425                 430                 435 ctc gtc cgc gac ggc gga aca ggc agc gag agc aac aag acc gag atc     1398
Leu Val Arg Asp Gly Gly Thr Gly Ser Glu Ser Asn Lys Thr Glu Ile
440                 445                 450 ttc aga ccc ggc gga ggc gac atg cgg gac aat tgg cgg agc gag ctg     1446
Phe Arg Pro Gly Gly Gly Asp Met Arg Asp Asn Trp Arg Ser Glu Leu
455                 460                 465                 470 tac aag tac aag gtg gtg gaa atc aag ccc ctg ggc gtg gcc ccc acc     1494
Tyr Lys Tyr Lys Val Val Glu Ile Lys Pro Leu Gly Val Ala Pro Thr
                475                 480                 485 aag gcc aag cgg aga gtg gtg gaa agc gag aag tcc gcc gtg gga atc     1542
Lys Ala Lys Arg Arg Val Val Glu Ser Glu Lys Ser Ala Val Gly Ile
        490                 495                 500 ggc gcc gtg ttc ctg ggc ttt ctg gga gcc gcc gga agc aca atg ggc     1590
Gly Ala Val Phe Leu Gly Phe Leu Gly Ala Ala Gly Ser Thr Met Gly
            505                 510                 515 gct gcc agc atc acc ctg acc gtg cag gcc aga cag ctg ctg agc ggc     1638
Ala Ala Ser Ile Thr Leu Thr Val Gln Ala Arg Gln Leu Leu Ser Gly
        520                 525                 530 atc gtg cag cag cag agc aac ctg ctg aga gct atc gag gcc cag cag     1686
Ile Val Gln Gln Gln Ser Asn Leu Leu Arg Ala Ile Glu Ala Gln Gln
535                 540                 545                 550 cat ctg ctg cag ctg acc gtg tgg ggc atc aag cag ctg cag acc cgg     1734
His Leu Leu Gln Leu Thr Val Trp Gly Ile Lys Gln Leu Gln Thr Arg
                555                 560                 565
```

```
gtg ctg gcc atc gag aga tac ctg aag gac cag cag ctc ctg gga atc      1782
Val Leu Ala Ile Glu Arg Tyr Leu Lys Asp Gln Gln Leu Leu Gly Ile
            570                 575                 580 tgg ggc tgc agc ggc aag ctg atc tgc acc acc gcc gtg ccc tgg aac      1830
Trp Gly Cys Ser Gly Lys Leu Ile Cys Thr Thr Ala Val Pro Trp Asn
        585                 590                 595 tac agc tgg tcc aac aga agc cag gac gac atc tgg gac aac atg acc      1878
Tyr Ser Trp Ser Asn Arg Ser Gln Asp Asp Ile Trp Asp Asn Met Thr
    600                 605                 610 tgg atg cag tgg gac aaa gag atc agc aac tac acc aac acc atc tac      1926
Trp Met Gln Trp Asp Lys Glu Ile Ser Asn Tyr Thr Asn Thr Ile Tyr
615                 620                 625                 630 aag ctg ctg gaa gat agc cag atc cag cag gaa aag aac gag aag gac      1974
Lys Leu Leu Glu Asp Ser Gln Ile Gln Gln Glu Lys Asn Glu Lys Asp
            635                 640                 645 ctg ctg gcc ctg gac agc tgg gag aac ctg tgg aac tgg ttc aac atc      2022
Leu Leu Ala Leu Asp Ser Trp Glu Asn Leu Trp Asn Trp Phe Asn Ile
        650                 655                 660 acc aac tgg ctg tgg tac atc aag atc ttc atc atc atc gtg ggc ggc      2070
Thr Asn Trp Leu Trp Tyr Ile Lys Ile Phe Ile Ile Ile Val Gly Gly
    665                 670                 675 ctg atc ggc ctg cgg atc atc ttc gcc gtg ctg ccc atc gtg gga ggc      2118
Leu Ile Gly Leu Arg Ile Ile Phe Ala Val Leu Pro Ile Val Gly Gly
680                 685                 690 gga gcc aag ttt gtg gcc gcc tgg acc ctg aaa gct gcc gct ggc ggc      2166
Gly Ala Lys Phe Val Ala Ala Trp Thr Leu Lys Ala Ala Ala Gly Gly
695                 700                 705                 710 acc gag aca tct cag gtg gcc cct gcc tgactcgagt ctagagggcc            2213
Thr Glu Thr Ser Gln Val Ala Pro Ala
                715 cgtttaaacc cgc                                                       2226

<210> SEQ ID NO 104
<211> LENGTH: 719
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
            20                  25                  30

Tyr Tyr Gly Val Pro Val Trp Lys Glu Ala Thr Thr Thr Leu Phe Cys
        35                  40                  45

Ala Ser Asp Ala Lys Ala Tyr Asp Lys Glu Val His Asn Val Trp Ala
    50                  55                  60

Thr His Ala Cys Val Pro Thr Asp Pro Asn Pro Gln Glu Met Val Leu
65                  70                  75                  80

Gly Asn Val Thr Glu Asn Phe Asn Met Trp Lys Asn Glu Met Val Asn
                85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu Glu Cys Ser Asn Val
        115                 120                 125

Thr Tyr Asn Glu Ser Met Lys Glu Val Lys Asn Cys Ser Phe Asn Leu
    130                 135                 140
```

```
              -continued

Thr Thr Glu Leu Arg Asp Lys Lys Gln Lys Val His Ala Leu Phe Tyr
145                 150                 155                 160

Arg Leu Asp Ile Val Pro Leu Asn Asp Thr Glu Lys Lys Asn Ser Ser
                165                 170                 175

Arg Pro Tyr Arg Leu Ile Asn Cys Asn Thr Ser Ala Ile Thr Gln Ala
            180                 185                 190

Cys Pro Lys Val Thr Phe Asp Pro Ile Pro Ile His Tyr Cys Thr Pro
        195                 200                 205

Ala Gly Tyr Ala Ile Leu Lys Cys Asn Asp Lys Lys Phe Asn Gly Thr
    210                 215                 220

Gly Pro Cys His Lys Val Ser Thr Val Gln Cys Thr His Gly Ile Lys
225                 230                 235                 240

Pro Val Val Ser Thr Gln Leu Leu Leu Asn Gly Ser Leu Ala Glu Gly
                245                 250                 255

Glu Ile Ile Ile Arg Ser Glu Asn Leu Thr Asn Asn Ala Lys Thr Ile
                260                 265                 270

Ile Val His Leu Asn Gln Ser Val Glu Ile Val Cys Ala Arg Pro Ser
                275                 280                 285

Asn Asn Thr Arg Thr Ser Ile Arg Ile Gly Pro Gly Gln Thr Phe Tyr
290                 295                 300

Ala Thr Gly Ala Ile Thr Gly Asp Ile Arg Gln Ala His Cys Asn Ile
305                 310                 315                 320

Ser Lys Asp Lys Trp Asn Glu Thr Leu Gln Arg Val Gly Glu Lys Leu
                325                 330                 335

Ala Glu His Phe Pro Asn Lys Thr Ile Lys Phe Asn Ser Ser Ser Gly
            340                 345                 350

Gly Asp Leu Glu Ile Thr Thr His Ser Phe Asn Cys Arg Gly Glu Phe
        355                 360                 365

Phe Tyr Cys Asn Thr Ser Gly Leu Phe Asn Gly Thr Phe Asn Gly Thr
    370                 375                 380

Tyr Val Ser Pro Asn Ser Thr Asp Ser Asn Ser Ser Ile Ile Thr
385                 390                 395                 400

Ile Pro Cys Arg Ile Lys Gln Ile Ile Asn Met Trp Gln Glu Val Gly
                405                 410                 415

Arg Ala Met Tyr Ala Pro Pro Ile Ala Gly Asn Ile Thr Cys Lys Ser
                420                 425                 430

Asn Ile Thr Gly Leu Leu Leu Val Arg Asp Gly Gly Thr Gly Ser Glu
                435                 440                 445

Ser Asn Lys Thr Glu Ile Phe Arg Pro Gly Gly Gly Asp Met Arg Asp
                450                 455                 460

Asn Trp Arg Ser Glu Leu Tyr Lys Tyr Lys Val Val Glu Ile Lys Pro
465                 470                 475                 480

Leu Gly Val Ala Pro Thr Lys Ala Lys Arg Arg Val Val Glu Ser Glu
                485                 490                 495

Lys Ser Ala Val Gly Ile Gly Ala Val Phe Leu Gly Phe Leu Gly Ala
                500                 505                 510

Ala Gly Ser Thr Met Gly Ala Ala Ser Ile Thr Leu Thr Val Gln Ala
            515                 520                 525

Arg Gln Leu Leu Ser Gly Ile Val Gln Gln Ser Asn Leu Leu Arg
        530                 535                 540

Ala Ile Glu Ala Gln Gln His Leu Leu Gln Leu Thr Val Trp Gly Ile
545                 550                 555                 560

Lys Gln Leu Gln Thr Arg Val Leu Ala Ile Glu Arg Tyr Leu Lys Asp
                565                 570                 575
```

```
Gln Gln Leu Leu Gly Ile Trp Gly Cys Ser Gly Lys Leu Ile Cys Thr
            580                 585                 590
Thr Ala Val Pro Trp Asn Tyr Ser Trp Ser Asn Arg Ser Gln Asp Asp
        595                 600                 605
Ile Trp Asp Asn Met Thr Trp Met Gln Trp Asp Lys Glu Ile Ser Asn
610                 615                 620
Tyr Thr Asn Thr Ile Tyr Lys Leu Leu Glu Asp Ser Gln Ile Gln Gln
625                 630                 635                 640
Glu Lys Asn Glu Lys Asp Leu Leu Ala Leu Asp Ser Trp Asn Leu
            645                 650                 655
Trp Asn Trp Phe Asn Ile Thr Asn Trp Leu Trp Tyr Ile Lys Ile Phe
            660                 665                 670
Ile Ile Ile Val Gly Gly Leu Ile Gly Leu Arg Ile Ile Phe Ala Val
            675                 680                 685
Leu Pro Ile Val Gly Gly Ala Lys Phe Val Ala Ala Trp Thr Leu
        690                 695                 700
Lys Ala Ala Ala Gly Gly Thr Glu Thr Ser Gln Val Ala Pro Ala
705                 710                 715
```

<210> SEQ ID NO 105
<211> LENGTH: 1589
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (42)..(1550)

<400> SEQUENCE: 105

```
gagcggaagg cccatgaggc cagttaatta agcttgccac c atg cct atg ggc agc      56
                                             Met Pro Met Gly Ser
                                             1               5 ctg cag cct ctg gcc acc ctg tac ctg ctg ggc atg ctg gtg gcc tcc     104
Leu Gln Pro Leu Ala Thr Leu Tyr Leu Leu Gly Met Leu Val Ala Ser
                10                  15                  20 gtg ctg gca gct ggc aac ctg tgg gtc aca gtg tac tac ggc gtg ccc     152
Val Leu Ala Ala Gly Asn Leu Trp Val Thr Val Tyr Tyr Gly Val Pro
            25                  30                  35 gtg tgg aaa gag gcc aag gcc aca ctg ttc tgc gcc agc gac gcc aag     200
Val Trp Lys Glu Ala Lys Ala Thr Leu Phe Cys Ala Ser Asp Ala Lys
        40                  45                  50 gcc tac gag aca gag gtg cac aac gtc tgg gcc acc cac gcc tgc gtg     248
Ala Tyr Glu Thr Glu Val His Asn Val Trp Ala Thr His Ala Cys Val
    55                  60                  65 ccc acc gac ccc aac ccc cag gaa atc gtc ctg gaa aac gtg acc gag     296
Pro Thr Asp Pro Asn Pro Gln Glu Ile Val Leu Glu Asn Val Thr Glu
70                  75                  80                  85 aac ttc aac atg tgg gag aac gac atg gtc aac cag atg cac gag gac     344
Asn Phe Asn Met Trp Glu Asn Asp Met Val Asn Gln Met His Glu Asp
                90                  95                 100 gtg atc agc ctg tgg gac cag agc ctg aag ccc tgc gtg aag ctg acc     392
Val Ile Ser Leu Trp Asp Gln Ser Leu Lys Pro Cys Val Lys Leu Thr
            105                 110                 115 ccc ctg tgc gtg acc ctg gac tgc gag aac gtg gac ggc aac gac acc     440
Pro Leu Cys Val Thr Leu Asp Cys Glu Asn Val Asp Gly Asn Asp Thr
        120                 125                 130 tac aac ggc acc aac gag atg aag aac tgc agc ttc aac acc acc acc     488
Tyr Asn Gly Thr Asn Glu Met Lys Asn Cys Ser Phe Asn Thr Thr Thr
```

```
                135                 140                 145
gag ctg cgg gac aag aaa cag aag gtg tcc gcc ctg ttc tac cgg ctg        536
Glu Leu Arg Asp Lys Lys Gln Lys Val Ser Ala Leu Phe Tyr Arg Leu
150                 155                 160                 165 gac atc gtg ccc ctg aac aga agc agc agc aac agc agc gac tac            584
Asp Ile Val Pro Leu Asn Arg Ser Ser Ser Asn Ser Ser Asp Tyr
                170                 175                 180 tac cgg ctg atc agc tgc aac acc agc gcc atc acc cag gcc tgc ccc        632
Tyr Arg Leu Ile Ser Cys Asn Thr Ser Ala Ile Thr Gln Ala Cys Pro
            185                 190                 195 aaa gtg acc ttc gac cct atc ccc atc cac tac tgc gcc cct gcc ggc        680
Lys Val Thr Phe Asp Pro Ile Pro Ile His Tyr Cys Ala Pro Ala Gly
200                 205                 210 ttc gcc atc ctg aag tgc aac aac aag acc ttc aat ggc acc ggc ccc        728
Phe Ala Ile Leu Lys Cys Asn Asn Lys Thr Phe Asn Gly Thr Gly Pro
215                 220                 225 tgc cac aac gtg tcc acc gtg cag tgc acc cac ggc atc aag ccc gtg        776
Cys His Asn Val Ser Thr Val Gln Cys Thr His Gly Ile Lys Pro Val
230                 235                 240                 245 gtg tcc acc cag ctg ctg ctg aat ggc agc ctg gcc gag aaa gag atc        824
Val Ser Thr Gln Leu Leu Leu Asn Gly Ser Leu Ala Glu Lys Glu Ile
                250                 255                 260 atc atc aga agc aag aac ctg agc gac aac gtg aaa acc atc att gtg        872
Ile Ile Arg Ser Lys Asn Leu Ser Asp Asn Val Lys Thr Ile Ile Val
            265                 270                 275 cac ctg aac gag agc gtg gaa atc gtg tgc acc cgg ccc aac aac aac        920
His Leu Asn Glu Ser Val Glu Ile Val Cys Thr Arg Pro Asn Asn Asn
280                 285                 290 acc aga aag agc atc cgg atc ggc cct ggc cag acc ttc tac gcc acc        968
Thr Arg Lys Ser Ile Arg Ile Gly Pro Gly Gln Thr Phe Tyr Ala Thr
295                 300                 305 ggc gcc atc atc ggc aac atc aga gag gcc cac tgc aac atc agc cgg       1016
Gly Ala Ile Ile Gly Asn Ile Arg Glu Ala His Cys Asn Ile Ser Arg
310                 315                 320                 325 gac aag tgg aac gag aca ctg cag aga gtg ggc aag aag ctg gaa gaa       1064
Asp Lys Trp Asn Glu Thr Leu Gln Arg Val Gly Lys Lys Leu Glu Glu
                330                 335                 340 cag ttc cct aac aag aca atc aac ttc acc tcc agc tct ggc ggc gac       1112
Gln Phe Pro Asn Lys Thr Ile Asn Phe Thr Ser Ser Ser Gly Gly Asp
            345                 350                 355 ctg gaa atc acc acc cac agc ttc aac tgc aga ggc gag ttc ttc tac       1160
Leu Glu Ile Thr Thr His Ser Phe Asn Cys Arg Gly Glu Phe Phe Tyr
360                 365                 370 tgc aac acc tcc aag ctg ttc aac agc acc tac atc ccc acc tac aga       1208
Cys Asn Thr Ser Lys Leu Phe Asn Ser Thr Tyr Ile Pro Thr Tyr Arg
375                 380                 385 ccc aac aac acc cag ggc aac agc tcc agc acc atc aca atc cct tgc       1256
Pro Asn Asn Thr Gln Gly Asn Ser Ser Ser Thr Ile Thr Ile Pro Cys
390                 395                 400                 405 cgg atc aag cag atc atc aat atg tgg cag gaa gtg ggc agg gct atg       1304
Arg Ile Lys Gln Ile Ile Asn Met Trp Gln Glu Val Gly Arg Ala Met
                410                 415                 420 tac gcc cct cct atc gcc ggc aac att acc tgc aag agc cac atc acc       1352
Tyr Ala Pro Pro Ile Ala Gly Asn Ile Thr Cys Lys Ser His Ile Thr
            425                 430                 435 ggc ctg ctg ctc gtc cgc gac ggc ggc aca ggc ctg aac agc agc acc       1400
Gly Leu Leu Leu Val Arg Asp Gly Gly Thr Gly Leu Asn Ser Ser Thr
440                 445                 450 gag aca ttc aga ccc ggc gga ggc gac atg cgg gac aat tgg cgg agc       1448
Glu Thr Phe Arg Pro Gly Gly Gly Asp Met Arg Asp Asn Trp Arg Ser
```

```
                    455                 460                 465
gag ctg tac aag tac aag gtg gtg gaa atc aag ccc ctg ggc gtg gcc    1496
Glu Leu Tyr Lys Tyr Lys Val Val Glu Ile Lys Pro Leu Gly Val Ala
470                 475                 480                 485 cct acc gcc gcc aag aga aga gtg gtg cag ggc gcc cac cac cac cat    1544
Pro Thr Ala Ala Lys Arg Arg Val Val Gln Gly Ala His His His His
                490                 495                 500 cac cac tgactcgagg cgcgcctagg ccttgacggc cttccgcca                 1589
His His

<210> SEQ ID NO 106
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
                20                  25                  30

Tyr Tyr Gly Val Pro Val Trp Lys Glu Ala Lys Ala Thr Leu Phe Cys
            35                  40                  45

Ala Ser Asp Ala Lys Ala Tyr Glu Thr Glu Val His Asn Val Trp Ala
        50                  55                  60

Thr His Ala Cys Val Pro Thr Asp Pro Asn Pro Gln Glu Ile Val Leu
65                  70                  75                  80

Glu Asn Val Thr Glu Asn Phe Asn Met Trp Glu Asn Asp Met Val Asn
                85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu Asp Cys Glu Asn Val
        115                 120                 125

Asp Gly Asn Asp Thr Tyr Asn Gly Thr Asn Glu Met Lys Asn Cys Ser
    130                 135                 140

Phe Asn Thr Thr Thr Glu Leu Arg Asp Lys Lys Gln Lys Val Ser Ala
145                 150                 155                 160

Leu Phe Tyr Arg Leu Asp Ile Val Pro Leu Asn Arg Ser Ser Ser Ser
                165                 170                 175

Asn Ser Ser Asp Tyr Tyr Arg Leu Ile Ser Cys Asn Thr Ser Ala Ile
            180                 185                 190

Thr Gln Ala Cys Pro Lys Val Thr Phe Asp Pro Ile Pro Ile His Tyr
        195                 200                 205

Cys Ala Pro Ala Gly Phe Ala Ile Leu Lys Cys Asn Asn Lys Thr Phe
    210                 215                 220

Asn Gly Thr Gly Pro Cys His Asn Val Ser Thr Val Gln Cys Thr His
225                 230                 235                 240

Gly Ile Lys Pro Val Val Ser Thr Gln Leu Leu Leu Asn Gly Ser Leu
                245                 250                 255

Ala Glu Lys Glu Ile Ile Ile Arg Ser Lys Asn Leu Ser Asp Asn Val
            260                 265                 270

Lys Thr Ile Ile Val His Leu Asn Glu Ser Val Glu Ile Val Cys Thr
        275                 280                 285

Arg Pro Asn Asn Asn Thr Arg Lys Ser Ile Arg Ile Gly Pro Gly Gln
    290                 295                 300
```

```
Thr Phe Tyr Ala Thr Gly Ala Ile Ile Gly Asn Ile Arg Glu Ala His
305                 310                 315                 320

Cys Asn Ile Ser Arg Asp Lys Trp Asn Glu Thr Leu Gln Arg Val Gly
                325                 330                 335

Lys Lys Leu Glu Gln Phe Pro Asn Lys Thr Ile Asn Phe Thr Ser
            340                 345                 350

Ser Ser Gly Gly Asp Leu Glu Ile Thr Thr His Ser Phe Asn Cys Arg
        355                 360                 365

Gly Glu Phe Phe Tyr Cys Asn Thr Ser Lys Leu Phe Asn Ser Thr Tyr
    370                 375                 380

Ile Pro Thr Tyr Arg Pro Asn Asn Thr Gln Gly Asn Ser Ser Ser Thr
385                 390                 395                 400

Ile Thr Ile Pro Cys Arg Ile Lys Gln Ile Ile Asn Met Trp Gln Glu
                405                 410                 415

Val Gly Arg Ala Met Tyr Ala Pro Pro Ile Ala Gly Asn Ile Thr Cys
            420                 425                 430

Lys Ser His Ile Thr Gly Leu Leu Leu Val Arg Asp Gly Gly Thr Gly
        435                 440                 445

Leu Asn Ser Ser Thr Glu Thr Phe Arg Pro Gly Gly Gly Asp Met Arg
450                 455                 460

Asp Asn Trp Arg Ser Glu Leu Tyr Lys Tyr Lys Val Val Glu Ile Lys
465                 470                 475                 480

Pro Leu Gly Val Ala Pro Thr Ala Ala Lys Arg Arg Val Val Gln Gly
                485                 490                 495

Ala His His His His His His
                500
```

```
<210> SEQ ID NO 107
<211> LENGTH: 1555
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
ttaattaagc ttgccaccat gcctatgggc agcctgcagc tctctggccac cctgtacctg      60 ctgggcatgc tggtggcctc cgtgctggca gctggcaacc tgtgggtcac agtgtactac     120
ggcgtgcccg tgtggaaaga ggccaagacc accctgttct cgccagcga cgccaaggcc      180 tacgagaaag aggtgcacaa cgtctgggcc acccacgcct gcgtgcccac cgaccccaac     240
ccccaggaaa tggtcctgga aaacgtgacc gagaacttca acatgtggaa gaacgacatg     300
gtggaacaga tgcacgagga cgtgatcagc ctgtgggacc agagcctgaa gccctgcgtg     360
aagctgaccc ccctgtgcgt gaccctggaa tgcagacagg tcaacaccac caacgccacc     420
agcagcgtga acgtgaccaa cggcgaggaa atcaagaact gcagcttcaa tgccaccacc     480
gagatccggg acaagaaaca gaaggtgtac gccctgttct accggctgga catcgtgccc     540
ctggaagagg aacggaaggg caacagcagc aagtaccggc tgatcaactg caacaccagc     600
gccatcaccc aggcctgccc caaagtgacc ttcgacccta tccccatcca ctactgcgcc     660
cctgccggct acgccatcct gaagtgcaac aacaagacct tcaacggcac cggccctgc      720 aacaacgtgt ccaccgtgca gtgcacccac ggcatcaagc cgtggtgtc acccagctg       780 ctgctgaatg cagcctggc cgagggcgag atcatcatca gaagcgagaa cctgaccaac      840
aacgtgaaaa ccatcatcgt gcacctgaac gagagcgtgg aaatcaactg cacccggccc     900
```

```
aacaacaaca ccagaaagag catccggatc ggccctggcc agaccttta cgccaccggc    960 gacatcatcg gcaacatccg gcaggcctac tgcaacatca gcaaggacga ctggatccgg   1020
accctgcaga gagtgggcaa gaagctggcc gagcacttcc ccagacggat catcaacttc   1080
accagccccg ctggcggcga cctggaaatc accacccaca gcttcaactg cagaggcgag   1140
ttcttctact gcaataccag cagcctgttc aacagcacct acaacccaa cgacaccaac    1200 agcaacagct ccagcagcaa ctccagcctg gacatcacca tcccttgccg gatcaagcag   1260
atcatcaata tgtggcagga agtgggcagg gctatgtacg cccctcccat cgagggcaac   1320
atcacatgca agagcaacat caccggcctg ctcctggtcc gcgacggcgg cgtggaaagc   1380
aacgagacag agatcttcag acccggcgga ggcgacatgc ggaacaactg gcggagcgag   1440
ctgtacaagt acaaggtggt ggaaatcaag ccctgggaa tcgccccac cgccgccaag    1500 cggagagtgg tggaaggcgc ccaccaccac catcaccact gactcgaggc gcgcc         1555
```

<210> SEQ ID NO 108
<211> LENGTH: 507
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 108

```
Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
            20                  25                  30

Tyr Tyr Gly Val Pro Val Trp Lys Glu Ala Lys Thr Thr Leu Phe Cys
        35                  40                  45

Ala Ser Asp Ala Lys Ala Tyr Glu Lys Glu Val His Asn Val Trp Ala
    50                  55                  60

Thr His Ala Cys Val Pro Thr Asp Pro Asn Pro Gln Glu Met Val Leu
65                  70                  75                  80

Glu Asn Val Thr Glu Asn Phe Asn Met Trp Lys Asn Asp Met Val Glu
                85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu Glu Cys Arg Gln Val
        115                 120                 125

Asn Thr Thr Asn Ala Thr Ser Ser Val Asn Val Thr Asn Gly Glu Glu
    130                 135                 140

Ile Lys Asn Cys Ser Phe Asn Ala Thr Thr Glu Ile Arg Asp Lys Lys
145                 150                 155                 160

Gln Lys Val Tyr Ala Leu Phe Tyr Arg Leu Asp Ile Val Pro Leu Glu
                165                 170                 175

Glu Glu Arg Lys Gly Asn Ser Ser Lys Tyr Arg Leu Ile Asn Cys Asn
            180                 185                 190

Thr Ser Ala Ile Thr Gln Ala Cys Pro Lys Val Thr Phe Asp Pro Ile
        195                 200                 205

Pro Ile His Tyr Cys Ala Pro Ala Gly Tyr Ala Ile Leu Lys Cys Asn
    210                 215                 220

Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu Leu
```

```
                245                 250                 255
Asn Gly Ser Leu Ala Glu Gly Glu Ile Ile Ile Arg Ser Glu Asn Leu
            260                 265                 270

Thr Asn Asn Val Lys Thr Ile Ile Val His Leu Asn Glu Ser Val Glu
        275                 280                 285

Ile Asn Cys Thr Arg Pro Asn Asn Asn Thr Arg Lys Ser Ile Arg Ile
    290                 295                 300

Gly Pro Gly Gln Thr Phe Tyr Ala Thr Gly Asp Ile Ile Gly Asn Ile
305                 310                 315                 320

Arg Gln Ala Tyr Cys Asn Ile Ser Lys Asp Asp Trp Ile Arg Thr Leu
                325                 330                 335

Gln Arg Val Gly Lys Lys Leu Ala Glu His Phe Pro Arg Arg Ile Ile
            340                 345                 350

Asn Phe Thr Ser Pro Ala Gly Gly Asp Leu Glu Ile Thr Thr His Ser
        355                 360                 365

Phe Asn Cys Arg Gly Glu Phe Phe Tyr Cys Asn Thr Ser Ser Leu Phe
    370                 375                 380

Asn Ser Thr Tyr Asn Pro Asn Asp Thr Asn Ser Asn Ser Ser Ser Ser
385                 390                 395                 400

Asn Ser Ser Leu Asp Ile Thr Ile Pro Cys Arg Ile Lys Gln Ile Ile
                405                 410                 415

Asn Met Trp Gln Glu Val Gly Arg Ala Met Tyr Ala Pro Pro Ile Glu
            420                 425                 430

Gly Asn Ile Thr Cys Lys Ser Asn Ile Thr Gly Leu Leu Leu Val Arg
        435                 440                 445

Asp Gly Gly Val Glu Ser Asn Glu Thr Glu Ile Phe Arg Pro Gly Gly
    450                 455                 460

Gly Asp Met Arg Asn Asn Trp Arg Ser Glu Leu Tyr Lys Tyr Lys Val
465                 470                 475                 480

Val Glu Ile Lys Pro Leu Gly Ile Ala Pro Thr Ala Ala Lys Arg Arg
                485                 490                 495

Val Val Glu Gly Ala His His His His His His
            500                 505

<210> SEQ ID NO 109
<211> LENGTH: 850
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
            20                  25                  30

Tyr Tyr Gly Val Pro Val Trp Lys Glu Ala Lys Thr Thr Leu Phe Cys
        35                  40                  45

Ala Ser Asp Ala Lys Ala Tyr Glu Thr Glu Val His Asn Val Trp Ala
    50                  55                  60

Thr His Ala Cys Val Pro Thr Asp Pro Asn Pro Gln Glu Leu Val Leu
65                  70                  75                  80

Glu Asn Val Thr Glu Asn Phe Asn Met Trp Arg Asn Asp Met Val Asp
                85                  90                  95

Gln Met His Glu Asp Val Ile Ser Leu Trp Asp Gln Ser Leu Lys Pro
```

```
                100             105              110
Cys Val Lys Leu Thr Pro Leu Cys Val Thr Leu Glu Cys Arg Gln Val
            115             120             125
Asn Thr Thr Asn Ala Thr Ser Ser Val Asn Val Thr Asn Gly Glu Glu
        130             135             140
Ile Lys Asn Cys Ser Phe Asn Ala Thr Thr Glu Ile Arg Asp Lys Lys
145             150             155             160
Gln Lys Val Tyr Ala Leu Phe Tyr Arg Leu Asp Ile Val Pro Leu Glu
            165             170             175
Glu Glu Arg Lys Gly Asn Ser Ser Lys Tyr Arg Leu Ile Asn Cys Asn
            180             185             190
Thr Ser Ala Ile Thr Gln Ala Cys Pro Lys Val Asn Phe Asp Pro Ile
            195             200             205
Pro Ile His Tyr Cys Thr Pro Ala Gly Tyr Ala Ile Leu Lys Cys Asn
        210             215             220
Asn Lys Thr Phe Asn Gly Thr Gly Pro Cys Ser Asn Val Ser Thr Val
225             230             235             240
Gln Cys Thr His Gly Ile Lys Pro Val Val Ser Thr Gln Leu Leu Leu
            245             250             255
Asn Gly Ser Leu Ala Glu Glu Gly Ile Ile Ile Arg Ser Glu Asn Leu
            260             265             270
Thr Asp Asn Val Lys Thr Ile Ile Val His Leu Glu Glu Pro Val Glu
            275             280             285
Ile Val Cys Thr Arg Pro Asn Asn Asn Thr Arg Lys Ser Ile Arg Ile
            290             295             300
Gly Pro Gly Gln Thr Phe Tyr Ala Thr Gly Asp Ile Ile Gly Asn Ile
305             310             315             320
Arg Gln Ala Tyr Cys Asn Ile Ser Glu Ala Lys Trp Asn Glu Thr Leu
            325             330             335
Gln Asn Val Thr Lys Lys Leu Lys Glu His Phe Pro Asn Lys Thr Ile
            340             345             350
Ile Phe Asn Ser Ser Ser Gly Gly Asp Leu Glu Ile Thr Thr His Ser
        355             360             365
Phe Asn Cys Arg Gly Glu Phe Phe Tyr Cys Asn Thr Ser Lys Leu Phe
        370             375             380
Asn Gly Ile Tyr Asn Gly Thr Gln Ser Asn Ser Ser Asn Ser Asn Ser
385             390             395             400
Thr Ile Ile Ile Pro Cys Lys Ile Lys Gln Ile Val Asn Met Trp Gln
            405             410             415
Lys Val Gly Arg Ala Met Tyr Ala Pro Pro Ile Ala Gly Asn Ile Thr
            420             425             430
Cys Thr Ser Asn Ile Thr Gly Leu Leu Leu Val Arg Asp Gly Gly Pro
        435             440             445
Asp Asn Val Thr Glu Ile Phe Arg Pro Gly Gly Asp Met Arg Asp
            450             455             460
Asn Trp Arg Ser Glu Leu Tyr Lys Tyr Lys Val Val Glu Ile Lys Pro
465             470             475             480
Leu Gly Ile Ala Pro Thr Gly Ala Lys Arg Arg Val Val Glu Arg Glu
            485             490             495
Lys Arg Ala Val Gly Leu Gly Ala Val Phe Leu Gly Phe Leu Gly Ala
            500             505             510
Ala Gly Ser Thr Met Gly Ala Ala Ser Ile Thr Leu Thr Val Gln Ala
        515             520             525
```

```
Arg Gln Leu Leu Ser Gly Ile Val Gln Gln Ser Asn Leu Leu Arg
            530             535             540
Ala Ile Glu Ala Gln Gln His Met Leu Gln Leu Thr Val Trp Gly Ile
545             550             555             560
Lys Gln Leu Gln Thr Arg Val Leu Ala Ile Glu Arg Tyr Leu Lys Asp
                565             570             575
Gln Gln Leu Leu Gly Ile Trp Gly Cys Ser Gly Lys Leu Ile Cys Thr
            580             585             590
Thr Ala Val Pro Trp Asn Ala Ser Trp Ser Asn Arg Ser His Asp Asp
            595             600             605
Ile Trp Asn Asn Met Thr Trp Met Gln Trp Asp Arg Glu Ile Ser Asn
        610             615             620
Tyr Thr Asn Thr Ile Tyr Arg Leu Leu Glu Glu Ser Gln Asn Gln Gln
625             630             635             640
Glu Arg Asn Glu Lys Asp Leu Leu Ala Leu Asp Ser Trp Gly Asn Leu
                645             650             655
Trp Asn Trp Phe Ser Ile Thr Asn Trp Leu Trp Tyr Ile Lys Ile Phe
            660             665             670
Ile Met Ile Val Gly Gly Leu Ile Gly Leu Arg Ile Ile Phe Ala Val
            675             680             685
Leu Ser Ile Val Asn Arg Val Arg Gln Gly Tyr Ser Pro Leu Ser Phe
        690             695             700
Gln Thr Pro Thr Pro Asn Pro Arg Glu Ala Asp Arg Leu Gly Gly Ile
705             710             715             720
Glu Glu Glu Gly Gly Glu Gln Asp Arg Thr Arg Ser Ile Arg Leu Val
                725             730             735
Asn Gly Phe Leu Ala Leu Ala Trp Asp Asp Leu Arg Ser Leu Cys Leu
            740             745             750
Phe Ser Tyr His Arg Leu Arg Asp Phe Ile Leu Val Val Ala Arg Ala
            755             760             765
Val Glu Leu Leu Gly Arg Ser Leu Leu Arg Gly Leu Gln Lys Gly Trp
    770             775             780
Glu Ala Leu Lys Tyr Leu Gly Gly Leu Val Gln Tyr Trp Gly Leu Glu
785             790             795             800
Leu Lys Lys Ser Ala Ile Ser Leu Leu Asp Thr Thr Ala Ile Ala Val
                805             810             815
Ala Glu Gly Thr Asp Arg Ile Ile Ala Val Ile Gln Gly Ile Cys Arg
            820             825             830
Ala Ile Arg Asn Ile Pro Arg Arg Ile Arg Gln Gly Phe Glu Thr Ile
            835             840             845
Leu Gln
    850
```

What is claimed is:

1. An isolated or non-naturally occurring soluble HIV-1 envelope glycoprotein having the amino acid sequence of SEQ ID NO. 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108 or 109.

2. A method of eliciting an immune response comprising administering to a mammal the glycoprotein of claim 1.

3. The method of claim 2, further comprising administering an adjuvant.

4. The method of claim 3 wherein the adjuvant comprises a lecithin.

5. The method of claim 4 wherein the adjuvant is a lecithin combined with an acrylic polymer, a lecithin coated oil droplet in an oil-in-water emulsion or a lecithin and an acrylic polymer in an oil-in-water emulsion.

6. The method of claim 5 wherein the adjuvant is Adjuplex-LAP, Adjuplex-LE or Adjuplex-LAO.

7. An isolated or non-naturally occurring soluble HIV-1 envelope glycoprotein wherein the glycoprotein is gp120 BG505 Clade A in SEQ ID NO:74.

8. The envelope glycoprotein of claim 1 having an amino acid sequence of SEQ ID NO:74.

* * * * *